United States Patent
Miller et al.

(10) Patent No.: US 11,781,135 B2
(45) Date of Patent: *Oct. 10, 2023

(54) METHODS FOR TREATING ALZHEIMER'S DISEASE

(71) Applicants: Washington University, St. Louis, MO (US); Biogen MA Inc., Cambridge, MA (US)

(72) Inventors: Timothy M. Miller, St. Louis, MO (US); Sarah Devos, St. Louis, MO (US); C. Frank Bennett, Carlsbad, CA (US); Frank Rigo, Carlsbad, CA (US)

(73) Assignees: Washington University, St. Louis, MO (US); Biogen MA Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/298,607

(22) Filed: Mar. 11, 2019

(65) Prior Publication Data

US 2020/0032257 A1 Jan. 30, 2020

Related U.S. Application Data

(63) Continuation of application No. 14/387,853, filed as application No. PCT/US2013/031500 on Mar. 14, 2013, now Pat. No. 10,273,474.

(60) Provisional application No. 61/719,149, filed on Oct. 26, 2012, provisional application No. 61/660,676, filed on Jun. 15, 2012, provisional application No. 61/618,435, filed on Mar. 30, 2012.

(51) Int. Cl.
*C12N 15/113* (2010.01)
*C07H 21/02* (2006.01)
*C07H 21/04* (2006.01)

(52) U.S. Cl.
CPC .......... *C12N 15/113* (2013.01); *C07H 21/02* (2013.01); *C07H 21/04* (2013.01); *C12N 2310/11* (2013.01); *C12N 2310/315* (2013.01); *C12N 2310/321* (2013.01); *C12N 2310/3341* (2013.01); *C12N 2310/341* (2013.01); *C12N 2310/346* (2013.01)

(58) Field of Classification Search
CPC .......... C12N 15/113; C12N 2310/321; C12N 2310/11; C12N 2310/315; C12N 2310/3341; C12N 2310/341; C12N 2310/346; C07H 21/02; C07H 21/04; A61P 43/00; A61P 35/00; A61P 25/28; A61P 25/16; A61P 25/00; A61P 25/08; A61P 25/00
See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Huynh Dinh et al. |
| 4,880,635 A | 11/1989 | Janoff et al. |
| 4,906,477 A | 3/1990 | Kurono et al. |
| 4,911,928 A | 3/1990 | Wallach |
| 4,917,951 A | 4/1990 | Wallach |
| 4,920,016 A | 4/1990 | Allen et al. |
| 4,921,757 A | 5/1990 | Wheatley et al. |
| 5,034,506 A | 7/1991 | Summerton et al. |
| 5,130,302 A | 7/1992 | Spielvogel et al. |
| 5,134,066 A | 7/1992 | Rogers et al. |
| 5,149,797 A | 9/1992 | Pederson et al. |
| 5,166,315 A | 11/1992 | Summerton et al. |
| 5,175,273 A | 12/1992 | Bischofberger et al. |
| 5,185,444 A | 2/1993 | Summerton et al. |
| 5,367,066 A | 11/1994 | Urdea et al. |
| 5,432,272 A | 7/1995 | Benner |
| 5,434,257 A | 7/1995 | Matteucci et al. |
| 5,457,187 A | 10/1995 | Gmelner et al. |
| 5,457,191 A | 10/1995 | Cook et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook et al. |
| 5,587,470 A | 12/1996 | Cook et al. |

(Continued)

FOREIGN PATENT DOCUMENTS

| | | |
|---|---|---|
| BR | PI0801674 | 2/2010 |
| BR | PI0901526 | 1/2011 |

(Continued)

OTHER PUBLICATIONS

Prakash (Chemistry & Biodiversity (2011) vol. 8:1616-1641). (Year: 2011).*

(Continued)

*Primary Examiner* — J. E. Angell
(74) *Attorney, Agent, or Firm* — Fish & Richardson P.C.

(57) ABSTRACT

Disclosed herein are methods for reducing expression of Tau mRNA and protein in an animal with Tau antisense compounds. Also disclosed are methods for modulating splicing of Tau mRNA in an animal with Tau antisense compounds. Such methods are useful to treat, prevent, or ameliorate neurodegenerative diseases in an individual in need thereof. Examples of neurodegenerative diseases that can be treated, prevented, and ameliorated with the administration Tau antisense oligonucleotides include Alzheimer's Disease, Fronto-temporal Dementia (FTD), FTDP-17, Progressive Supranuclear Palsy, Chronic Traumatic Encephalopathy, Epilepsy, and Dravet's Syndrome.

38 Claims, 46 Drawing Sheets

Specification includes a Sequence Listing.

(56) References Cited

U.S. PATENT DOCUMENTS

| | | |
|---|---|---|
| 5,594,121 A | 1/1997 | Froehler et al. |
| 5,596,091 A | 1/1997 | Switzer |
| 5,614,617 A | 3/1997 | Cook et al. |
| 5,645,985 A | 7/1997 | Froehler et al. |
| 5,681,941 A | 10/1997 | Cook et al. |
| 5,698,685 A | 12/1997 | Summerton et al. |
| 5,750,692 A | 5/1998 | Cook et al. |
| 5,763,588 A | 6/1998 | Matteucci et al. |
| 5,801,154 A | 9/1998 | Baracchini et al. |
| 5,808,027 A | 9/1998 | Cook et al. |
| 5,811,534 A | 9/1998 | Cook et al. |
| 5,830,653 A | 11/1998 | Froehler et al. |
| 5,837,853 A | 11/1998 | Takashima et al. |
| 5,859,221 A | 1/1999 | Cook et al. |
| 5,948,903 A | 9/1999 | Cook et al. |
| 6,005,087 A | 12/1999 | Cook et al. |
| 6,005,096 A | 12/1999 | Matteucci et al. |
| 6,166,199 A | 12/2000 | Cook et al. |
| 6,268,490 B1 | 7/2001 | Imanishi et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,617,162 B2 | 9/2003 | Dobie et al. |
| 6,670,461 B1 | 12/2003 | Wengel et al. |
| 6,673,661 B1 | 1/2004 | Liu et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,084,125 B2 | 8/2006 | Wengel |
| 7,217,805 B2 | 5/2007 | Imanishi et al. |
| 7,314,923 B2 | 1/2008 | Kaneko et al. |
| 7,399,845 B2 | 7/2008 | Seth et al. |
| 7,427,672 B2 | 9/2008 | Imanishi et al. |
| 7,547,684 B2 | 6/2009 | Seth et al. |
| 7,569,575 B2 | 8/2009 | Sorensen et al. |
| 7,569,686 B1 | 8/2009 | Bhat et al. |
| 7,572,582 B2 | 8/2009 | Wengel et al. |
| 7,666,854 B2 | 2/2010 | Seth et al. |
| 7,696,345 B2 | 4/2010 | Allerson et al. |
| 7,741,457 B2 | 6/2010 | Seth et al. |
| 7,745,391 B2 | 6/2010 | Mintz et al. |
| 7,750,131 B2 | 7/2010 | Woldike et al. |
| 7,858,747 B2 | 12/2010 | Woldike et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,034,909 B2 | 10/2011 | Wengel et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,124,745 B2 | 2/2012 | Allerson et al. |
| 8,153,365 B2 | 4/2012 | Wengel et al. |
| 8,178,503 B2 | 5/2012 | Rigoutsos et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,329,890 B2 | 12/2012 | Davidson et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,796,437 B2 | 8/2014 | Swayze et al. |
| 8,871,729 B2 * | 10/2014 | Sesto Yague ............ A61P 25/28 514/44 A |
| 9,005,906 B2 | 4/2015 | Swayze et al. |
| 9,012,421 B2 | 4/2015 | Migawa et al. |
| 9,084,813 B2 | 7/2015 | Roberson et al. |
| 9,198,982 B2 | 12/2015 | Roberson et al. |
| 9,644,207 B2 | 5/2017 | Rigo et al. |
| 9,683,235 B2 | 6/2017 | Freier |
| 10,273,474 B2 * | 4/2019 | Miller ................ A61P 25/28 |
| 10,407,680 B2 | 9/2019 | Kordasiewicz |
| 11,591,595 B2 | 2/2023 | Kordasiewicz et al. |
| 2001/0053519 A1 | 12/2001 | Fodor et al. |
| 2002/0018995 A1 | 2/2002 | Ghetti et al. |
| 2002/0045575 A1 | 4/2002 | Skov |
| 2003/0158403 A1 | 8/2003 | Manoharan et al. |
| 2003/0175906 A1 | 9/2003 | Manoharan et al. |
| 2003/0219770 A1 | 11/2003 | Eshleman et al. |
| 2003/0228597 A1 | 12/2003 | Cowsert et al. |
| 2004/0054156 A1 | 3/2004 | Draper et al. |
| 2004/0171570 A1 | 9/2004 | Allerson et al. |
| 2004/0241651 A1 | 12/2004 | Olek et al. |
| 2005/0108783 A1 | 5/2005 | Koike et al. |
| 2005/0130923 A1 | 6/2005 | Bhat et al. |
| 2005/0153336 A1 | 7/2005 | Bennett et al. |
| 2005/0244851 A1 | 11/2005 | Blume et al. |
| 2005/0255487 A1 | 11/2005 | Khvorova et al. |
| 2006/0216722 A1 | 9/2006 | Betsholtz et al. |
| 2007/0031844 A1 | 2/2007 | Khvorova et al. |
| 2007/0203333 A1 | 8/2007 | McSwiggen et al. |
| 2007/0287831 A1 | 12/2007 | Seth et al. |
| 2008/0003570 A1 | 1/2008 | Rogers et al. |
| 2008/0015162 A1 * | 1/2008 | Bhanot .................. A61P 3/10 514/44 A |
| 2008/0039618 A1 | 2/2008 | Allerson et al. |
| 2008/0249058 A1 | 10/2008 | Roberson et al. |
| 2008/0318210 A1 | 12/2008 | Bentwich |
| 2009/0012281 A1 | 1/2009 | Swayze et al. |
| 2009/0162365 A1 | 6/2009 | Feinstein |
| 2009/0076725 A1 | 7/2009 | Morrissey et al. |
| 2009/0176728 A1 | 7/2009 | Yague et al. |
| 2010/0261175 A1 | 10/2010 | Rasmussen et al. |
| 2011/0054005 A1 | 3/2011 | Naito et al. |
| 2011/0150897 A1 | 6/2011 | Meyer et al. |
| 2011/0244561 A1 | 10/2011 | Davidson et al. |
| 2011/0263687 A1 | 10/2011 | Mattick et al. |
| 2013/0046007 A1 | 2/2013 | Bennett |
| 2013/0078359 A1 | 3/2013 | Rajesh et al. |
| 2013/0123133 A1 | 5/2013 | Ward et al. |
| 2013/0130378 A1 | 5/2013 | Manoharan et al. |
| 2013/0203836 A1 | 8/2013 | Rajeev et al. |
| 2014/0155462 A1 | 6/2014 | Brown et al. |
| 2014/0315983 A1 | 10/2014 | Brown et al. |
| 2015/0057329 A1 | 2/2015 | Bhanot et al. |
| 2015/0191727 A1 | 7/2015 | Migawa et al. |
| 2015/0275205 A1 | 10/2015 | Miller et al. |
| 2016/0032285 A1 | 2/2016 | Rigo et al. |
| 2016/0145617 A1 | 5/2016 | Kordasiewicz et al. |
| 2017/0211064 A1 | 7/2017 | Rigo et al. |
| 2018/0051283 A1 | 2/2018 | Rigo et al. |
| 2018/0094261 A1 | 4/2018 | Kordasiewicz et al. |
| 2018/0119145 A1 | 5/2018 | Kordasiewicz et al. |
| 2019/0211332 A1 | 7/2019 | Kordasiewicz |
| 2021/0071176 A1 | 3/2021 | Kordasiewicz et al. |

FOREIGN PATENT DOCUMENTS

| | | |
|---|---|---|
| CN | 1696294 | 11/2005 |
| EP | 0653169 | 5/1995 |
| EP | 1152009 | 11/2001 |
| GB | 2471149 | 12/2010 |
| IT | GE20130015 | 1/2015 |
| JP | H06329551 | 11/1994 |
| JP | 2000297097 | 10/2000 |
| JP | 2004187609 | 7/2004 |
| JP | 2008520191 | 6/2008 |
| JP | 2011502514 | 1/2011 |
| JP | 2013107902 | 6/2013 |
| JP | 2016527154 | 9/2016 |
| WO | WO9839352 | 9/1998 |
| WO | WO 1998039352 | 9/1998 |
| WO | WO9914226 | 3/1999 |
| WO | WO 1999014226 | 3/1999 |
| WO | WO 9921439 | 5/1999 |
| WO | WO1999062548 | 12/1999 |
| WO | WO0063364 | 10/2000 |
| WO | WO2001032703 | 5/2001 |
| WO | WO01072765 | 10/2001 |
| WO | WO 2002066672 | 8/2002 |

(56) References Cited

FOREIGN PATENT DOCUMENTS

| | | |
|---|---|---|
| WO | WO02081494 | 10/2002 |
| WO | WO03004602 | 1/2003 |
| WO | WO2004017072 | 2/2004 |
| WO | WO2004035765 | 4/2004 |
| WO | WO2004058940 | 7/2004 |
| WO | WO2004011613 | 9/2004 |
| WO | WO2004106356 | 12/2004 |
| WO | WO2005017143 | 2/2005 |
| WO | WO2005021570 | 3/2005 |
| WO | WO2005040180 | 5/2005 |
| WO | WO2006047673 | 5/2006 |
| WO | WO2007027775 | 3/2007 |
| WO | WO2007107789 | 9/2007 |
| WO | WO2007134181 | 11/2007 |
| WO | WO2008101157 | 8/2008 |
| WO | WO2008124066 | 10/2008 |
| WO | WO2008131807 | 11/2008 |
| WO | WO2008150729 | 12/2008 |
| WO | WO2008154401 | 12/2008 |
| WO | WO2009006478 | 1/2009 |
| WO | WO 2009061851 | 5/2009 |
| WO | WO2009067647 | 5/2009 |
| WO | WO2009100320 | 8/2009 |
| WO | WO2010036698 | 4/2010 |
| WO | WO 2010048497 | 4/2010 |
| WO | WO2010148249 | 12/2010 |
| WO | WO 2011/005786 | 1/2011 |
| WO | WO 2011/005793 | 1/2011 |
| WO | WO 2011022606 | 2/2011 |
| WO | WO2011017521 | 5/2011 |
| WO | WO 2011079263 | 6/2011 |
| WO | WO 2011107993 | 9/2011 |
| WO | WO2011131693 | 10/2011 |
| WO | WO201113 9702 | 11/2011 |
| WO | WO 2012/005898 | 1/2012 |
| WO | WO2012018881 | 2/2012 |
| WO | WO2012177639 | 12/2012 |
| WO | WO2013078441 | 5/2013 |
| WO | WO 2013 079716 | 6/2013 |
| WO | WO2013148260 | 10/2013 |
| WO | WO2013173647 | 11/2013 |
| WO | WO2014012081 | 1/2014 |
| WO | WO2014114937 | 7/2014 |
| WO | WO2014153236 | 9/2014 |
| WO | WO2014179620 | 11/2014 |
| WO | WO 2014200909 | 12/2014 |
| WO | WO2015010135 | 1/2015 |
| WO | WO 2015072913 | 5/2015 |
| WO | WO2015106128 | 7/2015 |
| WO | WO2016019063 | 2/2016 |
| WO | WO2016126995 | 8/2016 |
| WO | WO2016127002 | 8/2016 |
| WO | WO2016151523 | 9/2016 |
| WO | WO2017015555 | 1/2017 |
| WO | WO 2017055102 | 4/2017 |
| WO | WO2017109679 | 6/2017 |
| WO | WO2013148283 | 10/2017 |
| WO | WO2018064593 | 4/2018 |
| WO | WO 2019175260 | 9/2019 |
| WO | WO 2020007892 | 1/2020 |
| WO | WO 2020227618 | 11/2020 |

OTHER PUBLICATIONS

Bennett, "Pharmacological Properties of 2'-O-Methoxyethyl-Modified Oligonucleotides" in "Antisense Drug Technology: Principles, Strategies, and Applications" 2nd Edition, Ed. Crooke, CRC Press Boca Raton (2007), pp. 273-303. (Year: 2007).*
Gagnon; IDrugs. 2010;13:219-223. (Year: 2010).*
Vickers et al. (Journ. Biol. Chem. (2003) 279(9); pp. 7108-7118. (Year: 2003).*
Southwell et al. Trends in Molecular Medicine (2012) 18(11) 634-643. (Year: 2012).*

U.S. Appl. No. 60/130,377, filed Apr. 21, 1999, Pachuk et al.
U.S. Appl. No. 60/399,998, filed Jul. 31, 2002, Pachuk et al.
U.S. Appl. No. 60/419,532, filed Oct. 18, 2002, Pachuk et al.
Agrawal, S. et al., Proc. Natl. Acad. Sci. USA 87, 1401-1405 (1990).
Albaek et al., J. Org. Chem., 2006, 71, 7731-7740.
Allshire, 2002, Science 297, 1818-1819.
Altmann et al., Biochem. Soc. Trans., 1996, 24, 630-637.
Altmann et al., Chimia, 1996, 50, 168-176.
Altmann et al., Nucleosides Nucleotides, 1997, 16, 917-926.
Altschul et al., J. Mol. Biol., 1990, 215, 403-410.
Andorfer et al., "Hyper phosphorylation and aggregation of tau in mice expressing normal human tau isoforms" Journal of Neurochemistiy (2003) 86: 582-590.
Australian Patent Examination Report for Application No. 2013202595 dated Jul. 4, 2014 (15 pages).
Australian Patent Examination Report for Application No. 2013202595, dated Mar. 17, 2016, 3 pages.
Australian Patent Examination Report for Application No. 2016202220, dated Jan. 12, 2017, 4 pages.
Badiola et al., "Tau phosphorylation and aggregation as a therapeutic target in Tauopathies," CNS Neurol, Disord. Drug Targets, Dec. 2010, vol. 9, No. 6, pp. 727-740.
Baker et al., J. Biol. Chem., 1997, 272, 11944-12000.
Baker, C. et al., Nucleic Acids Res. 18, 3537-3543 (1990).
Bevins, R.A. and Besheer, J., J. Nature Protocols, 2006, 1: 1306-1311.
Bi et al., Tau-Targeted Immunization Impedes Progression of Neurofibrillary Histopathology in Aged P30 IL Tau Transgenic Mice Plos ONE (2011) 6(12):e26860.
Boiziau et al., "Antisense 2-0-alkyl oligoribonucleotides are efficient inhibitors of reverse transcription", Nucleic Acids Research, 1995, 23(1):64-71.
Braasch et al., "Novel antisense and peptide nucleic acid strategies for controlling gene expression" Biochemistiy (2002) 41(14):4503-4510.
Braasch et al., Chem. Biol., 2001, 8, 1-7.
Branch et al., "A good antisense molecule is hard to find," TIBS (1998) 23:45-50.
Buck et al., "Design strategies and performance of custom DNA sequencing primers", Bio techniques, 1999, 27(3):528-536.
Caceres et al., "Inhibition of neurite polarity by tau antisense oligonucleotides in primary cerebellar neurons" Nature (1990) 343:461-463.
Caceres et al., "The Effect of Tau antisense Oligonucleotides on Neurite Formation of Cultured Cerebellar Macro-neurons" J. Neuroscience (1991) 11(6):1515-1523.
Canadian Patent Office Action for Application No. 2866392, dated Feb. 5, 2018, 6 pages.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
ClinicalTrials.gov, "Safety, Tolerability, Pharmacokinetics, and Pharmacodynamics of Ionis-Maptrx inpatients with mild Alzheimer's Disease", NCT03186989 online Jun. 14, 2017.
Craig et al., "Towards a small molecule inhibitor of tan exon 10 splicing: Identification of compounds that stabilize the 5'-splice site stem-loop" Alzheimer's & Dementia: The Journal of the Alzheimer's Association (2012) 8(4): p. 636.
Crooke et al., "Antisense Drug Technology", Second Edition, CRC Press, 2008, Chapters 1-28.
Crooke et al., "Basic Principles of Antisense Therapeutics" Antisense Research and Application (1998) Chapter 1:1-50.
Crooke et al., "Pharmacokinetic Properties of Several Novel Oligonucleotide Analogs in mice" J. Pharmacol. Exp. Ther. (1996) 277(2):923-937.
Davies et al., "Hyperphosphorylation and aggregation of tan in mice expressing normal human tau isoforms", Journal of Neurochemistry, 2003, 86:582-590.
Dawson, "Tau Exon 10 Splicing Tauopathy", presentation given at CurePSP 2010 International Research Symposium, Nov. 18, 2010, San Diego, CA.

(56) References Cited

OTHER PUBLICATIONS

Dawson, "The Effects of the CBD-Associated Tan Gene H1 Haplotype on Tau Expression, "Abstract presented at CurePSP 2010 International Research Symposium, Nov. 18, 2010, San Diego, CA (retrieved online Jan. 13, 2016), 39 pages.
Dawson, H.N. et al., J. Neurosci. 27: 9155-9168, 2007.
Deacon, R. M., Nat. Protocol. 2006, 1:1117-9.
DeVos et al., "Antisense oligonucleotides: treating neurodegeneration at the level of RNA" Neurotherapeutics (2013) 10(3): 486-497.
Devos et al., "Antisense Reduction of Human Tan in the CNS of P301S mice both Prevents and Reverses Hyperphosphorylated Tau Deposition" abstract presented at Keystone Symposium: Long Noncoding RNAs: Marching toward Mechanism, Feb. 27-Mar. 4, 2014, Santa Fe, NM, 1 page.
Devos et al., "Antisense Reduction of Tau in Adult Mice Protects against Seizures" J. Neuroscience (2013) 33(31): 12887-12897.
Devos et al., "Antisense Reduction of the Human Tau Transgene in the CNS of P301S mice Robustly Decreases Tau Deposition" abstract presented at Keystone Symposia: New Frontiers in Neurodegenerative Disease Research, Feb. 3-8, 2013, Santa Fe, NM,1 page.
Devos et al., "Reducing Human Tan in the CNS of P301S mice Dramatically Reverses Tau Pathology" abstract presented atl4th International Conference on Alzheimer's Drug Discovery, Sep. 9-10, 2013, Jersey City, NJ, 1 page.
DeVos et al., "Tau reduction prevents neuronal loss and reverses pathological tau deposition and seeding in mice with tauopathy", Science Translational Medicine, 2017, 9(374): 1-14.
Devos et al., "Using antisense oligonucleotides to knockdown endogenous brain tan in vivo" Alzheimer's & Dementia: The Journal of the Alzheimer's Association (2012) 8(4): p. 205.
Devos et al., "Using antisense oligonucleotides to knockdown endogenous brain tau in vivo" poster presentation at AAIC 2012; Jul. 14-19, 2012, 1 page.
Donahue et al., "Stabilization of the Tau Exon 10 Stem Loop Alters Pre-mRNA Splicing" J. Biol. Chem. (2006) 281(33):23302-23306.
Duff et al., "Characterization of Pathology in Transgenic Mice Over Expression Human Genomic and cDNA Tau Transgenes", Neurobiology of Disease, 2000, 7:87-98.
Elayadi et al., Curr. Opinion Inves. Drugs, 2001, 2, 558-561.
Englisch et al., "Chemically Modified Oligonucleotides as Probes and Inhibitors" Angewandte Chemie, International Edition (1991) 30(6): 613-629.
European Patent Office Action for Application No. 13770075.3 dated Aug. 16, 2018, 8 pages.
European Patent Office Action for Application No. 13770075.3 dated Feb. 8, 2018, 5 pages.
Extended European Search Report for Application No. 13770075.3 dated Oct. 2, 2015, 8 pages.
Extended European Search Report for Application No. 14767904.7, dated Sep. 19, 2016, 10 pages.
Freier et al., Nucleic Acids Research, 1997, 25(22), 4429-4443.
Frieden et al., Nucleic Acids Research, 2003, 21, 6365-6372.
Frost, S. Digital Telerential Screen, 2012, 91-100.
Furdon, P. et al., Nucleic Acids Res. 17, 9193-9204 (1989).
Gautschi et al., J. Natl. Cancer Inst., 93:463-471, 2001.
GenBank Accession No. AK22613 9.1 (2007), 3 pages.
GenBank Accession No. NM_001123066.3 (2015), 6 pages.
GenBank Accession No. NM_001123067.3 (2015), 5 pages.
GenBank Accession No. NM_001203251.1 (2015), 5 pages.
GenBank Accession No. NM_001203252.1 (2015), 6 pages.
GenBank Accession No. NM_001285455.1, 2013, 4 pages.
GenBank Accession No. NM_005910.5 (2015), 6 pages.
GenBank Accession No. NM_016834.4 (2015), 4 pages.
GenBank Accession No. NM_016835.4 (2015), 19 pages.
GenBank Accession NT_010783.15 (2013), 5 pages.
GenBank Accession NT010783.14 (2008)., 7 pages.
GenkBank Accession No. NM_16841.4 (2015)., 3 pages.
Goedert et al., "Cloning and Sequencing of the cDNA Encoding a Core Protein of the Paired Helical Filament of Alzheimer's Disease: Identification as the Microtubule-Associated Protein Tau" PNAS (1988) 85(11):4051-4055.
Goedert, M. et al., Neurosci. Lett. 1995, 167-9.
Gordon et al., "Antisense suppression of tau in cultured ray oligodendrocytes inhibits process formation", Journal of Neuroscience Research, May 2008, 86(12):2591-2601.
Gupta, N. et al., Can. J. Ophthalmol., 2008, 43:53-60.
Hall et al., 2002, Science, 297, 2232-2237.
Hatta et al., "Mechanisms of the inhibition of reverse transcription by unmodified and modified antisense oligonucleotides", 1993, 330(2):161-164.
Ho, W. L. et al., Molecular Vision, 2012, 18:2700-2710.
International Search Report and Written Opinion for Application No. PCT/US2013/31500 dated Jun. 5, 2013 (12 pages).
International Search Report and Written Opinion for Application No. PCT/US2014/047486, dated Feb. 9, 2015, 12 pages.
International Search Report and Written Opinion for Application No. PCT/US2015/042740, dated Dec. 15, 2015, 13 pages.
International Search Report and Written Opinion for Application No. PCT/US2015/042740, dated Feb. 4, 2016, 13 pages.
International Search Report for application PCT/US2014/029752 dated Sep. 18, 2014, 10 pages.
International Search Report for Application PCT/US2017/054540 dated Jan. 18, 2018, 11 pages.
Japanese Patent Office Action for Application No. 2015503306, dated Jun. 12, 2018, 13 pages with English Translation.
Japanese Patent Office Action for Application No. 2015503306, dated Nov. 22, 2016, 5 pages with English Translation.
Jenuwein, 2002, Science, 297, 2215-2218.
Jones et al., "Targeting hyper phosphorylated tau with sodium selenate suppresses seizures in rodent models" Neurobiology of Disease (2012) 897-901.
Jones, L.J. et al., Analytical Biochemistry, 1998, 265, 368-374.
Kabanov et al., "A new class of antivirals: antisense oligonucleotides combined with a hydrophobic substituent effectively inhibit influenza vims reproduction and synthesis of vims-specific proteins inMDCK cells" FEBS Lett. (1990) 259:327-330.
Kalbfuss, B. et al., "Correction of Alternative Splicing of Tau in Frontotemporal Dementia and Parkinsonism Linked to Chromosome 17," Journal of Biological Chemistry, 2001, vol. 276, pp. 42986-42993.
Koshkin et al., Tetrahedron, 1998, 54, 3607-3630.
Kroschwitz, The Concise Encyclopedia of Polymer Science and Engineering, John Wiley & Sons, 1990, 858-859.
Kumar et al., Bioorg. Med. Chem. Lett., 1998, 8, 2219-2222.
Lane et al., "Discovery and early clinical development of Ionis-Maptrx, The first tau-lowering antisense oligonucleotide, in patients with mild AD", abstract presented at the Alzheimer's Association International Conference, Jul. 2017, London, England.
Letsinger et al., "Cholesteryl-conjugated oligonucleotides: Synthesis, properties, and activity as inhibitors of replication of human immunodeficiency vims in cell culture" PNAS (1989) 86:6553-6556.
Leumann, J. C., Bioorganic & Medicinal Chemistry, 2002, 10, 841-854.
Maher and Dolnick, Nuc. Acid. Res. 16:3341-3358, 1988.
Manoharan et al., "Chemical Modifications to Improve Uptake and Bioavailability of Antisense Oligonucleotides" Ann, N.Y. Acad. Sci. (1992) 660:306.
Manoharan et al., "Cholic Acid-Oligonucleotide Conjugates for Antisense Applications" Bioorg. Med. Chem. Lett. (1994) 4:1053-1060.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Lipidic Nucleic Acids", Tetrahedron Lett., 1995, 36(21):3651-3564.
Martin, P., Helv. Chim Acta, 1995, 78, 486-504.
Mishra et al., "Improved leishmanicidal effect of phosphorotioate antisense oligonucleotides by LDL-mediated delivery" Biochem. Biophys. Acta (1995) 1264:229-237.

(56) References Cited

OTHER PUBLICATIONS

Morita et al., Bioorganic Medicinal Chemistry, 2003, 11, 2211-2226.
New England Biolabs 1998/99 Catalog (cover page and pp. 121 and 284).
Nishina et al., "Chimeric antisense oligonucleotide conjugated to alpha-tocopherol", Molecular Therapy Nucleic Acids, 2015, 4:e220.
Nishina et al., "Efficient in vivo delivery of siRNA to the liver by conjugation of alpha-tocopherol", Molecular Therapy, 2008, 16(4):734-740.
Oberhauser et al., "Effective incorporation of 2'-0-methyl-oligoribonucleotides into liposomes and enhanced cell association through modifications with thiocholesterol" Nucl. Acids Res. (1992) 20(3):533-538.
Oka et al., "An Oxazaphospholidine approach for the steroid controlled synthesis of oligonucleotide phosphorothioates", J. Am. Chem. Soc., 2003, 125:8307-8317.
Orum et al., Curr. Opinion Mol. Ther., 2001, 3, 239-243.
Pal-Bhadra et al., 2004, Science, 303, 669-672.
Peacey et al., "Targeting a pre-mRNA structure with bipartite antisense molecules modulates tau alternative splicing" Nucleic Acids Research (2012) 40(19):9836-9849.
Pizzi et al., "Antisense Strategy Unravels Tau Proteins as Molecular Risk Factors for Glutamate-Induced Neurodegeneration" Cellular and Molecular Neurobiology (1994) 14(5):569-578.
Reynolds et al., "Rational siRNA design for RNA interference" Nature Biotechnology (2004) 22(3):326-330.
Rodriguez-Martin, T. et al., Reprograming of tau alternative splicing by spliceosome-mediated RNA trans-splicing: Implications for Tauopathies, Proceedings of the National Academy of Sciences, 2005, Vo. 102, No. 43, pp. 15659-15664.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sanghvi et al., "Heterocyclic Base Modifications in Nucleic Acids and Their Applications in Antisense Oligonucleotides" Antisense Research and Applications (1993) pp. 273-288.
Sapir et al., "Tau's role in the developing brain: implications for intellectual disability" Human Molecular Genetics (2012) 21(8):1681-1692.
Sazani et al., "Therapeutic potential of antisense oligonucleotides as modulators of alternative splicing", J. Clinical Invest, 2003, 112:491-486.
Schoch et al., "Antisense oligonucleotide-mediated tau splicing reduces behavioral deficits and tau pathology in a Tauopathy model" abstract presented at Keystone Symposium: Alzheimer's Disease, Mar. 2-7, 2014, Keystone, CO.
Schoch et al., "Antisense oligonucleotide-mediated tau splicing reduces behavioral deficits and tau pathology in a Tauopathy model" poster presented at Keystone Symposium: Alzheimer's Disease, Mar. 2-7, 2014, Keystone, CO.
Shea et al., "Synthesis, hybridization properties and antiviral activity of lipid-oligodeoxynucleotide conjugates" Nucl. Acids Res. (1990) 18(13):3777-3783.
Singh et al., Chem. Commun., 1998, 4, 455-456.
Singh et al., J. Org. Chem., 1998, 63, 10035-10039.
Smith and Waterman, Adv. Appl. Math., 1981, 2, 482-489.
Spicakova et al., "Expression and silencing of the Microtubule-Associated Protein Tau in breast cancer cells", Molecular Cancer Therapeutics, Nov. 2010, 9(11):2970-2981.
Sproat, B. et al., Nucleic Acids Res. 17, 3373-3386 (1989).
Srivastava et al., J. Am Chem. Soc., 2007, 129(26), 8362-8379.
Svinarchuk et al., "Inhibition of HIV proliferation in MT-4 cells by antisense oligonucleotide conjugated to lipophilic groups" Biochem. (1993) 75:49-54.
Usman et al., "Exploiting the chemical synthesis of RNA", Trends in Biochemical Sciences, Sep. 1992, 17(9):334-339.
Verdel et al., 2004, Science, 303, 672-676.
Volpe et al., 2002, Science, 297, 1833-1837.
Wahlestedt et al., Proc. Natl. Acad. Sci. U.S.A., 2000, 97, 5633-5638.
Walder, R. and Walder, J., Proc. Natl. Acad. Sci. USA 85, 5011-5015 (1988).
Wan et al., "Synthesis, biophysical properties and biological activity of second generation antisense oligonucleotides containing chiral phosphorothioate linkages", Nucleic Acids Research, 2014, 42(22):13456-12468.
Wang et al., "A Novel Tau Transcript in Cultured Human Neuroblastoma Cells Expression Nuclear Tau" J. Cell Biol. (1993) 121(2):257-267.
Wolfe et al., "Tau Mutations in Neurodegenerative Diseases", J. Biol Chem, 2009, 284(10):3021-3025.
Wolfe M.S., "The Roll of Tau in Neurodegenerative Diseases and Its Potential as a Therapeutic Target" Scientifica (2012) 1-20.
Woolf et al., Proc. Natl. Acad. Sci. USA 89:7305-7309, 1992.
Yamada et al., Neurosci. 2011, 31: 13110-117.
Yoshiyama, Y. et al., Neuron 53: 337-351, 2007.
Zhang and Madden, Genome Res., 1997, 7, 649-656.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
Chernolovskaya et al., "Chemical modification of siRNA" Current Opinion in Molecular Therapeutics (2010) 12(2): 1-10.
U.S. Appl. No. 15/593,173, filed May 11, 2017, Kordasiewicz.
U.S. Appl. No. 16/527,574, filed Jul. 31, 2019, Kordasiewicz.
U.S. Appl. No. 16/986,770, filed Aug. 6, 2020, Kordasiewicz.
Extended Examination Report for EP 14826839.4 dated Jul. 6, 2017, 11 pages.
Kumar et al., "Design, synthesis, biophysical and primer extension studies of novel acyclic butyl nucleic acid (BuNA)," Org. Biomol. Chem, 2013, 11:5853-5865.
Manoharan et al., "Oligonucleotide Conjugates: Alteration of the Pharmacokinetic Properties of Antisense Agents" Nucleosides & Nucleotides (1995) 14(3-5): 969-973.
Sanghvi and P.D. Cook Eds. ACS Symposium Series 580; Chapters 3 and 4, (pp. 40-65).
U.S. Appl. No. 16/986,770, filed Aug. 6, 2022, Kordasiewicz.
Cummings et al., "Alzheimer's disease drug development pipeline: 2021," Alzheimer's & Dementia: Translational Research & Clinical Interventions, May 2021, 7(10):1-24.
International Search Report and Written Opinion in International Application No. PCT/US2022/074014, dated Nov. 29, 2022, 16 pages.
Mignon et al., "Design of the First-in-Human Study of IONIS-MAPTRx, a Tau-lowering Antisense Oligonucleotide, in Patients With Alzheimer Disease (S2.006)," Neurology, Apr. 2018, 7 pages.
Soeda et al., "New Insights Into Drug Discovery Targeting Tau Protein," Frontiers in Molecular Neuroscience, Dec. 2020, 13:1-24.
U.S. Appl. No. 14/387,853, U.S. Pat. No. 10,273,474, filed Sep. 25, 2014, Miller.
U.S. Appl. No. 14/906,047, U.S. Pat. No. 9,683,235, filed Jan. 19, 2016, Kordasiewicz.
U.S. Appl. No. 15/593,173, U.S. Pat. No. 10,793,856, filed May 11, 2017. Kordasiewicz.
U.S. Appl. No. 16/986,770, U.S. Pat. No. 11,591,595, filed Aug. 6, 2022, Kordasiewicz.
U.S. Appl. No. 18/155,945, filed Jan. 18, 2023, Kordasiewicz.
U.S. Appl. No. 16/336,443, filed Mar. 25, 2019, Kordasiewicz.
U.S. Appl. No. 15/721,366, U.S. Pat. No. 10,407,680, filed Sep. 29, 2017, Kordasiewicz.
U.S. Appl. No. 16/527,574, U.S. Pat. No. 11,053,498, filed Jul. 31, 2019, Kordasiewicz.
U.S. Appl. No. 17/339,475, filed Jun. 4, 2021, Kordasiewicz.
U.S. Appl. No. 17/574,681, filed Jan. 13, 2022, Kordasiewicz.
U.S. Appl. No. 17/821,512, filed Aug. 23, 2022, Kordasiewicz.

* cited by examiner

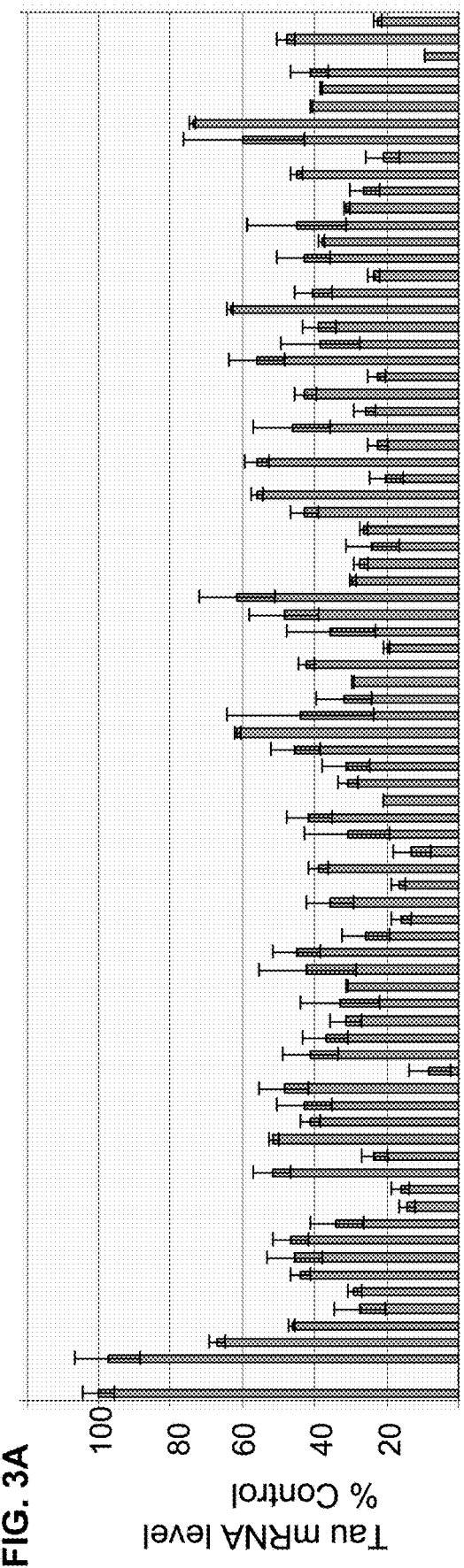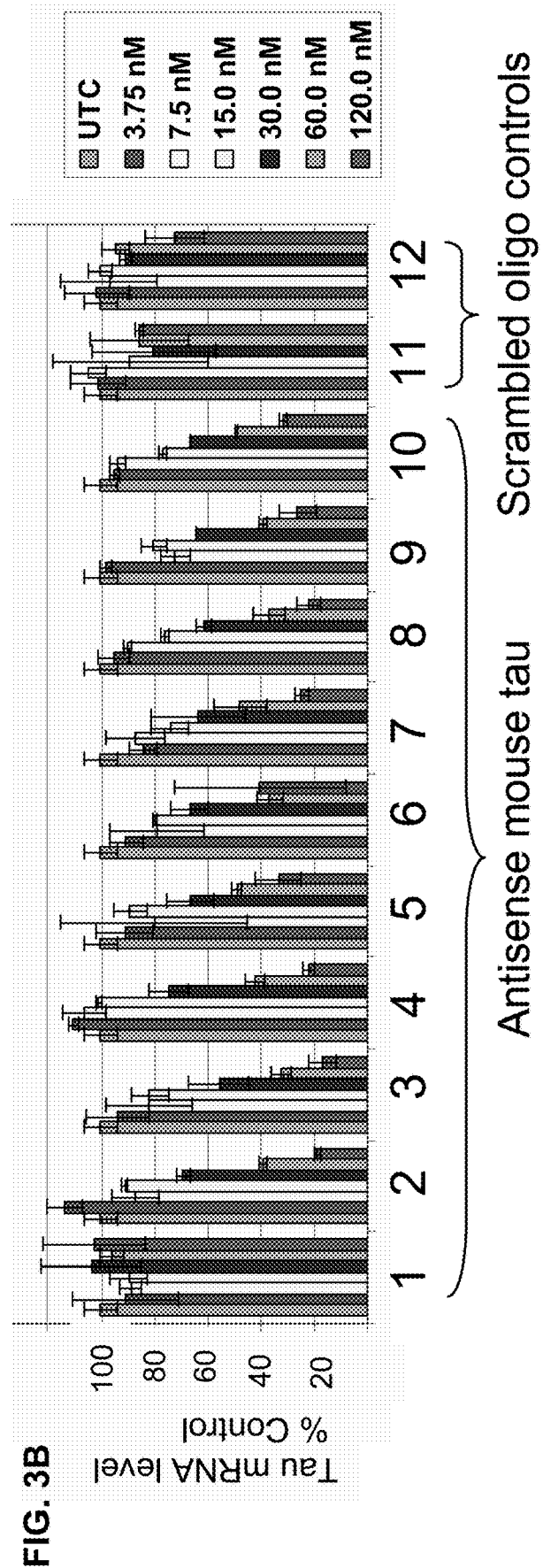

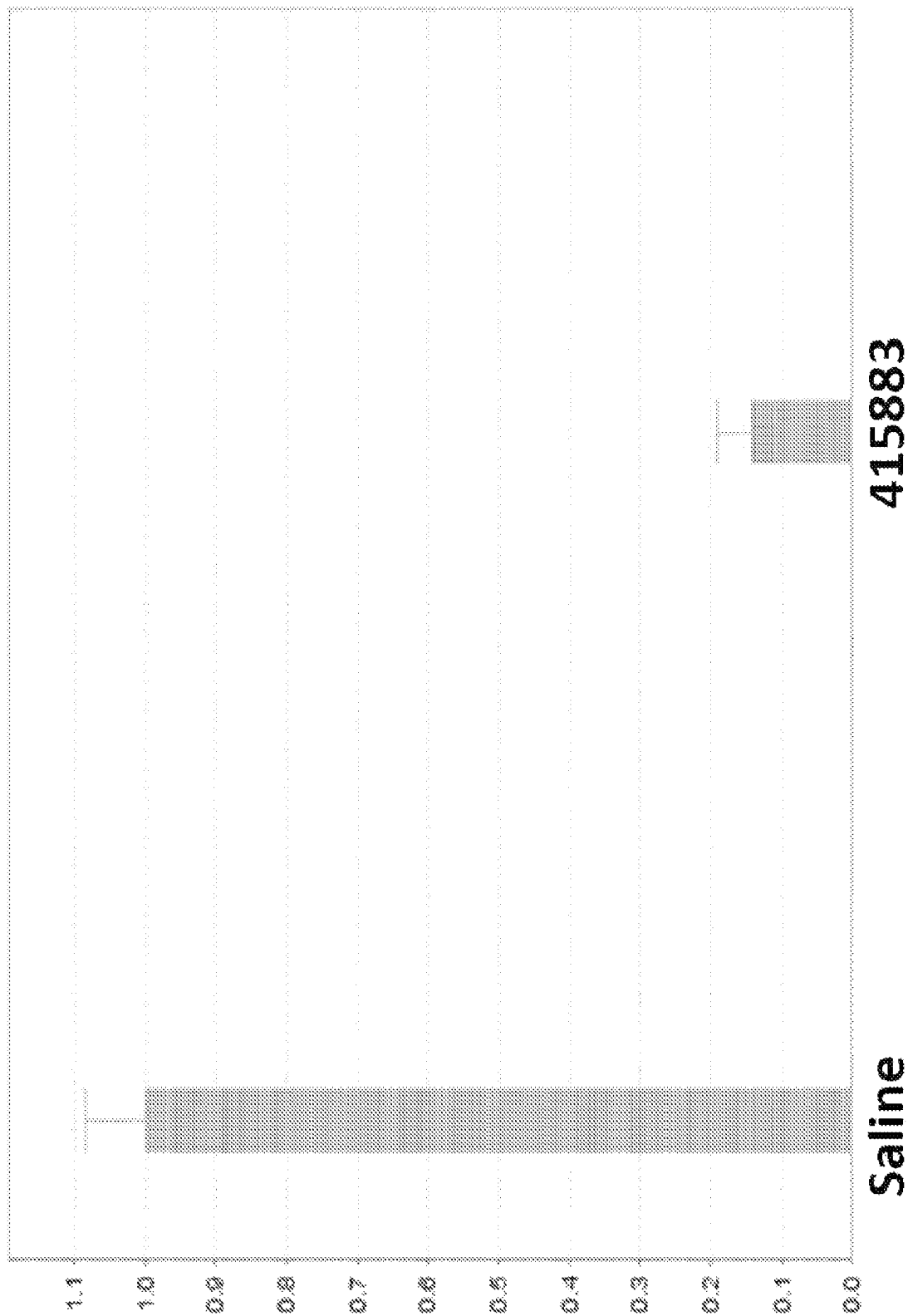

No significant effects involving Genotype.

No significant effects involving Genotype.

mRNA Tau Levels

Protein Tau Levels

SEQUENCE LISTING

<160> NUMBER OF SEQ ID NOS: 32

<210> SEQ ID NO 1
<211> LENGTH: 137001
<212> TYPE: DNA
<213> ORGANISM: homo sapiens

<400> SEQUENCE: 1

```
caaaaattag ccgggagtgg tggcatatgc ctgtaatccc agtagctggg aggctgagac      60
aggaaaatcg cttgaacccg ggaaacaggt tgcagtgagc cgagatcgtg ccactgcact     120
ccagcctggg caacagagcg agactccatc tcaaaaaaac aaaacaaaca cacacaaaaa     180
accaaaaata aataaataaa atgatcactt ctgaatactg atctaactag gggttgcagg     240
gtgggctgat atagggagaa actggagagc aaggagatca ctaaggtccc tacatgtcca     300
```

```
gaaccaagat agaggtcttg aactaggatg gtggcagtta gaacaacaac aacaaaaagt    360
caattccagg ctgagtgcag tggctcatgc ttgtaatccc aacgctttgg gaggctgagg    420
tgggagttag aaagcagcct gggcaacact gcaagacctc ctctctaaaa aaaaaaaaa    480
aaaaaagtta gccaggtgtg gtggtgccca cctgtagtcc cagcaactca gaaggctgag    540
gtgggaagat tgcttgagcc ccaggagttc aagcttgccg tgagctacga ttgtgccact    600
gcactccagc ctgagcaaga ccttgtctcc aaaaaaggt caattccact gacttttcta    660
aggtgtacac catcaagggg cagctccatc tccaggccat ggctcatga acattctgt    720
agtcagaagg ctagggcaga ttgctttgag caagccccca tggtggttct cactcctact    780
tctttgggta tatgcccctc tgtttaaaaa taaagttaat atgcatttaa aaaaaaaag    840
gagaaaaagg tcagttccag aaactgtgtg aataaagcat tttacttgct ttttctatta    900
atctataaca tatgttgatt ttttaaaaag aatataagag ctatgcaaat tggagcttca    960
agacaacttc ccatctccct aggaggagat ggctgcccta accccccta catagaaatc   1020
atcccactgc ttgggcttaa acttgatgtt ggggaaatga aaaatccaag ctaaggccga   1080
agcctggggc ctgggcgacc agcagaatga ggaccactgg tcagtttcag gctgaggtgc   1140
gtcttccagg ggacaatctc tagctggccc ttaaacattc agacttcaag ctctatttac   1200
agcataaagg tgtttcaaaa gacgtgatac aaataactgc aaatgctctg cgatgtgtta   1260
agcactgttt gaaattcgtc taattttaaga tttttttttc tgacgtaacg gttagattca   1320
cgtttctttt tttttaagta cagttctact gtattgtaac tgagttagct tgctttaagc   1380
cgatttgtta aggaaaggat tcaccttggt cagtaacaaa aaaggtggga aaaagcaag   1440
gagaaaggaa gcagcctggg ggaaagagac cttagccagg ggggcggttt cgggactacg   1500
aagggtcggg gcggacggac tcgagggccg gccacgtgga aggccgctca ggacttctgt   1560
aggagaggac accgcccag gctgactgaa agtaaagggc agcggaccca gcggcggagc   1620
cactggcctt gccccgaccc cgcatggccc gaaggaggac acccacccc acaacgacac   1680
aaagactcca actacaggag gtggagaaag cgcgtgcgcc acggaacgcg cgtgcgcgct   1740
gcggtcagcg ccgcggcctg aggcgtagcg gggagggggac cgcgaaaggg cagcgccgag   1800
aggaacgagc cgggagacgc cggacggccg agcggcaggg cgctcgcgcg cgcccactag   1860
tggccggagg agaaggctcc gcggaggcc gcgctgcccg ccccctcccc tggggaggct   1920
cgcgttcccg ctgctcgcgc ctgcgccgcc cgccggcctc aggaacgcgc cctcttcgcc   1980
ggcgcgcgcc ctcgcagtca ccgccaccca ccagctccgg caccaacagc agcgccgctg   2040
ccaccgccca ccttctgccg ccgccaccac agccaccttc tcctcctccg ctgtcctctc   2100
ccgtcctcgc ctctgtcgac tatcaggtaa gcgccgcggc tccgaaatct gcctcgccgt   2160
ccgcctctgt gcaccctgc gccgccgccc ctcgccctcc ctctccgcag actggggctt   2220
cgtgcgccgg gcatcggtcg gggccaccgc agggcccctc cctgcctccc ctgctcgggg   2280
gctggggcca gggcggcctg gaaagggacc tgagcaaggg atgcacgcac gcgtgagtgc   2340
gcgcgtgtgt gtgtgctgga gggtcttcac caccagattc gcgcagaccc caggtggagg   2400
ctgtgccggc agggtggggc gcggcggcgg tgacttgggg gaggggctg cccttcactc   2460
tcgactgcag ccttttgccg caatgggcgt gtgtgtgtgt gtgtgtgtgt gtgtgtgtgt   2520
gtgtgtgtgt gtggagggt ccgataacga ccccgaaac cgaatctgaa atccgctgtc   2580
cctgccgctg ttcgccatca gctctaagaa agacgtggat cgggtctag aaagatgac   2640
tccctgcacg cccctccctg cacctcccga gcagtgattc cgacagggcc ttcactgccc   2700
```

```
ctgattttag gcgggggccg gccccctccc cttttcctcc ttcagaaacc cgtagggggac    2760 atttgggggc tgggagaaat cgaggagatg gggaggggtc cacgcgctgt cactttagtt    2820
gcccttcccc ctgcgcacgc ctggcacaga gacgcgagca gcgccgtgcc tgagaacagt    2880
gcgcggatcc cactgtgcac gctcgcaaag gcagggttca cctggcctgg cgatgtggac    2940
ggactcggcg gccgctggtc cccgttcgcg ggcacgcaca gccgcagcca cgcacggatg    3000
ggcgcggggc tgcaggtgca tctcggggcg gatttctttc tcagcgctcg gagcgcaggg    3060
cgcccggcgt gtgcgctccc tgccggaggc gcggggctgg cgcgcagggc tcgcccctca    3120
ctgcggcagt gggtgtggac cctggtgggc gaggaagggg gaggataggc tgtgcctcct    3180
cccactcccg cccccagccc cccttttttt cccctcgga acgcgaggtg ccatcttttt    3240
tcggcgtgtc acgtctttac ggtgccatgc caaaccgggt ggccgggctt cataggacag    3300
ggcggggcct ggcattaaag ggaggggac aatcagcgct gaaatcttgg cgttttgctg    3360
ctgcgggcgt gagcactggg ggcgttcgcc cagcaccttc ttcggggggct ctttgctttg    3420 tctgtagagg ttacgtgatc tgcgctccca gccctggttt ctggctttta ttctgagggt    3480
gttcagtcaa cctccccct acgcccatgc gcctctcttt ccttttttcgc tcctcatttc    3540 cgagcccatt gttggatctc gaggcttgct gggttcgatg aactcgagtc aaccccccga    3600
cccccggcac gcatggaacg ggcgtgaccg cgcgcagcct cgtctcggag tctgccggcg    3660
ccgggaagct tctgaaggga tgggattcga gtctccgtgc gcgctgcggg cggcggcaga    3720
gggatctcgc ccctccctac accccaagtg tcctgagggc cacgccacac caggttgccc    3780
agcgagggac gctggctacc catccgggga tgggtgggga gccctggcgg ggcctctccg    3840
gctttacgcc ctgttgcttc gcctggccgg agaatgtgag gaaggggcat aaggttactg    3900
gtgcttcggc cacacccatc tttctgagcc cactggactg ggcgcagagg ggggattgcc    3960
atggaaacca caggtgtccg gagaggggat cttgggctg gcctcaccc ttccctgcgg    4020 agattgggga ccctggggta gggggagccg cgcccagtcg gcctcctgga ggacacggga    4080 ggaagcccg aaccccgcg cctgaggctg tttctgattg gccccctggag gccgcagaca    4140 cgcagatagg cggccctggg tgtattttta ttaatattat gtccgtactg attaatatta    4200
tttatcttaa ataaatttca cccgtgtcca agttcaccgc gcccccaaaa ccgagtctgg    4260
ggcggcaggg ggaactcctg gccaacgaat ccatgcctcg ccctcctgtg atgaacctgg    4320
tacgcacggt tttctggtta attctatcgc tgaaaactgg tgcgggggc gcacttctga    4380 gacgaagag catctaggag ctgaatcctc cacgcgggtc gcccaggttg atctgaattt    4440
ctggggaatg gcttggctgc ccgcccggga ccaggccgac cctccttgac ggtggcgtag    4500
agggctggag cctgggtact gcgaggctcc tcgcatggct gggcccgccg cgaggggttg    4560
cagagcggct cagggatcga ttcaagcatc gtctctcctc cctcgccccc agacagagct    4620
gggcgcgggg ttcccccttcc agatggacg agggtctcgg ggtggcccg gaaaagggga    4680 gcccgcggcc acggctacgt attgccatct cgcgagcaga gatgtcacct cctgcctttg    4740
gaggaaaggg agcccggtgg ggatgagcgc atttagccca atgctgggaa caaagcgcac    4800
tccgcgcttc tgcgatttcg ctccattttg aaatgtgttg gcgctttggt ggggccgctg    4860
cggtgggcaa ggccggggc gctgttaatg gaggaacctc agggggacgg tccttcgtag    4920
gaaactctat cctggctctg cgcgcgcttt aaggaaatgg cttccctcca ggacctcgag    4980
ggatgcagct tttgcgcgga tgacggtggg gtgctgaacc agccggtgcg cctctggaaa    5040
```

```
tgtctgggca cggatcctgg ggccatcgac gactcctccc cattcccagc aggcgggagc    5100
tcttacattc cgagcgagtg acccctctca ccctctggcg ctcacacacc tgtaactcca    5160
aacctccgtc tcagaatggt ccaggctgga agggatgatg ggggctccga cagcgactgc    5220
ctagctcacc cctctgcgtg ctcaggctcc aggctcagca ggaccaattt gagttctatc    5280
tgatccccct cggccccta actgacccat cctacaggag acagggaaat gtctttccta    5340
ccgcggttga ttctgggtg tcattttgtg ttttgtgatg ctgcttata tttactgtat    5400 aagcattgta tttactgtat aagcattgta ttataattac tgtataagct gcttatattt    5460
actgtataag catctccaaa tcctccctct acgtaaacaa attaatggat aaacagataa    5520
gtgtatcccc tgcccccacc cctgctacgc aggtccggag tgactcttga agctcataca    5580
ttccttggcc aagtttgctt ctctaacaga tgtttatata gcaataaacct ggcttggctc    5640 ttgggttcac ctttggacga tttggggaag gggcttgttg gctttgctgg ttttggatg    5700 agtgacagtc catgactgtt cctgctggaa gggcgtgact tttaagtggt ttctaatatc    5760
aggcattgct cctccgacag gaacaaaaga aatggatact gcccataaat tgttagaaaa    5820
cttagaatcg ctttgattga ggaaaggtta gatttattcc ggttggaaaa agtggccttt    5880
ctattaaacg tgccctttga ccctcatgcc cttggaggtc ggtgccagcc tggagatggg    5940
ataagattgt ggttttcctt ctgccttttt aacatctgtt gttacagtcc atttgttgaa    6000
aatttaaaga aactgtttta ttccactttc cctcagcatt tatgtgtgtg gtttcagtag    6060
ctctgtggct atatgtacga acacgtgtta tttttccaat tggacatgtg ataatttcc    6120 aactggacct tgccttctat tgatgtattt atttagcatc ttccttactc cctccttgaa    6180
aaagaatcac tcaaaaacaa ataaaaacag ccgtaggggc ctaatacagt gctagacata    6240
caagaggtat tcggtccata ccaaatggat tttatccatg aaggataaat ggggaaatac    6300
agtgggaagc aggtgggaaa ctgcgtttga ctctgctctt tcctccacca ccactttcct    6360
catcaccgtg ttcagagacc cccaaagccc cctcacactc cagaaacac cccctggcc    6420 actcctaact tgccatgccc aggagttagg tgcttccact agtgacatgg agctggcgtt    6480 tgggggcac ctcagcaggt gacgggaaga gaagacccca gcctcaccag ctgggctgca    6540
gcagggagag gagtcctcat gttccagcag ggactctcag ctgttttcct gtaaaaccat    6600
ggttctcaac tggggccac tgagatgtct agagagatgt ttttgttttc acaactcggg    6660
gagggtgcta ctgacatctt gtgggtagag gccaggaatg ctgttaaaca tcctacaagg    6720
aaggcacagg acagtctcct acatcaaaat atgacccagt cccaatgtca ccactgctgg    6780
ggttgacact ggcactgcta tcttaattac attcattgag tgtcttttag gaggccctat    6840
tctaagtgct tgctaagatt atctcattta atcctcacaa cacttccgct atgtagcagg    6900
tgctgttatt atctccgtga tggggaaact gaagcacaga gagggttagt aacttgctaa    6960
aggtcacaga gccagtgggt ggtggagctg gttgcctgac actagttccc tcccctctca    7020
gccacatgtg ggtttacttg gccattgtgg actagtctgg gaaccagat atgatctata    7080 acattgaccc agtagaatat tgattccaaa accactgtct cacaaatgaa tttttacaag    7140
agtctgtaat cggagcatga cccagaataa ggttagggaa atgtggagtt aaagctctca    7200
atttcttatc tggccccgac acagagagca aggcatttca ctctacattg gtgctctgtt    7260
tataaaacaa agagcaaata tctcttccta aggtccttaa acctcttccc ccaatccagg    7320
gtttctggac tgctctgcca tatgacgggg cagctggttt gattgaccca gggaaggctg    7380
gaaatcaaga ctgggggatc aagacgtaga ttcagtgtgg ccaaggtcaa gtctctgagg    7440
```

```
tttagggaca tcagatcccc agcttaggtt ctgtacctcg gcaaggtgaa agcgttggcg    7500
cccactgatg aggcctgctc tgagattgtg ggtgtgggtt gagttgggtg ggcataggca    7560
agtcctcttg taagaatctt ttggcaaaga tgggcctggg aggcttttct cacttcctgg    7620
ggcccaggct ttgcaataag tattccatta tactgtggta ccttggggct acctgagaat    7680
cctctgtctc gcccctgttg ccttgccaaa gagtttgctg tccaagaatt cctttcctgt    7740
ctccaggtgc catgctcctg ccacctctgc caggttccct gcctgccag atggctccca     7800 actgagtgtg aggaggaatt tgagacaggt tttgagcttt ctgggttctc cagttaggaa    7860
actttctgta agcatgcaga tagaatgggc ttcagcaaaa tacaaactcg aacaacttcc    7920
atgtatagtc ccttaatttt ctttgctttt tcatatttc atcaggctcc atgctgagcc     7980
caatcaggga cccgatagaa atccaaacac catgtcagcg agtccccaag aaatgcattt    8040
tgtgccaagg ctattcaagg aaggtttggg agcagctcaa gggcagacac tgttaccctc    8100
ccccaggtcc ccagtgcagg gcagtgttct gcatgtggag gcagtttggc ctaatggtta    8160
aggaggtagg ctctgatcgg gcctcctggg cacaaatccc agctccctgc tcactgtgag    8220
acctaagcca tattgtttag ctgcttggag agttttttgt catccacaac ttggagtatg    8280
atggtacctg tctcacgggt tgccatgggg ttcacacaag ctaacccggt actcactagg    8340
gccaagcaca tagtaactgc tcagtaaatg gcatcatcgg cggtgtcctg tggatgagtg    8400
cttgtgattg gctgaatgac cagaggggtc taaagatcct ggtgatggaa tcagttgtac    8460
agataaattg ttacactgag tagggatcaa gataggaaaa gtcggcaact acccagctcc    8520
cctgcaccaa actgggcaga agtggatcct ctgaaaattg cacacaccca tgtttaaatg    8580
tacacacaga actcttgcca caggcaagcg gagatttgtc atctgctgtc cctgcctcat    8640
cttcttcctg aaatccactc catgccagga ataaactgca tgctctccac cagcccaaac    8700
tgacctgcct tcccgccagc catcccgggc agggtgacct ggcttagtac atcgggttca    8760
gagatctttc cagtttactc gttgaataaa aagtgagggc tgatcgagaa agtaatggca    8820 gtcaggaag gcgaaggagg taaagaagag attttacaaa tgaagtaatt caacagagtg      8880
ctgacattgg taaactggca aacagatttc agggtggttg gttgagagta gagtagaaaa    8940
ggattaaata aagcaaactt gtggtgtact gaatcttagg aattccatgt atccaataag    9000
tatagtcatt tatgaattaa taaattcggc ctaagaagcc ttcttatcgc ttaaatcaag    9060
actaagtaac aatatatcag ttttaaaaag tcattatatc agaaaatcat ttaaatgata    9120
cacatagatt tccaagattt tactttaacc gaaactatat aaatgtgaat tgttcaccc     9180 atcttttgac acagggctca ggtcttctct tggtgtctgg atcagccagt tgaaatttct    9240
tgtctgtttt gcctatgcca cattaataat gcactgtctg ggtcctccga tttcagtttg   9300
gattttgggt ttacattgtg gagtcatctg aatgcagaat ccttcaggga ttttactttt    9360
tttttttttt ttcatggtct ttaccatccc atttgatagt aaatattact cacctttatg    9420
aagtctttcc aaaacattca actaaatttt cttaaaatca ttgaatgatt tgaagagctt    9480
attcctcagc acttttactc catcagcttg caccttattt tttaatcttt ttttgagacg    9540
gagtctcgct ctatcgccca ggcttaagtg caatggcgcg atcttggctc actgcgacct    9600
ccacctcctg ggttcaagca attccgcctc agcctccgcc gtagccggga ctacaggtac    9660
acaccataat gctcggctga ttttgtatt tttgtaggga tggggtatcg ccatgttggc      9720
caggctggtc ccgaacttct gacccaagtg atccaccca ctcggcctcc caaagtgctg      9780
```

```
ggattacagg tgtgagccac cgcgcccggc cagcttgcac cttatttagg atatgtgatt    9840
attatagcaa gtctggtgta catacaagat tttgaatggg cacagatgac ctttagtaag    9900
tgcttggctg tgataagagg cagtcctgac tgcagatcag gctgtgtgga ccccagcctt    9960
gcatgtttac agaccttcat gtcttattct tacagggtat cagaagaaca cctactgggg   10020
aaacttataa attagtaaaa ggtgggcatt ctccccgccc atcttctgtc tgtctgccag   10080
gactagcaca gcactttgaa gtcattcaca tagaatccca acttaagagg gtaaaatcct   10140
cctcaacaga ctgaaaataa gtttaaattc cctttgctat attaactccc ctgaggaaag   10200
agtcttagat caatgtccaa cactaaaaac agtttttaaat cagcaagtga gaattaaaatc   10260
tgaagcaatt gataataatg tttcattcat tcctctcctt tggccccgtc cacccctactg   10320
ctaaatccag gcatcaaaga gaagagggac ataattatct ctagtcccag ctgctggttt   10380
tccttccagc ctatggccca gttttctgtt ttactgagaa ggctggtgat gttatcttgg   10440
gatctaagtc tgcagtttca ccacaaaaag tccagggatg cactttcatg cttgtgtcct   10500
cctccctggg atagcaagga tattagaaga ccccctggctc tgtaattgct tgtcatgtgc   10560
tctacagacg ccacagaatg ccaagaacga agtgctggga aggacaaaatt catggaaccg   10620
tgggacggtg ctcctccccc agcgtaaagg acagctcctc ctcctgaatt ggagccagcg   10680
ttctaaaatca tgtgtcaaca gagttgtcct ggatcggatc cagttctgcc attgatttgc   10740
aggtcatttc agtggtacct gtttccagtt gttcttaatt gaacagtggc accaaaactat   10800
tgtcttgcct catcccctc ccatggcctg tcccccaaaa agagacttct tgggtaatta   10860
atcagggcaa catcaggcag tctggcgcg gtggctcacg cctgtaatcc cagcactttg   10920
ggaggccgag gcgggcagat catgaggtta ggagattgag accatcctgg ctttgtgaaa   10980
ccccgtctct actaaaaata caaaaaatta gccgggcgtg gtggcgggcg cctgtagtcc   11040
cagctactcg agaggctgag gcaggggaat ggcgtgaacc cgggaggtgg aggttgcagt   11100
gagccgagat cgcaccactg cactctagcc tgggcgacag agctagactt cttctcaaaa   11160
aaaaaaaaaa aaaggaatct ctttggtttt atatattttt tttatatat ataatatata   11220
ttaaaatata atatatatat ttatataata taatatataa atatattata tattatatat   11280
ttttatatat tatatattat atatattata tattatatat ttatatatat atatattata   11340
tatatttata tattatatat ttatatatat tatatatttta tatataatat atattatata   11400
ttatatatta tatattatat attatatatt tatatatatt atatattata tatattatat   11460
attatatatt tatatattat atatttatatt attatatatat ttatatatta tatatttata   11520
tattatatat ttatatatta tatatattta tatatattat atattatata ttatatatgt   11580
atatattata tatgttatatt attatatata tttatatata taatatattg tatatattat   11640
atatctaata tattatatat attatatata ttatatatta ataatatat tatatatattat   11700
atatatatttt atatatataa tatgtataat atataatata tataaaaaca tatataatat   11760
atattatata ttatatatat attatatata ttatatatatt taaatatatt ttatatatat   11820
tatatatatt atatatatta aatatatttt atatatatta tatatatata cacatatata   11880
tatataaatg aggccaggct cggtggctca cacttgtaat cccagcactg tgggaggatc   11940
acttgaagcc aggagtctga gactagcctg gcaacaaaaa caagatcctg tctctacaaa   12000
aggaaactgt aaaaattagc tgggcatgat ggcatgtgtc tgtagcccta gctacttggg   12060
aggccgaagc aggaggatcg cttgagccca ggagttcaag gctacagtga gctatgattg   12120
tcccatagca ctccagcctg ggtaacacag caaggccctg tctctaaaact ttttttttt   12180
```

```
aattctattt atatttacat gtatttaaat gtgaatattc actacctatt tgttgcatgc    12240
ctgcattttt tatactgggc ttgccaaaaa cccgaacagc tttctacttt gacaatgtat    12300
cagaatttaa atcagcaata tgttaataag ccaagcaaag gttatatatg caaataaaac    12360
tgttgtctat aacctcctgt tacactgggg cacagcaaaa gtcatggtgt agtcgcatgt    12420
gaacctgtcc ctttcatagc tgctcattgc caggaaacat caggaatagc catttggaag    12480
agtcatcagc cctcccacca tccgttttct gtcttgtctt ttccctatga gcaggggaaa    12540
ttccacgctg gccccaatcc ccagtgcagc ggctcagcct ctgcctctgc tgctggtccc    12600
catgaggcca gcttagaaac ggaggatttt gcagaacatc cctaaatccg cttgaataat    12660
gaagtgatca ttcataaact cacctgaacc ttattaaaac ctatttaata tttttcctgg    12720
ataatcctat agggataact tgcctcctgg gcttctctcc accgggttca gttcttcctt    12780
tagtggtgaa gttcctccct tcttagcatc tcaactgtgc ctgagaaaag gccagtggcg    12840
gctgcactct gttccctgtg gagtgttaat aaagactgaa taaattgaaa taaatcccTT    12900
tcaatgtcat taagtgctat aaataatcat gaaccaatgt tcgatggctg atgagaaatg    12960
caagaaaaaa ttttTaatca gtaggattca taagttgaca atctgggcca agttaaaaaa    13020
aataaaaata aaaagacttt taaaaagatc ttatcgtttg ttaccagtaa gactgaattc    13080
cagaagcaag ctactccctc atttgtgggc ccctgttatc actggctgct tagggttgcc    13140
aagccctgaa ttcatttgtc aactaagaga ttttTggcca agattaagat ttcccatgcc    13200
tccatatttc catctgagaa atggagatta tactgtcttc cccctcagaa tggatgataa    13260
tgtggtctct cttctgttcg catagtcata gaactgaaat aaaacaactt aagagaattc    13320
ctttgagctt tcagaagtg ctgcagggct gggggatgcc tcccaggagc cgcagtcagg    13380
tgctgatctg aagtctttgg tgggctgact ttagcctgac ctgaaatagt atagctgctg    13440
ccacctggct cccttagcgt cagtcagacg gtgcagctgg ttcctagggg tgagggctga    13500
gccagcaggg tccgtgccca ggagggatgc atgggtggcc acagcccagc ctgcactgat    13560
cttgtctgtc ccctcttttg gaaggaagga gccccaaacc agggtgcaag acagtgggtg    13620
ggggtgcctt gagcatgacc tcaagtgatt ccagcccct gccagtgctg acttctctgg    13680
ggaagggctg ggacttcctt ctgggctcaa gtcacgaccc ttggatggaa ttcctgggga    13740
gcttttctgt ttttctgga gttttcagtt ttttcctaac cagacaggga cttggtacag    13800
aatctcatat tctaattatg cctaggagca gcctctcccc accactcaca gtgtttagca    13860
tgtgacagga atcgattaag gcatgagtga ttaaattaaa gccaggcatt gacttggatg    13920
gtgtaatatt ctgacatctg tttggtgtca aaggcacggg gcaggcgcgt taattgaact    13980
gcttgcacct ggcatttgaa ttgagccaga gcggggctaa agtcagtttg ccttcaccct    14040
gtaaatggag ggtttctccg gagcgtggat ggtgggaggt atttcagggt gtatgcataa    14100
cccccaccct gacaatggcc catctcttct ccagcgtggc caggtttgag tgccagtcct    14160
gggtgtccag tggccccata gccttgcgtt ttagtaaaat gctgccccca ttaccacctg    14220
gtctgtgcac ttcggtcact ggaatttgcc atcttccagt cccgaatgtg gcaagccatg    14280
gagccttaag ctcttctccc tccacatcct ggaacagacc cgccagtttc ttccaggcat    14340
tgcctcagtt tgcccctctg tttccagtca cactctcacc agcgataaaa tgatttaga    14400 ccttatcatc tcacctcgg atccttatgg aaacaataat gagttgttcc ctgtttcaat    14460
tccaaaattc atatccaatc cgttttgcat gccattgcca aattcctccc agagcaaccc    14520
```

```
cgtcacctgc cctggccctc tccaagtgtg gtcctgccat gggcatcgcc tgctaagcca    14580
agctggcctc gagctgcctg cccgggtccc cacaccttgg ctcacctccc tgcccagtcc    14640
cgcctcctgc cagcctgccc tgtggctcct tcatagatgc cgtgctcttt ctgccccttg    14700
ctcacccatg gcagccttgc ccctctctcc ctgccccacc ccctatttaa attgacctga    14760
ccttcctcag tgtccatctt ccccgaagct ttccccagcc ttggcactca aggtccagag    14820
gctacgcgtt tcctctcacc tgtggcagcg ccgtgcctcc cagtgcctca cagtttcctt    14880
cttgcccccg cttcctgtgt aggactcatc tgcccacagg ttgcacgtcc tgtgagggca    14940
aggactgtgt cttatgtgac tttccttctc cagtcacaga gctgggcaca tagatagctc    15000
aaaaccctct ttattaacac agttggatgt tgagaaatca acaggccaa tgtcaaatga     15060 gctctcctta tttaaatcaa gtcagttctc cacctcctag cactcagttc cagtactcta    15120
tatacatgga aataataaaa aacacatttc ctttgaaaca ttctataatc gttcctttgc    15180
cctacttcag accaacttaa cgcactcccc attggtccaa atgagttttg ctatacgaag    15240
atgctgataa taatagcagc agtggattat tctgctaaaa ccattgcctc gttaatcctc    15300
agtcccgagg tggggattat tatcctcatt ttgcagagaa gcaaactgag actcagagat    15360
ttcacagctg ggagggagc cagctcatcc ctctgtccag gcccaagctc tctcccgctt     15420
gccttcctgc ctctgcaacc tcagagcatc ccccatctgg ttctactgcc tgtgctagtc    15480
gtgcaggagc caaaagacac gtctttagtg ctaaggactg gagaagccat gcctccagc    15540 ctctgtgaat gggtcatatg taacatgagc ctggagaaat tatttgaaac caaaggcaag    15600
cctctaaacc aggctgctgc ttcatggcgc cggtgacggc agaaccaaat ttagtgctgt    15660
gggcaggtcc acacttatca aatagagaag ctcattttc ttccggctca catcaagcat     15720
gaaaaatgtt cacacatacc ccccacacac acatgctttc cggaggggtc catgtggcta    15780
gaggctggaa gatgtggatg agaggagcct ggcaggtaag cccagggaag atgacattca    15840
gcttcccaga cagcatctac agggagaaat ttaattaaaa gtggggcggt ttccctgagc    15900
aaggcagaca aagtcagccc tctactgtta agaaaaaggg tcacagtgag aggggaggtg    15960
aggagactga gtctgtattt tctagtctgt tgggctacac tacctgatcc cccttcctca    16020
aaaatccact ttactttccc catgtctaca ccaatgtggt tcacactctg ggaccaggaa    16080
aagggggagt gatggggaac agagaaggga ggagctcaca cagctgaggc tggggttatg    16140
catatcgaat tacttagaat ttgcaacctc acagggtact ttcatggcgt tgaaatacac    16200
ttcccacagc cacccctccct ctaactaaaa gcaagagtca tttctcagtt ctggtcttgc    16260
ctcccacgtt ctcctccaca tttaagaaaa tccaccagct acaaagtgaa gataccatat    16320
gtgatatccc accctagttt ctgttttatc agggtttgga gcaggtggag caggcagagg    16380
gatcatttca gcctataaat tgtattaagg gtgagtactg agtcattctt caagaaaagt    16440
tttagaagca tccaaaactg aagggtggag ccacctggag acagtatcat cagtcctggc    16500
cccgagcatg gcctgcatag gccccatgg atcccagcgg gagctgcaga gtgcgggcac     16560
cttggcacac agccctgagt gcaaaattag gagctgggca gagggcatct ctctgtcgcc    16620
attgggcagc ccagggcaca ctggtcatag ccttagccaa cgaacaccct gtgcccgggg    16680
gacagatgca accagtgtgc cctgggctgc ccaatggcaa cagagagatc gacacctgga    16740
ccccatgtca cggggactcc actactaagg ctcctaagac tgccaccttc cagtgggata    16800
agccctgcct cctactgggc ccacaatgtg cagagaaaca ttgggactac ctggctttct    16860
ggatacacaa atattgatcc aatctggact aattagaagg tcagtcccaa taacaaatcg    16920
```

```
aagtcagctg ggcgtgatgg ctcactccta taatcccagc actttgggag gctgaggtgg    16980
gcagatcatt tgaagccaga agttcaagac cagcctgggc aacatagcaa aaccctgtct    17040
ctactaaaaa tacaaataat taggctgggt gtggtggctc atgcctgtaa tcccaacagt    17100
ttgggaggct gaggcaggtg gtcacctgag gtcaggagtt tgagaccagc ctggccaaca    17160
gggtgaaacc ccgtgtctac taaaaacata aaaattagcc aagcatgatg gcatgtgcct    17220
ataatcctgg ctactaggga ggctgagaca ggagagaatc gcttgaatcc aggaggtggt    17280
tgcagtgagc tgagatggtg ccactgcact ccagcctggt tgacagagca agactctgtc    17340
tcaaaaaaaa aaaaaaaaaa aaaaaagcc atgcctggtg gagcactacg tgtaatctca    17400
gctatttggg aggctgaggc acgagaatca cttgaacctg ggaggcagtg gttgcagtga    17460
gctgagatcg cgccactgca ctccagcctg ggcgacagag tgagtgagac tccatttcaa    17520
aaaaataata aatctgagtc actttaatat tgttatttgg atgtcaacct ctaggtgttt    17580
gagacaggag agtgatatgg gggcactgga aacacacagg cacggggtgt cctcacactt    17640
gggtagccca cacgatgtga tttcaggtgt ctgggaggtc cccccactcc ccaaattact    17700
aacaagtgga tagtacttta cagtttatat gatctcattt gattcttaac atgagcctgt    17760
gagtgaaaaa ttccttcccc tcttctacag attaggacgt tgagattcag ggaggttcag    17820
agggattcag ggaagtcaag tggcacctgg agtcccgtgg ctaatttgag gccggtaggg    17880
gattcgaacc caggatttgt gcttcttatg cctgggcttc tgctccctgg ggcatggtct    17940 tcccctagc tttcccattc actgctttag cctaggggtc ctaccctta ttaaactgcc     18000 agtgcctcac tgcttttctc ccccaaagac aaaaaaaaag tgttttgct tttgttttgt     18060 ttttcatggg cagagacctg gaatttcagc ttgagaattt gtgccatatg ataaataaat    18120
caacagatgg cttttcctt aaaaaaaaaa aaaaaaaaa ctaagatgta tttgcagtga     18180
ggcataattt gtaccaaaaa gtgctcacca cactgtagtc atgggggcag gaggcagccg    18240
cgggtgaagg gagaaatctt ggagtccagg cagccccctt ctgggctgaa ctggggagct    18300
gggggtgctg ccagccctgc caggttctcc taggaggcgg cagctcatat ggctgtggga    18360
ggaggcagag ggagcctcat atgcacccac atttccaggg atctagaaga cagaaggagg    18420
aaaaccacca tcatgttaaa gcagacagtt aggtaacaca tcctgtaata caagttattt    18480
tttccacatc taaaggctaa aaatagttgt tagaatttaa agataattgg taaatgagtt    18540
tctatccttc tagtttcaca tcaaatggaa tcatgctgcc ttcacatcac tagtgcccgt    18600
tatttgtgtt taatttccac aatgttgtct aattccactc tttgggcttc cccagggatc    18660
cagcctccct cactcgccca tcgcagggag atgctttatt catctttgtg tcttctgtgc    18720
cgggcatagc gcatggcaca gaataagcac tcagtaattg attcacgagt gaataaatgg    18780
atgagtgggt gagttcaata ttgactacaa aaaccctaag gccacactgg tgagtggctg    18840
cgcctgtagt cccagctgct ggggaatctg aggcaggagg atctcttgag cccaggagtt    18900
tgaaactagc ctgggcgata tagcgagaac ctgtctcaaa tgacaaaaac agggccaggt    18960
gcagtggctc acgcctggaa tcccagcact ttaggaggcc aagatgggag gatcacttga    19020
ggccaggagt ccgagaccag cctggcaac ataggggagac cctgtctcta caaaaaattt    19080
tttaaaaatt agctgggcat ggcggtgtgc gcttgtagtc ccagctactc aggaggctga    19140
ggcaggagga tcacttgagc ccaggaaatt gaggctgcag cgagccatga tggcaccact    19200
gcactgcagc ctgggcgtca gaacgagacc tgctctcaaa aaacaaaca aacaacaaaa    19260
```

```
aaaaaggctt tcttaaagag acttgagaac agaaagggga acagatacat aacttatata   19320
tttatttgtt catctttcca ccttcctgga gggtggaggg gaacaggtct gtatttggag   19380
ttttgaatgc taaaagtggg aatacatgta ctgtttgcca tgatctgttc aaaagttaag   19440
ccaaatgcct tagattctcc tgaaaactgg aatgccactg taaactataa gccccacttc   19500
aaagataaaa gatcttgatg aacagggctg ggtctgtgga ctgggcctct ccccaccaca   19560
caaggaaggg tggtgccagt tgaaggaaaa tcacttaaat ccttgctgtc tcctaataag   19620
gtgtggtccc aggtagggct gtcagaatta gcaaattaaa acacagggca tctgtgaaaa   19680
ttagaatttc agataacaac aaataattgg cataggctgc ataatgtccc tcaaagatat   19740
caggtcctaa tctccagaac ctgtaaatgt gatcttattt ggaaagggg tctttgtaga    19800
tgtggttaaa ttaaggattt tgagatgggg ggattatcct gtattatcta ggtaggtcct   19860
aaatgcagtc acactcatcc ttgtaagagg aaggaagaga gagatggaaa acacagaaga   19920
gaagacaatg tggtgatgga ggcagagatt ggagtgaggt ggccacaagc caaggactgc   19980
tggcagctac cagcagccag aaaagtccag gaaccaattc tctcttggag ctccagaggg   20040
agtgtggccc tgctgacacc ttagcttcaa cctagtgatc ctgattttgg actttggcct   20100
tcagaagtgt gagggaatga atatctgttg ttttaagcca ccaagtttat ggtcatttcc   20160
tacagcagcc acaggaatca aaacagtaa gtatgtccca tgcaatgttt gtgacacaca    20220
ccaaaatat tacttgttgt tcacctgaaa ttcaaattta actgggtctc ctgtatttta    20280
tttggccaac ctagttccca ggcccaaaga agaggctttt gaaatttgc aagaaagctg     20340
gttggagctg tcagaaagtg gactttgtaa acacagtacc accgaaccaa tttgaactgt   20400
actacctcta gacaaaagag agggcagtca gacagttgtt cgtgatttct tctttcaaca   20460
gtcatttgag cacttactac aaaacagaag ctatgtgtaa gggtggaggc gttagctgtt   20520
aatcaggacc tccaggctaa gtttctgtat tagtccgttt tcacgctgct gataaagaca   20580
tacccgagac tggggaattt acaaaagaaa gaggtttaat tggacttaca gttccaagtg   20640
gctggggaag cctcacaatc atggcagaag gcaaggagga gcaagccaca tcttacatgg   20700
atggcagcag acagacaggg agagagagct tgtgcagggg aactcctctt tttaaaacca   20760
tcagatctcg ttagacttat tcactatcaa gagaacagca cagaaaagac ctgcccccat   20820
gattcagtta cttcccacca gatccctccc acaacatgtg ggaattcaag atgagatttg   20880
ttaccatatc agttaccaac ccttccagat aaatcacgtg aaatatcgcc attaacagag   20940
tgagctcagg tggttcttca gtgcatttct gatacctgaa ccttccctgg gaatttcaca   21000
gaccatcagg ctctccaccc tttgatagca ggatagcagg gcccaggttc tgcaggagga   21060
gatgttacca caggcctgaa agggagggag gggcagatgc tacaggaaga tgctggctct   21120
ggattcgctg gaggagcttt caagggaagt agatacacac tgtctccatc atttcatgtc   21180
catcacactc taaatgcttt tggacaagaa gcaaatgtta aagacaaatg tggcccattt   21240
tcctgtacaa agagggctgc tcccatgcca ggctattggc actggtgggc atgaggcttc   21300
tctgctgccc tggccggggg gttctctcac tcaccattgg ctctctgaca cctggagaga   21360
ccaccaccct tgggctttca tgatgctcac agaatccaca ctgttggagc tttaaggagc   21420
ctggatcaac tggaacaggc agggagtact aggacagccc agcattgccc caaaatatcc   21480
aggcctgata aaagagaaaa acaggtagct cacaggaaaa ggataaaaaa aggaggaggg   21540
atttaacatg aaaaggtgct tgatctccct cataataaaa agactgctga ttccatccag   21600
gcaagtgaca gaaaaaaaaa atttaattta aaaagactgc tgataaaacc acagcgagac   21660
```

```
actgctgctc agggatctga gggtgtgggc agccaggctg ccacgcatca tgggtcggag   21720
aggaagacca caccCctgga gcagagggcg gctgatctgt cagatgccct ttgacagcac   21780
ctcagcttcc aagaattaac cctttctatg tgagcagagg catccatggg gggacacact   21840
ggtgaatcat ctgttatgta gaagtctgga aaacatcagg atggaactgg tgaaataagt   21900
gtggcctctg acggaatgga gcggtccgtc tgcactgctg cgggtgcccc tcagatcctg   21960
tgggtcagtg agaaaagcag tgaggaacaa ggcaggtact gtgtactgtc ctctgcgtgc   22020
aaggaaggcc agcgcatgca acagagtcca cacagacata gcctaactct ggaaggaaga   22080
atgagaatgc agtttcagtg gtggcctctg gtggggagaa actgggtgaa gggagatgtc   22140
atttccattt ctctactatt aattttgtat taccatgctt aaatgttact ttttaccttt   22200
tttttttttt ttgagacagg gtctctctct gttgcccagg caggagtgca gtggtacaat   22260
catggttcac tgcagcctga acctcccagg ctcaagcaat cctcccacct cagcctcctg   22320
agtagctggg actataggca cgcataccac cgtgcccagc tattttttt aatcaagatg    22380 gagttttct atgttgccca ggctggtctc aagctcctgg actcaagcaa tcctcctgcc   22440
tcagcctccc aaagggctga gattaaaacg tgagtcaccc tgcccagcca attgcttttt   22500
aaaaaagatt aaatgcatgt atacgctcag gcatcagcac acttggaaag gatgaaaata   22560
tccggaagaa gggttctttt aaaaggctcc tcaagtgatg ctggcaggca tgacgaatgt   22620
ccctggtcac aaaagctctg atctggccta accctgtcat gttagagact ggagtgcgtg   22680
tgtgtgcgcg caaagtgtgg ggggatgggg gtgagtgtgt gtggtgtgta agcatgagtg   22740
tgtatgtgtg tggtgtgggg gtgtgtgctg tgtgagcgtg tgtgagtctg tgtgtgtagt   22800
gtgtgtgtga agtatgtggt gtgtatgtgt gacgtgaggt gtgtgtggtg tgtgagttgt   22860
gtatggtgtg tgcatgagca tgtgtgtggg catgtgatgt gtgtgtggtg tgtaagcatg   22920
tgtgagtgtg tatgtttgag catgtgtggt gtgttgtgat atgtgtgtgg tgtgtgagca   22980
tgtgtgtgtg atgtgtctgt gtgtggtgtg tgtgagcatg tgtgttgtgt gtgtggtgca   23040
tgtgtgtggc gtgtgagcgt gtgtgtgcat tgtgtctgtg agcatgtgtg agtgtgtgtg   23100
tgttcagcat atataaggca tgtaactgaa cacagcactt tagagggctc tcctggagtc   23160
agagggggtg ggtaggagga gaagggaggt gggctagtgt gctgaagtat ctactccttg   23220
tcatagtctg tgacaaccca gactagccca tgagccaccc tgttccctgc atttccaatg   23280
agacctcggt ggacatgttc cctgaggtga ggctgactga tgtcatttga cgatcttgat   23340
gccaaatcct tttatatcaa aaacaaccag aacactctct tttctcttag tgctttcacc   23400
cagatgacca catttcatcc tcccagccac tctgggccag gtggcactgc tggtttgaaa   23460
gggaggtctc ccctggagta acttccgtgg gcggattcac accctgccca cagtcctgtc   23520
ccagtcagcc caccatggtg gtctccggtt cctccagaat tcccgctttt cagctcatcc   23580
ccacattccc ggagggactg agagcgcagc cccagggccc tgctctttgg gggccgtctc   23640
tacacccaga gaagcagcaa ggcattccta ggtttctctt tcagatgcag aacttcagtg   23700
ttcagagatg ttcccactgg tcctgagagg gctcagttca gctttaatga ctgcgctgtt   23760
gcgtgtgctc tgcagagggc gggtggccca gcgtggctga ctgcagtttt cctgacgtgg   23820
agcccgagcc tgccccgctg tttattaatt aaggatcact ctgcttgcag aaccctgaac   23880
tccccagaac tgtgaggtgg gagaaccccg agaggccacc tggccccact tcccacctgc   23940
tgcccaaacc ccctctctgc cttcctgaca gtcaccccaa ctcccagtga tccccatcaa   24000
```

```
ccatctgaca agggggactga gagggaagag aaaggagggg cccaaagagg aaggtaaaac   24060
tgtcgggaac agcccccaaa tgtgtgacag ccttcagtgg agttgcccac tttcccttt    24120
ctcctccctg caggacctcc cttctcccca gtcctcccca acttctgagg ttacattgag   24180
aaaagtctgc agagaggtgc cagcatcaca aggtgttaag gaccacgagt ttggcatttt   24240
aacagatgcc agagccactt gagaaatgtg gtaactaagc ccagagaggt acagttaacc   24300
tccccagagt cacacagcag gttcatggca aagctggact agcacaggtg tccttcccct   24360
gcagatcccc ttctgtgccc cacatcacct ccctccagtg tctgggccac ctggagatgg   24420
gccctcagac tcacccggcc agaggtgcca tctcatggga gaggtctggc caggaagcat   24480
cgatatttga gatcccaaga aatgaagact tggcctgtca gatgacagac ttcggtcatg   24540
ggaacacgtg atctgtttta cacatgcgtc ccctcagcag cagctttcca gaacattccc   24600
actttcttct gtagtgagaa gaactctttc cctgcagcct cctgcccaac tcctccttca   24660
gtgtctttgc ttcagtgtct ttgataaacc attctgcttt gcagagtgcg agctctgcct   24720
tgcagggttc gcatctgcct gtgctgagta accaacgcta aggtcgagtg gtcggtcacc   24780
tctcataaga gctagggttg tctcatgctg atgactagga cttgccctca aggagaaaaa   24840
taaatcaaaa caaaagcaaa aacagcaaac atgcatctct taaagaaggc tctgagtcca   24900
ggtaaatttc cttccactga agcagccagg ctgaattcga attatctttg ccctgctta    24960
aaaactaatg caaattttcc tagagaatat ccactaattc ctggaggggg catgggcatt   25020
cctgatgccc atgagaggac catttgctct tccctcagta tgctaaataa cagaagcgac   25080
atttgttgct ggaaagtatc agtgaagtta ataaggtttt tcttgcccag ggtgagggaa   25140
cagttcccaa tgacaaatgc tgtatgggaa ggggctgtag aactgccagc cccttggtc    25200
catccgtaaa gtgaactctg tggatcctgg aggattccag cgtctttttt tttttttctt   25260
ttttttaag acagagcctt gctgtcaccc aggctggagt gcagtggcac gatctcagtt   25320
cactgcaacc tccgcctccc gggttcaagc gattctcatg tctcggcctc ccgagcagca   25380
agactacagg tgcgcaccac catgcccgac taatttttgt attattagta gagacggggg   25440
tttcactctg ttggccaggc tggtctcaaa ctcctgacct caggtgatcc acccgcctca   25500
gcctcccaaa gtgctgggat tacaggcatg agccaccatg cccagccagc atctttcatt   25560
tttctgtctg ctttggccct ttcctctctc actgtcttcc ttttccattt ccaaagtcag   25620
tccatctcac tattagcaca aaaactgcta gagcgcttgt cattggtcat ctctccctgc   25680
acctggctgg tctgttcttg gccactgaag cgtttccccc agctgttgct ttaatcattt   25740
tattgttatt atgccttact taagaaatgg atatgagatg catttacctg tctcttcctg   25800
ccactctgca gagccagtaa gatgtggtgg aaagggccca ggcttttggag gagggctggc   25860
tggggttgga tcttggctgc cccctactag ctgtgtgacc ttgggtaagt agctggacct   25920
ctctgagcct ggttcggaat catagcacct ctctttcagg gctgctgtaa ggaatagcag   25980
tggtgtgtat aaagcagagc gcacagccag caactggccc ctagccacac tgctgagcac   26040
ctactgtgat aagctgccat tgtggtgtgt gaagcaaagg ggaaacatgc ctgctgtagt   26100
gagcttcctg tagggcaggt tgtagaacca gaggtgggtt ccaaggttac aaagggactc   26160
ttagtgtatt agtctgttct cacattacta taaagaccta cctgagactg gatcatttat   26220
aaagaaaaga ggtttaattg gctcacattg gctgggtgcg gtggctcacg cctgtaatcc   26280
cagcattttg ggaggccaag gccggcggat cacttgaggt caggaatttg agaccagcct   26340
ggccaacatg gtgaaaccct gtctcttcta aaataaaata caaaaattag ctgggcatgg   26400
```

```
tggtgtgcgc ctggaatccc agctactcag gaggctgagg tggaagaatt gcttgagccc   26460
gggaggtgga ggttgcagtg agccaagatc gccccactgc actctagcct gggcagcaga   26520
ctgagactct gtctcaataa aaaaaaaaaa aagaaaaga aaagaattg caagaaataa     26580 attattgttt atgagctata tggtctgtgg taccttgttg tgggactggg agtcttggcg   26640
tctccctgac cctgcctgtt gctgcagcac cgctcagccc tgcctgctcc ctacctgcct   26700
cccctcggcc tctcctgcct ccaccgggcc cctggtgcct cctctagaga cagtcctcct   26760
gggaccgatt gtgttctcac ttacacgagg catccaggac tacagataac cagaggaagg   26820 ggcgccccc ccgcctgccc tcctccctgg catcctcacg ctgcagaggt cagagcctca    26880
tcccagcccc ttacctgccc ctactctgtg gagaaccgtg gtcagttcgc caggccggat   26940
ccacgaacgg ccttgtggaa gatggtgagc tcacacccag agctggctcc gatgaccctg   27000
tctcctttac atgtttctac cttcccctcc ctaccttccc ccactgctgg gcgcagagtg   27060
gaggcagatg aggtttaaag ctcagaaggg cttaaacggg ttgggcgca gtggctcatg    27120 cctgtaatcc cggcactttg ggaggccaag gcagaggatc acttgagccc aggagttcga   27180
gaccaacctg agcaacatag tgagaccgcg tctctacaaa aaataaaata aataaaatta   27240
gctttgcagg gtggcatgca cctgcagtcc ctgctactca gaaggctgag gtgggaggat   27300
cgcttgtgcc caggagtttg aggctgcagt gagctatgct ggcaccacag cactccagcc   27360
tgagtaacag aatgagatcc tgtctcaaaa caaacaaaca aacaaacaaa agaaggctta   27420
aagggggctc caggtgggct tggcagcaca aagctatgaa gttctatctt agacacaagt   27480
tctgttactg ggcctttgca ggctggcctg ggtacctggc tgccatagac agggaacctt   27540
ccagatgagc tgcaggcgtg gagcacagga gccagggtgc tcttcctggg ctctgtccac   27600
aggcagaacg tacacagtct ttgtacacgt ccggcggctc tggtgcctat ttttgtttgt   27660
gttttctttt tgtttggggg gatggatttg gtttcccccg agccctctgt cctcctgtca   27720
cctggctggt gctcggcaat gttgaccagc tgcctggctg gagttggcag tggctaaggc   27780
tgtgacagct aacatgttcc tgagtcctct catttcttca ccataatgcc ctgttgagtt   27840
tgcagatact gtctctgttt ttatctcccg gggaaactga ggctcagagt ggctaggcca   27900
ccttcccatg gtccctcagc tcatgagggc cacacagggc attgcggtgg ccttctcctc   27960
agccttgacc ctccggcccc agcattgctg cctcaagggg tctcctctgc tgagccgtgc   28020
accttctgcc tggcagctcc aactctgtgg ctgtgttcag tggctcagca ctgccccttg   28080
accctccctg gccttctgcg gatgccagac tggagcactc tgacaaggtc tggggtggtt   28140
gtatgggtcc tgtgacctct atacacctcc cagtgcctgg gaatcctgca gatacaccct   28200
ccttagccgt ccctaaccat agaggacatt tctgaggtcc ccgagagagt ggggcacccc   28260
tgcaggatcc aactgctggg cccaggaagg atagcagcag catgaggggt tccattagcc   28320
acaaactcac ggcatggaac cttcacccac ctcgcccctc atctgctgtt tagcacctgg   28380
cacgccgtgt atacttactg attattacat tttaatggca aattatagtg gcaaacgtat   28440
gcatctttgc acaattgttg tacagcatga tgaacaagtc attaatagta aagaataaat   28500
gtgaaagtga gaaaaatctg actgccaaag tttttactcc ttccttccct ccccagactt   28560
ttaaatgaaa gtttagggat aatcccttag ttgtcctgct agtaggactt gcaattaaaa   28620
gaattgggcc aagaacactt ctacgcttct ccttttaggt ttgggtgtaa attcggggta   28680
tttctcactg atgaaagcct ggtgcagggc agaccgtggg aagctttcat ttccggaatg   28740
```

```
gaccatcaac atcccttgga gaagaattct cttctccaga cccagacctg gtgtcctggc   28800
acccattggg caagtgggtc ctagaagaca aacctggtca gagcctggag gctgcttagc   28860
attccccacg cacattagca gctcggagag ctcaggaagc cgcagcccct ccttgcctca   28920
ccagcctgga tcaggacagc atccctggaa gacacacag ggcctggcct ctgattaccc    28980
agcctggagg gaaagctcaa tcgagcatca tgtcacccgg tgccccatg cagggtggca    29040 ctggtgagac ccccaagcca atgataccac ctcacaggag tgcaggccca ttgtggccag   29100
atcatcttga cttttcaaga taaatcagaa atcgtatttc catgagatat ccctatttgc   29160
aagtgatggt gactaaatta gaagttttg aatattgtaa catgttcgta ggctgtttgt    29220
ctggtttaaa ctctatctgg aggaattcaa gctagacttc aggaataact tcttgaggca   29280
aggattttga gaccttaggg aaagaaggac gtcttggggg tattctgact gttgtcctcc   29340
tggaagggaa gaacagagaa ctagaagact gcccttagcg aagttcaaag cacctaagcc   29400
cgggaccctc agcaagtgtt cttgagtcac agattctccc tgaggcgcct ctttctggct   29460
ccatagaatg gctgattctg taactcggtg agtttgcttt ttttttttcc tccatcaccc   29520
aggctggagt gcagtgaagc tggagtgccg tggagcgatc actgcaacct ctgtctccca   29580
ggttcaagca attctccttc ctcagcctcc caagtagctg ggattacaag catgcagcac   29640
cacacctggc taattttgt gttttaata gagacggccc gaagtgctag gattacaggc    29700
atgagccacc gcggccagcc ataactctgt gactcttgtt acaaaggcct tatattttgc   29760
tctttgaggg tggttttggt ttgatgcctg ttggttgcca tcttttaact agggatgttt   29820
tatcaaaatg cccagccaaa gtgtccaaac aaattatacc ttaaagtttg aaaatgtctg   29880
gcacttctaa ttcaatgcct gttgtgccag gcactgggct gctgaggaac tgagtcccgt   29940
ccctgcaggc tagctagaga acacacacac acacacacac acacacacac acagagtggt   30000
cttacaagtc agttttatat tctacctata tgcaataaag gtattattat gttgaggtgc   30060
cttgatataa aaattttct taaggagag gatgcctaaa acaggcatta cctgaaacct    30120
cctctctcca gcattggttg tcttctgtca tgactcaggg ttttcactga gaatgggatg   30180
gaaatgtggt ctaaagatag ggccaatgtt gggactggat cccctctggg aagtcagacc   30240
aggctagggc aggtccttga agccatcagg aaaagcctct ggagccagaa acaaaacaaa   30300
aaaaaaatgg tgttaactaa actcagtctc aaatcctgaa taggactcaa gtcaagcaaa   30360
ataattaaag gagttagcaa agggcaagtc agagagaccg agcaacacca atgtcttccg   30420
ggagccctgt ggcgagtgac agagcctgga ctctggagta gaactcatct tgtgtcttct   30480
tctgccactc gttagctggg tgaccttgag ccaagcccct taacctcttg gaccctatgt   30540
tcttatctct aagtagggc tggtaatatc ttccccttg aggaatgccc tctaagggt    30600 gttgtgaaga ttcggtaagg tggcaggggt aggactcctg gccagaaaca ggcacataat   30660
aaatgctaag tctctccttc tctccacctg ctggatgctg tagatactaa ggatttcgat   30720
gtgaatgaga caaaacccct gccttccagg agcctttgag aatcagagaa ctagaccat    30780 ttccagaaca aggggatgca gggtctggat aaagttttgg ggatcaatag agcagagggc   30840
tcccagagga tcccataggg ttgactccta actcaagggc atgagacaac ccccaggaag   30900
ggcaccctgg aaggggtccg gctgtccctg atttacttgt gggcactggg ggaatgcccg   30960
gagccatcca gccctcaggg ctctgtgtga ttctgggttc ctcccataaa agataatcag   31020 attcttttcac gttaatgtct ttctccacct cattgcacat catgcagcta ttcattgact  31080
cagcaagtat cagctttgca tgcgaccttg gcctacccac tttagctttt agtaatagct   31140
```

```
cccttcttga ataatacaac cagtggggaa acagaaccta actcttacct ctgggaggct    31200
tatttgcttt gagaacatat gtcctgcagt tttgttcata tggcagtgaa gtttcgtgca    31260
cacactctag agccaggcag cctgggttca aagcgcagct ctgccaggtc ctaactgcat    31320
gaatttgggc aagtcgctca acctctccat gcctgagttt cctcatctgt aagattggag    31380
caatggtaat acctgctttt tagggttgag aagagaatta aatgaattaa gatgggtaaa    31440
gtgcttagag tggagctttg caagtagtaa gtgctatgta agtgttcgat ttaaaatgaa    31500
agacccttaa atacattctt tgttcatttc acaagccctt catttcacaa ccttacattt    31560
cacaaccaag ctctgtctcc cctggaatcc agccataact ctgctcacaa gtgtgagaca    31620
ggccccagca gagctgcacg aagaggagag aaggcagccc cccagactcc caaccccctg    31680
tccaagatgg caaaaccaga acacagcctc tgtaccaccc cagcaggtat tcagaatctg    31740
caatctccaa agcccacttc aattgtaaat gtagagccac gtgcgcttta agtcacctgt    31800
cactctggag gctcttttgc tcagttcctc accattagca gggatgacag ggagtgcagg    31860
agtgcggtcg actcccagat attggagagc gctgggctag ctgcccattc tcccggcctc    31920
cactcctctt tgctgtccag ccatcacttg ctctttgaag gcaaacaaaa cagaaaacag    31980
tgccaaaagt atgggaagaa agccagcttc tcccctgggg tgcctgtgat gccatgccca    32040
ccctccctga ccacgcagcc cctgtggacc ctcagggccc caagccccca tttccatcac    32100
atgcgtacac ccatgtgtgt ccatagccgc ccatctcagt caataaggct gctcctgccc    32160
acttggaata gtggtgacaa ccaggagtgg cttatgggaa ctatcccaat ggcctgacag    32220
catgtccgct gcaaaccgct gaggtaggac actgccctca tgtctagctg atcagcaaga    32280
ggcgcagttg ctttcttagg taacattgct gctgtgtcct ggccattgct ggggggtggc    32340
acttaatcta caccagattt ttccctcctg tatcttccaa gctgcttgga tcttggtgct    32400
gaattaggtt ggactttgtc ttgtggggaa gggaggacta tagaccctca acgtaagcaa    32460
tggtcagact attctaagaa aactcgccga attaaagcat gaggtaaatt tagttctgac    32520
ttctgtccac cccactgcca ctgtccccett ttatcccatg atcccttgct tttcttttcc    32580
tcctctctcc ctatctcttg tgtttgacgc atgataggaa ttcagaaata tatgtttgtg    32640
gatttgttta ttcacgtagc aaaccatttc ttgagtgcct accatgggcc aggtagaatg    32700
ggcggccccg ggctgcagtg gtttcttcag cccctctcca gggtttacac tgtgcaagac    32760
ggtttgtgat gggtcctccc atcgaggacc acactcttct ttctctgtgc cccttggtcc    32820
tcagtctctg accccacttc aaaggcagca ttcactcagg gaagctccca tacaatgcta    32880
gtcagagtaa aagtttggac aaattgccag gaagcagctt gtcagtatgc ataaacagcc    32940
tttaaaatat tactactctt tgacccgaaa tttcacttct aggaatctgt cctaaggaag    33000
tagtcacatg caaaagattt atgtaccaag atgttcatca aagtgttgtt ttataacagg    33060
aagtctcaga agctggataa atatccaacc tctggaaatg gttagataga atagtatgta    33120
gccattagaa aattatgtct atggggttta aaatgtcatg ggaaaacact tctgacataa    33180
aagagcatga gaactgtata tttagcataa tcttaactat gttttagaat gcacaggaaa    33240
aaaatgtaca aacatattca tagtgatgtc tctggtggta ggattatgat cagtaagtac    33300
ttctgtctct tcatattttc ctgtatttga taatacatgc atatgttgtt tttaaaataa    33360
gaaaaatttt aagtttaaaa ttggagctga aaagtgtttt taggtcaggc gaggtggctc    33420
acacctgtaa tagcaccact ttgggaggct gaggcagtca gatcacttga gcccaggagt    33480
```

```
tcgagaccag cctggccaac atggtgaaac cccatctcta ctaaaaataa aaaaattagc   33540
catgtgtggt ggcacacatc tgtaatccca gctacttggg aggctgaggc atgagaattg   33600
cttgaaccca ggaggtggag gttgcagtga gccaagatcg tgccactgca ctctagtctg   33660
ggcaacagag taagactcta tgtcaaagaa aaaaaaaaa gaaaagcctt tttaaacagt    33720
agcagacata actatataat ccttactaag ctgtcggtca aatttttatt tatatattta   33780
ttttattcat ttattatttt tagacagggt ctcactctgt tgcccaggct ggagtacagt   33840
ggcgtgatca tggctctctt caaacttgac ctcccgggct caagtgatcc tcccatctta   33900
gcctcccaag tagatgggac cacaggtgca taccaccaca cctggctaat tttttttatt   33960
ttttattttt agagatggtg tttactatgt tgcccaggct agtctcaaac tcctgggctc   34020
aagctatcct cccacctcgg cctcccgaag tgctggggtt accagcatga gccactgtac   34080
ccagccctca aatttttaaa aatctataag agacattatt ggacaattag agaaattcac   34140
atatggactt ataatagtat cagagtgtgt ggtgtgatgg ttctggaggg aatggacttt   34200
ttctttggag acaggctttt ctatgccacc cctttatct tgctaactta tcatcatcca    34260
ggttccagca gaaacattac ttcccccagg aaatttctta agggtgcagt atcatgatgt   34320
ctgcagcaaa ttctcaaata gctcaggaaa aaagtacgtg tgtggtatga gtgtgtgtat   34380
gtatgtgtgt atatatatac acatatatac acatatatat acatatatgt gtatatatat   34440
acatatatgt gtatatatat acacacacat acacatatat atacacacac acatacatac   34500 atgtatttt atataattat atatgcagag agtgcaaatg ttgccaagtt aaagattggt    34560
gagtctaggt gaagggaata tggtatttat tgtattattt gtgcaactt tcttaagttt    34620 gaaaatttt aaaacaaaaa attggaggaa gaaggcatgc cagtctaccc caagccctcc    34680
attggaatgc tgaaaatcta acaatgtga tttggcaatt tcatttcttt tctgttgtgg    34740
gccagtagtc cttagatgtt ggggaagggg gtagtcgctg aggtgtggtt gacttaggat   34800
ggaagaagca gaagtcaaga ctcccagggt caaagtggtt tgctctgctg acccaagtgt   34860
gggaggccca gagtcagcgt ttcaggtgtg ctaattcagc atggttctat tcacggccaa   34920
agtccaccct gggcacctct ctggcagcaa tcttgggtga ctctactaag gccaggcctc   34980
catgacccta tgtctggatc ccatatctcc acctctccca ctgtctcagg aacggtgctt   35040
agctttttct tttccctctc ctgtcttctt tgccagcatg tagaaagttt aaataattcc   35100
cctctttaca acaaaacaaa acatacccc ttcagtcaac caccctagct ctcttctcct    35160
tttcccagcc agatttttt aaaagcatcc taggccaggc gcggtgactc acgcctgtaa    35220
ttccagcact tgggaggcc aaggtgggtg gatcacaagg tcaggagatc gagaccatcc    35280
tggctaacat ggtgaaaccc catctctact aaaaatacaa aaaagtagcc gggagtggtg   35340
gcaggtgcct gtagtcccag ctactcggga ggctgaggca ggagaatggc gtgaacctgg   35400
taggcggagg ttgcagtgag ccgagatggc gccactgcac tccagcctgg gtgacagagt   35460
gagactccgt ctcaggaaaa aaaaaaaaa aaaaaaaaa agcatcctca gcactttggc     35520
aactccatct cctcccaaca tgtccctgtt actggaatcc agccaggact cagccccgat   35580
ctttctactc taaccagttg tctcagttaa caaggacagg tttatgctgc agtgacaaac   35640
aagatcccaa attcttgtgg cttcacacat ctggcaccac ctcatcttcc agccttagga   35700
gtcatctttt agttccttga aaactctta cagttttctg ttggggcctt gtcatatact    35760
attcccctgg aatgttcttt cctatcccct cccctttcacc ttgctaactt gtgcccatcc   35820
ttcaggtctc agcagaaaca tcacttcctt ggggaagttt tctccaacac ccacactaca   35880
```

```
caggtgtccc atctacactc ctatgacttt gtggtacttg tctcacttca ttttccactg   35940
ccttccccac aaggcacctg cacaagggca aggaccgtac cactgtacct atgtcactca   36000
ttgctgtggt cacctgcact ctggctgcct accttaacta cacattagaa tcacctgagg   36060
agcttttaaa gccacaatgc aagactccac cctaggccaa ttggatccaa atccctgggg   36120
tagggccaga catcagtgga gttatatata catatatata ttttgtttgt ttgtttgttt   36180
gttttttgag acagagtttt gctctgtcac ccaggctgga gtgcagtggc gcgatcttgg   36240
ctcactgcaa gctccgcctc tcgggttcac accattctcc tgcctcagcc tcctgagtgg   36300
ctggaactac aagtgctcgc caccacgccc agctaatttt tttgtgtttt tagtagagat   36360
ggggtttcac cgtgttagcc aggatggtct cgatctcctg acctcatgat ctgcctgcct   36420
catcagcctc ccagagtgct gggattacag gcatgagcca ctgcacccgg ccatcagtgg   36480 atatatttt aaagcactgc agagaattct gttgcatcag cttgagaacc actgatctgc   36540
cttgtgcttc acatttaaaa cttttttta atgaataaat aaaccccaaa aaattaatct   36600
ccctaagcct ccctagaaga taggatggta aggatatttt cctaggtaaa aatatgttaa   36660
tttcatattt catgaaattt catgtttcat ttcaatcaag ctctgtcata caccttacat   36720
ggggcaagcc cagtgcctgg gcagggtgta attatactca ttacacaggc aaggaaaagt   36780
cacattaggt gatggagcac aaataggcag ttaatggttt cagggctagt taggatatgt   36840
ttgtctttca attgcaagta atagaagccc aaagaaattg gttatttata taatataatt   36900
gattggttcc caaatttgaa aaattcagga atagacccag cttaggtaca gctggatcca   36960
gtcactcaaa caatgtcaca aagaacccctt tgacaggaat gtatcctgtg ttgactctac   37020
tttgctctga gtagtctttc cccaggtgat gataaaaatg gtcatcatcg ccaggcttgt   37080
gtcctgttta gtaggaatat acaagaagag ctcagtaaat gctggcccca ccactaagca   37140
aaaacaaaac ttttgttgtt gttattgttg ttttaaataa cagcttagac cttttcttctt   37200 tccttgttat tctcttcat ctgtaatcca gttttctact tctgaagtat agaatgttct   37260
gatgatttat tcttcattac ccacaacttg cacatgttta tttaaaaatg ccaggattgc   37320
ctggccgttg tgtgctgtta acctttgttt gctgttagtg gatccctgaa gttcaggctc   37380
ccaggggagc agataatggg tatccagttc ctgcaatatc caccctctgg caagccaagt   37440
tccttcctgg gtaaggtttt gcctacctgc attcctaggg aagtttctgg gcctgaccac   37500
caagccagct ctgagaaggg gtgcataagc cccaccatgc tttggctctg tccctataga   37560
atattttatg ttgttactga aaactaaagg aagatgggtg cggtggctca tgcctgtaat   37620
cccagcactt tgggaggcca agacagattg atcactcgat gccaggagtt caagaccagc   37680
ctggccaaca tggtgaaacc ttgtctctac aaaaacaaaa caaaacaaaa attagccggg   37740
tatggtggca tgcacctgtg gtaccagcta ctcaagaggc tgaggcacaa gaatctcttg   37800
aacctgggag gtagaggttg cagtgagccg agatcgcact actgcattcc agcctgggtg   37860
acagagcaag attctgtctc caaaaaaaaa aaaaaaaga aaaggaaagc taaaggagag   37920
agactaaaat gatatcaggt tcctggagaa caaacagaca tgattttgct tcatggcagg   37980
acagccggaa gaagtgggat tatatcctca cattacaaat aagaaaactg agactcagaa   38040
tggttaagtc acttgtccca ggccacacag ccagtaaatt acagaaacag aatttgaacc   38100
caaatcttcc agctccaaag cttgtgttct tttcactacc tcctgcttaa ttttttaatt   38160
tctaagatta gacccttcat ctatccatga cacctgcctg tcatcccctg aaaaaaggtg   38220
```

```
aacgccgttc agaaattttt ctagcctgag ctcactccca gttcacttat ttttgctttg   38280
tcatggctgc ccagtcccca cttgtagacc aggaataggt catggctgcg gggactacac   38340
gctgtcgctg ctgcaagggc cggcctctgt ttccggggct gagtgggggc cagacctgcc   38400
aggagcacca tcttctgtgg gtcctgcctg gatgtcacat cccggcccca agaagtcact   38460
gcaaaccttc gtattattga gcttcacatc ctagaatttg ctgtcactgt ggctgctgca   38520
tgaagttgtc ctgagagaaa cgggcattgt cattaacagg gaaattgatg gtctggggga   38580
aaagtcatcc tcattctctt gcagatctat gggtgattga gactggctga tgttgaaggg   38640
gtttctcagc catcgtgtgc catgttatgg aacagtggtg tagccagcca tttgacaccc   38700
agcgctgacc tttgtttaac aacctcacct atatatgaca aaatgattgt cagaaataat   38760
cgtgtaatga aatgactgta ataatggcca gaaagaaac gcagatagta aaatgtttct   38820
cttgttgaac tctgtacata taattgcacc aggatttttt tcaaataaaa agtaaatatt   38880
atactacaaa aaagggaaaa agcacaagca tttattaaat agctttctat atctttctga   38940
gttttgatcc tttgattgca gactgatgta atattttatg taaatcattg cttggttact   39000
aagtgaactt taagaaaagt gagacgtctg cagaagttgc ccataattta gcagctactg   39060
tattgtacca ttgatgtacg gctttatttt cttgattaat tatttaaaca ataattca    39120 caattttaaa ataataaatt tccacttaaa atggtattta aactcagcaa aatatatcat   39180
ctatgagtaa aatttgtatt taccaagcaa aaatattaca gtttgtggtt cacatgctgt   39240
ctcactgttt taaatttaa atacaaaaac tccaagtagg ctgggtgtgg tggctcacac   39300
ctgtaatccc agtactttgg gaggctgagg caggcatatc gcttgagttc aggagttcaa   39360
gatttgcctg ggcaacatag tgagatcctg tctctactga aaacaattag ctgggtgtgg   39420
tggcacatgc ctgcggtccc agctactcag gaggctgaga taggaggatc acttgaaccc   39480
tgggggacag aggttgcagt gaggcaagat tgcaccactg cactccagcc tgggtgacag   39540
attgagaccc tgtctcaaaa aaagaaaaaa aaaaagaaa cacaaaaact ccaggtggtc   39600
gcacagaatg acaggactga agtaacttag ctccaatttc tgtcttcata atcactgtcc   39660
taccattgtc tgtgcttaga atctacttgc ttaatgcagg aacatgtgtt ctcacagaga   39720
tggaaaatgc aaatggcgcc agaagcaagc tggaaattct gaaccattaa gaatttactc   39780
tctgccaggc acggtggctc acgcctgtaa tcccaggact tgggaggct gaggcaggca   39840 gatcatctga ggtcaggagt tcaagaccag cctggccaac atggtgaaac ttcatctcta   39900
caaaaataca aaaattagcc aggcatgatg gtgggtgcct gtaatcccag ctactcggga   39960
ggctgaggca ggagaatcgc ttgcacctga gaggtggagg ttgcagtgag ccgagatcta   40020
tctgcaccat tgcacttcag cctgggagac agagtaagac tccatctcaa aaaaaaaaa   40080 aaaaaaaag aacttactct caaaataaat acgtgtggct gactccacat atggtagggc   40140
caactgtata actagaagtt ctccaaataa cttctgtgga gaaaaaaag tttattaaag   40200 gttaactttt ttaaagtgct aactagaacc ttactaacac tgagatcgca ccaattgttt   40260
ataacttaga cagggccggg tgcagtggct catgcctata atcccaacac tttgggaggc   40320
cgaggcaggt ggatcacttg atgtcaggag ttcgagacca gcctaaccaa catgatgaaa   40380
ccccatctct actaaaaata caaaaattag ccaggcacgg tggtacacgc ctgtaatccc   40440
agctactggg gagggtgagg caggagaatc tcttgaaccc aggaggcgga gattgcagtg   40500
ggccaagatc gcaccattgc actctagccc cagcaacaag agtgaaactc tgtttcaaac   40560
aaacaaacaa aaaaaaaaac ctcttggacc aggaaaatat ttttaaggg aggagtattt   40620
```

```
tatcactggc attgtttagg attgcaggca catgatgcta atgaaaagca gactaactat   40680
tagttggttt tattactgtt tttgaactct ctctctccct tttttttttt tttgagacag   40740
agtctctctc tctgtcaccc aggctggaat gcagtgactg cagtctcagc tcactacatc   40800
ctctgcctcc tcagttcaag tgattctcgt gcctcagcct cccgagtagc tgggattaca   40860
gggcaccaca ccaggctaag ttttttgtatt tttagtagag cagggtttc accatgttgc   40920 ccaggctggt ctcaaactcc tggcctcaag cgatctgccc atcttgacct cccaaagtgt   40980
tgggattaca ggcgtgagcc accgtgccta gccctgtttt tgaactctct agagacagtc   41040 cagccccta ttacttgtcc tgaggcagct gctcccttca cctggccccc cgcattgtgt   41100
tccggaccct tgtcctggtg gtgctaaaga atatctctgt cgatcctttg gggactgggg   41160
aaactgaggc ccagtgccac gcgatgccat ttgttcaggg aagattaggt catctgctag   41220
gtccccagtc acttgaccct cttcccagac aggaagaagc tgctctgggt ctctcagtgc   41280
tccacgtgtc tttgcacatt gaaatgtttt ctgatttttt ttttttttttt tttgctgtta   41340 catttacttt taaaaaataa caagcaataa aatgttacat ttgagaaggt tgaaatgaga   41400
attgatttga gttaaattct agcagatttt tcttagaaga atgatatcat catctccagc   41460
tacctgcaat tgatctactc tgaattaaga aagagacttc catttgttgt ttatattttg   41520
cactcttgat gtgtttcttt aaattatggt catgggccag gtgtaggagc tcacacctgt   41580
aatcccagca ccttgggact ctgaggaggg aggatcactg gaggccagga gttcaagacc   41640
tcgtctgtac agtaaatttt aaaaattagc caggcatggt agcattcacc tgtagtctta   41700
gctacttggg aggctgagat gggaggattg cttgagccag aactttgagg ctacagtgag   41760
ttattttcac gccactgccc tctagcctgg ctgacagagc aagacctgcc tcaaaaaaat   41820
aagtaaaaaa taaattaaat ttcaatcatt agcagtcatt aggatattta aatacagtat   41880
gttgaatcaa agttacgcat gtgtgtattt ttttttccag agagttgttt atcatgtggg   41940
ttttaattta actttaaaaa aatgttggct ggacagttgc ccaaatggta tcatcagcca   42000
tttggttgag aacgtatgtc ctgcgggctc ctctgtcact ggagttttgc tagctgacag   42060
ccactggcta gttagagact gcagtcagca cagatgcagg cgtggacttg cgcacgtaac   42120
catgtcaatg caaagccatc acttcttaaa aattctgaac cctgctgtct gagatggtgg   42180
tgcagcggat agaactctgc tctaagaggc agtagctaat tccatgtctt ctttgccctt   42240
gactagctga gtgactttgc acatggggct tgcctctctg ttgccttgtc tgcaaagtgg   42300
aatcatcttt tccttgctag acagaaggtg gaccctggac ctatggcctt tttgagtttc   42360
ccccccgctt cttagaagga cctctgatcc tactgagttt aatacccacg ggttaataat   42420
tgggaaaagc aaaggaagcg cttctgttta ggtaattata tgcatgtttt tgtctttttc   42480
tggctggaaa gatatccaag ccactgggaa ggtccgtggc tacccagggt agccctctct   42540
ggggagggct gctatatcca agagcccctc atgagaattt gaaaatcgac catggtaggg   42600
cctgctgact tttgacagct aatggtgtgc tgagaattgt ccctccaaag atgcctttcc   42660
attccctcgg gagagtctgg gcagccccta ctggggcctg ggatgctggc tcttccctca   42720
gcctccaccc caactgctct cttccctcct cccctcccca gccccctaat ttctctcaca   42780
aggctttgtt ctgcagcaac ctttcctaat gcagtcctgg cctcttcgca gcttcattac   42840
ataaccttcc gtggactcct ggtccaagga tcacccaga aagccagtca gaggtaggca   42900
cgcagctggg gtccatttac ttaccttccc cacccctcg gaactcagag gtggtgcagg   42960
```

```
aatttggact ccaagaatta acagctccac caccatcacc agagccaaaa ctcaggatgc    43020
atgtgcttca tctgctgctt atttccagct gagagccagt ggtgccatgg ttccttaggg    43080
agccggtccc ctgatgccgg ctcctggccc caaatctctc tgatccgggc tcttccagaa    43140
tgtcttgtct ccaccatcgc ctttgaccaa tggtgtccct ttgcctggta atgtcccctt    43200
tgcctgatga tggccctgtc actcctctct ttagcacaga ggaggctgtt tcatcccttc    43260
aagcctgccc tcccttcaag tcttagctca agttcacctt ctccgcagag ccttctccaa    43320
tcttcttgac tacgtctcct ctcagctcca gcaacctctg tctctggcac tgattcctta    43380
cttagctaag agaatcacag acacttgggg ctcaggacaa tctgcttcct ctcttcttac    43440
ccatggcctt ggactgtgtg tacctctttg tctccactcc caaacccaac ccccagaggg    43500
cagagagcat gttgtctgtc cctttgctca gcatgaagcc atgcgtgtgg tagatcggca    43560
gagttccata acttgtgttg accgaggggt cactttgctc tgaaattacc cctgtgtcct    43620
tcagtatttg cacagatagc ttcctggcca gaccgaatat atccaagggc atggcccacc    43680
tctgctcctg tttccaggtc cctggtgggg gttagttcat gccttcctca taatctgccc    43740
actggcctgg tcctcaaggt cttcccaact gctcagccag agttgagaaa atgggtcgct    43800
ccatcctgtt tgtgtcgttc tctccttcct ggcccactct cctgcccaca ggtatccagg    43860
ggctgcctgt agcattagag gacatacatg cacatgcgtg ggcatgggac actcacgtag    43920
cctccaagca cagcatcaat aatgcattct gtgctttata gcatggaaag ctgctctaaa    43980
ctttattaca cagtggacat gtctgaagca gctcccaaat ccaccctga gtgtgttgga    44040 attggcaagc ctatcacttg ggagtctagt tttttgttc gttaataata gatgcttcct    44100
gtggccccag cttggcaatt ttgatttaaa gtgatcttaa ctgaagagac taatggacgg    44160
gtctgaattt gtgccttta agcacaaagt attgctctta attaactgga ttctatcctt    44220
tgagcaggca gaggccttcc cccaagggcg tcattaacga tccacatctg gacatcttcc    44280
aaagccttct tctgtttcag gccaaccgca ggtgtgttcc tgaacaccca ggaggctatg    44340
agagccacat atgcctccca aatacacaca gtgtgcatgc ccagggacat agagcagtgt    44400
gcaaagtccc attccatctc tctccacctg ggagaggatg gctcttctgt ctgattcatg    44460
gctcaaagtg gtaaaggagc tccccactcc ccgtcccacg cctactcaga gtctgcaaat    44520
atgtatgcga tatgagagct cgtcagttag ctgtcttcag tgtggcgcac atttgaggag    44580
tctgactccc ctccagcaca ggccaatgtg cactgctctc tatctttgt accccactg    44640 ttgcactgtg cagaggttgg agccatagaa gtaccagagc tgtgaaagga gaggcccct    44700 ctcacctctg ccctggtctc catccccact ttctctagga agctagtagg tgctgacagg    44760
ggagagaagg gagggaggg gtccagaaac agtggctcat gcctgcaatc ctagcacttt    44820
gggaggctga ggcaggagga tcatttgagg tcaggagttt gagaccagcc tgggcaatgt    44880
agcaagaccc tatctctaca aaagaaaaa atgtaattag ctgggtgtgg tggtgggcac    44940
ctgtagtcct agctacttgg gaggatgagg tgggaggatt gcttgagccc aagagtttga    45000
ggttacagta agctgtgatt gcaccactgc actccagcct gggcaacaga gctgagaccc    45060
tatctcaaaa aagaaaaaa aaaagaaag gagagagaga gaaagaaaag aaaagaaaaa    45120 aaaaaagaa gggaagggaa agcccagaag agtgtgggga gaggaggcgg ccgtcattct    45180
ggggccctca gtgtgcacaa ccagataaca catgctctgt gggcttttgt accattttgc    45240
ttgagcataa agaaaggaag gctgcccta aatagaaagc actctggagg caaacaaatc    45300
tgactccaat cctggccctg ccactttccc agctgaggac ttagacaagc accctagcct    45360
```

```
cttggacatt ctcagagcca tctgctgcaa gtgggtgctg ccatacccac cttactgggc   45420
aggcttgggg gaccaagggt ggtaaatggc tcagtctttc atgatgcggc cacacagcag   45480
gtgcgccatc caggtccatt tctttccttc ctttcccccca aatcaagttg tcattaaagt  45540
actagtccac attaatgaaa tcaactgtat taattttcta tttgctgcta taataaatca   45600
tcagaaattt agtggcttaa accaacacaa atgtattacc ttacagttct ggaggccaga   45660
agccctccat aggtgtcact gggctgaaat caaggttttg gcaaggttgc ggtcctttct   45720
ggagggtcca ggggagaatc cattttcttc cttttccag cttctaaagg tttcatgcat    45780
tccttggctc atgatcttct atagctatag tcagaaaaat tttccatcaa tcatcttcaa   45840
agccagcaat ggcaggatga gtcctcacat caccttgctc tgacaccagt tctctgcctc   45900
cctcttccac atgtcaggac cctcatgatt actttgggct cactctgata atctgggatg   45960
atctctctat tttagagtca gctgactggg aaccttaatt ccatctacaa ccccaattcc   46020
tctttgccat gtacagtgac atattcacag gttctgggga ttaggacgag cctgtctctg   46080
aaaggctact ttacatgaaa attcattttt ttaattaaga ttttttttttc ctcttgagac   46140 aaggtctcac tctatggttc aggctggagt gcagtggtat gatcacagct cactgcagcc   46200
tcgacgtctc tgggctcagg tgatcctccc acctcagctt ccctagtagc tggaactaca   46260
ggggtgagcc cccatgccca gctaattttt tttttttttt tttttgaga cagagtctca   46320 ctcagtcacc caggctggtg tgcagtggtg caatctcagc tcacagcaac ctccgcctcc   46380
tgggttcaag tgattcttgt gcctcagcct cccaaggagc tgggactaca ggtgtgcacc   46440
accacgcccg actaattttt gtatttttag taaagatggg gtttcaccat gttggccagg   46500
ctggtctcaa actcctgatc tcaagtgatc caccaacctc agcctctcaa agtgctggga   46560
ttacaggtgt aagccaacat gcccggcccc agctaatttt taaatatttt ttttgtagag   46620
atggggtttt accattttgt ctaggctggt cttgaactcc tgggctcaag caaacctccc   46680
accttggtct cccaaagtgc tgggattaca gcatgagcca ctgcactcgg ccttaagaga   46740
agatttaata attaatactt tacaacaaga tctggaagag gtgggatgag taactaaatg   46800
aggatacaag taacccgggt catatttgct aatacccttg gtcacattga acttgatatc   46860
ttatcagatt ttcctaatca gctcctttag cagcagtgtt gcagcatctt atctcatttt   46920
gttttttgtt ttttttgccta gcacatgcct gtaaatcact ggattgaggt gtttagatgt   46980
ttgttgtcct ttggatgctt cttataaatc catatttcat ggctccctgg aaagtgctat   47040
gcaaatgata agctgcaagg atggaaagga aattgcagtg ctcctgaatt gtaaatgggc   47100
ttttacgagg aggtttctaa ttactcgctc tttctcttga actgaggagt tgaagtgtag   47160
gtggcagatc cataacagat aatcatgtgt gtgatgtgac ttcagcctga gcgtcgagga   47220
ccaagtcaca gagcaggaac agccactctc cagtgtcctt ggggctacgt ctgaggagaa   47280
cctgggattt catatatgac ctgcactggc tgggggggctc tcttgacgta acgtgttccc   47340
tctgagcatg ttacagattc tgacattctt atgttccttc tgtggagaga catgtactta   47400
gtgacctaac tcacttttagc atattttttgc tcatcgtttg tgtagcttaa aggaatcaga   47460
taattacccc ctccccacta ctttcggaag cacaaatgca atgccctaga attgtactgg   47520
ggactcaaaa agaaaagaga gtagtaaaat ctattaaagg ggacaaagac agcctatata   47580
ctacaagctt tctatttttta tggcagagaa tgccattttc taagtaaaca gagaactgca   47640
tttgacctgc aatatcaaat gcatggattt gatgctttgg aaagcaactg ttttctgcgt   47700
```

| | |
|---|---|
| taatctgggt gtcttccgtg aaatgtcctc ctgcctttgg cttaaacact agctttgtct | 47760 |
| acagccattc catcctgaac ctgcccaatc ttgtctgaat cctggtttca ccactgacaa | 47820 |
| gctgtgtgtc cttgggcaag ttacttcacc tgtctgtgct tcagagtcct catctgtgag | 47880 |
| ttggggaatc tggacagaat ctaccccata gggcgtagtg aggatgtgtt gaattatccc | 47940 |
| aagtggctac acagagtaag cactcaaatg atgtcatcgt tgtcatgatt gctgttacca | 48000 |
| gagcctagag ttcattctga tactcgagtc tgtggcccat ccagcccagg taaggaatag | 48060 |
| ttggaggagt tgggcatgtt cagcttgaag aggagacgac aggggatatg ggatagttga | 48120 |
| atctgtgaag ggcccctgg gatgaagaac tggcatgttc tgtgtggctc cagggcactg | 48180 |
| agcaggaccc atttgccaaa gtctcaggga cacagtttct agctatagac agaaaaattt | 48240 |
| tctgtcactc agaggatgaa aatagaatga gccccttaa gaggtaatga gctccctgtc | 48300 |
| attggaagga ttccagaaga gctaggtaac cactttaggt gctatcaagg gcttttttc | 48360 |
| tttaaagtcc tttccaaaag cttctgagat tgcataaaca ataggaagcc atcttggtgc | 48420 |
| tttaacacaa actctcccca gtgatgaggg ttgagccaaa gccagattgg caagcagaga | 48480 |
| ggagacttgt gtacaaggag ttcctcgagt caattgcttt ttccttgttc tagccagcca | 48540 |
| gagggctcct gttggaaaac aggagaccgg agaggctgag gcctgaccaa accagcttct | 48600 |
| gcaggccagc tgggaggcca caactcctac ctacgggaaa actgaagggc atctctattt | 48660 |
| ttagattagc aaaagaaaat aaatttaagt ttgagtctcc tttgcaactt ttaaaagaca | 48720 |
| tctttattga gatgatcatt cacattctat aaaattcccc cactttgagt tacaattcag | 48780 |
| tggttttagt cttccttgat gattttgatg gtcttttctt aaggctcttg gaagacccag | 48840 |
| aagcctctca gacacaggtg ggtgtggagg gcgtagcaca gaggcagact tctcatttcc | 48900 |
| tgggtctccc ctttaatgac tctcagagac ccctccttcc ccctgcccct ggcttctacc | 48960 |
| ccaggggtgt agagttttgc cattttccaa gcagaacttc atttcctctt ctgtgtctac | 49020 |
| actctttgtg cttcttctt gccagctttt tctccttttgc ccgcccttcc ttccttcctt | 49080 |
| ccctccctcc ctccttccct ccttccctct ttcctcctt ccccccttcc acccttcccc | 49140 |
| ccttccccc ttccctcctt ccttccttcc ctccttcctt ccttccttcc tgccttcctt | 49200 |
| ccttcctgcc ttccttcctt cctgccttcc ttccttcctt ccttccttcc ttccttcctt | 49260 |
| cctggtatgt gactaatttc tgtttcagga cataaatgtt gtccaggctg ttctttggtc | 49320 |
| tttctgttgg ataatggaca tttggcattg agagaggctg ctttttctga aatcatgttc | 49380 |
| ttggggccca gaacctaggt gtgtgcttct gactttgttt tcttcctgat ccaaattctg | 49440 |
| atatgtccat ttaaattgat ctagacccac agggcactgt gggacagatc ctcagtggaa | 49500 |
| catgactctg taacgagagc attttgtttt gtcaaaatga gaacatatta ttgccttca | 49560 |
| tctgattgta aacataatac atgtttataa aacagtataa tgagacaaaa atgtagacac | 49620 |
| taataaggga aaatctccct aattgtattt ctcttcacag agaaagcccc tgttgggcat | 49680 |
| atatactcta gtttgtttat ttgtttgact acacatatat gtattctttt cttatgtata | 49740 |
| aaaattctga acatgcacat ttctgcaact actgttttca cttgatgatg catggacctc | 49800 |
| tctagagtgt acgtttcttc ttccttacaa agcagttggc ttcgcccagg gtacaccagg | 49860 |
| acacggtttt ggctctgtcc ccagggtgtc acggaccag gggatgatct cacagggtct | 49920 |
| gccatctgcc ctgcctggcc ggaggctgca tcgagagggc caaggggcac cacgtgtcgt | 49980 |
| gggtactgtc aaacaagagc cttcagagcc ttccacagtc tttctttttgc ttcccagcat | 50040 |
| tgcttccccg ctggtggact ctgaatctag aactagctcc aggcgcctct ccaaaattcag | 50100 |

| | |
|---|---|
| acgggagctg gggcactatt ataatgcaaa tctaggcaaa gccctcccaa taccaggatc | 50160 |
| cagaatgggg tggggcccct tgccctgaaa agctgtttag tttgaaaata caaacaggag | 50220 |
| acagaaaagt ttggctaaat taatggataa agttttaacg atggtaacca tagtagggtt | 50280 |
| catcgacagc cagcgatggt tctgaacact tgacatgtat taactcacct aatccccaca | 50340 |
| ttttacagac aatgcaaagg aggctctggg aggttgagtg acttgcccca aagtcgcaca | 50400 |
| gctcctaagt gaaggattcg gagtggactc caggcagcct ggtctgactc cctgcactgc | 50460 |
| gctgtgctta tctctggccc caatgccgcc atgcagaagt gtctggggc actttgtctc | 50520 |
| tgtcagacag aattcggaga tgtgtatgct tgccctggta tggcacttct ctttttttga | 50580 |
| gacagaatct cactctgtca ccctggctgg agtgcagtgg catgatctca gctcactgca | 50640 |
| acctccgcct cccaggttca agcaattctt gtgcctcagc ctcccaagta gctgggatta | 50700 |
| tagatgtgca ccatcgtgcc tagctaaatt tttgtacttt tagtaaagat gttgttttgc | 50760 |
| tgtgttggcc aagctgatct cgaactttg gcctcaagtg atctgcctac ctcagcctcc | 50820 |
| caaagtgctg ggattacagg catgagccac catgcctggc agtgtggcac ttcttacgtg | 50880 |
| tgttcagcgg acactgttta tcttctgtcc ctccaagacg tgctgagct caggtcgttc | 50940 |
| attactggca gacaactgct gatttccaac agaattgcca tcctcttctc ccctgcgact | 51000 |
| ttcagagtgt gacctcagac tcaaaaatta gaagtgaaaa catcttaaaa actatccact | 51060 |
| tttcttccta atcctcctct cccctccctg tcttccttgt tgtccccatc taatgaacta | 51120 |
| tcatggcaaa aagagcccat ttctggtcat tttctgtggc ctttcaaact cccacctacc | 51180 |
| ccactgctcc tgggtgcatt acccgaaagc tgagacttca gtgcagaaag tgccaggccc | 51240 |
| tctgtccccc cagatcgcct tccttgtctt ccctgtgctt gcctgtcaca ttgtgtgggt | 51300 |
| tccagcgctg gaaggaatga ggaacagatt ctctggttct cctttttgaag tttaccttcg | 51360 |
| ctccaccact tctgagacct tcccggaagt tgcccctttgt ttctctcctc tccagggctg | 51420 |
| ccccagagct gcctctcacc tcttcctgct gtcaccccac caccatcagg gcagaagttg | 51480 |
| ggacaaagcc tctcctactg gctcctgctt ttctccctta ggtccagcct cctcttctcc | 51540 |
| atcttcagga gtctccttct ccactcacac gtcatgactt cagcacctcg catcagtcca | 51600 |
| gaatatgact gcttgttcaa gtgccaccctt tctcatgcat tttttttctag tgacaatcac | 51660 |
| agccaccctg tggggcagga gtgtcatcat ccccatgttt caaatgaaga attgcagttc | 51720 |
| agagagggca agtgactggc ccagcctcaa cagctagcca gtggaccca ccagggcttc | 51780 |
| tgactccagt ccgggttccc tttccaccca aatccatgga gggagctgag ccgagaacag | 51840 |
| gtgtccttca ggaagacgtg aagccaaagc ctccacctcc aaactcaggg gcccagggag | 51900 |
| tccaggcacc catccactca caaggctgga tatggtgcat tccaggagag gggttggggg | 51960 |
| cgagtggcct ctctgtgtac ccgtggggat agatgcgcaa gtggcatcgc cacatcgtga | 52020 |
| gtcctggctt catgggtgag ctccaggtcc aacgagaagc caagcagggg gcccttcaag | 52080 |
| ctcagctttg ggcccgggtc ggggtacagg gtagagcggg cctccccagc ccctgccatg | 52140 |
| aggccaaggc agtgcatcgt tcgcagcgta cattcagaaa ccaaagccta ggagctggtt | 52200 |
| atcattccgg tttacagctg atggaagagc aggtgcttcc gagaacccac agtgctcttt | 52260 |
| ggccagtgac ccaagggtgc ctctgagagg cctcgcagca cccggaggtg ctgctgaggc | 52320 |
| aacgccctga ctgtaagaag gaccattcat cctcagagag tggccgtgat gctgctgcga | 52380 |
| cagtcccacc atccctcccg actctcactc ccaacagact tcccactgta aagctgaact | 52440 |

```
ctccagcaaa tcacctctcg ccagactctc tcctcactct ctctgggtcc actagaggtt  52500
cctcagcctc tctttgcctt ggttttccca gctgtaaaat ggagcaaaga gggcctatgt  52560
acccacaaag gtgtggttgg agcgactcct cctacattag ggcctcgagt ggggcttcat  52620
gattggttgg tggaggtctc caaacccacc cagtgccacc gaaggctgag actgcagatg  52680
caatgccaca ggtgtccttc ctcagcctgg gcagctgaac atcatgtgta aaacgggat  52740 aataagataa taacagcccc ttgcacctat gtggctgtga ggattaaaca agataaatgt  52800
gtaacagtgc ctggctatag aaatatttac tcttgttatt aagggaagaa tatgtgtggc  52860
taaaaaggga tcgaagatgt aaaagccaat ccctcccct ctagcatatt aagggtaat  52920 gttgagttgg tttgtggacc atttgctgcc tgttagagct ggaaggtagg gaccccctct  52980
caacagcgat gctacaaatt atcccattg gaggtcaacc aaaagacaaa gcttattggc  53040
tggacatggt ggctcacacc tgtaatccta gcactttggg aggccaaggc aggcggatca  53100
cttgagatca ggagttcgag accagcctgg ccaacatggt gaaacccat ccctactaaa  53160 aatacaaaaa ttagctgggc gtggtggtgc acacctgtaa tcccagctac tcaggaggct  53220
gaggcaggag aatcactaga acccaggagg tgaaggttgc agtgagccga gatcgcacca  53280
ctgtactcaa accgagcaa cagagggaga cgcaatctca aaaaaagaa aaaagacaa  53340 agcttgttaa taccagcata ttgttaaggg aataaagtag gctgcagaac aactggtgta  53400
atatggtgcc atgtagggaa aattacatgt gtgcatagga gaggggtctg caaggttgtg  53460
ccctaagatg ttagagtggt tcctttgctt ttctcttta taattttgta tttgacttt  53520 aaataaggac cataaatcac ttttataaaa tacattctct ccagcccta ctactccttt  53580 aaagaataag agtggtttgc ccaagaaaga cagttttttt tgctctggtt ttcttgattc  53640
tgacatcaga ggaaactcct tctcatccac ttggggtctc gggttcaggg gattcatttc  53700
aggcagatta aagtggtgac caggggcatt cgtggacaca gggagggaca ggagcaccat  53760
cagtttgtct cacacaacca ctgtcatcct cactgaaggc tgttgcctga tcaaaaacag  53820
tattgggcca ggcacggtgg ctcacacctg taataccacc actttgggag gctgaggtga  53880
gtggatcact tgaggtcagg agttcgagat caacctggcc aacatggtga aaccttgtct  53940
ctactaaaag ttcaaaaatt agccaggcgt ggtgggtgcc tgtagtccca gctacttggg  54000
aggctgaggc aggagaattg cttgaacccg agaggtagag gttgcagtga gccgagatgg  54060
caccaccaca ctccagcctg ggcgaccgag ggggactctg tcttaaaaaa aaaaaaaa  54120 aaaaaaata tatatatata tatatgtcaa aaatgggta gttttagat ctatagtagt  54180 tctaaaaaca aaggccatcc aagcatgaca gatttacaag cactattggc tattccagta  54240
gttacaatgg aggagagaag cttttagtta aaacaaacaa acaacacaac aaacccagaa  54300
accttaggtc aaaaccaaaa ttgtcctctc agacacaatc tgggaatttt ctcatgacag  54360
tgggcattag ccaactgaca tcagcagcaa ccatccgtgt gcacacagtg gcaccacctc  54420
ctcccaaaaa gcagccttca tctatgccct catacaatcg ttgattattc tctttggatt  54480
gaggcccgga attatttaag tttcttcttg ccagcatgag tctttccttt ctgtatgctc  54540
cttatcttct ctctttaatt tggcagttct gcttgaaatc tgggtctttc attagtagta  54600 gttcaattttg gttccagaac attctgtggt gtgatgcaat gtgaccagag ctcacacttc  54660
agagctcttc aagggccagt cttactgagc acctcccagt ggctgcctgt gtgctgggcg  54720
ccacttgtgg tgggcaggag agaggagggg acacaaaagg agacacagct ccttcttaga  54780
agctcaaagt tggggaccag ctgccacaga agagtatgtt tagcatctga gacaccaaga  54840
```

```
tccagcgtca caagggtgtt tattaagcct cctcatctct ttcttttct ttttttttt      54900 ttttttcctc aggcagtctt actctgtcac ccaggctgga gtgcagtggc atgatctcgg    54960
ctcactgcat gcaaccacca cctcccgggt ttaagcaatt ctcctgcctc agcctcccca    55020
gtagctggga ttacaggtgc ccaccaccac acccagctaa tttttgtgtt tttagtagag    55080
acagggtttc accatgttgg tcaggctggt ctcgaactcc tgacctcaga tgattcaccc    55140
acctcggcct cccagtgtgc tgggattaca ggtgtgagcc accgcgcctg gccttgctgt    55200
tgattcatct atagtatgtt tgacttgatg acctccagtt accttagaca gaggttctca    55260
tctaagctcc aactttccat ttcctttgtc ctcgtctttc cccttaaccc ctccacattt    55320
ctctcaaaat caccccactt ctaaaaaata ctgtttattt ttcttttaaa tttcaaatta    55380
tctatactca ttgaaataaa tcaaaatagc atggaataag cgaaaaaaat ggatcccacc    55440
cttccccact cccattccct agggctaacc atagttaacc atttaatgac taggtttttt    55500
tgttgttgtt atttttatt tatttatttt gagacagagt cttactctgt cacccaggct    55560
ggagtgcagt ggtgtgatct cggctcactg caacctctgc ctcccaggtt caagcattct    55620
cctgcctctg cctcctgagt agctgggatt acaggtgcct gccaccacac ctggctaatt    55680
tttgtacttt tggtagagac agggtttctc aatgttagcc aggctggtct cgaactcctg    55740
gcctcaagtg atctgcccac cttggccttc caaaatactg gattaaggt atgagccacc     55800 gcacccagcc ctcctgggct cttttccttt agttgcactc gctccccgct cctggagtag    55860
agggatttcc gagagactgt gggctccagc cttcacctag gcccaggact aggatgcctg    55920
ccctaacatt tatctttata ccttaaagca aaacagctgg accataagca ttcaagaaca    55980
aactgtgaat aaggagaaag ttctcccagg aaacaagagc tttagttatg ttgggccagc    56040
ccttatattc cttagctgtt accagtcact gcttgattta atctcggcta tcacttggcc    56100
tgacaggtct gctgctggtg ccaggatgtc tgggttttga agcctggctc cattacatac    56160
ttcctgtgtg accttgggca acttactcaa cctgtctgtt cctcagtttc cccagctgta    56220
ttatgtcagc ataatagttt gttgtgtgaa ttaaatgagg taataactgg aaatgcttca    56280
aacatggttc ctatcatgag aaatcctgct ttccgcctaa atgtgctgga aaattcctgg    56340
tggtgcagaa caggagacca gagcaaagga aagacagggt gcagaagcca aaaattacct    56400
tggagaacaa agcgcatgtt aaggttattt ttggattcta ggtttatctc tgcttggtct    56460
tcagttacct acaagagatc catttagggg attttttgttt gttttttaacg atagctttat   56520 tgagatataa ttcatatgcc ataaaagtca ctcttttaaa atgtttccgg tatattcaca    56580
aggctgtgca gccttccctg tccttgattc cagtctgagt ttttaactga agggataagg    56640
aggaccacgc tttcccccaga ccagaaccgc gggccagggg gcgattccgc tgagtcaccg    56700
cgggcgcctg gtgcgcggcg gcggagcccg ggaccttcct tggctgcccc ctagcgaggg    56760
ccgcagcgca gcctgagaca cccgccgggg ccgctccacg gccgtcggat ttagactgga    56820
agctcggtcc aggtccccag cttgatgcgc ccgcggtgta ggagaccagc ccgactcgag    56880
cttcccctga gcccctggac tcttgactcc agcagggcct gggtaatgaa cgtcagctcc    56940
cctttcccaa aggggttgct ctgttgggaa ggcacccgtt tgatacagta gcatagagat    57000
gggttttagc atcaaaatat cagaattcaa gccttgctct ctgcttacta gctgtgtgac    57060
cctaaaaagg tttctgaacg tctctgagct tcagttccct catcattcct tctcacgggg    57120
tggttgtgag cattacagag atcctctctg tgaagcccct gtgagtggct catcctgagg    57180
```

```
gctgaaataa acatgttatt aataatccaa aactggcaag ggatgttgac tggtccccct   57240
cccttgccca aggagctttc tagaacctga gttatcatta ccaaactgta ctgccttgag   57300
taagaaagtt agaaggaatg ggaaggatgg tggcaggtgg aggaaggcgg attggtcatc   57360
acctccttgc agcaagaaac agccccagat cgtgggaaac ctacagacct gctagacaga   57420
ctaggagcaa aagctggggc tttaagaatc cccagggagg ttctcctgag agagtagcca   57480
gttggatttt gtaagcagag atttgtttgg ggaggaggtg acaacgtagg gagcagaggg   57540
gcaaagctgt cgggaatcct gccttgaggg cagggatgtg tgttgggggg agttgggtca   57600
ctggggctcg gtggccttgg gcaagtttct acctctcagg tcctttaccc acctagggtc   57660
gccatcctgc ccacctcaca ggttacagtg agcctggatg cactgtcatg ggcaggtgcc   57720
caggaaaatg gcagacatgt tccaaacagc acgcagcatt ccccagtgat gcccagggtc   57780
accttggagg tgggcgagat gcctggggtt tctcgtccac cccacaacac ctcaggggac   57840
agccaaagct gtcccttcag gtaagctgca cagaagatgt gaactctgct gcaaagactc   57900
tattctttgg gagcaaaagg gacccagggt ctcacctgca catccctgtc cctgagggcc   57960
taggggttct tggaggcccc agccttggca aaatgaggaa gaaggtgaag gttgtctggg   58020
cccctgccag gctccttcct cggccacgca ctccccttcc tgcacacaca ccttctccc    58080 tccaccccat ctccattgtt gtcagaaaag tcacaataaa aaggtccata ttgtctagtt   58140
cccatacttt taattttaa aattttattt atttatttat ttatgtattt tttgagacag    58200
agtcttaacc caggctggag ttcagtggca tgatctaggc tcactgcaac ctctccctcc   58260
tgggttcaag tgattctcat gcctcagcct cccgagtagc tgagattaca gatatgtgcc   58320
actatgccca gctaattttt gtattttag tagagacggg gtttcaccat gttggccagg    58380
ctggtctcga actcctggcc tcaagtgatc tgcctgcctg agcctccgga agtgctggga   58440
tttcaggtgt gagccaccgc actcggctcc acacttttca cttattaaaa gactgtggtg   58500
tccatcaatg gatgaatgaa taaaccaatg tggactatcc ctcccattac ccaaggaatg   58560
aagcacggag ccgtgccaag atctggattc acagtgaaag aagccagtca ccaaaagcca   58620
cgtgctgtgt gacttccctt atacgaaata tccagaagag atacatccat ggtgacagaa   58680
agtagatgag cagctgggga ctggcgaagg ggagaagggg gagcagctgt ctatgaggtc   58740 cagccttttct tctgggtttg gtgagaatgt tttggaacta gatagaggtg atagttgtac   58800
aacattgtga atgtactaaa tgccactgaa tcattcattt taaatcgttc tttacgttgc   58860 atgaattta agtcaatcaa aaacagttgt ttgaaaagag aaaagcctat gggtagcggc    58920
agcagtgatt ggatttatga ttcgattcca tggctcatcc ctcccctgcc tcacccctc    58980 gccctccgac gtcttcttct tttactctga actgttatct ttgttctcat ctctctctct   59040
ctctctcaac cctgcagaca cttttccctt tctttgtctg cccccaccct ccagatttcc   59100
gtgtctccag tgtctcccta cgaggcatga attgagactg ggagggtgtg attctgaaga   59160
aggcaccaac agtgactcag ctagccccctt ccccacccc gccccccggg cctcaatta    59220 gctaaaaaac cacagggacg gactcaggag gcaataacctt tccaagggtc cctaaaaaat   59280
gtcccatttt agtgtccagg tttcactcaa ctttagtgcc tccctaaaa tgtgttcctt    59340 acctcccacc ccactgcatc taagtcactg cctgagaaaa caggattgag gaaaggagaa   59400
aggaagagag agagagagga ggagagagag agagagggag gaaggctgat ggatttagaa   59460
aagaagaaaa caagtggtct gaggaaaaca gccttggtgt gtttattttc ctgtctgtgt   59520
atcgcttctc ggccttttgg ctaagatcaa gtgtattttc ctgtctgtgt gtctcgctta   59580
```

```
gattacaggg atctgtgggt gatgacacgt ctggtccagg ctgcgtagtc acctcaaggg   59640
catgcttatt gatgtgtttt tcaattcact atctttgcat gggagtccca ggccaagagg   59700
cacagctgcg ccatttgtct gttggtttag atatccttta tccagttctt ccagagaaat   59760
catcctgccc ttctggagga ggtgggcagc aggggtcaga gatgggaggg aaaggaagga   59820
gccaggtcct tggctaggat gccagggtcc cctgcctctc acctggcctg ggctggaggc   59880
ctcctgctgt cctgtcactg atcactaccc cgccccagcc tcctgagtta gaagacacag   59940
gctaaagtag agtatttctt cattgaaaaa cccatacaaa ataaaggttc ataaaaaata   60000
aaaatttaga ctgggtgctg tggctcacac ctgtgatccc agcactttgg gaggccaagg   60060
caggtggatc gcttgagccc tggggttcat gaccagcctg ggcaacatag tgaaacccca   60120
tctctacaaa aaatacaaaa aattagccag gcatggtggt gcatacctgt ggtcccagct   60180
tctcagccta tggacccaca tagaatacaa tgtcagcata agaagggagc cctggggtca   60240
ccaaatggtt tgggcggcaa agaacctgaa ggttgagaga agtggcttgg ttacccagct   60300
gttggatgtg agacctggcc actgcttctt ccatacccta gacctgcacc ctgacatctc   60360
aagtaaaaag ttgggggatg ttttatggtc caggatgaag gaagggcagt gaggggcagc   60420
ggagcatcac tttgcatttc tgtctgcctc ttactggctg tgtgacctgg ggcaggtaac   60480
ttcccagact cctgggaatc ataacaccta tgatgatgat gatgatgatg atgatgatga   60540
tgatgacacc tacctcaagg attgccctga agggtcacag agatgcctgc aaggcacctg   60600
catggagcaa gcgcccctcc tctggcaggt gctgggtgag cactacctgc tgccaggccc   60660
tggggctatg gcactgcgtg accctgcaag tcctacctgg cgaagctgtc gttcttgtgc   60720
tcagtcagtg ttggttgtaa gactgagaag agtcacttca ttttgctctc cagggacatc   60780
tttctgggtc ctatttctg cctatgtcaa gtagcgcctc aaggatgctc ctgaaaatgg   60840
gcttgtcttt cttaacatgg caggtaggtc ccaaagcatt agcatgggc agctgaccta   60900 gcccagccaa tgcagtgcag tgactcttgc aaccgagtct aatcagaagg tccatgaacc   60960
tacgagcatt tcctgtccca ggatcagggt ggaggctgag cctccctgct tagagattct   61020
tcccatgcat tccactttt tccccaaaag aaaatattga cccttgagag gcacacagtt   61080
tatttatttt gcatagtaaa tagtagcctg tattttaagg atgagttgat ttctgcatca   61140
gcccctgtag gtcatcagcc ttctattggt gcatctgact ctctctagcc ctgcagggat   61200
ggtggagggg gaggggaagg agggatctt attggaaacc aggacagtga gactcattgc   61260
cctgtcatct gctctgtggt gctgaatgag gcagcccaac agagaaatac cctgagcgag   61320
catccccagc ctccaaaaca gtggcgcatt gccctgagtc ctgggaatga cctttgattc   61380
tcctgctcct gacttggaac ccatggaaac ctctagaagc agctgaggaa acccaacat   61440 gaaaagcaga actccacact gagaatatag gaggtgatcg gaacatacaa tgattcttgc   61500
taagaccgat tcacagttttt tctttttttt cgatcgaaga aatactggag aagcctaaag   61560
aaggagtcta aaaactctgg cacgtgggcc aaaactgtcc ttgagctaag aatgattttc   61620 acattttaa gtggttgaaa aatgaaataa aataagatga tgttttgtga cacatgaaag   61680
ctatgggaaa ttcaaattct aatatctata aatagtgttt tatcagaaca cagtcatgct   61740 catttatta tgctcgatgg ctgctttccc gctacaatta cgttgagcag ttacaacaga   61800
gaccacgtgg cccacaaagc cttacaatat ttactatctg gcccttttcca gaaaaaaatg   61860 tgccgactct tgaccttaac ctcagcaatt tgggaggccg aggcaggcgg atcgcttgag   61920
```

```
ctctggagtt catgaccagc ctgggcaaca tagtaagact ccatctctac aaaaaataca   61980
aaacattagc caggcatggt ggtgcacacc tgtggtccta gccactcggg agactgaggt   62040
gggaggatcg cctgagccca ggaagtcgag gctgcagtga gctgtgatgg caccactgca   62100
cctcagcctg ggcgacagag caagaccttg tctccaaata aataaataat gcaaagtaaa   62160
ataaataaaa ccatataaaa aggaatcaat ttaaaattat aatgaaagct ggccgggcat   62220
ggtggctcac gcctgtaatc ccagcacttt gggaggctga ggtgggtgga tcacgaggcc   62280
aggagatcga gaccatcttg gctaacacgg tgaaaccccg tctctactaa aaatacaaaa   62340
aaaaaattag ccgggcacag tggcgggcgc ctgtagtccc agctactcgg gaggctgagg   62400
caggagaatg tcttgaaccc gggaggtgga gcttgcagtg agccgagatc gtgccacttg   62460
cagtccagcc tgggcgaaag agcgagactc cgtctcaaaa acaaaaacaa aacaaaaac    62520
aaaaaaaat tataatgaaa gccaaggggc atagtagaac aaattttcta gagctcatta    62580
agtcaaatga gtcaccagtt agtaaaacgc agtcacgggg aagagagggc aggattcttt   62640
gaagcagcgg ctctcctaaa aacaacccac ccttgtccag ctgccttccc tcctgagggt   62700
gttccctttg actgtgtgac ccccatcccc tatttcccaa ccgtccaagc ccacctctag   62760
cataatacga gcttttaatc cctctccctg accccaaccc gattttgaag cccagtctag   62820
tattttctca aatacacttc ttggctccat tccttccttt ccatcacctc tgccttttca   62880
ctgcatgctt ggaccactgc agtcagctcc ctatgaacga ttgctctcta cccatccaat   62940
cggccccgcc tgctgctgcc aaattcaccg agggcacctc tgtggtgctg cctgtggaca   63000
aagtccaagc cagccacctc acccacctac aggtgagtgg ggagcagcca gcgtgtccag   63060
tggtttaccc catcgccaca gacttggtga tgtgtcgatg tgcagagaag gggtgttggc   63120
agccacaaca caagcaaccc cgccccatgt gagatctaag atgggcgtgc tgggagccac   63180
ctctgagaat ccaacagaag gcagagggga gaacggctca cacggcacaa acactccttc   63240
cttttttttt tttcttttc cttttgaaa ggagtctcac tctattgccc aggcaggagt    63300
gcagtggtgc aatctcagct cactgcaacc tccgcctcct aggttcaagc gattctccag   63360
cctcagcttc ccaagtagct gggattacag gtacactcca ccatgcccgg ctaattttg    63420
tgtttttagt agagacgggg tttccctatg ttggccaggc tggtcttgag ctcctgacct   63480
caggtgatct gcctgccttg gcctcccaaa gtgctgggat tacaggtgtg agccatgggg   63540
cctagcctcc ttccatttaa atgtatgcct aatttgccca ttgagaacgg ctgagacgca   63600
ttttaagtgg ccagggtcta cttagagtta gtgctcatga ccaggccag gtcaagcctg    63660
gctggccaga tggtgccttt gacctgctct gtctctgtgc aaaggaatga gctgaaggat   63720
gggggtgcag tgtgtgggca gtgggctggg gctggcagga ctcagtgact aagggaagag   63780
aactttcctc actaccagcc tgtcttttca gggcaccgcg gggggctttg ggacttggtg   63840
atgaacacag cacagagagc tgtccagcat gcgggtccct ggcttctcac acttcccagg   63900
ctccttcaga ggctctctcc aaagggagct gctctctcta gaacccatga atttggaata   63960
taggcaacca ctgcattggg gaccactgac ctcaaacata gagaccagag caaatggggc   64020
tcatcacgtg aaactcatct ggaactctag caggttcttt tatatatata tatatatata   64080
tatattttt attattatac tttaagttct agggtacatg tgcacaacat gcaggtttgt    64140
tacatatgta tacatgtgcc atgttggtgt gctgcaccca ttaattcatc atttacatta   64200
ggtatatctc ctaatgctat ccctccccac tcccccacc ccacaacagg cccagtgtg     64260
tgatgttccc cttcctgtgt ccaagtgttc tcattgttca attcccacct acgagtgaga   64320
```

```
acatgctgtg tttggttttt ttgtccttgc gatagtttgc tgagaatgat ggtttccagc   64380
ttcatccatg tccctacaaa ggacatgaac tcatcatttt ttatggctgc atagtattcc   64440
atggtgtata tgtgccacat tttcttaatc cagtctatca ttgttggaca tttgggttgg   64500
ttccaagtct ttgctattgt gaatagtgcc gcaataaaca tacgtgtgca tgtgtcttta   64560
taacagcatg atttatattc ctttggttat atacccagta atgagatggc tgggtcaaat   64620
ggtatttcta gttctagatc cctgaggaat cgccacactg tcttccacaa tggttgaact   64680
agtttacagt cctaccaaca gtgtaaaagt gttcctattt ctccacatcc tctccagcag   64740
ctgttgtttc ctgactttt aatgatcgcc attctaactg gtgtgagatg ttatctcatg    64800
gtggttttga tttgcatttc tctgatggcc agtgatgatg agcatttttt cacatgtctg   64860
ttggcgaact ctagcagctt cttttcacaa gttcatggag agaggtttcc cactgaggga   64920
atcacatctg tctgatcaaa agaggcttgg gaaatggctc tcctgttcat tccctgaaaa   64980
cctctgatgg aaccactgcc actgtggcag ccccagcact ggcacccag ccatgattgg     65040 tgccccagcc acatctctgc tgtgagcccc agagccctgg ttaattaatc atccacgtgt   65100
tgatggggag aggcccattc acaaaagcga cataaagccc agggagacgt ggccgtggca   65160
agaagggtgt gggactacat tccgccccca actgagagat tcagaaacca gaaaaaaatg   65220
gaaaaacata ctgtgctctt gggtgggaaa actaaatatc atgaagggag caatttttat   65280
agttttggcc tataatacaa ttccagccga aatcccagtg gaactttgag aatttgcagg   65340
aaaaaaaaaa atgtctaaag tacatctgga agacaaactt acaagaaggt caaataattt   65400 tgaaaagaa aatgatatct aagcccacct agagaataag acttgagatc caaagctaaa    65460
tcaggaggct ctagcaaaat tgacagataa gcaggacaga gtgcatggtg cattcacctg   65520
gggaagaggg cagattggtc tacaaatagg cctgggtcca ctgactttag ctgttatatt   65580
tggggagaaa cttttcaacc tcactccatc ttaaacctaa aaatattcca gatgaattaa   65640
taaatataaa aaattagacc actaaaaatg tagaagaaaa tggatgatct ttctatacca   65700
tagagcaatg gaataaatca caaggaaaa cagatttgac tatataaaac ttaaaccctg     65760
cccatcaaaa accatcagaa accaaaataa aaggcaacca actggagaag atagttgcca   65820
caaatatgat caagggttaa tgttattcat aaattaagag cccacacaag tcattagaat   65880
aagcactgag acctgaacag acaagcaaaa agaatgagag tgggtcggcg cggcggctca   65940
tgcctgtaat cccagcactt tggaaggctg aagcaggcgg atcacttgat cccaggagtt   66000
ccaacaccag cctgagcaac atggtgaaac cctgcctcta caaagtcat aaatattagc     66060 cgggtgtgat ggcacacgcc tgtagtccca gctactcagg aggctgaggt gggtggatca   66120
cttgagcccg ggaggtagag tctgcagtga gccaagatca caccgctgca ctccagctgg   66180
agcaacagag tgagaccctg acttaaaaga aaaaaaaaa aaagaggag aaaaatgctg      66240 atctcactag taattaaaac atcaggccag gcgcagtggc tcacaccttt aatcccagca   66300
ctctgggagg ctgaggcagg cagatcactt gagatcagga gttctagacc agcttggcca   66360
acatggtgaa atcccgtctc tacaaaaaat acaaaaattc gccaagcgtg gtggcacatg   66420
cctgtgatcc cagctactcg ggaggctgag acaggagaat tgcttgaaca cgggaggcag   66480
aggttgcagt aagctgagat cgtaccattc cagtccagcc tgggctacag agcgagactc   66540
tgtcccagaa aaaattaaaa catcacatat ttaaacaact ctaggatatc atttaaaaaa   66600
acattaatag actgtttttt agagcacttt taggttcaca gtgaaactga gtggaaggta   66660
```

```
cagagacttc cgtatgttc cctgccctcc acgtacagcc tcccccactg ccaacgtcct   66720
gcaccagagt ggtacacttg ttacaaccaa tgaatcctca ttaacatatc attatcaccc   66780
aagttcatag tttacattag taaaacatca tctttcatct ataagcacaa aaattttttg   66840
gcatttattt aggtgtatga ttaactcagt gttgacaaga ctcacacttc atacccactt   66900
gcactgcatc tgagaagcaa ttggtgtcta cagccgctac accctcaaca agcccgatct   66960
tgtttgaaaa gcaattggtg atgcttctca aaattctatg acaaagtca gccgggcatg   67020 gtggctcatg cctgtaatcc ctaaactttg ggaggccgag gcaggcagat cacctgaggt   67080
ctggtgaaac cctgtctcta ctaaaaatgc aaaaattacc caggcatggt ggctgggcc    67140 tgtaatccca gctactcggg aggctgaggc aggagaatcg cttgaagcaa ggaggcggag   67200
gtttcagtga gccaagattg caccactgca ctccagcctg ggtgacaaga gtgaaactcc   67260
atctaaaaaa aaaaaattat ggacaaagtt tttcaaaaag atatttaatg caactttatt   67320
tgtaatattg gaacatctga ggccatttca gtgctaacta ttaggggatg gttaggaaaa   67380
tatggtacat atgtggaaag gaacatttgg tagttagtgc ccctgatgtt tacaaaggct   67440
tttagtgacc aacaaatgct catgctataa tcttatgtga aaaagcaag tagcataatt    67500 gcaactatat ttttaatgca tagaataaaa ggctagaagg aaatatcaca gatccttgac   67560
atacattccc aaacctttgt aaatccgcgg attcatgaaa acagacacat ttgcacaagt   67620
gcctgatctt ttctgttata cattcattag aagtcaagcc ctggtgccac aaagtatctg   67680 cctttcaaa tgtgatcaga atgttctctt ttgcttcaag gccattttc acgaagcagt     67740 ggcatttttg cctcttcatc agagtcaccg tgtgccctgg aggactgaga acagcagagc   67800
cgttttagga tgggacaggg cagccaggag gattgggctc actccctact gagtgcctca   67860
ctcccgtaca gccccatag aggaagaggg gttcaaattt attcctcagc cagatggcat    67920
gtgccgcctg tcctggaatt tcacatcact tatgatggac caaaattcca aaagctgaat   67980
ccatgattgt caaagtctgg tatggcagga tgtcaacagt aatcgtttct gggcagaggg   68040
atgattttct cttcccatct tgctttgtat aaatacattt tctataataa ggttgtatta   68100
cttttctcat caagaaatag caaagtactg ttttactcaa aatatgaata gagccaggca   68160
tggtggcagc ttatgcctgt aatcccaaca ctttgagagg cggatatggg aggatcactt   68220
tagcccagga gtttgagacc agcctgggca acatagtgag accccgtcc ccactcccc    68280 aaagaaaacc cacaaagcat ttatcctgga ttattcacag gggccaaaaa aaaaaaaaaa   68340
ttcaggcctc ctatagccat gagctacgaa tatgaaaata tgcaaatgtg taagaaaagc   68400
cagcacatcc gatttttact tttactttca cacctctgtc caccatgttc caagagaaga   68460
aacttggtca ttgaaaggaa tagatcaaat ccaaagaaca aaaccactgt gctcattaaa   68520
cttcttagtg ttcacaaagc tttagctgca ggttgaatgg gcaacccga attggctggc    68580 tcacctgggc tgcagggagc agagatcgcg acactgcact ccagcctggg caacaaagcg   68640
agactctatc tcaaaaaaaa aaagttcat aaattcaaag ttatgaatta tttttaaaat    68700
aataataatt tacaataaag atgaggacaa agtgtgagta aatggtggtt tctatccagc   68760
tctgttgagc tgaagtggca tctccctgct ggggcttttg ggaagaagg gtgtgtgttg    68820 ctcttcagat cccaagcctc atgcccctac tgggccctgt ggggtgcttc tcagcccacc   68880
aggagagcca ccgttggaac acacgtgg gggacctggt gggtgccggt gtggtgaatg     68940
ggggccacag cctgactcca ggaagccagc aaactcggag ctgaggagt caggacaccc    69000 ccgatgagtc aagagttggt tttgctgcca gttgacatct gattgaacca tctcttcact   69060
```

```
tctccgtgcc tcactttcct taccagacag gctctgctga tgctgtccct ctcctgttca    69120
gtcgtgccct caccgttaaa gagaaagagc aaactgctgg gcagcagcat tgattttttt    69180
aatgaagtgg aaagagagct gggaataaca agtcgggccc acctcacctg cctcacctgg    69240
tgggtttatt tgttttgttt ttttttttt gttttgagac agagtttcac cctgtcaccc     69300
aggctggagt gcagtggtgt aatctcagct cactgcaacc tccacctgcc aggttcaatt    69360
gattctcctg cctcagcctc ccagtagctg ggattacag gcacctgcca catgcctggc     69420
taattattgt atttttagta gagatggggt tttaccatgt tggccaggct ggtctcgatc    69480
tcctgacctc aggtgatcca cccacctcgg cctcccaaag tgctgagatc acaggcgtga    69540
gccaccatgc ctggccgtca cctggtggtg ttgaatatga actgctgcgg tgttggtaaa    69600
ttaagcaagc agatagatgt aaataacgct gggcaggaa tatggagcac gggatgagga     69660
tgggcggcca actgttagag agggtagcag ggaggctgag atctgcctgc catgaactgg    69720
gaggagaggc tcctctctct cttcacccc actctgcccc caacactcc tcagaactta      69780 tcctctcctc ttctttcccc aggtgaactt tgaaccagga tggctgagcc ccgccaggag    69840
ttcgaagtga tggaagatca cgctgggacg tacgggttgg gggacaggaa agatcagggg    69900
ggctacacca tgcaccaaga ccaagagggt gacacggacg ctggcctgaa aggttagtgg    69960
acagccatgc acagcaggcc cagatcactg caagccaagg ggtggcggga acagtttgca    70020
tccagaattg caaagaaatt ttaaatacat tattgtctta gactgtcagt aaagtaaagc    70080
ctcattaatt tgagtgggcc aagataactc aagcagtgag ataatggcca gacacggtgg    70140
ctcacgcctg taatcccagc actttggaag gcccaggcag gaggatccct tgaggccagg    70200
aatttgagac cggcctgggc aacatagcaa gaccccgtct ctaaaataat ttaaaaatta    70260
gccaggtgtt gtggtgcatg tctatagtcc tagctactca ggatgctgag gcagaaggat    70320
cacttgagcc caggagttca aggttgcagt aagctgtgat tataaaactg cactccagcc    70380
tgagcaacag agcaagaccc tgtcaaaaaa aaagaaaag aaaaagaaa gaaagaaatt      70440 taccttgagt tacccacatg agtgaatgta gggacagaga ttttagggcc ttaacaatct    70500
ctcaaataca gggtactttt tgaggcatta gccacacctg ttagcttata aatcagtggt    70560
attgattagc atgtaaaata tgtgacttta aacattgctt tttatctctt acttagatca    70620
ggcctgagtg gcctctcttt agcaagagtt ggttagccct gggattctta ctgtagccac    70680
attaataaac aacatcgact tctaaacatt ctataatacc atcttttggc caaattgact    70740
tcgcctcttc ctctctcttt ccaaatgaaa tgtgtttcat ttcactgtca gaccacatgg    70800
ttggggaccc cacagagcac acagccctcc ctctgccttc ccatgctggc ccttcaccca    70860
ctgctggagt gccaggttgg tccaagggtt ggaccaagtt gtctgaggtt gtctcaaggt    70920
tggtcgaggc tgtctccgcg ctgggttgtg ctacaaggag cccttctttc catgggtgtg    70980
gctggcagtg agtgctcaca gcaacagccc acagtcagc ccgagggcag gatggactca     71040
gtccctgcct ccatacccat ttctaaggag gcaaaatggc aaacactcta ctttctctt     71100 ttaatgctaa aaataagaaa acaccttgca gcccagggta tgggtagtgc atggaagccg    71160
tggagttgtg aggtgggaag tgacctctgc tggatatgtc tattcaggaa gattgctgga    71220
gtgggtgggg tctctgggag gtcccctgag tgtgggaagc tgggaccacc agctttctcg    71280
cacagggagt ggccatccca gcttggagag gttccaggac tggttgggag gcacgtttca    71340
gatttctatc tgttgaatca gcgaagatat tggattatga ggaatttggg aattaggaaa    71400
```

```
gtgggtgcag gtgggttggg ggtaggtgaa ggaagacatg ggcgtattgg gggagcaggg    71460
gctgctcaga ggtgttccag aagctctggg tgaggaggtg agagggaccg gggaatgcag    71520
ctcggcccag cctccctgcc tgaggtcagc catcacgtgg tgatggcaag atggaaatgt    71580
gctttctgac tgctccagcc agtgctgcca gattcagctc cccagggagg gcacctgaga    71640
ggctccaagc caggagatct gttttctcct ttgttttgtt ttttttttgtt ttgttttgtt    71700 ttattatact ttaagttcta gggtacatgt gcacaacgtg caggtttgtt acatatgtat    71760
acatgtgcca tgttggtgtg ctgcacccat caacttgtca tttacattag gtatatctcc    71820
taatgctatc cctccccct ccccccaccc cctgttttct cctttgaatc cttcttagag    71880
gccgggtgcg gtggctcacg cctgtaatcc cagcactttg ggaggctgcg gcaggaggat    71940
tgcttgagcc caggagttcc agaccagcct gggcaacata gtgagacctc gtctctacag    72000
ataataattt taaaaattat ccgggcatag tggcatgcac ctatagtccc agctactcaa    72060
gaggcagagg caggaggatc acttgagccc aggaggcgga ggttgccgtg agccaagatc    72120
ccaccactgc actccagcct gggcgacaga gaccccatg tcaaataata ataataataa    72180
ataaatcctt ctcagtccct tcctcactgt gtcccctcc actgaattt tccacctcct    72240 ctcccacttc ccccactccc gctttccctc tccttctctc cccactccat cttttctctt    72300
ctctgctgtt tctcgtccct ccctcctctc catcccacaa cactgcctac cctgtccctg    72360
ccccaccctg gtgctcagga tgtgtgaagt gaggggtggt agcccccaag acctcaaccc    72420
cgaaggttag cctgttgaaa ccactttctc ccagctgccc ccctggcagt tggtgctgct    72480
gggggaaact gggattgggg gccagatttt gcctcttttc ctgacaaaga gagatgaaga    72540
gttctctcac caggtgcctg ggactggggt gtgggtgtcc cagcctatcc cagcgcatct    72600
gttctgcatc atgattaata gtgctgctttt cagccgggcg cggtggctca cacctgtaat    72660
cccagcactt tgggaggcta aggtgggcag atcacaaggt caggagttcg agaccagcct    72720
ggccaacatg gtgaaacctc gtctctacta aaaatacaaa aattaaccag gtgtggtggt    72780
gggtgcctgt agtcccagct acttgggagg ctgaggcagg agaatcactt gaatctggga    72840
agcagaggtt gcagtgagcc aagatcgtgc cactgcactc cagcctgggt gacagagcga    72900
gactccgtcc taaaaaaaaa ggagttttgc tctgtcgccc aggctggagt gtagtggcgc    72960
catctcggct caccgcaacc tgcgcctccc gggtgcaagc gattctcctg cctcagcctc    73020
ccaagtagct aggattacag gcgcctacca ccacgcccgg ccagttcttg tattttttaga    73080 agagacgggg tttcacccctg ttggccaggc tcgtctggga ctcctgacct caggtaatcc    73140
gcccacctca gcctcccaaa gtgctgggat tgcaggcatg agccaccgtg cccagtcaac    73200
tccttctcaa aaaaaaaaaa atagtgctgc tttctctttc aagtgtcctg atttgggtga    73260
tagtaaatgc cactctactt ataagggatc tacctcagaa tgctaattgg gacattttg    73320 tagcactcta ctgttggcag caggtgatgc tcacaacagc ccgtgagggt ggatgacgtc    73380
cgcttcacag atgacaaagg agcctcatgc tcagaccgtg ggctgccaga gcaggtccat    73440
ggctgcagcc ccacatggac catatttccc ccttgtcact cttccacca agctccctttg    73500 gaacttcagt tattaagctc tcttgggtgg aatccaagtt agaatcacaa catgtgcctc    73560
atatggattg tgccagtgaa aaatgacatt ctatttagag gcagggcagc ctggcttaga    73620
gtcagtttaa aatatgtatt atgctgcaac aaatgtacca tgatcctgta agatgttcac    73680
aacaagggaa ctggatgtgg ggtatactgt ctgtactaac ttcacaagtt ttctgtaaat    73740
ctaaaactgt tccaaaataa caagttcgtt taaaattaac tccaggagac caggtacggt    73800
```

```
agctaatgcc tataatccca gcacttcgga aggctgaggc aggtggattg cttgagccca   73860
ggagtttgag acaagcctgg gcaacatggt gaaatcctgt ctctaaaaaa aatcacaaaa   73920
attagccagg tgtggtggcg cattcctgta gtcccagcta cttgcggggc tgaggtggga   73980
gaatcatctg agcccaggag tttgaggctg cagtgagctg tgattgtacc actgcactcc   74040
aacctgggca acagagcaag accctgtctc aaaaaacaaa aatgaaataa agtccaggaa   74100
agaagtaggt tttaccactc ttattttctg aagagaaaac taaatttaat gtgtaaagtg   74160
aggacaagtt caccaagtta gtgtttgagt tgcctaaaat atgtttgcta aaactattca   74220
aagctttcac ataaaacatg atcagaagtt ctatgccaaa acatatgtgt gtgtatatat   74280
atatgcacta tatatactgt atataaaaat gcaaatctaa aattgccaac cttttagaaa   74340
ttgctctgaa aggaaagcat ttcaagataa tttgcttacc caagaatat actttccaag    74400 aaagcaagta atacttaagg tgttcataat cctcatcaaa ttaattcttg ctactgaaag   74460
cttacaagga gctgtttga tgtcgggtgt gacaggtttg acttggcaga aggtgtcact    74520
ttactaacaa cattttaaat aagtgacaga agacaagaaa ctacacgtta aatgccagaa   74580
caaagagtgt ctaagtggat gctaagagtt gaaatatggc tggatacctg cccaagagag   74640
ctgaaaagta gatgaaagtt ggttacctat aaactagtgc accctaatga attaaaaggt   74700
gttgatgagt taacttgtta tgccttccag ataagacatg caaatggggc ttcttcctcc   74760
ttcactactt ccaagggatt taacaaggag accaatgcaa atgataagga ctgtagggct   74820
caagctgggg acagattggg gaaggggga ccatcatgcc catatagatg tccctgtgcc    74880
ctggcagtca aggctgctga aaaataacaa aacccagaag tctgcgtgat gctgcctctc   74940
catttgtcca aagccttctt gcggcagttt gcaggctttt gcaaaagctc caggaccaag   75000
gagctatgtt catgctggaa gcttgttcag gattagctgt tctttgtggg atgggtgcag   75060
ccagggccag gtgtccaggg acagtgtttt aacaaagggc atgaggtgtc tgatctcaca   75120
gtggaactcc acttgccttt ttttcatctt ctcattctgc ttcatgcaca gaaccagccc   75180
catcctgaaa ctgactctaa attactcccg ccccaggtgg agtgcctttc tcggagttca   75240
acagagcctt cctgtcgccc aagggacaac tccactgaat gcccaagcca cacccaaaac   75300
ctaacaagta aaaaccaaat tctgtgctcc cccatcctgg gccattcctg gtttctctac   75360
tgctgttggt gataccacca tcagcttgtc catcatgacc ctggccagtt cctcccacaa   75420
ccctccacag cacccaggga cctcacctcc attccatccg acacagatct cctcaccaca   75480
aaccttggtt ttgcaacagc agccatgaga ccttacacc ctccgccctt catcctgtcc    75540
cccactgagg ccccagagcc attccttaaa gcagcgcgcc acaaactata acccacaagc   75600
caattctggt acccagcctg ttttgcacag ccagtgaact gacaatgatc ttttcataca   75660
gccagaaaaa caaacaaaa caaaaaacaa caaaaaaaaa ccccaccatt ctgagcatgt    75720
gacttccatg ttcaagatgt ctcatgttca gaaaggcccc tggaaaagga ggaagggag    75780 ctggcacaa agggagaccc tctcagctga gctcctccca tccagacatt ttcctggact   75840
tcctatccaa tgacttccct tagcttctta tcagccaccc ctgtctgccc aggaggctgg   75900
aagatgtggc cttttaactg ggcacagctc tgtcctctat catatcaggg ctctgttccc   75960
aaggagggta gagagaatgg acaccaggtg gaccctcagc agtctgtgcc acagagggag   76020
tgtttgcaat ttccagacta aaagtcccca tgtgcttgac ggggtatgtg actacaacgt   76080
gatgcttgac ttttcctcat atgaccagag ccactttgtc catctggtac aatgtcagct   76140
```

```
atctgctagg ggccctccag gattcccagt caattccata tctgcatcac caccattggc    76200
actaaataaa ataaaatact caagttcctg ctggtgagca tgagcagtgc tacactgggc    76260
ccttcaacca aggtgacatg ataatgactg aaaataatca ctgccactta ttggggacgt    76320
ctcatctgcc aggcatggta caaagtgctt taaataagca ttcaacaatt tcatgctgac    76380
agaagccctg tgagccagtg gagctactac tatgcccatt atacagggga gaaaactgag    76440
gcagagagag gttaggtaat tcgctcagcc tcacacaacc aataggtggt ggagccagga    76500
tttgggcccc atctgcctga ctctctagag gctctatctt ccagtcttcc agagttgagt    76560
ctaagccatg aataggacaa ttagacagca gaggaaaccc attcagccac catgtgcatg    76620
aagagtaagg aatttctgtc atacagaggg gagtgaattc actgagctga gagctgagga    76680
accattgatc tgatggctga gacaccactg ggaagactgg agaggctttt ctgggcatgc    76740
agtgccaggc acaggaggag ctgagggaag atgactaaga ggtactggca aagaattcag    76800
aaattctgat ggaagcttta catgttacca tcacatccat ccatctatcc acccatccat    76860
ccacccatat cttcctccct ccacccaatc atgcatacat ccagtcatct atacaccacc    76920
cacccaccca tccatccatc catccatccc ttcatccatc ccatcatcca tccaattata    76980
catacatcca atcatatatc tgtacataat ccattcttcc ctcggttcat ccatccatcc    77040
attcatccat ccatccaccc atcccttcct tcatccttcc tatcatccat ccaatcatat    77100
atctgtacat aatccattct tccctcggtt catccatcca tccattcatc catccatcca    77160
cccatccctt ccttcatcct tcctatcatc catccaatca tacatatatc caatcataca    77220
tctgcacatc accagctcat ccatctatcc atttatccat ccatccttcc ttccatccat    77280
cattcatcca tcatacatac atctaaccat acatctctac atcattcatt cttccatcga    77340
ttcatccaat tatccatcat tccttcctcc atccatccca ttatccattt gatcatacat    77400
atatcatcta tacatcatcc attcatccat ccatccatcc atccacccat atcttcatcc    77460
aatcaatcat acatacatcg aatcatctac acatcaccca tccatccatc catccattca    77520
tctatccacc catccatcca tccatccatc cattcatcta tccacccatc catccatcca    77580
tccatccatc catccatgta accatccagt catatatcca attacacatc catccagtta    77640
tacattcata catgcatcta atcattcaat tatacataca cacatccata taattctaca    77700
tccaattata cctccatcca attacacatt catcacccca cctaataaat tattaattca    77760
tatatccatc catataatta tacatcaatt atacatccat ctaatcattc agtaattcac    77820
ccaccatcca gtcatctatc caataataca ttcatccaat catccatcca tccatccacc    77880
cattcatcca tccatccgtc cgtccaccca tcatggtatg agccatgatt taccacgatg    77940
gtcccctgtg gacagcccag gtggggcaga actgaaggga agcccagggc tgcccccata    78000
aacatttgcc tcctttacat ggatgagaac tagatccaca tgtataaatc ctcatgattt    78060
gaaggtgctt ttaccaacat tcactcatgg gattctccca ggagctctag gaggaggcag    78120
gtagagttga ggtcatctca cgcattttac agatgaggaa acggaggccc tgagaggcag    78180
gtccaaggcc acctgaccag aaagaagtgg aactgggact tgaacccagc catcttgccc    78240
cttggtccca tgctctctag cctgtaactc ctgcttcctg gtgggcatcc tccaggagga    78300
ccctatcggc tggccatggg cctgccctgg agtcttttgc tctgtgtggc catccttcct    78360
ccctcaggag agtgtgtgct cccagagcac aggctgtatc ttctgagcat tttgtccctt    78420
cccagtacct agcactcagc tctgtataca ttgggctctc aagaattctc aaccttccag    78480
agtgtaaggc cttgacctgc tcagccctgg atactgcatg atgcattgat aagcccataa    78540
```

| | | | | | |
|---|---|---|---|---|---|
| aataaccagg | gcagattgac | tcccagtggc | caaagtgcca | cagggaaggg | acaattcagc | 78600 |
| ccttctagga | ggaggaggag | gtagttttct | catttctatt | aaggcaacaa | aagctgcctt | 78660 |
| actaaggaca | ttcttggtgg | agggcgtgac | tgtcaaccac | tgtgatcatt | tgggcctctc | 78720 |
| ttgcccaggc | ttcccattct | gaaaggacag | ttttattgta | ggtacacatg | gctgccattt | 78780 |
| caaatgtaac | tcacagcttg | tccatcagtc | cttggaggtc | tttctatgaa | aggagcttgg | 78840 |
| tggcgtccaa | acaccaccca | atgtccactt | agaagtaagc | accgtgtctg | ccctgagctg | 78900 |
| actccttttc | caaggaaggg | gttggatcgc | tgagtgtttt | tccaggtgtc | tacttgttgt | 78960 |
| taattaatag | caatgacaaa | gcagaaggtt | catgcgtagc | tcggctttct | ggtatttgct | 79020 |
| gcccgttgac | caatggaaga | taaacctttg | cctcaggtgg | caccactagc | tggttaagag | 79080 |
| gcactttgtc | ctttcaccca | ggagcaaacg | cacatcacct | gtgtcctcat | ctgatggccc | 79140 |
| tggtgtgggg | cacagtcgtg | ttggcaggga | gggaggtggg | gttggtcccc | tttgtgggtt | 79200 |
| tgttgcgagg | ccgtgttcca | gctgtttcca | caggagcga | ttttcagctc | cacaggacac | 79260 |
| tgctccccag | ttcctcctga | gaacaaaagg | gggcgctggg | gagaggccac | cgttctgagg | 79320 |
| gctcactgta | tgtgttccag | aatctcccct | gcagaccccc | actgaggacg | gatctgagga | 79380 |
| accgggctct | gaaacctctg | atgctaagag | cactccaaca | gcggaaggtg | ggcccccctt | 79440 |
| cagacgcccc | ctccatgcct | ccagcctgtg | cttagccgtg | ctttgagcct | ccctcctggc | 79500 |
| tgcatctgct | gctcccctg | gctgagagat | gtgctcactc | cttcggtgct | ttgcaggaca | 79560 |
| gcgtggtggg | agctgagcct | tgcgtcgatg | ccttgcttgc | tggtgctgag | gtgtgggcacc | 79620 |
| ttcatcccgt | gtgtgctctg | gaggcagcca | cccttggaca | gtcccgcgca | cagctccaca | 79680 |
| aagccccgct | ccatacgatt | gtcctcccac | acccccttca | aaagccccct | cctctctctt | 79740 |
| tcttcagggg | ccagtaggtc | ccagagcagc | catttggctg | agggaagggg | caggtcagtg | 79800 |
| gacatctgat | cttggtttag | tatccttcat | tttgggggct | ctgggtgtgg | cctgggcctc | 79860 |
| tggactttgg | ccacggtgtt | tgttccagcc | cttctcctaa | cctgtccttt | ccagacactc | 79920 |
| ggcatctagg | ttattagcac | ctcgcatact | ttctgacatg | ctcctcagtc | ctgattttga | 79980 |
| ccatcttctc | ttgcttccca | tctgtgtcag | tcaagactgc | atttggctgt | aagaaacaga | 80040 |
| aaccccaact | aactgtggca | tttacatgaa | gaggtttact | tttctcacat | aatcagatgt | 80100 |
| ctagacttgg | ccagcacctc | aagggtcatt | gatgctctcc | tgtctttatt | ttctgtcatc | 80160 |
| tttagtggtt | ggattgttgc | ctcatggtta | caaagtggct | gctgcacttc | caggcatcac | 80220 |
| atctgccttt | gaagcaggaa | caagttgcaa | agtaaagtgg | ccaaaagggc | cctgaaacta | 80280 |
| aatgtgtccc | cttaggaaag | caggagtttt | cttgcaagtg | gcaatcttct | gcttatgtct | 80340 |
| cattggccag | agctgggtct | tacggccacc | ccttgctgcg | agcaaggctg | ggacattgag | 80400 |
| cattttgccg | tccaacctct | ttagcagaat | aaaccaaggg | ggaagaacgt | taatagtggc | 80460 |
| ttttgagtca | ctagttggca | gtatctgccc | ctctatcttt | ccatcctccc | catggagttt | 80520 |
| caaggttcct | ttctcagtac | ttcttcaggc | tctgcacgtt | catttggatc | ttgtgtcttg | 80580 |
| gggtgaaaaa | ctggcccaag | tgtctccca | agcatccacc | tttggattaa | tttggaaaat | 80640 |
| ggctgtcaag | tgcccgcctc | ttgcttggta | taatgctaca | gctttagagg | acgcagcagg | 80700 |
| catgggcctt | gccgctgagg | ttcttagcct | catgagaata | tccagatcag | attctcttgg | 80760 |
| ctccttctta | gagccagtga | tgcaagacac | ttcctgctca | tcttgtcggg | acggttttac | 80820 |
| aagttgcctg | ccatcctgag | aaagtctaca | aaacgatgcc | agacctcatg | ccagcttccc | 80880 |

```
aagccttgac tctcagtgct ccctcaacag gattctggaa gaatctccca aacaagtcgc   80940
aatcccctct ggaccctgtg caggcatgag actcaagagc attggctccc acccctggtg   81000
gagggaacac tgctggggct gggatcttgc ctggttgctc cgcctgcacc caagacaacc   81060
ataattaaaa tgtccttcat tgaacttgga aagccttcaa agctgacaac tccttatgtg   81120
tacccggaaa ggcctgggag tgtgccaggg cattgctcgg gagggacgct gatttggaag   81180
catttacctg atgagagact gacagcagct cctggtagcc gagctttccc tcctgcctct   81240
gctgtgaagg tggacccatc caacagtcaa atgcctgact ctggacagga gcggacctat   81300
ttattgccat gcaagggact ctgcactttt gaattgtggg tcatgggctt ggatttaggg   81360
gttagagctg ggagaagtct tggaagtcac ctagagatga cactgccatt ttgcagatga   81420
ggaaaccgtc caatcaaaat ggaccaagga cttgcccaaa gcctcacagc aaaaccatag   81480
gcccccgcac taacccccaga gtccctgtgc tgtcttaaga atcaaatagt tgtaagcaat   81540
catctggttt tcagtatttc ttcttttaaa atgcctgggg ccatgcccag cagtctgttt   81600
cactgcagcg tttacacagg gctgccgggc tttcctggtg gatgagctgg gcggttcatg   81660
agccagaacc actcagcagc atgtcagtgt gcttcctggg gagctggtag caggggctcc   81720
gggccctact tcagggctgc tttctggcat atggctgatc ccctcctcac tcctcctccc   81780
tgcattgctc ctgcgcaaga agcaaaggtg aggggctggg tatggctcgt cctggcccct   81840
ctaaggtgga tctcggtggt ttctagatgt gacagcaccc ttagtggatg agggagctcc   81900
cggcaagcag gctgccgcgc agccccacac ggagatccca gaaggaacca caggtgaggg   81960
taagccccag agacccccag gcagtcaagg ccctgctggg tgccccagct gacctgtgac   82020
agaagtgagg gagctttgcg tgtttatcct cctgtggggc aggaacatgg gtggattctg   82080
gctcctggga atcttgggtt gtgagtagct cgatgccttg gtgctcagtt acctccctgg   82140
ctgcctgcca gcctctcaga gcatttaggg ccttctggac ttctagatgc tcctcatctt   82200
gcctcagtca gcgcgtcagt tccagagact tctctgcagg gttttctggg gcaggtggtg   82260
gcagacccgt gccttcttga cacctgaggt cagtccaccc tcctgctcag actgcccagc   82320
acagggtcac ctcccaaggg gtggacccca agatcacctg agcgcacaga gggtgcagat   82380
gactggacca caccttttgg tgatcttaat gaggtggtcc cagaggagct cagacatgca   82440
atctagcatc cagttctggg actctgtctc cttttcaaac gtattcatgt agaacaggca   82500
tgacgagaat gccttgtcaa catgggtgat ggggaatcaa tcagacaggg cgccgggctc   82560
aaggctgcag tcacccaaga gtggctcagc ccaccaggcc ctaggaaacg cctgcacagc   82620
ctggagctcc tggagtcatt tccttcatgt cttcttcact gcacttacgt aaagatgcca   82680
gccattggtt tggtgatttg gagggtgccc agttgcccaa caagaaatgc agaagaggcc   82740
tagccaggat ttcaccagca gtggagagta gagaagatgt ggccagaaaa gagtttcctt   82800
tccctcctaa agatggtact ccctgcagct actggggaag cctgcagcat tctctagggc   82860
tctgtgtgtt gagagcagcc ccaccctggc cccttctgag tgcatttctg ctttgtgact   82920
tgatccgtga agtcccctga gatgggcaga ggggatgtcc tcgaagctgg ggcagagcct   82980
catccttgaa cgtgaaggac gtttgaagac tgtggcatga tcacaggatg agatcacagg   83040
gaacttgagt ttctctcctc ctctcccttc acagttattt cactgaggga aatccctccc   83100
ctgcccagaa tgaaaactct agccaactct tgacttttcc atcactccaa agtagttgaa   83160
agtacattag tctccacagt ggcaaaacag tgtgcaaaag ctaaataatt agaacagcca   83220
gtcccatgtg acagtcaaag cttctaactc cattcaaagt tgcagccatt cccctcgagg   83280
```

```
gctggcaggg aggggagggg taagagaaac aggaaggttc ttactgagtt ggtcctggtg    83340
tgagctgcgt cacactccct gcagaggttt caaggagact ctctctctct ctgtctccat    83400
ggggacctta tttgaattct tctactctta ccccagcctg ccatctccag ctatcctccc    83460
ctgaagagcc cttctgctgc gctggattct ggtggccatg tcatctcctc ggccccgtgg    83520
gagtctgaag atctggctgc agcctcacct ctgaggtcct gctagttgcc acctcttaaa    83580
catgatctga ggctcccatg cactctgacc tgtgcccaca tggggcccac gggaaacacg    83640
ctggcaagca aactgtgggt gtgcagacgg ttctcagggc tgcagcacct gtcctttgct    83700
ctgcccccaa agcaaggcca gcccatcttc catcctctag tgttccttgg tggggccctg    83760
accacagtcc accaggtccc taaccagagg ggacacacac caggtgtcct caatgtattg    83820
ccttgaaaca gttgtgctgg gactgtgatg gggggtggcc atgtagccac ccccaccacc    83880
cccaagccac tctctccaag gaaatcctcc taaagatccc tttacatcct ccatgtggtg    83940
gggaggttct agagttgggt gcatgtgtct tcagctactg acaatgcaga ccttagttgg    84000
cacctcgctc tggcctatcc tgtttgctgt tcttggcgct ccagtgaaac tccccatggg    84060
ccatccagtt ggggtgcagt gtggccaccc ccttgcaggt tcctgccttg ctggagagca    84120
cagggccctc ctggctcttg taaaacactc cccatggtac agagaggcca gcagtgatgt    84180
gaggcccaac ctccctccat ggtgttccca agcagctccc tttctggggt caaggggtgg    84240
caaagacagt gcagcgtcca atttctgact caagccgggc ctggctatcg cagctctgca    84300
ctgtgtgtga cagcaaggca actcacccag tgccgtggca gtgaccgtgt ccgaggaagc    84360
ctcctcacac cctctgtctc aaggactctg gcatttagct ggacttgctg tagctctgag    84420
cctttctgcc attgccatca ccttgtcaga aactcaggcc gaatctgcac tcagagttgt    84480
gcccaggcag ttgagccaac acttgctcag cgatattgtc acatgacaag gcactgtcac    84540
cactgggcgt cgtgggtagc gcagtgtcgg ctggatggac ccggagggtg tctgtgtcat    84600
gctagtgcta gtgatgggag ccccgtgagc ccattgcccg ccctcccatg ccctcagcag    84660
ctgcctgggg acagccaatg gcctgggtgt ttctgaggct accacatggc ttccaggaaa    84720
ctcgagaacc tttctctccc ttgcctacac tcttcacaca ggcctgtgct ggccagcggt    84780
ggggatccgg cattcctatc ttaggtgcag aaagtgactg actcattgca ggcctgggag    84840
ataagactga tggcccagcc agcaagatgt atggatttct cagaggcagt ggcctctgtc    84900
attgtcctca ggaaatgctg gtgattctgg tggcctgagg tcaatgcatg tcaacgtggc    84960
caacttgcct tataaacttt ttttctggac aattgcgtgc actgtcctgt aacagtgtcc    85020
tgttgtttat gatgcagaaa taggtgtttt taaagcctat tgattttggt actattaatg    85080
tggtcaggaa ctttctcagt cttcttgtt ggggtgagc tgtggcttcc taaacaggaa    85140
cccaagacac ccccaaaagc tgctcaccag cactgccagc ctccctctta ccaagtagca    85200
cccgttcagg acattctgcg aaaggcattt gcccagaagt tggaggaag gaaatgtaac    85260 attttggggc acctaccata tgccaggcac caggctaaac gtgttcacac aaattctctt    85320
actaaccctc accatccttc tacaagacaa actagtatct tcatcttggg gttcaagatg    85380
aggaaatgga ggctcagaga ggttgaatga atgccggtgc ctggatatga accccatctg    85440
cctgactccg caacccaggc aaagtctttc cttgaacttc ccagcagcca ctgcttagac    85500
acagcctcca caaccatggc tcagcagcaa attgcttctc tgacctcact cagcctgtgt    85560
gtccttgttg agtgaggcat tcaggaccct ggtcccaaag tggagaaagt ctttcctact    85620
```

```
aggtcatagc tacacctgca tgtgggtgct gtgccttttg tttagtgaac ttttatcacc   85680
agcatcctca gcaatgacat ttgcagagaa gccagagctg aggcaccttg gtattcttgg   85740
gatgtgactt tcctgaatgt ttaagggaaa atgcccgaag gtacagagag cttggtttct   85800
agtaaacaat aactgtcttg cttttacccc ccttcatttg ctgacacata caccagctga   85860
agaagcaggc attggagaca cccccagcct ggaagacgaa gctgctggtc acgtgaccca   85920
aggtcagtga actggaattg cctgccatga cttgggggtt gggggagggg acatggggtg   85980
ggctctgccc tgaaaagatc atttggacct gagctctaat tcacaagtcc aggagatttt   86040
agggagttgg ttcttatcaa aggttggcta ctcagatata gaaagagccc tagtggtttt   86100
tttctaatac catttctggg taattcctaa ggcatttagt gttctgaaag atgctagcct   86160
tgtccagcct gggagttgag aatgaatgtc taacagaaac tctaggccgg gcgtggtggc   86220
tcacgcctct aatcccagca ctatgggaga cccaggtggg cagatcacct gaggtcagga   86280
gtttgagacc agcctggcca acatgtgaaa tcctgtctca ctacaaataa aaaaattagc   86340
cgggtgtggt ggtaggtgcc tataatccca gctactcagg aggctgaggc aggacaatcg   86400
ctcgaaccca ggaggtggac gttgcagtga gccgagatcg catcattgca ctccagcctg   86460
ggcaacaaaa gcaaaactcc gtctcaaaaa aaaaaagaa actcaaatat gtgtgacagg   86520
cgattctcac tgcaggctgc cctgtggctg atccaggagc aaggccttaa ccatgtcatc   86580
cccaagcgat tgcttgtaaa cttcttctg tgcagccttc aacccttatt atgattttct   86640
tctcaggaac caaactgctg tattcaagaa aggcagcttt gtgtaatcat ttatcataaa   86700
tatcttaaga aaaatcctag agattcctaa ttttaggaaa tgggagacct atggtactga   86760
tataatgtgg gctgggcttg ttttctgtca tttgctagat aaatgaactt gagagcctac   86820
tgtaaaatgt ggaagcttct agattgcaga agggctggaa agacactgtt cttttctccc   86880
gagtgatggg atctgtccag tatttagagc tgcctctgag gccatctgat tctaggagac   86940
tctgcctcgt tgaggatatt ttgaggccta actacacatt cctgcccca gagaggtcac   87000
agcctatagc aggctgatgt ttctcatgtc acatggcaca gaaaggcaca ttttcgttct   87060
caggctaaca aagagcttca aaaactatta gaagggacag tggctataag agaagaacct   87120
cagtcaatgt gtgaaattaa ctaggaacct ggctcctgtt tcttttaggt catgttttc    87180
agcttaggta aaactagagg ctttgataaa gcatgacctc tagaaatcat tgcttttcat   87240
aaatggaagt gggtttgagt ttttctact gattgttagt gcaggtgatg tctacatgcc    87300
cccagaacat attccatgca acaaaaaag cccaggtcac cgtctttgct gggaacttga    87360
cttttgtgct cactgaattt taagcttct gacagcagcc tggaatcatg gagggataaa    87420
gtacctatta gtaagatgga aaaggtgtt tcaggttgga gctgcagtct gttgagagta    87480
agctatggga aggcctgtat acgaggggtg acttttctt ctgtaagtgt ccagagacca    87540
ggcctcctga agagggcatg ggggcttaac ttacctggac tactgtgttt acaatactca   87600
tttatcttga actcctccta acccctgaga attgctacat ttagtatttg ctgagtactt   87660
cctagcatcc tagggaatca atagaacatt ctcccaacca ggctgggtgc ggtggctcat   87720
gtctgtaatc ccagcacttt gggaggccaa ggtaggcaga tcccttgagg ccaggagtgc   87780
aagactagcc tggctgacat ggtgaaaccc cgtctttact aaaaatacaa aagttagcca   87840
ggcatggtgg tacacacctg taatcccagc tacatgggag gagtaggagg caggagaatt   87900
gcttgaacct gggaggtgga ggttgctgtg agccgagatc atgccactgc actccagcct   87960
gggcgacaga gtgagtgaga ctctgtttaa aaaaaaaaa aaaaagaac attctcctaa    88020
```

```
cctggcttct tcctccaggg gtgtaattaa tcatgtcagt ttcctcattg atacacacac   88080
acacacacta caatcctgta tccattactt ttcaaggtac atttactatt tacgtttggg   88140
gtccttgtct cttttttaat agtgtttctt aaagtcttgt attatatcag agtacagtaa   88200
catcccagtc aagagcactc tagtaagctc taggaggaaa gcgacttccg gaaggcagtg   88260
gagacctgtc ctgttggggc agcatagggg cagcccctgc ctctggtcag ttctggcgct   88320
caggctcagg gttgcctctg ggctgttctt cccagagact gacaaagggc tcccataagg   88380
cacctgcaga gcctgtgaga agctgaagtc aatgttttcc tgacaccagt tgatctgtgc   88440
aggatccatt gatttaacca cctgctgtgt ggcatgcact gtggtcgatg ccaggaacag   88500
gaattggagg ggcccatgag catggccagt atcacaggct ggaggtgctg ctgcgctctg   88560
accgggcctc ttggggatga gcccatgtca accaccttgc ctccgatggg gtcgggccca   88620
caggttacct ttgtgtgtcc atgaccacac cttcctcccc gacctcatcc aaatctcttt   88680
cttttccaag cccctgaatc cttcaggggct gcaggttttg tttaaagcag agctggtgag   88740
ttgcataggt tgttgcgttg ggactagatg gggtgttcaa agagttggga gttaaaaaac   88800
ataaagggta tttattagga gaaccaagga gtgtaattct cctgttctta atatgcggcc   88860
aggttaatga atgtcacgtg aatgaaccag aaaaaaatga agtgtgccct tgatcagctg   88920
ggttggtgtg cagcaagctg tgtgaccagg ggacagcagt ggtcctgagg gccgtcactg   88980
tctgccgtgc agagcccttc ctcccacggg ggcctacctc acctgtgcca agggcttgtc   89040
tgtggtcagt gacctggata gatctgaatg gggcttcttt ttcgaggagt cttatggcag   89100
gtctctcagt aaagactcca ttcttgatga tcacacattt tggattttcc aaatctgtca   89160
gagaatgggc ttgaggcggg gtttgtgggc actagtttca ctggtttcat ttaccaaaaa   89220
ggggagcaga agtcaagtat ggtggctcat ccctgtaatc ccagaggcaa gagaattgct   89280
tgagcccagg agttcgagac cagcctgagc aacataagga gaccccgtct ccacaaaaat   89340
gaaaaataac attttagtca gacgtggtgg catgcatctg tggtcccagc tgcttgggag   89400
ggtgagatgg gagggttgtt tgagccctgg agttaaagtt gcaatgagct gtgattgcac   89460
cactgcactc tagcctgggt gacagaacga gaccctgtct caaaaaaaaa aaaaagaaa   89520 gaaaaaaagg aaaaaaaaaa ctcatgcctg taatcccagc actttgggga ccggggtggg   89580
cagatcacga ggtcaggaga tcaagactat cctagccaac atggtgaaac cccgtttcta   89640
ctaaaaatac aaaaattagc caggtgtggt ggcacgtgcc tgtaatccca gttactcggg   89700
aggctgaggc aggagaatcg cttgaaccag ggagtcagag gttgcagtga gctgagatcg   89760
tgccactgta ctccagcctg ggcgacagag tgagactctg tctcaaacca aaaaaaggg   89820 gtgggggcg gggcaggag aacagtgaga ggtagggaga ggaaagggga ttctcgctac   89880
acccaaacca gataccatct agaggctaga atctttggga ggctcaaatt ccctagaaag   89940
caggagaagc ttctgtagcc ctcccgcttt cccagtagat taagcccagg gcggctccag   90000
atgtgtgaca tgctctgtgc ccaaccagag cccatcatag gcagaggaat aacacccaca   90060
ccagaagggc cctcggaggt caccacgtcc aagaaccctc tttacagatg aggaaactga   90120
ggcccagaga ggggagagcc acctagcgag ctggtggcgg ctagaccagg agagctgtca   90180
ttccaagcaa gcaaaggcaa cgagacgagc ccagagctgt gctcccatct ctttgttagg   90240
gggcctggga tgccctctca gtgtcatttt gtccaggatg atgctccctc tcttaagcga   90300
ttaatgcgcc cttgctaacc ttttgctatc gctgcctctt caaaccagag gagttgagag   90360
```

```
ttccgggccg gcagaggaag gcgcctgaaa ggcccctggc caatgagatt agcgcccacg    90420
tccagcctgg accctgcgga gaggcctctg gggtctctgg gccgtgcctc ggggagaaag    90480
agccagaagc tcccgtcccg ctgaccgcga gccttcctca gcaccgtccc gtttgcccag    90540
cgcctcctcc aacaggaggc cctcaggagc cctccctgga gtggggacaa aaaggcgggg    90600
actgggccga aagggtccg gccttccga agcccgccac cactgcgtat ctccacacag      90660
agcctgaaag tggtaaggtg gtccaggaag gcttcctccg agagccaggc cccccaggtc    90720
tgagccacca gctcatgtcc ggcatgcctg gggctcccct cctgcctgag ggccccagag    90780
aggccacacg ccaaccttcg gggacaggac ctgaggacac agagggcggc cgccacgccc    90840
ctgagctgct caagcaccag cttctaggag acctgcacca ggaggggccg ccgctgaagg    90900
gggcaggggg caaagagagg ccggggagca aggaggaggt ggatgaagac cgcgacgtcg    90960
atgagtcctc cccccaagac tcccctccct ccaaggcctc cccagcccaa gatgggcggc    91020
ctccccagac agccgccaga gaagccacca gcatcccagg cttcccagcg gagggtgcca    91080 tcccctccc tgtggatttc ctctccaaag tttccacaga gatcccagcc tcagagcccg      91140
acgggcccag tgtagggcgg gccaagggc aggatgcccc cctggagttc acgtttcacg      91200
tggaaatcac acccaacgtg cagaaggagc aggcgcactc ggaggagcat ttgggaaggg    91260
ctgcatttcc aggggcccct ggagaggggc cagaggcccg ggcccctct ttgggagagg      91320 acacaaaaga ggctgacctt ccagagccct ctgaaaagca gcctgctgct gctccgcggg    91380
ggaagcccgt cagccgggtc cctcaactca aaggtctgtg tcttgagctt cttcgctcct    91440
tccctgggga cctcccaggc ctcccaggct gcgggcactg ccactgagct tccaggcctc    91500
ccgactcctg ctgcttctga cgttcctagg acgccactaa atcgacacct gggtgcagct    91560
gctccactcc ctcggcctcc tcccgtgctc aggctgtggc cgcacgcgcc cctcacgctt    91620
gcccgccact ctgcatgtca ccagcacccc cgctccgtgc tccccacctt gtttgactct    91680
ctggccactt gatttgtcca caacggccca tcagcccaca ggaggtttgg tgggtgcctt    91740
ccaccgacag gatgacgggt gccctcatgg tgtctagaac tctccaaccc tcccatgtag    91800
gcataagcag ccccactttg cagatgagga aacggaggct cagagaagta cagtaacttg    91860
ccgaaggcca atgagtagta agtgacagag ccaggtttgg gatccaggta ggttgtctct    91920
gaaagacacg cctgtcctgc atcccacaac gcctcccagg aggtgctgga gtgtggacgc    91980
ctaacacaga gatgtgcagg gcacacacag caggtgacac acacagcatc cagaggtggc    92040
ccagagctca tgctgtgcct ttggcccagt gccctgcccc cacccactct gccttgtggc    92100
aggaagacaa ggagcagaca caagatctcc ctggtccaca tgccaccacc tccctctgca    92160
gaggacaagg ggatcctcat gctggcattg gaggggttg agcagggccc accttgagcc      92220
ctcaggagca cgaccacagc agccctgcag ggagggattg gtgggaggag agtcccaagt    92280
atcagggaga ggagagttgg tgtcccacag gagacctcag agccacaagg cgagcttgtt    92340
cataaatttg ggaccccttag catttcacag ttatttgcag agcccagaaa tggatgttac    92400
tgaagctcac agttgcaagc atctgttaaa tttttattag attttacttt tagggaaaac    92460
tttgaaatgc tataagaag cctgtgttta aagttaagaa cagaggctgg gggcgatggc     92520
tcacgcctgt aatctcagca ctttgggagg ccaaggcagg tggatcattt gaggttagga    92580
gttcgagacc agcctggcca acatggtgag accctgtctc tactaaaatt acaaaaaatt    92640
agctgggcgt ggtggcgggc acctgtagtc ccagctactg ggaggctga agcaggataa     92700 gtgcttgaac ccaggaggcg gaggttacag tgagccaaga tcacaccact gtaccctaag    92760
```

```
cctgggcgac agagtgagac tctgtctcaa aaataaaat aaaataaagt taagagagaa    92820
aaaaatatat cctatatcct ttgttaaatt ccaaaacagt aggggacaaa taactgactt    92880
gacaggttac tacaatattt cctgaaatga tgttttcttg aatactggcc tactagaggt    92940
tcataggtgt gtttggatta aaaaagagtt ccatggccca gtgactgggg gaaaaaaata    93000
aaagactaaa gtaagttaaa caggcttttc tgctgcagga cttgtcagag cctttaatgt    93060
actaatggcc attgtgaccc tctgagaagg tcacagagtg ggtttcccaa acttacttga    93120
ttctacctgc taacatttcc tggaggaagt ttgggaaatg ccgatttagc agattctttt    93180
gttgtgccgt ggatggtgct ggttgatgtg ggcaaaacaa agaacacgtg agtcagatcc    93240
gcctggggct cttactaaag tgcaggttcc caggtgccac tttaggctta cagacccagt    93300 tgtgggtaa gcctgggagt cttttagcag gtgattctgc cacatagtat agttggaaaa    93360
cctctgggca tactcattgc tggtccctct agaaatccag gtgacaatag ccaatgagaa    93420
gctccaagag acccagttgt ccatgggta gagggaatgt gatattgaaa ccaaagaaga    93480
aaatctatga tcagttttca gcagtgactg tcaagagaag gagaagggtg agttagcgct    93540
gatgctggct gacaggtcag cggggttggtt tcaccaagga gtgtgatgaa ggctgatgtt    93600
gtctgtggga atgtatgatg gtaactggtt tgtagctaat ttggggaagc agtgagaatt    93660
cgtgcccttt gaagaccagt aagtggcaag aaacccacca ggcctggctc agggctgggc    93720
tgggcttggc tcgtctcaga gcagctgggg ctggtggcca aagccaccat tagtgagggg    93780
caggccctgg gggtacaacc agcaactagg ggacaaagac aaccctgcca gcctctccta    93840
ttctggaggc gtgtgaccag aaatggagat gggttggtca gcataagatg gccaggaagg    93900
tggaaatcag gactgctggc aatctagcca catgggcagg ggagccgggt ggttccaggc    93960
agtttccaag gccaagaggg tgagcaggca cctcacaggg aatcagggcc aagcctggct    94020
gcagtgtgga gacaatgcac ccacccccat ccttggatct tgcaggaggc tgggtcctca    94080
ctgagctacc aacatccatg gccctgaggc ttttaaaaca cccatccatg gagtggggct    94140
ggtcccagtg gggtgaggct gaccctggca gaaacagggc aggagcctgt gggttaggga    94200
gactgcacct tccttagata gcctccatgc catcatgtcc ccgtgacagt ttctgctgcg    94260
tcccctctgc atggtcccac cctcggccag cctgctgccc cctcttgcca ggttgcgcta    94320
atcagtgacc ccagtgtgct gtgttgatac taacaatgcg aggcctagca gattcaaggg    94380
aaaagagaac caactgggtt tccaccagac ccaactaaac aaacatggac ctatcccaga    94440
gaaatccagc ttcaccacag ctggctttct gtgaacagtg aaaatggagt gtgacaagca    94500
ttcttatttt atattttatc agctcgcatg gtcagtaaaa gcaaagacgg gactggaagc    94560
gatgacaaaa aagccaaggt aagctgacga tgccacggag ctctgcagct ggtcaagttt    94620
acagagaagc tgtgctttat gtctgattca ttctcatata taatgtgggg agtatttgtc    94680
actaaagtac agctgtcatt taaagtgctt tgtattttgg ggcaggcttt taaaagtcc    94740 agcatttatt agttttgata cttaccccag ggaagagcag ttggcaggtt catgaagtca    94800
tgctcctaat tccagctttc ttagtgtact ttcagtgaga ccctgacagt aaatgaaggt    94860
gtgtttgaaa accaaaccca ggacagtaaa tgaaggtgtg tttgaaaacc agccctagga    94920
cagtaaatga agccatcttc tcactgcata aactgcaccc agatctttgc ccatccttct    94980
cagtatttca cttcacccat tgtttactgt ctcaatgact ggggaaatgt ctggggaaat    95040
gctcccgtaa ttgcacagtg gcgttttttcc tggaaaatcc caccatggct ctagataaga    95100
```

```
cctattttc  ttaaaggtat  ctaaaatttc  cagcataaat  tctgtctgaa  acacctgaat    95160
tttaatcagt  actggagccc  ggagggcatc  tccagttgcc  acatagctct  gagcattcag    95220
tggtgtgttg  agggctgctc  ccggaagtgc  ctgcagagtc  agggctcccc  agcctcatct    95280
agtgaggcag  tggaagggcc  tgtggggatt  tggagagctg  gcctgggtct  ctgaagtgat    95340
agtgacagct  gcttgtcaat  cacggtgcac  atttagtgcc  gggggcaggg  ggcagggaat    95400
accagcctca  tgcatgcatg  cattcatttg  ttccttcctt  cattcattca  ttcagtacac    95460
atgggtacaa  catccctgcc  ctggagttgc  ccagagtcta  gggaggggaa  agatctatta    95520
ccctgggcct  cggccagctg  gggagtgctg  ctggtggaga  ggggccgtgt  gcagcgaggg    95580
aaggaggagt  cgtcaatacc  cccacccag   ctttgctttc  ttgtcatcag  ccccagggcc    95640
ccagcctgtg  tccctcctct  cccattgcta  cttcatctcc  tgggtcctcc  ttaccaagcc    95700
tgaccacaca  gagggccttg  gccgcttcca  tggggaattg  gaaagcaata  agatagcatc    95760
ccctagaagc  ccagtgaagt  ctgggacagg  acccttctct  gagctctgac  ttgctcttgg    95820
aaacacttcg  aggcttagcc  tccccacttt  gtttcccaag  agtgtgacct  gttccctcc    95880 aaacaccccc  ttctcctcca  gggccatgcc  caccgtcaa   aatccccac   gggcaggacg    95940 aactgtgggt  gtcagtcacc  atctatcctg  catcctggtt  ccaggcccc   cccagcccc    96000 gcctccatag  ggacaggcgt  gcagacaccc  gtccctggct  gcttcctctt  gtggaatggg    96060
ttcaaaagta  agcagtgttg  tttacactga  caaactgaaa  aaaaaagaaa  aagagataac    96120
attggaggct  tggcacagtg  gctcatgcct  gtaatcccag  cactttggga  ggctaaggtg    96180
ggaggatgtc  cccagcccaa  gagttctaga  ccagcctggg  caacatagca  agaccccatc    96240
tcaaaaaaaa  aatttaattg  gccaggcaga  ggtgggagga  tcacttgaac  ccaaagggtg    96300
gaggctgcag  tgagccgtga  tggcaccact  gcactccagc  cagggcaaca  gagggagacc    96360
ctgtctctaa  acaaacaaa   caaacaaaca  aacaaagag   ttaacattgg  ccagattagg    96420
attcaccaga  tagtgttaat  attagtttga  tttgagactt  taatcagaaa  gcacatgtgt    96480
ggtgggggtg  ggtgtaacct  aagtcaggta  gaatctttcc  aacttggggg  gggcacactc    96540
ctgattgtag  ccatatgagt  ctgtcagtgt  ggtggaagag  accatgggtt  aatgggcagg    96600 taaaaagca   ccttgcctgg  aattgagtag  aaagtaaggc  ccttcagacc  ccgtgacaca    96660
cttggggaca  ttttcttgag  taacatccta  agattcatgt  accttgatga  tctccatcaa    96720
cttactcatg  tgaagcacct  ttaaaccagt  cgtctccaaa  ttcagggggca  cagtaacatc    96780 caacaggctg  gagaaagaac  gtactagaac  ttccattcct  ttttcatgtc  ctcttctaaa    96840
agctttgtca  gggccaggcg  cggtggctca  cgcctgtaat  cccagcactt  tgggaggccg    96900
agacgggtgg  atcacgaggt  caggagatcg  agaccatcct  ggctaacaca  gtgaaacccc    96960
atctctacta  aaaatacaaa  aaacgagcc   gggcgtggtg  gtgggcgcct  gtagtcccag    97020
ctactcggga  ggctgaggca  ggagaatggc  gtgaacccag  gaggcagagc  ttgcagtgag    97080
ccgagattgc  accactgcag  tccagcctgg  gcgacagagc  gagactccgt  ctcaaaaaag    97140
aaaaagaaaa  agaaaaagaa  ctgtgattgg  ggaggacggt  cactttcctg  ttcttactga    97200
tcagaaggga  tattaagggt  acctgattca  aacagcctgg  agatcactgc  tttcaaccat    97260
tacctgcctt  atttattttt  agttactgtc  ctttttcag   tttgtttccc  tcctccatgt    97320
gctgactttt  attttgattt  tatttatgtt  tatgtttaag  acatccacac  gttcctctgc    97380
taaaaccttg  aaaaataggc  cttgcctag   ccccaaacac  cccactcctg  gtagctcaga    97440
ccctctgatc  caaccctcca  gccctgctgt  gtgcccagag  ccaccttcct  ctcctaaaca    97500
```

```
cgtctcttct gtcacttccc gaactggcag ttctggagca aaggagatga aactcaaggt    97560
aaggaaacca cctttgaaaa gaaccaggct gctctgctgt ggtttgcaaa tgtggggttt    97620
gtttatttgt ttttagcct caaagacctt tcttcaaatg agttctggca tagaagcacc     97680
gtgtaaaata gttagaattc tgggcaaagg ggaaaagaga gctgggggcc atccctctca    97740
gcaccccaca ggctctcata gcagcagctc ctaagacacc tggtgggacc ttggtttcga    97800
aatcgctact ctaaggctgg gcacggtggc tcacacctgt aatcccagct ctttaggagg    97860
ccgaggaggg tggatcacct gagatcagga gttcgagacc agcctggcta acatggcaaa    97920
accctgtctc tactaaaaat acaaaaatta gccgggcgtg gtgttatgcg tggtggtaat    97980
cgcagctact cgggaggctg aggcacaagg attgcttgaa ccccagaggc agaggttgta    98040
gttagctcca gcttgggcga cagagcaaga ccctgtcgca aaaattgttt aaaaaacaaa    98100
cccaaaattg ctactctcat tgggttcctt tgcccattcc tgattttggc aagagaaatg    98160
cttccagatt gccctgatct gggtaggaca gcatcacgcc atagcaacac tgccccgtga    98220
gctcactgcc ccctcaacta gcttgtggtc cttggttaat gtcagtttct ttttgagtt     98280 tgtgttatgt ctaagggtca tctgctgggt aacggaaccc agggactgcc ctagtcccta    98340
gactgtgcca tgcccgactc tgccagcttt gtcagtgatg ctggtgctcg cctcctcggg    98400
tgctcgcctg gtctgagcac acccaaggag ttcttgaggc cttagggttg tttgcgagag    98460
aatgaaagaa cacgacctag ctctctttag catccttggt caggttcaac actgccccca    98520
ggggcctctg gtggagccaa ccaccatcag ccaaataaat ccataattag agtcagaaaa    98580
tggatgtctg catatgtgta gtgcactaat gtcctgccga tgattgacat ggagtggaga    98640
gtgacctgat cattgctgtg agctctgctg gccttggcac aactcatgct gataactaat    98700
gcacacagtt cctctgggag gaaatgtcct cagggaactt ggagtttggg tggggatgtg    98760
ggtttgtgtg cccagcaagc ccttgtggtt gtagcagaca ctagtggcat ctaggaggca    98820
aagggtcacc ccagtcttag ccacgttttg agtcaaggtg gcggagtggg gctggtgttg    98880
actcttggtg gcagtaactt tcccaatgg tgaaaaccc ctctatcatg tttcatttac       98940
agggggctga tggtaaaacg aagatcgcca caccgcgggg agcagcccct ccaggccaga    99000
agggccaggc caacgccacc aggattccag caaaaacccc gcccgctcca aagacaccac    99060
ccagctctgg taagaagaac gttctcttga atcttagagg aagctgaagc tctcagaggt    99120
acagccttca ttttaggagg ccttaggcca ctgagaatga ataacccctg gcagctggtc    99180
agcagcttgc agtttactaa gcactggagt cttcattgcc ttctcagtcc ttttgatttc    99240
tgaggcaaat gttgaatccc tacctttttt tttttttttc ttttgagaca gagtttcgct    99300
tttgttatcc aggccggagt gcagtggtgt gatctcagct cactgcatcc tccacctccc    99360
aggttcaagc gattctccta cctcagcctc cctagtagct gggattacag gcacctgcca    99420
ctatgcccgg ctaattttt gtattttag tagagacagg gtttcaccat gttggccagg      99480
ctggtctcga acgcctgacc tcaggtgatc cacctgcctc ggcctcccaa agtgctggga    99540
ttacaggcat gagccaccac tcccagcctg aatcctcact ttttatcaat gaagaaattg    99600
aggctgattc tgcagcatga taaaaaaaa tacagaaaaa ggaaaaaaaa gaagaaatc      99660 gagcctctga gagtttgctt gactgagtct aaccagctca ttttaaaccc gaggaaatg      99720 cagtcacatg actactaagt ggcagctctc ggagcctctc tggcccccaag tccagggttc   99780 catagaggca gccccagcat ggcatgtttt cagtccccaa atgagactct ggagacaaat    99840
```

```
gtctctggag acagagcagc agcctggata agtcacaatg ggtgacgtca ctcagggctc    99900
aacccctggg cagcttaact tgctagggac gttaggagtc tgctgcaaaa cctgagggtc    99960
ttagctgagc agtcacaggc tgggcccgtt gccctgggct cctgtgagta aacccagtc   100020
aattttgagt acccagtaag gcatccattg agttattttg cagccaggag tgctattaag   100080
aacagtcgcg gctgggcgtg gtggctcatg cctgtaatcc cagcactttg ggaggccaag   100140
gtgggcggat cacctgaggt caggagttcg agaccagctt ggccaacatg gcaaaacccc   100200
gtctctaata aaatacaaa ataattagct gggcgtggtg gcgggcgcct gtaatcccag   100260
cttctcagga gggtgaggaa ggagaatcac ttgaacccag gaggcagagg ttgcagtgag   100320
ctgagatcgc accattgcac tccagcctgg atgacaaaag tgagattcct tctcaaaaaa   100380
aaaaaaaaaa aaacagtcgt cctctttggg gattagggac agcctgcctg cctgcccgag   100440
cacttctctc ttccattgcc ccagtgaagt attccaggcc cctgggttta gactctgcac   100500
catgtagggg tgtctgacct gcacttgctc cttggtggca cgggcagcct atggcacttg   100560
ctgcgggctg tgaccaaagc ctggcctgga tcttggatct tggtgactct gcttctccct   100620
ggcctgaggg agctgcccag agcctgccca ccacctgctg cgtgtctttg cggtggcatt   100680
tctcgcacac atgccgtgcg gtggcacccc caaggatggc cattcactaa gcccattgt   100740
ttttgtcttt tcgcttcgtg ttttctggcc tggtgttttt ctcatataca tgtgatccag   100800
ggataattcc cagaattttg acaggatttt aagtagcgtt tggatcctgc tgtttttttt   100860
tcacttaaca tcgggccagt tgactcacac tctgtttttt gttgttgttt ttttgagacg   100920
gagtctcact gtgtcaccca ggctgaagtg cagtggcaca atcttggcat actgcaacct   100980
ctgcttccca aattcaagca gttttcctgc ctcagcctcc tgagtagctg ggactacagg   101040
cacaggccac cacgccctgc taattttgt attttagta aagacagggt ttcaccattt   101100
tggccagcct agtctcgaac tcctgacctc aagtgatccg cccacctcgg cctcccaaag   101160
tgctgggatt acagggact cacactttgt aacaacctga acaacgtga tgcatttccc   101220
tttgggtctt acctgctctt cggtggctgc ctgcaggtgg agagaccctc cccctttggc   101280
ccctcgacct tgtttcagaa tggggccccct gctgggccag ctgtgggtgc ctgccacgtg   101340
aaggactcat taaggccctg tttaagcctg atgataataa ggctttcgtg gatttttctc   101400
tttaagcgac taagcaagtc cagagaagac cacccccctgc agggcccaga tctgagagag   101460
gtactcggga gcctacttcg ctgggagcag cctccctttg cgtgtgtggc cattcactgg   101520
cttgtgtttc tagagccggg aggaccctt tctgcaatgc agggttcaca cagggttcgc   101580
agcctgaaga tggagcagtc cgaattctct tccctgtgca gtttgcgcag ctgtgtttgt   101640
ctgatgggct ttctaatcct gtgtgctctc cttgacttca gggacaatgg cattacaggc   101700
atgagccacc atgcctggct gtctccctat gtttcagatg aagacatagg cttaaggagg   101760
tcaggtgact tgcccacgac cactctgtaa ataagaggca tgaaaagtat ttggagccac   101820
caccaccaag cccactggtc accctgggtc tctgaagtca gggaggcagg aggatgggag   101880
gtctgaggag gcagagaggc tgagcctgga ggccctggag gccgaggccc catctgttgt   101940
ttccttatgt ggaaaataag aggcttcatt tgtcctattg ccacagagcg tactacttca   102000
ggaacatcca agacatggaa atccgcaggg cacggtggct cacgtctata atcccggcac   102060
tttgggaggt tgaggtggga gaatcgcttg aggccagaag ttcaagacca gcctgagcaa   102120
catagtcaga ccccgtctct ataaaaaaca ttatttttaa aaaagacatg gaagtcaaat   102180
tctaaaaact ggtgctggct gggtgcggtg gctcatgcct ataatcccag cactttggga   102240
```

```
ggccgaggcg ggtggatcac ctgaggtcag gagttcaaga ccagcctggc caacatggta 102300
aaacctctac taaagaaatc tttactgaaa atacaaaaat ccagtctcta ctaaaataag 102360
tctctactaa aaatacaaaa attagccagg cgtggtgctg cacacctgta atatcagcta 102420
ctcgggaggc tgaggcagga gactcgcttg atcccatgca gcggaggttg cagtgagccg 102480
agatcacgcc attgcactcc agcctgggca tcagaataag actccgtctc aaaaaaaaaa 102540
ccacaaaaaa acaaaacaac aacaaaagaa aactagtgct tattcgtcac tggccaagct 102600
gcccattggc tacatgggtg cttcaaagag ctgcccttct ccaggtctgg ccagcaggta 102660
tgtgttacag caaatgcctg gggcagcggc aggggcattg ctgcgggaag cttctggact 102720
tgcaggaaag ctaagttctc agactgcagg ggagctaagc acacctcggc acagggtgag 102780
gcctgcggtt ctcagacttc agtctttgtg gagcttgaga aaaatgaggc tttgcaggtc 102840 ccaccctag agattctgct ctatccactc ttgaagggga tcgagaaatt tgcattttgc 102900
aactcccact ttcctccttg aaagctccgg agattctgac gcagggttcc gtgggccaca 102960
ctttggaaaa tacagaccca tgagatagaa taccagactg ttgaagtgta acgggggcct 103020
gggaagtgca gtaacagaag caagtttgag ggtaaaggac acccagagga gggagggaca 103080
gcatctgcat ggagaggaga agagaccccc cagcagcttc cagggtgttg aagggtgcg 103140 ctagtaactg ctatgcatgg caggtgggga actgtacgtc agggcacagc agcatgaagc 103200
ggtatggctc gtgtggacag ctagggacag gcaggcgtgg agcaggcatc ctgttctgaa 103260
ggccaaatcc cacagaggag ccagggtgct ggcaggagcc ctgaactagc cgaacagctg 103320
aacagctgaa cattcaccct gtggggaaag ggtcagaagc gtccaggctt gagggcacag 103380
ctgggtctcg tcactgcatc acccttattt aggataaagg ccctgaagaa ttgtattaga 103440
ggttggcaaa gcatatctac cacctcctgg agccacgctg gccgcaggga ttataattat 103500
ttccattttc aaattaaggc ctctgagctc agagagggga agttacttgt ctgaggccac 103560
acagcttgtt ggagcccatc tcttgaccca aagactgtgg agccgagttg gccacctctc 103620
tgggagcggg tattggatgg tggttgatgg ttttccattg ctttcctggg aaagggtgt 103680 ctctgtccct aagcaaaaag gcagggagga agagatgctt cccagggca gccgtctgct 103740 gtagctgcgc ttccaacctg gcttccacct gcctaaccca gtggtgagcc tgggaatgga 103800
cccacgggac aggcagcccc cagggccttt tctgaccca cccactcgag tcctggcttc 103860
actcccttcc ttccttccca ggtgaacctc caaaatcagg ggatcgcagc ggctacagca 103920
gccccggctc cccaggcact cccggcagcc gctcccgcac cccgtccctt ccaacccac 103980 ccacccggga gcccaagaag gtggcagtgg tccgtactcc acccaagtcg ccgtcttccg 104040
ccaagagccg cctgcagaca gccccgtgc ccatgccaga cctgaagaat gtcaagtcca 104100
agatcggctc cactgagaac ctgaagcacc agccggggagg cgggaaggtg agagtggctg 104160
gctgcgcgtg gaggtgtggg gggctgcgcc tggaggggta gggctgtgcc tggaagggta 104220
gggctgcgcc tggaggtgcg cggttgagcg tggagtcgtg ggactgtgca tggaggtgtg 104280
gggctccccg cacctgagca cccccgcata cacccccagt cccctctgga ccctcttcaa 104340
ggaagttcag ttctttattg ggctctccac tacactgtga gtgccctcct caggcagag 104400 aacgttctgg ctcttctctt gccccttcag ccctgttaa tcggacagag atggcagggc 104460
tgtgtctcca cggccggagg ctctcatagt cagggcaccc acagcggttc cccacctgcc 104520
ttctgggcag aatacactgc cacccatagg tcagcatctc cactcgtggg ccatctgctt 104580
```

-continued

```
aggttgggtt cctctggatt ctggggagat tgggggttct gttttgatca gctgattctt 104640
ctgggagcaa gtgggtgctc gcgagctctc cagcttccta aaggtggaga agcacagact 104700
tcgggggcct ggcctggatc cctttcccca ttcctgtccc tgtgcccctc gtctgggtgc 104760
gttagggctg acatacaaag caccacagtg aaagaacagc agtatgcctc ctcactagcc 104820
aggtgtgggc gggtgggttt cttccaaggc ctctctgtgg ccgtgggtag ccacctctgt 104880
cctgcaccgc tgcagtcttc cctctgtgtg tgctcctggt agctctgcgc atgctcatct 104940
tcttataaga acaccatggc agctgggcgt agtggctcac gcctataatc ccagcacttt 105000
gggaggctga ggcaggcaga tcacgaggtc aggagttcga gaccaacctg accaacaggg 105060
tgaaacctcg tctctactaa aaatacaaaa atacctgggc gtggtggtgg tgcgcgccta 105120
taatcccagc tactcaggag gctgaggcag gagaatcgct tgaacccagg aggcagaggt 105180
tgcagtgagc cgagatagtg ccactgcact ccagtttgag caacagagcg agactctgtc 105240
tcaaaacaaa ataaaacaaa ccaaaaaaac ccaccatggc ttagggccca gcctgatgac 105300
ctcattttc acttagtcac ctctctaaag gccctgtctc caaatagagt cacattctaa 105360
ggtacgggg tgttggggag ggggttagg gcttcaacat gtgaatttgc ggggaccaca 105420
attcagccca ggacccgct cccgccaccc agcactgggg agctggggaa gggtgaagag 105480
gaggctgggg gtgagaagga ccacagctca ctctgaggct gcagatgtgc tgggccttct 105540
gggcactggg cctcggggag ctaggggct ttctggaacc ctgggcctgc gtgtcagctt 105600
gcctccccca cgcaggcgct ctccacacca ttgaagttct tatcacttgg gtctgagcct 105660
ggggcatttg gacggagggt ggccaccagt gcacatgggc accttgcctc aaaccctgcc 105720
acctccccc acccaggatc ccccctgccc ccgaacaagc ttgtgagtgc agtgtcacat 105780
cccatcggga tggaaatgga cggtcgggtt aaaaaggacg catgtgtaga ccctgcctct 105840
gtgcatcagg cctcttttga gagtccctgc gtgccaggcg gtgcacagag gtggagaaga 105900
ctcggctgtg cccagagca cctcctctca tcgaggaaag gacagacagt ggctcccctg 105960
tggctgtggg gacaagggca gagctccctg gaacacagga gggagggaag gaagagaaca 106020
tctcagaatc tccctcctga tggcaaacga tccgggttaa attaaggtcc ggccttttcc 106080
tgctcaggca tgtggagctt gtagtggaag aggctctctg gaccctcatc caccacagtg 106140
gcctggttag agaccttggg gaaataactc acaggtgacc cagggcctct gtcctgtacc 106200
gcagctgagg gaaactgtcc tgcgcttcca ctggggacaa tgcgctccct cgtctccaga 106260
ctttccagtc ctcattcggt tctcgaaagt cgcctccaga agcccatct tgggaccacc 106320
gtgactttca ttctccaggg tgcctggcct tggtgctgcc caagacccca gaggggccct 106380
cactggcctt tcctgccttt tctcccattg cccacccatg cacccccatc ctgctccagc 106440
acccagactg ccatccagga tctcctcaag tcacataaca agcagcaccc acaaggtgct 106500
cccttccccc tagcctgaat ctgctgctcc ccgtctgggg ttcccgccc atgcacctct 106560
gggggcccct gggttctgcc ataccctgcc ctgtgtccca tggtggggaa tgtccttctc 106620
tccttatctc ttccccttccc ttaaatccaa gttcagttgc catctcctcc aggaagtctt 106680
cctggattcc cctctctctt cttaaagccc ctgtaaactc tgaccacact gagcatgtgt 106740
ctgctgctcc ctagtctggg ccatgagtga gggtggaggc caagtctcat gcattttgc 106800
agccccaca agactgtgca ggtggccggc cctcattgaa tgcggggtta atttaactca 106860
gcctctgtgt gagtggatga ttcaggttgc cagagacaga accctcagct tagcatggga 106920
agtagcttcc ctgttgaccc tgagttcatc tgaggttggc ttggaaggtg tgggcaccat 106980
```

```
ttggcccagt tcttacagct ctgaagagag cagcaggaat ggggctgagc agggaagaca  107040
actttccatt gaaggcccct ttcagggcca gaactgtccc tcccaccctg cagctgccct  107100
gcctctgccc atgaggggtg agagtcaggc gacctcatgc caagtgtaga aaggggcaga  107160
cgggagcccc aggttatgac gtcaccatgc tgggtggagg cagcacgtcc aaatctacta  107220
aagggttaaa ggagaaaggg tgacttgact tttcttgaga tattttgggg gacgaagtgt  107280
ggaaaagtgg cagaggacac agtcacagcc tcccttaaat gccaggaaag cctagaaaaa  107340
ttgtctgaaa ctaaacctca gccataacaa agaccaacac atgaatctcc aggaaaaaag  107400
aaaaagaaaa atgtcataca gggtccatgc acaagagcct ttaaaatgac ccgctgaagg  107460
gtgtcaggcc tcctcctcct ggactggcct gaaggctcca cgagcttttg ctgagacctt  107520
tgggtccctg tggcctcatg tagtacccag tatgcagtaa gtgctcaata aatgtttggc  107580
tacaaaagag gcaaagctgg cggagtctga agaatccctc aaccgtgccg aacagatgc   107640
taacaccaaa gggaaaagag caggagccaa gtcacgtttg ggaacctgca gaggctgaaa  107700
actgccgcag attgctgcaa atcattgggg gaaaaacgga aaacgtctgt tttcccttt   107760
gtgctttttct ctgtttttctt ctttgtgctt ttctctgttt tcaggatttg ctacagtgaa  107820
catagattgc tttggggccc caaatggaat tattttgaaa ggaaaatgca gataatcagg  107880
tggccgcact ggagcaccag ctgggtaggg gtagagattg caggcaagga ggaggagctg  107940
ggtggggtgc caggcaggaa gagcccgtag gccccgccga tcttgtggga gtcgtgggtg  108000
gcagtgttcc ctccagactg taaaagggag cacctggcgg gaagagggaa ttcttttaaa  108060
catcattcca gtgcccgagc tcctggacc  tgttgtcatc ttgaggtggg cctccctgg   108120
gtgactctag tgtgcagcct ggctgagact cagtggccct gggttcttac tgctgacacc  108180
taccctcaac ctcaaccact gcggcctcct gtgcaccctg atccagtggc tcattttcca  108240
ctttcagtcc cagctctatc cctatttgca gtttccaagt gcctggtcct cagtcagctc  108300
agacccagcc aggccagccc ctggttccca catccccttt gccaagctca tccccgccct  108360
gtttggcctg cgggagtggg agtgtgtcca gacacagaga caaaggacca gcttttaaaa  108420
cattttgttg gggccaggtg tggtggctca cacctaatcc caacacctgg ggaggccaag  108480
gcagaaggat cacttgagtc caggagttca agaccagcct gggcaacata gggagaccct  108540
gtctctacaa tttttttttt aattagctgg gcctgttggc actctcctgt agttccagct  108600
actctagagg ctgaggtggg aggactgctt gagcctggga ggtcagggct gcaatgagcc  108660
atgttcacac cactgaacgc cagcctgggc gagaccctgt atcaaaaaag taagtaaaa   108720
tgaatcctgt acgttatatt aaggtgcccc aaattgtact tagaaggatt tcatagtttt  108780
aaatactttt gttatttaaa aaattaaatg actgcagcat ataaattagg ttcttaatgg  108840
agggaaaaa gagtacaaga aaagaaataa gaatctagaa acaaagataa gagcagaaat  108900
aaaccagaaa acacaacctt gcactcctaa cttaaaaaaa aaaatgaaga aaacacaacc  108960
agtaaaacaa catataacag cattaagagc tggctcctgg ctgggcgcgg tggcgcatgc  109020
ctgtaatccc aacactttgg gaggccgatg ctggaggatc acttgagacc aggagttcaa  109080
ggttgcagtg agctatgatc ataccactac accctagcct gggcaacaca gtgagactga  109140
gactctatta aaaaaaaaat gctggttcct tccttatttc attcctttat tcattcattc  109200
agacaacatt tatggggcac ttctgagcac caggctctgt gctaagagct tttgccccca  109260
gggtccaggc caggggacag gggcaggtga gcagagaaac agggccagtc acagcagcag  109320
```

```
gaggaatgta ggatggagag cttggccagg caaggacatg caggggagc agcctgcaca    109380 agtcagcaag ccagagaaga caggcagacc cttgtttggg acctgttcag tggcctttga    109440
aaggacagcc cccacccgga gtgctgggtg caggagctga aggaggatag tggaacactg    109500
caacgtggag ctcttcagag caaaagcaaa ataaacaact ggaggcagct ggggcagcag    109560
agggtgtgtg ttcagcacta aggggtgtga agcttgagcg ctaggagagt tcacactggc    109620
agaagagagg ttggggcagc tgcaagcctc tggacatcgc ccgacaggac agagggtggt    109680
ggacggtggc cctgaagaga ggctcagttc agctggcagt ggccgtggga gtgctgaagc    109740
aggcaggctg tcggcatctg ctggggacgg ttaagcaggg gtgagggccc agcctcagca    109800
gcccttcttg gggggtcgct gggaaacata gaggagaact gaagaagcag ggagtcccag    109860
ggtccatgca gggcgagaga gaagttgctc atgtggggcc caggctgcag gatcaggaga    109920
actggggacc ctgtgactgc cagcggggag aaggggggtgt gcaggatcat gcccagggaa    109980
gggcccaggg gcccaagcat ggggggggcct ggttggctct gagaagatgg agctaaagtc    110040
actttctcgg aggatgtcca ggccaatagt tgggatgtga agacgtgaag cagcacagag    110100
cctggaagcc caggatggac agaaacctac ctgagcagtg gggctttgaa agccttgggg    110160 cgggggtgc aatattcaag atggccacaa gatggcaata gaatgctgta actttcttgg    110220
ttctgggccg cagcctgggt ggctgcttcc ttccctgtgt gtattgattt gtttctcttt    110280
tttgagacag agtcttgctg ggttgcccag gctggagtgc agtggtgcga tcatagctca    110340
ctgcagcctt gaagtcctga gctcaagaga tccttccacc tcagcctcct gagtagttgg    110400
gaccacaggc ttgcaccaca gtgcccaact aatttcttat attttttgta gagatggggt    110460
ttcactgtgt cgcccaggat ggtcttgaac tcctgggctc aagtgatcct cctgcctcag    110520
cctcgcaaat tgctgggatt acaggtgtga gccaccatgc ccgaccttct ctttttaagg    110580
gcgtgtgtgt gtgtgtgtgt gtgtgggcgc actctcgtct tcaccttccc ccagccttgc    110640
tctgtctcta cccagtcacc tctgcccatc tctccgatct gtttctctct ccttttaccc    110700
ctctttcctc cctcctcata caccactgac cattatagag aactgagtat tctaaaaata    110760
cattttattt atttattttg agacagagtc tcactctgtc acccaggctg gagtgcagtg    110820
gtgcaatctc ggctcactgc aacctccgcc tcccaggttg aagcaactct cctgcctcag    110880 cctcccctagt agctgggatt acaagcacac accaccatgc ctagcaaatt tttatatttt    110940
tagtagagga ggagtgtcac catgtttgcc aagctggtct caaactcctg gcctcaggtg    111000
atctgcctac cttggtctcc caaagtgctg ggattacagg tgtgagccac cacgcctgcc    111060
cttaaaaata cattatattt aatagcaaag ccccagttgt cactttaaaa agcatctatg    111120
tagaacattt atgtgaaata aatacagtga atttgtacgt ggaatcgttt gcctctcctc    111180
aatcagggcc agggatgcag gtgagcttgg gctgagatgt cagaccccac agtaagtggg    111240
gggcagagcc aggctgggac cctcctctag gacagctctg taactctgag accctccagg    111300
catcttttcc tgtacctcag tgcttctgaa aaatctgtgt gaatcaaatc attttaaagg    111360
agcttgggtt catcactgtt taaggacag tgtaaataat tctgaaggtg actctaccct    111420
gttatttgat ctcttctttg gccagctgac ttaacaggac atagacaggt ttcctgtgt    111480 cagttcctaa gctgatcacc ttggacttga agaggaggct tgtgtgggca tccagtgccc    111540 acccccgggtt aaactcccag cagagtattg cactgggctt gctgagcctg gtgaggcaaa    111600
gcacagcaca gcgagcacca ggcagtgctg gagacaggcc aagtctgggc cagcctggga    111660
gccaactgtg aggcacggac ggggctgtgg ggctgtgggg ctgcaggctt ggggccaggg    111720
```

```
agggagggct gggctctttg aacagccttt gagagaactg aacccaaaca aaaccagatc    111780
aaggtctagt gagagcttag ggctgctttg ggtgctccag gaaattgatt aaaccaagtg    111840
gacacacacc cccagcccca cctcaccaca gcctctcctt cagggtcaaa ctctgaccac    111900
agacatttct cccctgacta ggagttccct ggatcaaaat tgggagcttg caacacatcg    111960
ttctctccct tgatggtttt tgtcagtgtc tatccagagc tgaagtgtaa tatatatgtt    112020
actgtagctg agaaattaaa tttcaggatt ctgatttcat aatgacaacc attcctcttt    112080
tctctcccct ctgtaaatct aagattctat aaacggtgtt gacttaatgt gacaattggc    112140
agtagttcag gtctgctttg taaatacct tgtgtctatt gtaaaatctc acaaaggctt    112200 gttgccttt ttgtggggtt agaacaagaa aaagccacat ggaaaaaaaa tttctttttt    112260 gttttttgt ttgcttgttt ttttgagaca gagtttcact ctgtcgccca ggctggagtg    112320
cagtggtgcg atctccgccc actgcaagct ccacctcccg ggttcatgct attctcctgt    112380
ctcagcctcc caagtagctg ggactgcagg tgcccgccac cacacctggc taattttttt    112440 gtattttttag tagagacggg gtttcaccgt gttagccagg atggtctcaa tctcctgacc    112500
tcgtcatctg cctgcctcgg cctcccaaag tgctgagatt acaggcgtga gccaccgtgc    112560
ccggccagaa aaaacatttt ctaagtatgt ggcagatact gaattattgc ttaatgtcct    112620
ttgattcatt tgtttaattt ctttaatgga ttagtacaga aaacaaagtt ctcttccttg    112680
aaaaactggt aagttttctt tgtcagataa ggagagttaa ataacccatg acatttccct    112740
ttttgcctcg gcttccagga agctcaaagt taaatgtaat gatcactctt gtaattatca    112800
gtgttgatgc ccttcccttc ttctaatgtt actctttaca ttttcctgct ttattattgt    112860
gtgtgttttc taattctaag ctgttccac tcctttctga aagcaggcaa atcttctaag    112920
ccttatccac tgaaaagtta tgaataaaaa atgatcgtca agcctacagg tgctgaggct    112980
actccagagg ctgaggccag aggaccactt gagcccagga atttgagacc tgggctgggc    113040
agcatagcaa gactctatct ccattaaaac tatttttttt tatttaaaaa ataatccgca    113100
aagaaggagt ttatgtggga ttccttaaaa tcggagggtg gcatgaattg attcaaagac    113160
ttgtgcagag ggcgacagtg actccttgag aagcagtgtg agaaagcctg tcccacctcc    113220
ttccgcagct ccagcctggg ctgaggcact gtcacagtgt ctccttgctg gcaggagaga    113280
atttcaacat tcaccaaaaa gtagtattgt ttttattagg tttatgaggc tgtagccttg    113340
aggacagccc aggacaactt tgttgtcaca tagatagcct gtggctacaa actctgagat    113400
ctagattctt ctgcggctgc ttctgacctg agaaagttgc ggaacctcag cgagcctcac    113460
atggcctcct tgtccttaac gtggggacgg tgggcaagaa aggtgatgtg gcactagaga    113520
tttatccatc tctaaaggag gagtggattg tacattgaaa caccagagaa ggaattcaa    113580 aggaagaatt tgagtatcta aaaatgtagg tcaggcgctc ctgtgttgat gcagggcta    113640 ttcacaatag ccaagatttg gaagcaaccc aagtgtccat caacagacaa atggataaag    113700
aaaatgtggt gcatatacac aatggaatac tattcagcca tgaaaagaa tgagaatctg    113760 tcatttgaaa caacatggat ggaactggag gacattatgt taagtgaaat aagccagaca    113820
gaaggacaga cttcacatgt tctcacacat ttgtgggagc taaaattaa actcatggag    113880 atagagagta gaaggatggt taccagaggc tgaggaggt ggaggggagc agggagaaag    113940
tagggatggt taatgggtac aaaaacgtag ttagcatgca tagatctagt attggatagc    114000
acagcagggt gacgacagcc aacagtaatt tatagtacat ttaaaaacaa ctaaaagagt    114060
```

```
gtaactggac tggctaacat ggtgaaaccc cgtctctact aaaaatacaa aaattagctg   114120
ggcacggtgg ctcacgcctg taatcccagc actttgggag gccgaggcgg gccgatcacg   114180
aggtcaggag atcgagacca tcctagctaa catggtgaaa ccccgtctct actacaaata   114240
caaaaaaaag aaaaaattag ccgggcatgg tggtgggcgc ctgtagtccc agctactcgg   114300
gaggctgagg caggagaatg gcgtgaaccc gggaggcgga gcttgcagtg agccgagatc   114360
gcgccactgc actccagcct gggcgacaag gcaagattct atctcaaaaa aataaaaata   114420
aaataaaata aaataataaa ataaaataaa ataaaataaa ataaaataaa taaaataaaa   114480
tgtataattg aatgttttat aacacaagaa atgataaatg cttgaggtga tagataccccc  114540 attcaccgtg atgtgattat tgcacaatgt atgtctgtat ctaaatatct catgtacccc   114600
acaagtatat acacctacta tgtacccata taaatttaaa attaaaaaat tataaaacaa   114660
aaataaataa gtaaattaaa atgtaggctg acaccgtgg ttcacgcctg taatcccagt    114720
gctttgtgag gctgaggtga gagaatcact tgagcccagg agtttgagac cggcctgggt   114780
gacatagcga gaccccatca tcacaaagaa ttttaaaaa ttagctgggc gtggtagcac     114840
ataccggtag ttccagctac ttgggagacc gaggcaggag gattgcttga gcccaggagt   114900
ttaaggctgc agtgagctac gatggcgcca ctgcattcca gcctgggtga cagagtgaga   114960
gcttgtctct atttttaaaaa taataaaaag aataaataaa aataaattaa aatgtaaata   115020
tgtgcatgtt agaaaaaata cacccatcag caaaaagggg gtaaaggagc gatttcagtc   115080
ataattggag agatgcagaa taagccagca atgcagtttc ttttatttttg gtcaaaaaaa   115140 ataagcaaaa caatgttgta aacacccagt gctggcagca atgtggtgag gctggctctc   115200
tcaccagggc tcacagggaa aactcatgca acccttttag aaagccatgt ggagagttgt   115260
accgagaggt tttagaatat ttataactttt gacccagaaa ttctattcta ggactctgtg   115320
ttatgaaaat aacccatcat atggaaaaag ctccctttcag aaagaggttc atgggaggct   115380
gtttgtattt ttttttttctt tgcatcaaat ccagctcctg caggactgtt tgtattattg   115440
aagtacaaag tggaatcaat acaaatgttg gatagcaggg gaacaatatt cacaaaatgg   115500
aatgggacat agtattaaac atagtgcttc tgatgaccgt agaccataga caatgcttag   115560
gatatgatat cacttctttt gttgttttttt gtattttgag acgaagtctc attctgtcac   115620
ccaggctgga gttcagtggc gccatctcag ctcactgcaa cctccatctc ccgggttcaa   115680
gctattctcc ttcctcaacc tcccgagtag ctgggttgcg caccaccatg cctggctaac   115740
ttttgtattt ttagtacaga cggggtttca ccacgttggc caggctgctc ttgaactcct   115800
gacgtcaggt gatccaccag ccttgacctc ccaaagtgct aggattacag gagccactgt   115860
acccagccta ggatatgata tcacttctta gagcaagata caaaattgca tgtgcacaat   115920
aattctacca agtataggta tacaggggta gttatatata aatgagactt caaggaaata   115980
caacaaaatg caatcgtgat tgtgttaggg tggtaagaaa acggttttg ctttgatgag    116040 ctctgttttt taaaatcgtt atattttcta ataaaaatac atagtctttt gaggaacat    116100 aaaagattat gaagaaatga gttagatatt gattcctatt gaagattcag acaagtaaaa   116160 ttaagggaa aaaaacggg atgaaccaga agtcaggctg gagttccaac cccagatccg     116220
acagcccagg ctgatggggc ctccagggca gtggtttcca cccagcattc tcaaaagagc   116280
cactgaggtc tcagtgccat tttcaagatt tcggaagcgg cctggcacg gctggtcctt    116340 cactgggatc accacttggc aattatttac acctgagacg aatgaaaacc agagtgctga   116400
gattacaggc atggtggctt acgcttgtaa tcggctttgg gaagccgagg tgggctgatt   116460
```

```
gcttgagccc aggagtttca aactatcctg acaacatag catgacctcg tctctacaaa    116520
aaatacaaaa aatttgccag gtgtggtggc atgtgcctgt ggtcccagct acttgggagg    116580
ctgaagtagg agaatcccct gagccctggg aagtcgaggc tgcactgagc cgtgatggtg    116640
tcactgcact ccagcctggg tgacaaagtg agacccatc tcacaaagaa aaaaacaaa     116700
acaaaaaacc caaagcacac tgtttccact gtttccagag ttcctgagag gaaaggtcac    116760
cgggtgagga agacgttctc actgatctgg cagagaaaat gtccagtttt tccaactccc    116820
taaaccatgg ttttctattt catagttctt aggcaaattg gtaaaaatca tttctcatca    116880
aaacgctgat attttcacac ctccctggtg tctgcagaaa gaaccttcca gaaatgcagt    116940
cgtgggagac ccatccaggc cacccctgct tatggaagag ctgagaaaaa gccccacggg    117000
agcatttgct cagcttccgt tacgcaccta gtggcattgt gggtgggaga gggctggtgg    117060
gtggatggaa ggagaaggca cagcccccc ttgcagggac agagccctcg tacagaaggg    117120
acacccccaca tttgtcttcc ccacaaagcg gcctgtgtcc tgcctacggg gtcagggctt    117180
ctcaaacctg gctgtgtgtc agaatcacca ggggaacttt tcaaaactag agagactgaa    117240
gccagactcc tagattctaa ttctaggtca gggctagggg ctgagattgt aaaaatccac    117300
aggtgattct gatgcccggc aggcttgaga acagccgcag ggagttctct gggaatgtgc    117360
cggtgggtct agccaggtgt gagtggagat gccggggaac ttcctattac tcactcgtca    117420
gtgtggccga acacattttt cacttgacct caggctggtg aacgctcccc tctggggttc    117480
aggcctcacg atgccatcct tttgtgaagt gaggacctgc aatcccagct tcgtaaagcc    117540
cgctggaaat cactcacact tctgggatgc cttcagagca gccctctatc ccttcagctc    117600
ccctgggatg tgactcgacc tcccgtcact ccccagactg cctctgccaa gtccgaaagt    117660
ggaggcatcc ttgcgagcaa gtaggcgggt ccagggtggc gcatgtcact catcgaaagt    117720
ggaggcgtcc ttgcgagcaa gcaggcgggt ccagggtggc gtgtcactca tcctttttc    117780
tggctaccaa aggtgcagat aattaataag aagctggatc ttagcaacgt ccagtccaag    117840
tgtggctcaa aggataatat caaacacgtc ccggggaggcg gcagtgtgag taccttcaca    117900
cgtcccatgc gccgtgctgt ggcttgaatt attaggaagt ggtgtgagtg cgtacacttg    117960
cgagacactg catagaataa atccttcttg ggctctcagg atctggctgc gacctctggg    118020
tgaatgtagc ccggctcccc acattccccc acacggtcca ctgttcccag aagcccttc     118080
ctcatattct aggagggggt gtcccagcat ttctgggtcc cccagcctgc gcaggctgtg    118140
tggacagaat agggcagatg acggaccctc tctccggacc ctgcctggga agctgagaat    118200
acccatcaaa gtctccttcc actcatgccc agccctgtcc ccaggagccc catagcccat    118260
tggaagttgg gctgaaggtg gtggcacctg agactgggct gccgcctcct ccccgacac    118320
ctgggcaggt tgacgttgag tggctccact gtggacaggt gacccgtttg ttctgatgag    118380
cggacaccaa ggtcttactg tcctgctcag ctgctgctcc tacacgttca aggcaggagc    118440
cgattcctaa gcctccagct tatgcttagc ctgcgccacc ctctggcaga gactccagat    118500
gcaaagagcc aaaccaaagt gcgacaggtc cctctgccca gcgttgaggt gtggcagaga    118560
aatgctgctt ttggcccttt tagatttggc tgcctcttgc caggagtggt ggctcgtgcc    118620
tgtaattcca gcactttggg agactaaggc gggaggttcg cttgagccca ggagttcaag    118680
accagcctgg gcaacaatga cccctgtgt ctacaaaaa gaattaaaat tagccaggtg      118740
tggtggcacg cacctgtagt cccagctact gggaggctg aggtgggagg attgcctgag    118800
```

```
tccgggaggc ggaagttgca aggagccatg atcgcgccac tgcacttcaa cctaggcaac   118860
agagtgagac tttgtctcaa aaaacaatca tataataatt ttaaaataaa tagatttggc   118920
ttcctctaaa tgtccccggg gactccgtgc atcttctgtg gagtgtctcc gtgagattcg   118980
ggactcagat cctcaagtgc aactgaccca cccgataagc tgaggcttca tcatcccctg   119040
gccggtctat gtcgactggg cacccgaggc tcctctccca ccagctctct tggtcagctg   119100
aaagcaaact gttaacaccc tggggagctg gacgtatgag acccttgggg tgggaggcgt   119160 tgattttga gagcaatcac ctggccctgg ctggcagtac cgggacactg ctgtggctcc   119220
ggggtgggct gtctccagaa aatgcctggc ctgaggcagc cacccgcatc cagcccagag   119280
ggtttattct tgcaatgtgc tgctgcttcc tgccctgagc acctggatcc cggcttctgc   119340
cctgaggccc cttgagtccc acaggtagca agcgcttgcc ctgcggctgc tgcatggggc   119400
taactaacgc ttcctcacca gtgtctgcta agtgtctcct ctgtctccca cgccctgctc   119460
tcctgtcccc ccagtttgtc tgctgtgagg ggacagaaga ggtgtgtgcc gcccccaccc   119520
ctgcccgggc ccttgttcct gggattgctg ttttcagctg tttgagcttt gatcctggtt   119580
ctctggcttc ctcaaagtga gctcggccag aggaggaagg ccatgtgctt tctggttgaa   119640
gtcaagtctg gtgccctggt ggaggctgtg ctgctgaggc ggagctgggg agagagtgca   119700
cacgggctgc gtggccaacc cctctgggta gctgatgccc aaagacgctg cagtgcccag   119760
gacatctggg acctccctgg ggcccgcccg tgtgtcccgc gctgtgttca tctgcgggct   119820
agcctgtgac ccgcgctgtg ctcgtctgcg ggctagcctg tgtcccgcgc tctgcttgtc   119880
tgcggtctag cctgtgacct ggcagagagc caccagatgt cccgggctga gcactgccct   119940
ctgagcacct tcacaggaag cccttctcct ggtgagaaga gatgccagcc cctggcatct   120000 ggggggcactg gatccctggc ctgagcccta gcctctcccc agcctggggg cccccttccca  120060 gcaggctggc cctgctcctt ctctacctgg gaccttctg cctcctggct ggaccctgga   120120
agctctgcag ggcctgctgt ccccctccct gccctccagg tatcctgacc accggccctg   120180
gctcccactg ccatccactc ctctcctttc tggccgttcc ctggtccctg tcccagcccc   120240
cctccccctc tcacgagtta cctcacccag gccagaggga agagggaagg aggccctggt   120300
cataccagca cgtcctccca cctccctcgg ccctggtcca cccctcagt gctggcctca    120360 gagcacagct ctctccaagc caggccgcgc gccatccatc ctccctgtcc cccaacgtcc   120420
ttgccacaga tcatgtccgc cctgacacac atgggtctca gccatctctg ccccagttaa   120480
ctccccatcc ataaagagca catgccagcc gacaccaaaa taattcggga tggttccagt   120540
ttagacctaa gtggaaggag aaaccaccac ctgccctgca ccttgttttt tggtgacctt   120600
gataaaccat cttcagccat gaagccagct gtctcccagg aagctccagg gcggtgcttc   120660
ctcgggagct gactgatagg tgggaggtgg ctgcccccctt gcaccctcag gtgacccac    120720 acaaggccac tgctggaggc cctggggact ccaggaatgt caatcagtga cctgccccc    120780 aggcccacaa cagccatggc tgcatagagg cctgcctcca agggacctgt ctgtctgcca   120840
ctgtggagtc cctacagcgt gccccccaca ggggagctgg ttctttgact gagatcagct   120900
ggcagctcag ggtcatcatt cccagaggga gcggtgccct ggaggccaca ggcctcctca   120960
tgtgtgtctg cgtccgctcg agcttactga gacactaaat ctgttggttt ctgctgtgcc   121020
acctacccac cctgttggtg ttgctttgtt cctattgcta aagacaggaa tgtccaggac   121080
actgagtgtg caggtgcctg ctggttctca cgtccgagct gctgaactcc gctgggtcct   121140
gcttactgat ggtctttgct ctagtgcttt ccagggtccg tggaagcttt tcctggaata   121200
```

```
aagcccacgc atcgaccctc acagcgcctc ccctctttga ggcccagcag atacccact  121260 cctgcctttc cagcaagatt tttcagatgc tgtgcatact catcatattg atcacttttt  121320
tcttcatgcc tgattgtgat ctgtcaattt catgtcagga aagggagtga cattttaca   121380 cttaagcgtt tgctgagcaa atgtctgggt cttgcacaat gacaatgggt ccctgttttt  121440
cccagaggct cttttgttct gcagggattg aagacactcc agtcccacag tccccagctc  121500
ccctggggca gggttggcag aatttcgaca acacattttt ccaccctgac taggatgtgc  121560
tcctcatggc agctgggaac cactgtccaa taagggcctg gcttacaca gctgcttctc   121620 attgagttac acccttaata aaataatccc attttatcct ttttgtctct ctgtcttcct  121680
ctctctctgc ctttcctctt ctctctcctc ctctctcatc tccaggtgca aatagtctac  121740
aaaccagttg acctgagcaa ggtgacctcc aagtgtggct cattaggcaa catccatcat  121800
aaaccaggta gccctgtgga aggtgagggt tgggacggga gggtgcaggg ggtggaggag  121860
tcctggtgag gctggaactg ctccagactt cagaagggc tggaaaggat atttaggta    121920 gacctacatc aaggaaagtg ttgagtgtga aacttgcggg agcccaggag gcgtggtggc  121980
tccagctcgc tcctgcccag gccatgctgc ccaagacaag gtgaggcggg agtgaagtga  122040
aataaggcag gcacagaaag aaagcacata ttctcggccg ggcgctgtgg ctcacgcctg  122100
taattccagc actttgggag gccaaggtgg gtggatcatg aggtcaggag attgagacca  122160
tcctggctaa cacagtgaaa ccccgtctct actaaaaata caaaaaatta gccgggcgtg  122220
gtggtgggcg cctgtagtcc cagctactcc ggaggctgag gcaggaaaat ggcgtgaacc  122280
cggaaggcgg agcttgcagt gagcggagtg agcagagatc gcgccactgc actccagcct  122340
gggcgacaga gcgagactcc gtctcaaaaa aaaaagcac atgttctcgc ttctttgtgg    122400
gatccaggag atagagaata aaggatggt taccagaggc tgggaaggt agtgagggga     122460 tggtgggggg atggtcaatg ggtacaaaaa aaatagaata agacctagta tttgatagtg  122520
caacagggtg actatagtca ataataattt aattgtacat ttaaaaataa ctaaaagata  122580
gccgggtgca gtggcttacg tctgtaatcc cagtactttg ggaggctgag gtgggcgttt  122640
gagaccagcc tggccaacat ggtgaaaccc catctctact aaaaatacaa aaattagcca  122700
ggcatggtgg cgggcgcctg taatcccagc tactcgggag gctgaggcag gagaatcact  122760
tgaacctggg aggcagaggt tgcagtgagc cgagatcttg ccactgcact ccagcctggg  122820
tgacagtgaa actccgtctc aaaaataaaa ataaaaatac agctgggcac ggtggctcac  122880
gcctgtaatc ccagcacttt gggaggccga ggcgagcgga tcacaaggtc aggagatata  122940
gaccatcctg gctaacacgg tgaaacccgg tctctactaa aaatacaaaa aattagccag  123000
gcgtggtggc aggtgcctat agtcccagct actcacaagg ctgaggcagg agaatggcat  123060
gaacctggga ggcggagctt gcagtgagcc gagattgtgc cactgcactc agcctgggc   123120 gagagagtga gactccgtct caaaacaaaa acaaaaacaa aaacaaaaac aaacacacaa  123180
caaaaaccta aagaatatata atggattgt ttgtaacaca aaggacaaat gtttgagggg   123240
atggataccc cattttccat gatgtgatta ttatacattg tgtgtctgta tcaaacatc   123300 tcatgagccc cataaatata tacacctaac tatgtaccca caaaaattaa aaaatatat    123360 tttttaaggt gaagagggag gcgagatgct ggccttaacc cctaacccgt tgttctccct  123420
gcaagctgtc cacagggcct ctcagactcg aggttcagct atatgaatgc atgagcttgg  123480
tccccagcca acatgggaga cacttcacca tcggcagcag ctacagcaca ggaaccctgg  123540
```

```
gtcactgcca tgtcccctct gtgactttgt ttaaacagaa aatgatgctc tgggccggct   123600
gtggtggccc acacctataa tcccagcacc ttgggaggcg ggggtgggca gattgcctga   123660
ggtcaggagt tggagatcag cctggccgac atggcgaaac cccatgtcta ctaaaaatac   123720
aaaaactagc caggcatggt ggcacatgcc tgtaatccca gctacttggg aggctgaagc   123780
aggagaatca cttgaaccca ggaggcagag gctgagtgag ccaagatcgt gccaatgcac   123840
tccagcttgg gtgagggagt gagactccgt ctcaaaaaaa aaaaaaaaga aagaaaaaga   123900
aaagaaagtg atcctactgg aaccatgctt actcccctcc ccacctcaca ctgtgtagaa   123960
attagtgctg tcggccaggc gcggtggctc atgcctgtaa tcgcagcact ttgggaggcc   124020
aaggcaggcg gatcacgagg tcaggagatc aagaccatcc tggctaacac agtgaaaccc   124080
tgtctctact aaaaatacaa aaaattagcc gggcatggtg gcaggcacct gtagtcccaa   124140
ctacttggga ggctgaggca ggagaatggc atgaacctgg gaggcggagc ttgcagtgag   124200
ccaagatcgc gccactgcat accagcctag gtgacagagt gagactcagc aaaaaaagaa   124260
agaaagaaag aaagaaatca gtgctgtcta tacttctttc tgcagtgatg gaaatattct   124320
gtatctgtgc tgtccagtat agtagccact agctacatgt ggcacttgaa acatggctgg   124380
tacagttgag gaagagtggc tgccatatcg gacgacacag ctatagattc tgtcacccca   124440
ccccgagagt ccagagcggg gacttctgcc ttaggcccta ttcagggctg attttttactt   124500 gaacccttac tgtgggaaga gaaggccatg agaagttcag tctagaatgt gactccttat   124560
tttctggctc ccttggacac tttgtgggat ttagtctccc tgtggaaagt attccacaag   124620
tggtgccact accccagctg tgagagcagc tgggagctgc ttttgtcatc tttccctgga   124680
aagtcctgtg ggctgtctct tcctcatgcc ttgtcccatg cttgggcatg tgtcaagcg    124740 tcaggaggga gaaagggtcc ttatttattt atttagagag ggaccttct tctgttccca   124800 ggctggagtg cagtggtgcg atctcggctc actgcaacct ccgcctcctg ggttcaagtg   124860
attctcctgc ctcagcctcc tgagtagctg agattacagg cacatgccaa catgcccggc   124920
taattttttt tttttttttt tttttttttt tttgagatgg agttgtactc              124980
tcattgccca ggctggaatg taatggcaca atctcggctc actgcaacct ccacctcctg   125040
gattcaagca attctcctgt ctcagcttcc caagtagctg ggattacagg tgcccgccac   125100
catgctcaac taattttttgt atttttttt tagtagagac gaggtttcac catgttggtc    125160
agactggtct caaactcctg acctcaggtg atccacctgc ctcggcctcc caaagtgcta   125220
ggattacagg catgagccac cacgcccggc ctgaaagggt tcttatttag tgtgcattttt  125280 gacattcaat ttaattccaa ggtcttgtgg ggtcatggtt tacaggatgt tgatatagaa   125340
aagacttcac ttaatgggcc gggcgcagtg gctcatgcct gtaatcccag cactttggga   125400
ggccgaggca ggcagatcag gaggtcagga gattgagacc atcctggcta acacagtgaa   125460
accccatctc tactgaaaat acaaaaaatt agctgggcgt ggtggcaggc acctgtagtc   125520
ccagccactc ggttggctga ggcaggagaa tggcatgaac ccgggaggcg gagcttgcag   125580
tgagcagaga ccatgccact gcactccagc ctgggcgaca gagcaagact ctgtctcaag   125640
aaaaaaaaaa aaaacagac tttacttact ggaagccaac caatgtatat ttagagtaat   125700
ttttcctggg ctgagctgtc atttacttttt gcagtatctc aagaagaaga gtttacagtg   125760
taaatatttg atgcacactt tgattatata gatgaagcaa actattttca agagctttgc   125820
aaggacttac ttgtatccaa acaccattct aaaaggagtc ttacctactt ctaaaggctg   125880
gtctctactt ggaaccactt gcttggccct ggttcaagtc ctgctgcaaa cctggaagtc   125940
```

```
ctgtcattgt cttcttccct ccagagcagt ggcacccaat ctaattttg ctgtgcccca    126000 gcagccctg gcactttgcc ctgtagactg cagacctcat gtaatgtatg ttaagtccac    126060
agaaccacag aagatgatgg caagatgctc ttgtgtgtgt tgtgttctag gaggtggcca    126120
ggtggaagta aaatctgaga agcttgactt caaggacaga gtccagtcga agattgggtc    126180
cctggacaat atcacccacg tccctggcgg aggaaataaa aaggtaaagg gggtagggtg    126240
ggttggatgc tgcccttggg tatatgggca ttaatcaagt tgagtggaca aaggctggtc    126300
cagttcccag aggaggaaaa cagaggcttc tgtgttgact ggctggatgt gggccctcag    126360
cagcatccag tgggtctcca ctgcctgtct caatcacctg gagctttagc acgtttcaca    126420
cctgggcccc aacctggaga ggctgaccaa tgggtctcag gggcagctcg gttgctggag    126480 ttttgtttt tatttatttt tatgtattta aggcagggtc tctgtattag tccattctca    126540
cactgctaat aaagacatac ccaagactgg gtaatttata aaggaaagag gtttaatgga    126600
ctcacagttc cacatggctg ggaggcctc aaaatcatgg cggaaggcaa aggagaagca    126660
aaggcatttc ttacatggcg acaggcaaga gagcgtgtgc aggggaactc ccatttataa    126720
aaccatcaga cctcatgaga tttattcact atcatgagaa cagcatggga aagacccgcc    126780
cccatgattc agttacctcc cactgggtcc ctcccatgac acatggaatt atgggagcta    126840
caattcaaga tgagatttgg gtggggacac agccaaacca tatcagtctc cctctgtcat    126900
ccaggctgga gtgcactggc atgatctcgg ctcactgcag cctctacctc cctgggtcag    126960
gtgatcttcc cacctcagcc tcccaggtag ctggaactac aggtacctgc cactatgcct    127020
ggctaaatat tttgtatttc ctgtggagac gaggttttgc cacgttgccc aggctggtct    127080
tgaactcctg aggtcaagca atatgcccac ctcggcctcc caaggtgctg ggattacagg    127140
tgtgagccac agtgctcggc ctaagtcact gcagttttta aagctcccag gtgattcttc    127200
agtgcagtca aaagtgagaa ctggctgggt gcggtggctc atgcctgtaa tcccagcacc    127260
ttgggaggcg aaggtgggca gatggcttga ggtcaggagt tcaagaccag cctggccaac    127320
atggtaaaac cccatctcta ctaaaaatac aaaagttagc tgggtgtggt ggtgcgtgcc    127380
tgtaatccca gctacttggg aggctgaggc atgagaattg cttgaaccca ggggacagag    127440
gttgtagtga gccgagatcg tgccactgca ctccagcctg gcaacagag tgagattcca    127500 tctcacaaaa aaaaaaaaaa gcgagaacca ctgtcctagg ccctgatgtt tgcaggcaac    127560
taaaaaggaa agtggacatc cccagtcagc tgtggcgcac caagaacaag tcatgggaac    127620
ataacctaat tttctaaatg ggttactagg cacttagagc aaaacaatga tgccgaaatc    127680
ctgatttcag caaagcctct gcctgcctgt cttggaagta tccacatgag gctgctgggg    127740
ccttggtgtc cccagcagtt tctagtctct aggtcttgct gtgggtgtct gtgcagtgag    127800
ggtgtgtgtg gcgctgggtg agctctgtct aggcctggca caggatgcgg tctggtagct    127860
gctgcttctc ttctgcagaa gcgcagccaa gcaccctctg gggtttcagg cccacaccca    127920
gcctgaagtt ctgggagtgg ctcactttcc aaccttcagg gtctcccagc agctgactgg    127980
ggagtggtgg agggaaaagg gattgtatta gtccgttttc acgccgctga tgaagacata    128040
cccgatactg ggcagtctaa aagatagagg tctgatggac tcacagttcc acgtgactgg    128100
ggaggcctga caatcatggt ggaaggtgaa aggcttgtct cacacggtgg cagacaagag    128160
aaaagagctt gtgcagggga actccccttt ataaaaccat cagatctcgg gagacttatt    128220
cactatcatg agaacagcac gggaaagacc ctcctctatg attcaattac ctcccaccag    128280
```

-continued

```
gtccctccca caacatgtag gaattgtggg aactacaatt caagatgaca tttgggtggg   128340
gacacagcca aaccatatca gggcgtccca gaaagggtat agggtctgag acccaagtca   128400
gcatgagaaa gtatgcttct catggtggcc cagttgggtg gaagtggcag ccgggccgtc   128460
tttccaccag gccactcaag tagcagctga gagaccctg ccctggccag tccccgccct    128520
cccctcttgc cactgcctct ggttctgaac agatgggcac cctcatcttg tatttgtgat   128580
taatgtctaa caatgtagtt ttgtgagaag ggtttgctga tacagccttg ctgcagatgc   128640
tgcgaactgt ggcctggggc agaccttacc tccagacacg ccctgaggca ggggagggca   128700
ctggcccgta gctggccgag agctctcggg ttgcgcgaca gggatacttt tcagcggctg   128760
ggtcgctatc caaagtgaga aaacgaggag ggaccaggag gctgtccgcc tcaagagatg   128820
tgggggccag gtccagttat ctggggaagc agtaagcttc tctgctgttt ctaaccccag   128880
gcctcccctg gtctaaggca gggcctccca gcctcggggc actttaaaga tatctgggcc   128940
tggccccatc cccacagtct gactgagtgg gtctggatag ggcctgagca ttggtgattt   129000
cctgggtgaa aggaggcccc tcacagtctc tggaagcttc tctgtgttag gaaaagctct   129060
gggcttgact ctgctttgaa agtcaagatc cgcaaatcct ctcagcctca gtttctcctt   129120
cagcaagatg aaatggaaat gctgtaccta cgtcccgggg tggttgtgag acccaaaaaa   129180
gacaatgttc tggaaggttc ctggtgcgtt gcagtcctct aagaacctga gttagagcca   129240
cgctgagtct cagcttcttg gctccttctg tttcaaactc gtccatgtga tagctcagga   129300
agggtaggca gggccctgcc ccctactcag aaaacaccat cctggtcctg gggatccccg   129360
cagcattagt cccctgtttt cccagtgtat tgagaaaaat tgctaacaag cagtgggca    129420 caccaccagc ctcctgggtt cctttcagtt tggggatttt tggacattcc caggaatgtc   129480
ttaaaaaaca cttcaaaaaa cattaacata aatatttta tcaaagcctg tattaaatgg    129540
tctttcaaga aaatacagta acaggtcagg catggtggct catgcctgta accccagcac   129600
tttgggaggc caaggcaggc agatcacctg aaatcaggag ttcaagacca acctggccaa   129660
cacagccaaa tccatctct acaaaaaata caaaaattag ctgggtgtgg tggcacacac    129720
ctgtagtccc agctacttgg gaggccgagg caggagaatt gcttgatccc ggaggcgag    129780 gttgcagtga gccgagatcg tgccactgca ctccagcgtg ggtgacaagg tgaatctttg   129840
tctcaaaaaa aaaaaaaaa aaaagataaa atacagtata cagtaataga gaacaatcct    129900
tttttcaaag tagtgacccc aaatgaacaa aatatgcatc tagcttaaat gcgaacctgg   129960
ttttctctac gcccattcaa gccctgcaa taggggccct tcaccccgca tccatggact    130020
cctaaaatta tatggaaaat ggctgtgtgt gagtgtggat ggacatgtgc acacatattt   130080
ttggctttac cagatgctca aagagcctag gacccaaaaa gggctgagaa tgaccgtgtc   130140
ggccacttca gggtcatcag gaattgctgt gcactgctca cttctccagt gaacactttc   130200
tgcttctgtg tttcctggta tcctttggga ctcctggcta ggtcatgtgt ttctctactt   130260 tcaaagggc ttcagccagg cacgatggca tgagcctgta gtcccagttg ctctggaggt    130320
taaggtggga agattgcttg agcccaggaa tttgaggcca gcctgggcaa gtagataggt   130380
agatgattga tagatagata gatagataaa tagatggata gataagtcgc tagacagtca   130440
tccatccacc catccacaca taaaaaggcc tttgtcatgt catgttttgt ggcccacctg   130500
ccagtgttgc ccacagttgc tgcccctcca aactcatcag tcactggcaa acaggaggaa   130560
tgtgtggctc atgtctgggc atcagtggct gtgggagaca tccttgatct tctccagctt   130620
ctccttccac attttccttt gcaatctggc aatatctatt aaaataaaat gtgcatgcct   130680
```

```
tttgacctaa gagcttcact tctaggaccc acttacacgt gtgtgacatg atgttcatac   130740
gggtttattt atctgaggtt gttcatacac accattgcct gtaatcacta aaggcgggag   130800
cagcctacac atccatccac agaggagtag atgccttttg gtacatccgt ggcgacggaa   130860
tactaagcag cctgtgtatc tatacactca cacgtgtttg tttatgtgtg gaatatctct   130920
ggagggtaca caagaaactt aaaatgatca ctgtctctgg ggagggtacc tgggtgcctg   130980
ggaggcaggt cagggaagga gtgggcacag gtattaccaa ttggaagaca ataaaaacaa   131040
cagctcctgg ccaggcgcag tggctcacgc ctgtaatggc agcactctga gaggctgagg   131100
cgggcagatt gcttgcgtcc aggagttcaa gaccagcctg gcaacatag caaaaccccg   131160 tttctattaa aaatacaaaa aattagccag gtgtggtggc atgcacctgt aatcccagct   131220
actcgggagg ctgaggtggg agaatcacct gagcctggga ggtcaaggct gcagtgaggt   131280
gagattgtgc caccgcactc tagcctgggc gatagagcaa gaccctgtct caaaaacaaa   131340
caaaaaacag tccctggcac tctgggccag gcctggcagg gcagttggca gggctggtct   131400
ttctctggca cttcatctca ccctccctcc cttcctcttc ttgcagattg aaacccacaa   131460
gctgaccttc cgcgagaacg ccaaagccaa gacagaccac ggggcggaga tcgtgtacaa   131520
gtcgccagtg gtgtctgggg acacgtctcc acggcatctc agcaatgtct cctccaccgg   131580
cagcatcgac atggtagact cgccccagct cgccacgcta gctgacgagg tgtctgcctc   131640
cctggccaag cagggtttgt gatcaggccc ctgggcggt caataattgt ggagaggaga   131700
gaatgagaga gtgtggaaaa aaaaagaata atgacccggc ccccgccctc tgcccccagc   131760
tgctcctcgc agttcggtta attggttaat cacttaacct gcttttgtca ctcggctttg   131820
gctcgggact tcaaaatcag tgatgggagt aagagcaaat ttcatctttc caaattgatg   131880
ggtgggctag taataaaata tttaaaaaaa aacattcaaa aacatggcca catccaacat   131940
ttcctcaggc aattccttt  gattcttttt tcttcccct ccatgtagaa gagggagaag    132000
gagaggctct gaaagctgct tctggggat ttcaaggac tggggtgcc aaccacctct       132060 ggccctgttg tgggggtgtc acagaggcag tggcagcaac aaaggatttg aaacttggtg   132120
tgttcgtgga gccacaggca gacgatgtca accttgtgtg agtgtgacgg gggttgggt    132180 ggggcgggag gccacggggg aggccgaggc aggggctggg cagagggag aggaagcaca     132240 agaagtggga gtgggagagg aagccacgtg ctggagagta gacatccccc tccttgccgc   132300
tgggagagcc aaggcctatg ccacctgcag cgtctgagcg gccgcctgtc cttggtggcc   132360
gggggtgggg gcctgctgtg ggtcagtgtg ccaccctctg cagggcagcc tgtgggagaa   132420
gggacagcgg gtaaaaagag aaggcaagct ggcaggaggg tggcacttcg tggatgacct   132480
ccttagaaaa gactgacctt gatgtcttga gagcgctggc ctcttcctcc ctccctgcag   132540 ggtaggggc ctgagttgag gggcttccct ctgctccaca gaaaccctgt tttattgagt    132600
tctgaaggtt ggaactgctg ccatgatttt ggccactttg cagacctggg actttagggc   132660
taaccagttc tctttgtaag gacttgtgcc tcttgggaga cgtccacccg tttccaagcc   132720
tgggccactg gcatctctgg agtgtgtggg ggtctgggag gcaggtcccg agccccctgt   132780
ccttcccacg gccactgcag tcaccctgt  ctgcgccgct gtgctgttgt ctgccgtgag    132840
agcccaatca ctgcctatac ccctcatcac acgtcacaat gtcccgaatt cccagcctca   132900
ccaccccttc tcagtaatga ccctggttgg ttgcaggagg tacctactcc atactgaggg   132960
tgaaattaag ggaaggcaaa gtccaggcac aagagtggga ccccagcctc tcactctcag   133020
```

```
ttccactcat ccaactggga ccctcaccac gaatctcatg atctgattcg gttccctgtc   133080
tcctcctccc gtcacagatg tgagccaggg cactgctcag ctgtgaccct aggtgtttct   133140
gccttgttga catggagaga gccctttccc ctgagaaggc ctggcccctt cctgtgctga   133200
gcccacagca gcaggctggg tgtcttggtt gtcagtggtg gcaccaggat ggaagggcaa   133260
ggcacccagg gcaggcccac agtcccgctg tcccccactt gcaccctagc ttgtagctgc   133320
caacctccca gacagcccag cccgctgctc agctccacat gcatagtatc agccctccac   133380
acccgacaaa ggggaacaca ccccttggaa aatggttctt ttcccccagt cccagctgga   133440
agccatgctg tctgttctgc tggagcagct gaacatatac atagatgttg ccctgccctc   133500
cccatctgca ccctgttgag ttgtagttgg atttgtctgt ttatgcttgg attcaccaga   133560
gtgactatga tagtgaaaag aaaaaaaaaa aaaaaaaagg acgcatgtat cttgaaatgc   133620
ttgtaaagag gtttctaacc caccctcacg aggtgtctct cacccccaca ctgggactcg   133680
tgtggcctgt gtggtgccac cctgctgggg cctcccaagt tttgaaaggc tttcctcagc   133740
acctgggacc caacagagac cagcttctag cagctaagga ggccgttcag ctgtgacgaa   133800
ggcctgaagc acaggattag gactgaagcg atgatgtccc cttccctact tcccccttggg   133860 gctccctgtg tcagggcaca gactaggtct tgtggctggt ctggcttgcg gcgcgaggat   133920
ggttctctct ggtcatagcc cgaagtctca tggcagtccc aaaggaggct tacaactcct   133980
gcatcacaag aaaaggaag ccactgccag ctgggggat ctgcagctcc cagaagctcc   134040
gtgagcctca gccacccctc agactgggtt cctctccaag ctcgccctct ggaggggcag   134100
cgcagcctcc caccaaggc cctgcgacca cagcagggat tgggatgaat tgcctgtcct   134160
ggatctgctc tagaggccca agctgcctgc ctgaggaagg atgacttgac aagtcaggag   134220
acactgttcc caaagccttg accagagcac ctcagcccgc tgaccttgca caaactccat   134280
ctgctgccat gagaaaggg aagccgcctt tgcaaaacat tgctgcctaa agaaactcag   134340
cagcctcagg cccaattctg ccacttctgg tttgggtaca gttaaaggca accctgaggg   134400
acttggcagt agaaatccag ggcctcccct ggggctggca gcttcgtgtg cagctagagc   134460
tttacctgaa aggaagtctc tgggcccaga actctccacc aagagcctcc ctgccgttcg   134520
ctgagtccca gcaattctcc taagttgaag ggatctgaga aggagaagga aatgtggggt   134580
agatttggtg gtggttagag atatgccccc ctcattactg ccaacagttt cggctgcatt   134640
tcttcacgca cctcggttcc tcttcctgaa gttcttgtgc cctgctcttc agcaccatgg   134700
gccttcttat acgaaggct ctgggatctc ccccttgtgg gggcaggctc ttgggggcag   134760
cctaagatca tggtttaggg tgatcagtgc tggcagataa attgaaaagg cacgctggct   134820
tgtgatctta aatgaggaca atcccccag ggctgggcac tcctccctc ccctcacttc   134880 tcccacctgc agagccagtg tccttgggtg ggctagatag gatatactgt atgccggctc   134940
cttcaagctg ctgactcact ttatcaatag ttccatttaa attgacttca gtggtgagac   135000
tgtatcctgt ttgctattgc ttgttgtgct atgggggag gggggaggaa tgtgtaagat   135060
agttaacatg ggcaaaggga gatcttgggg tgcagcactt aaactgcctc gtaaccctt   135120 tcatgatttc aaccacattt gctagaggga gggagcagcc acgagttag aggccttgg   135180 ggtttctctt ttccactgac aggctttccc aggcagctgg ctagttcatt ccctccccag   135240
ccaggtgcag gcgtaggaat atggacatct ggttgctttg gctgctgcc ctctttcagg   135300 ggtcctaagc ccacaatcat gcctcctaa gaccttggca tccttccctc taagccgttg   135360
gcacctctgt gccacctctc acactggctc cagacacaca gcctgtgctt ttggagctga   135420
```

```
gatcactcgc ttcaccctcc tcatctttgt tctccaagta aagccacgag gtcggggcga   135480
gggcagaggt gatcacctgc gtgtcccatc tacagacctg cggcttcata aaacttctga   135540
tttctcttca gctttgaaaa gggttaccct gggcactggc ctagagcctc acctcctaat   135600
agacttagcc ccatgagttt gccatgttga gcaggactat ttctggcact tgcaagtccc   135660
atgatttctt cggtaattct gagggtgggg ggagggacat gaaatcatct tagcttagct   135720
ttctgtctgt gaatgtctat atagtgtatt gtgtgtttta acaaatgatt tacactgact   135780
gttgctgtaa aagtgaattt ggaaataaag ttattactct gattaaataa ggtctccatt   135840
catggattcc aaggacaaga aagtcatata gaatgtctat ttttttaagtt ctttcccacg   135900 caccccttaga taatttagct cagaacagga aatgatagta ttaataaaag ctggacatca   135960
ggattaacag ctctctctgg ggccctgaag gtgagagttc tcagacttgc tcatttgcag   136020
ttgcttcttt gtgatgctgg caaaccatcc tagtcccatt caagggcaa tacaaagcct   136080 tgtggctgac ctcacgatgc agcactcagt ttgcaagacc ggcaccagtg tatgcaaacc   136140
tgagaaggtt ggggatgagg atatgggatc tttcatccct ggaaatttag tccagaggcc   136200
tggggctgga gcagaacacc aagccaatca gcttaatgaa tggcttagat tcctgctagg   136260
tttgcagagc tgccttcttt cctttggtac cttattatag attgaggagt atttctgcta   136320
aaccaagata gggataacca gatagcatct tcatagcaat gccacaaagg aaaacaaaaa   136380
caaaacagta atccatcata ttattcctta gtaactatgc caaggtcatg atactgaatc   136440
cttagattgt ttcaaaatac tacttttctt tgctcttcct gatgtgtttg ccaccgcagg   136500
cagatgttta agtaaaacag attttaactg cagctacaaa agcagcaaca ggccagcaaa   136560
agagaagtgc tatctcagag agcatggctt tcagagccac aagagacagc ctcactggct   136620
gtttcagctt gactgccatg caagaagag agcagaggga gaaccagccc cacccactta   136680
ttcatcttgt acaaaaaaaa agcacctacc agcctaggct acatagtgag acactatctc   136740
cacaaaaaac ccacgaaaac tagctgggta tggtggcaca tgcctacagt cccagctact   136800
ggtaaggctg tggtgggagg atctcttgag gccaggaagg agatccaggc tgcagtgagc   136860
caagattgca ccactgcact ccagtctgga caatcgagca agatccate tcaaacaata   136920 aaaaaaaaaa gcgtgtaacc tcctcagaag aaagatgtta taatctcagg cagcaggcaa   136980
gaaccaatcc aggctctaag c                                             137001
```

<210> SEQ ID NO 2
<211> LENGTH: 6794
<212> TYPE: DNA
<213> ORGANISM: homo sapiens

<400> SEQUENCE: 2

```
aagggccctg aaactaaatg tgtcccctta ggaaagcagg agttttcttg caagtggcaa      60
tcttctgctt atgtctcatt ggccagagct ggtcttacg gccacccctt gctgcgagca     120
aggctgggac attgagcatt ttgccgtcca acctctttag cagaataaac caaggggaa      180 gaacgttaat agtggctttt gagtcactag ttggcagtat ctgcccctct atctttccat     240
cctccccatg gagtttcaag gttcctttct cagtacttct tcaggctctg cacgttcatt     300
tggatcttgt gtcttggggt gaaaaactgg cccaagtgtc tccccaagca tccacctttg     360
gattaatttg gaaatggct gtcaagtgcc cgcctcttgc ttggtataat gctacagctt     420
tagaggacgc agcaggcatg ggccttgccg ctgaggttct tagcctcatg agaatatcca     480
```

```
gatcagattc tcttggctcc ttcttagagc cagtgatgca agacacttcc tgctcatctt    540
gtcgggacgg ttttacaagt tgcctgccat cctgagaaag tctacaaaac gatgccagac    600
ctcatgccag cttcccaagc cttgactctc agtgctccct caacaggatt ctggaagaat    660
ctcccaaaca agtcgcaatg ccctctggac cctgtgcagg catgagactc aagagcattg    720
gctcccaccc ctggtggagg gaacactgct ggggctggga tcttgcctgg ttgctccgcc    780
tgcacccaag acaaccataa ttaaaatgtc cttcattgaa cttggaaagc cttcaaagct    840
gacaactcct tatgtgtacc cggaaaggcc tgggagtgtg ccagggcatt gctcgggagg    900
gacgctgatt tggaagcatt tacctgatga gagactgaca gcagctcctg gtagccgagc    960
tttccctcct gcctctgctg tgaaggtgga cccatccaac agtcaaatgc ctgactctgg   1020
acaggagcgg acctatttat tgccatgcaa gggactctgc acttttgaat tgtgggtcat   1080
gggcttggat ttaggggtta gagctgggag aagtcttgga agtcacctag agatgacact   1140
gccattttgc agatgaggaa accgtccaat caaaatggac caaggacttg cccaaagcct   1200
cacagcaaaa ccataggccc ccgcactaac cccagagtcc ctgtgctgtc ttaaggatca   1260
aatagttgta agcaatcatc tggttttcag tatttcttct tttaaaatgc tggggccat   1320
gcccagcagt ctgtttcact gcagcgttta cacagggctg ccgggctttc ctggtggatg   1380
agctgggcgg ttcatgagcc agaaccactc agcagcatgt cagtgtgctt cctggggagc   1440
tggtagcagg ggctccgggc cctacttcag ggctgctttc tggcatatgg ctgatcccct   1500
cctcactcct cctccctgca ttgctcctgc gcaagaagca aaggtgaggg gctgggtatg   1560
gctcgtcctg gcccctctaa ggtggatctc ggtggtttct agatgtgaca gcacccttag   1620
tggatgaggg agctcccggc aagcaggctg ccgcgcagcc ccacacggag atcccagaag   1680
gaaccacagg tgagggtaag ccccagagac ccccaggcag tcaaggccct gctgggtgcc   1740
ccagctgacc tgtgacagaa gtgagggagc tttgcgtgtt tatcctcctg tggggcagga   1800
acatgggtgg attctggctc ctgggaatct tgggttgtga gtagctcgat gccttggtgc   1860
tcagttacct ccctggctgc ctgccagcct ctcagagcat ttagggcctt ctggacttct   1920
agatgctcct catcttgcct cagtcagcgc gtcagttcca gagacttctc tgcagggttt   1980
tctggggcag gtggtggcag acccgtgcct tcttgacacc tgaggtcagt ccaccctcct   2040
gctcagactg cccagcacag ggtcacctcc caagggtggg accccaagat cacctgagcg   2100
cacagagggt gcagatgact ggaccacacc ttttggtgat cttaatgagg tggtcccaga   2160
ggagctcaga catgcaatct agcatccagt tctgggactc tgtctccttt tcaaacgtat   2220
tcatgtagaa caggcatgac gagaatgcct tgtcaacatg ggtgatgggg aatcaatcag   2280
acagggcgcc gggctcaagg ctgcagtcac ccaagagtgg ctcagcccac caggccctag   2340
gaaacgcctg cacagcctgg agctcctgga gtcatttcct tcatgtcttc ttcactgcac   2400
ttacgtaaag atgccagcca ttggtttggt gatttggagg gtgccagtt gcccaacaag    2460
aaatgcagaa gaggcctagc caggatttca ccagcagtgg agagtagaga agatgtggcc   2520
agaaaagagt ttcctttccc tcctaaagat ggtactccct gcagctactg ggaagcctg    2580
cagcattctc tagggctctg tgtgttgaga gcagccccac cctggcccct tctgagtgca   2640
tttctgcttt gtgacttgat ccgtgaagtc ccctgagatg ggcagagggg atgtcctcga   2700
agctggggca gagcctcatc cttgaacgtg aaggacgttt gaagactgtg gcatgatcac   2760
aggatgagat cacagggaac ttgagtttct ctcctcctct cccttcacag ttatttcact   2820
gagggaaatc cctcccctgc ccagaatgaa aactctagcc aactcttgac ttttccatca   2880
```

```
ctccaaagta gttgaaagta cattagtctc cacagtggca aaacagtgtg caaaagctaa    2940
ataattagaa cagccagtcc catgtgacag tcaaagcttc taactccatt caaagttgca    3000
gccattcccc tcgagggctg gcagggaggg gaggggtaag agaaacagga aggttcttac    3060
tgagttggtc ctggtgtgag ctgcgtcaca ctccctgcag aggtttcaag agactctct    3120 ctctctctgt ctccatgggg accttatttg aattcttcta ctcttacccc agcctgccat    3180
ctccagctat cctcccctga agagcccttc tgctgcgctg gattctggtg gccatgtcat    3240
ctcctcggcc ccgtgggagt ctgaagatct ggctgcagcc tcacctctga ggtcctgcta    3300
gttgccacct cttaaacatg atctgaggct cccatgcact ctgacctgtg cccacatggg    3360
gcccacggga aacacgctgg caagcaaact gtgggtgtgc agacggttct cagggctgca    3420
gcacctgtcc tttgctctgc ccccaaagca aggccagccc atcttccatc ctctagtgtt    3480
ccttggtggg gccctgacca cagtccacca ggtccctaac cagaggggac acacaccagg    3540
tgtcctcaat gtattgcctt gaaacagttg tgctgggact gtgatggggg gtggccatgt    3600
agccaccccc accacccca agccactctc tccaaggaaa tcctcctaaa gatccctta    3660 catcctccat gtggtgggga ggttctagag ttgggtgcat gtgtcttcag ctactgacaa    3720
tgcagacctt agttggcacc tcgctctggc ctatcctgtt tgctgttctt ggcgctccag    3780
tgaaactccc catgggccat ccagttgggg tgcagtgtgg ccaccccctt gcaggttcct    3840
gccttgctgg agagcacagg gccctcctgg ctcttgtaaa acactcccca tggtacagag    3900
aggccagcag tgatgtgagg cccaacctcc ctccatggtg ttcccaagca gctccctttc    3960
tggggtcaag gggtggcaaa gacagtgcag cgtccaattt ctgactcaag ccgggcctgg    4020
ctatcgcagc tctgcactgt gtgtgacagc aaggcaactc acccagtgcc gtggcagtga    4080
ccgtgtccga ggaagcctcc tcacaccctc tgtctcaagg actctggcat ttagctggac    4140
ttgctgtagc tctgagcctt tctgccattg ccatcacctt gtcagaaact caggccgaat    4200
ctgcactcag agttgtgccc aggcagttga gccaacactt gctcagcgat attgtcacat    4260
gacaaggcac tgtcaccact gggcgtcgtg ggtagcgcag tgtcggctgg atggacccgg    4320
agggtgtctg tgtcatgcta gtgctagtga tgggagcccc gtgagcccat tgcccgccct    4380
cccatgccct cagcagctgc ctggggacag ccaatggcct gggtgtttct gaggctacca    4440
catggcttcc aggaaactcg agaacctttc tctcccttgc ctacactctt cacacaggcc    4500
tgtgctggcc agcggtgggg atccggcatt cctatcttag gtgcagaaag tgactgactc    4560
attgcaggcc tgggagataa gactgatggc ccagccagca agatgtatgg atttctcaga    4620
ggcagtggcc tctgtcattg tcctcaggaa atgctggtga ttctggtggc ctgaggtcaa    4680
tgcatgtcaa cgtggccaac ttgccttata aactttttt ctggacaatt gcgtacactg    4740
tcctgtaaca gtgtcctgtt gtttatgatg cagaaatagg tgtttttaaa gcctattgat    4800
tttggtacta ttaatgtggt caggaacttt ctcagtcttt cttgtttggg gtgagctgtg    4860
gcttcctaaa caggaaccca agacaccccc aaaagctgct caccagcact gccagcctcc    4920
ctcttaccaa gtagcacccg ttcaggacat tctgcgaaag gcatttgccc agaagttggg    4980
aggaaggaaa tgtaacattt tggggcacct accatatgcc aggcaccagg ctaaacgtgt    5040
tcacacaaat tctcttacta accctcacca tccttctaca agacaaacta gtatcttcat    5100
cttggggttc aagatgagga aatggaggct cagagaggtt gaatgaatgc cggtgcctgg    5160
atatgaaccc catctgcctg actccgcaac ccaggcaaag tctttccttg aacttcccag    5220
```

```
cagccactgc ttagacacag cctccacaac catggctcag cagcaaattg cttctctgac    5280
ctcactcagc ctgtgtgtcc ttgttgagtg aggcattcag gaccctggtc ccaaagtgga    5340
gaaagtcttt cctactaggt catagctaca cctgcatgtg ggtgctgtgc cttttgttta    5400
gtgaactttt atcaccagca tcctcagcaa tgacatttgc agagaagcca gagctgaggc    5460
accttggtat tcttgggatg tgactttcct gaatgtttaa gggaaaatgc ccgaaggtac    5520
agagagcttg gtttctagta aacaataact gtcttgcttt tacccccctt catttgctga    5580
cacatacacc agctgaagaa gcaggcattg agacacccc cagcctggaa gacgaagctg     5640
ctggtcacgt gacccaagct cgcatggtca gtaaaagcaa agacgggact ggaagcgatg    5700
acaaaaaagc caaggggggct gatggtaaaa cgaagatcgc cacaccgcgg ggagcagccc   5760
ctccaggcca aagggccag gccaacgcca ccaggattcc agcaaaaacc ccgcccgctc     5820
caaagacacc acccagctct ggtgaacctc caaaatcagg ggatcgcagc ggctacagca    5880
gccccggctc cccaggcact cccggcagcc gctcccgcac ccgtcccctt ccaaccccac    5940 ccaccccggga gcccaagaag gtggcagtgg tccgtactcc acccaagtcg ccgtcttccg    6000
ccaagagccg cctgcagaca gcccccgtgc ccatgccaga cctgaagaat gtcaagtcca    6060
agatcggctc cactgagaac ctgaagcacc agccgggagg cggaaggtg caaatagtct      6120 acaaaccagt tgacctgagc aaggtgacct ccaagtgtgg ctcattaggc aacatccatc    6180
ataaaccagg aggtggccag gtggaagtaa aatctgagaa gcttgacttc aaggacagag    6240
tccagtcgaa gattgggtcc ctggacaata tcacccacgt ccctggcgga ggaaataaaa    6300
agattgaaac ccacaagctg accttccgcg agaacgccaa agccaagaca gaccacgggg    6360
cggagatcgt gtacaagtcg ccagtggtgt ctggggacac gtctccacgg catctcagca    6420
atgtctcctc caccggcagc atcgacatgg tagactcgcc ccagctcgcc acgctagctg    6480
acgaggtgtc tgcctccctg gccaagcagg gtttgtgatc aggcccctgg ggcggtcaat    6540
aattgtggag aggagagaat gagagagtgt ggaaaaaaaa agaataatga cccggccccc    6600
gccctctgcc cccagctgct cctcgcagtt cggttaattg gttaatcact taacctgctt    6660
ttgtcactcg gctttggctc gggacttcaa aatcagtgat gggagtaaga gcaaatttca    6720
tctttccaaa ttgatgggtg ggctagtaat aaaatattta aaaaaaaaca ttcaaaaaaa    6780
aaaaaaaaaa aagg                                                      6794
```

<210> SEQ ID NO 3
<211> LENGTH: 6816
<212> TYPE: DNA
<213> ORGANISM: homo sapiens
<220> FEATURE:
<221> NAME/KEY: CDS
<222> LOCATION: (323)...(2653)

<400> SEQUENCE: 3

```
ggacggccga gcggcagggc gctcgcgcgc gcccactagt ggccggagga gaaggctccc     60
gcggaggccg cgctgcccgc cccctcccct ggggaggctc gcgttcccgc tgctcgcgcc    120
tgcgccgccc gccggcctca ggaacgcgcc ctcttcgccg gcgcgcgccc tcgcagtcac    180
cgccacccac cagctccggc accaacagca gcgccgctgc caccgccgcac cttctgccgc    240 cgccaccaca gccaccttct cctcctccgc tgtcctctcc cgtcctcgcc tctgtcgact    300
atcaggtgaa ctttgaacca gg atg gct gag ccc cgc cag gag ttc gaa gtg      352
                         Met Ala Glu Pro Arg Gln Glu Phe Glu Val
                          1               5                  10
```

```
atg gaa gat cac gct ggg acg tac ggg ttg ggg gac agg aaa gat cag      400
Met Glu Asp His Ala Gly Thr Tyr Gly Leu Gly Asp Arg Lys Asp Gln
             15                  20                  25 ggg ggc tac acc atg cac caa gac caa gag ggt gac acg gac gct ggc      448
Gly Gly Tyr Thr Met His Gln Asp Gln Glu Gly Asp Thr Asp Ala Gly
         30                  35                  40 ctg aaa gaa tct ccc ctg cag acc ccc act gag gac gga tct gag gaa      496
Leu Lys Glu Ser Pro Leu Gln Thr Pro Thr Glu Asp Gly Ser Glu Glu
             45                  50                  55 ccg ggc tct gaa acc tct gat gct aag agc act cca aca gcg gaa gat      544
Pro Gly Ser Glu Thr Ser Asp Ala Lys Ser Thr Pro Thr Ala Glu Asp
         60                  65                  70 gtg aca gca ccc tta gtg gat gag gga gct ccc ggc aag cag gct gcc      592
Val Thr Ala Pro Leu Val Asp Glu Gly Ala Pro Gly Lys Gln Ala Ala
 75                  80                  85                  90 gcg cag ccc cac acg gag atc cca gaa gga acc aca gct gaa gaa gca      640
Ala Gln Pro His Thr Glu Ile Pro Glu Gly Thr Thr Ala Glu Glu Ala
                 95                 100                 105 ggc att gga gac acc ccc agc ctg gaa gac gaa gct gct ggt cac gtg      688
Gly Ile Gly Asp Thr Pro Ser Leu Glu Asp Glu Ala Ala Gly His Val
            110                 115                 120 acc caa gag cct gaa agt ggt aag gtg gtc cag gaa ggc ttc ctc cga      736
Thr Gln Glu Pro Glu Ser Gly Lys Val Val Gln Glu Gly Phe Leu Arg
            125                 130                 135 gag cca ggc ccc cca ggt ctg agc cac cag ctc atg tcc ggc atg cct      784
Glu Pro Gly Pro Pro Gly Leu Ser His Gln Leu Met Ser Gly Met Pro
        140                 145                 150 ggg gct ccc ctc ctg cct gag ggc ccc aga gag gcc aca cgc caa cct      832
Gly Ala Pro Leu Leu Pro Glu Gly Pro Arg Glu Ala Thr Arg Gln Pro
155                 160                 165                 170 tcg ggg aca gga cct gag gac aca gag ggc ggc cgc cac gcc cct gag      880
Ser Gly Thr Gly Pro Glu Asp Thr Glu Gly Gly Arg His Ala Pro Glu
            175                 180                 185 ctg ctc aag cac cag ctt cta gga gac ctg cac cag gag ggg ccg ccg      928
Leu Leu Lys His Gln Leu Leu Gly Asp Leu His Gln Glu Gly Pro Pro
            190                 195                 200 ctg aag ggg gca ggg ggc aaa gag agg ccg ggg agc aag gag gag gtg      976
Leu Lys Gly Ala Gly Gly Lys Glu Arg Pro Gly Ser Lys Glu Glu Val
        205                 210                 215 gat gaa gac cgc gac gtc gat gag tcc tcc ccc caa gac tcc cct ccc     1024
Asp Glu Asp Arg Asp Val Asp Glu Ser Ser Pro Gln Asp Ser Pro Pro
        220                 225                 230 tcc aag gcc tcc cca gcc caa gat ggg cgg cct ccc cag aca gcc gcc     1072
Ser Lys Ala Ser Pro Ala Gln Asp Gly Arg Pro Pro Gln Thr Ala Ala
235                 240                 245                 250 aga gaa gcc acc agc atc cca ggc ttc cca gcg gag ggt gcc atc ccc     1120
Arg Glu Ala Thr Ser Ile Pro Gly Phe Pro Ala Glu Gly Ala Ile Pro
            255                 260                 265 ctc cct gtg gat ttc ctc tcc aaa gtt tcc aca gag atc cca gcc tca     1168
Leu Pro Val Asp Phe Leu Ser Lys Val Ser Thr Glu Ile Pro Ala Ser
            270                 275                 280 gag ccc gac ggg ccc agt gta ggg cgg gcc aaa ggg cag gat gcc ccc     1216
Glu Pro Asp Gly Pro Ser Val Gly Arg Ala Lys Gly Gln Asp Ala Pro
        285                 290                 295 ctg gag ttc acg ttt cac gtg gaa atc aca ccc aac gtg cag aag gag     1264
Leu Glu Phe Thr Phe His Val Glu Ile Thr Pro Asn Val Gln Lys Glu
        300                 305                 310 cag gcg cac tcg gag gag cat ttg gga agg gct gca ttt cca ggg gcc     1312
Gln Ala His Ser Glu Glu His Leu Gly Arg Ala Ala Phe Pro Gly Ala
        315                 320                 325                 330
```

-continued

| | | | | | | | | | | | | | | | |
|---|---|---|---|---|---|---|---|---|---|---|---|---|---|---|---|
| cct | gga | gag | ggg | cca | gag | gcc | cgg | ggc | ccc | tct | ttg | gga | gag | gac | aca | 1360 |
| Pro | Gly | Glu | Gly | Pro | Glu | Ala | Arg | Gly | Pro | Ser | Leu | Gly | Glu | Asp | Thr | |
| | | | | 335 | | | | | 340 | | | | | 345 | | |

| aaa | gag | gct | gac | ctt | cca | gag | ccc | tct | gaa | aag | cag | cct | gct | gct | gct | 1408 |
| Lys | Glu | Ala | Asp | Leu | Pro | Glu | Pro | Ser | Glu | Lys | Gln | Pro | Ala | Ala | Ala | |
| | | | 350 | | | | | 355 | | | | | 360 | | | |

| ccg | cgg | ggg | aag | ccc | gtc | agc | cgg | gtc | cct | caa | ctc | aaa | gct | cgc | atg | 1456 |
| Pro | Arg | Gly | Lys | Pro | Val | Ser | Arg | Val | Pro | Gln | Leu | Lys | Ala | Arg | Met | |
| | | 365 | | | | | 370 | | | | | 375 | | | | |

| gtc | agt | aaa | agc | aaa | gac | ggg | act | gga | agc | gat | gac | aaa | aaa | gcc | aag | 1504 |
| Val | Ser | Lys | Ser | Lys | Asp | Gly | Thr | Gly | Ser | Asp | Asp | Lys | Lys | Ala | Lys | |
| | 380 | | | | | 385 | | | | | 390 | | | | | |

| aca | tcc | aca | cgt | tcc | tct | gct | aaa | acc | ttg | aaa | aat | agg | cct | tgc | ctt | 1552 |
| Thr | Ser | Thr | Arg | Ser | Ser | Ala | Lys | Thr | Leu | Lys | Asn | Arg | Pro | Cys | Leu | |
| 395 | | | | | 400 | | | | | 405 | | | | | 410 | |

| agc | ccc | aaa | cac | ccc | act | cct | ggt | agc | tca | gac | cct | ctg | atc | caa | ccc | 1600 |
| Ser | Pro | Lys | His | Pro | Thr | Pro | Gly | Ser | Ser | Asp | Pro | Leu | Ile | Gln | Pro | |
| | | | | 415 | | | | | 420 | | | | | 425 | | |

| tcc | agc | cct | gct | gtg | tgc | cca | gag | cca | cct | tcc | tct | cct | aaa | tac | gtc | 1648 |
| Ser | Ser | Pro | Ala | Val | Cys | Pro | Glu | Pro | Pro | Ser | Ser | Pro | Lys | Tyr | Val | |
| | | | 430 | | | | | 435 | | | | | 440 | | | |

| tct | tct | gtc | act | tcc | cga | act | ggc | agt | tct | gga | gca | aag | gag | atg | aaa | 1696 |
| Ser | Ser | Val | Thr | Ser | Arg | Thr | Gly | Ser | Ser | Gly | Ala | Lys | Glu | Met | Lys | |
| | | 445 | | | | | 450 | | | | | 455 | | | | |

| ctc | aag | ggg | gct | gat | ggt | aaa | acg | aag | atc | gcc | aca | ccg | cgg | gga | gca | 1744 |
| Leu | Lys | Gly | Ala | Asp | Gly | Lys | Thr | Lys | Ile | Ala | Thr | Pro | Arg | Gly | Ala | |
| | 460 | | | | | 465 | | | | | 470 | | | | | |

| gcc | cct | cca | ggc | cag | aag | ggc | cag | gcc | aac | gcc | acc | agg | att | cca | gca | 1792 |
| Ala | Pro | Pro | Gly | Gln | Lys | Gly | Gln | Ala | Asn | Ala | Thr | Arg | Ile | Pro | Ala | |
| 475 | | | | | 480 | | | | | 485 | | | | | 490 | |

| aaa | acc | ccg | ccc | gct | cca | aag | aca | cca | ccc | agc | tct | gcg | act | aag | caa | 1840 |
| Lys | Thr | Pro | Pro | Ala | Pro | Lys | Thr | Pro | Pro | Ser | Ser | Ala | Thr | Lys | Gln | |
| | | | | 495 | | | | | 500 | | | | | 505 | | |

| gtc | cag | aga | aga | cca | ccc | cct | gca | ggg | ccc | aga | tct | gag | aga | ggt | gaa | 1888 |
| Val | Gln | Arg | Arg | Pro | Pro | Pro | Ala | Gly | Pro | Arg | Ser | Glu | Arg | Gly | Glu | |
| | | | 510 | | | | | 515 | | | | | 520 | | | |

| cct | cca | aaa | tca | ggg | gat | cgc | agc | ggc | tac | agc | agc | ccc | ggc | tcc | cca | 1936 |
| Pro | Pro | Lys | Ser | Gly | Asp | Arg | Ser | Gly | Tyr | Ser | Ser | Pro | Gly | Ser | Pro | |
| | | 525 | | | | | 530 | | | | | 535 | | | | |

| ggc | act | ccc | ggc | agc | cgc | tcc | cgc | acc | ccg | tcc | ctt | cca | acc | cca | ccc | 1984 |
| Gly | Thr | Pro | Gly | Ser | Arg | Ser | Arg | Thr | Pro | Ser | Leu | Pro | Thr | Pro | Pro | |
| | 540 | | | | | 545 | | | | | 550 | | | | | |

| acc | cgg | gag | ccc | aag | aag | gtg | gca | gtg | gtc | cgt | act | cca | ccc | aag | tcg | 2032 |
| Thr | Arg | Glu | Pro | Lys | Lys | Val | Ala | Val | Val | Arg | Thr | Pro | Pro | Lys | Ser | |
| 555 | | | | | 560 | | | | | 565 | | | | | 570 | |

| ccg | tct | tcc | gcc | aag | agc | cgc | ctg | cag | aca | gcc | ccc | gtg | ccc | atg | cca | 2080 |
| Pro | Ser | Ser | Ala | Lys | Ser | Arg | Leu | Gln | Thr | Ala | Pro | Val | Pro | Met | Pro | |
| | | | | 575 | | | | | 580 | | | | | 585 | | |

| gac | ctg | aag | aat | gtc | aag | tcc | aag | atc | ggc | tcc | act | gag | aac | ctg | aag | 2128 |
| Asp | Leu | Lys | Asn | Val | Lys | Ser | Lys | Ile | Gly | Ser | Thr | Glu | Asn | Leu | Lys | |
| | | | 590 | | | | | 595 | | | | | 600 | | | |

| cac | cag | ccg | gga | ggc | ggg | aag | gtg | cag | ata | att | aat | aag | aag | ctg | gat | 2176 |
| His | Gln | Pro | Gly | Gly | Gly | Lys | Val | Gln | Ile | Ile | Asn | Lys | Lys | Leu | Asp | |
| | | 605 | | | | | 610 | | | | | 615 | | | | |

| ctt | agc | aac | gtc | cag | tcc | aag | tgt | ggc | tca | aag | gat | aat | atc | aaa | cac | 2224 |
| Leu | Ser | Asn | Val | Gln | Ser | Lys | Cys | Gly | Ser | Lys | Asp | Asn | Ile | Lys | His | |
| | 620 | | | | | 625 | | | | | 630 | | | | | |

| gtc | ccg | gga | ggc | ggc | agt | gtg | caa | ata | gtc | tac | aaa | cca | gtt | gac | ctg | 2272 |
| Val | Pro | Gly | Gly | Gly | Ser | Val | Gln | Ile | Val | Tyr | Lys | Pro | Val | Asp | Leu | |

```
                635                 640                 645                 650
agc aag gtg acc tcc aag tgt ggc tca tta ggc aac atc cat cat aaa        2320
Ser Lys Val Thr Ser Lys Cys Gly Ser Leu Gly Asn Ile His His Lys
                        655                 660                 665 cca gga ggt ggc cag gtg gaa gta aaa tct gag aag ctt gac ttc aag        2368
Pro Gly Gly Gly Gln Val Glu Val Lys Ser Glu Lys Leu Asp Phe Lys
            670                 675                 680 gac aga gtc cag tcg aag att ggg tcc ctg gac aat atc acc cac gtc        2416
Asp Arg Val Gln Ser Lys Ile Gly Ser Leu Asp Asn Ile Thr His Val
        685                 690                 695 cct ggc gga gga aat aaa aag att gaa acc cac aag ctg acc ttc cgc        2464
Pro Gly Gly Gly Asn Lys Lys Ile Glu Thr His Lys Leu Thr Phe Arg
    700                 705                 710 gag aac gcc aaa gcc aag aca gac cac ggg gcg gag atc gtg tac aag        2512
Glu Asn Ala Lys Ala Lys Thr Asp His Gly Ala Glu Ile Val Tyr Lys
715                 720                 725                 730 tcg cca gtg gtg tct ggg gac acg tct cca cgg cat ctc agc aat gtc        2560
Ser Pro Val Val Ser Gly Asp Thr Ser Pro Arg His Leu Ser Asn Val
                735                 740                 745 tcc tcc acc ggc agc atc gac atg gta gac tcg ccc cag ctc gcc acg        2608
Ser Ser Thr Gly Ser Ile Asp Met Val Asp Ser Pro Gln Leu Ala Thr
            750                 755                 760 cta gct gac gag gtg tct gcc tcc ctg gcc aag cag ggt ttg tga            2653
Leu Ala Asp Glu Val Ser Ala Ser Leu Ala Lys Gln Gly Leu
        765                 770                 775 tcaggcccct ggggcggtca ataattgtgg agaggagaga atgagagagt gtggaaaaaa     2713
aaagaataat gacccggccc ccgccctctg cccccagctg ctcctcgcag ttcggttaat     2773
tggttaatca cttaacctgc ttttgtcact cggctttggc tcgggacttc aaaatcagtg     2833
atgggagtaa gagcaaattt catctttcca aattgatggg tgggctagta ataaaatatt     2893
taaaaaaaaa cattcaaaaa catggccaca tccaacattt cctcaggcaa ttccttttga     2953
ttctttttc ttcccctcc atgtagaaga gggagaagga gaggctctga aagctgcttc       3013
tgggggattt caagggactg ggggtgccaa ccacctctgg ccctgttgtg ggggtgtcac     3073
agaggcagtg gcagcaacaa aggatttgaa acttggtgtg ttcgtggagc acaggcaga     3133
cgatgtcaac cttgtgtgag tgtgacgggg gttggggtgg ggcgggaggc cacggggag     3193
gccgaggcag gggctgggca gaggggagag gaagcacaag aagtgggagt gggagaggaa     3253
gccacgtgct ggagagtaga catccccctc cttgccgctg ggagagccaa ggcctatgcc     3313
acctgcagcg tctgagcggc cgcctgtcct tggtggccgg gggtggggc ctgctgtggg     3373
tcagtgtgcc accctctgca gggcagcctg tgggagaagg gacagcgggt aaaaagagaa     3433
ggcaagctgg caggagggtg gcacttcgtg gatgacctcc ttagaaaaga ctgaccttga     3493
tgtcttgaga gcgctggcct cttcctccct ccctgcaggg tagggggcct gagttgaggg     3553
gcttccctct gctccacaga aaccctgttt tattgagttc tgaaggttgg aactgctgcc     3613
atgattttgg ccactttgca gacctgggac tttagggcta accagttctc tttgtaagga     3673
cttgtgcctc ttgggagacg tccacccgtt tccaagcctg ggccactggc atctctggag     3733
tgtgtggggg tctgggaggc aggtcccgag cccctgtcc ttcccacggc cactgcagtc      3793
accccgtctg cgccgctgtg ctgttgtctg ccgtgagagc ccaatcactg cctatacccc     3853
tcatcacacg tcacaatgtc ccgaattccc agcctcacca cccctctca gtaatgaccc     3913
tggttggttg caggaggtac ctactccata ctgagggtga aattaaggga aggcaaagtc     3973
caggcacaag agtgggaccc cagcctctca ctctcagttc cactcatcca actgggaccc     4033
```

```
tcaccacgaa tctcatgatc tgattcggtt ccctgtctcc tcctcccgtc acagatgtga    4093
gccagggcac tgctcagctg tgaccctagg tgtttctgcc ttgttgacat ggagagagcc    4153
ctttcccctg agaaggcctg gccccttcct gtgctgagcc cacagcagca ggctgggtgt    4213
cttggttgtc agtggtggca ccaggatgga agggcaaggc acccagggca ggcccacagt    4273
cccgctgtcc cccacttgca ccctagcttg tagctgccaa cctcccagac agcccagccc    4333
gctgctcagc tccacatgca tagtatcagc cctccacacc cgacaaaggg gaacacaccc    4393
ccttggaaat ggttcttttc ccccagtccc agctggaagc catgctgtct gttctgctgg    4453
agcagctgaa catatacata gatgttgccc tgccctcccc atctgcaccc tgttgagttg    4513
tagttggatt tgtctgttta tgcttggatt caccagagtg actatgatag tgaaaagaaa    4573
aaaaaaaaaa aaaaggacg catgtatctt gaaatgcttg taaagaggtt tctaacccac    4633
cctcacgagg tgtctctcac ccccacactg ggactcgtgt ggcctgtgtg gtgccaccct    4693 gctgggcct cccaagtttt gaaaggcttt cctcagcacc tgggacccaa cagagaccag    4753
cttctagcag ctaaggaggc cgttcagctg tgacgaaggc ctgaagcaca ggattaggac    4813
tgaagcgatg atgtcccctt ccctacttcc ccttgggggct ccctgtgtca gggcacagac    4873
taggtcttgt ggctggtctg gcttgcggcg cgaggatggt tctctctggt catagcccga    4933
agtctcatgg cagtcccaaa ggaggcttac aactcctgca tcacaagaaa aaggaagcca    4993
ctgccagctg gggggatctg cagctcccag aagctccgtg agcctcagcc acccctcaga    5053
ctgggttcct ctccaagctc gccctctgga ggggcagcgc agcctccac caagggccct    5113 gcgaccacag cagggattgg gatgaattgc ctgtcctgga tctgctctag aggcccaagc    5173
tgcctgcctg aggaaggatg acttgacaag tcaggagaca ctgttcccaa gccttgacc    5233 agagcacctc agcccgctga ccttgcacaa actccatctg ctgccatgag aaaagggaag    5293 ccgccttgc aaaacattgc tgcctaaaga aactcagcag cctcaggccc aattctgcca    5353
cttctggttt gggtacagtt aaaggcaacc ctgagggact tggcagtaga aatccagggc    5413
ctcccctggg gctggcagct tcgtgtgcag ctagagcttt acctgaaagg aagtctctgg    5473
gcccagaact ctccaccaag agcctccctg ccgttcgctg agtcccagca attctcctaa    5533
gttgaaggga tctgagaagg agaaggaaat gtggggtaga tttggtggtg gttagagata    5593 tgccccctc attactgcca acagtttcgg ctgcatttct tcacgcacct cggttcctct    5653
tcctgaagtt cttgtgccct gctcttcagc accatgggcc ttcttatacg gaaggctctg    5713
ggatctcccc cttgtgggc aggctcttgg ggccagccta agatcatggt ttagggtgat    5773
cagtgctggc agataaattg aaaaggcacg ctggcttgtg atcttaaatg aggacaatcc    5833
ccccagggct gggcactcct ccctcccct cacttctccc acctgcagag ccagtgtcct    5893
tgggtgggct agataggata tactgtatgc cggctccttc aagctgctga ctcactttat    5953
caatagttcc atttaaattg acttcagtgg tgagactgta tcctgtttgc tattgcttgt    6013
tgtgctatgg ggggagggg gaggaatgtg taagatagtt aacatgggca aagggagatc    6073
ttggggtgca gcacttaaac tgcctcgtaa ccctttttcat gatttcaacc acatttgcta    6133
gagggaggga gcagccacgg agttagaggc ccttgggggtt tctcttttcc actgacaggc    6193
tttcccaggc agctggctag ttcattccct ccccagccag gtgcaggcgt aggaatatgg    6253
acatctggtt gctttggcct gctgccctct ttcaggggtc ctaagcccac aatcatgcct    6313
ccctaagacc ttggcatcct tccctctaag ccgttggcac ctctgtgcca cctctcacac    6373
```

```
tggctccaga cacacagcct gtgcttttgg agctgagatc actcgcttca ccctcctcat    6433
ctttgttctc caagtaaagc cacgaggtcg gggcgagggc agaggtgatc acctgcgtgt    6493
cccatctaca gacctgcagc ttcataaaac ttctgatttc tcttcagctt tgaaaagggt    6553
taccctgggc actggcctag agcctcacct cctaatagac ttagccccat gagtttgcca    6613
tgttgagcag gactatttct ggcacttgca agtcccatga tttcttcggt aattctgagg    6673 gtgggggag ggacatgaaa tcatcttagc ttagctttct gtctgtgaat gtctatatag     6733
tgtattgtgt gttttaacaa atgatttaca ctgactgttg ctgtaaaagt gaatttggaa    6793
ataaagttat tactctgatt aaa                                            6816

<210> SEQ ID NO 4
<211> LENGTH: 5724
<212> TYPE: DNA
<213> ORGANISM: homo sapiens
<220> FEATURE:
<221> NAME/KEY: CDS
<222> LOCATION: (323)...(1561)

<400> SEQUENCE: 4
ggacggccga gcggcagggc gctcgcgcgc gcccactagt ggccggagga gaaggctccc    60
gcggaggccg cgctgcccgc cccctcccct ggggaggctc gcgttcccgc tgctcgcgcc   120
tgcgccgccc gccggcctca ggaacgcgcc ctcttgccg gcgcgcgccc tcgcagtcac    180
cgccacccac cagctccggc accaacagca gcgccgctgc caccgcccac cttctgccgc   240
cgccaccaca gccaccttct cctcctccgc tgtcctctcc cgtcctcgcc tctgtcgact   300
atcaggtgaa ctttgaacca gg atg gct gag ccc cgc cag gag ttc gaa gtg   352
                          Met Ala Glu Pro Arg Gln Glu Phe Glu Val
                           1               5                  10 atg gaa gat cac gct ggg acg tac ggg ttg ggg gac agg aaa gat cag    400
Met Glu Asp His Ala Gly Thr Tyr Gly Leu Gly Asp Arg Lys Asp Gln
              15                  20                  25 ggg ggc tac acc atg cac caa gac caa gag ggt gac acg gac gct ggc    448
Gly Gly Tyr Thr Met His Gln Asp Gln Glu Gly Asp Thr Asp Ala Gly
         30                  35                  40 ctg aaa gaa tct ccc ctg cag acc ccc act gag gac gga tct gag gaa    496
Leu Lys Glu Ser Pro Leu Gln Thr Pro Thr Glu Asp Gly Ser Glu Glu
     45                  50                  55 ccg ggc tct gaa acc tct gat gct aag agc act cca aca gcg gaa gct    544
Pro Gly Ser Glu Thr Ser Asp Ala Lys Ser Thr Pro Thr Ala Glu Ala
 60                  65                  70 gaa gaa gca ggc att gga gac acc ccc agc ctg gaa gac gaa gct gct    592
Glu Glu Ala Gly Ile Gly Asp Thr Pro Ser Leu Glu Asp Glu Ala Ala
 75                  80                  85                  90 ggt cac gtg acc caa gct cgc atg gtc agt aaa agc aaa gac ggg act    640
Gly His Val Thr Gln Ala Arg Met Val Ser Lys Ser Lys Asp Gly Thr
                 95                 100                 105 gga agc gat gac aaa aaa gcc aag ggg gct gat ggt aaa acg aag atc    688
Gly Ser Asp Asp Lys Lys Ala Lys Gly Ala Asp Gly Lys Thr Lys Ile
             110                 115                 120 gcc aca ccg cgg gga gca gcc cct cca ggc cag aag ggc cag gcc aac    736
Ala Thr Pro Arg Gly Ala Ala Pro Pro Gly Gln Lys Gly Gln Ala Asn
         125                 130                 135 gcc acc agg att cca gca aaa acc ccg ccc gct cca aag aca cca ccc    784
Ala Thr Arg Ile Pro Ala Lys Thr Pro Pro Ala Pro Lys Thr Pro Pro
     140                 145                 150 agc tct ggt gaa cct cca aaa tca ggg gat cgc agc ggc tac agc agc    832
Ser Ser Gly Glu Pro Pro Lys Ser Gly Asp Arg Ser Gly Tyr Ser Ser
```

```
             155                 160                 165                 170
ccc ggc tcc cca ggc act ccc ggc agc cgc tcc cgc acc ccg tcc ctt       880
Pro Gly Ser Pro Gly Thr Pro Gly Ser Arg Ser Arg Thr Pro Ser Leu
                175                 180                 185 cca acc cca ccc acc cgg gag ccc aag aag gtg gca gtg gtc cgt act       928
Pro Thr Pro Pro Thr Arg Glu Pro Lys Lys Val Ala Val Val Arg Thr
                190                 195                 200 cca ccc aag tcg ccg tct tcc gcc aag agc cgc ctg cag aca gcc ccc       976
Pro Pro Lys Ser Pro Ser Ser Ala Lys Ser Arg Leu Gln Thr Ala Pro
                205                 210                 215 gtg ccc atg cca gac ctg aag aat gtc aag tcc aag atc ggc tcc act      1024
Val Pro Met Pro Asp Leu Lys Asn Val Lys Ser Lys Ile Gly Ser Thr
            220                 225                 230 gag aac ctg aag cac cag ccg gga ggc ggg aag gtg cag ata att aat      1072
Glu Asn Leu Lys His Gln Pro Gly Gly Gly Lys Val Gln Ile Ile Asn
235                 240                 245                 250 aag aag ctg gat ctt agc aac gtc cag tcc aag tgt ggc tca aag gat      1120
Lys Lys Leu Asp Leu Ser Asn Val Gln Ser Lys Cys Gly Ser Lys Asp
                255                 260                 265 aat atc aaa cac gtc ccg gga ggc ggc agt gtg caa ata gtc tac aaa      1168
Asn Ile Lys His Val Pro Gly Gly Gly Ser Val Gln Ile Val Tyr Lys
                270                 275                 280 cca gtt gac ctg agc aag gtg acc tcc aag tgt ggc tca tta ggc aac      1216
Pro Val Asp Leu Ser Lys Val Thr Ser Lys Cys Gly Ser Leu Gly Asn
            285                 290                 295 atc cat cat aaa cca gga ggt ggc cag gtg gaa gta aaa tct gag aag      1264
Ile His His Lys Pro Gly Gly Gly Gln Val Glu Val Lys Ser Glu Lys
300                 305                 310 ctt gac ttc aag gac aga gtc cag tcg aag att ggg tcc ctg gac aat      1312
Leu Asp Phe Lys Asp Arg Val Gln Ser Lys Ile Gly Ser Leu Asp Asn
315                 320                 325                 330 atc acc cac gtc cct ggc gga gga aat aaa aag att gaa acc cac aag      1360
Ile Thr His Val Pro Gly Gly Gly Asn Lys Lys Ile Glu Thr His Lys
                335                 340                 345 ctg acc ttc cgc gag aac gcc aaa gcc aag aca gac cac ggg gcg gag      1408
Leu Thr Phe Arg Glu Asn Ala Lys Ala Lys Thr Asp His Gly Ala Glu
                350                 355                 360 atc gtg tac aag tcg cca gtg gtg tct ggg gac acg tct cca cgg cat      1456
Ile Val Tyr Lys Ser Pro Val Val Ser Gly Asp Thr Ser Pro Arg His
            365                 370                 375 ctc agc aat gtc tcc tcc acc ggc agc atc gac atg gta gac tcg ccc      1504
Leu Ser Asn Val Ser Ser Thr Gly Ser Ile Asp Met Val Asp Ser Pro
            380                 385                 390 cag ctc gcc acg cta gct gac gag gtg tct gcc tcc ctg gcc aag cag      1552
Gln Leu Ala Thr Leu Ala Asp Glu Val Ser Ala Ser Leu Ala Lys Gln
395                 400                 405                 410 ggt ttg tga tcaggcccct ggggcggtca ataattgtgg agaggagaga              1601
Gly Leu atgagagagt gtggaaaaaa aaagaataat gacccggccc cgccctctg ccccagctg     1661 ctcctcgcag ttcggttaat tggttaatca cttaacctgc ttttgtcact cggctttggc    1721
tcgggacttc aaaatcagtg atgggagtaa gagcaaattt catctttcca aattgatggg    1781
tgggctagta ataaaatatt taaaaaaaaa cattcaaaaa catggccaca tccaacattt    1841
cctcaggcaa ttccttttga ttcttttttc ttccccctcc atgtagaaga gggagaagga    1901
gaggctctga aagctgcttc tgggggattt caagggactg ggggtgccaa ccacctctgg    1961
ccctgttgtg ggggtgtcac agaggcagtg gcagcaacaa aggatttgaa acttggtgtg    2021
```

-continued

```
ttcgtggagc cacaggcaga cgatgtcaac cttgtgtgag tgtgacgggg gttggggtgg    2081
ggcgggaggc cacggggggag gccgaggcag gggctgggca gaggggagag gaagcacaag    2141
aagtgggagt gggagaggaa gccacgtgct ggagagtaga catcccccte cttgccgctg    2201 ggagagccaa ggcctatgcc acctgcagcg tctgagcggc cgcctgtcct tggtggccgg    2261 gggtggggc ctgctgtggg tcagtgtgcc accctctgca gggcagcctg tgggagaagg    2321
gacagcgggt aaaagagaa ggcaagctgg caggagggtg gcacttcgtg gatgacctcc    2381
ttagaaaaga ctgaccttga tgtcttgaga gcgctggcct cttcctccct ccctgcaggg    2441 taggggcct gagttgaggg gcttccctct gctccacaga aaccctgttt tattgagttc    2501
tgaaggttgg aactgctgcc atgattttgg ccactttgca gacctgggac tttagggcta    2561
accagttctc tttgtaagga cttgtgcctc ttgggagacg tccacccgtt tccaagcctg    2621
ggccactggc atctctggag tgtgtggggg tctggaggc aggtcccgag cccctgtcc    2681 ttcccacggc cactgcagtc accccgtctg cgccgctgtg ctgttgtctg ccgtgagagc    2741
ccaatcactg cctataccc tcatcacacg tcacaatgtc ccgaattccc agcctcacca    2801 cccttctca gtaatgaccc tggttggttg caggaggtac ctactccata ctgagggtga    2861
aattaaggga aggcaaagtc caggcacaag agtgggaccc cagcctctca ctctcagttc    2921
cactcatcca actgggaccc tcaccacgaa tctcatgatc tgattcggtt ccctgtctcc    2981
tcctcccgtc acagatgtga gccagggcac tgctcagctg tgaccctagg tgtttctgcc    3041
ttgttgacat ggagagagcc ctttcccctg agaaggcctg gccccttcct gtgctgagcc    3101
cacagcagca ggctgggtgt cttggttgtc agtggtggca ccaggatgga agggcaaggc    3161
acccagggca ggcccacagt cccgctgtcc cccacttgca ccctagcttg tagctgccaa    3221
cctcccagac agcccagccc gctgctcagc tccacatgca tagtatcagc cctccacacc    3281
cgacaaaggg gaacacaccc ccttggaaat ggttcttttc ccccagtccc agctggaagc    3341
catgctgtct gttctgctgg agcagctgaa catatacata gatgttgccc tgccctcccc    3401
atctgcaccc tgttgagttg tagttggatt tgtctgttta tgcttggatt caccagagtg    3461
actatgatag tgaaaagaaa aaaaaaaaa aaaaggacg catgtatctt gaaatgcttg    3521
taaagaggtt tctaacccac cctcacgagg tgtctctcac ccccacactg ggactcgtgt    3581
ggcctgtgtg gtgccaccct gctggggcct cccaagtttt gaaaggcttt cctcagcacc    3641
tgggacccaa cagagaccag cttctagcag ctaaggaggc cgttcagctg tgacgaaggc    3701
ctgaagcaca ggattaggac tgaagcgatg atgtccccttt ccctacttcc ccttggggct    3761
ccctgtgtca gggcacagac taggtcttgt ggctggtctg gcttgcggcg cgaggatggt    3821
tctctctggt catagcccga agtctcatgg cagtcccaaa ggaggcttac aactcctgca    3881
tcacaagaaa aaggaagcca ctgccagctg ggggatctg cagctcccag aagctccgtg    3941
agcctcagcc cccctcaga ctgggttcct ctccaagctc gccctctgga ggggcagcgc    4001
agcctcccac caagggccct gcgaccacag cagggattgg gatgaattgc ctgtcctgga    4061
tctgctctag aggccaagc tgcctgcctg aggaaggatg acttgacaag tcaggagaca    4121
ctgttcccaa agccttgacc agagcacctc agcccgctga ccttgcacaa actccatctg    4181
ctgccatgag aaaagggaag ccgcctttgc aaaacattgc tgcctaaaga aactcagcag    4241
cctcaggccc aattctgcca cttctggttt gggtacagtt aaaggcaacc ctgagggact    4301
tggcagtaga aatccagggc ctcccctggg gctggcagct tcgtgtgcag ctagagcttt    4361
acctgaaagg aagtctctgg gcccagaact ctccaccaag agcctccctg ccgttcgctg    4421
```

```
agtcccagca attctcctaa gttgaaggga tctgagaagg agaaggaaat gtggggtaga      4481
tttggtggtg gttagagata tgccccctc attactgcca acagtttcgg ctgcatttct      4541
tcacgcacct cggttcctct tcctgaagtt cttgtgccct gctcttcagc accatgggcc      4601
ttcttatacg gaaggctctg ggatctcccc cttgtggggc aggctcttgg ggccagccta      4661
agatcatggt ttagggtgat cagtgctggc agataaattg aaaaggcacg ctggcttgtg      4721
atcttaaatg aggacaatcc ccccagggct gggcactcct cccctcccct cacttctccc      4781
acctgcagag ccagtgtcct tgggtgggct agataggata tactgtatgc cggctccttc      4841
aagctgctga ctcactttat caatagttcc atttaaattg acttcagtgg tgagactgta      4901
tcctgtttgc tattgcttgt tgtgctatgg ggggaggggg gaggaatgtg taagatagtt      4961
aacatgggca aagggagatc ttggggtgca gcacttaaac tgcctcgtaa ccctttcat      5021 gatttcaacc acatttgcta gagggaggga gcagccacgg agttagaggc ccttggggtt      5081
tctcttttcc actgacaggc tttcccaggc agctggctag ttcattccct ccccagccag      5141
gtgcaggcgt aggaatatgg acatctggtt gctttggcct gctgccctct ttcagggtc       5201 ctaagcccac aatcatgcct ccctaagacc ttggcatcct tccctctaag ccgttggcac      5261
ctctgtgcca cctctcacac tggctccaga cacacagcct gtgcttttgg agctgagatc      5321
actcgcttca ccctcctcat ctttgttctc caagtaaagc cacgaggtcg gggcgagggc      5381
agaggtgatc acctgcgtgt cccatctaca gacctgcagc ttcataaaac ttctgatttc      5441
tcttcagctt tgaaaagggt taccctgggc actggcctag agcctcacct cctaatagac      5501
ttagccccat gagtttgcca tgttgagcag gactatttct ggcacttgca agtcccatga      5561
tttcttcggt aattctgagg gtgggggag ggacatgaaa tcatcttagc ttagcttttct      5621 gtctgtgaat gtctatatag tgtattgtgt gttttaacaa atgatttaca ctgactgttg      5681
ctgtaaaagt gaatttggaa ataaagttat tactctgatt aaa                        5724
```

<210> SEQ ID NO 5
<211> LENGTH: 5631
<212> TYPE: DNA
<213> ORGANISM: homo sapiens
<220> FEATURE:
<221> NAME/KEY: CDS
<222> LOCATION: (323)...(1468)

<400> SEQUENCE: 5

```
ggacggccga gcggcagggc gctcgcgcgc gcccactagt ggccggagga gaaggctccc       60
gcggaggccg cgctgcccgc ccctccccct ggggaggctc gcgttcccgc tgctcgcgcc      120
tgcgccgccc gccggcctca ggaacgcgcc ctcttcgccg gcgcgcgccc tgcagtcac       180 cgccacccac cagctccggc accaacagca gcgccgctgc caccgcccac cttctgccgc      240
cgccaccaca gccaccttct cctcctccgc tgtcctctcc cgtcctcgcc tctgtcgact      300
atcaggtgaa ctttgaacca gg atg gct gag ccc cgc cag gag ttc gaa gtg      352
                         Met Ala Glu Pro Arg Gln Glu Phe Glu Val
                           1               5                  10 atg gaa gat cac gct ggg acg tac ggg ttg ggg gac agg aaa gat cag       400
Met Glu Asp His Ala Gly Thr Tyr Gly Leu Gly Asp Arg Lys Asp Gln
        15                  20                  25 ggg ggc tac acc atg cac caa gac caa gag ggt gac acg gac gct ggc       448
Gly Gly Tyr Thr Met His Gln Asp Gln Glu Gly Asp Thr Asp Ala Gly
    30                  35                  40 ctg aaa gaa tct ccc ctg cag acc ccc act gag gac gga tct gag gaa       496
```

-continued

| | | |
|---|---|---|
| Leu Lys Glu Ser Pro Leu Gln Thr Pro Thr Glu Asp Gly Ser Glu Glu<br>45　　　　　　　50　　　　　　　55 | | |
| ccg ggc tct gaa acc tct gat gct aag agc act cca aca gcg gaa gct<br>Pro Gly Ser Glu Thr Ser Asp Ala Lys Ser Thr Pro Thr Ala Glu Ala<br>60　　　　　　　65　　　　　　　70 | 544 | |
| gaa gaa gca ggc att gga gac acc ccc agc ctg gaa gac gaa gct gct<br>Glu Glu Ala Gly Ile Gly Asp Thr Pro Ser Leu Glu Asp Glu Ala Ala<br>75　　　　　　　80　　　　　　　85　　　　　　　90 | 592 | |
| ggt cac gtg acc caa gct cgc atg gtc agt aaa agc aaa gac ggg act<br>Gly His Val Thr Gln Ala Arg Met Val Ser Lys Ser Lys Asp Gly Thr<br>　　95　　　　　　　100　　　　　　　105 | 640 | |
| gga agc gat gac aaa aaa gcc aag ggg gct gat ggt aaa acg aag atc<br>Gly Ser Asp Asp Lys Lys Ala Lys Gly Ala Asp Gly Lys Thr Lys Ile<br>110　　　　　　　115　　　　　　　120 | 688 | |
| gcc aca ccg cgg gga gca gcc cct cca ggc cag aag ggc cag gcc aac<br>Ala Thr Pro Arg Gly Ala Ala Pro Pro Gly Gln Lys Gly Gln Ala Asn<br>125　　　　　　　130　　　　　　　135 | 736 | |
| gcc acc agg att cca gca aaa acc ccg ccc gct cca aag aca cca ccc<br>Ala Thr Arg Ile Pro Ala Lys Thr Pro Pro Ala Pro Lys Thr Pro Pro<br>140　　　　　　　145　　　　　　　150 | 784 | |
| agc tct ggt gaa cct cca aaa tca ggg gat cgc agc ggc tac agc agc<br>Ser Ser Gly Glu Pro Pro Lys Ser Gly Asp Arg Ser Gly Tyr Ser Ser<br>155　　　　　　　160　　　　　　　165　　　　　　　170 | 832 | |
| ccc ggc tcc cca ggc act ccc ggc agc cgc tcc cgc acc ccg tcc ctt<br>Pro Gly Ser Pro Gly Thr Pro Gly Ser Arg Ser Arg Thr Pro Ser Leu<br>　　175　　　　　　　180　　　　　　　185 | 880 | |
| cca acc cca ccc acc cgg gag ccc aag aag gtg gca gtg gtc cgt act<br>Pro Thr Pro Pro Thr Arg Glu Pro Lys Lys Val Ala Val Val Arg Thr<br>190　　　　　　　195　　　　　　　200 | 928 | |
| cca ccc aag tcg ccg tct tcc gcc aag agc cgc ctg cag aca gcc ccc<br>Pro Pro Lys Ser Pro Ser Ser Ala Lys Ser Arg Leu Gln Thr Ala Pro<br>205　　　　　　　210　　　　　　　215 | 976 | |
| gtg ccc atg cca gac ctg aag aat gtc aag tcc aag atc ggc tcc act<br>Val Pro Met Pro Asp Leu Lys Asn Val Lys Ser Lys Ile Gly Ser Thr<br>220　　　　　　　225　　　　　　　230 | 1024 | |
| gag aac ctg aag cac cag ccg gga ggc ggg aag gtg caa ata gtc tac<br>Glu Asn Leu Lys His Gln Pro Gly Gly Gly Lys Val Gln Ile Val Tyr<br>235　　　　　　　240　　　　　　　245　　　　　　　250 | 1072 | |
| aaa cca gtt gac ctg agc aag gtg acc tcc aag tgt ggc tca tta ggc<br>Lys Pro Val Asp Leu Ser Lys Val Thr Ser Lys Cys Gly Ser Leu Gly<br>　　255　　　　　　　260　　　　　　　265 | 1120 | |
| aac atc cat cat aaa cca gga ggt ggc cag gtg gaa gta aaa tct gag<br>Asn Ile His His Lys Pro Gly Gly Gly Gln Val Glu Val Lys Ser Glu<br>270　　　　　　　275　　　　　　　280 | 1168 | |
| aag ctt gac ttc aag gac aga gtc cag tcg aag att ggg tcc ctg gac<br>Lys Leu Asp Phe Lys Asp Arg Val Gln Ser Lys Ile Gly Ser Leu Asp<br>285　　　　　　　290　　　　　　　295 | 1216 | |
| aat atc acc cac gtc cct ggc gga gga aat aaa aag att gaa acc cac<br>Asn Ile Thr His Val Pro Gly Gly Gly Asn Lys Lys Ile Glu Thr His<br>300　　　　　　　305　　　　　　　310 | 1264 | |
| aag ctg acc ttc cgc gag aac gcc aaa gcc aag aca gac cac ggg gcg<br>Lys Leu Thr Phe Arg Glu Asn Ala Lys Ala Lys Thr Asp His Gly Ala<br>315　　　　　　　320　　　　　　　325　　　　　　　330 | 1312 | |
| gag atc gtg tac aag tcg cca gtg gtg tct ggg gac acg tct cca cgg<br>Glu Ile Val Tyr Lys Ser Pro Val Val Ser Gly Asp Thr Ser Pro Arg<br>　　335　　　　　　　340　　　　　　　345 | 1360 | |
| cat ctc agc aat gtc tcc tcc acc ggc agc atc gac atg gta gac tcg<br>His Leu Ser Asn Val Ser Ser Thr Gly Ser Ile Asp Met Val Asp Ser<br>350　　　　　　　355　　　　　　　360 | 1408 | |

|  |  |
|---|---|
| ccc cag ctc gcc acg cta gct gac gag gtg tct gcc tcc ctg gcc aag<br>Pro Gln Leu Ala Thr Leu Ala Asp Glu Val Ser Ala Ser Leu Ala Lys<br>     365                 370                375 | 1456 |
| cag ggt ttg tga tcaggcccct ggggcggtca ataattgtgg agaggagaga<br>Gln Gly Leu<br>     380 | 1508 |
| atgagagagt gtggaaaaaa aaagaataat gacccggccc ccgccctctg cccccagctg | 1568 |
| ctcctcgcag ttcggttaat tggttaatca cttaacctgc ttttgtcact cggctttggc | 1628 |
| tcgggacttc aaaatcagtg atgggagtaa gagcaaattt catctttcca aattgatggg | 1688 |
| tgggctagta ataaaatatt taaaaaaaaa cattcaaaaa catggccaca tccaacattt | 1748 |
| cctcaggcaa ttccttttga ttcttttttc ttccccctcc atgtagaaga gggagaagga | 1808 |
| gaggctctga aagctgcttc tggggattt caagggactg ggggtgccaa ccacctctgg | 1868 |
| ccctgttgtg ggggtgtcac agaggcagtg gcagcaacaa aggatttgaa acttggtgtg | 1928 |
| ttcgtggagc cacaggcaga cgatgtcaac cttgtgtgag tgtgacgggg gttggggtgg | 1988 |
| ggcgggaggc cacgggggag gccgaggcag gggctgggca gaggggagag gaagcacaag | 2048 |
| aagtgggagt gggagaggaa gccacgtgct ggagagtaga catcccctc cttgccgctg | 2108 |
| ggagagccaa ggcctatgcc acctgcagcg tctgagcggc cgcctgtcct tggtggccgg | 2168 |
| gggtgggggc ctgctgtggg tcagtgtgcc accctctgca gggcagcctg tgggagaagg | 2228 |
| gacagcgggt aaaagagaa ggcaagctgg caggagggtg gcacttcgtg gatgacctcc | 2288 |
| ttagaaaaga ctgaccttga tgtcttgaga gcgctggcct cttcctccct ccctgcaggg | 2348 |
| taggggggcct gagttgaggg gcttccctct gctccacaga aaccctgttt tattgagttc | 2408 |
| tgaaggttgg aactgctgcc atgattttgg ccactttgca gacctgggac tttagggcta | 2468 |
| accagttctc tttgtaagga cttgtgcctc ttgggagacg tccacccgtt tccaagcctg | 2528 |
| ggccactggc atctctggag tgtgtggggg tctgggaggc aggtcccgag ccccctgtcc | 2588 |
| ttcccacggc cactgcagtc accccgtctg cgccgctgtg ctgttgtctg ccgtgagagc | 2648 |
| ccaatcactg cctataccc tcatcacacg tcacaatgtc ccgaattccc agcctcacca | 2708 |
| cccccttctca gtaatgaccc tggttggttg caggaggtac ctactccata ctgagggtga | 2768 |
| aattaaggga aggcaaagtc caggcacaag agtgggaccc cagcctctca ctctcagttc | 2828 |
| cactcatcca actgggaccc tcaccacgaa tctcatgatc tgattcggtt ccctgtctcc | 2888 |
| tcctcccgtc acagatgtga gccagggcac tgctcagctg tgaccctagg tgtttctgcc | 2948 |
| ttgttgacat ggagagagcc ctttcccctg agaaggcctg gccccttcct gtgctgagcc | 3008 |
| cacagcagca ggctgggtgt cttggttgtc agtggtggca ccaggatgga agggcaaggc | 3068 |
| acccagggca ggcccacagt cccgctgtcc cccacttgca ccctagcttg tagctgccaa | 3128 |
| cctcccagac agcccagccc gctgctcagc tccacatgca tagtatcagc cctccacacc | 3188 |
| cgacaaaggg gaacacaccc ccttggaaat ggttcttttc ccccagtccc agctggaagc | 3248 |
| catgctgtct gttctgctgg agcagctgaa catatacata gatgttgccc tgccctcccc | 3308 |
| atctgcaccc tgttgagttg tagttggatt tgtctgttta tgcttggatt caccagagtg | 3368 |
| actatgatag tgaaaagaaa aaaaaaaaa aaaaggacg catgtatctt gaaatgcttg | 3428 |
| taaagaggtt tctaacccac cctcacgagg tgtctctcac ccccacactg ggactcgtgt | 3488 |
| ggcctgtgtg gtgccaccct gctgggggcct cccaagtttt gaaaggcttt cctcagcacc | 3548 |
| tgggacccaa cagagaccag cttctagcag ctaaggaggc cgttcagctg tgacgaaggc | 3608 |
| ctgaagcaca ggattaggac tgaagcgatg atgtcccctt ccctacttcc ccttggggct | 3668 |

```
ccctgtgtca gggcacagac taggtcttgt ggctggtctg gcttgcggcg cgaggatggt    3728
tctctctggt catagcccga agtctcatgg cagtcccaaa ggaggcttac aactcctgca    3788
tcacaagaaa aaggaagcca ctgccagctg gggggatctg cagctcccag aagctccgtg    3848
agcctcagcc accoctcaga ctgggttcct ctccaagctc gccctctgga ggggcagcgc    3908
agcctcccac caagggccct gcgaccacag cagggattgg gatgaattgc ctgtcctgga    3968
tctgctctag aggcccaagc tgcctgcctg aggaaggatg acttgacaag tcaggagaca    4028
ctgttcccaa agccttgacc agagcacctc agcccgctga ccttgcacaa actccatctg    4088
ctgccatgag aaagggaag ccgcctttgc aaaacattgc tgcctaaaga aactcagcag    4148
cctcaggccc aattctgcca cttctggttt gggtacagtt aaaggcaacc ctgagggact    4208
tggcagtaga atccagggc ctcccctggg gctggcagct tcgtgtgcag ctagagcttt    4268
acctgaaagg aagtctctgg gcccagaact ctccaccaag agcctccctg ccgttcgctg    4328
agtcccagca attctcctaa gttgaaggga tctgagaagg agaaggaaat gtggggtaga    4388
tttggtggtg gttagagata tgccccctc attactgcca acagtttcgg ctgcatttct    4448
tcacgcacct cggttcctct tcctgaagtt cttgtgccct gctcttcagc accatgggcc    4508
ttcttatacg gaaggctctg ggatctcccc cttgtggggc aggctcttgg ggccagccta    4568
agatcatggt ttagggtgat cagtgctggc agataaattg aaaaggcacg ctggcttgtg    4628
atcttaaatg aggacaatcc ccccagggct gggcactcct cccctcccct cacttctccc    4688
acctgcagag ccagtgtcct tgggtgggct agataggata tactgtatgc cggctccttc    4748
aagctgctga ctcactttat caatagttcc atttaaattg acttcagtgg tgagactgta    4808 tcctgttttgc tattgcttgt tgtgctatgg ggggagggg gaggaatgtg taagatagtt    4868
aacatgggca aagggagatc ttggggtgca gcacttaaac tgcctcgtaa cccttttcat    4928
gatttcaacc acatttgcta gagggaggga gcagccacgg agttagaggc ccttggggtt    4988
tctcttttcc actgacaggc tttcccaggc agctggctag ttcattccct ccccagccag    5048
gtgcaggcgt aggaatatgg acatctggtt gctttggcct gctgccctct ttcaggggtc    5108
ctaagcccac aatcatgcct ccctaagacc ttggcatcct tccctctaag ccgttggcac    5168
ctctgtgcca cctctcacac tggctccaga cacacagcct gtgcttttgg agctgagatc    5228
actcgcttca ccctcctcat ctttgttctc caagtaaagc cacgaggtcg gggcgagggc    5288
agaggtgatc acctgcgtgt cccatctaca gacctgcagc ttcataaaac ttctgatttc    5348
tcttcagctt tgaaagggt taccctgggc actggcctag agcctcacct cctaatagac    5408
ttagccccat gagtttgcca tgttgagcag gactatttct ggcacttgca agtcccatga    5468
tttcttcggt aattctgagg gtgggggag ggacatgaaa tcatcttagc ttagcttttct    5528 gtctgtgaat gtctatatag tgtattgtgt gttttaacaa atgatttaca ctgactgttg    5588
ctgtaaaagt gaatttggaa ataaagttat tactctgatt aaa                     5631
```

<210> SEQ ID NO 6
<211> LENGTH: 5718
<212> TYPE: DNA
<213> ORGANISM: homo sapiens
<220> FEATURE:
<221> NAME/KEY: CDS
<222> LOCATION: (323)...(1555)

<400> SEQUENCE: 6

```
ggacggccga gcggcagggc gctcgcgcgc gcccactagt ggccggagga gaaggctccc      60
```

-continued

```
gcggaggccg cgctgcccgc ccctcccct ggggaggctc gcgttccgc tgctcgcgcc        120 tgcgccgccc gccggcctca ggaacgcgcc ctcttcgccg gcgcgcgccc tcgcagtcac        180
cgccacccac cagctccggc accaacagca gcgccgctgc caccgcccac cttctgccgc        240
cgccaccaca gccaccttct cctcctccgc tgtcctctcc cgtcctcgcc tctgtcgact        300
atcaggtgaa ctttgaacca gg atg gct gag ccc cgc cag gag ttc gaa gtg        352
                         Met Ala Glu Pro Arg Gln Glu Phe Glu Val
                          1               5                      10 atg gaa gat cac gct ggg acg tac ggg ttg ggg gac agg aaa gat cag        400
Met Glu Asp His Ala Gly Thr Tyr Gly Leu Gly Asp Arg Lys Asp Gln
              15                  20                  25 ggg ggc tac acc atg cac caa gac caa gag ggt gac acg gac gct ggc        448
Gly Gly Tyr Thr Met His Gln Asp Gln Glu Gly Asp Thr Asp Ala Gly
             30                  35                  40 ctg aaa gaa tct ccc ctg cag acc ccc act gag gac gga tct gag gaa        496
Leu Lys Glu Ser Pro Leu Gln Thr Pro Thr Glu Asp Gly Ser Glu Glu
         45                  50                  55 ccg ggc tct gaa acc tct gat gct aag agc act cca aca gcg gaa gat        544
Pro Gly Ser Glu Thr Ser Asp Ala Lys Ser Thr Pro Thr Ala Glu Asp
     60                  65                  70 gtg aca gca ccc tta gtg gat gag gga gct ccc ggc aag cag gct gcc        592
Val Thr Ala Pro Leu Val Asp Glu Gly Ala Pro Gly Lys Gln Ala Ala
 75                  80                  85                  90 gcg cag ccc cac acg gag atc cca gaa gga acc aca gct gaa gaa gca        640
Ala Gln Pro His Thr Glu Ile Pro Glu Gly Thr Thr Ala Glu Glu Ala
                 95                 100                 105 ggc att gga gac acc cca agc ctg gaa gac gaa gct gct ggt cac gtg        688
Gly Ile Gly Asp Thr Pro Ser Leu Glu Asp Glu Ala Ala Gly His Val
             110                 115                 120 acc caa gct cgc atg gtc agt aaa agc aaa gac ggg act gga agc gat        736
Thr Gln Ala Arg Met Val Ser Lys Ser Lys Asp Gly Thr Gly Ser Asp
         125                 130                 135 gac aaa aaa gcc aag ggg gct gat ggt aaa acg aag atc gcc aca ccg        784
Asp Lys Lys Ala Lys Gly Ala Asp Gly Lys Thr Lys Ile Ala Thr Pro
     140                 145                 150 cgg gga gca gcc cct cca ggc cag aag ggc cag gcc aac gcc acc agg        832
Arg Gly Ala Ala Pro Pro Gly Gln Lys Gly Gln Ala Asn Ala Thr Arg
155                 160                 165                 170 att cca gca aaa acc ccg ccc gct cca aag aca cca ccc agc tct ggt        880
Ile Pro Ala Lys Thr Pro Pro Ala Pro Lys Thr Pro Pro Ser Ser Gly
                 175                 180                 185 gaa cct cca aaa tca ggg gat cgc agc ggc tac agc agc ccc ggc tcc        928
Glu Pro Pro Lys Ser Gly Asp Arg Ser Gly Tyr Ser Ser Pro Gly Ser
             190                 195                 200 cca ggc act ccc ggc agc cgc tcc cgc acc ccg tcc ctt cca acc cca        976
Pro Gly Thr Pro Gly Ser Arg Ser Arg Thr Pro Ser Leu Pro Thr Pro
         205                 210                 215 ccc acc cgg gag ccc aag aag gtg gca gtg gtc cgt act cca ccc aag        1024
Pro Thr Arg Glu Pro Lys Lys Val Ala Val Val Arg Thr Pro Pro Lys
     220                 225                 230 tcg ccg tct tcc gcc aag agc cgc ctg cag aca gcc ccc gtg ccc atg        1072
Ser Pro Ser Ser Ala Lys Ser Arg Leu Gln Thr Ala Pro Val Pro Met
235                 240                 245                 250 cca gac ctg aag aat gtc aag tcc aag atc ggc tcc act gag aac ctg        1120
Pro Asp Leu Lys Asn Val Lys Ser Lys Ile Gly Ser Thr Glu Asn Leu
                 255                 260                 265 aag cac cag ccg gga ggc ggg aag gtg caa ata gtc tac aaa cca gtt        1168
Lys His Gln Pro Gly Gly Gly Lys Val Gln Ile Val Tyr Lys Pro Val
```

|  |  |  |  |  |  |  |  |  |  |  |  |  |  |  |  |
|---|---|---|---|---|---|---|---|---|---|---|---|---|---|---|---|
| gac | ctg | agc | aag | gtg | acc | tcc | aag | tgt | ggc | tca | tta | ggc | aac | atc | cat |
| Asp | Leu | Ser | Lys | Val | Thr | Ser | Lys | Cys | Gly | Ser | Leu | Gly | Asn | Ile | His |
|  |  | 285 |  |  |  |  | 290 |  |  |  |  | 295 |  |  |  |

1216

|  |  |  |  |  |  |  |  |  |  |  |  |  |  |  |  |
|---|---|---|---|---|---|---|---|---|---|---|---|---|---|---|---|
| cat | aaa | cca | gga | ggt | ggc | cag | gtg | gaa | gta | aaa | tct | gag | aag | ctt | gac |
| His | Lys | Pro | Gly | Gly | Gly | Gln | Val | Glu | Val | Lys | Ser | Glu | Lys | Leu | Asp |
| 300 |  |  |  |  |  | 305 |  |  |  |  | 310 |  |  |  |  |

1264

|  |  |  |  |  |  |  |  |  |  |  |  |  |  |  |  |
|---|---|---|---|---|---|---|---|---|---|---|---|---|---|---|---|
| ttc | aag | gac | aga | gtc | cag | tcg | aag | att | ggg | tcc | ctg | gac | aat | atc | acc |
| Phe | Lys | Asp | Arg | Val | Gln | Ser | Lys | Ile | Gly | Ser | Leu | Asp | Asn | Ile | Thr |
| 315 |  |  |  | 320 |  |  |  |  | 325 |  |  |  |  | 330 |  |

1312

|  |  |  |  |  |  |  |  |  |  |  |  |  |  |  |  |
|---|---|---|---|---|---|---|---|---|---|---|---|---|---|---|---|
| cac | gtc | cct | ggc | gga | gga | aat | aaa | aag | att | gaa | acc | cac | aag | ctg | acc |
| His | Val | Pro | Gly | Gly | Gly | Asn | Lys | Lys | Ile | Glu | Thr | His | Lys | Leu | Thr |
|  |  |  |  | 335 |  |  |  |  | 340 |  |  |  |  | 345 |  |

1360

|  |  |  |  |  |  |  |  |  |  |  |  |  |  |  |  |
|---|---|---|---|---|---|---|---|---|---|---|---|---|---|---|---|
| ttc | cgc | gag | aac | gcc | aaa | gcc | aag | aca | gac | cac | ggg | gcg | gag | atc | gtg |
| Phe | Arg | Glu | Asn | Ala | Lys | Ala | Lys | Thr | Asp | His | Gly | Ala | Glu | Ile | Val |
|  |  |  | 350 |  |  |  |  | 355 |  |  |  |  | 360 |  |  |

1408

|  |  |  |  |  |  |  |  |  |  |  |  |  |  |  |  |
|---|---|---|---|---|---|---|---|---|---|---|---|---|---|---|---|
| tac | aag | tcg | cca | gtg | gtg | tct | ggg | gac | acg | tct | cca | cgg | cat | ctc | agc |
| Tyr | Lys | Ser | Pro | Val | Val | Ser | Gly | Asp | Thr | Ser | Pro | Arg | His | Leu | Ser |
|  |  | 365 |  |  |  |  | 370 |  |  |  |  | 375 |  |  |  |

1456

|  |  |  |  |  |  |  |  |  |  |  |  |  |  |  |  |
|---|---|---|---|---|---|---|---|---|---|---|---|---|---|---|---|
| aat | gtc | tcc | tcc | acc | ggc | agc | atc | gac | atg | gta | gac | tcg | ccc | cag | ctc |
| Asn | Val | Ser | Ser | Thr | Gly | Ser | Ile | Asp | Met | Val | Asp | Ser | Pro | Gln | Leu |
| 380 |  |  |  |  | 385 |  |  |  |  | 390 |  |  |  |  |  |

1504

|  |  |  |  |  |  |  |  |  |  |  |  |  |  |  |  |
|---|---|---|---|---|---|---|---|---|---|---|---|---|---|---|---|
| gcc | acg | cta | gct | gac | gag | gtg | tct | gcc | tcc | ctg | gcc | aag | cag | ggt | ttg |
| Ala | Thr | Leu | Ala | Asp | Glu | Val | Ser | Ala | Ser | Leu | Ala | Lys | Gln | Gly | Leu |
| 395 |  |  |  | 400 |  |  |  |  | 405 |  |  |  |  | 410 |  |

1552

```
tga tcaggcccct ggggcggtca ataattgtgg agaggagaga atgagagagt      1605
gtggaaaaaa aaagaataat gacccggccc ccgccctctg cccccagctg ctcctcgcag 1665
ttcggttaat tggttaatca cttaacctgc ttttgtcact cggctttggc tcgggacttc  1725
aaaatcagtg atgggagtaa gagcaaattt catctttcca aattgatggg tgggctagta  1785
ataaaatatt taaaaaaaaa cattcaaaaa catggccaca tccaacattt cctcaggcaa  1845
ttccttttga ttcttttttc ttccccctcc atgtagaaga gggagaagga gaggctctga  1905
aagctgcttc tgggggattt caagggactg ggggtgccaa ccacctctgg ccctgttgtg  1965
ggggtgtcac agaggcagtg gcagcaacaa aggatttgaa acttggtgtg ttcgtggagc  2025
cacaggcaga cgatgtcaac cttgtgtgag tgtgacgggg gttggggtgg ggcgggaggc  2085
cacggggag gccgaggcag gggctgggca gaggggagg gaagcacaag aagtgggagt   2145
gggagaggaa gccacgtgct ggagagtaga catccccctc cttgccgctg ggagagccaa  2205
ggcctatgcc acctgcagcg tctgagcggc cgcctgtcct tggtggccgg gggtgggggc  2265
ctgctgtggg tcagtgtgcc accctctgca gggcagcctg tgggagaagg gacagcgggt  2325
aaaaagagaa ggcaagctgg caggagggtg gcacttcgtg gatgacctcc ttagaaaaga  2385
ctgaccttga tgtcttgaga gcgctggcct cttcctccct ccctgcaggg tagggggcct  2445
gagttgaggg gcttccctct gctccacaga aaccctgttt tattgagttc tgaaggttgg  2505
aactgctgcc atgattttgg ccactttgca gacctggac tttagggcta accagttctc    2565
tttgtaagga cttgtgcctc ttgggagacg tccacccgtt tccaagcctg gccactggc   2625
atctctggag tgtgtggggg tctgggaggc aggtcccgag cccctgtcc ttcccacggc   2685
cactgcagtc acccgtctg cgccgctgtg ctgttgtctg ccgtgagagc caatcactg    2745
cctataccc tcatcacacg tcacaatgtc ccgaattccc agcctcacca ccccttctca   2805
gtaatgaccc tggttggttg caggaggtac ctactccata ctgagggtga aattaaggga  2865
aggcaaagtc caggcacaag agtgggaccc cagcctctca ctctcagttc cactcatcca  2925
```

```
actgggaccc tcaccacgaa tctcatgatc tgattcggtt ccctgtctcc tcctcccgtc    2985
acagatgtga gccagggcac tgctcagctg tgacccatgg tgtttctgcc ttgttgacat    3045
ggagagagcc ctttcccctg agaaggcctg gccccttcct gtgctgagcc cacagcagca    3105
ggctgggtgt cttggttgtc agtggtggca ccaggatgga agggcaaggc acccagggca    3165
ggcccacagt cccgctgtcc cccacttgca ccctagcttg tagctgccaa cctcccagac    3225
agcccagccc gctgctcagc tccacatgca tagtatcagc cctccacacc cgacaaaggg    3285
gaacacaccc ccttggaaat ggttctttc cccagtccc agctggaagc catgctgtct     3345
gttctgctgg agcagctgaa catatacata gatgttgccc tgccctcccc atctgcaccc    3405
tgttgagttg tagttggatt tgtctgttta tgcttggatt caccagagtg actatgatag    3465
tgaaaagaaa aaaaaaaaa aaaaaggacg catgtatctt gaaatgcttg taaagaggtt    3525
tctaacccac cctcacgagg tgtctctcac ccccacactg ggactcgtgt ggcctgtgtg    3585
gtgccaccct gctggggcct cccaagtttt gaaaggcttt cctcagcacc tgggacccaa    3645
cagagaccag cttctagcag ctaaggaggc cgttcagctg tgacgaaggc ctgaagcaca    3705
ggattaggac tgaagcgatg atgtccccctt ccctacttcc ccttggggct ccctgtgtca   3765
gggcacagac taggtcttgt ggctggtctg gcttgcggcg cgaggatggt tctctctggt    3825
catagcccga agtctcatgg cagtcccaaa ggaggcttac aactcctgca tcacaagaaa    3885
aaggaagcca ctgccagctg gggggatctg cagctcccag aagctccgtg agcctcagcc    3945 accectcaga ctgggttcct ctccaagctc gccctctgga ggggcagcgc agcctcccac    4005
caagggccct gcgaccacag cagggattgg gatgaattgc ctgtcctgga tctgctctag    4065
aggcccaagc tgcctgcctg aggaaggatg acttgacaag tcaggagaca ctgttcccaa    4125
agccttgacc agagcacctc agcccgctga ccttgcacaa actccatctg ctgccatgag    4185
aaaagggaag ccgcctttgc aaaacattgc tgcctaaaga aactcagcag cctcaggccc    4245
aattctgcca cttctggttt gggtacagtt aaaggcaacc ctgagggact tggcagtaga    4305
aatccagggc ctcccctggg gctggcagct tcgtgtgcag ctagagcttt acctgaaagg    4365
aagtctctgg gcccagaact ctccaccaag agcctccctg ccgttcgctg agtcccagca    4425
attctcctaa gttgaaggga tctgagaagg agaaggaaat gtggggtaga tttggtggtg    4485
gttagagata tgccccctc attactgcca acagtttcgg ctgcatttct tcacgcacct    4545
cggttcctct tcctgaagtt cttgtgccct gctcttcagc accatgggcc ttcttatacg    4605
gaaggctctg ggatctcccc cttgtgggc aggctcttgg ggccagccta agatcatggt    4665
ttagggtgat cagtgctggc agataaattg aaaaggcacg ctggcttgtg atcttaaatg    4725
aggacaatcc ccccagggct gggcactcct cccctcccct cacttctccc acctgcagag    4785
ccagtgtcct tgggtgggct agataggata tactgtatgc cggctccttc aagctgctga    4845
ctcactttat caatagttcc atttaaattg acttcagtgg tgagactgta tcctgtttgc    4905
tattgcttgt tgtgctatgg ggggaggggg gaggaatgtg taagatagtt aacatgggca    4965
aagggagatc ttgggggtgca gcacttaaac tgcctcgtaa ccctttcat gatttcaacc     5025 acatttgcta gagggaggga gcagccacgg agttagaggc ccttggggtt tctcttttcc    5085
actgacaggc tttcccaggc agctggctag ttcattccct ccccagccag gtgcaggcgt    5145
aggaatatgg acatctggtt gctttggcct gctgccctct ttcaggggtc ctaagcccac    5205
aatcatgcct ccctaagacc ttggcatcct tccctctaag ccgttggcac ctctgtgcca    5265
```

-continued

| | |
|---|---|
| cctctcacac tggctccaga cacacagcct gtgcttttgg agctgagatc actcgcttca | 5325 |
| ccctcctcat ctttgttctc caagtaaagc cacgaggtcg gggcgaggc agaggtgatc | 5385 |
| acctgcgtgt cccatctaca gacctgcagc ttcataaaac ttctgatttc tcttcagctt | 5445 |
| tgaaaagggt taccctgggc actggcctag agcctcacct cctaatagac ttagccccat | 5505 |
| gagtttgcca tgttgagcag gactatttct ggcacttgca agtcccatga tttcttcggt | 5565 |
| aattctgagg gtgggggag ggacatgaaa tcatcttagc ttagcttct gtctgtgaat | 5625 |
| gtctatatag tgtattgtgt gttttaacaa atgatttaca ctgactgttg ctgtaaaagt | 5685 |
| gaatttggaa ataaagttat tactctgatt aaa | 5718 |

```
<210> SEQ ID NO 7
<211> LENGTH: 5811
<212> TYPE: DNA
<213> ORGANISM: homo sapiens
<220> FEATURE:
<221> NAME/KEY: CDS
<222> LOCATION: (323)...(1648)

<400> SEQUENCE: 7
```

| | |
|---|---|
| ggacggccga gcggcagggc gctcgcgcgc gcccactagt ggccggagga gaaggctccc | 60 |
| gcggaggccg cgctgcccgc cccctcccct ggggaggctc gcgttcccgc tgctcgcgcc | 120 |
| tgcgccgccc gccggcctca ggaacgcgcc ctcttgccg gcgcgcgccc tcgcagtcac | 180 |
| cgccacccac cagctccggc accaacagca gcgccgctgc caccgcccac cttctgccgc | 240 |
| cgccaccaca gccaccttct cctcctccgc tgtcctctcc cgtcctcgcc tctgtcgact | 300 |

| | | |
|---|---|---|
| atcaggtgaa ctttgaacca gg atg gct gag ccc cgc cag gag ttc gaa gtg<br>                               Met Ala Glu Pro Arg Gln Glu Phe Glu Val<br>                               1         5               10 | 352 |
| atg gaa gat cac gct ggg acg tac ggg ttg ggg gac agg aaa gat cag<br>Met Glu Asp His Ala Gly Thr Tyr Gly Leu Gly Asp Arg Lys Asp Gln<br>               15                    20                 25 | 400 |
| ggg ggc tac acc atg cac caa gac caa gag ggt gac acg gac gct ggc<br>Gly Gly Tyr Thr Met His Gln Asp Gln Glu Gly Asp Thr Asp Ala Gly<br>           30                   35                 40 | 448 |
| ctg aaa gaa tct ccc ctg cag acc ccc act gag gac gga tct gag gaa<br>Leu Lys Glu Ser Pro Leu Gln Thr Pro Thr Glu Asp Gly Ser Glu Glu<br>45                    50                    55 | 496 |
| ccg ggc tct gaa acc tct gat gct aag agc act cca aca gcg gaa gat<br>Pro Gly Ser Glu Thr Ser Asp Ala Lys Ser Thr Pro Thr Ala Glu Asp<br>   60                    65                    70 | 544 |
| gtg aca gca ccc tta gtg gat gag gga gct ccc ggc aag cag gct gcc<br>Val Thr Ala Pro Leu Val Asp Glu Gly Ala Pro Gly Lys Gln Ala Ala<br>75                    80                    85                 90 | 592 |
| gcg cag ccc cac acg gag atc cca gaa gga acc aca gct gaa gaa gca<br>Ala Gln Pro His Thr Glu Ile Pro Glu Gly Thr Thr Ala Glu Glu Ala<br>               95                   100              105 | 640 |
| ggc att gga gac acc ccc agc ctg gaa gac gaa gct gct ggt cac gtg<br>Gly Ile Gly Asp Thr Pro Ser Leu Glu Asp Glu Ala Ala Gly His Val<br>          110                   115               120 | 688 |
| acc caa gct cgc atg gtc agt aaa agc aaa gac ggg act gga agc gat<br>Thr Gln Ala Arg Met Val Ser Lys Ser Lys Asp Gly Thr Gly Ser Asp<br>        125                 130               135 | 736 |
| gac aaa aaa gcc aag ggg gct gat ggt aaa acg aag atc gcc aca ccg<br>Asp Lys Lys Ala Lys Gly Ala Asp Gly Lys Thr Lys Ile Ala Thr Pro<br>140                   145               150 | 784 |
| cgg gga gca gcc cct cca ggc cag aag ggc cag gcc aac gcc acc agg<br>Arg Gly Ala Ala Pro Pro Gly Gln Lys Gly Gln Ala Asn Ala Thr Arg | 832 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 155 |     |     |     |     | 160 |     |     |     |     | 165 |     |     |     |     | 170 |      |
| att | cca | gca | aaa | acc | ccg | ccc | gct | cca | aag | aca | cca | ccc | agc | tct | ggt | 880  |
| Ile | Pro | Ala | Lys | Thr | Pro | Pro | Ala | Pro | Lys | Thr | Pro | Pro | Ser | Ser | Gly |      |
|     |     |     | 175 |     |     |     |     | 180 |     |     |     |     | 185 |     |     |      |
| gaa | cct | cca | aaa | tca | ggg | gat | cgc | agc | ggc | tac | agc | agc | ccc | ggc | tcc | 928  |
| Glu | Pro | Pro | Lys | Ser | Gly | Asp | Arg | Ser | Gly | Tyr | Ser | Ser | Pro | Gly | Ser |      |
|     |     |     | 190 |     |     |     |     | 195 |     |     |     |     | 200 |     |     |      |
| cca | ggc | act | ccc | ggc | agc | cgc | tcc | cgc | acc | ccg | tcc | ctt | cca | acc | cca | 976  |
| Pro | Gly | Thr | Pro | Gly | Ser | Arg | Ser | Arg | Thr | Pro | Ser | Leu | Pro | Thr | Pro |      |
|     |     | 205 |     |     |     |     | 210 |     |     |     |     | 215 |     |     |     |      |
| ccc | acc | cgg | gag | ccc | aag | aag | gtg | gca | gtg | gtc | cgt | act | cca | ccc | aag | 1024 |
| Pro | Thr | Arg | Glu | Pro | Lys | Lys | Val | Ala | Val | Val | Arg | Thr | Pro | Pro | Lys |      |
|     | 220 |     |     |     |     | 225 |     |     |     |     | 230 |     |     |     |     |      |
| tcg | ccg | tct | tcc | gcc | aag | agc | cgc | ctg | cag | aca | gcc | ccc | gtg | ccc | atg | 1072 |
| Ser | Pro | Ser | Ser | Ala | Lys | Ser | Arg | Leu | Gln | Thr | Ala | Pro | Val | Pro | Met |      |
| 235 |     |     |     |     | 240 |     |     |     |     | 245 |     |     |     |     | 250 |      |
| cca | gac | ctg | aag | aat | gtc | aag | tcc | aag | atc | ggc | tcc | act | gag | aac | ctg | 1120 |
| Pro | Asp | Leu | Lys | Asn | Val | Lys | Ser | Lys | Ile | Gly | Ser | Thr | Glu | Asn | Leu |      |
|     |     |     |     | 255 |     |     |     |     | 260 |     |     |     |     | 265 |     |      |
| aag | cac | cag | ccg | gga | ggc | ggg | aag | gtg | cag | ata | att | aat | aag | aag | ctg | 1168 |
| Lys | His | Gln | Pro | Gly | Gly | Gly | Lys | Val | Gln | Ile | Ile | Asn | Lys | Lys | Leu |      |
|     |     |     | 270 |     |     |     |     | 275 |     |     |     |     | 280 |     |     |      |
| gat | ctt | agc | aac | gtc | cag | tcc | aag | tgt | ggc | tca | aag | gat | aat | atc | aaa | 1216 |
| Asp | Leu | Ser | Asn | Val | Gln | Ser | Lys | Cys | Gly | Ser | Lys | Asp | Asn | Ile | Lys |      |
|     |     | 285 |     |     |     |     | 290 |     |     |     |     | 295 |     |     |     |      |
| cac | gtc | ccg | gga | ggc | ggc | agt | gtg | caa | ata | gtc | tac | aaa | cca | gtt | gac | 1264 |
| His | Val | Pro | Gly | Gly | Gly | Ser | Val | Gln | Ile | Val | Tyr | Lys | Pro | Val | Asp |      |
|     | 300 |     |     |     |     | 305 |     |     |     |     | 310 |     |     |     |     |      |
| ctg | agc | aag | gtg | acc | tcc | aag | tgt | ggc | tca | tta | ggc | aac | atc | cat | cat | 1312 |
| Leu | Ser | Lys | Val | Thr | Ser | Lys | Cys | Gly | Ser | Leu | Gly | Asn | Ile | His | His |      |
| 315 |     |     |     |     | 320 |     |     |     |     | 325 |     |     |     |     | 330 |      |
| aaa | cca | gga | ggt | ggc | cag | gtg | gaa | gta | aaa | tct | gag | aag | ctt | gac | ttc | 1360 |
| Lys | Pro | Gly | Gly | Gly | Gln | Val | Glu | Val | Lys | Ser | Glu | Lys | Leu | Asp | Phe |      |
|     |     |     |     | 335 |     |     |     |     | 340 |     |     |     |     | 345 |     |      |
| aag | gac | aga | gtc | cag | tcg | aag | att | ggg | tcc | ctg | gac | aat | atc | acc | cac | 1408 |
| Lys | Asp | Arg | Val | Gln | Ser | Lys | Ile | Gly | Ser | Leu | Asp | Asn | Ile | Thr | His |      |
|     |     |     | 350 |     |     |     |     | 355 |     |     |     |     | 360 |     |     |      |
| gtc | cct | ggc | gga | gga | aat | aaa | aag | att | gaa | acc | cac | aag | ctg | acc | ttc | 1456 |
| Val | Pro | Gly | Gly | Gly | Asn | Lys | Lys | Ile | Glu | Thr | His | Lys | Leu | Thr | Phe |      |
|     |     | 365 |     |     |     |     | 370 |     |     |     |     | 375 |     |     |     |      |
| cgc | gag | aac | gcc | aaa | gcc | aag | aca | gac | cac | ggg | gcg | gag | atc | gtg | tac | 1504 |
| Arg | Glu | Asn | Ala | Lys | Ala | Lys | Thr | Asp | His | Gly | Ala | Glu | Ile | Val | Tyr |      |
|     | 380 |     |     |     |     | 385 |     |     |     |     | 390 |     |     |     |     |      |
| aag | tcg | cca | gtg | gtg | tct | ggg | gac | acg | tct | cca | cgg | cat | ctc | agc | aat | 1552 |
| Lys | Ser | Pro | Val | Val | Ser | Gly | Asp | Thr | Ser | Pro | Arg | His | Leu | Ser | Asn |      |
| 395 |     |     |     |     | 400 |     |     |     |     | 405 |     |     |     |     | 410 |      |
| gtc | tcc | tcc | acc | ggc | agc | atc | gac | atg | gta | gac | tcg | ccc | cag | ctc | gcc | 1600 |
| Val | Ser | Ser | Thr | Gly | Ser | Ile | Asp | Met | Val | Asp | Ser | Pro | Gln | Leu | Ala |      |
|     |     |     |     | 415 |     |     |     |     | 420 |     |     |     |     | 425 |     |      |
| acg | cta | gct | gac | gag | gtg | tct | gcc | tcc | ctg | gcc | aag | cag | ggt | ttg | tga | 1648 |
| Thr | Leu | Ala | Asp | Glu | Val | Ser | Ala | Ser | Leu | Ala | Lys | Gln | Gly | Leu |     |      |
|     |     |     | 430 |     |     |     |     | 435 |     |     |     |     | 440 |     |     |      |

```
tcaggcccct ggggcggtca ataattgtgg agaggagaga atgagagagt gtggaaaaaa    1708
aaagaataat gacccggccc cgccctctg cccccagctg ctcctcgcag ttcggttaat     1768
tggttaatca cttaacctgc ttttgtcact cggctttggc tcgggacttc aaaatcagtg    1828
atgggagtaa gagcaaattt catctttcca aattgatggg tgggctagta ataaaatatt    1888
taaaaaaaaa cattcaaaaa catggccaca tccaacattt cctcaggcaa ttccttttga    1948
```

```
ttcttttttc ttccccctcc atgtagaaga gggagaagga gaggctctga aagctgcttc   2008
tgggggattt caagggactg ggggtgccaa ccacctctgg ccctgttgtg ggggtgtcac   2068
agaggcagtg gcagcaacaa aggatttgaa acttggtgtg ttcgtggagc cacaggcaga   2128
cgatgtcaac cttgtgtgag tgtgacgggg gttggggtgg ggcgggaggc cacggggggag  2188 gccgaggcag gggctgggca gaggggagag gaagcacaag aagtgggagt gggagaggaa   2248
gccacgtgct ggagagtaga catccccctc cttgccgctg ggagagccaa ggcctatgcc   2308
acctgcagcg tctgagcggc cgcctgtcct ggtggccgg gggtgggggc ctgctgtggg    2368
tcagtgtgcc accctctgca gggcagcctg tgggagaagg gacagcgggt aaaaagagaa   2428
ggcaagctgg caggagggtg gcacttcgtg gatgacctcc ttagaaaaga ctgaccttga   2488
tgtcttgaga gcgctggcct cttcctccct ccctgcaggg tagggggcct gagttgaggg   2548
gcttccctct gctccacaga aaccctgttt tattgagttc tgaaggttgg aactgctgcc   2608
atgattttgg ccactttgca gacctgggac tttagggcta accagttctc tttgtaagga   2668
cttgtgcctc ttgggagacg tccacccgtt tccaagcctg ggccactggc atctctggag   2728
tgtgtggggg tctgggaggc aggtcccgag cccctgtcc ttcccacggc cactgcagtc    2788
accccgtctg cgccgctgtg ctgttgtctg ccgtgagagc ccaatcactg cctataccc    2848 tcatcacacg tcacaatgtc ccgaattccc agcctcacca cccttctca gtaatgaccc    2908 tggttggttg caggaggtac ctactccata ctgagggtga aattaaggga aggcaaagtc   2968
caggcacaag agtgggaccc cagcctctca ctctcagttc cactcatcca actgggaccc   3028
tcaccacgaa tctcatgatc tgattcggtt ccctgtctcc tcctcccgtc acagatgtga   3088
gccagggcac tgctcagctg tgaccctagg tgtttctgcc ttgttgacat ggagagagcc   3148
cttttccctg agaaggcctg gccccttcct gtgctgagcc cacagcagca ggctgggtgt   3208
cttggttgtc agtggtggca ccaggatgga agggcaaggc acccagggca ggcccacagt   3268
cccgctgtcc cccacttgca ccctagcttg tagctgccaa cctcccagac agcccagccc   3328
gctgctcagc tccacatgca tagtatcagc cctccacacc cgacaaaggg gaacacaccc   3388
ccttggaaat ggttctttc ccccagtccc agctggaagc catgctgtct gttctgctgg    3448
agcagctgaa catatacata gatgttgccc tgccctcccc atctgcaccc tgttgagttg   3508
tagttggatt tgtctgttta tgcttggatt caccagagtg actatgatag tgaaagaaa    3568 aaaaaaaaaa aaaaggacg catgtatctt gaaatgcttg taaagaggtt ctaacccac    3628 cctcacgagg tgtctctcac ccccacactg ggactcgtgt ggcctgtgtg gtgccaccct   3688 gctgggcct cccaagtttt gaaaggcttt cctcagcacc tgggacccaa cagagaccag    3748
cttctagcag ctaaggaggc cgttcagctg tgacgaaggc ctgaagcaca ggattaggac   3808
tgaagcgatg atgtcccctt ccctacttcc ccttggggct ccctgtgtca gggcacagac   3868
taggtcttgt ggctggtctg gcttgcgcg cgaggatggt tctctctggt catagcccga    3928
agtctcatgg cagtcccaaa ggaggcttac aactcctgca tcacaagaaa aaggaagcca   3988
ctgccagctg gggggatctg cagctcccag aagctccgtg agcctcagcc acccctcaga   4048
ctgggttcct ctccaagctc gccctctgga ggggcagcgc agcctccac caagggccct    4108 gcgaccacag cagggattgg gatgaattgc ctgtcctgga tctgctctag aggcccaagc   4168
tgcctgcctg aggaaggatg acttgacaag tcaggagaca ctgttcccaa gccttgacc    4228 agagcacctc agcccgctga ccttgcacaa actccatctg ctgccatgag aaaagggaag   4288
```

-continued

| | |
|---|---|
| ccgcctttgc aaaacattgc tgcctaaaga aactcagcag cctcaggccc aattctgcca | 4348 |
| cttctggttt gggtacagtt aaaggcaacc ctgagggact tggcagtaga aatccagggc | 4408 |
| ctcccctggg gctggcagct tcgtgtgcag ctagagcttt acctgaaagg aagtctctgg | 4468 |
| gcccagaact ctccaccaag agcctccctg ccgttcgctg agtcccagca attctcctaa | 4528 |
| gttgaaggga tctgagaagg agaaggaaat gtggggtaga tttggtggtg gttagagata | 4588 |
| tgccccctc attactgcca acagtttcgg ctgcatttct tcacgcacct cggttcctct | 4648 |
| tcctgaagtt cttgtgccct gctcttcagc accatgggcc ttcttatacg gaaggctctg | 4708 |
| ggatctcccc cttgtggggc aggctcttgg ggccagccta agatcatggt ttagggtgat | 4768 |
| cagtgctggc agataaattg aaaaggcacg ctggcttgtg atcttaaatg aggacaatcc | 4828 |
| ccccagggct gggcactcct cccctcccct cacttctccc acctgcagag ccagtgtcct | 4888 |
| tgggtgggct agataggata tactgtatgc cggctccttc aagctgctga ctcactttat | 4948 |
| caatagttcc atttaaattg acttcagtgg tgagactgta tcctgtttgc tattgcttgt | 5008 |
| tgtgctatgg ggggagggg gaggaatgtg taagatagtt aacatgggca aagggagatc | 5068 |
| ttggggtgca gcacttaaac tgcctcgtaa ccctttcat gatttcaacc acatttgcta | 5128 |
| gagggaggga gcagccacgg agttagaggc ccttgggggtt tctcttttcc actgacaggc | 5188 |
| tttcccaggc agctggctag ttcattccct ccccagccag gtgcaggcgt aggaatatgg | 5248 |
| acatctggtt gctttggcct gctgccctct ttcaggggtc ctaagcccac aatcatgcct | 5308 |
| ccctaagacc ttggcatcct tccctctaag ccgttggcac ctctgtgcca cctctcacac | 5368 |
| tggctccaga cacacagcct gtgcttttgg agctgagatc actcgcttca ccctcctcat | 5428 |
| ctttgttctc caagtaaagc cacgaggtcg gggcgagggc agaggtgatc acctgcgtgt | 5488 |
| cccatctaca gacctgcagc ttcataaaac ttctgatttc tcttcagctt tgaaaagggt | 5548 |
| taccctgggc actggcctag agcctcacct cctaatagac ttagccccat gagtttgcca | 5608 |
| tgttgagcag gactatttct ggcacttgca agtcccatga tttcttcggt aattctgagg | 5668 |
| gtgggggag ggacatgaaa tcatcttagc ttagcttttct gtctgtgaat gtctatatag | 5728 |
| tgtattgtgt gttttaacaa atgatttaca ctgactgttg ctgtaaaagt gaatttggaa | 5788 |
| ataaagttat tactctgatt aaa | 5811 |

<210> SEQ ID NO 8
<211> LENGTH: 5637
<212> TYPE: DNA
<213> ORGANISM: homo sapiens
<220> FEATURE:
<221> NAME/KEY: CDS
<222> LOCATION: (323)...(1474)

<400> SEQUENCE: 8

| | |
|---|---|
| ggacggccga gcggcagggc gctcgcgcgc gcccactagt ggccggagga gaaggctccc | 60 |
| gcggaggccg cgctgcccgc cccctcccct ggggaggctc gcgttcccgc tgctcgcgcc | 120 |
| tgcgccgccc gccggcctca ggaacgcgcc ctcttcgccg gcgcgcgccc tcgcagtcac | 180 |
| cgccacccac cagctccggc accaacagca gcgccgctgc caccgcccac cttctgccgc | 240 |
| cgccaccaca gccaccttct cctcctccgc tgtcctctcc cgtcctcgcc tctgtcgact | 300 |
| atcaggtgaa ctttgaacca gg atg gct gag ccc cgc cag gag ttc gaa gtg | 352 |
|                                   Met Ala Glu Pro Arg Gln Glu Phe Glu Val<br>                                  1              5                      10 | |
| atg gaa gat cac gct ggg acg tac ggg ttg ggg gac agg aaa gat cag<br>Met Glu Asp His Ala Gly Thr Tyr Gly Leu Gly Asp Arg Lys Asp Gln | 400 |

-continued

```
             15                  20                  25
ggg ggc tac acc atg cac caa gac caa gag ggt gac acg gac gct ggc      448
Gly Gly Tyr Thr Met His Gln Asp Gln Glu Gly Asp Thr Asp Ala Gly
             30                  35                  40 ctg aaa gct gaa gaa gca ggc att gga gac acc ccc agc ctg gaa gac      496
Leu Lys Ala Glu Glu Ala Gly Ile Gly Asp Thr Pro Ser Leu Glu Asp
             45                  50                  55 gaa gct gct ggt cac gtg acc caa gct cgc atg gtc agt aaa agc aaa      544
Glu Ala Ala Gly His Val Thr Gln Ala Arg Met Val Ser Lys Ser Lys
             60                  65                  70 gac ggg act gga agc gat gac aaa aaa gcc aag ggg gct gat ggt aaa      592
Asp Gly Thr Gly Ser Asp Asp Lys Lys Ala Lys Gly Ala Asp Gly Lys
 75                  80                  85                  90 acg aag atc gcc aca ccg cgg gga gca gcc cct cca ggc cag aag ggc      640
Thr Lys Ile Ala Thr Pro Arg Gly Ala Ala Pro Pro Gly Gln Lys Gly
                 95                 100                 105 cag gcc aac gcc acc agg att cca gca aaa acc ccg ccc gct cca aag      688
Gln Ala Asn Ala Thr Arg Ile Pro Ala Lys Thr Pro Pro Ala Pro Lys
                110                 115                 120 aca cca ccc agc tct ggt gaa cct cca aaa tca ggg gat cgc agc ggc      736
Thr Pro Pro Ser Ser Gly Glu Pro Pro Lys Ser Gly Asp Arg Ser Gly
                125                 130                 135 tac agc agc ccc ggc tcc cca ggc act ccc ggc agc cgc tcc cgc acc      784
Tyr Ser Ser Pro Gly Ser Pro Gly Thr Pro Gly Ser Arg Ser Arg Thr
            140                 145                 150 ccg tcc ctt cca acc cca ccc acc cgg gag ccc aag aag gtg gca gtg      832
Pro Ser Leu Pro Thr Pro Pro Thr Arg Glu Pro Lys Lys Val Ala Val
155                 160                 165                 170 gtc cgt act cca ccc aag tcg ccg tct tcc gcc aag agc cgc ctg cag      880
Val Arg Thr Pro Pro Lys Ser Pro Ser Ser Ala Lys Ser Arg Leu Gln
                175                 180                 185 aca gcc ccc gtg ccc atg cca gac ctg aag aat gtc aag tcc aag atc      928
Thr Ala Pro Val Pro Met Pro Asp Leu Lys Asn Val Lys Ser Lys Ile
                190                 195                 200 ggc tcc act gag aac ctg aag cac cag ccg gga ggc ggg aag gtg cag      976
Gly Ser Thr Glu Asn Leu Lys His Gln Pro Gly Gly Gly Lys Val Gln
                205                 210                 215 ata att aat aag aag ctg gat ctt agc aac gtc cag tcc aag tgt ggc     1024
Ile Ile Asn Lys Lys Leu Asp Leu Ser Asn Val Gln Ser Lys Cys Gly
        220                 225                 230 tca aag gat aat atc aaa cac gtc ccg gga ggc ggc agt gtg caa ata     1072
Ser Lys Asp Asn Ile Lys His Val Pro Gly Gly Gly Ser Val Gln Ile
235                 240                 245                 250 gtc tac aaa cca gtt gac ctg agc aag gtg acc tcc aag tgt ggc tca     1120
Val Tyr Lys Pro Val Asp Leu Ser Lys Val Thr Ser Lys Cys Gly Ser
                255                 260                 265 tta ggc aac atc cat cat aaa cca gga ggt ggc cag gtg gaa gta aaa     1168
Leu Gly Asn Ile His His Lys Pro Gly Gly Gly Gln Val Glu Val Lys
                270                 275                 280 tct gag aag ctt gac ttc aag gac aga gtc cag tcg aag att ggg tcc     1216
Ser Glu Lys Leu Asp Phe Lys Asp Arg Val Gln Ser Lys Ile Gly Ser
            285                 290                 295 ctg gac aat atc acc cac gtc cct ggc gga gga aat aaa aag att gaa     1264
Leu Asp Asn Ile Thr His Val Pro Gly Gly Gly Asn Lys Lys Ile Glu
            300                 305                 310 acc cac aag ctg acc ttc cgc gag aac gcc aaa gcc aag aca gac cac     1312
Thr His Lys Leu Thr Phe Arg Glu Asn Ala Lys Ala Lys Thr Asp His
315                 320                 325                 330 ggg gcg gag atc gtg tac aag tcg cca gtg gtg tct ggg gac acg tct     1360
```

```
Gly Ala Glu Ile Val Tyr Lys Ser Pro Val Val Ser Gly Asp Thr Ser
                335                 340                 345 cca cgg cat ctc agc aat gtc tcc tcc acc ggc agc atc gac atg gta    1408
Pro Arg His Leu Ser Asn Val Ser Ser Thr Gly Ser Ile Asp Met Val
        350                 355                 360 gac tcg ccc cag ctc gcc acg cta gct gac gag gtg tct gcc tcc ctg    1456
Asp Ser Pro Gln Leu Ala Thr Leu Ala Asp Glu Val Ser Ala Ser Leu
    365                 370                 375 gcc aag cag ggt ttg tga tcaggcccct ggggcggtca ataattgtgg           1504
Ala Lys Gln Gly Leu
        380 agaggagaga atgagagagt gtggaaaaaa aaagaataat gacccggccc cgccctctg    1564 cccccagctg ctcctcgcag ttcggttaat tggttaatca cttaacctgc ttttgtcact   1624 cggctttggc tcgggacttc aaaatcagtg atgggagtaa gagcaaattt catctttcca   1684 aattgatggg tgggctagta ataaaatatt taaaaaaaaa cattcaaaaa catggccaca   1744 tccaacattt cctcaggcaa ttccttttga ttcttttttc ttcccctcc atgtagaaga    1804 gggagaagga gaggctctga agctgcttc tggggattt caagggactg ggggtgccaa     1864 ccacctctgg ccctgttgtg ggggtgtcac agaggcagtg gcagcaacaa aggatttgaa   1924 acttggtgtg ttcgtggagc cacaggcaga cgatgtcaac cttgtgtgag tgtgacgggg   1984 gttgggggtgg ggcgggaggc cacggggag gccgaggcag gggctgggca gaggggagag   2044 gaagcacaag aagtgggagt gggagaggaa gccacgtgct ggagagtaga catcccctc    2104 cttgccgctg ggagagccaa ggcctatgcc acctgcagcg tctgagcggc cgcctgtcct   2164 tggtggccgg gggtgggggc ctgctgtggg tcagtgtgcc accctctgca gggcagcctg   2224 tgggagaagg gacagcgggt aaaaagagaa ggcaagctgg caggagggtg gcacttcgtg   2284 gatgacctcc ttagaaaaga ctgaccttga tgtcttgaga gcgctggcct cttcctccct   2344 ccctgcaggg taggggggcct gagttgaggg gcttccctct gctccacaga aaccctgttt  2404 tattgagttc tgaaggttgg aactgctgcc atgatttttgg ccactttgca gacctgggac  2464 tttagggcta accagttctc tttgtaagga cttgtgcctc ttgggagacg tccacccgtt   2524 tccaagcctg ggccactggc atctctggag tgtgtggggg tctgggaggc aggtcccgag   2584 ccccctgtcc ttcccacggc cactgcagtc acccgtctg cgccgctgtg ctgttgtctg    2644 ccgtgagagc ccaatcactg cctataccc tcatcacacg tcacaatgtc ccgaattccc    2704 agcctcacca ccccttctca gtaatgaccc tggttggttg caggaggtac ctactccata   2764 ctgagggtga aattaaggga aggcaaagtc caggcacaag agtgggaccc cagcctctca   2824 ctctcagttc cactcatcca actgggaccc tcaccacgaa tctcatgatc tgattcggtt   2884 ccctgtctcc tcctcccgtc acagatgtga gccagggcac tgctcagctg tgaccctagg   2944 tgtttctgcc ttgttgacat ggagagagcc ctttcccctg agaaggcctg gccccttcct   3004 gtgctgagcc cacagcagca ggctgggtgt cttggttgtc agtggtggca ccaggatgga   3064 agggcaaggc acccagggca ggcccacagt cccgctgtcc cccacttgca ccctagcttg   3124 tagctgccaa cctcccagac agcccagccc gctgctcagc tccacatgca agtatcagc    3184 cctccacacc cgacaaaggg gaacacaccc ccttggaaat ggttcttttc ccccagtccc   3244 agctggaagc catgctgtct gttctgctgg agcagctgaa catatacata gatgttgccc   3304 tgccctcccc atctgcaccc tgttgagttg tagttggatt tgtctgttta tgcttggatt   3364 caccagagtg actatgatag tgaaaagaaa aaaaaaaaa aaaaggacg catgtatctt     3424
```

-continued

```
gaaatgcttg taaagaggtt tctaacccac cctcacgagg tgtctctcac ccccacactg    3484
ggactcgtgt ggcctgtgtg gtgccaccct gctggggcct cccaagtttt gaaaggcttt    3544
cctcagcacc tgggacccaa cagagaccag cttctagcag ctaaggaggc cgttcagctg    3604
tgacgaaggc ctgaagcaca ggattaggac tgaagcgatg atgtcccctt ccctacttcc    3664
ccttggggct ccctgtgtca gggcacagac taggtcttgt ggctggtctg gcttgcggcg    3724
cgaggatggt tctctctggt catagcccga agtctcatgg cagtcccaaa ggaggcttac    3784
aactcctgca tcacaagaaa aaggaagcca ctgccagctg gggggatctg cagctcccag    3844
aagctccgtg agcctcagcc acccctcaga ctgggttcct ctccaagctc gccctctgga    3904
ggggcagcgc agcctcccac caagggccct gcgaccacag cagggattgg gatgaattgc    3964
ctgtcctgga tctgctctag aggcccaagc tgcctgcctg aggaaggatg acttgacaag    4024
tcaggagaca ctgttcccaa agccttgacc agagcacctc agcccgctga ccttgcacaa    4084
actccatctg ctgccatgag aaagggaag ccgcctttgc aaaacattgc tgcctaaaga    4144
aactcagcag cctcaggccc aattctgcca cttctggttt gggtacagtt aaaggcaacc    4204
ctgagggact tggcagtaga aatccagggc ctcccctggg gctggcagct tcgtgtgcag    4264
ctagagcttt acctgaaagg aagtctctgg gcccagaact ctccaccaag agcctccctg    4324
ccgttcgctg agtcccagca attctcctaa gttgaaggga tctgagaagg agaaggaaat    4384
gtggggtaga tttggtggtg gttagagata tgccccctc attactgcca acagtttcgg    4444
ctgcatttct tcacgcacct cggttcctct tcctgaagtt cttgtgccct gctcttcagc    4504
accatgggcc ttcttatacg gaaggctctg ggatctcccc cttgtggggc aggctcttgg    4564
ggccagccta agatcatggt ttagggtgat cagtgctggc agataaattg aaaaggcacg    4624
ctggcttgtg atcttaaatg aggacaatcc ccccagggct gggcactcct cccctccct    4684
cacttctccc acctgcagag ccagtgtcct tgggtgggct agataggata tactgtatgc    4744
cggctccttc aagctgctga ctcactttat caatagttcc atttaaattg acttcagtgg    4804
tgagactgta tcctgtttgc tattgcttgt tgtgctatgg ggggagggg gaggaatgtg    4864
taagatagtt aacatgggca aagggagatc ttggggtgca gcacttaaac tgcctcgtaa    4924
cccttttcat gatttcaacc acatttgcta gagggaggga gcagccacgg agttagaggc    4984
ccttggggtt tctcttttcc actgacaggc tttcccaggc agctggctag ttcattccct    5044
ccccagccag gtgcaggcgt aggaatatgg acatctggtt gctttggcct gctgccctct    5104
ttcaggggtc ctaagcccac aatcatgcct ccctaagacc ttggcatcct tccctctaag    5164
ccgttggcac ctctgtgcca cctctcacac tggctccaga cacacagcct gtgcttttgg    5224
agctgagatc actcgcttca ccctcctcat ctttgttctc caagtaaagc cacgaggtcg    5284
gggcgagggc agaggtgatc acctgcgtgt cccatctaca gacctgcagc ttcataaaac    5344
ttctgatttc tcttcagctt tgaaaagggt taccctgggc actggcctag agcctcacct    5404
cctaatagac ttagccccat gagtttgcca tgttgagcag gactatttct ggcacttgca    5464
agtcccatga tttcttcggt aattctgagg gtgggggag ggacatgaaa tcatcttagc    5524
ttagcttttct gtctgtgaat gtctatatag tgtattgtgt gttttaacaa atgatttaca    5584
ctgactgttg ctgtaaaagt gaatttggaa ataaagttat tactctgatt aaa           5637
```

<210> SEQ ID NO 9
<211> LENGTH: 6762
<212> TYPE: DNA
<213> ORGANISM: homo sapiens

```
<220> FEATURE:
<221> NAME/KEY: CDS
<222> LOCATION: (323)...(2599)

<400> SEQUENCE: 9
ggacggccga gcggcagggc gctcgcgcgc gcccactagt ggccggagga gaaggctccc      60
gcggaggccg cgctgcccgc ccctcccct ggggaggctc gcgttcccgc tgctcgcgcc     120
tgcgccgccc gccggcctca ggaacgcgcc ctcttcgccg gcgcgcgccc tcgcagtcac     180
cgccacccac cagctccggc accaacagca gcgccgctgc caccgcccac cttctgccgc     240
cgccaccaca gccaccttct cctcctccgc tgtcctctcc cgtcctcgcc tctgtcgact     300
atcaggtgaa ctttgaacca gg atg gct gag ccc cgc cag gag ttc gaa gtg     352
                         Met Ala Glu Pro Arg Gln Glu Phe Glu Val
                          1               5                  10 atg gaa gat cac gct ggg acg tac ggg ttg ggg gac agg aaa gat cag      400
Met Glu Asp His Ala Gly Thr Tyr Gly Leu Gly Asp Arg Lys Asp Gln
             15                  20                  25 ggg ggc tac acc atg cac caa gac caa gag ggt gac acg gac gct ggc      448
Gly Gly Tyr Thr Met His Gln Asp Gln Glu Gly Asp Thr Asp Ala Gly
         30                  35                  40 ctg aaa gaa tct ccc ctg cag acc ccc act gag gac gga tct gag gaa      496
Leu Lys Glu Ser Pro Leu Gln Thr Pro Thr Glu Asp Gly Ser Glu Glu
     45                  50                  55 ccg ggc tct gaa acc tct gat gct aag agc act cca aca gcg gaa gat      544
Pro Gly Ser Glu Thr Ser Asp Ala Lys Ser Thr Pro Thr Ala Glu Asp
 60                  65                  70 gtg aca gca ccc tta gtg gat gag gga gct ccc ggc aag cag gct gcc      592
Val Thr Ala Pro Leu Val Asp Glu Gly Ala Pro Gly Lys Gln Ala Ala
 75                  80                  85                  90 gcg cag ccc cac acg gag atc cca gaa gga acc aca gct gaa gaa gca      640
Ala Gln Pro His Thr Glu Ile Pro Glu Gly Thr Thr Ala Glu Glu Ala
                 95                 100                 105 ggc att gga gac acc ccc agc ctg gaa gac gaa gct gct ggt cac gtg      688
Gly Ile Gly Asp Thr Pro Ser Leu Glu Asp Glu Ala Ala Gly His Val
             110                 115                 120 acc caa gag cct gaa agt ggt aag gtg gtc cag gaa ggc ttc ctc cga      736
Thr Gln Glu Pro Glu Ser Gly Lys Val Val Gln Glu Gly Phe Leu Arg
         125                 130                 135 gag cca ggc ccc cca ggt ctg agc cac cag ctc atg tcc ggc atg cct      784
Glu Pro Gly Pro Pro Gly Leu Ser His Gln Leu Met Ser Gly Met Pro
     140                 145                 150 ggg gct ccc ctc ctg cct gag ggc ccc aga gag gcc aca cgc caa cct      832
Gly Ala Pro Leu Leu Pro Glu Gly Pro Arg Glu Ala Thr Arg Gln Pro
155                 160                 165                 170 tcg ggg aca gga cct gag gac aca gag ggc ggc cgc cac gcc cct gag      880
Ser Gly Thr Gly Pro Glu Asp Thr Glu Gly Gly Arg His Ala Pro Glu
                 175                 180                 185 ctg ctc aag cac cag ctt cta gga gac ctg cac cag gag ggg ccg ccg      928
Leu Leu Lys His Gln Leu Leu Gly Asp Leu His Gln Glu Gly Pro Pro
             190                 195                 200 ctg aag ggg gca ggg ggc aaa gag agg ccg ggg agc aag gag gag gtg      976
Leu Lys Gly Ala Gly Gly Lys Glu Arg Pro Gly Ser Lys Glu Glu Val
         205                 210                 215 gat gaa gac cgc gac gtc gat gag tcc tcc ccc caa gac tcc cct ccc     1024
Asp Glu Asp Arg Asp Val Asp Glu Ser Ser Pro Gln Asp Ser Pro Pro
     220                 225                 230 tcc aag gcc tcc cca gcc caa gat ggg cgg cct ccc cag aca gcc gcc     1072
Ser Lys Ala Ser Pro Ala Gln Asp Gly Arg Pro Pro Gln Thr Ala Ala
235                 240                 245                 250
```

-continued

```
aga gaa gcc acc agc atc cca ggc ttc cca gcg gag ggt gcc atc ccc      1120
Arg Glu Ala Thr Ser Ile Pro Gly Phe Pro Ala Glu Gly Ala Ile Pro
            255                 260                 265 ctc cct gtg gat ttc ctc tcc aaa gtt tcc aca gag atc cca gcc tca      1168
Leu Pro Val Asp Phe Leu Ser Lys Val Ser Thr Glu Ile Pro Ala Ser
        270                 275                 280 gag ccc gac ggg ccc agt gta ggg cgg gcc aaa ggg cag gat gcc ccc      1216
Glu Pro Asp Gly Pro Ser Val Gly Arg Ala Lys Gly Gln Asp Ala Pro
    285                 290                 295 ctg gag ttc acg ttt cac gtg gaa atc aca ccc aac gtg cag aag gag      1264
Leu Glu Phe Thr Phe His Val Glu Ile Thr Pro Asn Val Gln Lys Glu
300                 305                 310 cag gcg cac tcg gag gag cat ttg gga agg gct gca ttt cca ggg gcc      1312
Gln Ala His Ser Glu Glu His Leu Gly Arg Ala Ala Phe Pro Gly Ala
315                 320                 325                 330 cct gga gag ggg cca gag gcc cgg ggc ccc tct ttg gga gag gac aca      1360
Pro Gly Glu Gly Pro Glu Ala Arg Gly Pro Ser Leu Gly Glu Asp Thr
                335                 340                 345 aaa gag gct gac ctt cca gag ccc tct gaa aag cag cct gct gct gct      1408
Lys Glu Ala Asp Leu Pro Glu Pro Ser Glu Lys Gln Pro Ala Ala Ala
            350                 355                 360 ccg cgg ggg aag ccc gtc agc cgg gtc cct caa ctc aaa gct cgc atg      1456
Pro Arg Gly Lys Pro Val Ser Arg Val Pro Gln Leu Lys Ala Arg Met
        365                 370                 375 gtc agt aaa agc aaa gac ggg act gga agc gat gac aaa aaa gcc aag      1504
Val Ser Lys Ser Lys Asp Gly Thr Gly Ser Asp Asp Lys Lys Ala Lys
    380                 385                 390 aca tcc aca cgt tcc tct gct aaa acc ttg aaa aat agg cct tgc ctt      1552
Thr Ser Thr Arg Ser Ser Ala Lys Thr Leu Lys Asn Arg Pro Cys Leu
395                 400                 405                 410 agc ccc aaa cac ccc act cct ggt agc tca gac cct ctg atc caa ccc      1600
Ser Pro Lys His Pro Thr Pro Gly Ser Ser Asp Pro Leu Ile Gln Pro
                415                 420                 425 tcc agc cct gct gtg tgc cca gag cca cct tcc tct cct aaa tac gtc      1648
Ser Ser Pro Ala Val Cys Pro Glu Pro Pro Ser Ser Pro Lys Tyr Val
            430                 435                 440 tct tct gtc act tcc cga act ggc agt tct gga gca aag gag atg aaa      1696
Ser Ser Val Thr Ser Arg Thr Gly Ser Ser Gly Ala Lys Glu Met Lys
        445                 450                 455 ctc aag ggg gct gat ggt aaa acg aag atc gcc aca ccg cgg gga gca      1744
Leu Lys Gly Ala Asp Gly Lys Thr Lys Ile Ala Thr Pro Arg Gly Ala
    460                 465                 470 gcc cct cca ggc cag aag ggc cag gcc aac gcc acc agg att cca gca      1792
Ala Pro Pro Gly Gln Lys Gly Gln Ala Asn Ala Thr Arg Ile Pro Ala
475                 480                 485                 490 aaa acc ccg ccc gct cca aag aca cca ccc agc tct ggt gaa cct cca      1840
Lys Thr Pro Pro Ala Pro Lys Thr Pro Pro Ser Ser Gly Glu Pro Pro
                495                 500                 505 aaa tca ggg gat cgc agc ggc tac agc agc ccc ggc tcc cca ggc act      1888
Lys Ser Gly Asp Arg Ser Gly Tyr Ser Ser Pro Gly Ser Pro Gly Thr
            510                 515                 520 ccc ggc agc cgc tcc cgc acc ccg tcc ctt cca acc cca ccc acc cgg      1936
Pro Gly Ser Arg Ser Arg Thr Pro Ser Leu Pro Thr Pro Pro Thr Arg
        525                 530                 535 gag ccc aag aag gtg gca gtg gtc cgt act cca ccc aag tcg ccg tct      1984
Glu Pro Lys Lys Val Ala Val Val Arg Thr Pro Pro Lys Ser Pro Ser
    540                 545                 550 tcc gcc aag agc cgc ctg cag aca gcc ccc gtg ccc atg cca gac ctg      2032
Ser Ala Lys Ser Arg Leu Gln Thr Ala Pro Val Pro Met Pro Asp Leu
```

```
                555              560              565              570
aag aat gtc aag tcc aag atc ggc tcc act gag aac ctg aag cac cag           2080
Lys Asn Val Lys Ser Lys Ile Gly Ser Thr Glu Asn Leu Lys His Gln
                575              580              585 ccg gga ggc ggg aag gtg cag ata att aat aag aag ctg gat ctt agc           2128
Pro Gly Gly Gly Lys Val Gln Ile Ile Asn Lys Lys Leu Asp Leu Ser
            590              595              600 aac gtc cag tcc aag tgt ggc tca aag gat aat atc aaa cac gtc ccg           2176
Asn Val Gln Ser Lys Cys Gly Ser Lys Asp Asn Ile Lys His Val Pro
            605              610              615 gga ggc ggc agt gtg caa ata gtc tac aaa cca gtt gac ctg agc aag           2224
Gly Gly Gly Ser Val Gln Ile Val Tyr Lys Pro Val Asp Leu Ser Lys
        620              625              630 gtg acc tcc aag tgt ggc tca tta ggc aac atc cat cat aaa cca gga           2272
Val Thr Ser Lys Cys Gly Ser Leu Gly Asn Ile His His Lys Pro Gly
635              640              645              650 ggt ggc cag gtg gaa gta aaa tct gag aag ctt gac ttc aag gac aga           2320
Gly Gly Gln Val Glu Val Lys Ser Glu Lys Leu Asp Phe Lys Asp Arg
                655              660              665 gtc cag tcg aag att ggg tcc ctg gac aat atc acc cac gtc cct ggc           2368
Val Gln Ser Lys Ile Gly Ser Leu Asp Asn Ile Thr His Val Pro Gly
            670              675              680 gga gga aat aaa aag att gaa acc cac aag ctg acc ttc cgc gag aac           2416
Gly Gly Asn Lys Lys Ile Glu Thr His Lys Leu Thr Phe Arg Glu Asn
            685              690              695 gcc aaa gcc aag aca gac cac ggg gcg gag atc gtg tac aag tcg cca           2464
Ala Lys Ala Lys Thr Asp His Gly Ala Glu Ile Val Tyr Lys Ser Pro
        700              705              710 gtg gtg tct ggg gac acg tct cca cgg cat ctc agc aat gtc tcc tcc           2512
Val Val Ser Gly Asp Thr Ser Pro Arg His Leu Ser Asn Val Ser Ser
715              720              725              730 acc ggc agc atc gac atg gta gac tcg ccc cag ctc gcc acg cta gct           2560
Thr Gly Ser Ile Asp Met Val Asp Ser Pro Gln Leu Ala Thr Leu Ala
                735              740              745 gac gag gtg tct gcc tcc ctg gcc aag cag ggt ttg tga tcaggcccct           2609
Asp Glu Val Ser Ala Ser Leu Ala Lys Gln Gly Leu
            750              755 ggggcggtca ataattgtgg agaggagaga atgagagagt gtggaaaaaa aaagaataat        2669
gacccggccc ccgccctctg cccccagctg ctcctcgcag ttcggttaat tggttaatca        2729
cttaacctgc ttttgtcact cggctttggc tcgggacttc aaaatcagtg atgggagtaa        2789
gagcaaattt catctttcca aattgatggg tgggctagta ataaaatatt taaaaaaaaa        2849
cattcaaaaa catggccaca tccaacattt cctcaggcaa ttcctttga ttcttttttc         2909 ttcccctcc atgtagaaga gggagaagga gaggctctga aagctgcttc tgggggattt         2969
caagggactg ggggtgccaa ccacctctgg ccctgttgtg ggggtgtcac agaggcagtg        3029
gcagcaacaa aggatttgaa acttggtgtg ttcgtggagc cacaggcaga cgatgtcaac        3089
cttgtgtgag tgtgacgggg gttggggtgg ggcgggaggc cacgggggag ccgaggcag         3149 gggctgggca gaggggagag gaagcacaag aagtgggagt gggagaggaa gccacgtgct        3209
ggagagtaga catcccctc cttgccgctg ggagagccaa ggcctatgcc acctgcagcg         3269
tctgagcggc cgcctgtcct tggtggccgg gggtgggggc ctgctgtggg tcagtgtgcc        3329
accctctgca gggcagcctg tgggagaagg acagcgggt aaaaagagaa ggcaagctgg         3389
caggagggtg gcacttcgtg gatgacctcc ttagaaaaga ctgaccttga tgtcttgaga        3449
gcgctggcct cttcctccct ccctgcaggg tagggggcct gagttgaggg gcttccctct        3509
```

```
gctccacaga aaccctgttt tattgagttc tgaaggttgg aactgctgcc atgattttgg    3569
ccactttgca gacctgggac tttagggcta accagttctc tttgtaagga cttgtgcctc    3629
ttgggagacg tccacccgtt tccaagcctg ggccactggc atctctggag tgtgtggggg    3689
tctgggaggc aggtcccgag cccctgtcc ttcccacggc cactgcagtc accccgtctg    3749
cgccgctgtg ctgttgtctg ccgtgagagc ccaatcactg cctataccc tcatcacacg     3809 tcacaatgtc ccgaattccc agcctcacca cccttctca gtaatgaccc tggttggttg     3869
caggaggtac ctactccata ctgagggtga aattaaggga aggcaaagtc caggcacaag    3929
agtgggaccc cagcctctca ctctcagttc cactcatcca actgggaccc tcaccacgaa    3989
tctcatgatc tgattcggtt ccctgtctcc cctcccgtc acagatgtga gccagggcac     4049
tgctcagctg tgaccctagg tgtttctgcc ttgttgacat ggagagagcc ctttcccctg    4109
agaaggcctg gcccttcct gtgctgagcc cacagcagca ggctgggtgt cttggttgtc     4169
agtggtggca ccaggatgga agggcaaggc acccagggca ggcccacagt cccgctgtcc    4229
cccacttgca ccctagcttg tagctgccaa cctcccagac agcccagccc gctgctcagc    4289
tccacatgca tagtatcagc cctccacacc cgacaaaggg gaacacaccc ccttgggaaat   4349 ggttcttttc ccccagtccc agctggaagc catgctgtct gttctgctgg agcagctgaa    4409
catatacata gatgttgccc tgccctcccc atctgcaccc tgttgagttg tagttggatt    4469
tgtctgttta tgcttggatt caccagagtg actatgatag tgaaaagaaa aaaaaaaaa     4529 aaaaaggacg catgtatctt gaaatgcttg taaagaggtt tctaacccac cctcacgagg    4589
tgtctctcac ccccacactg ggactcgtgt ggcctgtgtg gtgccaccct gctggggcct    4649 cccaagttt gaaaggcttt cctcagcacc tgggacccaa cagagaccag cttctagcag    4709
ctaaggaggc cgttcagctg tgacgaaggc ctgaagcaca ggattaggac tgaagcgatg    4769 atgtccctt ccctacttcc ccttgggct ccctgtgtca gggcacagac taggtcttgt     4829
ggctggtctg gcttgcggcg cgaggatggt tctctctggt catagcccga agtctcatgg    4889
cagtcccaaa ggaggcttac aactcctgca tcacaagaaa aaggaagcca ctgccagctg    4949
gggggatctg cagctcccag aagctccgtg agcctcagcc accctcaga ctgggttcct     5009 ctccaagctc gccctctgga ggggcagcgc agcctccac caagggccct gcgaccacag     5069
cagggattgg gatgaattgc ctgtcctgga tctgctctag aggcccaagc tgcctgcctg    5129
aggaaggatg acttgacaag tcaggagaca ctgttcccaa agccttgacc agagcacctc    5189
agcccgctga ccttgcacaa actccatctg ctgccatgaa aaagggaag ccgccttgc      5249 aaaacattgc tgcctaaaga aactcagcag cctcaggccc aattctgcca cttctggttt    5309
gggtacagtt aaaggcaacc ctgagggact tggcagtaga atccagggc ctcccctggg     5369 gctggcagct tcgtgtgcag ctagagcttt acctgaaagg aagtctctgg gcccagaact    5429
ctccaccaag agcctccctg ccgttcgctg agtcccagca attctcctaa gttgaaggga    5489
tctgagaagg agaaggaaat gtggggtaga tttggtggtg gttagagata tgcccccctc    5549
attactgcca acagtttcgg ctgcatttct tcacgcacct cggttcctct tcctgaagtt    5609
cttgtgccct gctcttcagc accatgggcc ttcttatacg gaaggctctg ggatctcccc    5669
cttgtggggc aggctcttgg ggccagccta agatcatggt ttagggtgat cagtgctggc    5729
agataaattg aaaaggcacg ctggcttgtg atccttaaatg aggacaatcc ccccagggct   5789
gggcactcct cccctcccct cacttctccc acctgcagag ccagtgtcct tgggtgggct    5849
```

```
agataggata tactgtatgc cggctccttc aagctgctga ctcactttat caatagttcc    5909
atttaaattg acttcagtgg tgagactgta tcctgtttgc tattgcttgt tgtgctatgg    5969 ggggagggg gaggaatgtg taagatagtt aacatgggca aagggagatc ttggggtgca    6029
gcacttaaac tgcctcgtaa ccctttttcat gatttcaacc acatttgcta gagggaggga    6089
gcagccacgg agttagaggc ccttggggtt tctcttttcc actgacaggc tttcccaggc    6149
agctggctag ttcattccct ccccagccag gtgcaggcgt aggaatatgg acatctggtt    6209
gctttggcct gctgccctct ttcaggggtc ctaagcccac aatcatgcct ccctaagacc    6269
ttggcatcct tccctctaag ccgttggcac tctctgtgcca cctctcacac tggctccaga    6329
cacacagcct gtgcttttgg agctgagatc actcgcttca ccctcctcat ctttgttctc    6389
caagtaaagc cacgaggtcg gggcgagggc agaggtgatc acctgcgtgt cccatctaca    6449
gacctgcagc ttcataaaac ttctgatttc tcttcagctt tgaaagggt tacccctgggc    6509 actggcctag agcctcacct cctaatagac ttagccccat gagtttgcca tgttgagcag    6569
gactatttct ggcacttgca agtcccatga tttcttcggt aattctgagg gtggggggag    6629
ggacatgaaa tcatcttagc ttagctttct gtctgtgaat gtctatatag tgtattgtgt    6689
gttttaacaa atgatttaca ctgactgttg ctgtaaaagt gaatttggaa ataaagttat    6749
tactctgatt aaa                                                     6762

<210> SEQ ID NO 10
<211> LENGTH: 5544
<212> TYPE: DNA
<213> ORGANISM: homo sapiens
<220> FEATURE:
<221> NAME/KEY: CDS
<222> LOCATION: (323)...(1381)

<400> SEQUENCE: 10
ggacggccga gcggcagggc gctcgcgcgc gcccactagt ggccggagga gaaggctccc    60
gcggaggccg cgctgcccgc cccctcccct ggggaggctc gcgttcccgc tgctcgcgcc    120
tgcgccgccc gccggcctca ggaacgcgcc ctcttcgccg gcgcgcgccc tcgcagtcac    180
cgccacccac cagctccggc accaacagca gcgccgctgc caccgccccac cttctgccgc    240 cgccaccaca gccaccttct cctcctccgc tgtcctctcc cgtcctcgcc tctgtcgact    300
atcaggtgaa ctttgaacca gg atg gct gag ccc cgc cag gag ttc gaa gtg    352
                          Met Ala Glu Pro Arg Gln Glu Phe Glu Val
                            1               5                  10 atg gaa gat cac gct ggg acg tac ggg ttg ggg gac agg aaa gat cag    400
Met Glu Asp His Ala Gly Thr Tyr Gly Leu Gly Asp Arg Lys Asp Gln
             15                  20                  25 ggg ggc tac acc atg cac caa gac caa gag ggt gac acg gac gct ggc    448
Gly Gly Tyr Thr Met His Gln Asp Gln Glu Gly Asp Thr Asp Ala Gly
         30                  35                  40 ctg aaa gct gaa gaa gca ggc att gga gac acc ccc agc ctg gaa gac    496
Leu Lys Ala Glu Glu Ala Gly Ile Gly Asp Thr Pro Ser Leu Glu Asp
     45                  50                  55 gaa gct gct ggt cac gtg acc caa gct cgc atg gtc agt aaa agc aaa    544
Glu Ala Ala Gly His Val Thr Gln Ala Arg Met Val Ser Lys Ser Lys
 60                  65                  70 gac ggg act gga agc gat gac aaa aaa gcc aag ggg gct gat ggt aaa    592
Asp Gly Thr Gly Ser Asp Asp Lys Lys Ala Lys Gly Ala Asp Gly Lys
 75                  80                  85                  90 acg aag atc gcc aca ccg cgg gga gca gcc cct cca ggc cag aag ggc    640
Thr Lys Ile Ala Thr Pro Arg Gly Ala Ala Pro Pro Gly Gln Lys Gly
```

|  |  |  |  |  |  |  |  |  |  |  |  |  |
|---|---|---|---|---|---|---|---|---|---|---|---|---|
|  |  |  | 95 |  |  |  | 100 |  |  |  | 105 |  |
| cag | gcc | aac | gcc | acc | agg | att | cca | gca | aaa | acc | ccg | ccc | gct | cca | aag | 688 |
| Gln | Ala | Asn | Ala | Thr | Arg | Ile | Pro | Ala | Lys | Thr | Pro | Pro | Ala | Pro | Lys |  |
|  |  | 110 |  |  |  |  | 115 |  |  |  |  | 120 |  |  |  |  |

```
             95                 100                 105
cag gcc aac gcc acc agg att cca gca aaa acc ccg ccc gct cca aag     688
Gln Ala Asn Ala Thr Arg Ile Pro Ala Lys Thr Pro Pro Ala Pro Lys
        110                 115                 120 aca cca ccc agc tct ggt gaa cct cca aaa tca ggg gat cgc agc ggc     736
Thr Pro Pro Ser Ser Gly Glu Pro Pro Lys Ser Gly Asp Arg Ser Gly
    125                 130                 135 tac agc agc ccc ggc tcc cca ggc act ccc ggc agc cgc tcc cgc acc     784
Tyr Ser Ser Pro Gly Ser Pro Gly Thr Pro Gly Ser Arg Ser Arg Thr
140                 145                 150 ccg tcc ctt cca acc cca ccc acc cgg gag ccc aag aag gtg gca gtg     832
Pro Ser Leu Pro Thr Pro Pro Thr Arg Glu Pro Lys Lys Val Ala Val
155                 160                 165                 170 gtc cgt act cca ccc aag tcg ccg tct tcc gcc aag agc cgc ctg cag     880
Val Arg Thr Pro Pro Lys Ser Pro Ser Ser Ala Lys Ser Arg Leu Gln
            175                 180                 185 aca gcc ccc gtg ccc atg cca gac ctg aag aat gtc aag tcc aag atc     928
Thr Ala Pro Val Pro Met Pro Asp Leu Lys Asn Val Lys Ser Lys Ile
        190                 195                 200 ggc tcc act gag aac ctg aag cac cag ccg gga ggc ggg aag gtg caa     976
Gly Ser Thr Glu Asn Leu Lys His Gln Pro Gly Gly Gly Lys Val Gln
    205                 210                 215 ata gtc tac aaa cca gtt gac ctg agc aag gtg acc tcc aag tgt ggc    1024
Ile Val Tyr Lys Pro Val Asp Leu Ser Lys Val Thr Ser Lys Cys Gly
220                 225                 230 tca tta ggc aac atc cat cat aaa cca gga ggt ggc cag gtg gaa gta    1072
Ser Leu Gly Asn Ile His His Lys Pro Gly Gly Gly Gln Val Glu Val
235                 240                 245                 250 aaa tct gag aag ctt gac ttc aag gac aga gtc cag tcg aag att ggg    1120
Lys Ser Glu Lys Leu Asp Phe Lys Asp Arg Val Gln Ser Lys Ile Gly
            255                 260                 265 tcc ctg gac aat atc acc cac gtc cct ggc gga gga aat aaa aag att    1168
Ser Leu Asp Asn Ile Thr His Val Pro Gly Gly Gly Asn Lys Lys Ile
        270                 275                 280 gaa acc cac aag ctg acc ttc cgc gag aac gcc aaa gcc aag aca gac    1216
Glu Thr His Lys Leu Thr Phe Arg Glu Asn Ala Lys Ala Lys Thr Asp
    285                 290                 295 cac ggg gcg gag atc gtg tac aag tcg cca gtg gtg tct ggg gac acg    1264
His Gly Ala Glu Ile Val Tyr Lys Ser Pro Val Val Ser Gly Asp Thr
300                 305                 310 tct cca cgg cat ctc agc aat gtc tcc tcc acc ggc agc atc gac atg    1312
Ser Pro Arg His Leu Ser Asn Val Ser Ser Thr Gly Ser Ile Asp Met
315                 320                 325                 330 gta gac tcg ccc cag ctc gcc acg cta gct gac gag gtg tct gcc tcc    1360
Val Asp Ser Pro Gln Leu Ala Thr Leu Ala Asp Glu Val Ser Ala Ser
            335                 340                 345 ctg gcc aag cag ggt ttg tga tcaggcccct ggggcggtca ataattgtgg       1411
Leu Ala Lys Gln Gly Leu
            350 agaggagaga atgagagagt gtggaaaaaa aagaataat gacccggccc cgccctctg    1471 cccccagctg ctcctcgcag ttcggttaat tggttaatca cttaacctgc ttttgtcact  1531 cggctttggc tcgggacttc aaaatcagtg atgggagtaa gagcaaattt catctttcca  1591 aattgatggg tgggctagta ataaaatatt taaaaaaaaa cattcaaaaa catgccaca   1651 tccaacattt cctcaggcaa ttcctttga ttctttttc ttcccctcc atgtagaaga    1711 gggagaagga gaggctctga aagctgcttc tgggggattt caagggactg ggggtgccaa  1771 ccacctctgg ccctgttgtg ggggtgtcac agaggcagtg gcagcaacaa aggatttgaa  1831
```

```
acttggtgtg ttcgtggagc cacaggcaga cgatgtcaac cttgtgtgag tgtgacgggg    1891
gttggggtgg ggcgggaggc cacggggggag gccgaggcag gggctgggca gaggggagag    1951
gaagcacaag aagtgggagt gggagaggaa gccacgtgct ggagagtaga catcccctc     2011
cttgccgctg ggagagccaa ggcctatgcc acctgcagcg tctgagcggc cgcctgtcct    2071
tggtggccgg gggtggggggc ctgctgtggg tcagtgtgcc accctctgca gggcagcctg   2131
tgggagaagg gacagcgggt aaaaagagaa ggcaagctgg caggagggtg gcacttcgtg    2191
gatgacctcc ttagaaaaga ctgaccttga tgtcttgaga gcgctggcct cttcctccct   2251
ccctgcaggg taggggggcct gagttgaggg gcttccctct gctccacaga aaccctgttt   2311
tattgagttc tgaaggttgg aactgctgcc atgattttgg ccactttgca gacctgggac   2371
tttaggctta accagttctc tttgtaagga cttgtgcctc ttgggagacg tccaccccgtt  2431
tccaagcctg ggccactggc atctctggag tgtgtggggg tctgggaggc aggtcccgag    2491
ccccctgtcc ttcccacggc cactgcagtc accccgtctg cgccgctgtg ctgttgtctg    2551
ccgtgagagc ccaatcactg cctataccc tcatcacacg tcacaatgtc ccgaattccc    2611
agcctcacca ccccttctca gtaatgaccc tggttggttg caggaggtac ctactccata   2671
ctgagggtga aattaaggga aggcaaagtc caggcacaag agtgggaccc cagcctctca   2731
ctctcagttc cactcatcca actgggaccc tcaccacgaa tctcatgatc tgattcggtt   2791
ccctgtctcc tcctcccgtc acagatgtga gccagggcac tgctcagctg tgaccctagg   2851
tgtttctgcc ttgttgacat ggagagagcc ctttcccctg agaaggcctg gcccttcct    2911
gtgctgagcc cacagcagca ggctgggtgt cttggttgtc agtggtggca ccaggatgga   2971
agggcaaggc acccagggca ggcccacagt cccgctgtcc cccacttgca ccctagcttg   3031
tagctgccaa cctcccagac agcccagccc gctgctcagc tccacatgca tagtatcagc   3091
cctccacacc cgacaaaggg gaacacaccc ccttggaaat ggttcttttc ccccagtccc   3151
agctggaagc catgctgtct gttctgctgg agcagctgaa catatacata gatgttgccc   3211
tgccctcccc atctgcaccc tgttgagttg tagttggatt tgtctgttta tgcttggatt   3271
caccagagtg actatgatag tgaaaagaaa aaaaaaaaaa aaaaggacg catgtatctt    3331
gaaatgcttg taaagaggtt tctaacccac cctcacgagg tgtctctcac ccccacactg   3391
ggactcgtgt ggcctgtgtg gtgccaccct gctgggggcct cccaagtttt gaaaggcttt  3451
cctcagcacc tgggacccaa cagagaccag cttctagcag ctaaggaggc cgttcagctg   3511
tgacgaaggc ctgaagcaca ggattaggac tgaagcgatg atgtccccct ccctacttcc   3571
ccttggggct ccctgtgtca gggcacagac taggtcttgt ggctggtctg gcttgcggcg   3631
cgaggatggt tctctctggt catagcccga agtctcatgg cagtcccaaa ggaggcttac   3691
aactcctgca tcacaagaaa aaggaagcca ctgccagctg gggggatctg cagctcccag   3751
aagctccgtg agcctcagcc acccctcaga ctgggttcct ctccaagctc gccctctgga   3811
ggggcagcgc agcctcccac caagggccct gcgaccacag cagggattgg gatgaattgc   3871
ctgtcctgga tctgctctag aggcccaagc tgcctgcctg aggaaggatg acttgacaag   3931
tcaggagaca ctgttcccaa agccttgacc agagcacctc agcccgctga ccttgcacaa   3991
actccatctg ctgccatgag aaaagggaag ccgcctttgc aaaacattgc tgcctaaaga   4051
aactcagcag cctcaggccc aattctgcca cttctggttt gggtacagtt aaaggcaacc   4111
ctgagggact tggcagtaga aatccagggc ctccctggg gctggcagct tcgtgtgcag    4171
```

```
ctagagcttt acctgaaagg aagtctctgg gcccagaact ctccaccaag agcctccctg    4231
ccgttcgctg agtcccagca attctcctaa gttgaaggga tctgagaagg agaaggaaat    4291
gtggggtaga tttggtggtg gttagagata tgccccctc attactgcca acagtttcgg     4351
ctgcatttct tcacgcacct cggttcctct tcctgaagtt cttgtgccct gctcttcagc    4411
accatgggcc ttcttatacg gaaggctctg ggatctcccc cttgtggggc aggctcttgg    4471
ggccagccta agatcatggt ttagggtgat cagtgctggc agataaattg aaaaggcacg    4531
ctggcttgtg atcttaaatg aggacaatcc ccccagggct gggcactcct cccctcccct    4591
cacttctccc acctgcagag ccagtgtcct tgggtgggct agataggata tactgtatgc    4651
cggctccttc aagctgctga ctcactttat caatagttcc atttaaattg acttcagtgg    4711
tgagactgta tcctgtttgc tattgcttgt tgtgctatgg ggggaggggg gaggaatgtg    4771
taagatagtt aacatgggca aagggagatc ttggggtgca gcacttaaac tgcctcgtaa    4831
cccttttcat gatttcaacc acatttgcta gagggaggga gcagccacgg agttagaggc    4891
ccttggggtt tctcttttcc actgacaggc tttcccaggc agctggctag ttcattccct    4951
ccccagccag gtgcaggcgt aggaatatgg acatctggtt gctttggcct gctgccctct    5011 ttcagggtc ctaagcccac aatcatgcct cctaagacc ttggcatcct tccctctaag      5071
ccgttggcac ctctgtgcca cctctcacac tggctccaga cacacagcct gtgcttttgg    5131
agctgagatc actcgcttca ccctcctcat ctttgttctc caagtaaagc cacgaggtcg    5191
gggcgagggc agaggtgatc acctgcgtgt cccatctaca gacctgcagc ttcataaaac    5251
ttctgatttc tcttcagctt tgaaaagggt taccctgggc actggcctag agcctcacct    5311
cctaatagac ttagccccat gagtttgcca tgttgagcag gactatttct ggcacttgca    5371
agtcccatga tttcttcggt aattctgagg gtgggggag ggacatgaaa tcatcttagc     5431
ttagctttct gtctgtgaat gtctatatag tgtattgtgt gttttaacaa atgatttaca    5491
ctgactgttg ctgtaaaagt gaatttggaa ataaagttat tactctgatt aaa           5544
```

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 11
ccttccctga aggttcctcc                                                20

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
tcttattaat tatctgcacc                                                20

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13

```
ccagcttctt attaattatc                                          20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
taagatccag cttcttatta                                          20

<210> SEQ ID NO 15
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 15
ggacgtgtga aggtactc                                            18

<210> SEQ ID NO 16
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 16
gcccaagaag gatttatt                                            18

<210> SEQ ID NO 17
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 17
tcctgagagc ccaagaag                                            18

<210> SEQ ID NO 18
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 18
cagatcctga gagcccaa                                            18

<210> SEQ ID NO 19
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 19
tgaaggtact cacactgccg c                                        21

<210> SEQ ID NO 20
<211> LENGTH: 18
<212> TYPE: DNA
```

<213> ORGANISM: Artificial Sequence
<220> FEATURE:
<223> OTHER INFORMATION: Synthetic Oligonucleotide

<400> SEQUENCE: 20
tatctgcacc tttggtag                                            18

<210> SEQ ID NO 21
<211> LENGTH: 25
<212> TYPE: DNA
<213> ORGANISM: Artificial Sequence
<220> FEATURE:
<223> OTHER INFORMATION: Primer

<400> SEQUENCE: 21
cgggaaggtg cagataatta ataag                                    25

<210> SEQ ID NO 22
<211> LENGTH: 26
<212> TYPE: DNA
<213> ORGANISM: Artificial Sequence
<220> FEATURE:
<223> OTHER INFORMATION: Primer

<400> SEQUENCE: 22
ggacgtgttt gatattatcc tttgag                                   26

<210> SEQ ID NO 23
<211> LENGTH: 18
<212> TYPE: DNA
<213> ORGANISM: Artificial Sequence
<220> FEATURE:
<223> OTHER INFORMATION: Probe

<400> SEQUENCE: 23
agctggatct tagcaacg                                            18

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
cactgagaac ctgaagcacc                                          20

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
ggacgttgct aagatccagc t                                        21

<210> SEQ ID NO 26
<211> LENGTH: 26
<212> TYPE: DNA
<213> ORGANISM: Artificial Sequence
<220> FEATURE:
<223> OTHER INFORMATION: Probe

<400> SEQUENCE: 26
ttaattatct gcaccttccc gcctcc                                   26

```
<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
ggataatatc aaacacgtcc cg                                              22

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
tgcctaatga gccacacttg                                                 20

<210> SEQ ID NO 29
<211> LENGTH: 24
<212> TYPE: DNA
<213> ORGANISM: Artificial Sequence
<220> FEATURE:
<223> OTHER INFORMATION: Probe

<400> SEQUENCE: 29
gtctacaaac cagttgacct gagc                                            24

<210> SEQ ID NO 30
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 30
ugaagguacu cacacugccg c                                               21

<210> SEQ ID NO 31
<211> LENGTH: 18
<212> TYPE: RNA
<213> ORGANISM: Artificial Sequence
<220> FEATURE:
<223> OTHER INFORMATION: Synthetic Oligonucleotide

<400> SEQUENCE: 31
uaucugcacc uuugguag                                                   18

<210> SEQ ID NO 32
<211> LENGTH: 141001
<212> TYPE: DNA
<213> ORGANISM: homo sapiens

<400> SEQUENCE: 32
aatttataaa ggaaaaaggt ttaattgact cacagttcag catgtctggg gaagtgttag     60
gaaacttaca atcatggcag aagagaaagc aaaccatcct ttctcacatg gtgacaggaa    120
gagcaaagcg gggtaagccc cttacaaaac caccagatct catgagaact cactatcacg    180
agaacaccat ggaggtaact gccccccatga ttcaattacc tcccaccagg tccctcccac    240
gacatgtggg gattatgcga actccaactc aagatgagat ttgggtgggg acacagccaa    300
```

```
accatatcag aagcttaacc ttctttggag catgattatt cagttgaacc taagttcagt    360
agtcacccag ttatgctgtc ttcagctact attttccata tgtttctcaa acatctgata    420
tatcacactg gctagtgcac tttcttccac cagcatacca tctcaattta ccactttaac    480
aattggactg ccactttgtg tcagggacta tctgtgctcc aactactaca agtgataagg    540
tcctcactga cagccaggga gcaagtgatc cagctctaaa actcaccttα tcatctgctt    600 tcctagacca ctcctaacaa ccaactattc tgggttgagt tctccaagag gcagagagtt    660
caggatacag aatgttgttt tgttttttgtt gttgttgctg ttgttgtttg tgtgtgtgtt    720 tgggctttt tgagacggag tctcactctg ttgcccaggt agaagtgcag tggcatgatc     780
tcagctccct gcaacctcca cctcctgggt ttaagtgatt cccctgcctc cacctcctga    840
gtagctggga ctacaagtgt gcgccaccac acccagctaa ttttgtgtt tttagtagaa     900 atggggtttt accatgttgg ctaggctgct cccaaactcc tgacctccag tgatccacct    960
acctctgcct cccaaagtgc tgggattaca ggcgtgagcc accacaccca gcccagaatg    1020
tttattagaa tgcacaatta ataccagagg cagtggggaa ggaaggactg agcagaggag    1080
gaagttgagt tgtgattcaa cccaacaact gcctggctgg catggggagc tctggagtta    1140
aatagggcca tcagactttc ccagtgtggg gccaacatga ctgggtcttt atacccccac    1200
ctctgtcagt cactcaacgt ggtctccctg caacaaggtg actcttgcag ccgagacaat    1260
ccctgaaggg acagagggct gaagcctgtc tgccaacagc actcccagtg gctggaacaa    1320
gtccttccct ataggggaat ctgggcggca cacctccatc tccatgtcca tcacatacga    1380
tatcacagac atttaaatat tttgataact gtacataaga gtttccttta taatcttata    1440
gatcttattt tatgcatttg aaaatattct tctgagacag ggcttttatc atattgccat    1500
agggtgccac gatataaaaa aggttaaata ctctctgatt cagaagtatc caatgatgac    1560
ttctctctca tgcatttaat tgaaaatctg gttttctcc ttctctgcta gttctctacc     1620
tctctcccca cctcccacat catagcctat tcacatatgt ctgaatctca tgatagacaa    1680
gttcaggttc ttttcccagg ttctttttac cacatccccc cacccccaca taaaaagtat    1740
atatggcaca gcctaggttc cacccaaatc ctttctcctc ttcttcctgg gcccacaact    1800
ctcctacata cattggtata ccttgcgctt agggatggcc atgtgactaa gttctaacag    1860
tggaacatga tcagatgcca cttccagcct ctaagacagc cagtgtgttt cctccataag    1920
ctccttctct tcctcccaac tggagactct aaatgatgac cctgcctcaa gcaagcaaac    1980
aacaagtccc tcaggggtgg tgtaggctgc aaatggaagg agcttgagtc ccaaaccttc    2040
cacggagaag gctggctacc aacctggatc actcacccaa gactgctcga agagttggtt    2100
tgaaccattg tgtttggggg tctatttatt acaacagttt agcttgcttt gtgaatagat    2160
ttagtggcag agcctccaaa ttctatagat acattgatct cagtcctaac cgcatctgga    2220
acaccattaa ataaaggaat tgcaaaccca gagaaggtaa tgaatttgtc taaggtcata    2280
caagatggct aggatcagga cccaactctc cagttttctt tcttctctgc tattctgcct    2340
tctgtgatcc tacataagtg ggcatgattg tataacatat gcggccatga gatttctctt    2400
tcagcaagag aaagggacag gaagaaagag agggaatgca ttttcttggc ctgaattagt    2460
gtgagccatt agttacctac attgactaaa ttatctggaa tgaacattca actctacatc    2520
acatatagtt aaaatgacag atctgcttaa gattgtttct agcatacgtt atttcaattt    2580
aggcaaatgt gaccattcag tgtgaggggα ccatactgtc attaggtccc tgtcagttct    2640
caattatact gttatcttag aggggga aaa atgtgaaatt tgaatgtaga cgagtgttga    2700
```

-continued

```
tttgactgct acagtttatt ttacgtatag aaataaaata atgtgtagca aaagcattat    2760
tacaaagatg ataatgaaat aactagtatt tataatagta taatagtata gtatttataa    2820
tagtatgata gtttaatgac tatttgtcag atgttgtgta agaaacttta tacacacaca    2880
cacacacacc tcatttaatt cctgtatcaa tcaggataca ggacgctgtg gtaacaactc    2940
ctcaaatctc ggtggcttgc acaacaaatg cttatttctt tttttttttt gacaccaagt    3000
cttgctctgt aacaggctgg agtgcaatgg tgcaatctcg gctcactgca gcctctgcct    3060
cctgggttca agcgattctc ctgcctcagt ctctcgagta gctgggaaca caggcacgcg    3120
ccaccacatc tggctaattt ttgtgatttt agtagagatg ggatttcacc atgttgctca    3180
ggctggcctt gaactcctga cctcaagcga tccacccacc tcagcctccc aaagtgctgg    3240
gattacaggc atgagccact cgcccagcc caaatgtttt atttcttgct catgtgacat    3300
gtacttcctc gagttttcc ttcctgagat ctaagctgaa ggaacagctc tctggagcca    3360
cgccattctg gtggcggaaa ggaagagtaa aagtggtaga accttgcaat gctcttgaag    3420
cgcctatttg gaatgtctac atcatgtaaa tggtaatgga caagtatgta taatccccac    3480
accaaaaaaa ggggacacta ttggggacaa taaccacatt tcaatgctgc aagacggata    3540
ttgactgcac ccccttccca cttcagaaa gaagaagagt aattttgctg aactccttct    3600
agagactgga aatgtcccct tccagttgggg tgattaggga aggctttggt aaaatttgag    3660
ctagagtttg aaggttaggt agactactgg tgggtgaaga agaacaagg accttgtag    3720 gcaaaggaaa acctcagaat tacagaggtg gaaaaagagt tctagtcaag ccacttcagc    3780
tggctacaga gtaggtggga aagaaaatgg gaggacaagg gctcagatga tggggggttg    3840
gggcattggg gggacacttg aaagctaaac taagggggttg aacttaattt aggaggcagt    3900
tagaagcttt tacatatttt tgagcaagag agtgacataa ttaaaatgat ctgggccagg    3960
tgtggtggct cacacctgta atcccagcac tttgggaggc tgaggagctt gggtcacctg    4020
aggtcaggag atcgagacca gcctggccaa catggtgaaa tcccgtccta ctaaaaatac    4080
aaaaattagc cgggagtggt ggcatatgcc tgtaatccca gtagctggga ggctgagaca    4140
ggaaaatcgc ttgaacccgg gaaacaggtt gcagtgagcc gagatcgtgc cactgcactc    4200
cagcctgggc aacagagcga gactccatct caaaaaaaca aaacaaacac acacaaaaaa    4260
ccaaaaataa ataaataaaa tgatcacttc tgaatactga tctaactagg ggttgcaggg    4320
tgggctgata tagggagaaa ctggagagca aggagatcac taaggtccct acatgtccag    4380
aaccaagata gaggtcttga actaggatgg tgcagttag aacaacaaca acaaaaagtc    4440
aattccaggc tgagtgcagt ggctcatgcc tgtaatccca acgctttggg aggctgaggt    4500
gggagttaga aagcagcctg gcaacactg caagacctcc tctctaaaaa aaaaaaaaa    4560 aaaaagttag ccaggtgtgg tggtgcccac ctgtagtccc agcaactcag aaggctgagg    4620
tgggaagatt gcttgagccc caggagttca agcttgccgt gagctacgat tgtgccactg    4680
cactccagcc tgagcaagac cttgtctcca aaaaaggtc aattccactg actttctaa    4740 ggtgtacacc atcaaggggc agctccatct ccaggccatt ggctcatgag acattctgta    4800
gtcagaaggc tagggcagat tgctttgagc aagccccat ggtggttctc actcctactt    4860
ctttgggtat atgcccctct gtttaaaaat aaagttaata tgcatttaaa aaaaaaagg    4920 agaaaaggt cagttccaga aactgtgtga ataaagcatt ttacttgctt tttctattaa    4980
tctataacat atgttgattt tttaaaaga atataagagc tatgcaaatt ggagcttcaa    5040
```

```
gacaacttcc catctcccta ggaggagatg gctgccctaa accccctac atagaaatca    5100
tcccactgct tgggcttaaa cttgatgttg gggaaatgaa aaatccaagc taaggccgaa    5160
gcctggggcc tgggcgacca gcagaatgag gaccactggt cagtttcagg ctgaggtgcg    5220
tcttccaggg gacaatctct agctggccct taaacattca gacttcaagc tctatttaca    5280
gcataaaggt gttcaaaag acgtgataca aataactgca aatgctctgc gatgtgttaa     5340
gcactgtttg aaattcgtct aatttaagat ttttttttct gacgtaacgg ttagattcac    5400
gttctttttt ttttaagtac agttctactg tattgtaact gagttagctt gctttaagcc    5460
gatttgttaa ggaaaggatt caccttggtc agtaacaaaa aaggtgggaa aaaagcaagg    5520
agaaaggaag cagcctgggg gaaagagacc ttagccaggg gggcggtttc gggactacga    5580
agggtcgggg cggacggact cgagggccgg ccacgtggaa ggccgctcag gacttctgta    5640
ggagaggaca ccgccccagg ctgactgaaa gtaaagggca gcggacccag cggcggagcc    5700
actggccttg ccccgacccc gcatggcccg aaggaggaca cccaccccg caacgacaca     5760
aagactccaa ctacaggagg tggagaaagc gcgtgcgcca cggaacgcgc gtgcgcgctg    5820
cggtcagcgc cgcggcctga ggcgtagcgg gaggggacc gcgaaagggc agcgccgaga     5880
ggaacgagcc gggagacgcc ggacggccga gcggcagggc gctcgcgcgc gcccactagt    5940
ggccggagga gaaggctccc gcggaggccg cgctgcccgc ccctcccct ggggaggctc     6000
gcgttcccgc tgctcgcgcc tgcgccgccc gccggcctca ggaacgcgcc ctcttcgccg    6060
gcgcgcgccc tcgcagtcac cgccacccac cagctccggc accaacagca gcgccgctgc    6120
caccgcccac cttctgccgc cgccaccaca gccaccttct cctcctccgc tgtcctctcc    6180
cgtcctcgcc tctgtcgact atcaggtaag cgccgcggct ccgaaatctg cctcgccgtc    6240
cgcctctgtg cacccctgcg ccgccgcccc tcgcccctcc tctccgcaga ctggggcttc    6300
gtgcgccggg catcggtcgg ggccaccgca gggcccctcc ctgcctcccc tgctcggggg    6360
ctggggccag ggcggcctgg aaagggacct gagcaaggga tgcacgcacg cgtgagtgcg    6420
cgcgtgtgtg tgtgctggag ggtcttcacc accagattcg cgcagacccc aggtggaggc    6480
tgtgccggca gggtggggcg cggcggcggt gacttggggg aggggctgc ccttcactct     6540
cgactgcagc cttttgccgc aatgggcgtg tgtgtgtgtg tgtgtgtgtg tgtgtgtgtg    6600
tgtgtgtgtg gagggggtccg ataacgaccc ccgaaaccga atctgaaatc cgctgtccct   6660
gccgctgttc gccatcagct ctaagaaaga cgtggatcgg gttctagaaa agatgactcc    6720
ctgcacgccc ctccctgcac ctcccgagca gtgattccga cagggccttc actgcccctg    6780
attttaggcg ggggccggcc ccctcccctt tcctccttc agaaaccgt agggacatt       6840
tgggggctgg gagaaatcga ggagatgggg aggggtccac gcgctgtcac tttagttgcc    6900
cttccccctg cgcacgcctg gcacagagac gcgagcagcg ccgtgcctga aacagtgcg     6960
cggatcccac tgtgcacgct cgcaaaggca gggttcacct ggcctggcga tgtggacgga    7020
ctcggcggcc gctggtcccc gttcgcgggc acgcacagcc gcagccacgc acggatgggc    7080
gcggggctgc aggtgcatct cggggcggat ttctttctca gcgctcggag cgcagggcgc    7140
ccggcgtgtg cgctccctgc cggaggcgcg gggctggcgc gcaggctcg ccctcactg      7200
cggcagtggg tgtggaccct ggtgggcgag gaaggggag gataggctgt gcctcctccc    7260
actcccgccc ccagcccccc ttttttcccc cctcggaacg cgaggtgcca tcttttttcg    7320
gcgtgtcacg tctttacggt gccatgccaa accgggtggc cgggcttcat aggacagggc    7380
ggggcctggc attaaaggga gggggacaat cagcgctgaa atcttggcgt tttgctgctg    7440
```

| | |
|---|---|
| cgggcgtgag cactgggggc gttcgcccag caccttcttc gggggctctt tgctttgtct | 7500 |
| gtagaggtta cgtgatctgc gctcccagcc ctggtttctg gcttttattc tgagggtgtt | 7560 |
| cagtcaacct cccccctacg cccatgcgcc tctctttcct ttttcgctcc tcatttccga | 7620 |
| gcccattgtt ggatctcgag gcttgctggg ttcgatgaac tcgagtcaac cccccgaccc | 7680 |
| ccggcacgca tggaacgggc gtgaccgcgc gcagcctcgt ctcggagtct gccggcgccg | 7740 |
| ggaagcttct gaagggatgg gattcgagtc tccgtgcgcg ctgcgggcgg cggcagaggg | 7800 |
| atctcgcccc tccctacacc ccaagtgtcc tgagggccac gccacaccag gttgcccagc | 7860 |
| gagggacgct ggctacccat ccggggatgg gtggggagcc ctggcggggc ctctccggct | 7920 |
| ttacgccctg ttgcttcgcc tggccggaga atgtgaggaa ggggcataag gttactggtg | 7980 |
| cttcggccac acccatcttt ctgagcccac tggactgggc gcagaggggg gattgccatg | 8040 |
| gaaaccacag gtgtccggag aggggatctt ggggctggcc tcaccccttc cctgcggaga | 8100 |
| ttggggaccc tggggtaggg ggagccgcgc ccagtcggcc tcctggagga cacgggagga | 8160 |
| agccccgaac cccgcgcct gaggctgttt ctgattggcc cctggaggcc gcagacacgc | 8220 |
| agataggcgg ccctgggtgt atttttatta atattatgtc cgtactgatt aatattattt | 8280 |
| atcttaaata aatttcaccc gtgtccaagt tcaccgcgcc cccaaaaccg agtctggggc | 8340 |
| ggcaggggga actcctggcc aacgaatcca tgcctcgccc tcctgtgatg aacctggtac | 8400 |
| gcacggtttt ctggttaatt ctatcgctga aaactggtgc ggggggcgca cttctgagac | 8460 |
| ggaagagcat ctaggagctg aatcctccac gcggtcgcc caggttgatc tgaatttctg | 8520 |
| gggaatggct tggctgcccg cccgggacca ggccgaccct ccttgacggt ggcgtagagg | 8580 |
| gctggagcct gggtactgcg aggctcctcg catggctggg cccgccgcga ggggttgcag | 8640 |
| agcggctcag ggatcgattc aagcatcgtc tctcctccct cgcccccaga cagagctggg | 8700 |
| cgcggggttc cccttccaga tggagcgagg gtctcggggt ggcccggaa aaggggagcc | 8760 |
| cgcggccacg gctacgtatt gccatctcgc gagcagagat gtcacctcct gccttttggag | 8820 |
| gaaagggagc ccgtgggga tgagcgcatt tagcccaatg ctgggaacaa agcgcactcc | 8880 |
| gcgcttctgc gatttcgctc cattttgaaa tgtgttggcg ctttggtggg gccgctgcgg | 8940 |
| tgggcaaggc cggggcgct gttaatggag gaacctcagg gggacggtcc ttcgtaggaa | 9000 |
| actctatcct ggctctgcgc gcgctttaag gaaatggctt ccctccagga cctcgaggga | 9060 |
| tgcagctttt gcgcggatga cggtggggtg ctgaaccagc cggtgcgcct ctggaaatgt | 9120 |
| ctgggcacgg atcctgggc catcgacgac tcctccccat tcccagcagg cgggagctct | 9180 |
| tacattccga gcgagtgacc cctctcaccc tctggcgctc acacacctgt aactccaaac | 9240 |
| ctccgtctca gaatggtcca ggctggaagg gatgatgggg gctccgacag cgactgccta | 9300 |
| gctcacccct ctgcgtgctc aggctccagg ctcagcagga ccaatttgag ttctatctga | 9360 |
| tccccctcgg cccttaact gacccatcct acaggagaca gggaaatgtc tttcctaccg | 9420 |
| cggttgattc tggggtgtca ttttgtgttt tgtgatggct gcttatattt actgtataag | 9480 |
| cattgtattt actgtataag cattgtatta taattactgt ataagctgct tatatttact | 9540 |
| gtataagcat ctccaaatcc tccctctacg taaacaaatt aatggataaa cagataagtg | 9600 |
| tatccccctgc ccccacccct gctacgcagg tccggagtga ctcttgaagc tcatacattc | 9660 |
| cttggccaag tttgcttctc taacagatgt ttatatagca ataacctggc ttggctcttg | 9720 |
| ggttcacctt tggacgattt ggggaagggg cttgttggct ttgctgggtt ttggatgagt | 9780 |

```
gacagtccat gactgttcct gctggaaggg cgtgactttt aagtggtttc taatatcagg    9840
cattgctcct ccgacaggaa caaaagaaat ggatactgcc cataaattgt tagaaaactt    9900
agaatcgctt tgattgagga aaggttagat ttattccggt tggaaaaagt ggcctttcta    9960
ttaaacgtgc cctttgaccc tcatgccctt ggaggtcggt gccagcctgg agatgggata   10020
agattgtggt tttccttctg ccttttttaac atctgttgtt acagtccatt tgttgaaaat   10080
ttaaagaaac tgttttattc cactttccct cagcatttat gtgtgtggtt tcagtagctc   10140
tgtggctata tgtacgaaca cgtgttattt ttccaattgg acatgtgata attttccaac   10200
tggaccttgc cttctattga tgtatttatt tagcatcttc cttactccct ccttgaaaaa   10260
gaatcactca aaaacaaata aaaacagccg taggggccta atacagtgct agacatacaa   10320
gaggtattcg gtccatacca aatggatttt atccatgaag gataaatggg gaaatacagt   10380
gggaagcagg tgggaaactg cgtttgactc tgctctttcc tccaccacca ctttcctcat   10440
caccgtgttc agagaccccc aaagcccct cacactccca gaaacacccc cctggccact   10500
cctaacttgc catgcccagg agttaggtgc ttccactagt gacatggagc tggcgtttgg   10560
ggggcacctc agcaggtgac gggaagagaa gaccccagcc tcaccagctg gctgcagca   10620
gggagaggag tcctcatgtt ccagcaggga ctctcagctg ttttcctgta aaaccatggt   10680
tctcaactgg gggccactga gatgtctaga gagatgtttt tgttttcaca actcggggag   10740
ggtgctactg acatcttgtg ggtagaggcc aggaatgctg ttaaacatcc tacaaggaag   10800
gcacaggaca gtctcctaca tcaaaatatg acccagtccc aatgtcacca ctgctggggt   10860
tgacactggc actgctatct taattacatt cattgagtgt cttttaggag cccctattct   10920
aagtgcttgc taagattatc tcatttaatc ctcacaacac ttccgctatg tagcaggtgc   10980
tgttattatc tccgtgatgg ggaaactgaa gcacagagag ggttagtaac ttgctaaagg   11040
tcacagagcc agtgggtggt ggagctggtt gcctgacact agttccctcc cctctcagcc   11100
acatgtgggt ttacttggcc attgtggact agtctgggaa cccagatatg atctataaca   11160
ttgacccagt agaatattga ttccaaaacc actgtctcac aaatgaattt ttacaagagt   11220
ctgtaatcgg agcatgaccc agaataaggt tagggagatg tggagttaaa gctctcaatt   11280
tcttatctgg ccccgacaca gagagcaagg catttcactc tacattggtg ctctgtttat   11340
aaaacaaaga gcaaatatct cttcctaagg tccttaaacc tcttccccca atccaggggtt  11400
tctggactgc tctgccatat gacggggcag ctggtttgat tgacccaggg aaggctggaa   11460
atcaagactg ggggatcaag acgtagattc agtgtggcca aggtcaagtc tctgaggttt   11520
agggacatca gatccccagc ttaggttctg tacctcggca aggtgaaagc gttggcgccc   11580
actgatgagg cctgctctga gattgtgggt gtgggttgag ttgggtgggc ataggcaagt   11640
cctcttgtaa gaatcttttg gcaaagatgg gcctgggagg cttttctcac ttcctggggc   11700
ccaggctttg caataagtat tccattatac tgtggtacct tggggctacc tgagaatcct   11760
ctgtctcgcc cctgttgcct tgccaaagag tttgctgtcc aagaattcct ttcctgtctc   11820
caggtgccat gctcctgcca cctctgccag gttccctgcc tgcccagatg ctcccaact   11880
gagtgtgagg aggaatttga gacaggtttt gagctttctg ggttctccag ttaggaaact   11940
ttctgtaagc atgcagatag aatgggcttc agcaaaatac aaactcgaac aacttccatg   12000
tatagtccct taattttctt tgctttttc atatttcatc aggctccatg ctgagcccaa   12060
tcagggaccc gatagaaatc caaacaccat gtcagcgagt ccccaagaaa tgcattttgt   12120
gccaaggcta ttcaaggaag gtttgggagc agctcaaggg cagacactgt taccctcccc   12180
```

```
caggtcccca gtgcagggca gtgttctgca tgtggaggca gtttggccta atggttaagg   12240
aggtaggctc tgatcgggcc tcctgggcac aaatcccagc tccctgctca ctgtgagacc   12300
taagccatat tgtttagctg cttggagagt ttttgtcat ccacaacttg gagtatgatg    12360
gtacctgtct cacggggttgc catggggttc acacaagcta acccggtact cactagggcc  12420
aagcacatag taactgctca gtaaatggca tcatcggcgg tgtcctgtgg atgagtgctt   12480
gtgattggct gaatgaccag aggggtctaa agatcctggt gatggaatca gttgtacaga   12540
taaattgtta cactgagtag ggatcaagat aggaaaagtc ggcaactacc cagctcccct   12600
gcaccaaact gggcagaagt ggatcctctg aaaattgcac acacccatgt ttaaatgtac   12660
acacagaact cttgccacag gcaagcggag atttgtcatc tgctgtccct gcctcatctt   12720
cttcctgaaa tccactccat gccaggaata aactgcatgc tctccaccag cccaaactga   12780
cctgccttcc cgccagccat cccgggcagg gtgacctggc ttagtacatc gggttcagag   12840
atctttccag tttactcgtt gaataaaaag tgagggctga tcgagaaagt aatggcagtc   12900
agggaaggcg aaggaggtaa agaagagatt ttacaaatga agtaattcaa cagagtgctg   12960
acattggtaa actggcaaac agatttcagg gtggttggtt gagagtagag tagaaaagga   13020
ttaaataaag caaacttgtg gtgtactgaa tcttaggaat tccatgtatc caataagtat   13080
agtcatttat gaattaataa attcggccta agaagcctttc ttatcgctta aatcaagact   13140
aagtaacaat atatcagttt taaaaagtca ttatatcaga aaatcattta aatgatacac   13200
atagatttcc aagattttac tttaaccgaa actatataaa tgtgaatttg ttcacccatc   13260
ttttgacaca gggctcaggt cttctcttgg tgtctggatc agccagttga aatttcttgt   13320
ctgttttgcc tatgccacat taataatgca ctgtctgggt cctccgattt cagtttggat   13380
tttgggttta cattgtggag tcatctgaat gcagaatcct tcagggatttt actttttttt   13440
tttttttttc atggtcttta ccatcccatt tgatagtaaa tattactcac ctttatgaag   13500
tctttccaaa acattcaact aaattttctt aaaatcattg aatgatttga agagcttatt   13560
cctcagcact tttactccat cagcttgcac cttatttttt aatctttttt tgagacggag   13620
tctcgctcta tcgcccaggc ttaagtgcaa tggcgcgatc ttggctcact gcgacctcca   13680
cctcctgggt tcaagcaatt ccgcctcagc ctccgccgta gccgggacta caggtacaca   13740
ccataatgct cggctgattt ttgtattttt gtagggatgg ggtatcgcca tgttggccag   13800
gctggtcccg aacttctgac ccaagtgatc cacccacctc ggcctcccaa agtgctggga   13860
ttacaggtgt gagccaccgc gcccggccag cttgcaccttt atttaggata tgtgattatt  13920
atagcaagtc tggtgtacat acaagatttt gaatgggcac agatgacctt tagtaagtgc   13980
ttggctgtga taagaggcag tcctgactgc agatcaggct gtgtggaccc cagccttgca   14040
tgtttacaga ccttcatgtc ttattcttac agggtatcag aagaacacct actggggaaa   14100
cttataaatt agtaaaaggt gggcattctc cccgcccatc ttctgtctgt ctgccaggac   14160
tagcacagca ctttgaagtc attcacatag aatcccaact taagagggta aaatcctcct   14220
caacagactg aaaataagtt taaattccct ttgctatatt aactcccctg aggaaagagt   14280
cttagatcaa tgtccaacac taaaaacagt tttaaatcag caagtgagaa ttaaatctga   14340
agcaattgat aataatgttt cattcattcc tctcctttgg ccccgtccac cctactgcta   14400
aatccaggca tcaaagagaa gagggacata attatctcta gtcccagctg ctggttttcc   14460
ttccagccta tggcccagtt ttctgtttta ctgagaaggc tggtgatgtt atcttgggat   14520
```

```
ctaagtctgc agtttcacca caaaaagtcc agggatgcac tttcatgctt gtgtcctcct    14580
ccctgggata gcaaggatat tagaagaccc ctggctctgt aattgcttgt catgtgctct    14640
acagacgcca cagaatgcca agaacgaagt gctgggaagg acaaattcat ggaaccgtgg    14700
gacggtgctc ctcccccagc gtaaaggaca gctcctcctc ctgaattgga gccagcgttc    14760
taaatcatgt gtcaacagag ttgtcctgga tcggatccag ttctgccatt gatttgcagg    14820
tcatttcagt ggtacctgtt tccagttgtt cttaattgaa cagtggcacc aaactattgt    14880
cttgcctcat ccccctccca tggcctgtcc cccaaaaaga gacttcttgg gtaattaatc    14940
agggcaacat caggcagtct gggcgcggtg gctcacgcct gtaatcccag cactttggga    15000
ggccgaggcg ggcagatcat gaggttagga gattgagacc atcctggctt tgtgaaaccc    15060
cgtctctact aaaaatacaa aaaattagcc gggcgtggtg gcgggcgcct gtagtcccag    15120
ctactcgaga ggctgaggca ggggaatggc gtgaacccgg gaggtggagg ttgcagtgag    15180
ccgagatcgc accactgcac tctagcctgg gcgacagagc tagacttctt ctcaaaaaaa    15240
aaaaaaaaaa ggaatctctt tggttttata tatattttt ttatatatat aatatatatt    15300
aaaatataat atatatattt atataatata atatataaat atattatata ttatatattt    15360
tatatattat atattatata tattatatat tatatttta tatatttata tattatatat    15420
atttatatat tatatatttta tatatattat atttatat ataatatata ttatatatta    15480
tatattatat attatatatt atatatttat atatattata tattatatat attatatatt    15540
atatatttat atattatata tttatatata ttatatatta tatattatat atttatatat    15600
tatatattta tatattatat atatttatat atatatata ttatatatta tatatgtata    15660
tattatatat gttatatatt atatatattt atatatataa tatattgtat atattatata    15720
tctaatatat tatatatatt atatatatta tatattataa tatatattat atattatata    15780
ttatatatat ttttatatat ataatatgta taatatataa tatatataaa aacatatata    15840
atatatatta tatattatat atatattata tatattatat atattaaata tattttatat    15900
atattatata tatatacaca tatatatata taaatgaggc caggctcggt ggctcacact    15960
tgtaatccca gcactgtggg aggatcactt gaagccagga gtctgagact agcctgggca    16020
acaaaacaag atcctgtctc tacaaaagga aactgtaaaa attagctggg catgatggca    16080
tgtgtctgta gccctagcta cttgggaggc cgaagcagga ggatcgcttg agcccaggag    16140
ttcaaggcta cagtgagcta tgattgtccc atagcactcc agcctgggta acacagcaag    16200
gccctgtctc taaacttttt ttttttaatt ctatttatat ttacatgtat ttaaatgtga    16260
atattcacta cctatttgtt gcatgcctgc atttttata ctgggcttgc caaaaacccg    16320
aacagctttc tactttgaca atgtatcaga atttaaatca gcaatatgtt aataagccaa    16380
gcaaaggtta tatatgcaaa taaaactgtt gtctataacc tcctgttaca ctggggcaca    16440
gcaaaagtca tggtgtagtc gcatgtgaac ctgtcccttt catagctgct cattgccagg    16500
aaacatcagg aatagccatt tggaagagtc atcagccctc ccaccatccg tttctgtct    16560
tgtcttttcc ctatgagcag gggaaattcc acgctggccc caatcccag tgcagcggct    16620
cagcctctgc ctctgctgct ggtccccatg aggccagctt agaaacggag gattttgcag    16680
aacatcccta aatccgcttg aataatgaag tgatcattca taaactcacc tgaaccttat    16740
taaaacctat ttaatatttt tcctggataa tcctataggg ataacttgcc tcctgggctt    16800
ctctccaccg ggttcagttc ttcctttagt ggtgaagttc ctcccttctt agcatctcaa    16860
ctgtgcctga gaaaaggcca gtggcggctg cactctgttc cctgtggagt gttaataaag    16920
```

```
actgaataaa ttgaaataaa tcccttcaa tgtcattaag tgctataaat aatcatgaac    16980
caatgttcga tggctgatga gaaatgcaag aaaaaatttt taatcagtag gattcataag    17040
ttgacaatct gggccaagtt aaaaaaaata aaaataaaaa gacttttaaa aagatcttat    17100
cgtttgttac cagtaagact gaattccaga agcaagctac tccctcattt gtgggcccct    17160
gttatcactg gctgcttagg gttgccaagc cctgaattca tttgtcaact aagagatttt    17220
tggccaagat taagatttcc catgcctcca tatttccatc tgagaaatgg agattatact    17280
gtcttccccc tcagaatgga tgataatgtg gtctctcttc tgttcgcata gtcatagaac    17340
tgaaataaaa caacttaaga gaattccttt gagcttctca gaagtgctgc agggctgggg    17400
gatgcctccc aggagccgca gtcaggtgct gatctgaagt ctttggtggg ctgactttag    17460
cctgacctga aatagtatag ctgctgccac ctggctccct tagcgtcagt cagacggtgc    17520
agctggttcc taggggtgag ggctgagcca gcagggtccg tgcccaggag ggatgcatgg    17580
gtggccacag cccagcctgc actgatcttg tctgtcccct tctttggaag gaaggagccc    17640
caaaccaggg tgcaagacag tgggtggggg tgccttgagc atgacctcaa gtgatttcca    17700 gccctgcca gtgctgactt ctctggggaa gggctgggac ttccttctgg gctcaagtca    17760
cgacccttgg atggaatttc ctgggagctt ttctgttttt tctggagttt tcagttttt    17820 cctaaccaga cagggacttg gtacagaatc tcatattcta attatgccta ggagcagcct    17880
ctccccacca ctcacagtgt ttagcatgtg acaggaatcg attaaggcat gagtgattaa    17940
attaaagcca ggcattgact tggatggtgt aatattctga catctgtttg gtgtcaaagg    18000
cacggggcag gcgcgttaat tgaactgctt gcacctggca tttgaattga gccagagcgg    18060
ggctaaagtc agtttgcctt caccctgtaa atggagggtt tctccggagc gtggatggtg    18120
ggaggtattt cagggtgtat gcataacccc caccctgaca atggcccatc tcttctccag    18180
cgtggccagg tttgagtgcc agtcctgggt gtccagtggc cccatagcct tgcgttttag    18240
taaaatgctg cccccattac cacctggtct gtgcacttcg gtcactggaa tttgccatct    18300
tccagtcccg aatgtggcaa gccatggagc cttaagctct tctccctcca catcctggaa    18360
cagacccgcc agtttcttcc aggcattgcc tcagtttgcc cctctgtttc cagtcacact    18420
ctcaccagcg ataaaatgat tttagacctt atcatctcac cctcggatcc ttatggaaac    18480
aataatgagt tgttccctgt ttcaattcca aaattcatat ccaatccgtt ttgcatgcca    18540
ttgccaaatt cctcccagag caaccccgtc acctgccctg ccctctccaa agtgtggtcc    18600
tgccatgggc atcgcctgct aagccaagct ggcctcgagc tgcctgcccg ggtccccaca    18660
ccttggctca cctccctgcc cagtcccgcc tcctgccagc ctgccctgtg gctccttcat    18720
agatgccgtc tctttctgc cccttgctca cccatggcag ccttgcccct ctctccctgc    18780
cccaccccct atttaaattg acctgacctt cctcagtgtc catcttcccc gaagctttcc    18840
ccagccttgg cactcaaggt ccagaggcta cgcgtttcct ctcacctgtg gcagcgccgt    18900
gctccccagt gcctcacagt ttccttcttg ccccgcttc ctgtgtagga ctcatctgcc    18960
cacaggttgc acgtcctgtg agggcaagga ctgtgtctta tgtgactttc cttctccagt    19020
cacagagctg ggcacataga tagctcaaaa ccctctttat taacacagtt ggatgttgag    19080
aaatcaaaca ggccaatgtc aaatgagctc tccttattta aatcaagtca gttctccacc    19140
tcctagcact cagttccagt actctatata catggaaata ataaaaaaca catttccttt    19200
gaaacattct ataatcgttc ctttgcccta cttcagacca acttaacgca ctccccattg    19260
```

```
-continued gtccaaatga gttttgctat acgaagatgc tgataataat agcagcagtg gattattctg   19320
ctaaaaccat tgcctcgtta atcctcagtc ccgaggtggg gattattatc ctcattttgc   19380
agagaagcaa actgagactc agagatttca cagctgggga gggagccagc tcatccctct   19440
gtccaggccc aagctctctc ccgcttgcct tcctgcctct gcaacctcag agcatccccc   19500
atctggttct actgcctgtg ctagtcgtgc aggagccaaa agacacgtct ttagtgctaa   19560
ggactggaga agccatgccc tccagcctct gtgaatgggt catatgtaac atgagcctgg   19620
agaaattatt tgaaaccaaa ggcaagcctc taaaccaggc tgctgcttca tggcgccggt   19680
gacggcagaa ccaaatttag tgctgtgggc aggtccacac ttatcaaata gagaagctca   19740
tttttcttcc ggctcacatc aagcatgaaa aatgttcaca catacccccc acacacacat   19800
gctttccgga ggggtccatg tggctagagg ctggaagatg tggatgagag gagcctggca   19860
ggtaagccca gggaagatga cattcagctt cccagacagc atctacaggg agaaatttaa   19920
ttaaaagtgg ggcggtttcc ctgagcaagg cagacaaagt cagccctcta ctgttaagaa   19980
aaagggtcac agtgagaggg gaggtgagga gactgagtct gtattttcta gtctgttggg   20040
ctacactacc tgatcccccct tcctcaaaaa tccactttac tttccccatg tctacaccaa   20100
tgtggttcac actctgggac caggaaaagg gggagtgatg gggaacagag aagggaggag   20160
ctcacacagc tgaggctggg gttatgcata tcgaattact tagaatttgc aacctcacag   20220
ggtactttca tggcgttgaa atacacttcc cacagccacc ctccctctaa ctaaaagcaa   20280
gagtcatttc tcagttctgg tcttgcctcc cacgttctcc tccacattta agaaaatcca   20340
ccagctacaa agtgaagata ccatatgtga tatcccaccc tagtttctgt tttatcaggg   20400
tttggagcag gtggagcagg cagagggatc atttcagcct ataaattgta ttaagggtga   20460
gtactgagtc attcttcaag aaaagtttta gaagcatcca aaactgaagg gtggagccac   20520
ctggagacag tatcatcagt cctggccccg agcatggcct gcataggccc ccatggatcc   20580
cagcgggagc tgcagagtgc gggcaccttg cacacagcc ctgagtgcaa aattaggagc   20640
tgggcagagg gcatctctct gtcgccattg gcagcccag gcacactgg tcatagcctt   20700 agaccacgaa caccctgtgc ccgggggaca gatgcaacca gtgtgccctg gctgcccaa   20760 tggcaacaga gagatcgaca cctggacccc atgtcacggg gactccacta ctaaggctcc   20820
taagactgcc accttccagt gggataagcc ctgcctccta ctgggcccac aatgtgcaga   20880
gaacacttgg gactacctgg cttctggat acacaaatat tgatccaatc tggactaatt   20940
agaaggtcag tcccaataac aaatcgaagt cagctgggcg tgatggctca ctcctataat   21000
cccagcactt tgggaggctg aggtgggcag atcatttgaa gccagaagtt caagaccagc   21060
ctgggcaaca tagcaaaacc ctgtctctac taaaaataca aataattagg ctgggtgtgg   21120
tggctcatgc ctgtaatccc aacagtttgg gaggctgagg caggtggtca cctgaggtca   21180
ggagtttgag accagcctgg ccaacagggt gaaaccccgt gtctactaaa aacataaaaa   21240
ttagccaagc atgatggcat gtgcctataa tcctggctac tagggaggct gagacaggag   21300
agaatcgctt gaatccagga ggtggttgca gtgagctgag atggtgccac tgcactccag   21360
cctggttgac agagcaagac tctgtctcaa aaaaaaaaaa aaaaaaaaa aagccatgcc   21420 tggtggagca ctacgtgtaa tctcagctat tgggaggct gaggcacgag aatcacttga   21480
acctgggagg cagtggttgc agtgagctga gatcgcgcca ctgcactcca gcctgggcga   21540
cagagtgagt gagactccat ttcaaaaaaa taataaatct gagtcacttt aatattgtta   21600
tttggatgtc aacctctagg tgtttgagac aggagagtga tatgggggca ctggaaacac   21660
```

| | |
|---|---|
| acaggcacgg ggtgtcctca cacttgggta gcccacacga tgtgatttca gggtgctggg | 21720 |
| aggtccccca actccccaaa ttactaacaa gtggatagta ctttacagtt tatatgatct | 21780 |
| catttgattc ttaacatgag cctgtgagtg aaaaattcct tcccctcttc tacagattag | 21840 |
| gacgttgaga ttcagggagg ttcagaggga ttcaggaag tcaagtggca cctggagtcc | 21900 |
| cgtggctaat ttgaggccgg taggggattc gaacccagga tttgtgcttc ttatgcctgg | 21960 |
| gcttctgctc cctggggcat ggtcttcccc ctagctttcc cattcactgc tttagcctag | 22020 |
| gggtcctacc ctttattaaa ctgccagtgc ctcactgctt ttctccccca aagacaaaaa | 22080 |
| aaaagtgttt ttgcttttgt tttgttttc atgggcagag acctggaatt tcagcttgag | 22140 |
| aatttgtgcc atatgataaa taaatcaaca gatggctttt tccttaaaaa aaaaaaaaa | 22200 |
| aaaaactaag atgtatttgc agtgaggcat aatttgtacc aaaaagtgct caccacactg | 22260 |
| tagtcatggg ggcaggaggc agccgcgggt gaagggagaa atcttggagt ccaggcagcc | 22320 |
| cccttctggg ctgaactggg gagctggggg tgctgccagc cctgccaggt tctcctagga | 22380 |
| ggcggcagct catatggctg tgggaggagg cagagggagc ctcatatgca cccacatttc | 22440 |
| cagggatcta aagacagaa ggaggaaaac caccatcatg ttaaagcaga cagttaggta | 22500 |
| acacatcctg taatacaagt tatttttcc acatctaaag gctaaaaata gttgttagaa | 22560 |
| tttaaagata attggtaaat gagttctat ccttctagtt tcacatcaaa tggaatcatg | 22620 |
| ctgccttcac atcactagtg cccgttattt gtgtttaatt tccacaatgt tgtctaattc | 22680 |
| cactctttgg gcttcccag ggatccagcc tccctcactc gcccatcgca gggagatgct | 22740 |
| ttattcatct ttgtgtcttc tgtgccgggc atagcgcatg gcacagaata agcactcagt | 22800 |
| aattgattca cgagtgaata aatggatgag tgggtgagtt caatattgac tacaaaaacc | 22860 |
| ctaaggccac actggtgagt ggctgcgcct gtagtcccag ctgctgggga atctgaggca | 22920 |
| ggaggatctc ttgagcccag gagttttgaaa ctagcctggg cgatatagcg agaacctgtc | 22980 |
| tcaaatgaca aaaacagggc caggtgcagt ggctcacgcc tggaatccca gcactttagg | 23040 |
| aggccaagat gggaggatca cttgaggcca ggagtccgag accagcctgg gcaacatagg | 23100 |
| gagaccctgt ctctacaaaa aatttttaa aaattagctg gcatggcgg tgtgcgcttg | 23160 |
| tagtcccagc tactcaggag gctgaggcag gaggatcact tgagcccagg aaattgaggc | 23220 |
| tgcagcgagc catgatggca ccactgcact gcagcctggg cgtcagaacg agacctgctc | 23280 |
| tcaaaaaac aaacaaacaa caaaaaaaa ggctttctta aagagacttg agaacagaaa | 23340 |
| ggggaacaga tacataactt atatatttat ttgttcatct ttccaccttc ctggagggtg | 23400 |
| gaggggaaca ggtctgtatt tggagttttg aatgctaaaa gtgggaatac atgtactgtt | 23460 |
| tgccatgatc tgttcaaaag ttaagccaaa tgccttagat tctcctgaaa actggaatgc | 23520 |
| cactgtaaac tataagcccc acttcaaaga taaaagatct tgatgaacag gctgggtct | 23580 |
| gtggactggg cctctcccca ccacacaagg aagggtggtg ccagttgaag gaaaatcact | 23640 |
| taaatccttg ctgtctccta ataaggtgtg gtcccaggta gggctgtcag aattagcaaa | 23700 |
| ttaaaacaca gggcatctgt gaaaattaga atttcagata acaacaaata attggcatag | 23760 |
| gctgcataat gtccctcaaa gatatcaggt cctaatctcc agaacctgta aatgtgatct | 23820 |
| tatttggaaa aggggtcttt gtagatgtgg ttaaattaag gattttgaga tgggggatt | 23880 |
| atcctgtatt atctaggtag gtcctaaatg cagtcacact catccttgta agaggaagga | 23940 |
| agagagagat ggaaaacaca gaagagaaga caatgtggtg atggaggcag agattggagt | 24000 |

```
gaggtggcca caagccaagg actgctggca gctaccagca gccagaaaag tccaggaacc    24060
aattctctct tggagctcca gagggagtgt ggccctgctg acaccttagc ttcaacctag    24120
tgatcctgat tttggacttt ggccttcaga agtgtgaggg aatgaatatc tgttgtttta    24180
agccaccaag tttatggtca tttcctacag cagccacagg aatcaaaaac agtaagtatg    24240
tcccatgcaa tgtttgtgac acacaccaaa aatattactt gttgttcacc tgaaattcaa    24300
atttaactgg gtctcctgta ttttatttgg ccaacctagt tcccaggccc aaagaaagag    24360
gcttttgaaa tttgcaagaa agctggttgg agctgtcaga aagtggactt tgtaaacaca    24420
gtaccaccga accaatttga actgtactac ctctagacaa aagagagggc agtcagacag    24480
ttgttcgtga tttcttcttt caacagtcat ttgagcactt actacaaaac agaagctatg    24540
tgtaagggtg gaggcgttag ctgttaatca ggacctccag gctaagtttc tgtattagtc    24600
cgttttcacg ctgctgataa agacataccc gagactgggg aatttacaaa agaaagaggt    24660
ttaattggac ttacagttcc aagtggctgg ggaagcctca caatcatggc agaaggcaag    24720
gaggagcaag ccacatctta catggatggc agcagacaga cagggagaga gagcttgtgc    24780
aggggaactc ctcttttttaa aaccatcaga tctcgttaga cttattcact atcaagagaa    24840
cagcacagaa aagacctgcc cccatgattc agttacttcc caccagatcc ctcccacaac    24900
atgtgggaat tcaagatgag atttgttacc atatcagtta ccaacccttc cagataaatc    24960
acgtgaaata tcgccattaa cagagtgagc tcaggtggtt cttcagtgca tttctgatac    25020
ctgaaccttc cctgggaatt tcacagacca tcaggctctc cacccttttga tagcaggata    25080 gcagggccca ggttctgcag gaggagatgt taccacaggc ctgaaaggga gggaggggca    25140
gatgctacag gaagatgctg gctctggatt cgctggagga gctttcaagg gaagtagata    25200
cacactgtct ccatcatttc atgtccatca cactctaaaa tgctttggac aagaagcaaa    25260
tgttaaagac aaatgtggcc catttttcctg tacaaagagg gctgctccca tgccaggcta    25320
ttggcactgg tgggcatgag gcttctctgc tgccctggcc gggggggttct ctcactcacc    25380 attggctctc tgacacctgg agagaccacc acccttgggc tttcatgatg ctcacagaat    25440
ccacactgtt ggagctttaa ggagcctgga tcaactggaa caggcaggga gtactaggac    25500
agcccagcat tgccccaaaa tatccaggcc tgataaaaga gaaaaacagg tagctcacag    25560
gaaaaggata aaaaaaggag gagggattta acatgaaaag gtgcttgatc tccctcataa    25620
taaaaagact gctgattcca tccaggcaag tgacagaaaa aaaaaaatta atttaaaaag    25680
actgctgata aaaccacagc gagacactgc tgctcaggga tctgagggtg tgggcagcca    25740
ggctgccacg catcatgggt cggagaggaa gaccacaccc ctggagcaga gggcggctga    25800
tctgtcagat gcccttttgac agcacctcag cttccaagaa ttaacccttt ctatgtgagc    25860
agaggcatcc atgggggggac acactggtga atcatctgtt atgtagaagt ctggaaaaca    25920
tcaggatgga actggtgaaa taagtgtggc ctctgacgga atggagcggt ccgtctgcac    25980
tgctgcgggt gccctcaga tcctgtgggt cagtgagaaa agcagtgagg aacaaggcag    26040
gtactgtgta ctgtcctctg cgtgcaagga aggccagcgc atgcaacaga gtccacacag    26100
acatagccta actctggaag gaagaatgag aatgcagttt cagtggtggc ctctggtggg    26160
gagaaactgg gtgaagggag atgtcatttc catttctcta ctattaattt tgtattacca    26220
tgcttaaatg ttacttttta ccttttttttt tttttttgag acagggtctc tctctgttgc    26280
ccaggcagga gtgcagtggt acaatcatgg ttcactgcag cctgaacctc ccaggctcaa    26340
gcaatcctcc cacctcagcc tcctgagtag ctgggactat aggcacgcat accaccgtgc    26400
```

```
ccagctattt tttttaatca agatggagtt tttctatgtt gcccaggctg gtctcaagct   26460
cctggactca agcaatcctc ctgcctcagc ctcccaaagg gctgagatta aaacgtgagt   26520
caccctgccc agccaattgc tttttaaaaa agattaaatg catgtatacg ctcaggcatc   26580
agcacacttg gaaaggatga aaatatccgg aagaagggtt cttttaaaag gctcctcaag   26640
tgatgctggc aggcatgacg aatgtccctg gtcacaaaag ctctgatctg gcctaaccct   26700
gtcatgttag agactggagt gcgtgtgtgt gcgcgcaaag tgtgggggga tgggggtgag   26760
tgtgtgtggt gtgtaagcat gagtgtgtat gtgtgtggtg tgggggtgtg tgctgtgtga   26820
gcgtgtgtga gtctgtgtgt gtagtgtgtg tgtgaagtat gtggtgtgta tgtgtgacgt   26880
gaggtgtgtg tggtgtgtga gttgtgtatg gtgtgtgcat gagcatgtgt gtgggcatgt   26940
gatgtgtgtg tggtgtgtaa gcatgtgtga gtgtgtatgt ttgagcatgt gtggtgtgtt   27000
gtgatatgtg tgtggtgtgt gagcatgtgt gtgtgatgtg tctgtgtgtg gtgtgtgtga   27060
gcatgtgtgt tgtgtgtgtg gtgcatgtgt gtggcgtgtg agcgtgtgtg tgcattgtgt   27120
ctgtgagcat gtgtgagtgt gtgtgtgttc agcatatata aggcatgtaa ctgaacacag   27180
cactttagag ggctctcctg gagtcagagg gggtgggtag gaggagaagg gaggtgggct   27240
agtgtgctga agtatctact ccttgtcata gtctgtgaca acccagacta gcccatgagc   27300
caccctgttc cctgcatttc caatgagacc tcggtggaca tgttccctga ggtgaggctg   27360
actgatgtca tttgacgatc ttgatgccaa atccttttat atcaaaaaca accagaacac   27420
tctcttttct cttagtgctt tcacccagat gaccacattt catcctccca gccactctgg   27480
gccaggtggc actgctggtt tgaaagggag gtctcccctg gagtaacttc cgtgggcgga   27540
ttcacaccct gcccacagtc ctgtcccagt cagcccacca tggtggtctc cggttcctcc   27600
agaattcccg cttttcagct catccccaca ttcccggagg gactgagagc gcagcccag   27660 ggccctgctc tttgggggcc gtctctacac ccagagaagc agcaaggcat tcctaggttt   27720
ctctttcaga tgcagaactt cagtgttcag agatgttccc actggtcctg agagggctca   27780
gttcagcttt aatgactgcg ctgttgcgtg tgctctgcag agggcgggtg gcccagcgtg   27840
gctgactgca gttttcctga cgtggagccc gagcctgccc cgctgtttat taattaagga   27900
tcactctgct tgcagaaccc tgaactcccc agaactgtga ggtgggagaa ccccgagagg   27960
ccacctggcc ccacttccca cctgctgccc aaacccctc tctgccttcc tgacagtcac   28020
cccaactccc agtgatcccc atcaaccatc tgacaagggg actgagaggg aagagaaagg   28080
aggggcccaa agaggaaggt aaaactgtcg ggaacagccc ccaaatgtgt gacagccttc   28140
agtggagttg cccactttcc ctttttctcct ccctgcagga cctcccttct ccccagtcct   28200
ccccaacttc tgaggttaca ttgagaaaag tctgcagaga ggtgccagca tcacaaggtg   28260
ttaaggacca cgagtttggc attttaacag atgccagagc cacttgagaa atgtggtaac   28320
taagcccaga gaggtacagt taacctcccc agagtcacac agcaggttca tggcaaagct   28380
ggactagcac aggtgtcctt cccctgcaga tccccttctg tgccccacat cacctccctc   28440
cagtgtctgg gccacctgga gatgggccct cagactcacc cggccagagg tgccatctca   28500
tgggagaggt ctgccagga agcatcgata tttgagatcc caagaaatga agacttggcc   28560
tgtcagatga cagacttcgg tcatgggaac acgtgatctg ttttacacat gcgtcccctc   28620
agcagcagct ttccagaaaca ttcccacttt cttctgtagt gagaagaact ctttccctgc   28680
agcctcctgc ccaactcctc cttcagtgtc tttgcttcag tgtctttgat aaaccattct   28740
```

```
gctttgcaga gtgcgagctc tgccttgcag ggttcgcatc tgcctgtgct gagtaaccaa   28800
cgctaaggtc gagtggtcgg tcacctctca taagagctag ggttgtctca tgctgatgac   28860
taggacttgc cctcaaggag aaaaataaat caaaacaaaa gcaaaacag caaacatgca    28920 tctcttaaag aaggctctga gtccaggtaa atttccttcc actgaagcag ccaggctgaa   28980
ttcgaattat ctttgcccct gcttaaaaac taatgcaaat tttcctagag aatatccact   29040
aattcctgga gggggcatgg gcattcctga tgcccatgag aggaccattt gctcttccct   29100
cagtatgcta ataacagaa gcgacatttg ttgctggaaa gtatcagtga agttaataag    29160 gttttcttg cccagggtga gggaacagtt cccaatgaca aatgctgtat gggaaggggc    29220
tgtagaactg ccagcccctt tggtccatcc gtaaagtgaa ctctgtggat cctggaggat   29280
tccagcgtct tttttttttt ttctttttt ttaagacaga gccttgctgt cacccaggct    29340
ggagtgcagt ggcacgatct cagttcactg caacctccgc ctcccgggtt caagcgattc   29400
tcatgtctcg gcctcccgag cagcaagact acaggtgcgc accaccatgc ccgactaatt   29460
tttgtattat tagtagagac gggggtttca ctctgttggc caggctggtc tcaaactcct   29520
gacctcaggt gatccacccg cctcagcctc ccaaagtgct gggattacag gcatgagcca   29580
ccatgcccag ccagcatctt tcatttttct gtctgctttg gccctttcct ctctcactgt   29640
cttccttttc catttccaaa gtcagtccat ctcactatta gcacaaaaac tgctagagcg   29700
cttgtcattg gtcatctctc cctgcacctg gctggtctgt tcttggccac tgaagcgttt   29760
cccccagctg ttgctttaat cattttattg ttattatgcc ttacttaaga aatggatatg   29820
agatgcattt acctgtctct tcctgccact ctgcagagcc agtaagatgt ggtggaaagg   29880
gcccaggctt tggaggaggg ctggctgggg ttggatcttg gctgccccct actagctgtg   29940
tgaccttggg taagtagctg gacctctctg agcctggttc ggaatcatag cacctctctt   30000
tcagggctgc tgtaaggaat agcagtggtg tgtataaagc agagcgcaca gccagcaact   30060
ggcccctagc cacactgctg agcacctact gtgataagct gccattgtgg tgtgtgaagc   30120
aaaggggaaa catgcctgct gtagtgagct tcctgtaggg caggttgtag aaccagaggt   30180
gggttccaag gttacaaagg gactcttagt gtattagtct gttctcacat tactataaag   30240
acctacctga gactggatca tttataaaga aaagaggttt aattggctca cattggctgg   30300
gtgcggtggc tcacgcctgt aatcccagca ttttgggagg ccaaggccgg cggatcactt   30360
gaggtcagga atttgagacc agcctggcca acatggtgaa accctgtctc ttctaaaata   30420
aaatacaaaa attagctggc catggtggtg tgcgcctgga atcccagcta ctcaggaggc   30480
tgaggtggaa gaattgcttg agcccgggag gtggaggttg cagtgagcca agatcgcccc   30540
actgcactct agcctgggca gcagactgag actctgtctc aataaaaaaa aaaaaaaga   30600 aaagaaaaag aattgcaaga aataaattat tgtttatgag ctatatggtc tgtggtacct   30660
tgttgtggga ctgggagtct tggcgtctcc ctgaccctgc ctgttgctgc agcaccgctc   30720
agccctgcct gctccctacc tgcctcccct cggcctctcc tgcctccacc gggcccctgg   30780
tgcctcctct agagacagtc ctcctgggac cgattgtgtt ctcacttaca cgaggcatcc   30840
aggactacag ataaccagag gaaggggcgc cccccccgcc tgccctcctc cctgcatccc   30900
tcacgctgca gaggtcagag cctcatccca gccccttacc tgcccctact ctgtggagaa   30960
ccgtggtcag ttcgccaggc cggatccacg aacggccttg tggaagatgg tgagctcaca   31020
cccagagctg gctccgatga ccctgtctcc tttacatgtt tctaccttcc cctccctacc   31080
ttcccccact gctgggcgca gagtggaggc agatgaggtt taaagctcag aagggcttaa   31140
```

-continued

```
acgggttggg gcgcagtggc tcatgcctgt aatcccggca ctttgggagg ccaaggcaga  31200
ggatcacttg agcccaggag ttcgagacca acctgagcaa catagtgaga ccgcgtctct  31260
acaaaaaata aaataaataa aattagcttt gcagggtggc atgcacctgc agtccctgct  31320
actcagaagg ctgaggtggg aggatcgctt gtgcccagga gtttgaggct gcagtgagct  31380
atgctggcac cacagcactc cagcctgagt aacagaatga gatcctgtct caaaacaaac  31440
aaacaaacaa acaaaagaag gcttaaaggg ggctccaggt gggcttggca gcacaaagct  31500
atgaagttct atcttagaca caagttctgt tactgggcct ttgcaggctg gcctgggtac  31560
ctggctgcca tagacaggga accttccaga tgagctgcag gcgtggagca caggagccag  31620
ggtgctcttc ctgggctctg tccacaggca gaacgtacac agtctttgta cacgtccggc  31680
ggctctggtg cctatttttg tttgtgtttt tcttttgttt gggggatgg atttggtttc  31740 ccccgagccc tctgtcctcc tgtcacctgg ctggtgctcg gcaatgttga ccagctgcct  31800
ggctggagtt ggcagtggct aaggctgtga cagctaacat gttcctgagt cctctcattt  31860
cttcaccata atgccctgtt gagtttgcag atactgtctc tgtttttatc tcccggggaa  31920
actgaggctc agagtggcta ggccaccttc ccatggtccc tcagctcatg agggccacac  31980
agggcattgc ggtggccttc tcctcagcct tgaccctccg gccccagcat tgctgcctca  32040
aggggtctcc tctgctgagc cgtgcacctt ctgcctggca gctccaactc tgtggctgtg  32100
ttcagtggct cagcactgcc ccttgaccct ccctggcctt ctgcggatgc cagactggag  32160
cactctgaca aggtctgggg tggttgtatg ggtcctgtga cctctataca cctcccagtg  32220
cctgggaatc ctgcagatac accctcctta gccgtcccta accatagagg acatttctga  32280
ggtccccgag agagtggggc accctgcag gatccaactg ctgggcccag gaaggatagc  32340
agcagcatga ggggttccat tagccacaaa ctcacggcat ggaaccttca cccacctcgc  32400
ccctcatctg ctgtttagca cctggcacgc cgtgtatact tactgattat tacattttaa  32460
tggcaaatta tagtggcaaa cgtatgcatc tttgcacaat tgttgtacag catgatgaac  32520
aagtcattaa tagtaaagaa taaatgtgaa agtgagaaaa atctgactgc caaagttttt  32580
actccttcct tccctcccca gacttttaaa tgaaagttta gggataatcc cttagttgtc  32640
ctgctagtag gacttgcaat taaaagaatt gggccaagaa cacttctacg cttctccttt  32700
taggtttggg tgtaaattcg gggtatttct cactgatgaa agcctggtgc agggcagacc  32760
gtgggaagct ttcatttccg gaatggacca tcaacatccc ttggagaaga attctcttct  32820
ccagacccag acctggtgtc ctggcaccca ttgggcaagt gggtcctaga agacaaacct  32880
ggtcagagcc tggaggctgc ttagcattcc ccacgcacat tagcagctcg gagagctcag  32940
gaagccgcag cccctccttg cctcaccagc ctggatcagg acagcatccc ctggaagaca  33000
cacagggcct ggcctctgat tacccagcct ggagggaaag ctcaatcgag catcatgtca  33060
cccggtgccc ccatgcaggg tggcactggt gagaccccca agccaatgat accacctcac  33120
aggagtgcag gcccattgtg gccagatcat cttgactttt caagataaat cagaaatcgt  33180
atttccatga gatatcccta tttgcaagtg atggtgacta aattagaagt ttttgaatat  33240
tgtaacatgt tcgtaggctg tttgtctggt ttaaactcta tctggaggaa ttcaagctag  33300
acttcaggaa taacttcttg aggcaaggat tttgagacct tagggaaaga aggacgtctt  33360
gggggtattc tgactgttgt cctcctggaa gggaagaaca gagaactaga agactgccct  33420
tagcgaagtt caaagcacct aagcccggga ccctcagcaa gtgttcttga gtcacagatt  33480
```

```
ctccctgagg cgcctctttc tggctccata gaatggctga ttctgtaact cggtgagttt    33540 gcttttttt tttcctccat cacccaggct ggagtgcagt gaagctggag tgccgtggag     33600
cgatcactgc aacctctgtc tcccaggttc aagcaattct ccttcctcag cctcccaagt    33660
agctgggatt acaagcatgc agcaccacac ctggctaatt tttgtgtttt taatagagac    33720
ggcccgaagt gctaggatta caggcatgag ccaccgcggc cagccataac tctgtgactc    33780
ttgttacaaa ggccttatat tttgctcttt gagggtggtt ttggtttgat gcctgttggt    33840
tgccatcttt taactaggga tgttttatca aaatgcccag ccaaagtgtc caaacaaatt    33900
ataccttaaa gtttgaaaat gtctggcact tctaattcaa tgcctgttgt gccaggcact    33960
gggctgctga ggaactgagt cccgtccctg caggctagct agagaacaca cacacacaca    34020
cacacacaca cacacacaga gtggtcttac aagtcagttt tatattctac ctatatgcaa    34080
taaaggtatt attatgttga ggtgccttga tataaaaatt tttcttaaag gagaggatgc    34140 ctaaacagg cattacctga aacctcctct ctccagcatt ggttgtcttc tgtcatgact     34200
cagggttttc actgagaatg ggatggaaat gtggtctaaa gatagggcca atgttgggac    34260
tggatcccct ctgggaagtc agaccaggct agggcaggtc cttgaagcca tcaggaaaag    34320
cctctggagc cagaaacaaa acaaaaaaaa aatggtgtta actaaactca gtctcaaatc    34380
ctgaatagga ctcaagtcaa gcaaaataat taaaggagtt agcaagggc aagtcagaga     34440 gaccgagcaa caccaatgtc ttccgggagc cctgtggcga gtgacagagc ctggactctg    34500
gagtagaact catcttgtgt cttcttctgc cactcgttag ctgggtgacc ttgagccaag    34560 cccccttaacc tcttggaccc tatgttctta tctctaagta ggggctggta atatcttccc    34620
cttggaggaa tgccctctaa ggggtgttgt gaagattcgg taaggtggca ggggtaggac    34680
tcctggccag aaacaggcac ataataaatg ctaagtctct ccttctctcc acctgctgga    34740
tgctgtagat actaaggatt tcgatgtgaa tgagacaaaa ccctgccttt ccaggagcct    34800
ttgagaatca gagaactaga cccatttcca gaacaagggg atgcagggtc tggataaagt    34860
tttggggatc aatagagcag agggctccca gaggatccca tagggttgac tcctaactca    34920
agggcatgag acaaccccca ggaagggcac cctggaaggg gtccggctgt ccctgattta    34980
cttgtgggca ctgggggaat gcccggagcc atccagcct cagggctctg tgtgattctg     35040
ggttcctccc ataaaagata atcagattct ttcacgttaa tgtctttctc cacctcattg    35100
cacatcatgc agctattcat tgactcagca agtatcagct ttgcatgcga ccttggccta    35160
cccactttag cttttagtaa tagctcccctt cttgaataat acaaccagtg gggaaacaga   35220
acctaactct tacctctggg aggcttattt gctttgagaa catatgtcct gcagttttgt    35280
tcatatggca gtgaagtttc gtgcacacac tctagagcca ggcagcctgg gttcaaagcg    35340
cagctctgcc aggtcctaac tgcatgaatt tgggcaagtc gctcaacctc tccatgcctg    35400
agtttcctca tctgtaagat tggagcaatg gtaatacctg ctttttaggg ttgagaagag    35460
aattaaatga attaagatgg gtaaagtgct tagagtggag ctttgcaagt agtaagtgct    35520
atgtaagtgt tcgatttaaa atgaaagacc cttaaataca ttctttgttc atttcacaag    35580
cccttcattt cacaacctta catttcacaa ccaagctctg tctcccctgg aatccagcca    35640
taactctgct cacaagtgtg agacaggccc cagcagagct gcacgaagag gagagaaggc    35700
agccccccag actcccaacc ccctgtccaa gatggcaaaa ccagaacaca gcctctgtac    35760
caccccagca ggtattcaga atctgcaatc tccaaagccc acttcaattg taaatgtaga    35820
gccacgtgcg cttaagtca cctgtcactc tggaggctct tttgctcagt tcctcaccat     35880
```

```
tagcagggat gacagggagt gcaggagtgc ggtcgactcc cagatattgg agagcgctgg   35940
gctagctgcc cattctcccg gcctccactc ctctttgctg tccagccatc acttgctctt   36000
tgaaggcaaa caaaacagaa aacagtgcca aaagtatggg aagaaagcca gcttctcccc   36060
tggggtgcct gtgatgccat gcccaccctc cctgaccacg cagcccctgt ggaccctcag   36120
ggccccaagc ccccatttcc atcacatgcg tacacccatg tgtgtccata gccgccatc   36180 tcagtcaata aggctgctcc tgcccacttg gaatagtggt gacaaccagg agtggcttat   36240
gggaactatc ccaatggcct gacagcatgt ccgctgcaaa ccgctgaggt aggacactgc   36300
cctcatgtct agctgatcag caagaggcgc agttgctttc ttaggtaaca ttgctgctgt   36360
gtcctggcca ttgctggggg gtggcactta atctacacca gaattttccc tcctgtatct   36420
tccaagctgc ttggatcttg gtgctgaatt aggttggact ttgtcttgtg gggaagggag   36480
gactatagac cctcaacgta agcaatggtc agactattct aagaaaactc gccgaattaa   36540
agcatgaggt aaatttagtt ctgacttctg tccaccccac tgccactgtc ccctttatc   36600 ccatgatccc ttgcttttct tttcctcctc tctccctatc tcttgtgttt gacgcatgat   36660
aggaattcag aaatatatgt ttgtggattt gtttattcac gtagcaaacc atttcttgag   36720
tgcctaccat gggccaggta gaatgggcgg ccccgggctg cagtggtttc ttcagcccct   36780
ctccagggtt tacactgtgc aagacggttt gtgatgggtc ctcccatcga ggaccacact   36840
cttctttctc tgtgccccTT ggtcctcagt tctgacccc acttcaaagg cagcattcac   36900
tcagggaagc tcccatacaa tgctagtcag agtaaaagtt tggacaaatt gccaggaagc   36960
agcttgtcag tatgcataaa cagcctttaa aatattacta ctctttgacc cagaatttca   37020
cttctaggaa tctgtcctaa ggaagtagtc acatgcaaaa gatttatgta ccaagatgtt   37080
catcaaagtg ttgttttata acaggaagtc tcagaagctg gataaatatc caacctctgg   37140
aaatggttag atagaatagt atgtagccat tagaaaatta tgtctatggg gtttaaaatg   37200
tcatgggaaa acacttctga cataaaagag catgagaact gtatatttag cataatctta   37260
actatgtttt agaatgcaca ggaaaaaaat gtacaaacat attcatagtg atgtctctgg   37320
tggtaggatt atgatcagta agtacttctg tctcttcata ttttcctgta tttgataata   37380
catgcatatg ttgttttTaa aataagaaaa attttaagtt taaaattgga gctgaaaagt   37440 gttttaggt caggcgaggt ggctcacacc tgtaatagca ccactttggg aggctgaggc   37500
agtcagatca cttgagccca ggagttcgag accagcctgg ccaacatggt gaaaccccat   37560
ctctactaaa aataaaaaaa ttagccatgt gtggtggcac acatctgtaa tcccagctac   37620
ttgggaggct gaggcatgag aattgcttga acccaggagg tggaggttgc agtgagccaa   37680
gatcgtgcca ctgcactcta gtctgggcaa cagagtaaga ctctatgtca agaaaaaaaa   37740
aaaaagaaaa gcctttttaa acagtagcag acataactat ataatcctta ctaagctgtc   37800
ggtcaaattt ttatttatat atttatttta ttcattatt attttagac agggtctcac   37860 tctgttgccc aggctggagt acagtggcgt gatcatggct ctcttcaaac ttgacctccc   37920
gggctcaagt gatcctccca tcttagcctc ccaagtagat gggaccacag gtgcatacca   37980
ccacacctgg ctaattttt ttattttta tttttagaga tggtgtttac tatgttgccc   38040
aggctagtct caaactcctg ggctcaagct atcctcccac ctcggcctcc cgaagtgctg   38100
gggttaccag catgagccac tgtacccagc cctcaaattt ttaaaaatct ataagagaca   38160
ttattggaca attagagaaa ttcacatatg gacttataat agtatcagag tgtgtggtgt   38220
```

```
gatggttctg gagggaatgg acttttctt tggagacagg cttttctatg cccacccttt   38280
tatcttgcta acttatcatc atccaggttc cagcagaaac attacttccc ccaggaaatt   38340
tcttaagggt gcagtatcat gatgtctgca gcaaattctc aaatagctca ggaaaaaagt   38400
acgtgtgtgg tatgagtgtg tgtatgtatg tgtgtatata tatacacata tatacacata   38460
tatatacata tatgtgtata tatatacata tatgtgtata tatatacaca cacatacaca   38520
tatatataca cacacacata catacatgta ttttttatata attatatatg cagagagtgc   38580
aaatgttgcc aagttaaaga ttggtgagtc taggtgaagg gaatatggta tttattgtat   38640
tatttgtgca acttttctta agtttgaaaa ttttcaaaac aaaaaattgg aggaagaagg   38700
catgccagtc taccccaagc cctccattgg aatgctgaaa atctaaacaa tgtgatttgg   38760
caatttcatt tcttttctgt tgtgggccag tagtccttag atgttgggga aggggggtagt   38820
cgctgaggtg tggttgactt aggatggaag aagcagaagt caagactccc agggtcaaag   38880
tggtttgctc tgctgaccca agtgtgggag gcccagagtc agcgtttcag gtgtgctaat   38940
tcagcatggt tctattcacg gccaaagtcc accctgggca cctctctggc agcaatcttg   39000
ggtgactcta ctaaggccag gcctccatga ccctatgtct ggatcccata tctccacctc   39060
tcccactgtc tcaggaacgg tgcttagctt ttttctttttcc ctctcctgtc ttctttgcca   39120
gcatgtagaa agtttaaata attcccctct ttacaacaaa acaaaacata cccccttcag   39180
tcaaccaccc tagctctctt ctccttttcc cagccagatt tttttaaaag catcctaggc   39240
caggcgcggt gactcacgcc tgtaattcca gcactttggg aggccaaggt gggtggatca   39300
caaggtcagg agatcgagac catcctggct aacatggtga acccccatct ctactaaaaa   39360
tacaaaaaag tagccgggag tggtggcagg tgcctgtagt cccagctact cgggaggctg   39420
aggcaggaga atggcgtgaa cctggtaggc ggaggttgca gtgagccgag atggcgccac   39480
tgcactccag cctgggtgac agagtgagac tccgtctcag gaaaaaaaaa aaaaaaaaa   39540
aaaaagcat cctcagcact ttggcaactc catctcctcc caacatgtcc ctgttactgg   39600
aatccagcca ggactcagcc ccgatctttc tactctaacc agttgtctca gttaacaagg   39660
acaggtttat gctgcagtga caaacaagat cccaaattct tgtggcttca cacatctggc   39720
accacctcat cttccagcct taggagtcat ctttttagttc cttgaaaact ctttacagtt   39780
ttctgttggg gccttgtcat atactattcc cctggaatgt tctttcctat cccctcccctt   39840
tcaccttgct aacttgtgcc catccttcag gtctcagcag aaacatcact tccttgggga   39900
agttttctcc aacacccaca ctacacaggt gtcccatcta cactcctatg actttgtggt   39960
acttgtctca cttcattttc cactgccttc cccacaaggc acctgcacaa gggcaaggac   40020
cgtaccactg tacctatgtc actcattgct gtggtcacct gcactctggc tgcctacctt   40080
aactacacat tagaatcacc tgaggagctt ttaaagccac aatgcaagac tccaccctag   40140
gccaattgga tccaaatccc tggggtaggg ccagacatca gtggagttat atatacatat   40200
atatattttg tttgtttgtt tgtttgtttt ttgagacaga gttttgctct gtcacccagg   40260
ctggagtgca gtggcgcgat cttggctcac tgcaagctcc gcctctcggg ttcacaccat   40320
tctcctgcct cagcctcctg agtggctgga actacaagtg ctcgccacca cgcccagcta   40380
attttttttgt gttttttagta gagatggggt ttcaccgtgt tagccaggat ggtctcgatc   40440
tcctgacctc atgatctgcc tgcctcatca gcctcccaga gtgctgggat tacaggcatg   40500
agccactgca cccggccatc agtggatata ttttaaagc actgcagaga attctgttgc   40560
atcagcttga gaaccactga tctgccttgt gcttcacatt taaaactttt ttttaatgaa   40620
```

```
taaataaacc ccaaaaaatt aatctcccta agcctcccta gaagatagga tggtaaggat   40680
attttcctag gtaaaaatat gttaatttca tatttcatga aatttcatgt ttcatttcaa   40740
tcaagctctg tcatacacct tacatggggc aagcccagtg cctgggcagg gtgtaattat   40800
actcattaca caggcaagga aaagtcacat taggtgatgg agcacaaata ggcagttaat   40860
ggtttcaggg ctagttagga tatgtttgtc tttcaattgc aagtaataga agcccaaaga   40920
aattggttat ttatataata taattgattg gttcccaaat ttgaaaaatt caggaataga   40980
cccagcttag gtacagctgg atccagtcac tcaaacaatg tcacaaagaa cccttttgaca  41040 ggaatgtatc ctgtgttgac tctactttgc tctgagtagt cttcccccag gtgatgataa   41100
aaatggtcat catcgccagg cttgtgtcct gtttagtagg aatatacaag aagagctcag   41160
taaatgctgg ccccaccact aagcaaaaac aaaacttttg ttgttgttat tgttgtttta   41220
aataacagct tagacctttc ttctttcctt gttattctct ttcatctgta atccagtttt   41280
ctacttctga agtatagaat gttctgatga tttattcttc attacccaca acttgcacat   41340
gtttatttaa aaatgccagg attgcctggc cgttgtgtgc tgttaacctt tgtttgctgt   41400
tagtggatcc ctgaagttca ggctcccagg ggagcagata atgggtatcc agttcctgca   41460
atatccaccc tctggcaagc caagttcctt cctgggtaag gttttgccta cctgcattcc   41520
tagggaagtt tctgggcctg accaccaagc cagctctgag aagggggtgca taagccccac   41580 catgctttgg ctctgtccct atagaatatt ttatgttgtt actgaaaact aaaggaagat   41640
gggtgcggtg gctcatgcct gtaatcccag cactttggga ggccaagaca gattgatcac   41700
tcgatgccag gagttcaaga ccagcctggc caacatggtg aaaccttgtc tctacaaaaa   41760
caaaacaaaa caaaaattag ccgggtatgg tggcatgcac ctgtggtacc agctactcaa   41820
gaggctgagg cacaagaatc tcttgaacct gggaggtaga ggttgcagtg agccgagatc   41880
gcactactgc attccagcct gggtgacaga gcaagattct gtctccaaaa aaaaaaaaaa   41940
aaagaaaagg aaagctaaag gagagagact aaaatgatat caggttcctg gagaacaaac   42000
agacatgatt ttgcttcatg gcaggacagc cggaagaagt gggattatat cctcacatta   42060
caaataagaa aactgagact cagaatggtt aagtcacttg tcccaggcca cacagccagt   42120
aaattacaga aacagaattt gaacccaaat cttccagctc caaagcttgt gttcttttca   42180
ctacctcctg cttaattttt taatttctaa gattagaccc ttcatctatc catgacacct   42240
gcctgtcatc ccctgaaaaa aggtgaacgc cgttcagaaa ttttttctagc ctgagctcac   42300 tcccagttca cttattttg ctttgtcatg gctgcccagt ccccacttgt agaccaggaa   42360
taggtcatgg ctgcggggac tacacgctgt cgctgctgca agggccggcc tctgtttccg   42420
gggctgagtg ggggccagac ctgccaggag caccatcttc tgtgggtcct gcctggatgt   42480
cacatcccgg ccccaagaag tcactgcaaa ccttcgtatt attgagcttc acatcctaga   42540
atttgctgtc actgtggctg ctgcatgaag ttgtcctgag agaaacgggc attgtcatta   42600
acagggaaat tgatggtctg ggggaaaagt catcctcatt ctcttgcaga tctatgggtg   42660
attgagactg gctgatgttg aaggggtttc tcagccatcg tgtgccatgt tatgaacag    42720 tggtgtagcc agccatttga cacccagcgc tgaccttgt ttaacaacct cacctatata    42780
tgacaaaatg attgtcagaa ataatcgtgt aatgaaatga ctgtaataat ggccagaaaa   42840
gaaacgcaga tagtaaaatg tttctcttgt tgaactctgt acatataatt gcaccaggat   42900 tttttttcaaa taaaagtaa atattatact acaaaaaagg gaaaaagcac aagcatttat   42960
```

| | | | | | |
|---|---|---|---|---|---|
| taaatagctt | tctatatctt | tctgagtttt | gatcctttga | ttgcagactg | atgtaatatt | 43020 |
| ttatgtaaat | cattgcttgg | ttactaagtg | aactttaaga | aaagtgagac | gtctgcagaa | 43080 |
| gttgcccata | atttagcagc | tactgtattg | taccattgat | gtacggcttt | attttcttga | 43140 |
| ttaattattt | aaacaatata | attcacaatt | ttaaaataat | aaatttccac | ttaaaatggt | 43200 |
| atttaaactc | agcaaaatat | atcatctatg | agtaaaattt | gtatttacca | agcaaaaata | 43260 |
| ttacagtttg | tggttcacat | gctgtctcac | tgtttttaaat | tttaaataca | aaaactccaa | 43320 |
| gtaggctggg | tgtggtggct | cacacctgta | atcccagtac | tttgggaggc | tgaggcaggc | 43380 |
| atatcgcttg | agttcaggag | ttcaagattt | gcctgggcaa | catagtgaga | tcctgtctct | 43440 |
| actgaaaaca | attagctggg | tgtggtggca | catgcctgcg | gtcccagcta | ctcaggaggc | 43500 |
| tgagatagga | ggatcacttg | aaccctgggg | gacagaggtt | gcagtgaggc | aagattgcac | 43560 |
| cactgcactc | cagcctgggt | gacagattga | gaccctgtct | caaaaaaga | aaaaaaaaaa | 43620 |
| agaaacacaa | aaactccagg | tggtcgcaca | gaatgacagg | actgaagtaa | cttagctcca | 43680 |
| atttctgtct | tcataatcac | tgtcctacca | ttgtctgtgc | ttagaatcta | cttgcttaat | 43740 |
| gcaggaacat | gtgttctcac | agagatggaa | aatgcaaatg | gcgccagaag | caagctggaa | 43800 |
| attctgaacc | attaagaatt | tactctctgc | caggcacggt | ggctcacgcc | tgtaatccca | 43860 |
| ggactttggg | aggctgaggc | aggcagatca | tctgaggtca | ggagttcaag | accagcctgg | 43920 |
| ccaacatggt | gaaacttcat | ctctacaaaa | atacaaaaat | tagccaggca | tgatggtggg | 43980 |
| tgcctgtaat | cccagctact | cgggaggctg | aggcaggaga | atcgcttgca | cctgagaggt | 44040 |
| ggaggttgca | gtgagccgag | atctatctgc | accattgcac | ttcagcctgg | gagacagagt | 44100 |
| aagactccat | ctcaaaaaaa | aaaaaaaaa | aaaagaactt | actctcaaaa | taaatacgtg | 44160 |
| tggctgactc | cacatatggt | agggccaact | gtataactag | aagttctcca | aataacttct | 44220 |
| gtggagaaaa | aaaagtttat | taaaggttaa | cttttttaaa | gtgctaacta | gaaccttact | 44280 |
| aacactgaga | tcgcaccaat | tgtttataac | ttagacaggg | ccgggtgcag | tggctcatgc | 44340 |
| ctataatccc | aacactttgg | gaggccgagg | caggtggatc | acttgatgtc | aggagttcga | 44400 |
| gaccagccta | accaacatga | tgaaacccca | tctctactaa | aaatacaaaa | attagccagg | 44460 |
| cacggtggta | cacgcctgta | atcccagcta | ctggggaggg | tgaggcagga | gaatctcttg | 44520 |
| aacccaggag | gcggagattg | cagtgggcca | agatcgcacc | attgcactct | agccccagca | 44580 |
| acaagagtga | aactctgttt | caaacaaaca | aacaaaaaaa | aaaacctctt | ggaccaggaa | 44640 |
| aatatttttt | aagggaggag | tattttatca | ctggcattgt | ttaggattgc | aggcacatga | 44700 |
| tgctaatgaa | aagcagacta | actattagtt | ggttttatta | ctgttttttga | actctctctc | 44760 |
| tcccttttt | tttttttga | gacagagtct | ctctctctgt | cacccaggct | ggaatgcagt | 44820 |
| gactgcagtc | tcagctcact | acatcctctg | cctcctcagt | tcaagtgatt | ctcgtgcctc | 44880 |
| agcctcccga | gtagctggga | ttacaggca | ccacaccagg | ctaagttttt | gtattttag | 44940 |
| tagaggcagg | gtttcaccat | gttgcccagg | ctggtctcaa | actcctggcc | tcaagcgatc | 45000 |
| tgcccatctt | gacctcccaa | agtgttggga | ttacaggcgt | gagccaccgt | gcctagccct | 45060 |
| gttttttgaac | tctctagaga | cagtccagcc | ccttattact | tgtcctgagg | cagctgctcc | 45120 |
| cttcacctgg | ccccccgcat | tgtgttccgg | accctttgtcc | tggtggtgct | aaagaatatc | 45180 |
| tctgtcgatc | ctttgggac | tgggaaact | gaggcccagt | gccacgcgat | gccatttgtt | 45240 |
| cagggaagat | taggtcatct | gctaggtccc | cagtcacttg | accttcttcc | cagacaggaa | 45300 |
| gaagctgctc | tgggtctctc | agtgctccac | gtgtctttgc | acattgaaat | gttttctgat | 45360 |

```
tttttttttt ttttttttgct gttacattta cttttaaaaa ataacaagca ataaaatgtt    45420
acatttgaga aggttgaaat gagaattgat ttgagttaaa ttctagcaga ttttttcttag   45480 aagaatgata tcatcatctc cagctacctg caattgatct actctgaatt aagaaagaga   45540
cttccatttg ttgtttatat tttgcactct tgatgtgttt ctttaaatta tggtcatggg   45600
ccaggtgtag gagctcacac ctgtaatccc agcaccttgg gactctgagg agggaggatc   45660
actggaggcc aggagttcaa gacctcgtct gtacagtaaa ttttaaaaat tagccaggca   45720
tggtagcatt cacctgtagt cttagctact gggaggctg agatgggagg attgcttgag    45780
ccagaacttt gaggctacag tgagttattt tcacgccact gccctctagc ctggctgaca   45840
gagcaagacc tgcctcaaaa aaataagtaa aaaataaatt aaatttcaat cattagcagt   45900
cattaggata tttaaataca gtatgttgaa tcaaagttac gcatgtgtgt atttttttt    45960 ccagagagtt gtttatcatg tgggttttaa tttaacttta aaaaaatgtt ggctggacag   46020
ttgcccaaat ggtatcatca gccatttggt tgagaacgta tgtcctgcgg gctcctctgt   46080
cactggagtt ttgctagctg acagccactg gctagttaga gactgcagtc agcacagatg   46140
caggcgtgga cttgcgcacg taaccatgtc aatgcaaagc catcacttct taaaaattct   46200
gaaccctgct gtctgagatg gtggtgcagc ggatagaact ctgctctaag aggcagtagc   46260
taattccatg tcttctttgc ccttgactag ctgagtgact ttgcacatgg gcttgcctc    46320 tctgttgcct tgtctgcaaa gtggaatcat cttttccttg ctagacagaa ggtggaccct   46380
ggacctatgg ccttttgag tttccccccc gcttcttaga aggacctctg atcctactga    46440
gtttaatacc cacgggttaa taattgggaa aagcaaagga agcgcttctg tttaggtaat   46500
tatatgcatg ttttttgtctt tttctggctg gaaagatatc caagccactg ggaaggtccg   46560
tggctaccca gggtagccct ctctggggag ggctgctata tccaagagcc cctcatgaga   46620
atttgaaaat cgaccatggt agggcctgct gacttttgac agctaatggt gtgctgagaa   46680
ttgtccctcc aaagatgcct ttccattccc tcgggagagt ctgggcagcc cctactgggg   46740
gctgggatgc tggctcttcc ctcagcctcc accccaactg ctctcttccc tcctcccctc   46800 cccagcccc taatttctct cacaaggctt tgttctgcag caacctttcc taatgcagtc     46860
ctggcctctt cgcagcttca ttacataacc ttccgtggac tcctggtcca aggatcaccc   46920
cagaaagcca gtcagaggta ggcacgcagc tggggtccat ttacttacct tccccacccc   46980
ctcggaactc agaggtggtg caggaattg gactccaaga attaacagct ccaccaccat     47040
caccagagcc aaaactcagg atgcatgtgc ttcatctgct gcttatttcc agctgagagc   47100
cagtggtgcc atggttcctt agggagccgg tcccctgatg ccggctcctg gccccaaatc   47160
tctctgatcc gggctcttcc agaatgtctt gtctccacca tcgcctttga ccaatggtgt   47220 cccttttgcct ggtaatgtcc cctttgcctg atgatggccc tgtcactcct ctctttagca   47280 cagaggagc tgtttcatcc cttcaagcct gccctccctt caagtcttag ctcaagttca    47340
ccttctccgc agagccttct ccaatcttct tgactacgtc tcctctcagc tccagcaacc   47400
tctgtctctg gcactgattc cttacttagc taagagaatc acagacactt ggggctcagg   47460
acaatctgct ttctctcttc ttacccatgg ccttggactg tgtgtacctc tttgtctcca   47520
ctcccaaacc caacccccag agggcagaga gcatgttgtc tgtccctttg ctcagcatga   47580
agccatgcgt gtggtagatc ggcagagttc cataacttgt gttgaccgag gggtcacttt   47640
gctctgaaat tacccctgtg tccttcagta tttgcacaga tagcttcctg gccagaccga   47700
```

```
atatatccaa gggcatggcc cacctctgct cctgtttcca ggtccctggt gggggttagt   47760
tcatgccttc ctcataatct gcccactggc ctggtcctca aggtcttccc aactgctcag   47820
ccagagttga gaaaatgggt cgctccatcc tgtttgtgtc gttctctcct tcctggccca   47880
ctctcctgcc cacaggtatc caggggctgc ctgtagcatt agaggacata catgcacatg   47940
cgtgggcatg ggacactcac gtagcctcca agcacagcat caataatgca ttctgtgctt   48000
tatagcatgg aaagctgctc taaactttat tacacagtgg acatgtctga agcagctccc   48060
aaatccaccc ctgagtgtgt tggaattggc aagcctatca cttgggagtc tagttttttt   48120
gttcgttaat aatagatgct tcctgtggcc ccagcttggc aattttgatt taaagtgatc   48180
ttaactgaag agactaatgg acgggtctga atttgtgcct tttaagcaca aagtattgct   48240
cttaattaac tggattctat cctttgagca ggcagaggcc ttcccccaag ggcgtcatta   48300
acgatccaca tctggacatc ttccaaagcc ttcttctgtt tcaggccaac cgcaggtgtg   48360
ttcctgaaca cccaggaggc tatgagagca acatatgcct cccaaataca cacagtgtgc   48420
atgcccaggg acatagagca gtgtgcaaag tcccattcca tctctctcca cctgggagag   48480
gatggctctt ctgtctgatt catggctcaa agtggtaaag gagctcccca ctccccgtcc   48540
cacgcctact cagagtctgc aaatatgtat gcgatatgag agctcgtcag ttagctgtct   48600
tcagtgtggc gcacatttga ggagtctgac tcccctccag cacaggccaa tgtgcactgc   48660
tctcctatct ttgtaccccc actgttgcac tgtgcagagg ttggagccat agaagtacca   48720
gagctgtgaa aggagaggcc ccctctcacc tctgccctgg tctccatccc cactttctct   48780
aggaagctag taggtgctga caggggagag aagggagggg aggggtccag aaacagtggc   48840
tcatgcctgc aatcctagca ctttgggagg ctgaggcagg aggatcattt gaggtcagga   48900
gtttgagacc agcctgggca atgtagcaag accctatctc tacaaaaaga aaaatgtaa   48960
ttagctgggt gtggtggtgg gcacctgtag tcctagctac ttgggaggat gaggtgggag   49020
gattgcttga gcccaagagt ttgaggttac agtaagctgt gattgcacca ctgcactcca   49080
gcctgggcaa cagagctgag accctatctc aaaaaaagaa aaaaaaaag aaaggagaga   49140
gagagaaaga aagaaaaga aaaaaaaaaa agaagggaag ggaaagccca gaagagtgtg   49200
gggagaggag gcggccgtca ttctggggcc ctcagtgtgc acaaccagat aacacatgct   49260
ctgtgggctt ttgtaccatt ttgcttgagc ataaagaaag gaaggctgcc ctaaatagaa   49320
aagcactctg gaggcaaaca aatctgactc caatcctggc cctgccactt tcccagctga   49380
ggacttagac aagcacccta gcctcttgga cattctcaga gccatctgct gcaagtgggt   49440
gctgccatac ccaccttact gggcaggctt ggggggaccaa gggtggtaaa tggctcagtc   49500
tttcatgatg cggccacaca gcaggtgcgc catccaggtc catttctttc cttccttttcc   49560
cccaaatcaa gttgtcatta aagtactagt ccacattaat gaaatcaact gtattaattt   49620
tctatttgct gctataataa atcatcagaa atttagtggc ttaaaccaac acaaatgtat   49680
taccttacag ttctggaggc cagaagccct ccataggtgt cactgggctg aaatcaaggt   49740
tttggcaagg ttgcggtcct ttctggaggg tccaggggag aatccatttt cttccttttt   49800
ccagcttcta aaggtttcat gcattccttg gctcatgatc ttctatagct atagtcagaa   49860
aaattttcca tcaatcatct tcaaagccag caatggcagg atgagtcctc acatcacctt   49920
gctctgacac cagttctctg cctccctctt ccacatgtca ggaccctcat gattactttg   49980
ggctcactct gataatctgg gatgatctct ctattttaga gtcagctgac tgggaacctt   50040
aattccatct acaaccccaa ttcctctttg ccatgtacag tgacatattc acaggttctg   50100
```

```
gggattagga cgagcctgtc tctgaaaggc tactttacat gaaaattcat ttttttaatt    50160
aagatttttt tttcctcttg agacaaggtc tcactctatg gttcaggctg gagtgcagtg    50220
gtatgatcac agctcactgc agcctcgacg tctctgggct caggtgatcc tcccacctca    50280
gcttccctag tagctggaac tacaggggtg agcccccatg cccagctaat ttttttttt     50340
ttttttttt  gagacagagt ctcactcagt cacccaggct ggtgtgcagt ggtgcaatct    50400
cagctcacag caacctccgc ctcctgggtt caagtgattc ttgtgcctca gcctcccaag    50460
gagctgggac tacaggtgtg caccaccacg cccgactaat ttttgtattt ttagtaaaga    50520
tggggtttca ccatgttggc caggctggtc tcaaactcct gatctcaagt gatccaccaa    50580
cctcagcctc tcaaagtgct gggattacag gtgtaagcca acatgcccgg ccccagctaa    50640
ttttaaata  ttttttttgt agagatgggg ttttaccatt ttgtctaggc tggtcttgaa    50700
ctcctgggct caagcaaacc tcccaccttg gtctcccaaa gtgctgggat tacagcatga    50760
gccactgcac tcggccttaa gagaagattt aataattaat actttacaac aagatctgga    50820
agaggtggga tgagtaacta aatgaggata caagtaaccc gggtcatatt tgctaatacc    50880
cttggtcaca ttgaacttga tatcttatca gattttccta atcagctcct ttagcagcag    50940
tgttgcagca tcttatctca ttttgttttt tgttttttg  cctagcacat gcctgtaaat    51000
cactggattg aggtgtttag atgtttgttg tcctttggat gcttcttata aatccatatt    51060
tcatggctcc ctggaaagtg ctatgcaaat gataagctgc aaggatggaa aggaaattgc    51120
agtgctcctg aattgtaaat gggcttttac gaggaggttt ctaattactc gctctttctc    51180
ttgaactgag gagttgaagt gtaggtggca gatccataac agataatcat gtgtgtgatg    51240
tgacttcagc ctgagcgtcg aggaccaagt cacagagcag gaacagccac tctccagtgt    51300
ccttggggct acgtctgagg agaacctggg atttcatata tgacctgcac tggctggggg    51360
gctctcttga cgtaacgtgt tccctctgag catgttacag attctgacat tcttatgttc    51420
cttctgtgga gagacatgta cttagtgacc taactcactt tagcatattt ttgctcatcg    51480
tttgtgtagc ttaaaggaat cagataatta cccctcccc  actactttcg gaagcacaaa    51540
tgcaatgccc tagaattgta ctggggactc aaaaagaaaa gagagtagta aaatctatta    51600
aaggggacaa agacagccta tatactacaa gctttctatt tttatggcag agaatgccat    51660
tttctaagta aacagagaac tgcatttgac ctgcaatatc aaatgcatgg atttgatgct    51720
ttggaaagca actgttttct gcgttaatct gggtgtcttc cgtgaaatgt cctcctgcct    51780
ttggcttaaa cactagcttt gtctacagcc attccatcct gaacctgccc aatcttgtct    51840
gaatcctggt ttcaccactg acaagctgtg tgtccttggg caagttactt cacctgtctg    51900
tgcttcagag tcctcatctg tgagttgggg aatctggaca gaatctaccc catagggcgt    51960
agtgaggatg tgttgaatta tcccaagtgg ctacacagag taagcactca aatgatgtca    52020
tcgttgtcat gattgctgtt accagagcct agagttcatt ctgatactcg agtctgtggc    52080
ccatccagcc caggtaagga atagttggag gagttgggca tgttcagctt gaagaggaga    52140
cgacagggga tatgggatag ttgaatctgt gaagggcccc ctgggatgaa gaactggcat    52200
gttctgtgtg gctccagggc actgagcagg acccatttgc caaagtctca gggacacagt    52260
ttctagctat agacagaaaa attttctgtc actcagagga tgaaaataga atgagccccc    52320
ttaagaggta atgagctccc tgtcattgga aggattccag aagagctagg taaccacttt    52380
aggtgctatc aaggggcttt tttctttaaa gtcctttcca aaagcttctg agattgcata    52440
```

```
aacaatagga agccatcttg gtgctttaac acaaactctc cccagtgatg agggttgagc    52500
caaagccaga ttggcaagca gagaggagac ttgtgtacaa ggagttcctc gagtcaattg    52560 cttttteett gttctagcca gccagagggc teetgttgga aaacaggaga ccggagaggc    52620
tgaggcctga ccaaaccagc ttctgcaggc cagctgggag gccacaactc ctacctacgg    52680
gaaaactgaa gggcatctct attttttagat tagcaaaaga aaataaattt aagtttgagt    52740
ctcctttgca acttttaaaa gacatcttta ttgagatgat cattcacatt ctataaaatt    52800
cccccacttt gagttacaat tcagtggttt tagtcttcct tgatgatttt gatggtcttt    52860
tcttaaggct cttggaagac ccagaagcct ctcagacaca ggtgggtgtg gagggcgtag    52920
cacagaggca gacttctcat ttcctgggtc tcccctttaa tgactctcag agaccctcc     52980 ttccccctgc ccctggcttc taccccaggg gtgtagagtt ttgccatttt ccaagcagaa    53040
cttcatttcc tcttctgtgt ctacactctt tgtgcttctt tcttgccagc ttttttctcct    53100 ttgcccgccc ttccttcctt ccttccctcc ctccccccctt ccctccttcc ctctttccct  53160
cctccccccc ttccaccctt cccccttcc cccttccct ccttccttcc ttccttcctg      53220
cctgccttcc ttccttcctt ccttccttcc ttccttcctt ccttccttcc ttcctggtat   53280
gtgactaatt tctgtttcag gacataaatg ttgtccaggc tgttctttgg tctttctgtt   53340
ggataatgga catttggcat tgagagaggc tgcttttttct gaaatcatgt tcttggggcc   53400
cagaacctag gtgtgtgctt ctgactttgt tttcttcctg atccaaattc tgatatgtcc   53460
atttaaattg atctagaccc acagggcact gtgggacaga tcctcagtgg aacatgactc   53520
tgtaacgaga gcattttgtt ttgtcaaaat gagaacatat tattgccttt catctgattg    53580
taaacataat acatgtttat aaaacagtat aatgagacaa aaatgtagac actaataagg    53640
gaaaatctcc ctaattgtat ttctcttcac agagaaagcc cctgttgggc atatatactc    53700
tagtttgttt atttgtttga ctacacatat atgtattctt ttcttatgta taaaaattct    53760
gaacatgcac atttctgcaa ctactgtttt cacttgatga tgcatggacc tctctagagt    53820
gtacgtttct tcttccttac aaagcagttg gcttcgccca gggtgcacca ggacacggtt    53880
ttggctctgt cccagggtg tcacgggacc aggggatgat ctcacagggt ctgccatctg     53940
ccctgcctgg ccggaggctg catcgagagg gccaagggc accacgtgtc gtgggtactg    54000
tcaaacaaga gccttcagag ccttccacag tcttttcttttt gcttcccagc attgcttccc  54060
cgctggtgga ctctgaatct agaactagct ccaggcgcct ctccaaattc agacgggagc   54120
tggggcacta ttataatgca aatctaggca aagccctccc aataccagga tccagaatgg   54180
ggtggggccc tttgccctga aaagctgttt agtttgaaaa tacaaacagg agacagaaaa   54240
gtttggctaa attaatggat aaagttttaa cgatggtaac catagtaggg ttcatcgaca    54300
gccagcgatg gttctgaaca cttgacatgt attaactcac ctaatcccca catttacag    54360 acaatgcaaa ggaggctctg ggaggttgag tgacttgccc caaagtcgca cagctcctaa   54420
gtgaaggatt cggagtggac tccaggcagc ctggtctgac tccctgcact gcgctgtgct   54480
tatctctggc cccaatgccg ccatgcagaa gtgtctgggg gcactttgtc tctgtcagac   54540
agaattcgga gatgtgtatg cttgccctgg tatggcactt ctcttttttt gagacagaat   54600
ctcactctgt caccctggct ggagtgcagt ggcatgatct cagctcactg caacctccgc   54660
ctcccaggtt caagcaattc ttgtgcctca gcctcccaag tagctgggat tatagatgtg   54720
caccatcgtg cctagctaaa tttttgtact tttagtaaag atgttgtttt gctgtgttgg    54780
ccaagctgat ctcgaacttt tggcctcaag tgatctgcct acctcagcct cccaaagtgc    54840
```

```
tgggattaca ggcatgagcc accatgcctg gcagtgtggc acttcttacg tgtgttcagc    54900
ggacactgtt tatcttctgt ccctccaaga cggtgctgag ctcaggtcgt tcattactgg    54960
cagacaactg ctgatttcca acagaattgc catcctcttc tccctgcga ctttcagagt     55020 gtgacctcag actcaaaaat tagaagtgaa aacatcttaa aaactatcac cttttcttcc    55080
taatcctcct ctcccctccc tgtcttcctt gttgtcccca tctaatgaac tatcatggca    55140
aaaagagccc atttctggtc attttctgtg gcctttcaaa ctcccaccta ccccactgct    55200
cctgggtgca ttacccgaaa gctgagactt cagtgcagaa agtgccaggc cctctgtccc    55260
cccagatcgc cttccttgtc ttccctgtgc ttgcctgtca cattgtgtgg gttccagcgc    55320
tggaaggaat gaggaacaga ttctctggtt ctcctttga agtttacctt cgctccacca     55380
cttctgagac cttcccggaa gttgcccctt gtttctctcc tctccagggc tgccccagag    55440
ctgcctctca cctcttcctg ctgtcacccc accaccatca gggcagaagt tgggacaaag    55500
cctctcctac tggctcctgc ttttctccct taggtccagc ctcctcttct ccatcttcag    55560
gagtctcctt ctccactcac acgtcatgac ttcagcacct cgcatcagtc cagaatatga    55620
ctgcttgttc aagtgccacc tttctcatgc attttttct agtgacaatc acagccaccc    55680
tgtggggcag gagtgtcatc atccccatgt ttcaaatgaa gaattgcagt tcagagaggg    55740
caagtgactg gcccagcctc aacagctagc cagtggaccc caccagggct tctgactcca    55800
gtccgggttc ccttttccacc caaatccatg gagggagctg agccgagaac aggtgtcctt    55860
caggaagacg tgaagccaaa gcctccacct ccaaactcag gggcccaggg agtccaggca    55920
cccatccact cacaaggctg gatatggtgc attccaggag aggggttggg ggcgagtggc    55980
ctctctgtgt acccgtgggg atagatgcgc aagtggcatc gccacatcgt gagtcctggc    56040
ttcatgggtg agctccaggt ccaacgagaa gccaagcagg gggcccttca agctcagctt    56100
tgggcccggg tcggggtaca gggtagagcg ggcctcccca gccctgcca tgaggccaag     56160 gcagtgcatc gttcgcagcg tacattcaga aaccaaagcc taggagctgg ttatcattcc    56220
ggtttacagc tgatggaaga gcaggtgctt ccgagaaccc acagtgctct ttggccagtg    56280
acccaagggt gcctctgaga ggcctcgcag caccggagg tgctgctgag gcaacgccct     56340
gactgtaaga aggaccattc atcctcagag agtggccgtg atgctgctgc gacagtccca    56400
ccatccctcc cgactctcac tcccaacaga cttcccactg taaagctgaa ctctccagca    56460
aatcacctct cgccagactc tctcctcact ctctctgggt ccactagagg ttcctcagcc    56520
tctctttgcc ttggttttcc cagctgtaaa atggagcaaa gagggcctat gtacccacaa    56580
aggtgtggtt ggagcgactc ctcctacatt agggcctcga gtgggcttc atgattggtt     56640 ggtggaggtc tccaaaccca cccagtgcca ccgaaggctg agactgcaga tgcaatgcca    56700
caggtgtcct tcctcagcct gggcagctga acatcatgtg taaaacgggg ataataagat    56760
aataacagcc ccttgcacct atgtggctgt gaggattaaa caagataaat gtgtaacagt    56820
gcctggctat agaaatattt actcttgtta ttaagggaag aatatgtgtg gctaaaaagg    56880
gatcgaagat gtaaaagcca atccctcccc ctctagcata tttaagggta atgttgagtt    56940
ggtttgtgga ccatttgctg cctgttagag ctggaaggta gggacccccct ctcaacagcg    57000 atgctacaaa ttatacccat tggaggtcaa ccaaaagaca aagcttattg gctggacatg    57060
gtggctcaca cctgtaatcc tagcactttg ggaggccaag gcaggcggat cacttggagat    57120 caggagttcg agaccagcct ggccaacatg gtgaaacccc atccctacta aaaatacaaa    57180
```

```
aattagctgg gcgtggtggt gcacacctgt aatcccagct actcaggagg ctgaggcagg   57240
agaatcacta gaacccagga ggtgaaggtt gcagtgagcc gagatcgcac cactgtactc   57300
aaaccgaggc aacagaggga gacgcaatct caaaaaaaaa gaaaaaaaga caaagcttgt   57360
taataccagc atattgttaa gggaataaag taggctgcag aacaactggt gtaatatggt   57420
gccatgtagg gaaaattaca tgtgtgcata ggagaggggt ctgcaaggtt gtgccctaag   57480
atgttagagt ggttcctttg cttttctctt ttataatttt gtatttgact tttaaataag   57540
gaccataaat cacttttata aaatacattc tctccagccc ctactactcc tttaaagaat   57600
aagagtggtt tgcccaagaa agacagtttt ttttgctctg gtttttcttga ttctgacatc   57660
agaggaaact gcttctcatc cacttggggc tctgggttca ggggattcat ttcaggcaga   57720
ttaaagtggt gaccagggge attcgtggac acaggagggg acaggagcac catcagtttg   57780
tctcacacaa ccactgtcat cctcactgaa ggctgttgcc tgatcaaaaa cagtattggg   57840
ccaggcacgg tggctcacac ctgtaatacc accactttgg gaggctgagg tgagtggatc   57900
acttgaggtc aggagttcga gatcaacctg gccaacatgg tgaaaccttg tctctactaa   57960
aagttcaaaa attagccagg cgtggtgggt gcctgtagtc ccagctactt gggaggctga   58020
ggcaggagaa ttgcttgaac ccgagaggta gaggttgcag tgagccgaga tggcaccacc   58080
acactccagc ctgggcgacc gagggggact ctgtcttaaa aaaaaaaaa aaaaatatat   58140
atatatatat atatatatgt caaaatggg gtagttttta gatctatagt agttctaaaa   58200
acaaaggcca tccaagcatg acagatttac aagcactatt ggctattcca gtagttacaa   58260
tggaggagag aagcttttag ttaaaacaaa caaacaacac aacaaaccca gaaaccttag   58320
gtcaaaacca aaattgtcct ctcagacaca atctgggaat tttctcatga cagtgggcat   58380
tagccaactg acatcagcag caaccatccg tgtgcacaca gtggcaccac ctcctcccaa   58440
aaagcagcct tcatctatgc cctcatacaa tcgttgatta ttctctttgg attgaggccc   58500
ggaattattt aagtttcttc ttgccagcat gagtctttcc tttctgtatg ctccttatct   58560
tctctcttta atttggcagt tctgcttgaa atctgggtct ttcattagta gtagttcaat   58620
ttggttccag aacattctgt ggtgtgatgc aatgtgacca gagctcacac ttcagagctc   58680
ttcaagggcc agtcttactg agcacctccc agtggctgcc tgtgtgctgg gcgccacttg   58740
tggtgggcag gagagaggag gggacacaaa aggagacaca gctccttctt agaagctcaa   58800
agttggggac cagctgccac agaagagtat gtttagcatc tgagacacca agatccagcg   58860
tcacaagggt gtttattaag cctcctcatc tctttctttt tctttttttt ttttttttc   58920
ctcaggcagt cttactctgt cacccaggct ggagtgcagt ggcatgatct cggctcactg   58980
catgcaacca ccacctcccg ggtttaagca attctcctgc ctcagcctcc ccagtagctg   59040
ggattacagg tgcccaccac cacacccagc taattttgt gtttttagta gagacagggt   59100
ttcaccatgt tggtcaggct ggtctcgaac tcctgacctc agatgattca cccacctcgg   59160
cctcccagtg tgctgggatt acaggtgtga gccaccgcgc ctggccttgc tgttgattca   59220
tctatagtat gtttgacttg atgacctcca gttaccttag acagaggttc tcatctaagc   59280
tccaactttc catttccttt gtcctcgtct ttcccttaa cccctccaca tttctctcaa   59340
aatcacccca cttctaaaaa atactgttta ttttctttt aaatttcaaa ttatctatac   59400
tcattgaaat aaatcaaaat agcatggaat aagcgaaaaa aatggatccc acccttcccc   59460
actcccattc cctagggcta accatagtta accatttaat gactaggttt ttttgttgtt   59520
gttattttt atttatttat tttgagacag agtcttactc tgtcacccag gctggagtgc   59580
```

```
agtggtgtga tctcggctca ctgcaacctc tgcctcccag gttcaagcat tctcctgcct   59640
ctgcctcctg agtagctggg attacaggtg cctgccacca cacctggcta attttgtac    59700 ttttggtaga gacagggttt ctcaatgtta gccaggctgg tctcgaactc ctggcctcaa   59760
gtgatctgcc caccttggcc ttccaaaata ctgggattaa ggtatgagcc accgcaccca   59820
gccctcctgg gctcttttcc tttagttgca ctcgctcccc gctcctggag tagagggatt   59880
tccgagagac tgtgggctcc agccttcacc taggcccagg actaggatgc ctgccctaac   59940
atttatcttt ataccttaaa gcaaaacagc tggaccataa gcattcaaga acaaactgtg   60000
aataaggaga aagttctccc aggaaacaag agctttagtt ctgttgggcc agcccttata   60060
ttccttagct gttaccagtc actgcttgat ttaatctcgg ctatcacttg gcctgacagg   60120
tctgctgctg gtgccaggat gtctgggttt tgaagcctgg ctccattaca tacttcctgt   60180
gtgaccttgg gcaacttact caacctgtct gttcctcagt ttccccagct gtattatgtc   60240
agcataatag tttgttgtgt gaattaaatg aggtaataac tggaaatgct tcaaacatgg   60300
ttcctatcat gagaaatcct gctttccgcc taaatgtgct ggaaaattcc tggtggtgca   60360
gaacaggaga ccagagcaaa ggaaagacag ggtgcagaag ccaaaaatta ccttggagaa   60420
caaagcgcat gttaaggtta ttttggatt ctaggtttat ctctgcttgg tcttcagtta    60480
cctgcaagag atccatttag gggattttg tttgttttta acgatagctt tattgagata    60540
taattcatat gccataaaag tcactctttt aaaatgtttc cggtatattc acaaggctgt   60600
gcagccttcc ctgtccttga ttccagtctg agttttttaac tgaagggata aggaggacca   60660
cgctttcccc agaccagaac cgcgggccag ggggcgattc tgctgagtca ccgcgggcgc   60720
ctggtgcgcg gcggcggagc ccgggaccTt ccttggctgc ccctagcga gggccgcagc    60780 gcagcctgag acacccgccg gggccgctcc acggccgtcg gatttagact ggaagctcgg   60840
tccaggtccc cagcttgatg cgcccgcggt gtaggagacc agcccgactc gggcttcccc   60900
tgagcccctg gactcttgac tccagcaggg cctgggtaat gaacgtcagc tccccttccc   60960 caaagggggtt gctctgttgg gaaggcaccc gtttgataca gtagcataga gatgggtttt   61020
agcatcaaaa tatcagaatt caagccttgc tctctgctta ctagctgtgt gaccctaaaa   61080
aggtttctga acgtctctga gcttcagttt cctcatcatt ccttctcacg gggtggttgt    61140
gagcattaca gagatcctct ctgtgaagcc cctgtgagtg gctcatcctg agggctgaaa   61200
taaacatgtt attaataatc caaaactggc aagggatgtt gactggtccc cctcccttgc   61260
ccaaggagct ttctagaacc tgagttatca ttaccaaact gtactgcctt gagtaagaaa   61320
gttagaagga atgggaagga tggtggcagg tggaggaagg cggattggtc atcacctcct   61380
tgcagcaaga aacagcccca gatcgtggga aacctacaga cctgctagac agactaggag   61440
caaaagctgg ggctttaaga atccccaggg aggttctcct gagagagtag ccagttggat   61500
tttgtaagca gagatttgtt tggggaggag gtgacaacgt agggagcaga ggggcaaagc   61560
tgtcgggaat cctgccttga gggcagggat gtgtgttggg gggagttggg tcactggggc   61620
tcggtggcct tgggcaagtt tctacctctc aggtccttta cccacctagg gtcgccatcc   61680
tgcccacctc acaggttaca gtgagcctgg atgcactgtc atgggcaggt gcccaggaaa   61740
atggcagaca tgttccaaac agcacgcagc attccccagt gatgcccagg gtcaccttgg   61800
aggtgggcga gatgcctggg gtttctcgtc caccccacaa cacctcaggg gacagccaaa   61860
gctgtcccTt caggtaagct gcacagaaga tgtgaactct gctgcaaaga ctctattctt   61920
```

-continued

```
tgggagcaaa agggacccag ggtctcacct gcacatccct gtccctgagg gcctaggggt   61980
tcttggaggc cccagccttg gcaaaatgag gaagaaggtg aaggttgtct gggcccctgc   62040
caggctcctt cctcggccac gcactcccct tcctgcacac acaccttct ccctccaccc   62100
catctccatt gttgtcagaa aagtcacaat aaaaaggtcc atattgtcta gttcccatac   62160
ttttaatttt taaaatttta tttatttatt tatttatgta ttttttgaga cagagtctta   62220
acccaggctg gagttcagtg gcatgatcta ggctcactgc aacctctccc tcctgggttc   62280
aagtgattct catgcctcag cctcccgagt agctgagatt acagatatgt gccactatgc   62340
ccagctaatt tttgtatttt tagtagagac ggggtttcac catgttggcc aggctggtct   62400
cgaactcctg gcctcaagtg atctgcctgc ctgagcctcc ggaagtgctg ggatttcagg   62460
tgtgagccac cgcactcggc tccacacttt tcacttatta aaagactgtg gtgtccatca   62520
atggatgaat gaataaacca atgtggacta tccctcccat tacccaagga atgaagcacg   62580
gagccgtgcc aagatctgga ttcacagtga aagaagccag tcaccaaaag ccacgtgctg   62640
tgtgacttcc cttatacgaa atatccagaa gagatacatc catggtgaca gaaagtagat   62700
gagcagctgg ggactggcga aggggagaag ggggagcagc tgtctatgag gtccagcctt   62760
tcttctgggt ttggtgagaa tgttttggaa ctagatagag gtgatagttg tacaacattg   62820
tgaatgtact aaatgccact gaatcattca ttttaaatcg ttctttacgt tgcatgaatt   62880
ttaagtcaat caaaaacagt tgtttgaaaa gagaaaagcc tatgggtagc ggcagcagtg   62940
attggattta tgattcgatt ccatggctca tccctcccct gcctcacccc ctcgccctcc   63000
gacgtcttct tcttttactc tgaactgtta tctttgttct catctctctc tctctctctc   63060
aaccctgcag acactttttcc cttctttgt ctgccccac cctccagatt tccgtgtctc   63120
cagtgtctcc ctacgaggca tgaattgaga ctgggagggt gtgattctga agaaggcacc   63180
aacagtgact cagctagccc cttccccac cccgccccc gggcctcaat ttagctaaaa   63240
aaccacaggg acggactcag gaggcaatac cttttccaagg gtccctaaaa aatgtcccat   63300
tttagtgtcc aggtttcact caactttagt gcctcccta aaatgtgttc cttacctccc   63360
accccactgc atctaagtca ctgcctgaga aaacaggatt gaggaaagga gaaggaaga   63420
gagagagaga ggaggagaga gagagagagg gaggaaggct gatggattta gaaaagaaga   63480
aaacaagtgg tctgaggaaa acagccttgg tgtgtttatt ttcctgtctg tgtatcgctt   63540
ctcggccttt tggctaagat caagtgtatt ttcctgtctg tgtgtctcgc ttagattaca   63600
gggatctgtg ggtgatgaca cgtctggtcc aggctgcgta gtcacctcaa gggcatgctt   63660
attgatgtgt ttttcaattc actatctttg catgggagtc ccaggccaag aggcacagct   63720
gcgccatttg tctgttggtt tagatatcct ttatccagtt cttccagaga aatcatcctg   63780
cccttctgga ggaggtgggc agcaggggtc agagatggga gggaaaggaa ggagccaggt   63840
ccttggctag gatgccaggg tcccctgcct ctcacctggc ctgggctgga ggcctcctgc   63900
tgtcctgtca ctgatcacta ccccgcccca gcctcctgag ttagaagaca caggctaaag   63960
tagagtattt cttcattgaa aaacccatac aaaataaagg ttcataaaaa ataaaatttt   64020
agactgggtg ctgtggctca cacctgtgat cccagcactt tgggaggcca aggcaggtgg   64080
atcgcttgag ccctggggtt catgaccagc ctgggcaaca tagtgaaacc ccatctctac   64140
aaaaaataca aaaaattagc caggcatggt ggtgcatacc tgtggtccca gcttctcagc   64200
ctatggaccc acatagaata caatgtcagc ataagaaggg agccctgggg tcaccaaatg   64260
gtttgggcgg caaagaacct gaaggttgag agaagtggct tggttaccca gctgttggat   64320
```

```
gtgagacctg gccactgctt cttccatacc ctagacctgc accctgacat ctcaagtaaa   64380
aagttggggg atgttttatg gtccaggatg aaggaagggc agtgaggggc agcggagcat   64440
cactttgcat ttctgtctgc ctcttactgg ctgtgtgacc tggggcaggt aacttcccag   64500
actcctggga atcataacac ctatgatgat gatgatgatg atgatgatga tgacacctac   64560
ctcaaggatt gccctgaagg gtcacagaga tgcctgcaag gcacctgcat ggagcaagcg   64620 cccctcct ggcaggtgct gggtgagcac tacctgctgc caggccctgg ggctatggca    64680
ctgcgtgacc ctgcaagtcc tacctggcga agctgtcgtt cttgtgctca gtcagtgttg   64740
gttgtaagac tgagaagagt cacttcattt tgctctccag ggacatcttt ctgggtccta   64800
ttttctgcct atgtcaagta gcgcctcaag gatgctcctg aaaatgggct tgtctttctt   64860
aacatggcag gtaggtccca aagcattagc atggggcagc tgacctagcc cagccaatgc   64920
agtgcagtga ctcttgcaac cgagtctaat cagaaggtcc atgaacctac gagcatttcc   64980
tgtcccagga tcagggtgga ggctgagcct ccctgcttag agattcttcc catgcattcc   65040 actttttcc ccaaaagaaa atattgaccc ttgagaggca cacagtttat ttatttgca    65100 tagtaaatag tagcctgtat tttaaggatg agttgatttc tgcatcagcc cctgtaggtc   65160
atcagccttc tattggtgca tctgactctc tctagccctg cagggatggt ggaggggag    65220 gggaaggagg gatctttatt ggaaaccagg acagtgagac tcattgccct gtcatctgct   65280
ctgtggtgct gaatgaggca gcccaacaga gaaataccct gagcgagcat ccccagcctc   65340
caaaacagtg gcgcattgcc ctgagtcctg ggaatgacct ttgattctcc tgctcctgac   65400
ttggaaccca tggaaacctc tagaagcagc tgaggaaaac ccaacatgaa aagcagaact   65460
ccacactgag aatataggag gtgatcggaa catacaatga ttcttgctaa gaccgattca   65520
cagtttttct tttttttcga tcgaagaaat actggagaag cctaaagaag gagtctaaaa   65580
actctggcac gtgggccaaa actgtccttg agctaagaat gattttcaca tttttaagtg   65640
gttgaaaaat gaaataaaat aagatgatgt tttgtgacac atgaaagcta tgggaaattc   65700
aaattctaat atctataaat agtgttttat cagaacacag tcatgctcat ttatttatgc   65760
tcgatggctg ctttcccgct acaattacgt tgagcagtta caacagagac cacgtggccc   65820
acaaagcctt acaatattta ctatctggcc ctttccagaa aaaaatgtgc cgactcttga   65880
ccttaacctc agcaatttgg gaggccgagg caggcggatc gcttgagctc tggagttcat   65940
gaccagcctg gcaacatag taagactcca tctctacaaa aaatacaaaa cattagccag   66000
gcatggtggt gcacacctgt ggtcctagcc actcgggaga ctgaggtggg aggatcgcct   66060
gagcccagga agtcgaggct gcagtgagct gtgatggcac cactgcacct cagcctgggc   66120
gacagagcaa gaccttgtct ccaaataaat aaataatgca aagtaaaata aataaaacca   66180
tataaaaagg aatcaattta aaattataat gaaagctggc cgggcatggt ggctcacgcc   66240
tgtaatccca gcactttggg aggctgaggt gggtggatca cgaggccagg agatcgagac   66300
catcttggct aacacggtga aaccccgtct ctactaaaaa tacaaaaaaa aattagccg    66360 ggcacagtgg cgggcgcctg tagtcccagc tactcgggag gctgaggcag gagaatgtct   66420
tgaacccggg aggtggagct tgcagtgagc cgagatcgtg ccacttgcag tccagcctgg   66480
gcgaaagagc gagactccgt ctcaaaaaca aaacaaaaa caaaaacaaa aaaaattat     66540 aatgaaagcc aaggggcata gtagaacaaa ttttctagag ctcattaagt caaatgagtc   66600
accagttagt aaaacgcagt cacggggaag agagggcagg attctttgaa gcagcggctc   66660
```

```
tcctaaaaac aacccaccct tgtccagctg ccttccctcc tgagggtgtt ccctttgact    66720
gtgtgacccc catcccctat ttcccaaccg tccaagccca cctctagcat aatacgagct    66780
tttaatccct ctccctgacc ccaacccgat tttgaagccc agtctagtat tttctcaaat    66840
acacttcttg gctccattcc ttcctttcca tcacctctgc cttttcactg catgcttgga    66900
ccactgcagt cagctcccta tgaacagttg ctctctaccc atccaatcgg cccgcctgc    66960 tgctgccaaa ttcaccgagg gcacctctgt ggtgctgcct gtggacaaag tccaagccag    67020
ccacctcacc cacctacagg tgagtgggga gcagccagcg tgtccagtgg tttacccat    67080 cgccacagac ttggtgatgt gtcgatgtgc agagaagggg tgttggcagc cacaacacaa    67140
gcaaccccgc cccatgtgag atctaagatg ggcgtgctgg gagccacctc tgagaatcca    67200
acagaaggca gagggagaa cggctcacac ggcacaaaca ctccttcctt tttttttttt    67260 cttttttcctt tttgaaagga gtctcactct attgcccagg caggagtgca gtggtgcaat    67320
ctcagctcac tgcaacctcc gcctcctagg ttcaagcgat tctccagcct cagcttccca    67380
agtagctggg attacaggta cactccacca tgcccggcta ttttttgtgt ttttagtaga    67440
gacggggttt ccctatgttg gccaggctgg tcttgagctc ctgacctcag gtgatctgcc    67500
tgccttggcc tcccaaagtg ctgggattac aggtgtgagc catggggcct agcctccttc    67560
catttaaatg tatgcctaat ttgcccattg agaacggctg agacgcattt taagtggcca    67620
gggtctactt agagttagtg ctcatgacca ggcccaggtc aagcctggct ggccagatgg    67680
tgcctttgac ctgctctgtc tctgtgcaaa ggaatgagct gaaggatggg ggtgcagtgt    67740
gtgggcagtg ggctggggct ggcaggactc agtgactaag ggaagagaac tttcctcact    67800
accagcctgt ctttcaggg caccgcgggg ggctttggga cttggtgatg aacacagcac    67860
agagagctgt ccagcatgcg ggtccctggc ttctcacact tcccaggctc cttcagaggc    67920
tctctccaaa gggagctgct ctctctagaa cccatgaatt tggaatatag caaccactg    67980 cattggggac cactgacctc aaacatagag accagagcaa atggggctca tcacgtgaaa    68040
ctcatctgga actctagcag gttcttttat atatatatat atatatatat atatatatat    68100
atatatatat atatatatat ttttattat tatactttaa gttctagggt acatgtgcac    68160
aacatgcagg tttgttacat atgtatacat gtgccatgtt ggtgtgctgc acccattaat    68220
tcatcattta cattaggtat atctcctaat gctatccctc cccactcccc caccccaca    68280 acaggcccca gtgtgtgatg ttccccttcc tgtgtccaag tgttctcatt gttcaattcc    68340
cacctacgag tgagaacatg ctgtgtttgg ttttttttgtc cttgcgatag tttgctgaga    68400
atgatggttt ccagcttcat ccatgtccct acaaaggaca tgaactcatc attttttatg    68460
gctgcatagt attccatggt gtatatgtgc cacattttct taatccagtc tatcattgtt    68520
ggacatttgg gttggttcca agtctttgct attgtgaata gtgccgcaat aaacatacgt    68580
gtgcatgtgt ctttataaca gcatgattta tattcctttg gttatatacc cagtaatgag    68640
atggctgggt caaatggtat ttctagttct agatccctga ggaatcgcca cactgtcttc    68700
cacaatggtt gaactagttt acagtcctac caacagtgta aaagtgttcc tatttctcca    68760
catcctctcc agcagctgtt gtttcctgac ttttttaatga tcgccattct aactggtgtg    68820
agatgttatc tcatggtggt tttgatttgc atttctctga tggccagtga tgatgagcat    68880
tttttcacgt gtctgttggc gaactctagc agcttctttt cacaagttca tggagagagg    68940
tttcccactg agggaatcac atctgtctga tcaaagagg cttgggaaat ggctctcctg    69000
ttcattccct gaaaacctct gatggaacca ctgccactgt ggcagcccca gcactggcac    69060
```

```
cccagccatg attggtgccc cagccacatc tctgctgtga gccccagagc cctggttaat    69120
taatcatcca cgtgttgatg gggagaggcc cattcacaaa agcgacataa agcccaggga    69180
gacgtggccg tggcaagaag ggtgtgggac tacattccgc ccccaactga gagattcaga    69240
aaccagaaaa aaatggaaaa acatactgtg ctcttgggtg ggaaaactaa atatcatgaa    69300
gggagcaatt tttatagttt tggcctataa tacaattcca gccgaaatcc cagtggaact    69360
ttgagaattt gcaggaaaaa aaaaaatgtc taaagtacat ctggaagaca aacttacaag    69420
aaggtcaaat aattttgaaa agaaaatga tatctaagcc cacctagaga ataagacttg    69480
agatccaaag ctaaatcagg aggctctagc aaaattgaca gataagcagg acagagtgca    69540
tggtgcattc acctggggaa gagggcagat tggtctacaa ataggcctgg gtccactgac    69600
tttagctgtt atatttgggg agaaactttt caacctcact ccatcttaaa cctaaaaata    69660
ttccagatga attaataaat ataaaaaatt agaccactaa aaatgtagaa gaaaatggat    69720
gatctttcta taccatagag caatggaata aatcacaaag gaaaacagat ttgactatat    69780
aaaacttaaa ccctgcccat caaaaaccat cagaaaccaa aataaaaggc aaccaactgg    69840
agaagatagt tgccacaaat atgatcaagg gttaatgtta ttcataaatt aagagcccac    69900
acaagtcatt agaataagca ctgagacctg aacagacaag caaaaagaat gagagtgggt    69960
cggcgcggcg gctcatgcct gtaatcccag cactttggaa ggctgaagca ggcggatcac    70020
ttgatcccag gagttccaac accagcctga gcaacatggt gaaaccctgc tctacaaaa    70080 gtcataaata ttagccgggt gtgatggcac acgcctgtag tcccagctac tcaggaggct    70140
gaggtgggtg gatcacttga gcccggggagg tagagtctgc agtgagccaa gatcacaccg    70200
ctgcactcca gctggagcaa cagagtgaga ccctgactta aagaaaaaa aaaaaaaaag    70260 aggagaaaaa tgctgatctc actagtaatt aaaacatcag gccaggcgca gtggctcaca    70320
cctttaatcc cagcactctg ggaggctgag gcaggcagat cacttgagat caggagttct    70380
agaccagctt ggccaacatg gtgaaatccc gtctctacaa aaaatacaaa aattcgccaa    70440
gcgtggtggc acatgcctgt gatcccagct actcgggagg ctgagacagg agaattgctt    70500
gaacacggga ggcagaggtt gcagtaagct gagatcgtac cattccagtc cagcctgggc    70560
tacagagcga gactctgtcc cagaaaaaat aaaacatca catatttaaa caactctagg    70620
atatcattta aaaaaacatt aatagactgt ttttagagc acttttaggt tcacagtgaa    70680
actgagtgga aggtacagag acttcccgta tgttccctgc cctccacgta cagcctcccc    70740
cactgccaac gtcctgcacc agagtggtac acttgttaca accaatgaat cctcattaac    70800
atatcattat cacccaagtt catagtttac attagtaaaa catcatcttt catctataag    70860
cacaaaaatt ttttggcatt tatttaggtg tatgattaac tcagtgttga caagactcac    70920
acttcatacc cacttgcact gcatctgaga agcaattggt gtctacagcc gctacaccct    70980
caacaagccc gatcttgttt gaaaagcaat tggtgatgct tctcaaaatt ctatggacaa    71040
agtcagccgg gcatggtggc tcatgcctgt aatccctaaa ctttgggagg ccgaggcagg    71100
cagatcacct gaggtctggt gaaaccctgt ctctactaaa aatgcaaaaa ttacccaggc    71160
atggtggctg gggcctgtaa tcccagctac tcggaggct gaggcaggag aatcgcttga    71220
agcaaggagg cggaggtttc agtgagccaa gattgcacca ctgcactcca gcctgggtga    71280
caagagtgaa actccatcta aaaaaaaaa attatgagca aagttttca aaagatatt    71340 taatgcaact ttatttgtaa tattggaaca tctgaggcca tttcagtgct aactattagg    71400
```

```
ggatggttag gaaaatatgg tacatatgtg gaaaggaaca tttggtagtt agtgcccctg   71460
atgtttacaa aggcttttag tgaccaacaa atgctcatgc tataatctta tgtgaaaaaa   71520
gcaagtagca taattgcaac tatattttta atgcatagaa taaaaggcta gaaggaaata   71580
tcacagatcc ttgacataca ttcccaaacc tttgtaaatc cgcggattca tgaaaacaga   71640
cacatttgca caagtgcctg atcttttctg ttatacattc attagaagtc aagccctggt   71700
gccacaaagt atctgccttt tcaaatgtga tcagaatgtt ctcttttgct tcaaggccat   71760
ttttcacgaa gcagtggcat ttttgcctct tcatcagagt caccgtgtgc cctggaggac   71820
tgagaacagc agagccgttt taggatggga cagggcagcc aggaggattg gctcactcc    71880 ctactgagtg cctcactccc gtacagcccc catagaggaa gaggggttca aatttattcc   71940
tcagccagat ggcatgtgcc gcctgtcctg gaatttcaca tcacttatga tggaccaaaa   72000
ttccaaaagc tgaatccatg attgtcaaag tctggtatgg caggatgtca acagtaatcg   72060
tttctgggca gagggatgat tttctcttcc catcttgctt tgtataaata catttctat    72120 aataaggttg tattactttt ctcatcaaga aatagcaaag tactgtttta ctcaaaatat   72180
gaatagagcc aggcatggtg gcagcttatg cctgtaatcc caacactttg agaggcggat   72240
atgggaggat cactttagcc caggagtttg agaccagcct gggcaacata gtgagacccc   72300
cgtccccact cccccaaaga aaacccacaa agcatttatc ctggattatt cacaggggcc   72360
aaaaaaaaaa aaaaaaattc aggcctccta tagccatgag ctacgaatat gaaaatatgc   72420
aaatgtgtaa gaaaagccag cacatccgat ttttactttt actttcacac ctctgtccac   72480
catgttccaa gagaagaaac ttggtcattg aaaggaatag atcaaatcca agaacaaaa    72540 ccactgtgct cattaaactt cttagtgttc acaaagcttt agctgcaggt tgaatggggc   72600
aacccgaatt ggctggctca cctgggctgc agggagcaga gatcgcgaca ctgcactcca   72660
gcctgggcaa caaagcgaga ctctatctca aaaaaaaaaa agttcataaa ttcaaagtta   72720
tgaattattt ttaaaataat aataatttac aataaagatg aggacaaagt gtgagtaaat   72780
ggtggtttct atccagctct gttgagctga agtggcatct ccctgctggg cttttgggg    72840 aagaagggtg tgtgttgctc ttcagatccc aagcctcatg cccctactgg gcccgtgggg   72900
gtgcttctca gcccaccagg agagccaccg ttggaacaca cacgtggggg acctggtggg   72960
tgccggtgtg gtgaatgggg gccacagcct gactccagga agccagcaaa ctcggagctg   73020
gaggagtcag gacaccccg atgagtcaag agttggtttt gctgccagtt gacatctgat    73080
tgaaccatct cttcacttct ccgtgcctca ctttccttac cagacaggct ctgctgatgc   73140
tgtccctctc ctgttcagtc gtgccctcac cgttaaagag aaagagcaaa ctgctgggca   73200
gcagcattga ttttttttaat gaagtggaaa gagagctggg aataacaagt cgggcccacc   73260
tcacctgcct cacctggtgg gtttatttgt tttgttttt tttttttgtt ttgagacaga    73320
gtttcaccct gtcacccagg ctggagtgca gtggtgtaat ctcagctcac tgcaacctcc   73380
acctgccagg ttcaattgat tctcctgcct cagcctcccc agtagctggg attacaggca   73440
cctgccacat gcctggctaa ttattgtatt tttagtagag atggggtttt accatgttgg   73500
ccaggctggt ctcgatcccc tgacctcagg tgatccaccc acctcggcct cccaaagtgc   73560
tgagatcaca ggcgtgagcc accatgcctg gccgtcacct ggtggtgttg aatatgaact   73620
gctgcggtgt tggtaaatta agcaagcaga tagatgtaaa taacgcttgg gcaggaatat   73680
ggagcacggg atgaggatgg gcggccaact gttagagagg gtagcaggga ggctgagatc   73740
tgcctgccat gaactgggag gagaggctcc tctctctctt caccccccact ctgcccccca   73800
```

```
acactcctca gaacttatcc tctcctcttc tttccccagg tgaactttga accaggatgg   73860
ctgagccccg ccaggagttc gaagtgatgg aagatcacgc tgggacgtac ggggttgggggg  73920 acaggaaaga tcagggggc tacaccatgc accaagacca agagggtgac acggacgctg    73980
gcctgaaagg ttagtggaca gccatgcaca gcaggcccag atcactgcaa gccaaggggt   74040
ggcgggaaca gtttgcatcc agaattgcaa agaaatttta aatacattat tgtcttagac   74100
tgtcagtaaa gtaaagcctc attaatttga gtgggccaag ataactcaag cagtgagata   74160
atggccagac acgtggctc acgcctgtaa tcccagcact ttggaaggcc caggcaggag    74220
gatcccttga ggccaggaat ttgagaccgg cctgggcaac atagcaagac cccgtctcta   74280
aaataattta aaaattagcc aggtgttgtg gtgcatgtct atagtcctag ctactcagga   74340
tgctgaggca aaggatcac ttgagcccag gagttcaagg ttgcagtaag ctgtgattat    74400
aaaactgcac tccagcctga gcaacagagc aagaccctgt caaaaaaaaa agaaaagaaa   74460
aaagaaagaa agaaatttac cttgagttac ccacatgagt gaatgtaggg acagagattt   74520
tagggcctta acaatctctc aaatacaggg tactttttga ggcattagcc acacctgtta   74580
gcttataaat cagtggtatt gattagcatg taaaatatgt gactttaaac attgcttttt   74640
atctcttact tagatcaggc ctgagtggcc tctctttagc aagagttggt tagccctggg   74700
attcttactg tagccacatt aataaacaac atcgacttct aaacattcta taataccatc   74760
ttttggccaa attgacttcg cctcttcctc tctctttcca aatgaaatgt gtttcatttc   74820
actgtcagac cacatggttg gggacccccac agagcacaca gccctccctc tgccttccca   74880
tgctggccct tcacccactg ctggagtgcc aggttggtcc aagggttgga ccaagttgtc   74940
tgaggttgtc tcaaggttgg tcgaggctgt ctccgcgctg ggttgtgcta caaggagccc   75000 ttcttttccat gggtgtggct ggcagtgagt gctcacagca acagcccaca gtgcagcccg   75060
agggcaggat ggactcagtc cctgcctcca tacccatttc taaggaggca aaatggcaaa   75120
cactctactt ttctctttta atgctaaaaa taagaaaaca ccttgcagcc cagggtatgg   75180
gtagtgcatg gaagccgtgg agttgtgagg tgggaagtga cctctgctgg atatgtctat   75240
tcaggaagat tgctggagtg ggtggggtct ctggaggtc ccctgagtgt gggaagctgg    75300
gaccaccagc tttctcgcac agggagtggc catcccagct tggagaggtt ccaggactgg   75360
ttgggaggca cgtttcagat ttctatctgt tgaatcagcg aagatattgg attatgagga   75420
atttgggaat taggaaagtg ggtgcaggtg ggttgggggt aggtgaagga agacatgggc   75480
gtattggggg agcaggggct gctcagaggt gttccagaag ctctgggtga ggaggtgaga   75540
gggaccgggg aatgcagctc ggcccagcct ccctgcctga ggtcagccat cacgtggtga   75600
tggcaagatg gaaatgtgct ttctgactgc tccagccagt gctgccagat tcagctcccc   75660
agggagggca cctgagaggc tccaagccag gagatctgtt ttctcctttg tttttgtttt    75720
ttttgttttg ttttgtttta ttatacttta agttctaggg tacatgtgca caacgtgcag   75780
gtttgttaca tatgtataca tgtgccatgt tggtgtgctg cacccatcaa cttgtcattt   75840
acattaggta tatctcctaa tgctatccct ccccccctccc cccacccccct gttttctcct   75900 ttgaatcctt cttagaggcc gggcgcggtg gctcacgcct gtaatcccag cactttggga   75960
ggctgcggca ggaggattgc ttgagcccag gagttccaga ccagcctggg caacatagtg   76020
agacctcgtc tctacagata ataattttaa aaattatccg ggcatagtgg catgcaccta   76080
tagtcccagc tactcaagag gcagaggcag gaggatcact tgagcccagg aggcggaggt   76140
```

-continued

| | |
|---|---|
| tgccgtgagc caagatccca ccactgcact ccagcctggg cgacagagac ccccatgtca | 76200 |
| aataataata ataataaata aatccttctc agtcccttcc tcactgtgtc ccctccact | 76260 |
| gaattttcc acctcctctc ccacttcccc cactcccgct ttccctctcc ttctctcccc | 76320 |
| actccatctt tttctttctc tgctgtttct cgtccctccc tcctctccat cccacaacac | 76380 |
| tgcctaccct gtccctgccc caccctggtg ctcaggatgt gtgaagtgag gggtggtagc | 76440 |
| ccccaagacc tcaaccccga aggttagcct gttgaaacca ctttctccca gctgcccccc | 76500 |
| tggcagttgg tgctgctggg ggaaactggg attgggggcc agattttgcc tcttttcctg | 76560 |
| acaaagagag atgaagagtt ctctcaccag gtgcctggga ctggggtgtg ggtgtcccag | 76620 |
| cctatcccag cgcatctgtt ctgcatcatg attaatagtg ctgctttcag ccgggcgcgg | 76680 |
| tggctcacac ctgtaatccc agcactttgg gaggctaagg tgggcagatc acaaggtcag | 76740 |
| gagttcgaga ccagcctggc caacatggtg aaacctcgtc tctactaaaa atacaaaaat | 76800 |
| taaccaggtg tggtggtggg tgcctgtagt cccagctact tgggaggctg aggcaggaga | 76860 |
| atcacttgaa tctgggaagc agaggttgca gtgagccaag atcgtgccac tgcactccag | 76920 |
| cctgggtgac agagtgagac tccgtcctaa aaaaaaagga gttttgctct gtcgcccagg | 76980 |
| ctggagtgta gtggcgccat ctcggctcac cgcaacctgc gcctcccggg tgcaagcgat | 77040 |
| tctcctgcct cagcctccca gtagctagg attacaggcg cctaccacca cgcctggcca | 77100 |
| gttcttgtat ttttagaaga gacggggttt caccctgttg gccaggctcg tctgggactc | 77160 |
| ctgacctcag gtaatccgcc cacctcagcc tcccaaagtg ctgggattgc aggcatgagc | 77220 |
| caccgtgccc agtcaactcc ttctcaaaaa aaaaaaaata gtgctgcttt ctctttcaag | 77280 |
| tgtcctgatt tgggtgatag taaatgccac tctacttata agggatctac ctcagaatgc | 77340 |
| taattgggac attttgtag cactctactg ttggcagcag gtgatgctca caacagcccg | 77400 |
| tgagggtgga tgacgtccgc ttcacagatg acaaggagc ctcatgctca gaccgtgggc | 77460 |
| tgccagagca ggtccatggc tgcagcccca catggaccat atttcccct tgtcactctt | 77520 |
| tccaccaagc tcccttggaa cttcagttat taagctctct tgggtggaat ccaagttaga | 77580 |
| atcacaaacat gtgcctcata tggattgtgc cagtgaaaaa tgacattcta tttagaggca | 77640 |
| gggcagcctg gcttagagtc agtttaaaat atgtattatg ctgcaacaaa tgtaccatga | 77700 |
| tcctgtaaga tgttcacaac aagggaactg gatgtgggt atactgtctg tactaacttc | 77760 |
| acaagttttc tgtaaatcta aaactgttcc aaaataacaa gttcgtttaa aattaactcc | 77820 |
| aggagaccag gtacggtagc taatgcctat aatcccagca cttcggaagg ctgaggcagg | 77880 |
| tggattgctt gagcccagga gtttgagaca agcctgggca acatggtgaa atcctgtctc | 77940 |
| taaaaaaat cacaaaaatt agccaggtgt ggtggcgcat tcctgtagtc ccagctactt | 78000 |
| gcggggctga ggtgggagaa tcatctgagc ccaggagttt gaggctgcag tgagctgtga | 78060 |
| ttgtaccact gcactccaac ctgggcaaca gagcaagacc ctgtctcaaa aacaaaaat | 78120 |
| gaaataaagt ccaggaaaga agtaggtttt accactctta ttttctgaag agaaaactaa | 78180 |
| atttaatgtg taaagtgagg acaagttcac caagttagtg tttgagttgc ctaaaatatg | 78240 |
| tttgctaaaa ctattcaaag ctttcacata aacatgatc agaagttcta tgccaaaaca | 78300 |
| tatgtgtgtg tatatatata tgcactatat atactgtata taaaaatgca aaatctaaat | 78360 |
| tgccaacctt ttagaaattg ctctgaaagg aaagcatttc aagataattt gcttacccaa | 78420 |
| agaatatact ttccaagaaa gcaagtaata cttaaggtgt tcataatcct catcaaatta | 78480 |
| attcttgcta ctgaaagctt acaaggagct gttttgatgt cgggtgtgac aggtttgact | 78540 |

```
tggcagaagg tgtcacttta ctaacaacat tttaaataag tgacagaaga caagaaacta   78600
cacgttaaat gccagaacaa agagtgtcta agtggatgct aagagttgaa atatggctgg   78660
atacctgccc aagagagctg aaaagtagat gaaagttggt tacctataaa ctagtgcacc   78720
ctaatgaatt aaaaggtgtt gatgagttaa cttgttatgc cttccagata agacatgcaa   78780
atggggcttc ttcctccttc actacttcca agggatttaa caaggagacc aatgcaaatg   78840
ataaggactg tagggctcaa gctggggaca gattggggaa aggggacca tcatgcccat    78900 atagatgtcc ctgtgccctg gcagtcaagg ctgctgaaaa ataacaaaac ccagaagtct   78960
gcgtgatgct gcctctccat ttgtccaaag ccttcttgcg gcagtttgca ggcttttgca   79020
aaagctccag gaccaaggag ctatgttcat gctggaagct tgttcaggat tagctgttct   79080
ttgtgggatg ggtgcagcca gggccaggtg tccaggaca gtgttttaac aaagggcatg    79140
aggtgtctga tctcacagtg gaactccact tgccttttt tcatcttctc attctgcttc    79200
atgcacagaa ccagccccat cctgaaactg actctaaatt actcccgccc caggtggagt   79260
gcctttctcg gagttcaaca gagccttcct gtcgcccaag ggacaactcc actgaatgcc   79320
caagccacac ccaaaaccta acaagtaaaa accaaattct gtgctccccc atcctgggcc   79380
attcctggtt tctctactgc tgttggtgat accaccatca gcttgtccat catgaccctg   79440
gccagttcct cccacaaccc tccacagcac ccagggacct cacctccatt ccatccgaca   79500
cagatctcct caccacaaac cttggttttg caacagcagc catgagacct ttacaccctc   79560
cgcccttcat cctgtccccc actgaggccc cagagccatt ccttaaagca gcgcgccaca   79620
aactataacc cacaagccaa ttctggtacc cagcctgttt tgcacagcca gtgaactgac   79680
aatgatcttt tcatacagcc agaaaaacaa aacaaaacaa aaacaacaa aaaaaaccc     79740 caccattctg agcatgtgac ttccatgttc aagatgtctc atgttcagaa aggccctgg    79800 aaaaggagga aggggagctg ggcacaaagg gagaccctct cagctgagct cctcccatcc   79860
agacattttc ctggacttcc tatccaatga cttcccttag cttcttatca gccacccctg   79920
tctgcccagg aggctggaag atgtggcctt ttaactgggc acagtctgt cctctatcat    79980 atcagggctc tgttcccaag gagggtagag agaatggaca ccaggtggac cctcagcagt   80040
ctgtgccaca gagggagtgt ttgcaatttc cagactaaaa gtccccatgt gcttgacggg   80100
gtatgtgact acaacgtgat gcttgacttt tcctcatatg accagagcca ctttgtccat   80160
ctggtacaat gtcagctatc tgctaggggc cctccaggat tcccagtcaa ttccatatct   80220
gcatcaccac cattggcact aaataaaata aaatactcaa gttcctgctg gtgagcatga   80280
gcagtgctac actgggccct tcaaccaagg tgacatgata atgactgaaa ataatcactg   80340
ccacttattg gggacgtctc atctgccagg catggtacaa agtgctttaa ataagcattc   80400
aacaatttca tgctgacaga agccctgtga gccagtggag ctactactat gcccattata   80460 cagggagaa aactgaggca gagagaggtt aggtaattcg ctcagcctca cacaaccaat    80520
aggtggtgga gccaggattt gggcccatc tgcctgactc tctagaggct ctatcttcca    80580
gtcttccaga gttgagtcta agccatgaat aggacaatta gacagcagag gaaacccatt   80640
cagccaccat gtgcatgaag agtaaggaat ttctgtcata cagaggggag tgaattcact   80700
gagctgagag ctgaggaacc attgatctga tggctgagac accactggga agactggaga   80760
ggcttttctg ggcatgcagt gccaggcaca ggaggagctg agggaagatg actaagaggt   80820
actggcaaag aattcagaaa ttctgatgga agctttacat gttaccatca catccatcca   80880
```

```
tctatccacc catccatcca cccatatctt cctccctcca cccaatcatg catacatcca    80940
gtcatctata caccacccac ccacccatcc atccatccat ccatcccttc atccatccca    81000
tcatccatcc aattatacat acatccaatc atatatctgt acataatcca ttcttccctc    81060
ggttcatcca tccatccatt catccatcca tccacccatc ccttccttca tccttcctat    81120
catccatcca atcatatatc tgtacataat ccattcttcc ctcggttcat ccatccatcc    81180
attcatccat ccatccaccc atcccttcct tcatccttcc tatcatccat ccaatcatac    81240
atatatccaa tcatacatct gcacatcacc agctcatcca tctatccatt tatccatcca    81300
tccttccttc catccatcat tcatccatca tacatacatc taaccataca tctctacatc    81360
attcattctt ccatcgattc atccaattat ccatcattcc ttcctccatc catcccatta    81420
tccatttgat catacatata tcatctatac atcatccatt catccatcca tccatccatc    81480
cacccatatc ttcatccaat caatcataca tacatcgaat catctacaca tcacccatcc    81540
atccatccat ccattcatct atccacccat ccatccatcc atccatccat tcatctatcc    81600
acccatccat ccatccatcc atccatccat ccatgtaacc atccagtcat atatccaatt    81660
acacatccat ccagttatac attcatacat gcatctaatc attcaattat acatacacac    81720
atccatataa ttctacatcc aattatacct ccatccaatt acacattcat acacccacct    81780
aataaattat taattcatat atccatccat ataattatac atcaattata catccatcta    81840
atcattcagt aattcaccca ccatccagtc atctatccaa taatacattc atccaatcat    81900
ccatccatcc atccacccat tcatccatcc atccgtccgt ccacccatca tggtatgagc    81960
catgatttac cacgatggtc ccctgtggac agcccaggtg gggcagaact gaagggaagc    82020
ccagggctgc ccccataaac atttgcctcc tttacatgga tgagaactag atccacatgt    82080
ataaatcctc atgatttgaa ggtgctttta ccaacattca ctcatgggat tctcccagga    82140
gctctaggag gaggcaggta gagttgaggt catctcacgc attttacaga tgaggaaacg    82200
gaggccctga gaggcaggtc caaggccacc tgaccagaaa gaagtggaac tgggacttga    82260
acccagccat cttgcccctt ggtcccatgc tctctagcct gtaactcctg cttcctggtg    82320
gggcatctcc aggaggaccc tatcggctgg ccatgggcct gccctggagt cttttgctct    82380
gtgtggccat ccttcctccc tcaggagagt gtgtgctccc agagcacagg ctgtatcttc    82440
tgagcatttt gtcccttccc agtacctagc actcagctct gtatacattg ggctctcaag    82500
aattctcaac cttccagagt gtaaggcctt gacctgctca gccctggata ctgcatgatg    82560
cattgataag cccataaaat aaccagggca gattgactcc cagtggccaa agtgccacag    82620
ggaagggaca attcagccct tctaggagga ggaggaggta gttttctcat ttctattaag    82680
gcaacaaaag ctgccttact aaggacattc ttggtggagg gcgtgactgt caaccactgt    82740
gatcatttgg gcctctcttg cccaggcttc ccattctgaa aggacagttt tattgtaggt    82800
acacatggct gccatttcaa atgtaactca cagcttgtcc atcagtcctt ggaggtcttt    82860
ctatgaaagg agcttggtgg cgtccaaaca ccacccaatg tccacttaga agtaagcacc    82920
gtgtctgccc tgagctgact ccttttccaa ggaaggggtt ggatcgctga gtgttttcc     82980 aggtgtctac ttgttgttaa ttaatagcaa tgacaaagca gaaggttcat gcgtagctcg    83040
gctttctggt atttgctgcc cgttgaccaa tggaagataa acctttgcct caggtggcac    83100
cactagctgg ttaagaggca ctttgtcctt tcacccagga gcaaacgcac atcacctgtg    83160
tcctcatctg atgccctggg tgtggggcac agtcgtgttg gcaggagggg aggtggggtt    83220
ggtccccttt gtgggtttgt tgcgaggccg tgttccagct gttttccacag ggagcgattt    83280
```

```
tcagctccac aggacactgc tccccagttc ctcctgagaa caaaagggg cgctggggag    83340
aggccaccgt tctgagggct cactgtatgt gttccagaat ctcccctgca gaccccact    83400
gaggacggat ctgaggaacc gggctctgaa acctctgatg ctaagagcac tccaacagcg    83460
gaaggtgggc cccccttcag acgcccctc catgcctcca gcctgtgctt agccgtgctt    83520
tgagcctccc tcctggctgc atctgctgct cccctggct gagagatgtg ctcactcctt    83580
cggtgctttg caggacagcg tggtgggagc tgagccttgc gtcgatgcct tgcttgctgg    83640
tgctgagtgt gggcaccttc atcccgtgtg tgctctggag gcagccaccc ttggacagtc    83700
ccgcgcacag ctccacaaag ccccgctcca tacgattgtc ctcccacacc ccttcaaaa    83760
gccccctcct ctctctttct caggggcca gtaggtccca gagcagccat ttggctgagg    83820
gaaggggcag gtcagtggac atctgatctt ggtttagtat ccttcatttt gggggctctg    83880
ggtgtggcct gggcctctgg actttggcca cggtgtttgt tccagcccctt ctcctaacct    83940
gtcctttcca gacactcggc atctaggtta ttagcacctc gcatactttc tgacatgctc    84000
ctcagtcctg attttgacca tcttctcttg cttcccatct gtgtcagtca agactgcatt    84060
tggctgtaag aaacagaaac cccaactaac tgtggcattt acatgaagag gtttactttt    84120
ctcacataat cagatgtcta gacttggcca gcacctcaag ggtcattgat gctctcctgt    84180
ctttattttc tgtcatcttt agtggttgga ttgttgcctc atggttacaa agtggctgct    84240
gcacttccag gcatcacatc tgcctttgaa gcaggaacaa gttgcaaagt aaagtggcca    84300
aaagggccct gaaactaaat gtgtcccctt aggaaagcag gagttttctt gcaagtggca    84360
atcttctgct tatgtctcat tggccagagc tgggtcttac ggccaccct tgctgcgagc    84420
aaggctggga cattgagcat tttgccgtcc aacctcttta gcagaataaa ccaaggggga    84480
agaacgttaa tagtggcttt tgagtcacta gttggcagta tctgcccctc tatctttcca    84540
tcctccccat ggagtttcaa ggttcctttc tcagtacttc ttcaggctct gcacgttcat    84600
ttggatcttg tgtcttgggg tgaaaaactg gcccaagtgt ctccccaagc atccacctt    84660
ggattaattt ggaaaatggc tgtcaagtgc ccgcctcttg cttggtataa tgctacagct    84720
ttagaggacg cagcaggcat gggccttgcc gctgaggttc ttagcctcat gagaatatcc    84780
agatcagatt ctcttggctc cttcttagag ccagtgatgc aagacacttc ctgctcatct    84840
tgtcgggacg gttttacaag ttgcctgcca tcctgagaaa gtctacaaaa cgatgccaga    84900
cctcatgcca gcttcccaag ccttgactct cagtgctccc tcaacaggat tctggaagaa    84960
tctcccaaac aagtcgcaat gccctctgga ccctgtgcag gcatgagact caagagcatt    85020
ggctcccacc cctggtggag ggaacactgc tggggctggg atcttgcctg gttgctccgc    85080
ctgcacccaa gacaaccata attaaaatgt ccttcattga acttggaaag ccttcaaagc    85140
tgacaactcc ttatgtgtac ccggaaaggc ctgggagtgt gccagggcat tgctcgggag    85200
ggacgctgat ttggaagcat ttacctgatg agagactgac agcagctcct ggtagccgag    85260
ctttccctcc tgcctctgct gtgaaggtgg accatccaa cagtcaaatg cctgactctg    85320
gacaggagcg gacctattta ttgccatgca agggactctg cacttttgaa ttgtgggtca    85380
tgggcttgga tttaggggtt agagctggga gaagtcttgg aagtcaccta gagatgacac    85440
tgccattttg cagatgagga aaccgtccaa tcaaaatgga ccaaggactt gcccaaagcc    85500
tcacagcaaa accataggcc cccgcactaa ccccagagtc cctgtgctgt cttaaggatc    85560
atatagttgt aagcaatcat ctggttttca gtatttcttc tttaaaatg cctgggggcca    85620
```

```
tgcccagcag tctgtttcac tgcagcgttt acacagggct gccgggcttt cctggtggat    85680
gagctgggcg gttcatgagc cagaaccact cagcagcatg tcagtgtgct tcctggggag    85740
ctggtagcag gggctccggg ccctacttca gggctgcttt ctggcatatg gctgatcccc    85800
tcctcactcc tcctccctgc attgctcctg cgcaagaagc aaaggtgagg ggctgggtat    85860
ggctcgtcct ggcccctcta aggtggatct cggtggtttc tagatgtgac agcaccctta    85920
gtggatgagg gagctcccgg caagcaggct gccgcgcagc cccacacgga gatcccagaa    85980
ggaaccacag gtgagggtaa gccccagaga cccccaggca gtcaaggccc tgctgggtgc    86040
cccagctgac ctgtgacaga agtgagggag ctttgcgtgt ttatcctcct gtggggcagg    86100
aacatgggtg gattctggct cctgggaatc ttgggttgtg agtagctcga tgccttggtg    86160
ctcagttacc tccctggctg cctgccagcc tctcagagca tttagggcct tctggacttc    86220
tagatgctcc tcatcttgcc tcagtcagcg cgtcagttcc agagacttct ctgcagggtt    86280
ttctggggca ggtggtggca gacccgtgcc ttcttgacac ctgaggtcag tccaccctcc    86340
tgctcagact gcccagcaca gggtcacctc ccaaggggtg gaccccaaga tcacctgagc    86400
gcacagaggg tgcagatgac tggaccacac cttttggtga tcttaatgag gtggtcccag    86460
aggagctcag acatgcaatc tagcatccag ttctgggact ctgtctcctt ttcaaacgta    86520
ttcatgtaga acaggcatga cgagaatgcc ttgtcaacat gggtgatggg gaatcaatca    86580
gacagggcgc cgggctcaag gctgcagtca cccaagagtg gctcagccca ccaggcccta    86640
ggaaacgcct gcacagcctg gagctcctgg agtcatttcc ttcatgtctt cttcactgca    86700
cttacgtaaa gatgccagcc attggtttgg tgatttggag ggtgcccagt tgcccaacaa    86760
gaaatgcaga agaggcctag ccaggatttc accagcagtg gagagtagag aagatgtggc    86820
cagaaaagag tttcctttcc ctcctaaaga tggtactccc tgcagctact ggggaagcct    86880
gcagcattct ctagggctct gtgtgttgag agcagcccca ccctggcccc ttctgagtgc    86940
atttctgctt tgtgacttga tccgtgaagt ccccctgagat gggcagaggg gatgtcctcg    87000
aagctggggc agagcctcat ccttgaacgt gaaggacgtt tgaagactgt ggcatgatca    87060
caggatgaga tcacagggaa cttgagtttc tctcctcctc tcccttcaca gttatttcac    87120
tgagggaaat ccctcccctg cccagaatga aaactctagc caactcttga cttttccatc    87180
actccaaagt agttgaaagt acattagtct ccacagtggc aaaacagtgt gcaaaagcta    87240
aataattaga acagccagtc ccatgtgaca gtcaaagctt ctaactccat tcaaagttgc    87300
agccattccc ctcgagggct ggcagggagg ggaggggtaa gagaaacagg aaggttctta    87360
ctgagttggt cctggtgtga gctgcgtcac actccctgca gaggtttcaa ggagactctc    87420
tctctctctg tctccatggg gaccttattt gaattcttct actcttaccc cagcctgcca    87480
tctccagcta tcctcccctg aagagccctt ctgctgcgct ggattctggt ggccatgtca    87540
tctcctcggc cccgtgggag tctgaagatc tggctgcagc ctcacctctg aggtcctgct    87600
agttgccacc tcttaaacat gatctgaggc tcccatgcac tctgacctgt gcccacatgg    87660
ggcccacggg aaaacgctg gcaagcaaac tgtgggtgtg cagacggttc tcagggctgc    87720
agcacctgtc ctttgctctg cccccaaagc aaggccagcc catcttccat cctctagtgt    87780
tccttggtgg ggccctgacc acagtccacc aggtccctaa ccagagggga cacacaccag    87840
gtgtcctcaa tgtattgcct tgaaacagtt gtgctgggac tgtgatgggg ggtggccatg    87900
tagccacccc caccaccccc aagccactct ctccaaggaa atcctcctaa agatcccttt    87960
acatcctcca tgtggtgggg aggttctaga gttgggtgca tgtgtcttca gctactgaca    88020
```

```
atgcagacct tagttggcac ctcgctctgg cctatcctgt ttgctgttct tggcgctcca    88080
gtgaaactcc ccatgggcca tccagttggg gtgcagtgtg gccacccct tgcaggttcc     88140
tgccttgctg gagagcacag ggccctcctg gctcttgtaa aacactcccc atggtacaga    88200
gaggccagca gtgatgtgag gcccaacctc cctccatggt gttcccaagc agctccctt     88260
ctggggtcaa ggggtggcaa agacagtgca gcgtccaatt tctgactcaa gccgggcctg    88320
gctatcgcag ctctgcactg tgtgtgacag caaggcaact cacccagtgc cgtggcagtg    88380
accgtgtccg aggaagcctc ctcacaccct ctgtctcaag gactctggca tttagctgga    88440
cttgctgtag ctctgagcct ttctgccatt gccatcacct tgtcagaaac tcaggccgaa    88500
tctgcactca gagttgtgcc caggcagttg agccaacact tgctcagcga tattgtcaca    88560
tgacaaggca ctgtcaccac tgggcatcgt gggtagcgca gtgtcggctg gatggacccg    88620
gagggtgtct gtgtcatgct agtgctagtg atgggagccc cgtgagccca ttgcccgccc    88680
tcccatgccc tcagcagctg cctggggaca gccaatggcc tgggtgtttc tgaggctacc    88740
acatggcttc caggaaactc gagaaccttt ctctcccttg cctacactct tcacacaggc    88800
ctgtgctggc cagcggtggg gatccggcat tcctatctta ggtgcagaga gtgactgact    88860
cattgcaggc ctgggagata agactgatgg cccagccagc aagatgtatg gatttctcag    88920
aggcagtggc ctctgtcatt gtcctcagga aatgctggtg attctggtgg cctgaggtca    88980
atgcatgtca acgtggccaa cttgccttat aaactttttt tctggacaat tgcgtgcact    89040
gtcctgtaac agtgtcctgt tgtttatgat gcagaaatag gtgttttaa agcctattga     89100
ttttggtact attaatgtgg tcaggaactt tctcagtctt tcttgtttgg ggtgagctgt    89160
ggcttcctaa acaggaaccc aagacacccc caaaagctgc tcaccagcac tgccagcctc    89220
cctcttacca gtagcaccc gttcaggaca ttctgcgaaa ggcatttgcc cagaagttgg     89280
gaggaaggaa atgtaacatt ttggggcacc taccatatgc caggcaccag gctaaacgtg    89340
ttcacacaaa ttctcttact aaccctcacc atccttctac aagacaaact agtatcttca    89400
tcttggggtt caagatgagg aaatggaggc tcagagaggt tgaatgaatg ccggtgcctg    89460
gatatgaacc ccatctgcct gactccgcaa cccaggcaaa gtctttcctt gaacttccca    89520
gcagccactg cttagacaca gcctccacaa ccatggctca gcagcaaatt gcttctctga    89580
cctcactcag cctgtgtgtc cttgttgagt gaggcattca ggaccctggt cccaaagtgg    89640
agaaagtctt tcctactagg tcatagctac acctgcatgt gggtgctgtg ccttttgttt    89700
agtgaacttt tatcaccagc atcctcagca atgacatttg cagagaagcc agagctgagg    89760
caccttggta ttcttgggat gtgactttcc tgaatgttta agggaaaatg cccgaaggta    89820
cagagagctt ggtttctagt aaacaataac tgtcttgctt ttacccccct tcatttgctg    89880
acacatacac cagctgaaga agcaggcatt ggagacaccc ccagcctgga agacgaagct    89940
gctggtcacg tgacccaagg tcagtgaact ggaattgcct gccatgactt gggggttggg    90000
gggagggaca tggggtgggc tctgccctga aaagatcatt tggacctgag ctctaattca    90060
caagtccagg agattttagg gagttggttc ttatcaaagg ttggctactc agatatagaa    90120
agagccctag tggttttttt ctaataccat ttctgggtaa ttcctaaggc atttagtgtt    90180
ctgaaagatg ctagccttgt ccagcctggg agttgagaat gaatgtctaa cagaaactct    90240
aggccgggcc tggtggctca cgcctctaat cccagcacta tggagaccc aggtgggcag     90300
atcacctgag gtcaggagtt tgagaccagc ctggccaaca tgtgaaatcc tgtctcacta    90360
```

```
caaataaaaa aattagccgg gtgtggtggt aggtgcctat aatcccagct actcaggagg    90420
ctgaggcagg acaatcgctc gaacccagga ggtggacgtt gcagtgagcc gagatcgcat    90480
cattgcactc cagcctgggc aacaaaagca aaactccgtc tcaaaaaaaa aaagaaact     90540 caaatatgtg tgacaggcga ttctcactgc aggctgccct gtggctgatc caggagcaag    90600
gccttaacca tgtcatcccc aagcgattgc ttgtaaactt tcttctgtgc agccttcaac    90660
ccttattatg attttcttct caggaaccaa actgctgtat tcaagaaagg cagctttgtg    90720
taatcattta tcataaatat cttaagaaaa atcctagaga ttcctaattt taggaaatgg    90780
gagacctatg gtactgatat aatgtgggct gggcttgttt tctgtcattt gctagataaa    90840
tgaacttgag agcctactgt aaaatgtgga agcttctaga ttgcagaagg gctggaaaga    90900
cactgttctt ttctcccgag tgatgggatc tgtccagtat ttagagctgc ctctgaggcc    90960
atctgattct aggagactct gcctcgttga ggatattttg aggcctaact acacattcct    91020
gcccccagag aggtcacagc ctatagcagg ctgatgtttc tcatgtcaca tggcacagaa    91080
aggcacattt tcgttctcag gctaacaaag agcttcaaaa actattagaa gggacagtgg    91140
ctataagaga agaacctcag tcaatgtgtg aaattaacta ggaacctggc tcctgtttct    91200
tttaggtcat gtttttcagc ttaggtaaaa ctagaggctt tgataaagca tgacctctag    91260
aaatcattgc ttttcataaa tggaagtggg tttgagtttt ttctactgat tgttagtgca    91320
ggtgatgtct acatgcccccc agaacatatt ccatgcaaca aaaaagccc aggtcaccgt    91380 ctttgctggg aacttgactt ttgtgctcac tgaattttaa gctttctgac agcagcctgg    91440
aatcatggag ggataaagta cctattagta agatggaaaa aggtgtttca ggttggagct    91500
gcagtctgtt gagagtaagc tatgggaagg cctgtatacg aggggtggac ttttcttctg    91560
taagtgtcca gagaccaggc ctcctgaaga gggcatgggg gcttaactta cctggactac    91620
tgtgtttaca atactcattt atcttgaact cctcctaacc cctgagaatt gctacattta    91680
gtatttgctg agtacttcct agcatccag ggaatcaata gaacattctc ccaaccaggc    91740
tgggtgcggt ggctcatgtc tgtaatccca gcactttggg aggccaaggt aggcagatcc    91800
cttgaggcca ggagtgcaag actagcctgg ctgacatggt gaaacccgt ctttactaaa    91860 aatacaaaag ttagccaggc atggtggtac acacctgtaa tcccagctac atgggaggag    91920
taggaggcag gagaattgct tgaacctggg aggtggaggt tgctgtgagc cgagatcatg    91980
ccactgcact ccagcctggg cgacagagtg agtgagactc tgtttaaaaa aaaaaaaaa    92040 aagaacattc tcctaacctg gcttcttcct ccaggggtgt aattaatcat gtcagtttcc    92100
tcattgatac acacacacac acactacaat cctgtatcca ttacttttca aggtacattt    92160
actatttacg tttggggtcc ttgtctcttt tttaatagtg tttcttaaag tcttgtatta    92220
tatcagagta cagtaacatc ccagtcaaga gcactctagt aagctctagg aggaaagcga    92280
cttccggaag gcagtggaga cctgtcctgt tggggcagca tagggcagc ccctgcctct    92340 ggtcagttct ggcgctcagg ctcagggttg cctctgggct gttcttccca gagactgaca    92400
aagggctccc ataaggcacc tgcagagcct gtgagaagct gaagtcaatg ttttcctgac    92460
accagttgat ctgtgcagga tccattgatt taaccacctg ctgtgtggca tgcactgtgg    92520
tcgatgccag gaacaggaat tggaggggcc catgagcatg gccagtatca caggctggag    92580
gtgctgctgc gctctgaccg ggcctcttgg ggatgagccc atgtcaacca ccttgcctcc    92640 gatgggtcg ggcccacagg ttaccttgt gtgtccatga ccacacccttc ctccccgacc    92700 tcatccaaat ctctttcttt tccaagcccc tgaatccttc agggctgcag gttttgttta    92760
```

```
aagcagagct ggtgagttgc ataggttgtt gcattgggac tagatggggt gttcaaagag   92820
ttgggagtta aaaacataa agggtattta ttaggagaac caaggagtgt aattctcctg   92880
ttcttaatat gcggccaggt taatgaatgt cacgtgaatg aaccagaaaa aaatgaagtg   92940
tgcccttgat cagctgggtt ggtgtgcagc aagctgtgtg accaggggac agcagtggtc   93000
ctgagggccg tcactgtctg ccgtgcagag cccttcctcc cacggggcc tacctcacct    93060 gtgccaaggg cttgtctgtg gtcagtgacc tggatagatc tgaatggggc ttcttttcg    93120 aggagtctta tggcaggtct ctcagtaaag actccattct tgatgatcac acattttgga   93180 tttttccaaat ctgtcagaga atgggcttga ggcggggttt gtgggcacta gtttcactgg  93240
tttcatttac caaaaggggg agcagaagtc aagtatggtg gctcatccct gtaatcccag   93300
aggcaagaga attgcttgag cccaggagtt cgagaccagc ctgagcaaca taaggagacc   93360
ccgtctccac aaaaatgaaa aataacattt tagtcagacg tggtggcatg catctgtggt   93420
cccagctgct tgggagggtg agatggggagg gttgtttgag ccctggagtt aaagttgcaa  93480
tgagctgtga ttgcaccact gcactctagc ctgggtgaca gaacgagacc ctgtctcaaa   93540
aaaaaaaaaa aagaaagaaa gaaggaaaa aaaaaactca tgcctgtaat cccagcactt    93600
tggggaccgg ggtgggcaga tcacgaggtc aggagatcaa gactatcctg gccaacatgg   93660 tgaaccccg tttctactaa aaatacaaaa attagccagg tgtggtggca cgtgcctgta    93720
atcccagtta ctcgggaggc tgaggcagga gaatcgcttg aaccagggag tcagaggttg   93780
cagtgagctg agatcgtgcc actgtactcc agcctgggcg acagagtgag actctgtctc   93840
aaaccaaaaa aaggggtgg ggggcggggg caggagaaca gtgagaggta gggagaggaa    93900
aggggattct cgctacaccc aaaccagata ccatctagag gctagaatct ttgggaggct   93960
caaattccct agaaagcagg agaagcttct gtagccctcc cgctttccca gtagattaag   94020
cccagggcgg ctccagatgt gtgacatgct ctgtgcccaa ccagagccca tcataggcag   94080
aggaataaca cccacaccag aagggccctc ggaggtcacc acgtccaaga accctcttta   94140
cagatgagga aactgaggcc cagagagggg agagccacct agcgagctgg tggcggctag   94200
accaggagag ctgtcattcc aagcaagcaa aggcaacgag acgagcccag agctgtgctc   94260
ccatctcttt gttagggggc ctgggatgcc ctctcagtgt cattttgtcc aggatgatgc    94320
tccctctctt aagcgattaa tgcgcccttg ctaaccttt gctatcgctg cctcttcaaa    94380
ccagaggagt tgagagttcc gggccggcag aggaaggcgc ctgaaaggcc cctggccaat   94440
gagattagcg cccacgtcca gcctggaccc tgcggagagg cctctggggt ctctgggccg    94500
tgcctcgggg agaaagagcc agaagctccc gtcccgctga ccgcgagcct tcctcagcac    94560
cgtcccgttt gcccagcgcc tcctccaaca ggaggccctc aggagccctc cctggagtgg   94620
ggacaaaaag gcgggactg ggccgagaag ggtccggcct ttccgaagcc cgccaccact    94680
gcgtatctcc acacagagcc tgaaagtggt aaggtggtcc aggaaggctt cctccgagag   94740
ccaggccccc caggtctgag ccaccagctc atgtccggca tgcctggggc tcccctcctg   94800
cctgagggcc ccagagaggc cacacgccaa ccttcgggga caggacctga ggacacagag   94860
ggcggccgcc acgcccctga gctgctcaag caccagcttc taggagacct gcaccaggag   94920
gggccgccgc tgaaggggc aggggcaaa gagaggccgg ggagcaagga ggaggtggat    94980
gaagaccgcg acgtcgatga gtcctcccccc caagactccc ctccctccaa ggcctcccca    95040
gcccaagatg ggcggcctcc ccagacagcc gccagagaag ccaccagcat cccaggcttc    95100
```

```
ccagcggagg gtgccatccc cctccctgtg gatttcctct ccaaagtttc cacagagatc    95160
ccagcctcag agcccgacgg gcccagtgta gggcgggcca aagggcagga tgccccctg     95220 gagttcacgt ttcacgtgga aatcacaccc aacgtgcaga aggagcaggc gcactcggag    95280
gagcatttgg gaagggctgc atttccaggg gcccctggag aggggccaga ggcccggggc    95340
ccctctttgg gagaggacac aaaagaggct gaccttccag agccctctga aaagcagcct    95400
gctgctgctc cgcggggggaa gcccgtcagc cgggtccctc aactcaaagg tctgtgtctt   95460
gagcttcttc gctccttccc tggggacctc ccaggcctcc caggctgcgg gcactgccac    95520
tgagcttcca ggcctcccga ctcctgctgc ttctgacgtt cctaggacgc cactaaatcg    95580
acacctgggt gcagctgctc cactccctcg gcctcctccc gtgctcaggc tgtggccgca    95640
cgcgcccctc acgcttgccc gccactctgc atgtcaccag cacccccgct ccgtgctacc    95700
caccttgttt gactctctgg ccacttgatt tgtccacaac ggcccatcag cccacaggag    95760
gtttggtggg tgccttccac cgacaggatg acgggtgccc tcatggtgtc tagaactctc    95820
caaccctccc atgtaggcat aagcagcccc actttgcaga tgaggaaacg gaggctcaga    95880
gaagtacagt aacttgccga aggccaatga gtagtaagtg acagagccag gtttgggatc    95940
caggtaggtt gtctctgaaa gacacgcctg tcctgcatcc cacaacgcct cccaggaggt    96000
gctggagtgt ggacgcctaa cacagagatg tgcagggcac acacagcagg tgacacacac    96060
agcatccaga ggtggcccag agctcatgct gtgccttggg cccagtgccc tgcccccacc    96120
cactctgcct tgtggcagga agacaaggag cagacacaag atctccctgg tccacatgcc    96180
accacctccc tctgcagagg acaagggggat cctcatgctg gcattggagg gggttgagca    96240
gggcccacct tgagccctca ggagcacgac cacagcagcc ctgcagggag ggattggtgg    96300
gaggagagtc ccaagtatca gggagaggag agttggtgtc ccacaggaga cctcagagcc    96360
acaaggcgag cttgttcata aatttgggac ccttagcatt tcacagttat ttgcagagcc    96420
cagaaatgga tgttactgaa gctcacagtt gcaagcatct gttaaatttt tattagattt    96480 tactttagg gaaaactttg aaatgctata agaagcctg tgtttaaaag ttaagacaga     96540
ggctgggggc gatggctcac gcctgtaatc tcagcacttt gggaggccaa ggcaggtgga    96600
tcatttgagg ttaggagttc gagaccagcc tggccaacat ggtgagaccc tgtctctact    96660 aaaaattacaa aaaattagct gggcgtggtg gcgggcacct gtagtcccag ctactgggga   96720
ggctgaagca ggataagtgc ttgaacccag gaggcagagg ttacagtgag ccaagatcac    96780
accactgtac cctaagcctg ggcgacagag tgagactctg tctcaaaaaa taaaataaaa    96840
taaagttaag agagaaaaaa atatatccta tatcctttgt taaattccaa aacagtaggg    96900
gacaaataac tgacttgaca ggttactaca atatttcctg aaatgatgtt ttcttgaata    96960
ctggcctact agaggttcat aggtgtgttt ggattaaaaa agagttccat ggcccagtga    97020 ctggggggaaa aaaataaaag actaaagtaa gttaaacagg cttttctgct gcaggacttg    97080
tcagagcctt taatgtacta atggccattg tgaccctctg agaaggtcac agagtgggtt    97140
tcccaaactt acttgattct acctgctaac atttcctgga ggaagtttgg gaaatgccga    97200
tttagcagat tcttttgttg tgccgtggat ggtgctggtt gatgtgggca aaacaaagaa    97260
cacgtgagtc agatccgcct ggggctctta ctaaagtgca ggttcccagg tgccactttta    97320 ggcttacaga cccagttgtg gggtaagcct gggagtcttt tagcaggtga ttctgccaca    97380
tagtatagtt ggaaaacctc tgggcatact cattgctggt ccctctagaa atccaggtga    97440
caatagccaa tgagaagctc caagagaccc agttgtccat ggggtagagg gaatgtgata    97500
```

```
ttgaaaccaa agaagaaaat ctatgatcag ttttcagcag tgactgtcaa gagaaggaga   97560
agggtgagtt agcgctgatg ctggctgaca ggtcagcggg ttggtttcac caaggagtgt   97620
gatgaaggct gatgttgtct gtgggaatgt atgatggtaa ctggtttgta gctaatttgg   97680
ggaagcagtg agaattcgtg ccctttgaag accagtaagt ggcaagaaac ccaccaggcc   97740
tggctcaggg ctgggctggg cttggctcgt ctcagagcag ctggggctgg tggccaaagc   97800
caccattagt gaggggcagg ccctgggggt acaaccagca actaggggac aaagacaacc   97860
ctgccagcct ctcctattct ggaggcgtgt gaccagaaat ggagatgggt tggtcagcat   97920
aagatggcca ggaaggtgga aatcaggact gctggcaatc tagccacatg ggcaggggag   97980
ccgggtggtt ccaggcagtt tccaaggcca agagggtgag caggcacctc acagggaatc   98040
agggccaagc ctggctgcag tgtggagaca atgcacccac ccccatcctt ggatcttgca   98100
ggaggctggg tcctcactga gctaccaaca tccatggccc tgaggctttt aaaacaccca   98160
tccatggagt ggggctggtc ccagtggggt gaggctgacc ctggcagaaa cagggcagga   98220
gcctgtgggt tagggagact gcaccttcct tagatagcct ccatgccatc atgtccccgt   98280
gacagtttct gctgcgtccc ctctgcatgg tcccaccctc ggccagcctg ctgcccctc    98340 ttgccaggtt gcgctaatca gtgaccccag tgtgctgtgt tgatactaac aatgcgaggc   98400
ctagcagatt caagggaaaa gagaaccaac tgggtttcca ccagacccaa ctaaacaaac   98460
atggacctat cccagagaaa tccagcttca ccacagctgg ctttctgtga acagtgaaaa   98520
tggagtgtga caagcattct tattttatat tttatcagct cgcatggtca gtaaaagcaa   98580
agacgggact ggaagcgatg acaaaaaagc caaggtaagc tgacgatgcc acggagctct   98640
gcagctggtc aagtttacag agaagctgtg ctttatgtct gattcattct catatataat   98700
gtggggagta tttgtcacta aagtacagct gtcatttaaa gtgctttgta ttttggggca   98760
ggcttttaaa aagtccagca tttattagtt ttgatactta ccccagggaa gagcagttgg   98820
caggttcatg aagtcatgct cctaattcca gctttcttag tgtactttca gtgagaccct   98880
gacagtaaat gaaggtgtgt ttgaaaacca aacccaggac agtaaatgaa ggtgtgtttg   98940
aaaaccagcc ctaggacagt aaatgaagcc atcttctcac tgcataaact gcacccagat   99000
cttcgcccat ccttctcagt atttcacttc acccattgtt tactgtctca atgactgggg   99060
aaatgtctgg ggaaatgctc ccgtaattgc acagtggcgt ttttcctgga aaatcccacc   99120
atggctctag ataagaccta ttttctcttaa aggtatctaa aatttccagc ataaattctg   99180
tctgaaacac ctgaattta atcagtactg gagcccggag ggcatctcca gttgccacat   99240
agctctgagc attcagtggt gtgttgaggg ctgctcccgg aagtgcctgc agagtcaggg   99300
ctccccagcc tcatctagtg aggcagtgga agggcctgtg gggatttgga gagctggcct   99360
gggtctctga agtgatagtg acagctgctt gtcaatcacg gtgcacattt agtgctgggg   99420
gcagggggca gggaatacca gcctcatgca tgcatgcatt catttgttcc ttccttcatt   99480
cattcattca gtacacatgg gtacaacatc cctgccctgg agttgcccag agtctaggga   99540
ggggaaagat ctattaccct gggcctcggc cagctgggga gtgctgctgg tggagagggg   99600
ccgtgtgcag cgagggaagg aggagtcgtc aatacccca ccccagcttt gctttcttgt    99660
catcagcccc agggcccag cctgtgtccc tcctctccca ttgctacttc atctcctggg    99720
tcctccttac caagcctgac cacacagagg gccttggccg cttccatggg gaattggaaa   99780
gcaataagat agcatcccct agaagcccag tgaagtctgg gacaggaccc ttctctgagc   99840
```

```
tctgacttgc tcttggaaac acttcgaggc ttagcctccc cactttgttt cccgagagtg  99900
tgacctgttc ccctccaaac accccttct cctccaggc catgcccacc cgtcaaaatc   99960
ccccacgggc aggacgaact gtgggtgtca gtcaccatct atcctgcatc ctggttccag 100020
ggccccccc agccccgcct ccatagggac aggcgtgcag acaccccgtcc ctggctgctt 100080
cctcttgtgg aatgggttca aaagtaagca gtgttgttta cactgacaaa ctgaaaaaaa 100140
aagaaaaaga gataacattg gaggcttggc acagtggctc atgcctgtaa tcccagcact 100200
ttgggaggct aaggtgggag gatgtcccca gcccaagagt tctagaccag cctgggcaac 100260
atagcaagac cccatctcaa aaaaaaaatt taattggcca ggcagaggtg ggaggatcac 100320
ttgaacccaa agggtggagg ctgcagtgag ccgtgatggc accactgcac tccagccagg 100380
gcaacagagg gagaccctgt ctctaaaaca aacaaacaaa caaacaaaca aaagagttaa 100440
cattggccag attaggattc accagatagt gttaatatta gtttgatttg agactttaat 100500
cagaaagcac atgtgtggtg ggggtgggtg taacctaagt caggtagaat ctttccaact 100560
tgggggggc acactcctga ttgtagccat atgagtctgt cagtgtggtg gaagaggcca 100620
tgggttaatg ggcaggtaaa aaagcacctt gcctggaatt gagtagaaag taaggccctt 100680
cagaccccgt gacacacttg gggacatttt cttgagtaac atcctaagat tcatgtacct 100740
tgatgatctc catcaactta ctcatgtgaa gcacctttaa accagtcgtc tccaaattca 100800
ggggcacagt aacatccaac aggctggaga agaacgtac tagaacttcc attccttttt 100860
catgtcctct tctaaaagct ttgtcagggc caggcgcggt ggctcacgcc tgtaatccca 100920
gcactttggg aggccgagac gggtggatca cgaggtcagg agatcgagac catcctggct 100980
aacacagtga aaccccatct ctactaaaaa tacaaaaaaa cgagccgggc gtggtggtgg 101040
gcgcctgtag tcccagctac tcgggaggct gaggcaggga aatggcgtga acccaggagg 101100
cagagcttgc agtgagccga gattgcacca ctgcagtcca gcctgggcga cagagcgaga 101160
ctccgtctca aaaagaaaa agaaaagaa aaagaactgt gattggggag gacggtcact 101220
ttcctgttct tactgatcag aagggatatt aagggtacct gattcaaaca gcctggagat 101280
cactgctttc aaccattacc tgccttattt attttagtt actgtccttt tttcagtttg 101340
tttccctcct ccatgtgctg acttttattt tgatttttatt tatgtttatg tttaagacat 101400
ccacacgttc ctctgctaaa accttgaaaa ataggccttg ccttagcccc aaacaccca 101460
ctcctggtag ctcagaccct ctgatccaac cctccagccc tgctgtgtgc ccagagccac 101520
cttcctctcc taaatacgtc tcttctgtca ctttcccgaac tggcagttct ggagcaaagg 101580
agatgaaact caaggtaagg aaaccacctt tgaaagaac caggctgctc tgctgtggtt 101640
tgcaaatgtg gggtttgttt atttgttttt tagcctcaaa gacctttctt caaatgagtt 101700
ctggcataga agcaccgtgt aaaatagtta gaattctggg caaggggaa aagagagctg 101760
ggggccatcc ctctcagcac cccacaggct ctcatagcag cagctcctaa gacacctggt 101820
gggaccttgg tttcgaaatc gctactctaa ggctgggcac ggtggctcac acctgtaatc 101880
ccagctcttt aggaggccga ggagggtgga tcacctgaga tcaggagttc gagaccagcc 101940
tggctaacat ggcaaaaccc tgtctctact aaaaatacaa aaattagccg ggcgtggtgg 102000
tatgcgtggt ggtaatcgca gctactcggg aggctgaggc acaaggattg cttgaacccc 102060
agaggcagag gttgtagtta gctccagctt gggcgacaga gcaagaccct gtcgcaaaaa 102120
ttgtttaaaa aacaaaccca aaattgctac tctcattggg ttccttttgcc cattcctgat 102180
ttttggcaaga gaaatgcttc cagattgccc tgatctgggt aggacagcat cacgccatag 102240
```

```
caacactgcc ccgtgagctc actgcccect caactagett gtggtccttg gttaatgtca 102300
gtttctttt tgagtttgtg ttatgtctaa gggtcatctg ctgggtaacg gaacccaggg 102360
actgccctag tccctagact gtgccatgcc cgactctgcc agctttgtca gtgatgctgg 102420
tgctcgcctc ctcgggtgct cgcctggtct gagcacaccc aaggagttct tgaggcctta 102480
gggttgtttg cgagagaatg aaagaacacg acctagctct cttagcatc cttggtcagg 102540
ttcaacactg cccccagggg cctctggtgg agccaaccac catcagccaa ataaatccat 102600
aattagagtc agaaaatgga tgtctgcata tgtgtagtgc actaatgtcc tgccgatgat 102660
tgacatggag tggagagtga cctgatcatt gctgtgagct ctgctggcct tggcacaact 102720
catgctgata actaatgcac acagttcctc tgggaggaaa tgtcctcagg gaacttggag 102780
tttgggtggg gatgtgggtt tgtgtgccca gcaagccctt gtggttgtag cagacactag 102840
tggcatctag gaggcaaagg gtcaccccag tcttagccac gttttgagtc aaggtggcgg 102900
agtgggctg tgtgttgactc ttggtggcag taacttttcc caatggtgaa aaacccctct 102960
atcatgtttc atttacaggg ggctgatggt aaaacgaaga tcgccacacc gcggggagca 103020
gcccctccag gccagaaggg ccaggccaac gccaccagga ttccagcaaa acccccgccc 103080
gctccaaaga caccacccag ctctggtaag aagaacgttc tcttgaatct tagaggaagc 103140
tgaagctctc agaggtacag ccttcatttt aggaggcctt aggccactga gaatgaataa 103200
cccctggcag ctggtcagca gcttgcagtt tactaagcac tggagtcttc attgccttct 103260
cagtccttt gatttctgag gcaaatgttg aatccctacc ttttttttt tttttctttt 103320
gagacagagt ttcgcttttg ttatccaggc cggagtgcag tggtgtgatc tcagctcact 103380
gcatcctcca cctcccaggt tcaagcgatt ctcctacctc agcctcccta gtagctggga 103440
ttacaggcac ctgccactat gcccggctaa ttttttgtat ttttagtaga gacagggttt 103500
caccatgttg gccaggctgg tctcgaacgc ctgacctcag gtgatccacc tgcctcggcc 103560
tcccaaagtg ctgggattac aggcatgagc caccactccc agcctgaatc ctcactttt 103620
atcaatgaag aaattgaggc tgattctgca gcatgataaa aaaaaataca gaaaaggaa 103680
aaaaagaaa gaaatcgagc ctctgagagt ttgcttgact gagtctaacc agctcatttt 103740
aaacccgagg aaaatgcagt cacatgacta ctaagtggca gctctcggag cctctctggc 103800
cccaagtcca gggttccata gaggcagccc cagcatggca tgttttcagt ccccaaatga 103860
gactctggag acaaatgtct ctggagacag agcagcagcc tggataagtc acaatgggtg 103920
acgtcactca gggctcaacc cctgggcagc ttaacttgct agggacgtta ggagtctgct 103980
gcaaaacctg agggtcttag ctgagcagtc acaggctggg cccgttgccc tgggctcctg 104040
tgagtaaaac ccagtcaatt ttgagtaccc agtaaggcat ccattgagtt attttgcagc 104100
caggagtgct attaagaaca gtcgcggctg ggcgtggtgg ctcatgcctg taatcccagc 104160
actttgggag gccaaggtgg gcggatcacc tgaggtcagg agttcgagac cagcttggcc 104220
aacatggcaa aaccccgtct ctaataaaaa tacaaaataa ttagctgggc gtggtggcgg 104280
gcgcctgtaa tcccagcttc tcaggagggt gaggaaggag aatcacttga acccaggagg 104340
cagaggttgc agtgagctga gatcgcacca ttgcactcca gcctggatga caaagtgag 104400
attccttctc aaaaaaaaaa aaaaaaaaac agtcgtcctc tttggggatt agggacagcc 104460
tgcctgcctg cccgagcact tctctcttcc attgccccag tgaagtattc caggcccctg 104520
ggtttagact ctgcaccatg taggggtgtc tgacctgcac ttgctccttg gtggcacggg 104580
```

-continued

```
cagcctatgg cacttgctgc gggctgtgac caaagcctgg cctggatctt ggatcttggt 104640
gactctgctt ctccctggcc tgagggagct gcccagagcc tgcccaccac ctgctgcgtg 104700
tctttgcggt ggcatttctc gcacacatgc cgtgcagtgg cacccccaag gatggccatt 104760
cactaaggcc cattgttttt gtcttttcgc ttcgtgtttt ctggcctggt gtttttctca 104820
tatacatgtg atccagggat aattcccaga attttgacag gattttaagt agcgtttgga 104880
tcctgctgtt ttttttcac ttaacatcgg gccagttgac tcacactctg ttttttgttg 104940
ttgtttttt gagacggagt ctcactgtgt cacccaggct gaagtgcagt ggcacaatct 105000
tggcatactg caacctctgc ttcccaaatt caagcagttt tcctgcctca gcctcctgag 105060
tagctgggac tacaggcaca ggccaccacg ccctgctaat ttttgtattt ttagtaaaga 105120
cagggtttca ccattttggc cagcctagtc tcgaactcct gacctcaagt gatccgccca 105180
cctcggcctc ccaaagtgct gggattacag gggactcaca ctttgtaaca acctgaaaca 105240
acgtgatgca tttcccttg ggtcttacct gctcttcggt ggctgcctgc aggtggagag 105300
acccctcccc ttgggcccct cgaccttgtt tcagaatggg gccctgctg ggccagctgt 105360
gggtgcctgc cacgtgaagg actcattaag gccctgttta gcctgatga taataaggct 105420
ttcgtggatt tttctcttta agcgactaag caagtccaga gaagaccacc ccctgcaggg 105480
cccagatctg agagaggtac tcgggagcct acttcgctgg gagcagcctc cctttgcgtg 105540
tgtggccatt cactggcttg tgtttctaga gccgggagga cccttttctg caatgcaggg 105600
ttcacacagg gttcgcagcc tgaagatgga gcagtccgaa ttctcttccc tgtgcagttt 105660
gcgcagctgt gtttgtctga tgggcttcct aatcctgtgt gctctccttg acttcaggga 105720
caatggcatt acaggcatga gccaccatgc ctggctgtct ccctatgttt cagatgaaga 105780
cataggctta aggaggtcag gtgacttgcc cacgaccact ctgtaaataa gaggcatgaa 105840
aagtatttgg agccaccacc accaagccca ctggtcaccc tgggtctctg aagtcaggga 105900
ggcaggagga tgggaggtct gaggaggcag agaggctgag cctggaggcc ctggaggccg 105960
aggccccatc tgttgtttcc ttatgtggaa aataagaggc ttcgtttgtc ctattgccac 106020
agagcgtact acttcaggaa catccaagac atggaaatcc gcagggcacg gtggctcacg 106080
tctataatcc cggcactttg ggaggttgag gtgggagaat cgcttgaggc cagaagttca 106140
agaccagcct gagcaacata gtcagacccc gtctctataa aaacattat ttttaaaaaa 106200
gacatggaag tcaaattcta aaaactggtg ctggctgggt gcggtggctc atgcctataa 106260
tcccagcact ttgggaggcc gaggcgggtg gatcacctga ggtcaggagt tcaagaccag 106320
cctggccaac atggtaaaac ctctactaaa gaaatcttta ctgaaaatac aaaaatccag 106380
tctctactaa aataagtctc tactaaaaat acaaaaatta gccaggcgtg gtgctgcaca 106440
cctgtaatat cagctactcg ggaggctgag gcaggagact cgcttgatcc catgcagcgg 106500
aggttgcagt gagccgagat cacgccattg cactccagcc tgggcatcag aataagactc 106560
cgtctcaaaa aaaaaccac aaaaaaacaa aacaacaaca aagaaaact agtgcttatt 106620
cgtcactggc caagctgccc attggctaca tgggtgcttc aaagagctgc ccttctccag 106680
gtctggccag caggtatgtg ttacagcaaa tgcctgggc agcggcaggg gcattgctgc 106740
gggaagcttc tggacttgca ggaaagctaa gttctcagac tgcaggggag ctaagcacac 106800
ctcggcacag ggtgaggcct gcggttctca gacttcagtc tttgtggagc ttgagaaaaa 106860
tgaggctttg caggtcccac ccctagagat tctgctctat ccactcttga aggggatcga 106920
gaaatttgca ttttgcaact cccactttcc tccttgaaag ctccggagat tctgacgcag 106980
```

```
ggttccgtgg gccacacttt ggaaaataca gacccatgag atagaatacc agactgttga   107040
agtgtaacgg gggcctggga agtgcagtaa cagaagcaag tttgagggta aaggacaccc   107100
agaggaggga gggacagcat ctgcatggag aggagaagag accccccagc agcttccagg   107160
gtgttggaag ggtgcgctag taactgctat gcatggcagg tggggaactg tacgtcaggg   107220
cacagcagca tgaagcggta tggctcgtgt ggacagctag ggacaggcag gcgtggagca   107280
ggcatcctgt tctgaaggcc aaatcccaca gaggagccag ggtgctggca ggagccctga   107340
actagccgaa cagctgaaca gctgaacatt caccctgtgg ggaaagggtc agaagcgtcc   107400
aggcttgagg gcacagctgg gtctcgtcac tgcatcaccc ttatttagga taaaggcccct  107460
gaagaattgt attagaggtt ggcaaagcat atctaccacc tcctggagcc acgctggccg   107520
cagggattat aattatttcc attttcaaat taaggcctct gagctcagag aggggaagtt   107580
acttgtctga ggccacacag cttgttggag cccatctctt gacccaaaga ctgtggagcc   107640
gagttggcca cctctctggg agcgggtatt ggatggtggt tgatggtttt ccattgcttt   107700
cctgggaaag gggtgtctct gtccctaagc aaaaaggcag ggaggaagag atgcttcccc   107760
agggcagccg tctgctgtag ctgcgcttcc aacctggctt ccacctgcct aacccagtgg   107820
tgagcctggg aatggaccca cgggacaggc agcccccagg gccttttctg accccaccca   107880
ctcgagtcct ggcttcactc ccttccttcc ttcccaggtg aacctccaaa atcagggat    107940
cgcagcggct acagcagccc cggctcccca ggcactcccg gcagccgctc ccgcaccccg   108000
tcccttccaa ccccacccac ccgggagccc aagaaggtgg cagtggtccg tactccaccc   108060
aagtcgccgt cttccgccaa gagccgcctg cagacagccc ccgtgcccat gccagacctg   108120
aagaatgtca agtccaagat cggctccact gagaacctga agcaccagcc gggaggcggg   108180
aaggtgagag tggctggctg cgcgtggagg tgtgggggc tgcgcctgga ggggtagggc    108240
tgtgcctgga agggtagggc tgcgcctgga ggtgcgcggt tgagcgtgga gtcgtgggac   108300
tgtgcatgga ggtgtggggc tccccgcacc tgagcaccc cgcataacac cccagtcccc    108360
tctggaccct cttcaaggaa gttcagttct ttattgggct ctccactaca ctgtgagtgc   108420
cctcctcagg cgagagaacg ttctggctct tctcttgccc cttcagcccc tgttaatcgg   108480
acagagatgg cagggctgtg tctccacggc cggaggctct catagtcagg gcacccacag   108540
cggttcccca cctgccttct gggcagaata cactgccacc cataggtcag catctccact   108600
cgtgggccat ctgcttaggt tgggttcctc tggattctgg ggagattggg ggttctgttt   108660
tgatcagctg attcttctgg gagcaagtgg gtgctcgcga gctctccagc ttcctaaagg   108720
tggagaagca cagacttcgg gggcctggcc tggatcccctt tccccattcc tgtccctgtg   108780
cccctcgtct gggtgcgtta gggctgacat acaaagcacc acagtgaaag aacagcagta   108840
tgcctcctca ctagccaggt gtgggcgggt gggtttcttc caaggcctct ctgtggccgt   108900
gggtagccac ctctgtcctg caccgctgca gtcttccctc tgtgtgtgct cctggtagct   108960
ctgcgcatgc tcatcttctt ataagaacac catggcagct gggcgtagtg gctcacgcct   109020
ataatcccag cactttggga ggctgaggca ggcagatcac gaggtcagga gttcgagacc   109080
aacctgacca acagggtgaa acctcgtctc tactaaaaat acaaaaatac ctgggcgtgg   109140
tggtggtgcg cgcctataat cccagctact caggaggctg aggcaggaga atcgcttgaa   109200
cccaggaggc agaggttgca gtgagccgag atagtgccac tgcactccag tttgagcaac   109260
agagcgagac tctgtctcaa aacaaaataa aacaaaccaa aaaacccac catggcttag    109320
```

-continued

```
ggcccagcct gatgacctca tttttcactt agtcacctct ctaaaggccc tgtctccaaa 109380
tagagtcaca ttctaaggta cgggggtgtt ggggaggggg gttagggctt caacatgtga 109440
atttgcgggg accacaattc agcccaggac cccgctcccg ccacccagca ctggggagct 109500
ggggaagggt gaagaggagg ctgggggtga aaggaccac agctcactct gaggctgcag 109560
atgtgctggg ccttctgggc actgggcctc ggggagctag ggggcttct ggaaccctgg 109620 gcctgcgtgt cagcttgcct cccccacgca ggcgctctcc acaccattga agttcttatc 109680
acttgggtct gagcctgggg catttggacg gagggtggcc accagtgcac atgggcacct 109740
tgcctcaaac cctgccacct cccccccaccc aggatccccc ctgcccccga caagcttgt 109800 gagtgcagtg tcacatccca tcgggatgga aatggacggt cgggttaaaa gggacgcatg 109860
tgtagaccct gcctctgtgc atcaggcctc ttttgagagt ccctgcgtgc caggcggtgc 109920
acagaggtgg agaagactcg gctgtgcccc agagcacctc ctctcatcga ggaaaggaca 109980
gacagtggct cccctgtggc tgtggggaca agggcagagc tccctggaac acaggaggga 110040
gggaaggaag agaacatctc agaatctccc tcctgatggc aaacgatccg ggttaaatta 110100
aggtccggcc ttttcctgct caggcatgtg gagcttgtag tggaagaggc tctctggacc 110160
ctcatccacc acagtggcct ggttagagac cttggggaaa taactcacag gtgacccagg 110220
gcctctgtcc tgtaccgcag ctgagggaaa ctgtcctgcg cttccactgg ggacaatgcg 110280
ctccctcgtc tccagacttt ccagtcctca ttcggttctc gaaagtcgcc tccagaagcc 110340
ccatcttggg accaccgtga ctttcattct ccagggtgcc tggccttggt gctgcccaag 110400
accccagagg ggccctcact ggcctttcct gccttttctc ccattgccca cccatgcacc 110460
cccatcctgc tccagcaccc agactgccat ccaggatctc ctcaagtcac ataacaagca 110520
gcacccacaa ggtgctccct tcccctagc ctgaatctgc tgctccccgt ctggggttcc 110580
ccgcccatgc acctctgggg gccctgggt tctgccatac cctgccctgt gtcccatggt 110640 gggaatgtc cttctctcct tatctcttcc cttcccttaa atccaagttc agttgccatc 110700
tcctccagga agtcttcctg gattcccctc tctcttctta aagcccctgt aaactctgac 110760
cacactgagc atgtgtctgc tgctccctag tctgggccat gagtgagggt ggaggccaag 110820
tctcatgcat ttttgcagcc cccacaagac tgtgcaggtg gccggccctc attgaatgcg 110880
gggttaattt aactcagcct ctgtgtgagt ggatgattca ggttgccaga gacagaaccc 110940
tcagcttagc atgggaagta gcttccctgt tgaccctgag ttcatctgag gttggcttgg 111000
aaggtgtggg caccatttgg cccagttctt acagctctga agagagcagc aggaatgggg 111060
ctgagcaggg aagacaactt tccattgaag gccccttca gggccagaac tgtccctccc 111120
accctgcagc tgccctgcct ctgcccatga ggggtgagag tcaggcgacc tcatgccaag 111180
tgtagaaagg ggcagatggg agcccaggt tatgacgtca ccatgctggg tggaggcagc 111240
acgtccaaat ctactaaagg gttaaaggag aaagggtgac ttgacttttc ttgagatatt 111300 ttggggggacg aagtgtggaa aagtggcaga ggacacagtc acagcctccc ttaaatgcca 111360
ggaaagccta gaaaaattgt ctgaaactaa acctcagcca taacaaagac caacacatga 111420
atctccagga aaaagaaaaa agaaaaatgt catacagggt ccatgcacaa gagcctttaa 111480
aatgacccgc tgaagggtgt caggcctcct cctcctggac tggcctgaag gctccacgag 111540
cttttgctga gacctttggg tccctgtggc ctcatgtagt acccagtatg cagtaagtgc 111600
tcaataaatg tttggctaca aaagaggcaa agctggcgga gtctgaagaa tccctcaacc 111660
gtgccggaac agatgctaac accaaaggga aaagagcagg agccaagtca cgtttgggaa 111720
```

```
cctgcagagg ctgaaaactg ccgcagattg ctgcaaatca ttgggggaaa aacggaaaac 111780
gtctgttttc cccttttgtgc ttttctctgt tttcttcttt gtgcttttct ctgttttcag 111840
gatttgctac agtgaacata gattgctttg gggcccccaaa tggaattatt ttgaaaggaa 111900
aatgcagata atcaggtggc cgcactggag caccagctgg gtaggggtag agattgcagg 111960
caaggaggag gagctgggtg gggtgccagg caggaagagc ccgtaggccc cgccgatctt 112020
gtgggagtcg tgggtggcag tgttccctcc agactgtaaa agggagcacc tggcgggaag 112080
agggaattct tttaaacatc attccagtgc ccgagcctcc tggacctgtt gtcatcttga 112140
ggtgggcctc ccctgggtga ctctagtgtg cagcctggct gagactcagt ggccctgggt 112200
tcttactgct gacacctacc ctcaacctca accactgcgg cctcctgtgc accctgatcc 112260
agtggctcat tttccacttt cagtcccagc tctatcccta tttgcagttt ccaagtgcct 112320
ggtcctcagt cagctcagac ccagccaggc cagcccctgg ttcccacatc cctttgcca 112380
agctcatccc cgcccgtttt ggcctgcggg agtgggagtg tgtccagaca cagagacaaa 112440
ggaccagctt ttaaaacatt ttgttggggc caggtgtggt ggctcacacc taatcccaac 112500
acctggggag gccaaggcag aaggatcact tgagtccagg agttcaagac cagcctgggc 112560
aacataggga gaccctgtct ctacaatttt tttttttaatt agctgggcct gttggcactc 112620
tcctgtagtt ccagctactc tagaggctga ggtgggagga ctgcttgagc ctgggaggtc 112680
agggctgcaa tgagccatgt tcacaccact gaacgccagc ctgggcgaga ccctgtatca 112740
aaaaagtaaa gtaaatgaa tcctgtacgt tatattaagg tgccccaaat tgtacttaga 112800
aggattttcat agttttaaat acttttgtta tttaaaaaat taaatgactg cagcatataa 112860
attaggttct taatggaggg gaaaaagagt acaagaaaag aaataagaat ctagaaacaa 112920
agataagagc agaaataaac cagaaaacac aaccttgcac tcctaactta aaaaaaaaaa 112980
tgaagaaaac acaaccagta aaacaacata taacagcatt aagagctggc tcctggctgg 113040
gcgcggtggc gcatgcctgt aatcccaaca ctttgggagg ccgatgctgg aggatcactt 113100
gagaccagga gttcaaggtt gcagtgagct atgatcatac cactcaccc tagcctgggc 113160
aacacagtga gactgagact ctattaaaaa aaaaatgctg gttccttcct tatttcattc 113220
ctttattcat tcattcagac aacatttatg gggcacttct gagcaccagg ctctgtgcta 113280
agagcttttg cccccagggt ccaggccagg ggacagggc aggtgagcag agaaacaggg 113340
ccagtcacag cagcaggagg aatgtaggat ggagagcttg gccaggcaag gacatgcagg 113400
gggagcagcc tgcacaagtc agcaagccag agaagacagg cagacccttg tttgggacct 113460
gttcagtggc cttttgaaagg acagcccccca ccggagtgc tgggtgcagg agctgaagga 113520
ggatagtgga acactgcaac gtggagctct tcagagcaaa agcaaaataa acaactggag 113580
gcagctgggg cagcagaggg tgtgtgttca gcactaaggg gtgtgaagct tgagcgctag 113640
gagagttcac actggcagaa gagaggttgg ggcagctgca agcctctgga catcgcccga 113700
caggacagag ggtggtggac ggtggccctg aagagaggct cagttcagct ggcagtggcc 113760
gtgggagtgc tgaagcaggc aggctgtcgg catctgctgg ggacggttaa gcaggggtga 113820
gggcccagcc tcagcagccc ttcttggggg gtcgctggga aacatagagg agaactgaag 113880
aagcagggag tcccagggtc catgcagggc gagagagaag ttgctcatgt ggggcccagg 113940
ctgcaggatc aggagaactg gggacccgt gactgccagc gggagaagg gggtgtgcag 114000
gatcatgccc agggaagggc ccaggggccc aagcatgggg gggcctggtt ggctctgaga 114060
```

```
agatggagct aaagtcactt tctcggagga tgtccaggcc aatagttggg atgtgaagac  114120
gtgaagcagc acagagcctg gaagcccagg atggacagaa acctacctga gcagtggggc  114180
tttgaaagcc ttggggcggg gggtgcaata ttcaagatgg ccacaagatg gcaatagaat  114240
gctgtaactt tcttggttct gggccgcagc ctgggtggct gcttccttcc ctgtgtgtat  114300
tgatttgttt ctcttttttg agacagagtc ttgctgggtt gcccaggctg gagtgcagtg  114360
gtgcgatcat agctcactgc agccttgaag tcctgagctc aagagatcct tccacctcag  114420
cctcctgagt agttgggacc acaggcttgc accacagtgc caactaatt tcttatattt  114480 tttgtagaga tggggtttca ctgtgtcgcc caggatggtc ttgaactcct gggctcaagt  114540
gatcctcctg cctcagcctc gcaaattgct gggattacag gtgtgagcca ccatgcccga  114600
ccttctcttt ttaagggcgt gtgtgtgtgt gtgtgtgtgt gggcgcactc tcgtcttcac  114660 cttccccag ccttgctctg tctctaccca gtcacctctg cccatctctc cgatctgttt  114720
ctctctcctt ttaccctct ttcctccctc ctcatacacc actgaccatt atagagaact  114780
gagtattcta aaaatacatt ttatttattt attttgagac agagtctcac tctgtcaccc  114840
aggctggagt gcagtggtgc aatctcggct cactgcaacc tccgcctccc aggttgaagc  114900
aactctcctg cctcagcctc cctagtagct gggattacaa gcacacacca ccatgcctag  114960 caaatttta tatttttagt agaggagggg tgtcaccatg tttgccaagc tggtctcaaa  115020
ctcctggcct caggtgatct gcctaccttg gtctcccaaa gtgctgggat tacaggtgtg  115080
agccaccacg cctgccctta aaaatacatt atattaata gcaaagcccc agttgtcact  115140
ttaaaaagca tctatgtaga acatttatgt ggaataaata cagtgaattt gtacgtggaa  115200
tcgtttgcct ctcctcaatc agggccaggg atgcaggtga gcttgggctg agatgtcaga  115260
ccccacagta agtgggggc agagccaggc tgggaccctc ctctaggaca gctctgtaac  115320
tctgagaccc tccaggcatc ttttcctgta cctcagtgct tctgaaaaat ctgtgtgaat  115380
caaatcattt taaaggagct tgggttcatc actgtttaaa ggacagtgta aataattctg  115440
aaggtgactc taccctgtta tttgatctct tctttggcca gctgacttaa caggacatag  115500
acaggttttc ctgtgtcagt tcctaagctg atcaccttgg acttgaagag gaggcttgtg  115560
tgggcatcca gtgcccaccc cgggttaaac tcccagcaga gtattgcact gggcttgctg  115620
agcctggtga ggcaaagcac agcacagcga gcaccaggca gtgctggaga caggccaagt  115680
ctgggccagc ctgggagcca actgtgaggc acggacgggg ctgtggggct gtgggctgc  115740 aggcttgggg ccagggaggg agggctgggc tctttggaac agccttgaga gaactgaacc  115800
caaacaaaac cagatcaagg tctagtgaga gcttagggct gctttgggtg ctccaggaaa  115860
ttgattaaac caagtggaca cacccccca gccccacctc accacagcct ctccttcagg  115920
gtcaaactct gaccacagac atttctcccc tgactaggag ttccctggat caaaattggg  115980
agcttgcaac acatcgttct ctcccttgat ggttttgtc agtgtctatc cagagctgaa  116040
gtgtaatata tatgttactg tagctgagaa attaaatttc aggattctga tttcataatg  116100
acaaccattc ctcttttctc tcccttctgt aaatctaaga ttctataaac ggtgttgact  116160
taatgtgaca attggcagta gttcaggtct gctttgtaaa tacccttgtg tctattgtaa  116220
aatctcacaa aggcttgttg ccttttttgt ggggttagaa caagaaaaag ccacatggaa  116280 aaaaatttc ttttttgttt tttgtttgc ttgttttttt gagacagagt ttcactctgt  116340
cgcccaggct ggagtgcagt ggtgcgatct ccgcccactg caagctccac ctcccggtt  116400 catgctattc tcctgtctca gcctcccaag tagctgggac tgcaggtgcc cgccaccaca  116460
```

```
cctggctaat ttttttgtat ttttagtaga dacggggttt caccgtgtta gccaggatgg  116520
tctcaatctc ctgacctcgt catctgcctg cctcggcctc ccaaagtgct gagattacag  116580
gcgtgagcca ccgtgcccgg ccagaaaaaa acatttctaa gtatgtggca gatactgaat  116640
tattgcttaa tgtcctttga ttcatttgtt taatttcttt aatggattag tacagaaaac  116700
aaagttctct tccttgaaaa actggtaagt tttctttgtc agataaggag agttaaataa  116760
cccatgacat ttccctttt gcctcggctt ccaggaagct caaagttaaa tgtaatgatc  116820
actcttgtaa ttatcagtgt tgatgcccct cccttcttct aatgttactc tttacatttt  116880
cctgctttat tattgtgtgt gttttctaat tctaagctgt tcccactcct ttctgaaagc  116940
aggcaaatct tctaagcctt atccactgaa aagttatgaa taaaaaatga tcgtcaagcc  117000
tacaggtgct gaggctactc cagaggctga ggccagagga ccacttgagc ccaggaattt  117060
gagacctggg ctgggcagca tagcaagact ctatctccat taaaactatt ttttttatt  117120 taaaaaataa tccgcaaaga aggagtttat gtgggattcc ttaaaatcgg agggtggcat  117180
gaattgattc aaagacttgt gcagagggcg acagtgactc cttgagaagc agtgtgagaa  117240
agcctgtccc acctccttcc gcagctccag cctgggctga ggcactgtca cagtgtctcc  117300
ttgctggcag gagagaattt caacattcac caaaaagtag tattgttttt attaggttta  117360
tgaggctgta gccttgagga cagcccagga caactttgtt gtcacataga tagcctgtgg  117420
ctacaaactc tgagatctag attcttctgt ggctgcttct gacctgagaa agttgcggaa  117480
cctcagcgag cctcacatgg cctccttgtc cttaacgtgg ggacggtggg caagaaaggt  117540
gatgtggcac tagagattta tccatctcta aaggaggagt ggattgtaca ttgaaacacc  117600
agagaaggaa ttacaaagga agaatttgag tatctaaaaa tgtaggtcag gcgctcctgt  117660
gttgattgca gggctattca caatagccaa gatttggaag caacccaagt gtccatcaac  117720
agacaaatgg ataagaaaa tgtggtgcat atacacaatg gaatactatt cagccatgaa  117780
aaagaatgag aatctgtcat ttgaaacaac atggatggaa ctggaggaca ttatgttaag  117840
tgaaataagc cagacagaag gacagacttc acatgttctc acacatttgt gggagctaaa  117900
aattaaactc atggagatag agagtagaag gatggttacc agaggctgag gagggtggag  117960
gggagcaggg agaaagtagg gatggttaat gggtacaaaa acgtagttag catgcataga  118020
tctagtattg gatagcacag cagggtgacg acagccaaca gtaatttata gtacatttaa  118080
aaacaactaa aagagtgtaa ttggactggc taacatggtg aaaccccgtc tctactaaaa  118140
atacaaaaat tagctgggca tggtggctca cgcctgtaat cccagcactt tgggaggccg  118200
aggcgggccg atcacgaggt caggagatcg agaccatcct agctaacatg gtgaaacccc  118260
gtctctacta caaatacaaa aaaagaaaa aattagccgg gcatggtggt gggcgcctgt  118320
agtcccagct actcgggagg ctgaggcagg agaatggcgt gaacccggga ggcggagctt  118380
gcagtgagcc gagatcgcgc cactgcactc cagcctgggc gacaaggcaa gattctatct  118440
caaaaaaata aaaataaaat aaaataaaat aataaaataa aataaaataa aataaaataa  118500
ataaaataaa ataaaatgta taattggaat gtttataaca caagaaatga taaatgcttg  118560
aggtgataga taccccattc accgtgatgt gattattgca caatgtatgt ctgtatctaa  118620
atatctcatg taccccacaa gtatatacac ctactatgta cccatataaa tttaaaatta  118680 aaaattata aaacaaaaat aaataagtaa attaaaatgt aggctggaca ccgtggttca  118740
cgcctgtaat cccagtgctt tgtgaggctg aggtgagaga atcacttgag cccaggagtt  118800
```

```
tgagaccggc ctgggtgaca tagcgagacc ccatcatcac aaagaatttt taaaaattag    118860
ctgggcgtgg tagcacatac cggtagttcc agctacttgg gagaccgagg caggaggatt    118920
gcttgagccc aggagtttaa ggctgcagtg agctacgatg gcgccactgc attccagcct    118980
gggtgacaga gtgagagctt gtctctattt taaaaataat aaaagaata  aataaaaata    119040
aattaaaatg taaatatgtg catgttagaa aaaatacacc catcagcaaa aaggggggtaa   119100
aggagcgatt tcagtcataa ttggagagat gcagaataag ccagcaatgc agtttctttt    119160
attttggtca aaaaaaataa gcaaaacaat gttgtaaaca cccagtgctg gcagcaatgt    119220
ggtgaggctg gctctctcac cagggctcac agggaaaact catgcaaccc ttttagaaag    119280
ccatgtggag agttgtaccg agaggtttta gaatatttat aactttgacc cagaaattct    119340
attctaggac tctgtgttat gaaaataacc catcatatgg aaaaagctcc tttcagaaag    119400
aggttcatgg gaggctgttt gtattttttt tttctttgca tcaaatccag ctcctgcagg    119460
actgtttgta ttattgaagt acaaagtgga atcaatacaa atgttggata gcagggggaac   119520
aatattcaca aaatggaatg ggacatagta ttaaacatag tgcttctgat gaccgtagac    119580
catagacaat gcttaggata tgatatcact tcttttgttg tttttttgtat tttgagacga   119640
agtctcattc tgtcacccag gctggagttc agtggcgcca tctcagctca ctgcaacctc    119700
catctcccgg gttcaagcta ttctccttcc tcaacctccc gagtagctgg gttgcgcacc    119760
accatgcctg gctaactttt gtattttttag tacagacggg gtttcaccac gttggccagg    119820
ctgctcttga actcctgacg tcaggtgatc caccagcctt gacctcccaa agtgctagga    119880
ttacaggagc cactgtaccc agcctaggat atgatatcac ttcttagagc aagatacaaa    119940
attgcatgtg cacaataatt ctaccaagta taggtataca ggggtagtta tatataaatg    120000
agacttcaag gaaatacaac aaaatgcaat cgtgattgtg ttagggtggt aagaaaacgg    120060
tttttgcttt gatgagctct gttttttaaa atcgttatat tttctaataa aaatacatag    120120
tcttttgaag gaacataaaa gattatgaag aaatgagtta gatattgatt cctattgaag    120180
attcagacaa gtaaaattaa ggggaaaaaa aacgggatga accagaagtc aggctggagt    120240
tccaaccccca gatccgacag cccaggctga tggggcctcc agggcagtgg tttccaccca    120300
gcattctcaa aagagccact gaggtctcag tgccattttc aagatttcgg aagcggcctg    120360
ggcacggctg gtccttcact gggatcacca cttggcaatt atttacacct gagacgaata    120420
aaaaccagag tgctgagatt acaggcatgg tggcttacgc ttgtaatcgg ctttgggaag    120480
ccgaggtggg ctgattgctt gagcccagga gtttcaaact atcctggaca acatagcatg    120540
acctcgtctc tacaaaaaat acaaaaaatt gccaggtgt  ggtggcatgt gcctgtggtc    120600
ccagctactt gggaggctga agtaggaaa  tcccctgagc cctgggaagt cgaggctgca    120660
ctgagccgtg atggtgtcac tgcactccag cctgggtgac aaagtgagac cctatctcac    120720
aaagaaaaaa aacaaaacaa aaacccaaa  gcacactgtt tccactgttt ccagagttcc    120780
tgagaggaaa ggtcaccggg tgaggaagac gttctcactg atctggcaga gaaaatgtcc    120840
agttttccca actccctaaa ccatggtttt ctatttcata gttcttaggc aaattggtaa    120900
aaatcatttc tcatcaaaac gctgatattt tcacacctcc ctggtgtctg cagaaagaac    120960
cttccagaaa tgcagtcgtg ggagacccat ccaggccacc cctgcttatg gaagagctga    121020
gaaaagccc  cacgggagca tttgctcagc ttccgttacg cacctagtgg cattgtgggt    121080
gggagagggc tggtgggtgg atggaaggag aaggcacagc ccccccttgc agggacagag    121140
ccctcgtaca gaagggacac cccacatttg tcttccccac aaagcggcct gtgtcctgcc    121200
```

```
tacggggtca gggcttctca aacctggctg tgtgtcagaa tcaccagggg aacttttcaa   121260
aactagagag actgaagcca gactcctaga ttctaattct aggtcagggc taggggctga   121320
gattgtaaaa atccacaggt gattctgatg cccggcaggc ttgagaacag ccgcagggag   121380
ttctctggga atgtgccggt gggtctagcc aggtgtgagt ggagatgccg gggaacttcc   121440
tattactcac tcgtcagtgt ggccgaacac attttttcact tgacctcagg ctggtgaacg   121500
ctcccctctg gggttcaggc ctcacgatgc catcctttg tgaagtgagg acctgcaatc   121560
ccagcttcgt aaagcccgct ggaaatcact cacacttctg ggatgccttc agagcagccc   121620
tctatccctt cagctcccct gggatgtgac tcaacctccc gtcactcccc agactgcctc   121680
tgccaagtcc gaaagtggag gcatccttgc gagcaagtag gcgggtccag ggtggcgcat   121740
gtcactcatc gaaagtggag gcgtccttgc gagcaagcag gcgggtccag ggtggcgtgt   121800
cactcatcct tttttctggc taccaaaggt gcagataatt aataagaagc tggatcttag   121860
caacgtccag tccaagtgtg gctcaaagga taatatcaaa cacgtcccgg gaggcggcag   121920
tgtgagtacc ttcacacgtc ccatgcgccg tgctgtggct tgaattatta ggaagtggtg   121980
tgagtgcgta cacttgcgag acactgcata gaataaatcc ttcttgggct ctcaggatct   122040
ggctgcgacc tctgggtgaa tgtagcccgg ctccccacat tcccccacac ggtccactgt   122100
tcccagaagc cccttcctca tattctagga ggggtgtcc cagcatttct gggtccccca   122160
gcctgcgcag gctgtgtgga cagaataggg cagatgacgg accctctctc cggaccctgc   122220
ctgggaagct gagaataccc atcaaagtct ccttccactc atgcccagcc ctgtccccag   122280
gagccccata gcccattgga agttgggctg aaggtggtgg cacctgagac tgggctgccg   122340
cctcctcccc cgacacctgg gcaggttgac gttgagtggc tccactgtgg acaggtgacc   122400
cgtttgttct gatgagcgga caccaaggtc ttactgtcct gctcagctgc tgctcctaca   122460
cgttcaaggc aggagccgat tcctaagcct ccagcttatg cttagcctgc gccaccctct   122520
ggcagagact ccagatgcaa agagccaaac caaagtgcga caggtccctc tgcccagcgt   122580
tgaggtgtgg cagagaaatg ctgcttttgg ccctttaga tttggctgcc tcttgccagg   122640
agtggtggct cgtgcctgta attccagcac tttgggagac taaggcggga ggttcgcttg   122700
agcccaggag ttcaagacca gcctgggcaa caatgagacc cctgtgtcta caaaagaat   122760 taaaattagc caggtgtggt ggcacgcacc tgtagtccca gctacttggg aggctgaggt   122820
gggaggattg cctgagtccg ggaggcggaa gttgcaagga gccatgatcg cgccactgca   122880
cttcaaccta ggcaacagag tgagactttg tctcaaaaaa caatcatata ataatttaa   122940 aataaataga tttggcttcc tctaaatgtc cccggggact ccgtgcatct tctgtggagt   123000
gtctccgtga gattcgggac tcagatcctc aagtgcaact gacccacccg ataagctgag   123060
gcttcatcat cccctggccg gtctatgtcg actgggcacc cgaggctcct ctcccaccag   123120
ctctcttggt cagctgaaag caaactgtta acacccctggg gagctggacg tatgagaccc   123180
ttggggtggg aggcgttgat ttttgagagc aatcacctgg ccctggctgg cagtaccggg   123240
acactgctgt ggctccgggg tgggctgtct ccagaaaatg cctggcctga ggcagccacc   123300
cgcatccagc ccagagggtt tattcttgca atgtgctgct gcttcctgcc ctgagcacct   123360
ggatcccggc ttctgccctg aggccccttg agtcccacag gtagcaagcg cttgccctgc   123420
ggctgctgca tggggctaac taacgcttcc tcaccagtgt ctgctaagtg tctcctctgt   123480
ctcccacgcc ctgctctcct gtccccccag tttgtctgct gtgaggggac agaagaggtg   123540
```

```
tgtgccgccc ccacccctgc ccgggcccct tgttcctggga ttgctgtttt cagctgtttg   123600
agctttgatc ctggttctct ggcttcctca aagtgagctc ggccagagga ggaaggccat   123660
gtgctttctg gttgaagtca agtctggtgc cctggtggag gctgtgctgc tgaggcggag   123720
ctggggagag agtgcacacg ggctgcgtgg ccaacccctc tgggtagctg atgcccaaag   123780
acgctgcagt gcccaggaca tctgggacct ccctggggcc cgcccgtgtg tcccgcgctg   123840
tgttcatctg cgggctagcc tgtgacccgc gctgtgctcg tctgcgggct agcctgtgtc   123900
ccgcgctctg cttgtctgcg gtctagcctg tgacctggca gagagccacc agatgtcccg   123960
ggctgagcac tgccctctga gcaccttcac aggaagccct tctcctggtg agaagagatg   124020
ccagcccctg gcatctgggg gcactggatc cctggcctga gccctagcct ctccccagcc   124080
tgggggcccc ttcccagcag gctggccctg ctccttctct acctgggacc cttctgcctc   124140
ctggctggac cctggaagct ctgcagggcc tgctgtcccc ctccctgccc tccaggtatc   124200
ctgaccaccg gccctggctc ccactgccat ccactcctct cctttctggc cgttccctgg   124260
tccctgtccc agcccccctc cccctctcac gagttacctc acccaggcca gagggaagag   124320
ggaaggaggc cctggtcata ccagcacgtc ctcccacctc cctcggccct ggtccacccc   124380
ctcagtgctg gcctcagagc acagctctct ccaagccagg ccgcgcgcca tccatcctcc   124440
ctgtccccca acgtccttgc cacagatcat gtccgccctg acacacatgg gtctcagcca   124500
tctctgcccc agttaactcc ccatccataa agagcacatg ccagctgaca ccaaaataat   124560
tcgggatggt tccagtttag acctaagtgg aaggagaaac caccacctgc cctgcacctt   124620
gtttttggt gaccttgata aaccatcttc agccatgaag ccagctgtct cccaggaagc   124680
tccagggcgg tgcttcctcg ggagctgact gataggtggg aggtggctgc cccttgcac    124740
cctcaggtga ccccacacaa ggccactgct ggaggccctg gggactccag gaatgtcaat   124800
cagtgacctg ccccccaggc cccacacagc catggctgca tagaggcctg cctccaaggg   124860
acctgtctgt ctgccactgt ggagtcccta cagcgtgccc cccacagggg agctggttct   124920
ttgactgaga tcagctggca gctcagggtc atcattccca gagggagcgg tgccctggag   124980
gccacaggcc tcctcatgtg tgtctgcgtc cgctcgagct tactgagaca ctaaatctgt   125040
tggtttctgc tgtgccacct acccaccctg ttggtgttgc tttgttccta ttgctaaaga   125100
caggaatgtc caggacactg agtgtgcagg tgcctgctgg ttctcacgtc cgagctgctg   125160
aactccgctg ggtcctgctt actgatggtc tttgctctag tgctttccag ggtccgtgga   125220
agcttttcct ggaataaagc ccacgcatcg accctcacag cgcctcccct ctttgaggcc   125280
cagcagatac cccactcctg cctttccagc aagatttttc agatgctgtg catactcatc   125340
atattgatca cttttttctt catgcctgat tgtgatctgt caatttcatg tcaggaaagg   125400
gagtgacatt tttacactta agcgtttgct gagcaaatgt ctgggtcttg cacaatgaca   125460
atgggtccct gttttcccca gaggctcttt tgttctgcag ggattgaaga cactccagtc   125520
ccacagtccc cagctcccct ggggcagggt tggcagaatt tcgacaacac attttttccac  125580
cctgactagg atgtgctcct catggcagct gggaaccact gtccaataag ggcctgggct   125640
tacacagctg cttctcattg agttacaccc ttaataaaat aatcccatt tatcctttt     125700
gtctctctgt cttcctctct ctctgccttt cctcttctct ctcctcctct ctcatctcca   125760
ggtgcaaata gtctacaaac cagttgacct gagcaaggtg acctccaagt gtggctcatt   125820
aggcaacatc catcataaac caggtagccc tgtggaaggt gagggttggg acggagggt    125880
gcaggggggtg gaggagtcct ggtgaggctg gaactgctcc agacttcaga agggctgga    125940
```

```
aaggatattt taggtagacc tacatcaagg aaagtgttga gtgtgaaact tgcgggagcc 126000
caggaggcgt ggtggctcca gctcgctcct gcccaggcca tgctgcccaa gacaaggtga 126060
ggcgggagtg aagtgaaata aggcaggcac agaaagaaag cacatattct cggccgggcg 126120
ctgtggctca cgcctgtaat tccagcactt tgggaggcca aggtgggtgg atcatgaggt 126180
caggagattg agaccatcct ggctaacaca gtgaaacccc gtctctacta aaaatacaaa 126240
aaattagccg ggcgtggtgg tgggcgcctg tagtcccagc tactccggag ctgaggcag 126300 gaaaatggcg tgaacccgga aggcggagct tgcagtgagc ggagtgagca gagatcgcgc 126360
cactgcactc cagcctgggc gacagagcga gactccgtct caaaaaaaaa aagcacatgt 126420
tctcgcttct ttgtgggatc caggagatag agaatagaag gatggttacc agaggctggg 126480
aagggtagtg aggggatggt gggggatgg tcaatgggta caaaaaaaat agaataagac 126540
ctagtatttg atagtgcaac agggtgacta tagtcaataa taatttaatt gtacatttaa 126600
aaataactaa aagatagccg ggtgcagtgg cttacgtctg taatcccagt actttggag 126660 gctgaggtgg gcgtttgaga ccagcctggc caacatggtg aaaccccatc tctactaaaa 126720
atacaaaaat tagccaggca tggtggcggg cgcctgtaat cccagctact cgggaggctg 126780
aggcaggaga atcacttgaa cctgggaggc agaggttgca gtgagccgag atcttgccac 126840
tgcactccag cctgggtgac agtgaaactc cgtctcaaaa ataaaataa aaatacagct 126900 gggcacggtg gctcacgcct gtaatcccag cactttggga ggccgaggcg agcggatcac 126960
aaggtcagga gatatagacc atcctggcta acacggtgaa accggtctc tactaaaaat 127020 acaaaaatt agccaggcgt ggtggcaggt gcctatagtc ccagctactc acaaggctga 127080
ggcaggagaa tggcatgaac ctgggaggcg gagcttgcag tgagccgaga ttgtgccact 127140
gcactccagc ctgggcgaga gagtgagact ccgtctcaaa acaaaaacaa aacaaaaac 127200 aaaaacaaac acacaacaaa aacctaaaag aatataaatg gattgtttgt aacacaaagg 127260
acaaatgttt gagggatgg atacccatt ttccatgatg tgattattat acattgtgtg 127320
tctgtatcaa aacatctcat gagccccata aatatataca cctaactatg tacccacaaa 127380
aattaaaaaa atatatttt taaggtgaag agggaggcga gatgctggcc ttaaccccta 127440
acccgttgtt ctccctgcaa gctgtccaca gggcctctca gactcgaggt tcagctatat 127500
ggatgcatga gcttggtccc cagccaacat gggagacact tcaccatcgg cagcagctac 127560
agcacaggaa ccctgggtca ctgccatgtc ccctctgtga ctttgtttaa acagaaaatg 127620
atgctctggg ccggctgtgg tggcccacac ctataatccc agcacttgg gaggcggggg 127680 tgggcagatt gcctgaggtc aggagttgga gatcagcctg gccgacatgg cgaaacccca 127740
tgtctactaa aaatacaaaa actagccagg catggtggca catgcctgta atcccagcta 127800
cttgggaggc tgaagcagga gaatcacttg aacccaggag gcagaggctg agtgagccaa 127860
gatcgtgcca tgcactcca gcttgggtga gggagtgaga ctccgtctca aaaaaaaaa 127920 aaaagaaaga aaaagaaaag aaagtgatcc tactggaacc atgcttactc ccctccccac 127980
ctcacactgt gtagaaatta gtgctgtcgg ccaggcgcgg tggctcatgc ctgtaatcgc 128040
agcactttgg gaggccaagg caggcggatc acgaggtcag gagatcaaga ccatcctggc 128100
taacacagtg aaaccctgtc tctactaaaa atacaaaaaa ttagccgggc atggtggcag 128160
gcacctgtag tcccaactac ttgggaggct gaggcaggag aatggcatga acctgggagg 128220
cggagcttgc agtgagccaa gatcgcgcca ctgcatacca gcctaggtga cagagtgaga 128280
```

-continued

```
ctcagcaaaa aaagaaagaa agaaagaaag aaatcagtgc tgtctatact tctttctgca 128340
gtgatggaaa tattctgtat ctgtgctgtc cagtatagta gccactagct acatgtggca 128400
cttgaaacat ggctggtaca gttgaggaag agtggctgcc atatcggacg acacagctat 128460
agattctgtc accccacccc gagagtccag agcgggact tctgccttag ccctattca 128520 gggctgattt ttacttgaac ccttactgtg ggaagagaag gccatgagaa gttcagtcta 128580
gaatgtgact ccttattttc tggctccctt ggacactttg tgggatttag tctccctgtg 128640
gaaagtattc cacaagtggt gccaccaccc cagctgtgag agcagctggg agctgctttt 128700
gtcatctttc cctggaaagt cctgtgggct gtctcttcct catgccttgt cccatgcttg 128760
ggcatggtgt caagcgtcag gagggagaaa gggtccttat ttatttattt agagagggac 128820
ccttcttctg ttcccaggct ggagtgcagt ggtgcgatct cggctcactg caacctccgc 128880
ctcctgggtt caagtgattc tcctgcctca gcctcctgag tagctgagat tacaggcaca 128940
tgccaacatg cctggctaat tttttttttt tttttttttt tttttttttg agatggagtt 129000
gtactctcat tgcccaggct ggaatgtaat ggcacaatct cggctcactg caacctccac 129060
ctcctggatt caagcaattc tcctgtctca gcttcccaag tagctgggat tacaggtgcc 129120
cgccaccatg ctcaactaat ttttgtattt ttttttagt agagacgagg tttcaccatg 129180
ttggtcagac tggtctcaaa ctcctgacct caggtgatcc acctgcctcg gcctcccaaa 129240
gtgctaggat tacaggcatg agccaccacg cccggcctga aagggttctt atttagtgtg 129300
cattttgaca ttcaatttaa ttccaaggtc ttgtggggtc atggtttaca ggatgttgat 129360
atagaaaaga cttcacttaa tgggccgggc gcagtggctc atgcctgtaa tcccagcact 129420
ttgggaggcc gaggcaggca gatcaggagg tcaggagatt gagaccatcc tggctaacac 129480
agtgaaaccc catctctact gaaaatacaa aaaattagct gggcgtggtg gcaggcacct 129540
gtagtcccag ccactcggtt ggctgaggca ggagaatggc atgaacccgg gaggcggagc 129600
ttgcagtgag cagagaccat gccactgcac tccagcctgg gcgacagagc aagactctgt 129660
ctcaagaaaa aaaaaaaaa aacagacttt acttactgga agccaaccaa tgtatattta 129720
gagtaatttt tcctgggctg agctgtcatt tacttttgca gtatctcaag aagaagagtt 129780
tacagtgtaa atatttgatg cacactttga ttatatagat gaagcaaact attttcaaga 129840
gctttgcaag gacttacttg tatccaaaca ccattctaaa ggagtcttac ctacttctaa 129900
aggctggtct ctacttggaa ccacttgctt ggccctggtt caagtcctgc tgcaaacctg 129960
gaagtcctgt cattgtcttc ttccctccag agcagtggca cccaatctaa ttttgctgt 130020 gccccagcag cccctggcac tttgccctgt agactgcaga cctcatgtaa tgtatgttaa 130080
gtccacagaa ccacagaaga tgatggcaag atgctcttgt gtgtgttgtg ttctaggagg 130140
tggccaggtg gaagtaaaat ctgagaagct tgacttcaag gacagagtcc agtcgaagat 130200
tgggtccctg acaatatca cccacgtccc tggcggagga aataaaaagg taaggggggt 130260
agggtgggtt ggatgctgcc cttgggtata tgggcattaa tcaagttgag tggacaaagg 130320
ctggtccagt tcccagagga ggaaaacaga ggcttctgtg ttgactggct ggatgtgggc 130380
cctcagcagc atccagtggg tctccactgc ctgtctcaat cacctggagc tttagcacgt 130440
ttcacacctg ggccccaacc tggagaggct gaccaatggg tctcagggc agctcggttg 130500 ctggagtttt tgttttttatt tattttatg tatttaaggc agggtctctg tattagtcca 130560
ttctcacact gctaataaag acatacccaa gactgggtaa tttataaagg aaagaggttt 130620
aatggactca cagttccaca tggctgggga ggcctcaaaa tcatggcgga aggcaaagga 130680
```

```
gaagcaaagg catttcttac atggcgacag gcaagagagc gtgtgcaggg gaactcccat    130740
ttataaaacc atcagacctc atgagattta ttcactatca tgagaacagc atgggaaaga    130800
cccgccccca tgattcagtt acctcccact gggtccctcc catgacacat ggaattatgg    130860
gagctacaat tcaagatgag atttgggtgg ggacacagcc aaaccatatc agtctccctc    130920
tgtcatccag gctggagtgc actggcatga tctcggctca ctgcagcctc tacctccctg    130980
ggtcaggtga tcttcccacc tcagcctccc aggtagctgg aactacaggt acctgccact    131040
atgcctggct aaatattttg tatttcctgt ggagacgagg ttttgccacg ttgcccaggc    131100
tggtcttgaa ctcctgaggt caagcaatat gcccacctcg gcctcccaag gtgctgggat    131160
tacaggtgtg agccacagtg ctcggcctaa gtcactgcag ttttttaaagc tcccaggtga    131220
ttcttcagtg cagtcaaaag tgagaactgg ctgggtgcgg tggctcatgc ctgtaatccc    131280
agcaccttgg gaggcgaagg tgggcagatg gcttgaggtc aggagttcaa gaccagcctg    131340
gccaacatgg taaaacccca tctctactaa aaatacaaaa gttagctggg tgtggtggtg    131400
cgtgcctgta atcccagcta cttgggaggc tgaggcatga gaattgcttg aacccagggg    131460
acagaggtta tagtgagccg agatcgtgcc actgcactcc agcctgggca acagagtgag    131520
attccatctc acaaaaaaaa aaaaaaagc gagaaccact gtcctaggcc ctgatgtttg    131580
caggcaacta aaaaggaag tggacatccc cagtcagctg tggcgcacca agaacaagtc    131640
atgggaacat aacctaattt tctaaatggg ttactaggca cttagagcaa acaatgatg    131700
ccgaaatcct gatttcagca aagcctctgc ctgcctgtct tggaagtatc cacatgaggc    131760
tgctggggcc ttggtgtccc cagcagtttc tagtctctag gtcttgctgt gggtgtctgt    131820
gcagtgaggg tgtgtgtggc gctgggtgag ctctgtctag gcctggcaca ggatgcggtc    131880
tggtagctgc tgcttctctt ctgcagaagc gcagccaagc accctctggg gtttcaggcc    131940
cacacccagc ctgaagttct gggagtggct cactttccaa ccttcagggt ctcccagcag    132000
ctgactgggg agtggtggag ggaaaaggga ttgtattagt ccgttttcac gccgctgatg    132060
aagacatacc cgatactggg cagtctaaaa gatagaggtc tgatggactc acagttccac    132120
gtgactgggg aggcctgaca atcatggtgg aaggtgaaag gcttgtctca cacggtggca    132180
gacaagagaa aagagcttgt gcaggggaac tccccttat aaaaccatca gatctcggga    132240
gacttattca ctatcatgag aacagcacgg gaaagaccct cctctatgat tcaattcct    132300
cccaccaggt ccctcccaca acatgtagga attgtgggaa ctacaattca agatgacatt    132360
tgggtgggga cacagccaaa ccatatcagg gcgtcccaga aagggtatag ggtctgagac    132420
ccaagtcagc atgagaaagt atgcttctca tggtggccca gttgggtgga agtggcagcc    132480
gggccgtctt tccaccaggc cactcaagta gcagctgaga gacccctgcc ctggccagtc    132540
cccgccctcc cctcttgcca ctgcctctgg ttctgaacag atgggcaccc tcatcttgta    132600
tttgtgatta atgtctaaca atgtagtttt gtgagaaggg tttgctgata cagccttgct    132660
gcagatgctg cgaactgtgg cctggggcag accttacctc cagacacgcc ctgaggcagg    132720
ggagggcact ggcccgtagc tggccgagag ctctcgggtt gcgcgacagg atacttttc    132780
agcggctggg tcgctatcca aagtgagaaa acgaggaggg accaggaggc tgtccgcctc    132840
aagagatgtg gggggccaggt ccagttatct ggggaagcag taagcttctc tgctgtttct    132900
aaccccaggc ctccctggt ctaaggcagg gcctcccagc ctcggggcac tttaaagata    132960
tctgggcctg gccccatccc cacagtctga ctgagtgggt ctggataggg cctgagcatt    133020
```

```
ggtgatttcc tgggtgaaag gaggcccctc acagtctctg gaagcttctc tgtgttagga    133080
aaagctctgg gcttgactct gctttgaaag tcaagatccg caaatcctct cagcctcagt    133140
ttctccttca gcaagatgaa atggaaatgc tgtacctacg tcccggggtg gttgtgagac    133200
ccaaaaaaga caatgttctg gaaggttcct ggtgcgttgc agtcctctaa gaacctgagt    133260
tagagccacg ctgagtctca gcttcttggc tccttctgtt tcaaactcgt ccatgtgata    133320
gctcaggaag ggtaggcagg gccctgcccc tactcagaa acaccatcc tggtcctggg      133380
gatccccgca gcattagtcc cctgttttcc cagtgtattg agaaaaattg ctaacaagca    133440
gtggggcaca ccaccagcct cctgggttcc tttcagtttg gggattttg gacattccca     133500
ggaatgtctt aaaaaacact tcaaaaaaca ttaacataaa tattttatc aaagcctgta     133560
ttaaatggtc tttcaagaaa atacagtaac aggtcaggca tggtggctca tgcctgtaac    133620
cccagcactt tgggaggcca aggcaggcag atcacctgaa atcaggagtt caagaccaac    133680
ctggccaaca cagccaaatc ccatctctac aaaaaataca aaattagct gggtgtggtg     133740
gcacacacct gtagtcccag ctacttggga ggccgaggca ggagaattgc ttgatcccgg    133800
aggcggaggt tgcagtgagc tgagatcgtg ccactgcact ccagcgtggg tgacaaggtg    133860
aatctttgtc tcaaaaaaaa aaaaaaaaa aagataaaat acagtataca gtaatagaga     133920
acaatccttt tttcaaagta gtgaccccaa atgaacaaaa tatgcatcta gcttaaatgc    133980
gaacctggtt ttctctacgc ccattcaagc ccctgcaata ggggcccttc accccgcatc    134040
catggactcc taaaattata tggaaaatgg ctgtgtgtga gtgtggatgg acatgtgcac    134100
acatattttt ggctttacca gatgctcaaa gagcctagga cccaaaaagg gctgagaatg    134160
accgtgtcgg ccacttcagg gtcatcagga attgctgtgc actgctcact tctccagtga    134220
acactttctg cttctgtgtt tcctggtatc ctttgggact cctggctagg tcatgtgttt    134280
ctctactttc aaaagggctt cagccaggca cgatggcatg agcctgtagt cccagttgct    134340
ctggaggtta aggtgggaag attgcttgag cccaggaatt tgaggccagc ctgggcaagt    134400
agataggtag atgattgata gatagataga tagataaata gatggataga taagtcgcta    134460
gacagtcatc catccaccca tccacacata aaaaggcctt tgtcatgtca tgttttgtgg    134520
cccacctgcc agtgttgccc acagttgctg cccctccaaa ctcatcagtc actggcaaac    134580
aggaggaatg tgtggctcat gtctgggcat cagtggctgt gggagacatc cttgatcttc    134640
tccagcttct ccttccacat tttcctttgc aatctggcaa tatctattaa aataaaatgt    134700
gcatgccttt tgacctaaga gcttcacttc taggacccac ttacgcgtgt gtgacatgat    134760
gttcatacgg gtttatttat ctgaggttgt tcatacacac cattgcctgt aatcactaaa    134820
ggcgggagca gcctacacat ccatccacag aggagtagat gccttttggt acatccgtgg    134880
cgacggaata ctaagcagcc tgtgtatcta tacactcaca cgtgtttgtt tatgtgtgga    134940
atatctctgg agggtacaca agaaacttaa aatgatcact gtctctgggg agggtacctg    135000
ggtgcctggg aggcaggtca gggaaggagt gggcacaggt attaccaatt ggaagacaat    135060
aaaaacaaca gctcctggcc aggcgcagtg gctcacgcct gtaatggcag cactctgaga    135120
ggctgaggcg ggcagattgc ttgcgtccag gagttcaaga ccagcctggg caacatagca    135180
aaaccccgtt tctattaaaa atacaaaaaa ttagccaggt gtggtggcat gcacctgtaa    135240
tcccagctac tcggaggct gaggtgggag aatcacctga gcctgggagg tcaaggctgc    135300
agtgaggtga gattgtgcca ccgcactcta gcctgggcga tagagcaaga ccctgtctca    135360
aaaacaaaca aaaacagtc cctggcactc tgggccaggc ctggcagggc agttggcagg    135420
```

```
gctggtcttt ctctggcact tcatctcacc ctccctccct tcctcttctt gcagattgaa   135480
acccacaagc tgaccttccg cgagaacgcc aaagccaaga cagaccacgg ggcggagatc   135540
gtgtacaagt cgccagtggt gtctggggac acgtctccac ggcatctcag caatgtctcc   135600
tccaccggca gcatcgacat ggtagactcg ccccagctcg ccacgctagc tgacgaggtg   135660
tctgcctccc tggccaagca gggtttgtga tcaggcccct ggggcggtca ataattgtgg   135720
agaggagaga atgagagagt gtggaaaaaa aagaataat acccggccc cgccctctg    135780 cccccagctg ctcctcgcag ttcggttaat tggttaatca cttaacctgc ttttgtcact   135840
cggctttggc tcgggacttc aaaatcagtg atgggagtaa gagcaaattt catctttcca   135900
aattgatggg tgggctagta ataaaatatt taaaaaaaaa cattcaaaaa catggccaca   135960
tccaacattt cctcaggcaa ttccttttga ttctttttc ttcccctcc atgtagaaga    136020 gggagaagga gaggctctga aagctgcttc tgggggattt caagggactg ggggtgccaa   136080
ccacctctgg ccctgttgtg ggggtgtcac agaggcagtg gcagcaacaa aggatttgaa   136140
acttggtgtg ttcgtggagc cacaggcaga cgatgtcaac cttgtgtgag tgtgacgggg   136200
gttggggtgg ggcgggaggc cacggggag gccgaggcag gggctgggca gaggggagag    136260
gaagcacaag aagtgggagt gggagaggaa gccacgtgct ggagagtaga catccccctc   136320
cttgccgctg ggagagccaa ggcctatgcc acctgcagcg tctgagcggc cgcctgtcct   136380
tggtggccgg gggtgggggc ctgctgtggg tcagtgtgcc accctctgca gggcagcctg   136440
tgggagaagg gacagcgggt aaaaagagaa ggcaagctgg caggagggtg gcacttcgtg   136500
gatgacctcc ttagaaaaga ctgaccttga tgtcttgaga gcgctggcct cttcctccct   136560
ccctgcaggg taggggccct gagttgaggg gcttccctct gctccacaga aaccctgttt   136620
tattgagttc tgaaggttgg aactgctgcc atgatttttgg ccactttgca gacctgggac   136680
tttagggcta accagttctc tttgtaagga cttgtgcctc ttgggagacg tccaccgtt    136740 tccaagcctg ggccactggc atctctggag tgtgtggggg tctgggaggc aggtcccgag   136800 cccctgtcc ttcccacggc cactgcagtc accccgtctg cgccgctgtg ctgttgtctg    136860
ccgtgagagc ccaatcactg cctataccc tcatcacacg tcacaatgtc ccgaattccc    136920
agcctcacca cccttctca gtaatgaccc tggttggttg caggaggtac ctactccata    136980
ctgagggtga aattaaggga aggcaaagtc caggcacaag agtgggaccc cagcctctca   137040
ctctcagttc cactcatcca actgggaccc tcaccacgaa tctcatgatc tgattcggtt   137100
ccctgtctcc tcctcccgtc acagatgtga gccaggcac tgctcagctg tgaccctagg    137160
tgtttctgcc ttgttgacat ggagagagcc ctttcccctg agaaggcctg gccccttcct   137220
gtgctgagcc cacagcagca ggctgggtgt cttggttgtc agtggtggca ccaggatgga   137280
agggcaaggc acccagggca ggcccacagt cccgctgtcc cccacttgca ccctagcttg   137340
tagctgccaa cctcccagac agcccagccc gctgctcagc tccacatgca tagtatcagc   137400
cctccacacc cgacaaaggg gaacacaccc ccttggaaat ggttcttttc ccccagtccc   137460
agctggaagc catgctgtct gttctgctgg agcagctgaa catatacata gatgttgccc   137520
tgccctcccc atctgcaccc tgttgagttg tagttggatt tgtctgtttta tgcttggatt   137580 caccagagtg actatgatag tgaaaagaaa aaaaaaaaa aaaaggacg catgtatctt    137640 gaaatgcttg taaagaggtt tctaacccac cctcacgagg tgtctctcac ccccacactg   137700
ggactcgtgt ggcctgtgtg gtgccaccct gctggggcct cccaagtttt gaaaggcttt   137760
```

```
cctcagcacc tgggacccaa cagagaccag cttctagcag ctaaggaggc cgttcagctg   137820
tgacgaaggc ctgaagcaca ggattaggac tgaagcgatg atgtcccctt ccctacttcc   137880
ccttggggct ccctgtgtca gggcacagac taggtcttgt ggctggtctg gcttgcggcg   137940
cgaggatggt tctctctggt catagcccga agtctcatgg cagtcccaaa ggaggcttac   138000
aactcctgca tcacaagaaa aaggaagcca ctgccagctg gggggatctg cagctcccag   138060
aagctccgtg agcctcagcc acccctcaga ctgggttcct ctccaagctc gccctctgga   138120
ggggcagcgc agcctcccac caagggccct gcgaccacag cagggattgg gatgaattgc   138180
ctgtcctgga tctgctctag aggcccaagc tgcctgcctg aggaaggatg acttgacaag   138240
tcaggagaca ctgttcccaa agccttgacc agagcacctc agcccgctga ccttgcacaa   138300
actccatctg ctgccatgag aaaagggaag ccgcctttgc aaaacattgc tgcctaaaga   138360
aactcagcag cctcaggccc aattctgcca cttctggttt gggtacagtt aaaggcaacc   138420
ctgagggact tggcagtaga atccagggc ctcccctggg gctggcagct tcgtgtgcag   138480
ctagagcttt acctgaaagg aagtctctgg gcccagaact ctccaccaag agcctccctg   138540
ccgttcgctg agtcccagca attctcctaa gttgaaggga tctgagaagg agaaggaaat   138600
gtggggtaga tttggtggtg gttagagata tgccccctc attactgcca acagtttcgg   138660
ctgcatttct tcacgcacct cggttcctct tcctgaagtt cttgtgccct gctcttcagc   138720
accatgggcc ttcttatacg gaaggctctg ggatctcccc cttgtgggc aggctcttgg   138780 ggccagccta agatcatggt ttagggtgat cagtgctggc agataaattg aaaaggcacg   138840
ctggcttgtg atcttaaatg aggacaatcc ccccagggct gggcactcct cccctcccct   138900
cacttctccc acctgcagag ccagtgtcct tgggtgggct agataggata tactgtatgc   138960
cggctccttc aagctgctga ctcactttat caatagttcc atttaaattg acttcagtgg   139020
tgagactgta tcctgtttgc tattgcttgt tgtgctatgg ggggagggg gaggaatgtg   139080 taagatagtt aacatgggca aagggagatc ttggggtgca gcacttaaac tgcctcgtaa   139140 ccctttttcat gatttcaacc acatttgcta gagggaggga gcagccacgg agttagaggc   139200
ccttggggtt tctctttttcc actgacaggc tttcccaggc agctggctag ttcattccct   139260
ccccagccag gtgcaggcgt aggaatatgg acatctggtt gctttggcct gctgccctct   139320
ttcaggggtc ctaagcccac aatcatgcct ccctaagacc ttggcatcct tccctctaag   139380
ccgttggcac ctctgtgcca cctctcacac tggctccaga cacacagcct gtgcttttgg   139440
agctgagatc actcgcttca ccctcctcat cttttgttctc caagtaaagc cacgaggtcg   139500
gggcgagggc agaggtgatc acctgcgtgt cccatctaca gacctgcagc ttcataaaac   139560
ttctgatttc tcttcagctt tgaaaagggt taccctgggc actggcctag agcctcacct   139620
cctaatagac ttagccccat gagtttgcca tgttgagcag gactatttct ggcacttgca   139680
agtcccatga tttcttcggt aattctgagg gtgggggag ggacatgaaa tcatcttagc   139740
ttagctttct gtctgtgaat gtctatatag tgtattgtgt gttttaacaa atgatttaca   139800
ctgactgttg ctgtaaaagt gaatttggaa ataaagttat tactctgatt aaataaggtc   139860
tccattcatg gattccaagg acaagaaagt catatagaat gtctattttt taagttcttt   139920
cccacgcacc cttagataat ttagctcaga acaggaaatg atagtattaa taaaagctgg   139980
acatcaggat taacagctct ctctggggcc ctgaaggtga gagttctcag acttgctcat   140040
ttgcagttgc ttctttgtga tgctggcaaa ccatcctagt cccattcaaa gggcaataca   140100
aagccttgtg gctgacctca cgatgcagca ctcagtttgc aagaccggca ccagtgtatg   140160
```

-continued

```
caaacctgag aaggttgggg atgaggatat gggatctttc atccctggaa atttagtcca    140220
gaggcctggg gctggagcag aacaccaagc caatcagctt aatgaatggc ttagattcct    140280
gctaggtttg cagagctgcc ttctttcctt tggtacctta ttatagattg aggagtattt    140340
ctgctaaacc aagatgggga taaccagata gcatcttcat agcaatgcca caaaggaaaa    140400
caaaaacaaa acagtaatcc atcatattat tccttagtaa ctatgccaag gtcatgatac    140460
tgaatcctta gattgtttca aaatactact tttctttgct cttcctgatg tgtttgccac    140520
cgcaggcaga tgtttaagta aaacagattt taactgcagc tacaaaagca gcaacaggcc    140580
agcaaaagag aagtgctatc tcagagagca tggctttcag agccacaaga gacagcctca    140640
ctggctgttt cagcttgact gccatgcaaa gaagagagca gagggagaac cagcccacc    140700 cacttattca tcttgtacaa aaaaaaagca cctaccagcc taggctacat agtgagacac    140760
tatctccaca aaaaacccac gaaaactagc tgggtatggt ggcacatgcc tacagtccca    140820
gctactggta aggctgtggt gggaggatct cttgaggcca ggaaggagat ccaggctgca    140880
gtgagccaag attgcaccac tgcactccag tctggacaat cgagcaagat cccatctcaa    140940
acaataaaaa aaaaaagcgt gtaacctcct cagaagaaag atgttataat ctcaggcagc    141000
a                                                                  141001
```

METHODS FOR TREATING ALZHEIMER'S DISEASE

CROSS-REFERENCE TO RELATED APPLICATION(S)

This is a continuation of U.S. patent application Ser. No. 14/387,853, filed on Sep. 25, 2014, which is a U.S. national stage entry of International Patent Application No. PCT/US2013/031500, filed on Mar. 14, 2013, which claims priority to U.S. Provisional Patent Application No. 61/719,149, filed on Oct. 26, 2012, U.S. Provisional Patent Application No. 61/660,676, filed on Jun. 15, 2012, and U.S. Provisional Patent Application No. 61/618,435, filed on Mar. 30, 2012, the entire contents of each of which are fully incorporated herein by reference.

GOVERNMENTAL RIGHTS

This invention was made with government support under AG005681 and NS074194 awarded by the National Institutes of Health. The government has certain rights in the invention.

SEQUENCE LISTING

Incorporated by reference herein in its entirety is a computer-readable nucleotide/amino acid sequence listing submitted concurrently herewith and identified as follows: One 444,816 Byte ASCII (Text) file named "206335-9002-US04-SEQ-LIST-03-11-19.txt," created on Mar. 11, 2019.

FIELD

Provided are methods for treating, preventing, or ameliorating neurodegenerative diseases, including tauopathies, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, and Dravet's Syndrome by inhibiting expression of Tau or modulating the splicing of Tau in an animal. Certain embodiments are directed to methods, compounds and compositions for treating, preventing or ameliorating a seizure disorder by inhibiting expression of Tau or modulating the splicing of Tau in an animal.

BACKGROUND

The primary function of Tau is to bind to and stabilize microtubules, which are important structural components of the cytoskeleton involved in mitosis, cytokinesis, and vesicular transport. Tau is found in multiple tissues, but is particularly abundant in axons of neurons. In humans, there are six isoforms of Tau that are generated by alternative splicing of exons 2, 3, and 10. Splicing of exons 2 and 3 at the N-terminus of the protein leads to inclusion of zero, one, or two 29 amino acid acidic domains and is termed 0N, 1N, or 2N Tau respectively. The influence of these domains on Tau function is not fully clear, though may play a role in interactions with the plasma membrane. Inclusion of exon 10 at the C-terminus leads to inclusion of the microtubule binding domain encoded by exon 10. Since there are 3 microtubule binding domains elsewhere in Tau, this Tau isoform (with exon 10 included) is termed 4R Tau, where 'R' refers to the number of repeats of microtubule binding domains. Tau without exon 10 is termed 3R Tau. Since more microtubule binding domains (4R compared with 3R) increases the binding to microtubules, 4R Tau presumably significantly increases microtubule binding and assembly. The ratio of 3R/4R Tau is developmentally regulated, with fetal tissues expressing exclusively 3R Tau and adult human tissues expressing approximately equal levels of 3R/4R Tau. Deviations from the normal ratio of 3R/4R Tau are characteristic of neurodegenerative FTD Tauopathies. It is not known how changing the 3R/4R Tau ratio at a later stage in the adult animal will affect Tau pathogenesis.

Serine-threonine directed phosphorylation regulates the microtubule binding ability of Tau. Hyperphosphorylation promotes detachment of Tau from microtubules. Other post translational modifications of Tau have been described; however the significance of these is unclear. Phosphorylation of Tau is also developmentally regulated with higher phosphorylation in fetal tissues and much lower phosphorylation in the adult. One characteristic of neurodegenerative disorders is aberrantly increased Tau phosphorylation.

The microtubule network is involved in many important processes within the cell including structural integrity needed for maintaining morphology of cells and operating transport machinery. Since binding of Tau to microtubules stabilizes microtubules, Tau is likely to be a key mediator of some of these processes and disruption of normal Tau in neurodegenerative diseases may disrupt some of these key cellular processes.

One of the early indicators that Tau may be important in neurodegenerative syndromes was the recognition that Tau is a key component of neurofibrillary inclusions in Alzheimer's disease. In fact, neurofibrillary inclusions are aggregates of hyperphosphorylated Tau protein. Along with amyloid beta containing plaques, neurofibrillary inclusions are a hallmark of Alzheimer's disease and correlate significantly with cognitive impairment. 95% of Tau accumulations in AD are found in neuronal processes and is termed neuritic dystrophy. The process(es) whereby this microtubule associated protein becomes disengaged from microtubules and forms accumulations of proteins and how this relates to neuronal toxicity is not well understood.

Neuronal Tau inclusions are a pathological characteristic of not only Alzheimer's disease, but also a subset of Frontotemporal dementia (FTD), PSP, and CBD. The link between Tau and neurodegeneration was solidified by the discovery that mutations in the Tau gene cause a subset of FTD. These genetic data have also highlighted the importance of the 3R:4R ratio of Tau. Many of the Tau mutations that cause FTD lead to a change in Tau splicing which leads to preferential inclusion of exon 10, and thus to increased 4R Tau. The overall Tau levels are normal. Whether the Tau isoform change or the amino acid change or both cause neurodegeneration remains unknown. Recent data suggest that PSP may also be associated with an increased 4R:3R Tau ratio and thus may be amenable to a similar splicing strategy.

To help understand the influence of Tau ratios on neurodegeneration, a mouse model based on one of the splicing Tau mutations (N279K) has been generated using a minigene that includes the Tau promoter and the flanking intronic sequences of exon 10. As in humans, these mice demonstrate increased levels of 4R Tau compared with transgenics expressing WT Tau and develop behavioral and motor abnormalities as well as accumulations of aggregated Tau in the brain and spinal cord.

The protein "Tau" has been associated with multiple diseases of the brain including Alzheimer's disease, frontotemporal dementia, progressive supranuclear palsy, corticobasal ganglionic degeneration, dementia pugilistica, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, argyrophilic grain disease, corticobasal degeneration or frontotemporal lobar degeneration and others. Tau-associated disorders such as AD are the most common cause of dementia in the elderly. AD affects an estimated 15 million people worldwide and 40% of the population above 85 years of age. AD is characterized by two pathological hallmarks: Tau neurofibrillary inclusions (NFT) and amyloid-β (Aβ) plaques.

In seizure disorders, the brain's electrical activity is periodically disturbed, resulting in some degree of temporary brain dysfunction. Normal brain function requires an orderly, organized, coordinated discharge of electrical impulses. Electrical impulses enable the brain to communicate with the spinal cord, nerves, and muscles as well as within itself. Seizures may result when the brain's electrical activity is disrupted. There are two basic types of seizures; epileptic and nonepileptic. Epileptic seizures have no apparent cause or trigger and occur repeatedly. Nonepileptic seizures are triggered or provoked by a disorder or another condition that irritates the brain. Certain mental disorders can cause seizure symptoms referred to as psychogenic nonepileptic seizures.

Alzheimer's Disease (AD) is known to be a clinical risk factor for late onset seizures. Multiple AD mouse models recapitulate this increased seizure susceptibility. Within the last 5 years, many of these AD models have been studied in the setting of mouse tau knockout (tau−/−). Increased seizure susceptibility was ameliorated in these amyloid-depositing tau knockout lines. Further, tau−/− alone interestingly appeared to be protective against chemically induced seizures.

Anticonvulsants represent the common treatment regime for seizures. However, anticonvulsants are ineffective in a significant percent of people with a seizure disorder and for these individuals, surgery is the only option. Amidst the lack of available treatments for seizure disorders and neurodegenerative diseases, certain methods of the present embodiments provide methods for treating, preventing or ameliorating a seizure disorder and neurodegenerative diseases by inhibiting expression of Tau or modulating the splicing of Tau in an animal.

SUMMARY

Provided herein are methods for modulating levels of Tau mRNA and protein in cells, tissues, and animals. Also provided herein are methods for modulating splicing of Tau mRNA in cells, tissues, and animals. Also provided herein are methods for modulating the expression product of a Tau mRNA in cells, tissues, and animals.

In certain embodiments, modulation can occur in a cell or tissue. In certain embodiments, the cell or tissue is in an animal. In certain embodiments, the animal is human. In certain embodiments, Tau mRNA levels are reduced. In certain embodiments, Tau protein levels are reduced. In certain embodiments, splicing of Tau mRNA is modulated. In certain embodiments, the expression product of a Tau mRNA is modulated. In certain embodiments, exclusion of Tau exon 10 is promoted. In certain embodiments, expression of the 4R isoform of Tau RNA or protein is reduced. In certain embodiments, expression of the 3R isoform of Tau RNA or protein is increased. In certain embodiments, expression of the 4R isoform of Tau RNA or protein is reduced and expression of the 3R isoform of Tau RNA or protein is increased. In certain embodiments, hyperphosphorylated Tau is reduced. Such reduction and modulation can occur in a time-dependent manner or in a dose-dependent manner.

Several embodiments are drawn to methods of reducing or decreasing seizures in a subject. In certain embodiments, methods are provided for reducing the risk for seizure in a subject. In certain embodiments, the seizures are related to neurodegenerative disorders. In certain embodiments, the neurodegenerative disorder is a tau-associated disorder. In certain embodiments, the tau-associated disorder or neurodegenerative disorder is Alzheimer's disease, frontotemporal dementia, progressive supranuclear palsy, corticobasal ganglionic degeneration, dementia pugilistica, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, argyrophilic grain disease, corticobasal degeneration or frontotemporal lobar degeneration. Certain embodiments are drawn to a method of decreasing seizures in a subject with a high 4R:3R tau isoform ratio. In certain embodiments, the methods comprise administering an antisense agent to the subject, wherein the agent decreases expression of tau or decreases the 4R:3R tau ratio in the central nervous system of the subject.

Also provided are methods useful for preventing, treating, and ameliorating diseases, disorders, and conditions associated with Tau. In certain embodiments, such diseases, disorders, and conditions associated with Tau are neurodegenerative diseases. In certain embodiments, the neurodegenerative disease is any of Alzheimer's Disease, Fronto-temporal Dementia (FTD), FTDP-17, Progressive Supranuclear Palsy, Chronic Traumatic Encephalopathy, Epilepsy, or Dravet's Syndrome. In certain embodiments, one or more symptoms of a neurodegenerative disease is ameliorated, prevented, or delayed (progression slowed). In certain embodiments, the symptom is memory loss, anxiety, or loss of motor function. In certain embodiments, neurodegenerative function is improved. In certain embodiments, neurofibrillary inclusions are reduced.

Such diseases, disorders, and conditions can have one or more risk factors, causes, or outcomes in common. Certain risk factors and causes for development of a neurodegenerative disease include genetic predisposition and older age.

In certain embodiments, methods of treatment include administering a Tau antisense compound to an individual in need thereof. The antisense compound may inhibit expression of Tau or modulate splicing of Tau. In certain embodiments, the antisense compound is a single-stranded antisense oligonucleotide. In certain embodiments, the single-stranded antisense oligonucleotide is complementary to a Tau nucleic acid.

The present disclosure provides the following non-limiting numbered embodiments:

Embodiment 1

A method of reducing seizures or risk of seizures in an animal comprising administering a Tau-specific inhibitor to the subject, wherein incidence of seizures or severity of seizures is reduced.

Embodiment 2

The method of embodiment 1, wherein the animal is a human.

Embodiment 3

The method of embodiments 1-2, wherein the Tau-specific inhibitor is an antisense compound.

Embodiment 4

A method comprising administering a Tau antisense compound to an animal for treating a Tau associated disease and thereby ameliorating at least one symptom of the Tau associated disease.

Embodiment 5

A method comprising:
(a) identifying an animal having a Tau associated disease; and
(b) administering a Tau antisense compound and thereby ameliorating at least one symptom of the Tau associated disease.

Embodiment 6

The method of embodiments 4-5, wherein the animal is a human.

Embodiment 7

The method of embodiments 4-6, wherein the symptom is any one of incidence of seizures, seizure severity, presence of neurofibrillary inclusions, loss of memory, loss of cognition, decreased motor function, or bradykinesia.

Embodiment 8

The method of embodiments 4-8, wherein the Tau associated disease is a neurodegenerative disease.

Embodiment 9

The method of embodiment 8, wherein the neurodegenerative disease is selected from among Alzheimer's Disease, Fronto-temporal Dementia (FTD), FTDP-17, Progressive Supranuclear Palsy, Chronic Traumatic Encephalopathy, Epilepsy, and Dravet's Syndrome.

Embodiment 10

The method of embodiments 3-9, wherein the antisense compound comprises a single-stranded antisense oligonucleotide complementary to a Tau nucleic acid.

Embodiment 11

The method of embodiments 1-10, wherein expression of Tau RNA or expression of Tau protein is reduced.

Embodiment 12

The method of embodiments 1-10, wherein expression of the 4R isoform of Tau RNA or expression of the 4R isoform of Tau protein is reduced.

Embodiment 13

The method of embodiments 1-10, wherein expression of the 3R isoform of Tau RNA or expression of the 3R isoform of Tau protein is increased.

Embodiment 14

The method of embodiments 1-10, wherein expression of the 4R isoform of Tau RNA is reduced and expression of the 3R isoform of Tau RNA is increased.

Embodiment 15

The method of embodiments 1-10, wherein expression of the 4R isoform of Tau protein is reduced and expression of the 3R isoform of Tau protein is increased.

Embodiment 16

The method of embodiments 10-15, wherein the single-stranded antisense oligonucleotide comprises at least one modification.

Embodiment 17

The method of embodiment 10-16, wherein the single-stranded antisense oligonucleotide is specifically hybridizable to a human Tau nucleic acid.

Embodiment 18

The method of embodiments 10-17, wherein the single-stranded antisense oligonucleotide is at least 75%, at least 80%, at least 85%, at least 90%, or at least 95% complementary to an equal length portion of a human Tau nucleic acid.

Embodiment 19

The method of embodiments 10-18, wherein the single-stranded antisense oligonucleotide is 100% complementary to a human Tau nucleic acid.

Embodiment 20

The method of embodiments 16-19, wherein the single-stranded antisense oligonucleotide comprises at least one modified internucleoside linkage.

Embodiment 21

The method of embodiment 20, wherein each internucleoside linkage of the single-stranded antisense oligonucleotide is a modified internucleoside linkage.

Embodiment 22

The method of embodiments 20-21, wherein the modified internucleoside linkage is a phosphorothioate internucleoside linkage.

Embodiment 23

The method of embodiments 16-22, comprising at least one modified nucleoside.

Embodiment 24

The method of embodiments 16-23, wherein the single-stranded antisense oligonucleotide comprises at least one modified nucleoside having a modified sugar.

Embodiment 25

The method of embodiment 24, wherein the single-stranded antisense oligonucleotide comprises at least one modified nucleoside comprising a bicyclic sugar.

Embodiment 26

The method of embodiment 25, wherein the bicyclic sugar comprises a 4' to 2' bridge selected from among: 4'-(CH2)n-O-2', wherein n is 1 or 2; and 4'-CH2-O—CH2-2'.

Embodiment 27

The method of embodiment 25, wherein the bicyclic sugar comprises a 4'-CH(CH3)-O-2' bridge.

Embodiment 28

The method of embodiment 24, wherein the at least one modified nucleoside having a modified sugar comprises a non-bicyclic 2'-modified sugar moiety.

Embodiment 29

The method of embodiment 28, wherein the 2'-modified sugar moiety comprises a 2'-O-methoxyethyl group.

Embodiment 30

The method of embodiment 28, wherein the 2'-modified sugar moiety comprises a 2'-O-methyl group.

Embodiment 31

The method of embodiment 24, wherein the at least one modified nucleoside having a modified sugar comprises a sugar surrogate.

Embodiment 32

The method of embodiment 31, wherein the sugar surrogate is a morpholino.

Embodiment 33

The method of embodiment 31, wherein the sugar surrogate is a peptide nucleic acid.

Embodiment 34

The method of embodiments 23-33, wherein each nucleoside is modified.

Embodiment 35

The method of embodiments 10-34, wherein the single-stranded antisense oligonucleotide comprises at least one modified nucleobase.

Embodiment 36

The method of embodiment 35, wherein the modified nucleobase is a 5'-methylcytosine.

Embodiment 37

The method of embodiment 16-35, wherein the single-stranded antisense oligonucleotide comprises:
(a) a gap segment consisting of linked deoxynucleosides;
(b) a 5' wing segment consisting of linked nucleosides;
(c) a 3' wing segment consisting of linked nucleosides;
wherein the gap segment is positioned immediately adjacent to and between the 5' wing segment and the 3' wing segment and wherein each nucleoside of each wing segment comprises a modified sugar.

Embodiment 38

The method of embodiment 37, wherein the single-stranded antisense oligonucleotide comprises:
(a) a gap segment consisting of ten linked deoxynucleosides;
(b) a 5' wing segment consisting of five linked nucleosides;
(c) a 3' wing segment consisting of five linked nucleosides;
wherein the gap segment is positioned immediately adjacent and between the 5' wing segment and the 3' wing segment, wherein each nucleoside of each wing segment comprises a 2'-O-methoxyethyl sugar; and wherein each internucleoside linkage is a phosphorothioate linkage.

Embodiment 39

The method of embodiments 10-37, wherein the single-stranded antisense oligonucleotide consists of 15, 16, 17, 18, 19, 20, 21, 22, 23, 24, or 25 linked nucleosides.

Embodiment 40

The method of any preceding embodiment, wherein the administering is parenteral administration.

Embodiment 41

The method of embodiment 40, wherein the parenteral administration is any of injection or infusion.

Embodiment 42

The method of embodiments 40-41, wherein the parenteral administration is any of intrathecal administration or intracerebroventricular administration.

Embodiment 43

A method comprising administering a Tau antisense compound to an animal for treating a Tau associated disease and thereby reducing neurofibrillary inclusions.

Embodiment 44

A method comprising administering a Tau antisense compound to an animal for treating a Tau associated disease and thereby improving neurological function.

Embodiment 45

A method comprising:
(a) identifying an animal having a Tau associated disease; and
(b) administering a Tau antisense compound and thereby reducing neurofibrillary inclusions.

Embodiment 46

A method comprising:
(a) identifying an animal having a Tau associated disease; and
(b) administering a Tau antisense compound and thereby improving neurological function.

Embodiment 47

The method of embodiments 43-46, wherein the animal is a human.

Embodiment 48

The method of embodiments 43-47, wherein the antisense compound comprises a single-stranded antisense oligonucleotide complementary to a Tau nucleic acid.

Embodiment 49

The method of embodiments 43-48, wherein the Tau associated disease is a neurodegenerative disease.

Embodiment 50

The method of embodiment 49, wherein the neurodegenerative disease is selected from among Alzheimer's Disease, Fronto-temporal Dementia (FTD), FTDP-17, Progressive Supranuclear Palsy, Chronic Traumatic Encephalopathy, Epilepsy, and Dravet's Syndrome.

Embodiment 51

The method of embodiments 43-50, wherein the expression of Tau RNA or expression of Tau protein is reduced.

Embodiment 52

The method of embodiments 43-50, wherein expression of the 4R isoform of Tau RNA or expression of the 4R isoform of Tau protein is reduced.

Embodiment 53

The method of embodiments 43-50, wherein expression of the 3R isoform of Tau RNA or expression of the 3R isoform of Tau protein is increased.

Embodiment 54

The method of embodiments 43-50, wherein expression of the 4R isoform of Tau RNA is reduced and expression of the 3R isoform of Tau RNA is increased.

Embodiment 55

The method of embodiments 43-50, wherein expression of the 4R isoform of Tau protein is reduced and expression of the 3R isoform of Tau protein is increased.

Embodiment 56

The method of embodiments 48-55, wherein the single-stranded antisense oligonucleotide comprises at least one modification.

Embodiment 57

The method of embodiment 48-56, wherein the single-stranded antisense oligonucleotide is specifically hybridizable to a human Tau nucleic acid.

Embodiment 58

The method of embodiments 48-57, wherein the single-stranded antisense oligonucleotide is at least 75%, at least 80%, at least 85%, at least 90%, or at least 95% complementary to an equal length portion of a human Tau nucleic acid.

Embodiment 59

The method of embodiments 48-58, wherein the single-stranded antisense oligonucleotide is 100% complementary to a human Tau nucleic acid.

Embodiment 60

The method of embodiments 56-59, wherein the single-stranded antisense oligonucleotide comprises at least one modified internucleoside linkage.

Embodiment 61

The method of embodiment 60, wherein each internucleoside linkage of the single-stranded antisense oligonucleotide is a modified internucleoside linkage.

Embodiment 62

The method of embodiments 60-61, wherein the modified internucleoside linkage is a phosphorothioate internucleoside linkage.

Embodiment 63

The method of embodiments 56-62, comprising at least one modified nucleoside.

Embodiment 64

The method of embodiments 56-63, wherein the single-stranded antisense oligonucleotide comprises at least one modified nucleoside having a modified sugar.

Embodiment 65

The method of embodiment 64, wherein the single-stranded antisense oligonucleotide comprises at least one modified nucleoside comprising a bicyclic sugar.

Embodiment 66

The method of embodiment 65, wherein the bicyclic sugar comprises a 4' to 2' bridge selected from among: 4'-(CH2)n-O-2', wherein n is 1 or 2; and 4'-CH2-O—CH2-2'.

Embodiment 67

The method of embodiment 65, wherein the bicyclic sugar comprises a 4'-CH(CH3)-O-2' bridge.

Embodiment 68

The method of embodiment 64, wherein the at least one modified nucleoside having a modified sugar comprises a non-bicyclic 2'-modified sugar moiety.

Embodiment 69

The method of embodiment 68, wherein the 2'-modified sugar moiety comprises a 2'-O-methoxyethyl group.

Embodiment 70

The method of embodiment 68, wherein the 2'-modified sugar moiety comprises a 2'-O-methyl group.

Embodiment 71

The method of embodiment 64, wherein the at least one modified nucleoside having a modified sugar comprises a sugar surrogate.

Embodiment 72

The method of embodiment 71, wherein the sugar surrogate is a morpholino.

Embodiment 73

The method of embodiment 71, wherein the sugar surrogate is a peptide nucleic acid.

Embodiment 74

The method of embodiments 63-73, wherein each nucleoside is modified.

Embodiment 75

The method of embodiments 48-74, wherein the single-stranded antisense oligonucleotide comprises at least one modified nucleobase.

Embodiment 76

The method of embodiment 75, wherein the modified nucleobase is a 5'-methylcytosine.

Embodiment 77

The method of embodiment 56-75, wherein the single-stranded antisense oligonucleotide comprises:
(a) a gap segment consisting of linked deoxynucleosides;
(b) a 5' wing segment consisting of linked nucleosides;
(c) a 3' wing segment consisting of linked nucleosides;
wherein the gap segment is positioned immediately adjacent to and between the 5' wing segment and the 3' wing segment and wherein each nucleoside of each wing segment comprises a modified sugar.

Embodiment 78

The method of embodiment 77, wherein the single-stranded antisense oligonucleotide comprises:
(a) a gap segment consisting of ten linked deoxynucleosides;
(b) a 5' wing segment consisting of five linked nucleosides;
(c) a 3' wing segment consisting of five linked nucleosides;
wherein the gap segment is positioned immediately adjacent and between the 5' wing segment and the 3' wing segment, wherein each nucleoside of each wing segment comprises a 2'-O-methoxyethyl sugar; and wherein each internucleoside linkage is a phosphorothioate linkage.

Embodiment 79

The method of embodiments 48-77, wherein the single-stranded antisense oligonucleotide consists of 15, 16, 17, 18, or 19 linked nucleosides.

Embodiment 80

The method of embodiments 48-78, wherein the single-stranded antisense oligonucleotide consists of 20 linked nucleosides.

Embodiment 81

The method of embodiments 48-77, wherein the single-stranded antisense oligonucleotide consists of 21, 22, 23, 24, or 25 linked nucleosides.

Embodiment 82

The method of embodiments 43-82 preceding embodiment, wherein the administering is parenteral administration.

Embodiment 83

The method of embodiment 82, wherein the parenteral administration is any of injection or infusion.

Embodiment 84

The method of embodiments 82-83, wherein the parenteral administration is any of intrathecal administration or intracerebroventricular administration.

Embodiment 85

The method of embodiments 43-84, wherein at least one symptom of a Tau associated disease is ameliorated.

Embodiment 86

The method of embodiments 43-85, wherein at least one symptom of a Tau associated disease is prevented.

Embodiment 87

The method of embodiments 43-86, wherein progression of at least one symptom of a Tau associated disease is slowed.

Embodiment 88

The method of embodiments 85-87, wherein the at least one symptom is any of memory loss, anxiety, loss of motor function, incidence of seizures, severity of seizures, and excitotoxicity.

Embodiment 89

A method of decreasing seizures in a subject with a high 4R:3R tau isoform ratio, the method comprising administering an antisense oligonucleotide to the subject, wherein the method decreases the 4R:3R tau ratio in the central nervous system of the subject.

Embodiment 90

The method of embodiment 89, wherein the high 4R:3R tau isoform ratio in the subject is caused by a splicing defect.

Embodiment 91

The method of embodiment 89, further comprising decreasing the accumulation of aggregated tau in the brain and spinal cord of the subject.

Embodiment 92

The method of embodiment 89, wherein the antisense oligonucleotide is an o methyl oligonucleotide.

Embodiment 93

The method of embodiment 89, wherein the oligonucleotide is administered using a single bolus administration.

Embodiment 94

The method of embodiment 89, wherein the oligonucleotide is administered using a pump.

Embodiment 95

The method of embodiment 89, wherein the total amount of tau in the central nervous system is not changed.

Embodiment 96

A method of modifying a neurodegenerative syndrome in a subject with a high 4R:3R tau isoform ratio, the method comprising administering an antisense oligonucleotide to the central nervous system of the subject, wherein the antisense oligonucleotide decreases the high 4R:3R tau ratio in the central nervous system of the subject.

Embodiment 97

The method of embodiment 89, wherein the high 4R:3R tau isoform ratio in the subject is caused by a splicing defect.

Embodiment 98

The method of embodiment 89, wherein the neurodegenerative syndrome is a neurodegenerative syndrome associated with tau.

Embodiment 99

The method of embodiment 91, wherein the neurodegenerative syndrome neurodegenerative syndrome associated with tau is associated with tau multimerization.

Embodiment 100

The method of embodiment 89, wherein the neurodegenerative syndrome is Alzheimer's disease, progressive supranuclear palsy, dementia pugilistica, frontotemporal dementia, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, corticobasal degeneration, argyrophilic grain disease, supranuclear palsy, corticobasal degeneration, frontotemporal dementia, or frontotemporal lobar degeneration.

Embodiment 101

The method of embodiment 89, wherein the neurodegenerative syndrome is Alzheimer's disease, progressive supranuclear palsy, corticobasal degeneration, or frontotemporal dementia.

Embodiment 102

The method of embodiment 89, wherein modifying a neurodegenerative disease improves the behavioral phenotype of the subject.

Embodiment 103

The method of embodiment 95, wherein the behavioral phenotype of the subject is seizures.

Embodiment 104

The method of embodiment 89, wherein modifying a neurodegenerative disease slows the progression of neurodegenerative disease development in the subject.

Embodiment 105

The method of embodiment 89, wherein modifying a neurodegenerative disease decreases the accumulation of aggregated tau in the brain and spinal cord of the subject.

Embodiment 106

The method of embodiment 89, wherein the antisense oligonucleotide is an o methyl oligonucleotide.

Embodiment 107

The method of embodiment 89, wherein the oligonucleotide is administered using a single bolus administration.

Embodiment 108

The method of embodiment 89, wherein the oligonucleotide is administered using a pump.

Embodiment 109

The method of embodiment 89, wherein the abnormal 4R:3R tau ratio in the central nervous system is decreased without decreasing the total amount of tau in the central nervous system.

Embodiment 110

The method of embodiment 89, wherein the antisense oligo alters the splicing of a nucleic acid encoding tau.

Embodiment 111

A method of reducing seizures or risk of seizures in a subject comprising administering tau-specific inhibitor to the subject, wherein seizures or risk of seizures in the subject is reduced.

Embodiment 112

The method of embodiment 111, wherein the tau-specific inhibitor is a transcriptional inhibitor.

Embodiment 113

The method of embodiment 112, wherein the transcriptional inhibitor is an oligonucleotide.

Embodiment 114

The method of embodiment 113, wherein the oligonucleotide comprises a nucleobase sequence at least 80%, at least 85%, at least 90%, at least 95%, at least 96%, at least 97%, at least 98%, 99% or at least 100% complementary to an equal length portion of a nucleic acid encoding Tau such as any one of SEQ ID NOs: 1-10.

Embodiment 115

The method of embodiment 113 or 114, wherein the oligonucleotide is a modified oligonucleotide.

Embodiment 116

The method of embodiment 113 or 114, wherein the oligonucleotide is an antisense oligonucleotide.

Embodiment 117

The method of any of embodiment 113-115, wherein the oligonucleotide is a single-stranded oligonucleotide.

Embodiment 118

The method of any of embodiments 113-116, wherein the oligonucleotide consists of 12 to 30 linked nucleosides.

Embodiment 119

The method of any of embodiments 113-118, wherein oligonucleotide comprises at least one modified internucleoside linkage.

Embodiment 120

The method of any of embodiments 119, wherein the modified internucleoside linkage is a phosphorothioate internucleoside linkage.

Embodiment 121

The method of any of embodiments 119, wherein each modified internucleoside linkage is a phosphorothioate internucleoside linkage.

Embodiment 122

The method of any of embodiments 113-121, wherein the oligonucleotide comprises at least one modified sugar moiety.

Embodiment 123

The method of embodiment 122, wherein the modified sugar moiety is a bicyclic sugar moiety.

Embodiment 124

The method of embodiment 122, wherein the modified sugar moiety is a 2' substituted sugar moiety.

Embodiment 125

The method of embodiment 124, wherein the 2' substituted sugar moiety is selected from among: 2'-O-methoxyethyl (2'-MOE), 2'-OMe, or 2'-Fl.

Embodiment 126

The method of any of embodiments 113-124, wherein the oligonucleotide comprises at least one modified nucleobase.

Embodiment 127

The method of embodiment 126, wherein the modified nucleobase is a 5-methylcytosine.

Embodiment 128

The method of any of embodiment 113-126, wherein the oligonucleotide is a chimeric oligonucleotide.

Embodiment 129

The method of any of embodiments 113-127, wherein the oligonucleotide comprises: (i) a gap segment consisting of linked deoxynucleosides; (ii) a 5' wing segment consisting of linked nucleosides; (iii) a 3' wing segment consisting of linked nucleosides, wherein the gap segment is positioned immediately adjacent to and between the 5' wing segment and the 3' wing segment and wherein each nucleoside of each wing segment comprises a modified sugar.

Embodiment 130

The method of embodiment 128, wherein the oligonucleotide comprises: (i) a gap segment consisting of ten linked deoxynucleosides; (ii) a 5' wing segment consisting of five linked nucleosides; (iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

Embodiment 131

The method of embodiment 111-130, wherein the inhibitor is administered to the CNS of the subject.

Embodiment 132

The method of embodiment 131, wherein the inhibitor is administered by intrathecal or intracerebral vascular administration.

Embodiment 133

The method of embodiment 131 or 132, wherein the administration is by bolus or infusion.

Embodiment 134

The method of any of embodiments 131-133, wherein the administration is by a pump.

Embodiment 135

A method of reducing seizures or the risk of seizures in a subject comprising administering a tau splice modulating agent to the subject, wherein the seizures or risk of seizures in the subject is reduced.

Embodiment 136

A method of reducing seizures or the risk of seizures in a subject comprising administering an oligonucleotide consists of 12 to 30 linked nucleosides, wherein the oligonucleotide comprises a nucleobase sequence at least 80%, at least 85%, at least 90%, at least 95%, at least 96%, at least 97%, at least 98%, 99% or at least 100% complementary to an equal length portion of a nucleic acid encoding Tau such as any one of SEQ ID NOs:1-10 and, wherein the seizures or risk of seizures in the subject is reduced.

Embodiment 137

The method of embodiment 135, wherein the tau splice modulating agent is an oligonucleotide.

Embodiment 138

The method of embodiment 136-137, wherein the oligonucleotide comprises at least one modified nucleoside.

Embodiment 139

The method of embodiment 138, wherein at least one modified nucleoside comprises a modified sugar moiety.

Embodiment 140

The method of embodiment 139, wherein at least one modified sugar moiety is a 2'-substituted sugar moiety.

Embodiment 141

The method of embodiment 140, wherein the 2'-substitutent of at least one 2'-substituted sugar moiety is selected from among: 2'-OMe, 2'-F, and 2'-MOE.

Embodiment 142

The method of embodiment 140, wherein the 2'-substituent of at least one 2'-substituted sugar moiety is a 2'-MOE.

Embodiment 143

The method of embodiments 139, wherein at least one modified sugar moiety is a bicyclic sugar moiety.

Embodiment 144

The method of embodiment 143, wherein at least one bicyclic sugar moiety is LNA or cEt.

Embodiment 145

The method of embodiment 139, wherein at least one modified sugar moiety is a sugar surrogate.

Embodiment 146

The method of embodiment 145, wherein at least one sugar surrogate is a morpholino.

Embodiment 147

The method of embodiment 145, wherein at least one sugar surrogate is a modified morpholino.

Embodiment 148

The method of embodiments 136-147, wherein the oligonucleotide comprises at least 5 modified nucleosides, each independently comprising a modified sugar moiety.

Embodiment 149

The method of embodiments 136-148, wherein the oligonucleotide comprises at least 10 modified nucleosides, each independently comprising a modified sugar moiety.

Embodiment 150

The method of embodiments 136-499, wherein the oligonucleotide comprises at least 15 modified nucleosides, each independently comprising a modified sugar moiety.

Embodiment 151

The method of embodiments 136-150, wherein each nucleoside of the oligonucleotide is a modified nucleoside, each independently comprising a modified sugar moiety Embodiment 152

The method of embodiments 136-141, wherein the oligonucleotide comprises at least two modified nucleosides comprising modified sugar moieties that are the same as one another.

Embodiment 153

The method of embodiments 136-147, wherein the oligonucleotide comprises at least two modified nucleosides comprising modified sugar moieties that are different from one another.

Embodiment 154

The method of embodiments 136-147, wherein the oligonucleotide comprises a modified region of at least 5 contiguous modified nucleosides.

Embodiment 155

The method of embodiments 136-147, wherein the oligonucleotide comprises a modified region of at least 10 contiguous modified nucleosides.

Embodiment 156

The method of embodiments 136-147, wherein the oligonucleotide comprises a modified region of at least 15 contiguous modified nucleosides.

Embodiment 157

The method of embodiments 136-147, wherein the oligonucleotide comprises a modified region of at least 20 contiguous modified nucleosides.

Embodiment 158

The method of embodiments 154-157, wherein each modified nucleoside of the modified region has a modified sugar moiety independently selected from among: 2'-F, 2'-OMe, 2'-MOE, cEt, LNA, morpholino, and modified morpholino.

Embodiment 159

The method of embodiments 154-158, wherein the modified nucleosides of the modified region each comprise the same modification as one another.

Embodiment 160

The method of embodiment 159, wherein the modified nucleosides of the modified region each comprise the same 2'-substituted sugar moiety.

Embodiment 161

The method of embodiment 160, wherein the 2'-substituted sugar moiety of the modified nucleosides of the region of modified nucleosides is selected from 2'-F, 2'-OMe, and 2'-MOE.

Embodiment 162

The method of embodiment 160, wherein the 2'-substituted sugar moiety of the modified nucleosides of the region of modified nucleosides is 2'-MOE.

Embodiment 163

The method of embodiment 159, wherein the modified nucleosides of the region of modified nucleosides each comprise the same bicyclic sugar moiety.

Embodiment 164

The method of embodiment 163, wherein the bicyclic sugar moiety of the modified nucleosides of the region of modified nucleosides is selected from LNA and cEt.

Embodiment 165

The method of embodiment 159, wherein the modified nucleosides of the region of modified nucleosides each comprises a sugar surrogate.

Embodiment 166

The method of embodiment 165, wherein the sugar surrogate of the modified nucleosides of the region of modified nucleosides is a morpholino.

Embodiment 167

The method of embodiment 165, wherein the sugar surrogate of the modified nucleosides of the region of modified nucleosides is a modified morpholino.

Embodiment 168

The method of embodiments 136-167, wherein the oligonucleotide comprises no more than 4 contiguous naturally occurring nucleosides.

Embodiment 169

The method of embodiments 136-167, wherein each nucleoside of the oligonucleotide is a modified nucleoside.

Embodiment 170

The method of embodiment 169, wherein each modified nucleoside comprises a modified sugar moiety.

Embodiment 171

The method of embodiment 170, wherein the modified nucleosides of the modified oligonucleotide comprise the same modification as one another.

Embodiment 172

The method of embodiment 171, wherein the modified nucleosides of the modified oligonucleotide each comprise the same 2'-substituted sugar moiety.

Embodiment 173

The method of embodiment 172, wherein the 2'-substituted sugar moiety of the modified oligonucleotide is selected from 2'-F, 2'-OMe, and 2'-MOE.

Embodiment 174

The method of embodiment 172, wherein the 2'-substituted sugar moiety of the modified oligonucleotide is 2'-MOE.

Embodiment 175

The method of embodiment 171, wherein the modified nucleosides of the oligonucleotide each comprise the same bicyclic sugar moiety.

Embodiment 176

The method of embodiment 175, wherein the bicyclic sugar moiety is selected from LNA and cEt.

Embodiment 177

The method of embodiment 169, wherein the modified nucleosides of the oligonucleotide each comprises a sugar surrogate.

Embodiment 178

The method of embodiment 177, wherein the sugar surrogate is a morpholino.

Embodiment 179

The method of embodiment 178, wherein the sugar surrogate is a modified morpholino.

Embodiment 180

The method of embodiments 136-179, wherein the oligonucleotide comprises at least one modified internucleoside linkage.

Embodiment 181

The method of embodiments 136-180, wherein each internucleoside linkage is a modified internucleoside linkage.

Embodiment 182

The method of embodiments 178-181, the modified internucleoside linkage is a phosphorothioate internucleoside linkage.

Embodiment 183

The method of embodiments 136-149, wherein each internucleoside linkage is a modified internucleoside linkage and wherein each internucleoside linkage comprises the same modification.

Embodiment 184

The method of embodiment 183, wherein each internucleoside linkage is a phosphorothioate internucleoside linkage.

Embodiment 185

The method of embodiment 135-184, wherein the subject has a high 4R-3R tau isoform ratio.

Embodiment 186

The method of embodiments 135-185, wherein 4R:3R tau ratio is reduced in the central nervous system of the subject.

Embodiment 187

The method of embodiments 185, wherein the high 4R:3R tau isoform ratio in the subject is caused by a splicing defect.

Embodiment 188

The method of embodiments 135-187, wherein the total amount of tau in the central nervous system is not changed.

Embodiment 189

The method of embodiments 111-188, wherein the agent, inhibitor or oligonucleotide is administered to the CNS of the subject.

Embodiment 190

The method of embodiment 189, wherein the inhibitor is administered by intrathecal or intracerebral vascular administration.

Embodiment 191

The method of embodiments 189-190, wherein the administration is by bolus or infusion.

Embodiment 192

The method of embodiments 189-191, wherein the oligonucleotide is administered using a pump.

Embodiment 193

The method of embodiments 111-192, wherein the subject has a tau-associated disease.

Embodiment 194

The method of embodiment 193, wherein the tau-associated disease is selected from among: Alzheimer's disease, progressive supranuclear palsy, dementia pugilistica, frontotemporal dementia, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, corticobasal degeneration, argyrophilic grain disease, supranuclear palsy, corticobasal degeneration, frontotemporal dementia, or frontotemporal lobar degeneration.

Embodiment 195

The method of embodiments 111-194 wherein the subject has a seizure disorder.

Embodiment 196

The method of embodiment 195, wherein the seizure disorder is selected from among: epilepsy, meningitis, brain strokes, injury-associated seizures, brain injury, juvenile myoclonic epilepsy, infantile spasms, reflex epilepsy, and febrile seizures.

Embodiment 197

The method of embodiments 111-196 wherein the subject has a neurological disorder.

Embodiment 198

The method of any of the preceding embodiments, wherein the antisense oligonucleotide has the nucleobase sequence of SEQ ID NO: 12.

Embodiment 199

The method of any of the preceding embodiments, wherein the antisense oligonucleotide has the nucleobase sequence of SEQ ID NO: 13.

Embodiment 200

The method of any of the preceding embodiments, wherein the antisense oligonucleotide has the nucleobase sequence of SEQ ID NO: 14.

Embodiment 201

The method of any of the preceding embodiments, wherein the antisense oligonucleotide has the nucleobase sequence of SEQ ID NO: 15.

Embodiment 202

The method of any of the preceding embodiments, wherein the antisense oligonucleotide has the nucleobase sequence of SEQ ID NO: 16.

Embodiment 203

The method of any of the preceding embodiments, wherein the antisense oligonucleotide has the nucleobase sequence of SEQ ID NO: 17.

Embodiment 204

The method of any of the preceding embodiments, wherein the antisense oligonucleotide has the nucleobase sequence of SEQ ID NO: 18.

Embodiment 205

An antisense oligonucleotide comprising 20 linked modified nucleosides and having the sequence of SEQ ID NO: 12, wherein each internucleoside linkage is a phosphorothioate linkage and each modified nucleoside comprises a 2'-O-methoxyethyl group.

Embodiment 206

An antisense oligonucleotide comprising 20 linked modified nucleosides and having the sequence of SEQ ID NO: 13, wherein each internucleoside linkage is a phosphorothioate linkage and each modified nucleoside comprises a 2'-O-methoxyethyl group.

Embodiment 207

An antisense oligonucleotide comprising 20 linked modified nucleosides and having the sequence of SEQ ID NO: 14, wherein each internucleoside linkage is a phosphorothioate linkage and each modified nucleoside comprises a 2'-O-methoxyethyl group.

Embodiment 208

An antisense oligonucleotide comprising 18 linked modified nucleosides and having the sequence of SEQ ID NO: 15, wherein each internucleoside linkage is a phosphorothioate linkage and each modified nucleoside comprises a 2'-O-methoxyethyl group.

Embodiment 209

An antisense oligonucleotide comprising 18 linked modified nucleosides and having the sequence of SEQ ID NO: 16, wherein each internucleoside linkage is a phosphorothioate linkage and each modified nucleoside comprises a 2'-O-methoxyethyl group.

Embodiment 210

An antisense oligonucleotide comprising 18 linked modified nucleosides and having the sequence of SEQ ID NO: 17, wherein each internucleoside linkage is a phosphorothioate linkage and each modified nucleoside comprises a 2'-O-methoxyethyl group.

Embodiment 211

An antisense oligonucleotide comprising 18 linked modified nucleosides and having the sequence of SEQ ID NO: 18, wherein each internucleoside linkage is a phosphorothioate linkage and each modified nucleoside comprises a 2'-O-methoxyethyl group.

BRIEF DESCRIPTION OF THE FIGURES

FIG. 3A-3B depict two plots showing mouse tau mRNA levels are decreased by mouse tau antisense oligos in vitro. (A) 80 antisense oligonucleotides, 120 nM, against mouse tau were transfected by cytofectin into cultured B16-F10 (murine melanoma cells). Each bar represents tau mRNA levels 48 hours after transfection with a different antisense oligonucleotide measured in triplicate cultures compared with untransfected cells (UTC, 100%). (B) Mouse tau mRNA 48 hours after transfection. Antisense oligos against mouse tau that demonstrated decreased levels of mouse tau in the initial screen (part A) were tested in cultured B16-F10 (murine melanoma cells line) cells transfected by cytofectin with increasing antisense oligos to mouse tau (1-10) or two scrambled oligonucleotide controls, (11, 12). Nine of 10 oligos showed an appropriate dose response in this subsequent screen. Untransfected cells=100%. These oligos are excellent candidates for in vivo testing of mouse tau knockdown.

FIG. 8 depicts a plot representing the relative brain 4R tau levels after a one month intraventricular infusion of the splicing oligo.

DETAILED DESCRIPTION

Figure 1:
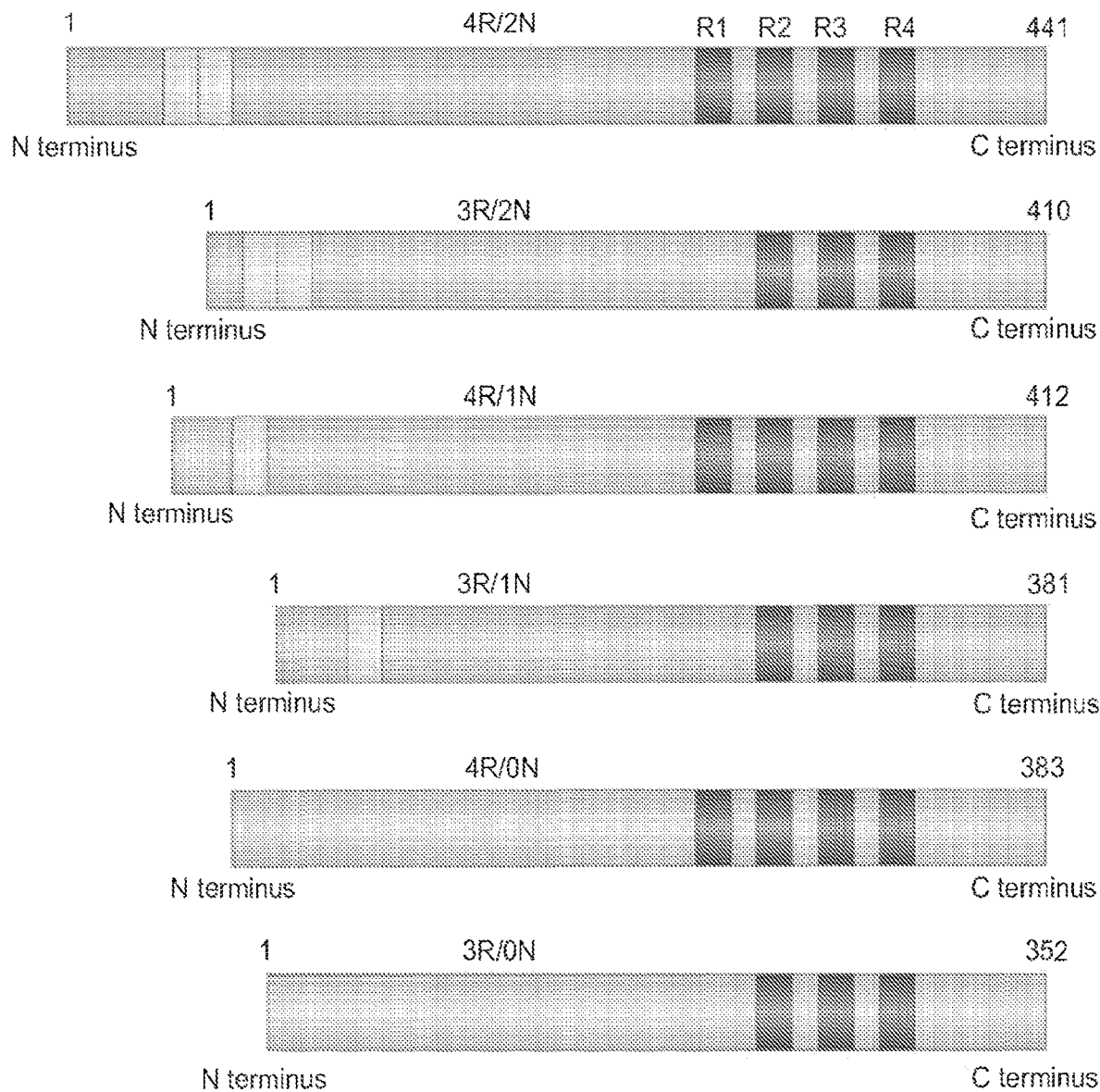
FIG. 1 depicts a graphical representation of Tau isoforms. The isoforms can differ from each other in the number of tubulin-binding domains (three or four repeats located in the C-terminal half of the protein) and are referred to as 3R or 4R Tau isoforms, respectively. They can also differ in the presence or absence of either one or two 29-amino-acid-long, highly acidic inserts at the N-terminal portion of the protein (the projection domain). Between the projection domain and the microtubule-binding domain lies a basic proline-rich region.

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. Where permitted, all documents, or portions of documents, cited in this disclosure, including, but not limited to, patents, patent applications, published patent applications, articles, books, treatises, and GEN BANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Treatment of Neurodegenerative Syndrome and Seizures

A method of modifying neurodegenerative disease has been developed. Using the methods of the invention, it is now possible to alter the ratio of tau isoforms associated with multiple diseases of the brain. Advantageously, the invention provides a method of bypassing the blood brain barrier to specifically target the generation of certain tau isoforms in the central nervous system, may be administered for an extended period of time using proven technology, and has been demonstrated to provide widespread distribution of therapy throughout the brain and spinal cord where it is most efficient.

I. Method

The present invention provides a method of modifying a neurodegenerative syndrome in a subject by administering an antisense oligonucleotide to the central nervous system. Generally speaking, the antisense oligonucleotide alters splicing of the nucleic acid encoding tau and decreases the abnormal 4R:3R tau ratio in the central nervous system of the subject.

(a) Subject

According to the invention, the subject may be any subject that expresses 3R and 4R isoforms of tau. In some embodiments, a subject is a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In an exemplary embodiment, the subject may be a human.

The subject may be suffering from a neurodegenerative syndrome or may be at risk of developing a neurodegenerative syndrome. In some embodiments, the subject may be suffering from a neurodegenerative syndrome. In other embodiments, the subject may be at risk of developing a neurodegenerative syndrome. Neurodegenerative syndromes are as described further below.

(b) Neurodegenerative Syndrome

The method of the invention comprises modifying a neurodegenerative syndrome. In some embodiments, a neurodegenerative syndrome may be any neurodegenerative syndrome associated with tau. Non limiting examples of a neurodegenerative disorder associated with tau may include Alzheimer's disease, progressive supranuclear palsy, dementia pugilistica, frontotemporal dementia, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, corticobasal ganglionic degeneration, argyrophilic grain disease, supranuclear palsy, corticobasal degeneration, frontotemporal dementia, or frontotemporal lobar degeneration. In some embodiments, the method of the invention comprises modifying frontotemporal dementia (FTD). In other embodiments, the method of the invention comprises modifying Alzheimer's disease (AD). In yet other embodiments, the method of the invention comprises modifying progressive supranuclear palsy. In other embodiments, the method of the invention comprises modifying corticobasalganglionic degeneration.

As used herein, the term "modifying a neurodegenerative syndrome" may refer to curing the neurodegenerative syndrome, slowing the course of development of the syndrome, reversing the course of the syndrome, or improving the behavioral phenotype of a subject having a neurodegenerative syndrome. In some embodiments, the method of the invention modifies a neurodegenerative syndrome by curing the neurodegenerative syndrome. In other embodiments, the method of the invention modifies a neurodegenerative syndrome by slowing the progression of the syndrome.

In yet other embodiments, the method of the invention modifies a neurodegenerative syndrome by improving the behavioral phenotype of a subject having a neurodegenerative syndrome. For instance, the symptoms for subjects suffering from Alzheimer's disease may be the mild early symptoms associated with the neurodegenerative syndrome such as mild forgetfulness of recent events, activities, the names of familiar people or things, and the inability to solve simple math problems. The symptoms may also be the moderate symptoms associated with the neurodegenerative syndrome such as forgetting how to do simple tasks such as grooming, speaking, understanding, reading, or writing. Alternatively, the symptoms may be the severe symptoms associated with the neurodegenerative syndrome such as becoming anxious or aggressive, and wandering away from home. Subjects with AD may also have an increased risk of seizures. The symptoms for subjects suffering from progressive supranuclear palsy may include loss of balance, lunging forward when mobilizing, fast walking, bumping into objects or people, falls, changes in personality, general slowing of movement, visual symptoms, dementia (typically including loss of inhibition and ability to organize information), slurring of speech, difficulty swallowing, and difficulty moving the eyes, particularly in the vertical direction, poor eyelid function, contracture of the facial muscles, a backward tilt of the head with stiffening of the neck muscles, sleep disruption, urinary incontinence and constipation. The symptoms for subjects suffering from FTD may include personality changes, cognitive impairment, and motor symptoms. The symptoms for subjects suffering from corticobasalganglionic degeneration are similar to symptoms in patients suffering from FTD and Parkinson's disease and may include shaking, rigidity, slowness of movement and difficulty with walking and gait, cognitive and behavioural problems, dementia, sensory, sleep and emotional problems. In preferred embodiments, the method of the invention modifies a neurodegenerative syndrome by decreasing the risk of seizures.

(c) Differential Splicing in Tau

The invention describes a method of modifying a neurodegenerative syndrome by altering the splicing of a nucleic acid encoding tau. Tau is a protein found in multiple tissues, but is particularly abundant in axons of neurons. The primary function of tau is to bind to and stabilize microtubules, which are important structural components of the cytoskeleton involved in mitosis, cytokinesis and vesicular transport. In humans, there are six isoforms of tau that are generated by alternative splicing of exons 2, 3, and 10. Splicing of exons 2 and 3 at the N-terminus of the protein leads to inclusion of zero, one or two 29 amino acid, acidic domains and is termed 0N, 1N, or 2N tau respectively. Inclusion of exon 10 at the C-terminus leads to inclusion of the microtubule binding domain encoded by exon 10. Since there are 3 mictrotubule binding domains elsewhere in tau, this tau isoform (with exon 10 included) is termed 4R tau, where R refers to the number of repeats of microtubule binding domains. (FIG. 1). Tau without exon 10 is termed 3R tau. In healthy subjects, the ratio of 3R:4R tau is developmentally regulated, with fetal tissues expressing almost exclusively 3R tau and adult human tissues expressing approximately equal levels of 3R/4R tau. Deviations from the normal ratio of 3R/4R tau are characteristic of neurodegenerative syndromes such as FTD tauopathies. In essence, the method decreases the 4R:3R tau ratio in the central nervous system of the subject.

The 4R:3R tau ratio in the central nervous system of the subject may be normal, low or high. As used herein, a "normal 4R:3R tau ratio" in the central nervous system signifies a 4R:3R tau ratio in the central nervous system that is substantially the same as the 4R:3R tau ratio in the central nervous system of a subject from the same species and of approximately the same age not suffering from a neurodegenerative disease. In some embodiments, the method decreases the normal 4R:3R tau ratio in the central nervous system of a subject. In other embodiments, the method decreases an low 4R:3R tau ratio in the central nervous system of a subject.

In preferred embodiments, the method decreases a high 4R:3R tau ratio in the central nervous system of a subject. In exemplary embodiments, the method decreases a high 4R:3R tau ratio caused by a defect in splicing of the nucleic acid encoding tau in the subject. Defects in splicing of the nucleic acid encoding tau in the subject may be caused, for instance, by genetic mutations altering the splicing of the nucleic acid encoding tau and leading to a high 4R:3R tau ratio. A mutation may be either a substitution mutation or a deletion mutation which creates a new, aberrant, splice element. Non-limiting examples of genetic mutations that may alter the splicing of the nucleic acid encoding tau and lead to a high 4R:3R tau ratio may include N279K, P301S, 280, L284L, N296H, N296N, 296N, P301S, G303V, E10+11, E10+12, E10+13, E+10+14 and E10+16, and E10+19.

(d) Antisense Oligonucleotide

A method of the invention decreases the 4R:3R tau ratio in the central nervous system of a subject by altering the splicing of a nucleic acid encoding tau using an antisense oligonucleotide. An antisense oligonucleotide is a single stranded ribonucleic acid or deoxyribonucleic acid complementary to a chosen sequence. Antisense oligonucleotides may target a specific, complementary, coding or non-coding, nucleic acid. Depending on the antisense oligonucleotide used, the binding of the oligonucleotide to its target nucleic acid sequence may or may not activate RNAse H. In some embodiments, the antisense oligonucleotide activates RNAse H, which degrades the target nucleic acid. In preferred embodiments, the antisense oligonucleotide does not activate RNAse H. In an exemplary embodiment, the antisense oligonucleotide of the invention is complementary to the nucleic acid sequence encoding tau, does not activate RNAse H, and disrupts the splicing of the nucleic acid encoding tau to reduce the 4R:3R tau ratio.

Methods of making antisense oligonucleotides which do not activate RNase H are known in the art. See, e.g., U.S. Pat. No. 5,149,797 incorporated herein by reference. Such antisense oligonucleotides may contain one or more structural modification which sterically hinders or prevents binding of RNase H to a duplex molecule comprising the oligonucleotide, but does not substantially hinder or disrupt duplex formation. Antisense oligonucleotides that do not activate RNAse H may include oligonucleotides wherein at least one, two or more of the internucleotide bridging phosphate residues are modified phosphates, such as methyl phosphonates, methyl phosphonothioates, phosphoromorpholidates, phosphoropiperazidates and phosphoramidates. For instance, every other one of the internucleotide bridging phosphate residues may be a modified phosphate, contain a 2' loweralkyl moiety (e.g., C1-C4, linear or branched, saturated or unsaturated alkyl, such as methyl, ethyl, ethenyl, propyl, 1-propenyl, 2-propenyl, and isopropyl) or a combination thereof. In preferred embodiments, the antisense oligonucleotide of the invention that does not activate RNAse H, and disrupts the splicing of the nucleic acid encoding tau to reduce the 4R:3R tau ratio is a 2'-O-(2-methoxyethyl) (MOE)-modified antisense oligonucleotide.

Other methods of modifying an oligonucleotide to hinder binding of RNAse H may be found in P. Furdon et al., Nucleic Acids Res. 17, 9193-9204 (1989); S. Agrawal et al., Proc. Natl. Acad. Sci. USA 87, 1401-1405 (1990); C. Baker et al., Nucleic Acids Res. 18, 3537-3543 (1990); B. Sproat et al., Nucleic Acids Res. 17, 3373-3386 (1989); R. Walder and J. Walder, Proc. Natl. Acad. Sci. USA 85, 5011-5015 (1988) the disclosures of all of which are incorporated herein, in their entirety, by reference.

The antisense oligonucleotide of the invention may be a deoxyribonucleotide oligonucleotide or a ribonucleotide oligonucleotide. The antisense oligonucleotide may be any length provided it binds selectively to the intended location. In general, the antisense oligonucleotide may be from 8, 10 or 12 nucleotides in length up to 20, 30, or 50 nucleotides in length.

The antisense oligonucleotide of the invention may disrupt the splicing of the nucleic acid encoding tau to reduce the 4R:3R tau ratio. The splicing process is a series of reactions, mediated by splicing factors, which is carried out on RNA after transcription but before translation, in which the intron(s) are removed, and the exons joined together sequentially so that the protein may be translated. Each intron is defined by a 5' splice site, a 3' splice site, and a branch point situated there between. An antisense oligonucleotide may block these splice elements when the oligonucleotide either fully or partially overlaps the element, or binds to the pre-mRNA at a position sufficiently close to the element to disrupt the binding and function of the splicing factors which would ordinarily mediate the particular splicing reaction which occurs at that element. The antisense oligonucleotide may block a variety of different splice elements to carry out the instant invention. For instance, the antisense oligonucleotide may block a mutated element, a cryptic element, or a native element; it may block a 5' splice site, a 3' splice site, or a branch point.

The term "antisense oligonucleotide" includes the physiologically and pharmaceutically acceptable salts thereof:

i.e., salts that retain the desired biological activity of the parent compound and do not impart undesired toxicological effects thereto. Examples of such salts are (a) salts formed with cations such as sodium, potassium, NH4+, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

(e) Administration

Antisense oligonucleotides of the invention may be administered to a subject by several different means. For instance, oligonucleotides may generally be administered parenterally, intraperitoneally, intravascularly, or intrapulmonarily in dosage unit formulations containing conventional nontoxic pharmaceutically acceptable carriers, adjuvants, and vehicles as desired. In a preferred embodiment, the oligonucleotide may be administered parenterally. The term parenteral as used herein includes subcutaneous, intravenous, intramuscular, intrathecal, or intrasternal injection, or infusion techniques. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

Delivery methods are preferably those that are effective to circumvent the blood-brain barrier and are effective to deliver agents to the central nervous system. For example, delivery methods may include the use of nanoparticles. The particles may be of any suitable structure, such as unilamellar or plurilamellar, so long as the antisense oligonucleotide is contained therein. Positively charged lipids such as N-[1-(2,3-dioleoyloxi)propyl]-N, N,N-trimethyl-ammoniummethylsulfate, or "DOTAP," are particularly preferred for such particles and vesicles. The preparation of such lipid particles is well known in the art. See, e.g., U.S. Pat. No. 4,880,635 to Janoff et al.; U.S. Pat. No. 4,906,477 to Kurono et al.; U.S. Pat. No. 4,911,928 to Wallach; U.S. Pat. No. 4,917,951 to Wallach; U.S. Pat. No. 4,920,016 to Allen et al.; U.S. Pat. No. 4,921,757 to Wheatley et al.; etc.

In one preferred embodiment, the oligonucleotide may be administered in a bolus directly into the central nervous system. The oligonucleotides may be administered to the subject in a bolus once, or multiple times. In some preferred embodiments, the oligonucleotides may be administered once. In other preferred embodiments, the oligonucleotides may be administered multiple times. When administered multiple times, the oligonucleotides may be administered at regular intervals or at intervals that may vary during the treatment of a subject. In some embodiments, the oligonucleotides may be administered multiple times at intervals that may vary during the treatment of a subject. In some embodiments, the oligonucleotides may be administered multiple times at regular intervals.

In another preferred embodiment, the oligonucleotide may be administered by continuous infusion into the central nervous system. Non-limiting examples of methods that may be used to deliver the oligonucleotide into the central nervous system by continuous infusion may include pumps, wafers, gels, foams and fibrin clots. In a preferred embodiment, the oligonucleotide may be delivered into the central nervous system by continuous infusion using an osmotic pump. An osmotic minipump contains a high-osmolality chamber that surrounds a flexible, yet impermeable, reservoir filled with the targeted delivery composition-containing vehicle. Subsequent to the subcutaneous implantation of this minipump, extracellular fluid enters through an outer semipermeable membrane into the high-osmolality chamber, thereby compressing the reservoir to release the targeted delivery composition at a controlled, pre-determined rate. The targeted delivery composition, released from the pump, may be directed via a catheter to a stereotaxically placed cannula for infusion into the cerebroventricular space. In an exemplary embodiment, the oligonucleotide may be delivered into the central nervous system by continuous infusion using a pump as described in the Examples.

One of skill in the art will recognize that the amount and concentration of the composition administered to a subject will depend in part on the subject, the reason for the administration, and the method of administration. In some embodiments, when the oligonucleotide is administered in a bolus into the central nervous system, the oligonucleotide may be administered to the subject in an amount of about 0.1, 0.2, 0.3, 0.4, 0.5, 1, 1.5, 2, 2.5, 3, 3.5, 4, 4.5, 5, 6.5, 7, 7.5, 8, 8.5, 9, 9.5, 10, 10.5, 11, 11.5, 12, 12.5, 13, 13.5, 14, 14.5, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 mg/kg or more.

In other embodiments, when the oligonucleotide is administered by continuous infusion using a pump into the central nervous system, the oligonucleotide may be administered to the subject in an amount of about 0.1, 0.2, 0.3, 0.4, 0.5, 1, 1.5, 2, 2.5, 3, 3.5, 4, 4.5, 5, 6.5, 7, 7.5, 8, 8.5, 9, 9.5, 10, 10.5, 11, 11.5, 12, 12.5, 13, 13.5, 14, 14.5, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 mg/kg or more. In some embodiments, the oligonucleotide may be administered by continuous infusion for 1, 2, 3, 4, 5, 6, 7, 8, 9, 10, 11, 12, 13, 14, 15, 16, 178, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 days or longer. In one embodiment, the oligonucleotide may be administered by continuous infusion for 20, 21, 22, 23, 24, 25, 26, 27, 28, 29, 30, 31, 32, 33, 34, 35 days or longer. In another embodiment, the oligonucleotide may be administered by continuous infusion for 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65 days or longer. In yet another embodiment, the oligonucleotide may be administered by continuous infusion for 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 days or longer. Longer continuous infusions of the antisense oligonucleotide may also be envisioned using existing pump technology as is known in the art.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE and 2'-O(CH2)2-OCH3 and MOE) refers to an O-methoxy-ethyl modification at the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position of the furanosyl ring other than H or OH. In certain embodiments, 2' substituted nucleosides include nucleosides with bicyclic sugar modifications.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5 position. A 5-methylcytosine is a modified nucleobase.

"About" means within ±7% of a value. For example, if it is stated, "the compounds affected at least about 70% inhibition of Tau", it is implied that the Tau levels are inhibited within a range of 63% and 77%.

"Acceptable safety profile" means a pattern of side effects that is within clinically acceptable limits.

"Active pharmaceutical agent" means the substance or substances in a pharmaceutical composition that provide a therapeutic benefit when administered to an individual. For example, in certain embodiments an antisense oligonucleotide targeted to Tau is an active pharmaceutical agent.

"Active target region" means a target region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to, administering by a medical professional and self-administering.

"Agent" means an active substance that can provide a therapeutic benefit when administered to an animal. "First Agent" means a therapeutic compound described herein. For example, a first agent can be an antisense oligonucleotide targeting Tau. "Second agent" means a second therapeutic compound described herein (e.g. a second antisense oligonucleotide targeting Tau) and/or a non-Tau therapeutic compound.

"Amelioration" or "ameliorate" or "ameliorating" refers to a lessening of at least one indicator, sign, or symptom of a disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing. Antisense mechanisms include, without limitation, RNase H mediated antisense; RNAi mechanisms, which utilize the RISC pathway and include, without limitation, siRNA, ssRNA, and microRNA mechanisms; and occupancy based mechanisms, including, without limitation uniform modified olionucleotides. Certain antisense compounds may act through more than one such mechanism and/or through additional mechanisms.

"Antisense oligonucleotide" (also "oligo") means a single-stranded oligonucleotide having a nucleobase sequence that permits hybridization to a corresponding region or segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar" means a furanosyl ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon on the sugar ring.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH(CH3)-O-2'.

"Constrained ethyl nucleoside" (also cEt nucleoside) means a nucleoside comprising a bicyclic sugar moiety comprising a 4'-CH(CH3)-O-2' bridge.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses administration in parallel or sequentially.

"Complementarity" means the capacity for pairing between nucleobases of a first nucleic acid and a second nucleic acid.

"Comply" means the adherence with a recommended therapy by an individual.

"Comprise," "comprises" and "comprising" will be understood to imply the inclusion of a stated step or element or group of steps or elements but not the exclusion of any other step or element or group of steps or elements.

"Contiguous nucleobases" means nucleobases immediately adjacent to each other.

"Cure" means a method or course that restores health or a prescribed treatment for an illness.

"Deoxyribonucleotide" means a nucleotide having a hydrogen at the 2' position of the sugar portion of the nucleotide. Deoxyribonucleotides may be modified with any of a variety of substituents.

"Designing" or "Designed to" refer to the process of designing an oligomeric compound that specifically hybridizes with a selected nucleic acid molecule.

"Diluent" means an ingredient in a composition that lacks pharmacological activity, but is pharmaceutically necessary or desirable. For example, in drugs that are injected, the diluent may be a liquid, e.g. saline solution.

"Dosage unit" means a form in which a pharmaceutical agent is provided, e.g. pill, tablet, or other dosage unit known in the art.

"Dose" means a specified quantity of a pharmaceutical agent provided in a single administration, or in a specified time period. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual. In other embodiments, the pharmaceutical agent is administered by infusion over an extended period of time or continuously. Doses may be stated as the amount of pharmaceutical agent per hour, day, week or month.

"Dosing regimen" is a combination of doses designed to achieve one or more desired effects.

"Duration" means the period of time during which an activity or event continues. In certain embodiments, the duration of treatment is the period of time during which doses of a pharmaceutical agent are administered.

"Effective amount" in the context of modulating an activity or of treating or preventing a condition means the administration of that amount of active ingredient to a subject in need of such modulation, treatment or prophylaxis, either in a single dose or as part of a series, that is effective for modulation of that effect, or for treatment or prophylaxis or improvement of that condition. The effective amount will vary depending upon the health and physical condition of the subject to be treated, the taxonomic group of subjects to be treated, the formulation of the composition, the assessment of the medical situation, and other relevant factors.

"Efficacy" means the ability to produce a desired effect.

"Excitotoxicity" the pathological process by which nerve cells are damaged and killed by excessive stimulation by neurotransmitters.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Fully modified motif" refers to an antisense compound comprising a contiguous sequence of nucleosides wherein essentially each nucleoside is a sugar modified nucleoside having uniform modification.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Tau nucleic acid" or Tau DNA" means any nucleic acid encoding Tau. For example, in certain embodiments, a Tau nucleic acid includes, without limitation, any viral DNA sequence encoding a Tau genome or portion thereof, any RNA sequence transcribed from a DNA sequence including any mRNA sequence encoding a Tau protein.

"Hybridization" means the annealing of complementary nucleic acid molecules. In certain embodiments, complementary nucleic acid molecules include, but are not limited to, an antisense compound and a nucleic acid target. In certain embodiments, complementary nucleic acid molecules include, but are not limited to, an antisense oligonucleotide and a nucleic acid target.

"Identifying an animal having a Tau-related disease or disorder" means identifying an animal having been diagnosed with a Tau-related disease or disorder; or, identifying an animal having any symptom of Tau-related disease or disorder including, but not limited to a neurodegenerative disorder associated with Tau.

"Immediately adjacent" means there are no intervening elements between the immediately adjacent elements.

"Individual" means a human or non-human animal selected for treatment or therapy.

"Individual compliance" means adherence to a recommended or prescribed therapy by an individual.

"Induce", "inhibit", "potentiate", "elevate", "increase", "decrease" or the like, e.g., which denote quantitative differences between two states, refer to at least statistically significant differences between the two states. For example, "an amount effective to inhibit the activity or expression of Tau" means that the level of activity or expression of Tau in a treated sample will differ statistically significantly from the level of Tau activity or expression in untreated cells. Such terms are applied to, for example, levels of expression, and levels of activity.

"Inhibiting Tau" means reducing the level or expression of a Tau mRNA, DNA and/or protein. In certain embodiments, Tau is inhibited in the presence of an antisense compound targeting Tau, including an antisense oligonucleotide targeting Tau, as compared to expression of Tau mRNA, DNA and/or protein levels in the absence of a Tau antisense compound, such as an antisense oligonucleotide.

"Inhibiting the expression or activity" refers to a reduction, blockade of the expression or activity and does not necessarily indicate a total elimination of expression or activity.

"Internucleoside linkage" refers to the chemical bond between nucleosides.

"Intraperitoneal administration" means administration through infusion or injection into the peritoneum.

"Intravenous administration" means administration into a vein.

"Lengthened" antisense oligonucleotides are those that have one or more additional nucleosides relative to an antisense oligonucleotide disclosed herein.

"Linked deoxynucleoside" means a nucleic acid base (A, G, C, T, U) substituted by deoxyribose linked by a phosphate ester to form a nucleotide.

"Linked nucleosides" means adjacent nucleosides linked together by an internucleoside linkage.

"Locked nucleic acid" or "LNA" or "LNA nucleosides" means nucleic acid monomers having a bridge connecting two carbon atoms between the 4' and 2'position of the nucleoside sugar unit, thereby forming a bicyclic sugar. Examples of such bicyclic sugar include, but are not limited to A) α-L-Methyleneoxy (4'-CH2-O-2') LNA, (B) β-D-Methyleneoxy (4'-CH2-O-2') LNA, (C) Ethyleneoxy (4'-(CH2)2-O-2') LNA, (D) Aminooxy (4'-CH2-O—N(R)-2') LNA and (E) Oxyamino (4'-CH2-N(R)—O-2') LNA, as depicted below.

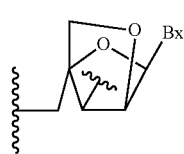
(A)

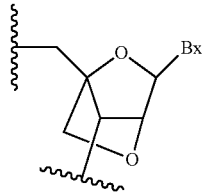
(B)

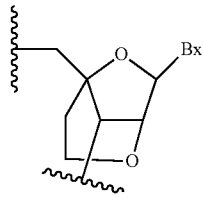
(C)

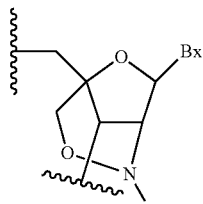
(D)

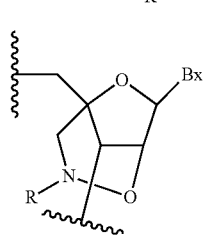
(E)

As used herein, LNA compounds include, but are not limited to, compounds having at least one bridge between the 4' and the 2' position of the sugar wherein each of the bridges independently comprises 1 or from 2 to 4 linked groups independently selected from —[C(R$_1$)(R$_2$)]$_n$—, —C(R$_1$)=C(R$_2$)—, —C(R$_1$)=N—, —C(=NR$_1$)—, —C(=O)—, —C(=S)—, —O—, —Si(R$_1$)$_2$—, —S(=O)$_x$— and —N(R$_1$)—; wherein: x is 0, 1, or 2; n is 1, 2, 3, or 4; each R$_1$ and R$_2$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, a heterocycle radical, a substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

Examples of 4'-2' bridging groups encompassed within the definition of LNA include, but are not limited to one of formulae: —[C(R$_1$)(R$_2$)]$_n$—, —[C(R$_1$)(R$_2$)]$_n$—O—, —C(R$_1$R$_2$)—N(R$_1$)—O— or —C(R$_1$R$_2$)—O—N(R$_1$)—. Furthermore, other bridging groups encompassed with the definition of LNA are 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R$_1$)-2' and 4'-CH2-N($R_1$)—O-2'-bridges, wherein each $R_1$ and $R_2$ is, independently, H, a protecting group or $C_1$-$C_{12}$ alkyl.

Also included within the definition of LNA according to the invention are LNAs in which the 2'-hydroxyl group of the ribosyl sugar ring is connected to the 4' carbon atom of the sugar ring, thereby forming a methyleneoxy (4'-$CH_2$—O-2') bridge to form the bicyclic sugar moiety. The bridge can also be a methylene (—$CH_2$—) group connecting the 2' oxygen atom and the 4' carbon atom, for which the term methyleneoxy (4'-$CH_2$—O-2') LNA is used. Furthermore; in the case of the bicyclic sugar moiety having an ethylene bridging group in this position, the term ethyleneoxy (4'-$CH_2CH_2$—O-2') LNA is used. α-L-methyleneoxy (4'-$CH_2$—O-2'), an isomer of methyleneoxy (4'-$CH_2$—O-2') LNA is also encompassed within the definition of LNA, as used herein.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, or modified nucleobase.

"Modified oligonucleotide" means an oligonucleotide comprising at least one modified internucleoside linkage, a modified sugar, and/or a modified nucleobase.

"Modified sugar" means substitution and/or any change from a natural sugar moiety.

"Monomer" refers to a single unit of an oligomer. Monomers include, but are not limited to, nucleosides and nucleotides, whether naturally occurring or modified.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Neurodegenerative disorder" means a chronic progressive neuropathy characterized by selective loss of neurons in motor, sensory, or cognitive systems. Neurodegenerative disorders include, but are not limited to, Tau-associated disorders.

"Neurofibrillary inclusion" means intraneuronal aggregates largely composed of insoluble hyperphosphorylated tau protein. In certain embodiments, neurofibrillary inclusions may be measured through various means including SPECT perfusion imaging, functional MRI, and PET scans. In certain embodiments, reduction of neurofibrillary inclusions may be inferred by improved scores on cognitive exams such as the Mini-Mental State Exam (MMSE) and the Alzheimer's Disease Assessment Scale Cognitive Behavior Section (ADAS-cog).

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" means a polymer of linked monomeric subunits which is capable of hybridizing to at least a region of a nucleic acid molecule.

"Oligonucleoside" means an oligonucleotide in which the internucleoside linkages do not contain a phosphorus atom.

"Oligonucleotide" (also "oligo") means a polymer of linked nucleosides each of which can be modified or unmodified, independent one from another.

"Parenteral administration" means administration through injection (e.g., bolus injection) or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Without limitation, as used herein, "peptide" refers to polypeptides and proteins.

"Pharmaceutically acceptable carrier" means a medium or diluent that does not interfere with the structure of the oligonucleotide. Certain such carriers enable pharmaceutical compositions to be formulated as, for example, tablets, pills, dragees, capsules, liquids, gels, syrups, slurries, suspension and lozenges for the oral ingestion by a subject.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Pharmaceutical agent" means a substance that provides a therapeutic benefit when administered to an individual. For example, in certain embodiments, an antisense oligonucleotide targeted to Tau is a pharmaceutical agent.

"Pharmaceutical composition" means a mixture of substances suitable for administering to a subject. For example, a pharmaceutical composition may comprise an antisense oligonucleotide and a sterile aqueous solution. In certain embodiments, a pharmaceutical composition shows activity in free uptake assay in certain cell lines.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevention" or "preventing" refers to delaying or forestalling the onset or development of a condition or disease for a period of time from hours to days, preferably weeks to months.

"Prodrug" means a therapeutic agent that is prepared in an inactive form that is converted to an active form (i.e., drug) within the body or cells thereof by the action of endogenous enzymes or other chemicals and/or conditions.

"Prophylactically effective amount" refers to an amount of a pharmaceutical agent that provides a prophylactic or preventative benefit to an animal.

"Recommended therapy" means a therapeutic regimen recommended by a medical professional for the treatment, amelioration, or prevention of a disease.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Salts" mean a physiologically and pharmaceutically acceptable salts of antisense compounds, i.e., salts that retain the desired biological activity of the parent oligonucleotide and do not impart undesired toxicological effects thereto.

"Scrambled oligo" or "scrambled" or "ISIS 141923" is a 5-10-5 MOE gapmer with no known target having the sequence of SEQ ID NO: 11.

"Segments" are defined as smaller or sub-portions of regions within a target nucleic acid.

"Shortened" or "truncated" versions of antisense oligonucleotides Taught herein have one, two or more nucleosides deleted.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

"Sites," as used herein, are defined as unique nucleobase positions within a target nucleic acid.

"Slows progression" means decrease in the development of the said disease.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Stringent hybridization conditions" or "stringent conditions" refer to conditions under which an oligomeric compound will hybridize to its target sequence, but to a minimal number of other sequences.

"Subcutaneous administration" means administration just below the skin.

"Subject" means a human or non-human animal selected for treatment or therapy.

"Target" refers to a protein, the modulation of which is desired.

"Target gene" refers to a gene encoding a target.

"Targeting" means the process of design and selection of an antisense compound that will specifically hybridize to a target nucleic acid and induce a desired effect.

"Target nucleic acid," "target RNA," "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Tau-associated disease" means any neurological or neurodegenerative disease associated with Tau. Non-limiting examples of Tau-associated disorders include Alzheimer's disease, progressive supranuclear palsy, dementia pugilistica, frontotemporal dementia, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, corticobasal ganglionic degeneration, argyrophilic grain disease, supranuclear palsy, corticobasal degeneration, frontotemporal dementia, or frontotemporal lobar degeneration.

"Tauopathy" means disorders characterized by a build-up of Tau protein in the brain.

"Tau-specific inhibitor" includes but is not limited to a "antisense compound" targeted to Tau.

"Therapeutically effective amount" means an amount of a pharmaceutical agent that provides a therapeutic benefit to an individual.

"Treatment" refers to administering a composition to effect an alteration or improvement of the disease or condition.

"Unmodified" nucleobases mean the purine bases adenine (A) and guanine (G), and the pyrimidine bases thymine (T), cytosine (C) and uracil (U).

"Unmodified nucleotide" means a nucleotide composed of naturally occuring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Validated target segment" is defined as at least an 8-nucleobase portion (i.e. 8 consecutive nucleobases) of a target region to which an active oligomeric compound is targeted.

"Wing segment" means a plurality of nucleosides modified to impart to an oligonucleotide properties such as enhanced inhibitory activity, increased binding affinity for a target nucleic acid, or resistance to degradation by in vivo nucleases.

Certain Embodiments

Certain embodiments provide for methods of administering a Tau antisense compound targeting a Tau nucleic acid for the treatment of a Tau associated disease. In certain embodiments, the Tau nucleic acid is any of the sequences set forth in GENBANK Accession NT_010783.14 truncated from nucleotides 2624000 to U.S. Pat. No. 2,761,000 (incorporated herein as SEQ ID NO: 1); GENBANK Accession No. AK226139.1 (incorporated herein as SEQ ID NO: 2); GENBANK Accession No. NM_001123066.3 (incorporated herein as SEQ ID NO: 3); GENBANK Accession No. NM_001123067.3 (incorporated herein as SEQ ID NO: 4); GENBANK Accession No. NM_001203251.1 (incorporated herein as SEQ ID NO: 5); GENBANK Accession No. NM_001203252.1 (incorporated herein as SEQ ID NO: 6); GENBANK Accession No. NM_005910.5 (incorporated herein as SEQ ID NO: 7); GENBANK Accession No. NM_016834.4 (incorporated herein as SEQ ID NO: 8); GENBANK Accession No. NM_016835.4 (incorporated herein as SEQ ID NO: 9); or GENBANK Accession No. NM_016841.4 (incorporated herein as SEQ ID NO: 10).

A method of treating a Tau associated disease with antisense compounds has been developed. In certain embodiments, neurofibrillary inclusions are reduced. In certain embodiments, neurological function is improved. In certain embodiments, the antisense compounds reduce expression of Tau mRNA and protein. In certain embodiments, the antisense compounds alter the ratio of Tau isoforms. In certain embodiments, the splicing alteration is a decrease in 4R:3R Tau ratio in the central nervous system of the subject. In certain embodiments, the splicing alteration results in a normal 4R:3R Tau ratio. Advantageously, several embodiments provide methods of bypassing the blood brain barrier to specifically target Tau in the central nervous system, administer for an extended period of time, and achieve widespread distribution of therapy throughout the brain and spinal cord where it is most effective.

Certain embodiments provide methods for the treatment, prevention, or amelioration of diseases, disorders, and conditions associated with Tau in an individual in need thereof. Also contemplated are methods for the preparation of a medicament for the treatment, prevention, or amelioration of a disease, disorder, or condition associated with Tau. Tau associated diseases, disorders, and conditions include neurodegenerative diseases. In certain embodiments, the neurodegenerative disease may be any of Alzheimer's Disease, frontotemporal Dementia (FTD), FTDP-17, Progressive Supranuclear Palsy (PSP), Chronic Traumatic Encephalopathy (CTE), Corticobasal Ganglionic Degeneration (CBD), epilepsy, Dravet's Syndrome, dementia pugilistica, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, argyrophilic grain disease, supranuclear palsy, corticobasal degeneration, or frontotemporal lobar degeneration.

Described herein are methods comprising administering a Tau antisense compound to an animal for treating a Tau associated disease and thereby reducing neurofibrillary inclusions.

Described herein are methods comprising administering a Tau antisense compound to an animal for treating a Tau associated disease and thereby improving neurological function.

Described herein are methods comprising: (i) identifying an animal having a Tau associated disease; and (ii) administering a Tau antisense compound and thereby reducing neurofibrillary inclusions.

Described herein are methods comprising: (i) identifying an animal having a Tau associated disease; and (ii) administering a Tau antisense compound and thereby improving neurological function.

In certain embodiments, the animal is a human.

In certain embodiments, the antisense compound comprises a single-stranded antisense oligonucleotide complementary to a Tau nucleic acid.

In certain embodiments, the Tau nucleic acid is any of SEQ ID NO: 1-10.

In certain embodiments, the antisense compounds for use in the methods may comprise a single-stranded antisense oligonucleotide comprising a nucleobase sequence at least 80%, at least 85%, at least 90%, at least 95%, at least 96%, at least 97%, at least 98%, or at least 99% complementary to an equal length portion of SEQ ID NOs:1-10. In certain embodiments, the compound may comprise a single-stranded antisense oligonucleotide comprising a nucleobase sequence 100% complementary to an equal length portion of SEQ ID NOs: 1-10.

In certain embodiments, the Tau associated disease is a neurodegenerative disease.

In certain embodiments, the neurodegenerative disease is selected from among Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, or Dravet's Syndrome.

In certain embodiments, expression of Tau RNA or expression of Tau protein is reduced.

In certain embodiments, expression of the 4R isoform of Tau RNA or expression of the 4R isoform of Tau protein is reduced.

In certain embodiments, expression of the 3R isoform of Tau RNA or expression of the 3R isoform of Tau protein is increased.

In certain embodiments, expression of the 4R isoform of Tau RNA is reduced and expression of the 3R isoform of Tau RNA is increased.

In certain embodiments, expression of the 4R isoform of Tau protein is reduced and expression of the 3R isoform of Tau protein is increased.

In certain embodiments, the single-stranded antisense oligonucleotide comprises at least one modification.

In certain embodiments, the single-stranded antisense oligonucleotide is specifically hybridizable to a human Tau nucleic acid.

In certain embodiments, the single-stranded antisense oligonucleotide is at least 75%, at least 80%, at least 85%, at least 90%, or at least 95% complementary to an equal length portion of a human Tau nucleic acid.

In certain embodiments, the single-stranded antisense oligonucleotide is 100% complementary to a human Tau nucleic acid.

In certain embodiments, the single-stranded antisense oligonucleotide comprises at least one modified internucleoside linkage.

In certain embodiments, each internucleoside linkage of the single-stranded antisense oligonucleotide is a modified internucleoside linkage.

In certain embodiments, the modified internucleoside linkage is a phosphorothioate internucleoside linkage.

In certain embodiments, the antisense oligonucleotide comprises at least one modified nucleoside.

In certain embodiments, the single-stranded antisense oligonucleotide comprises at least one modified nucleoside having a modified sugar.

In certain embodiments, the single-stranded antisense oligonucleotide comprises at least one modified nucleoside comprising a bicyclic sugar.

In certain embodiments, the bicyclic sugar comprises a 4' to 2' bridge selected from among: 4'-(CH2)n-O-2', wherein n is 1 or 2; and 4'-CH2-O—CH2-2'.

In certain embodiments, the bicyclic sugar comprises a 4'-CH(CH3)-O-2' bridge.

In certain embodiments, the at least one modified nucleoside having a modified sugar comprises a non-bicyclic 2'-modified sugar moiety.

In certain embodiments, the 2'-modified sugar moiety comprises a 2'-O-methoxyethyl group.

In certain embodiments, the 2'-modified sugar moiety comprises a 2'-O-methyl group.

In certain embodiments, the at least one modified nucleoside having a modified sugar comprises a sugar surrogate.

In certain embodiments, the sugar surrogate is a morpholino.

In certain embodiments, the sugar surrogate is a peptide nucleic acid.

In certain embodiments, each nucleoside is modified.

In certain embodiments, the single-stranded antisense oligonucleotide comprises at least one modified nucleobase.

In certain embodiments, the modified nucleobase is a 5'-methylcytosine.

In certain embodiments, the single-stranded antisense oligonucleotide comprises:
a gap segment consisting of linked deoxynucleosides;
a 5' wing segment consisting of linked nucleosides;
a 3' wing segment consisting of linked nucleosides;

wherein the gap segment is positioned immediately adjacent to and between the 5' wing segment and the 3' wing segment and wherein each nucleoside of each wing segment comprises a modified sugar.

In certain embodiments, the single-stranded antisense oligonucleotide comprises:
a gap segment consisting of ten linked deoxynucleosides;
a 5' wing segment consisting of five linked nucleosides;
a 3' wing segment consisting of five linked nucleosides;
wherein the gap segment is positioned immediately adjacent and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the single-stranded antisense oligonucleotide consists of 15, 16, 17, 18, or 19 linked nucleosides.

In certain embodiments, the single-stranded antisense oligonucleotide consists of 20 linked nucleosides.

In certain embodiments, the single-stranded antisense oligonucleotide consists of 21, 22, 23, 24, or 25 linked nucleosides.

In certain embodiments, the administering is parenteral administration.

In certain embodiments, the parenteral administration is any of injection or infusion.

In certain embodiments, the parenteral administration is any of intrathecal administration or intracerebroventricular administration.

In certain embodiments, at least one symptom of a Tau associated disease is ameliorated.

In certain embodiments, at least one symptom of a Tau associated disease is prevented.

In certain embodiments, progression of at least one symptom of a Tau associated disease is slowed.

In certain embodiments, at least one symptom is any of memory loss, anxiety, loss of motor function, incidence of seizures, severity of seizures, and excitotoxicity.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a Tau nucleic acid is 10 to 30 subunits in length. In certain embodiments, an antisense compound targeted to a Tau nucleic acid is 12 to 30 subunits in length. In certain embodiments, an antisense compound targeted to a Tau nucleic acid is 12 to 22 subunits in length. In certain embodiments, an antisense compound targeted to a Tau nucleic acid is 14 to 30 subunits in length. In certain embodiments, an antisense compound targeted to a Tau nucleic acid is 14 to 20 subunits in length. In certain embodiments, an antisense compound targeted to a Tau nucleic acid is 15 to 30 subunits in length. In certain embodiments, an antisense compound targeted to a Tau nucleic acid is 15 to 20 subunits in length. In certain embodiments, an antisense compound targeted to a Tau nucleic acid is 16 to 30 subunits in length. In certain embodiments, an antisense compound targeted to a Tau nucleic acid is 16 to 20 subunits in length. In certain embodiments, an antisense compound targeted to a Tau nucleic acid is 17 to 30 subunits in length. In certain embodiments, an antisense compound targeted to a Tau nucleic acid is 17 to 20 subunits in length. In certain embodiments, an antisense compound targeted to a Tau nucleic acid is 18 to 30 subunits in length. In certain embodiments, an antisense compound targeted to a Tau nucleic acid is 18 to 21 subunits in length. In certain embodiments, an antisense compound targeted to a Tau nucleic acid is 18 to 20 subunits in length. In certain embodiments, an antisense compound targeted to a Tau nucleic acid is 20 to 30 subunits in length. In other words, such antisense compounds are from 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits, respectively. In certain embodiments, an antisense compound targeted to a Tau nucleic acid is 14 subunits in length. In certain embodiments, an antisense compound targeted to a Tau nucleic acid is 16 subunits in length. In certain embodiments, an antisense compound targeted to a Tau nucleic acid is 17 subunits in length. In certain embodiments, an antisense compound targeted to a Tau nucleic acid is 18 subunits in length. In certain embodiments, an antisense compound targeted to a Tau nucleic acid is 20 subunits in length. In other embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleosides.

In certain embodiments, an antisense compound targeted to a Tau nucleic acid is a single stranded ribonucleic acid or deoxyribonucleic acid antisense oligonucleotide.

Antisense oligonucleotides may target a specific, complementary, coding or non-coding, nucleic acid. Depending on the antisense oligonucleotide used, the binding of the oligonucleotide to its target nucleic acid sequence may or may not activate RNAse H. In some embodiments, the antisense oligonucleotide activates RNAse H, which degrades the target nucleic acid. The antisense oligonucleotides of several embodiments may be any length provided it binds selectively to the intended location. In general, the antisense oligonucleotide may be from 8, 10 or 12 nucleotides in length up to 20, 30, or 50 nucleotides in length.

In certain embodiments antisense oligonucleotides targeted to a Tau nucleic acid may be shortened or truncated. For example, a single subunit may be deleted from the 5' end (5' truncation), or alternatively from the 3' end (3' truncation). A shortened or truncated antisense compound targeted to a Tau nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al. (*J. Natl. Cancer Inst.* 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (*Nuc. Acid. Res.* 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a Tau nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

In certain embodiments, the antisense compounds are uniform sugar-modified oligonucleotides. Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—CH$_3$, among others), and bicyclic sugar modified nucleosides. In certain embodiments, wings may include several modified sugar moieties, including, for example 2'-MOE. In certain embodiments, wings may include several modified and unmodified sugar moieties. In certain embodiments, wings may include various combinations of 2'-MOE nucleosides and 2'-deoxynucleosides.

Each distinct region may comprise uniform sugar moieties, variant, or alternating sugar moieties. The wing-gap-wing motif is frequently described as "X—Y—Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X—Y—Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same; in other embodiments they are different. In certain embodiments, Y is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30, or more nucleosides. Thus, gapmers described herein include, but are not limited to, for example, 5-10-5, 5-10-4, 4-10-4, 4-10-3, 3-10-3, 2-10-2, 5-9-5, 5-9-4, 4-9-5, 5-8-5, 5-8-4, 4-8-5, 5-7-5, 4-7-5, 5-7-4, or 4-7-4.

In certain embodiments, antisense compounds targeted to a Tau nucleic acid possess a 5-8-5 gapmer motif.

In certain embodiments, an antisense compound targeted to a Tau nucleic acid has a gap-narrowed motif. In certain embodiments, a gap-narrowed antisense oligonucleotide targeted to a Tau nucleic acid has a gap segment of 9, 8, 7, or 6 2'-deoxynucleotides positioned immediately adjacent to and between wing segments of 5, 4, 3, 2, or 1 chemically modified nucleosides. In certain embodiments, the chemical modification comprises a bicyclic sugar. In certain embodiments, the bicyclic sugar comprises a 4' to 2' bridge selected from among: 4'-(CH2)n-O-2' bridge, wherein n is 1 or 2; and 4'-CH2-O—CH2-2'. In certain embodiments, the bicyclic sugar is comprises a 4'-CH(CH3)-O-2' bridge. In certain embodiments, the chemical modification comprises a non-bicyclic 2'-modified sugar moiety. In certain embodiments, the non-bicyclic 2'-modified sugar moiety comprises a 2'-O-methylethyl group or a 2'-O-methyl group.

In certain embodiments, an antisense compound targeted to a Tau nucleic acid is uniformly modified. In certain embodiments, the antisense compound comprises 12, 13, 14, 15, 16, 17, 18, 19, 20, 21, 22, 23, 24, or 25 nucleosides. In certain embodiments, each nucleoside is chemically modified. In certain embodiments, the chemical modification comprises a non-bicyclic 2'-modified sugar moiety. In certain embodiments, the 2'-modified sugar moiety comprises a 2'-O-methoxyethyl group. In certain embodiments, the 2'-modified sugar moiety comprises a 2'-O-methyl group.

Target Nucleic Acids, Target Regions and Nucleotide Sequences

Nucleotide sequences that encode Tau include, without limitation, the following: GENBANK Accession NT_010783.14 truncated from nucleotides 2624000 to 2761000 (incorporated herein as SEQ ID NO: 1); GENBANK Accession No. AK226139.1 (incorporated herein as SEQ ID NO: 2); GENBANK Accession No. NM_001123066.3 (incorporated herein as SEQ ID NO: 3); GENBANK Accession No. NM_001123067.3 (incorporated herein as SEQ ID NO: 4); GENBANK Accession No. NM_001203251.1 (incorporated herein as SEQ ID NO: 5); GENBANK Accession No. NM_001203252.1 (incorporated herein as SEQ ID NO: 6); GENBANK Accession No. NM_005910.5 (incorporated herein as SEQ ID NO: 7); GENBANK Accession No. NM_016834.4 (incorporated herein as SEQ ID NO: 8); GENBANK Accession No. NM_016835.4 (incorporated herein as SEQ ID NO: 9); or GENBANK Accession No. NM_016841.4 (incorporated herein as SEQ ID NO: 10).

It is understood that the sequence set forth in each SEQ ID NO contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for Tau can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in Tau mRNA levels are indicative of inhibition of Tau expression. Reductions in levels of a Tau protein are also indicative of inhibition of target mRNA expression. In certain embodiments, reductions in the 4R isoform of Tau mRNA levels are indicative of modulation of Tau splicing. Reductions in levels of the 4R isoform of Tau protein are also indicative of modulation of Tau splicing. In certain embodiments, increases in the 3R isoform of Tau mRNA levels are indicative of modulation of Tau splicing. Increases in levels of the 3R isoform of Tau protein are also indicative of modulation of Tau splicing. Reduction in percent of cells staining positive for hyperphosphorylated Tau are indicative of inhibition of Tau expression or modulation of Tau splicing. Improvement in neurological function is indicative of inhibition of Tau expression or modulation of Tau splicing. Improved memory and motor function are indicative of inhibition of Tau expression or modulation of Tau splicing. Reduction of neurofibrillary inclusions is indicative of inhibition of Tau expression or modulation of Tau splicing.

Hybridization

In some embodiments, hybridization occurs between an antisense compound disclosed herein and a Tau nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a Tau nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a Tau nucleic acid).

Non-complementary nucleobases between an antisense compound and a Tau nucleic acid may be tolerated provided that the antisense compound remains able to specifically hybridize to a target nucleic acid. Moreover, an antisense compound may hybridize over one or more segments of a Tau nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a Tau nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having four non-complementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound may be fully complementary to a Tau nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a Tau nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a Tau nucleic acid, or specified portion thereof.

The antisense compounds provided also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds are complementary to at least an 11 nucleobase portion of a target segment. In certain embodiments, the antisense compounds are complementary to at least a 12 nucleobase portion of a target segment. In certain embodiments, the antisense compounds are complementary to at least a 13 nucleobase portion of a target segment. In certain embodiments, the antisense compounds are complementary to at least a 14 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a Tau nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of an antisense compound is a phosphorothioate internucleoside linkage.

Modified Sugar Moieties

Oligomeric compounds provided herein may comprise one or more monomers, including a nucleoside or nucleotide, having a modified sugar moiety. For example, the furanosyl sugar ring of a nucleoside or nucleotide can be modified in a number of ways including, but not limited to, addition of a substituent group and bridging of two non-geminal ring atoms to form a Locked Nucleic Acid (LNA).

In certain embodiments, oligomeric compounds comprise one or more monomers having a bicyclic sugar. In certain embodiments, the monomer is an LNA. In certain such embodiments, LNAs include, but are not limited to, (A) α-L-Methyleneoxy (4'-CH$_2$—O-2') LNA, (B) β-D-Methyleneoxy (4'-CH$_2$—O-2') LNA, (C) Ethyleneoxy (4'-(CH$_2$)$_2$—O-2') LNA, (D) Aminooxy (4'-CH$_2$—O—N(R)-2') LNA and (E) Oxyamino (4'-CH$_2$—N(R)—O-2') LNA, as depicted below.

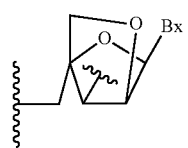
(A)

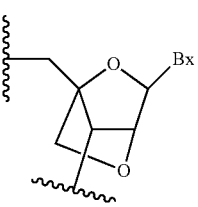
(B)

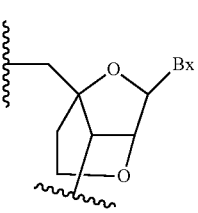
(C)

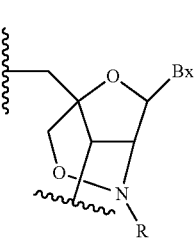
(D)

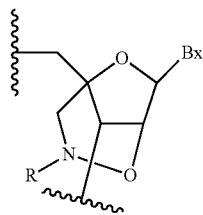
(E)

In certain embodiments, LNA compounds include, but are not limited to, compounds having at least one bridge between the 4' and the 2' position of the sugar wherein each of the bridges independently comprises 1 or from 2 to 4 linked groups independently selected from —[C(R$_1$)(R$_2$)]$_n$—, —C(R$_1$)=C(R$_2$)—, —C(R$_1$)=N—, —C(=NR$_1$)—, —C(=O)—, —C(=S)—, —O—, —Si(R$_1$)$_2$—, —S(=O)$_x$— and —N(R$_1$)—;

wherein:

x is 0, 1, or 2;

n is 1, 2, 3, or 4;

each R$_1$ and R$_2$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, a heterocycle radical, a substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)$_2$-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In one embodiment, each of the bridges of the LNA compounds is, independently, —[C(R$_1$)(R$_2$)]$_n$—, —[C(R$_1$)(R$_2$)]$_n$—O—, —C(R$_1$R$_2$)—N(R$_1$)—O— or —C(R$_1$R$_2$)—O—N(R$_1$)—. In another embodiment, each of said bridges is, independently, 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R$_1$)-2' and 4'-CH$_2$—N(R$_1$)—O-2'- wherein each R$_1$ is, independently, H, a protecting group or C$_1$-C$_{12}$ alkyl.

Certain LNA's have been prepared and disclosed in the patent literature as well as in scientific literature (see for example: issued U.S. Pat. Nos. 7,053,207; 6,268,490; 6,770,748; 6,794,499; 7,034,133; 6,525,191; 7,696,345; 7,569,575; 7,314,923; 7,217,805; and 7,084,125, hereby incorporated by reference herein in their entirety.

Also provided herein are LNAs in which the 2'-hydroxyl group is connected, to the 4' carbon atom of the ribosyl sugar ring, thereby forming a methyleneoxy (4'-CH$_2$—O-2') bridge to form the bicyclic sugar moiety (reviewed in Elayadi et al., Curr. Opinion Invens. Drugs, 2001, 2, 558-561; Braasch et al., Chem. Biol., 2001, 8 1-7; and Orum et al., Curr. Opinion Mol. Ther., 2001, 3, 239-243; see also U.S. Pat. No. 6,670,461). Furthermore, the bridge can also be a methylene (—CH$_2$—) group connecting the 2' oxygen atom to the 4' carbon atom of the sugar ring, for which the term methyleneoxy (4'-CH$_2$—O-2') LNA is used. In the case of the bicylic sugar moiety having an ethylene bridging group in this position, the term ethyleneoxy (4'-CH$_2$CH$_2$—O-2') LNA is used (Singh et al., Chem. Commun., 1998, 4, 455-456; Morita et al., *Bioorganic Medicinal Chemistry*, 2003, 11, 2211-2226). Methyleneoxy (4'-CH$_2$—O-2') LNA and other bicyclic sugar analogs display very high duplex thermal stabilities with complementary DNA and RNA (Tm=+3 to +10° C.), stability towards 3'-exonucleolytic degradation and good solubility properties. Potent and non-toxic antisense oligonucleotides comprising LNAs have been described (Wahlestedt et al., *Proc. Natl. Acad. Sci. U.S.A*, 2000, 97, 5633-5638).

An isomer of methyleneoxy (4'-CH$_2$—O-2') LNA that has also been discussed is α-L-methyleneoxy (4'-CH$_2$—O-2') LNA which has been shown to have superior stability against a 3'-exonuclease. The α-L-methyleneoxy (4'-CH$_2$—O-2') LNA's were incorporated into antisense gapmers and chimeras that showed potent antisense activity (Frieden et al., Nucleic Acids Research, 2003, 21, 6365-6372).

The synthesis and preparation of adenine, cytosine, guanine, 5-methyl-cytosine, thymine and uracil LNAs having a methyleneoxy (4'-CH$_2$—O-2') bridge, along with their oligomerization, and nucleic acid recognition properties have been described (Koshkin et al., Tetrahedron, 1998, 54, 3607-3630). LNAs and preparation thereof are also described in WO 98/39352 and WO 99/14226, incorporated by reference herein.

Analogs of various LNA nucleosides that have 4' to 2' bridging groups such as 4'-CH$_2$—O-2' (methyleneoxy) and 4'-CH$_2$—S-2' (methylene-thio), have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-LNA, a novel conformationally restricted high-affinity oligonucleotide analog has been described in the art (Singh et al., J. Org. Chem., 1998, 63, 10035-10039). In addition, 2'-amino- and 2'-methylamino-LNA's have been prepared and the thermal stability of their duplexes with complementary RNA and DNA strands has been previously reported.

As used herein, "bicyclic nucleoside" refers to a nucleoside comprising a bridge connecting two carbon atoms of the sugar ring, thereby forming a bicyclic sugar moiety. In certain embodiments, the bridge connects the 2' carbon and another carbon of the sugar ring.

As used herein, "4'-2' bicyclic nucleoside" or "4' to 2' bicyclic nucleoside" refers to a bicyclic nucleoside comprising a furanose ring comprising a bridge connecting the 2' carbon atom and the 4' carbon atom of the sugar ring.

One carbocyclic bicyclic nucleoside having a 4'-(CH$_2$)$_3$-2' bridge and the alkenyl analog, bridge 4'-CH═CH—CH$_2$-2', have been described (see, e.g., Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

Many other bicyclic and tricyclic sugar surrogate ring systems are also known in the art that can be used to modify nucleosides for incorporation into antisense compounds as provided herein (see, e.g., review article: Leumann, J. C, *Bioorganic & Medicinal Chemistry*, 2002, 10, 841-854). Such ring systems can undergo various additional substitutions to further enhance their activity. Such ring systems can undergo various additional substitutions to enhance activity.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[(CH$_2$)$_n$O]$_m$CH$_3$, O(CH$_2$)$_n$NH$_2$, O(CH$_2$)$_n$CH$_3$, O(CH$_2$)$_n$ONH$_2$, OCH$_2$C(═O)N(H)CH$_3$, and O(CH$_2$)$_n$ON[(CH$_2$)$_n$CH$_3$]$_2$, where n and m are from 1 to about 10. Other 2'-substituent groups can also be selected from: C$_1$-C$_{12}$ alkyl; substituted alkyl; alkenyl; alkynyl; alkaryl; aralkyl; O-alkaryl or O-aralkyl; SH; SCH$_3$; OCN; Cl; Br; CN; CF$_3$; OCF$_3$; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; a group for improving pharmacokinetic properties; and a group for improving the pharmacodynamic properties of an antisense compound, and other substituents having similar properties. In certain embodiments, modified nucleosides comprise a 2'-MOE side chain (see, e.g., Baker et al., J. Biol. Chem., 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (see, e.g., Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, "2'-modified nucleoside" or "2'-substituted nucleoside" refers to a nucleoside comprising a sugar comprising a substituent at the 2' position of a furanose ring other than H or OH. 2' modified nucleosides include, but are not limited to, nucleosides with non-bridging 2'substituents, such as allyl, amino, azido, thio, O-allyl, O—C$_1$-C$_{10}$ alkyl, —OCF$_3$, O—(CH$_2$)$_2$—O—CH$_3$, 2'-O(CH$_2$)$_2$SCH$_3$, O—(CH$_2$)$_2$—O—N(R$_m$)(R$_n$), or O—CH$_2$—C(═O)—N(R$_m$)(R$_n$), where each R$_m$ and R$_n$ is, independently, H or substituted or unsubstituted C$_1$-C$_{10}$ alkyl. 2'-modifed nucleosides may further comprise other modifications, for example, at other positions of the sugar and/or at the nucleobase.

As used herein, "2'-F" refers to modification of the 2' position of the furanosyl sugar ring to comprise a fluoro group.

As used herein, "2'-OMe" or "2'-OCH$_3$" or "2'-O-methyl" each refers to modification at the 2' position of the furanosyl sugar ring to comprise a —OCH$_3$ group.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA). Methods for the preparations of modified sugars are well known to those skilled in the art.

In nucleotides having modified sugar moieties, the nucleobase moieties (natural, modified, or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE.

RNAi Compounds

In certain embodiments, antisense compounds are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). In certain embodiments, antisense compounds comprise modifications that make them particularly suited for such mechanisms.

(I) ssRNA Compounds

In certain embodiments, antisense compounds including those particularly suited for use as single-stranded RNAi compounds (ssRNA) comprise a modified 5'-terminal end. In certain such embodiments, the 5'-terminal end comprises a modified phosphate moiety. In certain embodiments, such modified phosphate is stabilized (e.g., resistant to degradation/cleavage compared to unmodified 5'-phosphate). In certain embodiments, such 5'-terminal nucleosides stabilize the 5'-phosphorous moiety. Certain modified 5'-terminal nucleosides may be found in the art, for example in WO/2011/139702.

In certain embodiments, the 5'-nucleoside of an ssRNA compound has Formula IIc:

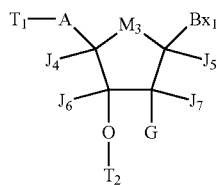

wherein:

$T_1$ is an optionally protected phosphorus moiety;

$T_2$ is an internucleoside linking group linking the compound of Formula IIc to the oligomeric compound;

A has one of the formulas:

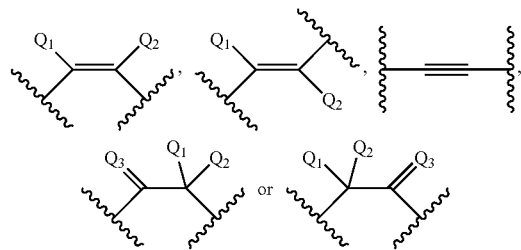

$Q_1$ and $Q_2$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or $N(R_3)(R_4)$;

$Q_3$ is O, S, $N(R_5)$ or $C(R_6)(R_7)$;

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;

$M_3$ is O, S, $NR_{14}$, $C(R_{15})(R_{16})$, $C(R_{15})(R_{16})C(R_{17})(R_{18})$, $C(R_{15})$=$C(R_{17})$, $OC(R_{15})(R_{16})$ or $OC(R_{15})(Bx_2)$;

$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$Bx_1$ is a heterocyclic base moiety;

or if $Bx_2$ is present then $Bx_2$ is a heterocyclic base moiety and $Bx_1$ is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

or $J_4$ forms a bridge with one of $J_5$ or $J_7$ wherein said bridge comprises from 1 to 3 linked biradical groups selected from O, S, $NR_{19}$, $C(R_{20})(R_{21})$, $C(R_{20})$=$C(R_{21})$, $C[$=$C(R_{20})(R_{21})]$ and $C($=$O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or O—$[C(R_8)(R_9)]_n$—$[(C$=$O)_m$—$X_1]_j$—Z;

each $R_8$ and $R_9$ is, independently, H, halogen, $C_1$-$C_6$ alkyl or substituted $C_1$-$C_6$ alkyl;

$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, =$NJ_1$, $SJ_1$, $N_3$, CN, $OC($=$X_2)J_1$, $OC($=$X_2)$—$N(J_1)(J_2)$ and $C($=$X_2)N(J_1)(J_2)$;

$X_2$ is O, S or $NJ_3$;

each $J_1$, $J_2$ and $J_3$ is, independently, H or $C_1$-$C_6$ alkyl;

when j is 1 then Z is other than halogen or $N(E_2)(E_3)$; and wherein said oligomeric compound comprises from 8 to 40 monomeric subunits and is hybridizable to at least a portion of a target nucleic acid.

In certain embodiments, $M_3$ is O, CH=CH, $OCH_2$ or $OC(H)(Bx_2)$. In certain embodiments, $M_3$ is O.

In certain embodiments, $J_4$, $J_5$, $J_6$ and $J_7$ are each H. In certain embodiments, $J_4$ forms a bridge with one of $J_5$ or $J_7$.

In certain embodiments, A has one of the formulas:

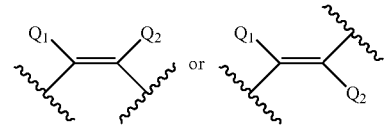

wherein:

$Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each H. In certain embodiments, $Q_1$ and $Q_2$ are each, independently, H or halogen. In certain embodiments, $Q_1$ and $Q_2$ is H and the other of $Q_1$ and $Q_2$ is F, $CH_3$ or $OCH_3$.

In certain embodiments, $T_1$ has the formula:

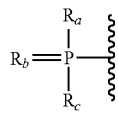

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and $R_b$ is O or S. In certain embodiments, $R_b$ is O and $R_a$ and $R_c$ are each, independently, $OCH_3$, $OCH_2CH_3$ or $CH(CH_3)_2$.

In certain embodiments, G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—$N(R_{10})(R_{11})$, $O(CH_2)_2$—$ON(R_{10})(R_{11})$, $O(CH_2)_2$—$O(CH_2)_2$—$N(R_{10})(R_{11})$, $OCH_2C(=O)$—$N(R_{10})(R_{11})$, $OCH_2C(=O)$—$N(R_{12})$—$(CH_2)_2$—$N(R_{10})(R_{11})$ or $O(CH_2)_2$—$N(R_{12})$—$C(=NR_{13})[N(R_{10})(R_{11})]$ wherein $R_{10}$, $R_{11}$, $R_{12}$ and $R_{13}$ are each, independently, H or $C_1$-$C_6$ alkyl. In certain embodiments, G is halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$ or $OCH_2$—$N(H)$—$C(=NH)NH_2$. In certain embodiments, G is F, $OCH_3$ or $O(CH_2)_2$—$OCH_3$. In certain embodiments, G is $O(CH_2)_2$—$OCH_3$.

In certain embodiments, the 5'-terminal nucleoside has Formula IIe:

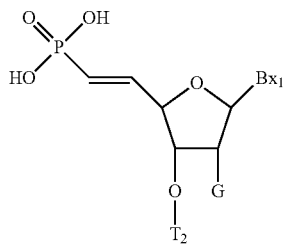

In certain embodiments, antisense compounds, including those particularly suitable for ssRNA comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modifications are 2'-F and 2'-OMe. Such regions may be contiguous or may be interrupted by differently modified nucleosides or conjugated nucleosides.

In certain embodiments, the alternating region of alternating modifications each consist of a single nucleoside (i.e., the pattern is $(AB)_xA_y$, wherein A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides may include one or more regions of any of the following nucleoside motifs:

AABBAA;
ABBABB;
AABAAB;
ABBABAABB;
ABABAA;
AABABAB;
ABABAA;
ABBAABBABABAA;
BABBAABBABABAA; or
ABABBAABBABABAA;

wherein A is a nucleoside of a first type and B is a nucleoside of a second type. In certain embodiments, A and B are each selected from 2'-F, 2'-OMe, BNA, and MOE.

In certain embodiments, oligonucleotides having such an alternating motif also comprise a modified 5' terminal nucleoside, such as those of formula IIc or IIe.

In certain embodiments, oligonucleotides comprise a region having a 2-2-3 motif. Such regions comprises the following motif:

-$(A)_2$-$(B)_x$-$(A)_2$-$(C)_y$-$(A)_3$- wherein: A is a first type of modifed nucleoside;

B and C, are nucleosides that are differently modified than A, however, B and C may have the same or different modifications as one another;

x and y are from 1 to 15.

In certain embodiments, A is a 2'-OMe modified nucleoside. In certain embodiments, B and C are both 2'-F modified nucleosides. In certain embodiments, A is a 2'-OMe modified nucleoside and B and C are both 2'-F modified nucleosides.

In certain embodiments, oligonucleosides have the following sugar motif:

5'-(Q)-$(AB)_xA_y$-$(D)_z$ wherein:

Q is a nucleoside comprising a stabilized phosphate moiety. In certain embodiments, Q is a nucleoside having Formula IIc or IIe;

A is a first type of modifed nucleoside;

B is a second type of modified nucleoside;

D is a modified nucleoside comprising a modification different from the nucleoside adjacent to it. Thus, if y is 0, then D must be differently modified than B and if y is 1, then D must be differently modified than A. In certain embodiments, D differs from both A and B.

X is 5-15;
Y is 0 or 1;
Z is 0-4.

In certain embodiments, oligonucleosides have the following sugar motif:

5'-(Q)-(A)$_x$-(D)$_z$ wherein:

Q is a nucleoside comprising a stabilized phosphate moiety. In certain embodiments, Q is a nucleoside having Formula IIc or IIe;

A is a first type of modified nucleoside;

D is a modified nucleoside comprising a modification different from A.

X is 11-30;
Z is 0-4.

In certain embodiments A, B, C, and D in the above motifs are selected from: 2'-OMe, 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine.

In certain embodiments, antisense compounds, including those particularly suited for use as ssRNA comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region | 3'-region |
|---|---|---|
| PS | Alternating PO/PS | 6 PS |
| PS | Alternating PO/PS | 7 PS |
| PS | Alternating PO/PS | 8 PS | siRNA Compounds

In certain embodiments, antisense compounds are double-stranded RNAi compounds (siRNA). In such embodiments, one or both strands may comprise any modification motif described above for ssRNA. In certain embodiments, ssRNA compounds may be unmodified RNA. In certain embodiments, siRNA compounds may comprise unmodified RNA nucleosides, but modified internucleoside linkages.

Several embodiments relate to double-stranded compositions wherein each strand comprises a motif defined by the location of one or more modified or unmodified nucleosides. In certain embodiments, compositions are provided comprising a first and a second oligomeric compound that are fully or at least partially hybridized to form a duplex region and further comprising a region that is complementary to and hybridizes to a nucleic acid target. It is suitable that such a composition comprise a first oligomeric compound that is an antisense strand having full or partial complementarity to a nucleic acid target and a second oligomeric compound that is a sense strand having one or more regions of complementarity to and forming at least one duplex region with the first oligomeric compound.

The compositions of several embodiments modulate gene expression by hybridizing to a nucleic acid target resulting in loss of its normal function. In some embodiments, the target nucleic acid is an eRNA. In certain embodiment, the degradation of the targeted eRNA is facilitated by an activated RISC complex that is formed with compositions of the invention.

Several embodiments are directed to double-stranded compositions wherein one of the strands is useful in, for example, influencing the preferential loading of the opposite strand into the RISC (or cleavage) complex. The compositions are useful for targeting selected nucleic acid molecules and modulating the expression of one or more genes. In some embodiments, the compositions of the present invention hybridize to a portion of a target RNA resulting in loss of normal function of the target RNA.

Certain embodiments are drawn to double-stranded compositions wherein both the strands comprises a hemimer motif, a fully modified motif, a positionally modified motif or an alternating motif. Each strand of the compositions of the present invention can be modified to fulfill a particular role in for example the siRNA pathway. Using a different motif in each strand or the same motif with different chemical modifications in each strand permits targeting the antisense strand for the RISC complex while inhibiting the incorporation of the sense strand. Within this model, each strand can be independently modified such that it is enhanced for its particular role. The antisense strand can be modified at the 5'-end to enhance its role in one region of the RISC while the 3'-end can be modified differentially to enhance its role in a different region of the RISC.

The double-stranded oligonucleotide molecules can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The double-stranded oligonucleotide molecules can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double-stranded structure, for example wherein the double-stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the double-stranded oligonucleotide molecule are complementary to the target nucleic acid or a portion thereof). Alternatively, the double-stranded oligonucleotide is assembled from a single oligonucleotide, where the self-complementary sense and antisense regions of the siRNA are linked by means of a nucleic acid based or non-nucleic acid-based linker(s).

The double-stranded oligonucleotide can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The double-stranded oligonucleotide can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNAi.

In certain embodiments, the double-stranded oligonucleotide comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the double-stranded oligonucleotide comprises nucleotide sequence that is complementary to nucleotide sequence of a target gene. In another embodiment, the double-stranded oligonucleotide interacts with nucleotide sequence of a target gene in a manner that causes inhibition of expression of the target gene.

As used herein, double-stranded oligonucleotides need not be limited to those molecules containing only RNA, but further encompasses chemically modified nucleotides and non-nucleotides. In certain embodiments, the short interfering nucleic acid molecules lack 2'-hydroxy (2'-OH) containing nucleotides. In certain embodiments short interfering nucleic acids optionally do not include any ribonucleotides (e.g., nucleotides having a 2'-OH group). Such double-stranded oligonucleotides that do not require the presence of ribonucleotides within the molecule to support RNAi can however have an attached linker or linkers or other attached or associated groups, moieties, or chains containing one or more nucleotides with 2'-OH groups. Optionally, double-stranded oligonucleotides can comprise ribonucleotides at about 5, 10, 20, 30, 40, or 50% of the nucleotide positions. As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, double-stranded oligonucleotides can be used to epigenetically silence genes at both the post-transcriptional level and the pre-transcriptional level. In a non-limiting example, epigenetic regulation of gene expression by siRNA molecules of the invention can result from siRNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

It is contemplated that compounds and compositions of several embodiments provided herein can target eRNAs by a dsRNA-mediated gene silencing or RNAi mechanism, including, e.g., "hairpin" or stem-loop double-stranded RNA effector molecules in which a single RNA strand with self-complementary sequences is capable of assuming a double-stranded conformation, or duplex dsRNA effector molecules comprising two separate strands of RNA. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000, or U.S. Ser. No. 60/130,377, filed Apr. 21, 1999. The dsRNA or dsRNA effector molecule may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other.

In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. In certain embodiments, the regions of complementarity are at least 70, 80, 90, 95, 98, or 100% complementary to each other and to a target nucleic acid sequence. In certain embodiments, the region of the dsRNA that is present in a double-stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a cDNA or other target nucleic acid sequence being represented in the dsRNA. In some embodiments, the dsRNA does not contain any single stranded regions, such as single stranded ends, or the dsRNA is a hairpin. In other embodiments, the dsRNA has one or more single stranded regions or overhangs. In certain embodiments, RNA/DNA hybrids include a DNA strand or region that is an antisense strand or region (e.g., has at least 70, 80, 90, 95, 98, or 100% complementarity to a target nucleic acid) and an RNA strand or region that is a sense strand or region (e.g., has at least 70, 80, 90, 95, 98, or 100% identity to a target nucleic acid), and vice versa.

In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as Taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999.

In other embodiments, the dsRNA can be any of the at least partially dsRNA molecules disclosed in WO 00/63364, as well as any of the dsRNA molecules described in U.S. Provisional Application 60/399,998; and U.S. Provisional Application 60/419,532, and PCT/US2003/033466, the teaching of which is hereby incorporated by reference. Any of the dsRNAs may be expressed in vitro or in vivo using the methods described herein or standard methods, such as those described in WO 00/63364.

Occupancy

In certain embodiments, antisense compounds are not expected to result in cleavage or the target nucleic acid via RNase H or to result in cleavage or sequestration through the RISC pathway. In certain such embodiments, antisense activity may result from occupancy, wherein the presence of the hybridized antisense compound disrupts the activity of the target nucleic acid. In certain such embodiments, the antisense compound may be uniformly modified or may comprise a mix of modifications and/or modified and unmodified nucleosides.

In certain embodiments, antisense oligonucleotides do not activate RNAse H. In several aspects, antisense oligonucleotides that do not activate RNAse H are complementary to a nucleic acid sequence encoding Tau and disrupts the splicing of the nucleic acid encoding Tau to reduce the 4R:3R Tau ratio.

The antisense oligonucleotide of several embodiments may disrupt the splicing of the nucleic acid encoding Tau to reduce the 4R:3R Tau ratio. The splicing process is a series of reactions, mediated by splicing factors, which is carried out on RNA after transcription but before translation, in which the intron(s) are removed, and the exons joined together sequentially so that the protein may be translated. Each intron is defined by a 5' splice site, a 3' splice site, and a branch point situated there between. An antisense oligonucleotide may block these splice elements when the oligonucleotide either fully or partially overlaps the element, or binds to the pre-mRNA at a position sufficiently close to the element to disrupt the binding and function of the splicing factors which would ordinarily mediate the particular splicing reaction which occurs at that element. The antisense oligonucleotide may block a variety of different splice elements to carry out certain embodiments. For instance, the antisense oligonucleotide may block a mutated element, a cryptic element, or a native element; it may block a 5' splice site, a 3' splice site, or a branch point.

Methods of making antisense oligonucleotides which do not activate RNase H are known in the art. See, e.g., U.S. Pat. No. 5,149,797 incorporated herein by reference. Such antisense oligonucleotides may contain one or more structural modification which sterically hinders or prevents binding of RNase H to a duplex molecule comprising the oligonucleotide, but does not substantially hinder or disrupt duplex formation. Antisense oligonucleotides that do not activate RNAse H may include oligonucleotides wherein at least one, two or more of the internucleotide bridging phosphate residues are modified phosphates, such as methyl phosphonates, methyl phosphonothioates, phosphoromorpholidates, phosphoropiperazidates and phosphoramidates. For instance, every other one of the internucleotide bridging phosphate residues may be a modified phosphate, contain a 2' loweralkyl moiety (e.g., C1-C4, linear or branched, saturated or unsaturated alkyl, such as methyl, ethyl, ethenyl, propyl, 1-propenyl, 2-propenyl, and isopropyl) or a combination thereof. In preferred embodiments, the antisense oligonucleotide of the invention that does not activate RNAse H, and disrupts the splicing of the nucleic acid encoding Tau to reduce the 4R:3R Tau ratio is a 2'-O-(2-methoxyethyl) (MOE)-modified antisense oligonucleotide.

Other methods of modifying an oligonucleotide to hinder binding of RNAse H may be found in P. Furdon et al., Nucleic Acids Res. 17, 9193-9204 (1989); S. Agrawal et al., Proc. Natl. Acad. Sci. USA 87, 1401-1405 (1990); C. Baker et al., Nucleic Acids Res. 18, 3537-3543 (1990); B. Sproat et al., Nucleic Acids Res. 17, 3373-3386 (1989); R. Walder and J. Walder, Proc. Natl. Acad. Sci. USA 85, 5011-5015 (1988) the disclosures of all of which are incorporated herein, in their entirety, by reference.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a Tau nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a Tau nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts. A prodrug can include the incorporation of additional nucleosides at one or both ends of an antisense compound which are cleaved by endogenous nucleases within the body, to form the active antisense compound.

In certain embodiments, an antisense oligonucleotide can include a physiologically and pharmaceutically acceptable salts thereof: i.e., salts that retain the desired biological activity of the parent compound and do not impart undesired toxicological effects thereto. Examples of such salts are (a) salts formed with cations such as sodium, potassium, NH4+, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

Administration

Antisense oligonucleotides of certain embodiments may be administered to a subject by several different means. For instance, oligonucleotides may generally be administered parenterally, intraperitoneally, intravascularly, or intrapulmonarily in dosage unit formulations containing conventional nontoxic pharmaceutically acceptable carriers, adjuvants, and vehicles as desired. In a preferred embodiment, the oligonucleotide may be administered parenterally.

The term parenteral as used herein includes subcutaneous, intravenous, intramuscular, intrathecal, or intrasternal injection, or infusion techniques. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

Delivery methods are preferably those that are effective to circumvent the blood-brain barrier and are effective to deliver agents to the central nervous system. For example, delivery methods may include the use of nanoparticles. The particles may be of any suitable structure, such as unilamellar or plurilamellar, so long as the antisense oligonucleotide is contained therein.

Positively charged lipids such as N-[1-(2,3-dioleoyloxi) propyl)-N, N,N-trimethylammoniummethylsulfate, or "DOTAP," are particularly preferred for such particles and vesicles. The preparation of such lipid particles is well known in the art. See, e.g., U.S. Pat. No. 4,880,635 to Janoff et al.; U.S. Pat. No. 4,906,477 to Kurono et al.: U.S. Pat. No. 4,911,928 to Wallach; U.S. Pat. No. 4,917,951 to Wallach; U.S. Pat. No. 4,920,016 to Allen et al.: U.S. Pat. No. 4,921,757 to Wheatley et al.; etc.

In one embodiment, the compounds provided herein may be administered in a bolus directly into the central nervous system. The compounds provided herein may be administered to the subject in a bolus once, or multiple times. In some preferred embodiments, the compounds provided herein may be administered once. In other preferred embodiments, the compounds provided herein may be administered multiple times. When administered multiple times, the compounds provided herein may be administered at regular intervals or at intervals that may vary during the treatment of a subject. In some embodiments, the compounds provided herein may be administered multiple times at intervals that may vary during the treatment of a subject. In some embodiments, the compounds provided herein may be administered multiple times at regular intervals.

In another preferred embodiment, the compounds provided herein may be administered by continuous infusion into the central nervous system. Non-limiting examples of methods that may be used to deliver the compounds provided herein into the central nervous system by continuous infusion may include pumps, wafers, gels, foams and fibrin clots. In a preferred embodiment, the compounds provided herein may be delivered into the central nervous system by continuous infusion using an osmotic pump. An osmotic mini pump contains a high-osmolality chamber that surrounds a flexible, yet impermeable, reservoir filled with the targeted delivery composition-containing vehicle. Subsequent to the subcutaneous implantation of this minipump, extracellular fluid enters through an outer semi-permeable membrane into the high-osmolality chamber, thereby compressing the reservoir to release the targeted delivery composition at a controlled, pre-determined rate. The targeted delivery composition, released from the pump, may be directed via a catheter to a stereotaxically placed cannula for infusion into the cerebroventricular space. In certain embodiments, the compounds provided herein may be delivered into the central nervous system by continuous infusion using a pump as described in the Examples.

In another preferred embodiment, the compounds provided herein may be delivered into the central nervous system by intrathecal administration. A catheter may be placed in the intrathecal lumbar space of the animal. The proximal end of the catheter may be attached to a dosing pedestal that may extend through the skin. In further embodiments, the compounds provided herein may be administered as a bolus injection. In other embodiments, the compounds provided herein may be administered as a continuous infusion.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of Tau nucleic acids can be tested in vitro in a variety of cell types. Cell types used for such analyses are available from commerical vendors (e.g. American Type Culture Collection, Manassas, Va.; Zen-Bio, Inc., Research Triangle Park, N.C.; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, SH-SY5Y and A172.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides may be mixed with LIPOFECTIN in OPTI-MEM 1 (Invitrogen, Carlsbad, Calif.) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that may range from 2 to 12 ug/mL per 100 nM antisense oligonucleotide.

Another technique used to introduce antisense oligonucleotides into cultured cells includes electroporation.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of a Tau nucleic acid can be assayed in a variety of ways known in the art. For example, target nucleic acid levels can be quantitated by, e.g., Northern blot analysis, competitive polymerase chain reaction (PCR), or quantitaive real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents may be obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invitrogen, Inc. Eugene, Oreg.). Methods of RNA quantification by RIBOGREEN are Taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a Tau nucleic acid. Methods for designing real-time PCR probes and primers are well known in the art, and may include the use of software such as PRIMER EXPRESS Software (Applied Biosystems, Foster City, Calif.).

Quantitative Real-Time PCR Analysis of Target DNA Levels

Quantitation of target DNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Gene (or DNA) target quantities obtained by real time PCR are normalized using either the expression level of a gene whose expression is constant, such as cyclophilin A, or by quantifying total DNA using RIBOGREEN (Invitrogen, Inc. Carlsbad, Calif.). Cyclophilin A expression is quantified by real time PCR, by being run simultaneously with the target, multiplexing, or separately. Total DNA is quantified using RIBOGREEN RNA quantification reagent (Invitrogen, Inc. Eugene, Oreg.). Methods of DNA quantification by RIBOGREEN are Taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a Tau nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of Tau nucleic acids can be assessed by measuring Tau protein levels. Protein levels of Tau can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of Tau and produce phenotypic changes. Testing may be performed in non-transgenic animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, subcutaneous, intrathecal, and intracerebroventricular. Calculation of antisense oligonucleotide dosage and dosing frequency is within the abilities of those skilled in the art, and depends upon factors such as route of administration and animal body weight. Following a period of treatment with antisense oligonucleotides, RNA is isolated from brain tissue and changes in Tau nucleic acid expression are measured. Changes in Tau DNA levels are also measured. Changes in Tau protein levels are also measured. Changes in Tau splicing are also measured.

Tau Splicing

Certain embodiments provided herein relate to differential splicing in tau. Accordingly, several embodiments provide methods of treating a tau associated disease by lowering tau or altering the splicing of a nucleic acid encoding tau. Tau is a protein found in multiple tissues, but is particularly abundant in axons of neurons. The primary function of tau is to bind to and stabilize microtubules, which are important structural components of the cytoskeleton involved in mitosis, cytokinesis and vesicular transport. In humans, there are six isoforms of tau that are generated by alternative splicing of exons 2, 3, and 10. Splicing of exons 2 and 3 at the N-terminus of the protein leads to inclusion of zero, one or two 29 amino acid, acidic domains and is termed 0N, 1N, or 2N tau respectively. Inclusion of exon 10 at the C-terminus leads to inclusion of the microtubule binding domain encoded by exon 10. Since there are 3 mictrotubule binding domains elsewhere in tau, this tau isoform (with exon 10 included) is termed 4R tau, where R refers to the number of repeats of microtubule binding domains. Tau without exon 10 is termed 3R tau. In healthy subjects, the ratio of 3R:4R tau is developmentally regulated, with fetal tissues expressing exclusively 3R tau and adult human tissues expressing approximately equal levels of 3R/4R tau. Deviations from the normal ratio of 3R:4R tau are characteristic of neurodegenerative syndromes such as FTD tauopathies. In essence, the method decreases the 4R:3R tau ratio in the central nervous system of the subject.

The 4R:3R tau ratio in the central nervous system of the subject may be normal, low or high. As used herein, a "normal 4R:3R tau ratio" in the central nervous system signifies a 4R:3R tau ratio in the central nervous system that is substantially the same as the 4R:3R tau ratio in the central nervous system of a subject from the same species and of approximately the same age not suffering from a neurodegenerative disease. In some embodiments, the method decreases the normal 4R:3R tau ratio in the central nervous system of a subject. In other embodiments, the method decreases a low 4R:3R tau ratio in the central nervous system of a subject.

In certain embodiments, the method decreases a high 4R:3R tau ratio in the central nervous system of a subject. In certain embodiments, the method decreases a high 4R:3R tau ratio caused by a defect in splicing of the nucleic acid encoding tau in the subject. Defects in splicing of the nucleic acid encoding tau in the subject may be caused, for instance, by genetic mutations altering the splicing of the nucleic acid encoding tau and leading to a high 4R:3R tau ratio. A mutation may be either a substitution mutation or a deletion mutation which creates a new, aberrant, splice element. Non-limiting examples of genetic mutations that may alter the splicing of the nucleic acid encoding tau and lead to a high 4R:3R tau ratio may include N279K, P301S, LI280, L284L, N296H, N296N, L1296N, P301 S, G303V, E10+11, E10+12, E10+13, E+10+14 and E10+16, and E10+19. Certain embodiments relate to a method of decreasing the 4R:3R tau ratio in the central nervous system of a subject by lowering expression of tau or altering the splicing of a nucleic acid encoding tau administering an antisense compound to the subject.

Certain Indications

In certain embodiments, provided herein are methods of treating an individual comprising administering one or more pharmaceutical compositions described herein. In certain embodiments, the individual has a neurodegenerative disease. In certain embodiments, the individual is at risk for developing a neurodegenerative disease, including, but not limited to, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, and Dravet's Syndrome. In certain embodiments, the individual has been identified as having a Tau associated disease. In certain embodiments, provided herein are methods for prophylactically reducing Tau expression in an individual. In certain embodiments, provided herein are methods for prophylactically modulating Tau splicing in an individual. Certain embodiments include treating an individual in need thereof by administering to an individual a therapeutically effective amount of an antisense compound targeted to a Tau nucleic acid.

In certain embodiments, administration of a therapeutically effective amount of an antisense compound targeted to a Tau nucleic acid is accompanied by monitoring of Tau levels and Tau isoform in an individual, to determine an individual's response to administration of the antisense compound. An individual's response to administration of the antisense compound may be used by a physician to determine the amount and duration of therapeutic intervention.

In certain embodiments, administration of an antisense compound targeted to a Tau nucleic acid results in reduction of Tau expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a Tau nucleic acid results in reduction of the 4R isoform of Tau expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a Tau nucleic acid results in reduced memory loss, reduced anxiety, improved motor function in an animal, and/or reduced incidence or severity of seizures. In certain embodiments, administration of a Tau antisense results in reduced memory loss, reduced anxiety, improved motor function; and/or reduced incidence or severity of seizures by at least 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to Tau are used for the preparation of a medicament for treating a patient suffering or susceptible to a neurodegenerative disease including Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, and Dravet's Syndrome.

Certain Splicing Compounds

In certain embodiments, splicing compounds are useful for treating neurodegenerative syndromes. In certain embodiments, such splicing compounds promote the exclusion of exon 10, resulting in shifting tau isoform from 4R Tau (which is associated with neurodegenerative syndrome) to 3R Tau. In certain embodiments, such splicing compounds are antisense oligonucleotides wherein each nucleoside comprises a high affinity modification. In certain embodiments, the splicing compound is complementary to a human Tau genetic sequence. In certain embodiments, the splicing compound is complementary to SEQ ID NO: 1 (GENBANK Accession No. NT_010783.14 truncated from nucleotides 2624000 to 2761000).

Certain splicing compounds for use in the claimed methods are described hereinbelow in the examples and include ISIS 415883, ISIS 415885, ISIS 415887, ISIS 549595, ISIS 549617, ISIS 549619, and ISIS 549620.

ISIS 415883 is 20 nucleobases in length having the sequence (5' to 3') TCTTATTAATTATCTGCACC (SEQ ID NO: 12) and each nucleoside comprises a 2'-MOE modification. Each internucleoside linkage is a phosphorothioate linkage and all cytosine residues are 5-methylcytosines.

ISIS 415885 is 20 nucleobases in length having the sequence (5' to 3') CCAGCTTCTTATTAATTATC (SEQ ID NO: 13) and each nucleoside comprises a 2'-MOE modification. Each internucleoside linkage is a phosphorothioate linkage and all cytosine residues are 5-methylcytosines.

ISIS 415887 is 20 nucleobases in length having the sequence (5' to 3') TAAGATCCAGCTTCTTATTA (SEQ ID NO: 14) and each nucleoside comprises a 2'-MOE modification. Each internucleoside linkage is a phosphorothioate linkage and all cytosine residues are 5-methylcytosines.

ISIS 549595 is 18 nucleobases in length having the sequence (5' to 3') GGACGTGTGAAGGTACTC (SEQ ID NO: 15) and each nucleoside comprises a 2'-MOE modification. Each internucleoside linkage is a phosphorothioate linkage and all cytosine residues are 5-methylcytosines.

ISIS 549617 is 18 nucleobases in length having the sequence (5' to 3') GCCCAAGAAGGATTTATT (SEQ ID NO: 16) and each nucleoside comprises a 2'-MOE modification. Each internucleoside linkage is a phosphorothioate linkage and all cytosine residues are 5-methylcytosines.

ISIS 549619 is 18 nucleobases in length having the sequence (5' to 3') TCCTGAGAGCCCAAGAAG (SEQ ID NO: 17) and each nucleoside comprises a 2'-MOE modification. Each internucleoside linkage is a phosphorothioate linkage and all cytosine residues are 5-methylcytosines.

ISIS 549620 is 18 nucleobases in length having the sequence (5' to 3') CAGATCCTGAGAGCCCAA (SEQ ID NO: 18) and each nucleoside comprises a 2'-MOE modification. Each internucleoside linkage is a phosphorothioate linkage and all cytosine residues are 5-methylcytosines.

Certain Comparator Compounds

In certain embodiments, splicing compounds described herein are compared to certain comparator compounds. In certain embodiments, the splicing compounds described herein perform better than comparator compounds in terms of in vitro or in vivo efficacy, potency, or tolerability. In certain embodiments, the comparator compound is complementary to a human Tau genetic sequence. In certain embodiments, the splicing compound is complementary to SEQ ID NO: 1 (GENBANK Accession No. NT_010783.14 truncated from nucleotides 2624000 to 2761000).

Certain comparator compounds are described hereinbelow in the examples and include ISIS 617782 and ISIS 617781.

ISIS 617782 is 21 nucleosides in length having the sequence (5' to 3') TGAAGGTACTCACACTGCCGC (SEQ ID NO: 19) and each nucleoside comprises a 2'-OCH$_3$ modification. Each internucleoside linkage is a phosphorothioate linkage and all cytosine residues are 5-methylcytosines.

ISIS 617781 is 18 nucleosides in length having the sequence (5' to 3') TATCTGCACCTTTGGTAG (SEQ ID NO: 20) and each nucleoside comprises a 2'-OCH$_3$ modification. Each internucleoside linkage is a phosphorothioate linkage and all cytosine residues are 5-methylcytosines.

As described hereinbelow, ISIS 415883 achieved an IC50 of 0.65 nM in a 6 point dose response curve (0, 0.1, 0.3, 1, 3, 10, or 30 nM) in cultured A172 cells transfected using Lipofectamine2000®, whereas ISIS 617781 achieved an IC50 of 20.25 nM. Human Tau primer probe set 10_11 was used. Thus, ISIS 415883 is more potent than the comparator compound ISIS 617781. See Example 8 hereinbelow.

As described hereinbelow, ISIS 549595, ISIS 549617, ISIS 549619, and ISIS 549620 achieved 20%, 31.8%, 41.7%, and 35.6% (respectively) Tau exon 10 mRNA expression relative to untreated control levels in cultured A172 cells transfected using Lipofectamine2000® with 5 nM oligonucleotide using human Tau primer probe set 10_11. ISIS 617781 achieved 65% Tau exon 10 mRNA expression relative to untreated control levels in cultured A172 cells transfected using Lipofectamine2000® with 10 nM oligonucleotide using human Tau primer probe set 10_11. Therefore, ISIS 549595, ISIS 549617, ISIS 549619, and ISIS 549620 are more efficacious than comparator compound ISIS 617781 even when ISIS 617781 is administered at 2x the dose of ISIS 549595, ISIS 549617, ISIS 549619, and ISIS 549620. See Examples 8 and 9 hereinbelow.

As described hereinbelow, ISIS 549595, ISIS 549619, ISIS 549620 achieved 26%, 42%, and 35% (respectively) Tau exon 10 mRNA expression relative to untreated control levels in cultured A172 cells transfected using Lipofectamine2000® with 5 nM oligonucleotide using human Tau primer probe set 9_10 R$_5$. ISIS 617782 achieved 55% Tau exon 10 mRNA expression relative to untreated control levels in cultured A172 cells transfected using Lipofectamine2000® with 3 nM and 34% Tau exon 10 mRNA expression relative to untreated control levels in cultured A172 cells transfected using Lipofectamine2000® with 10 nM oligonucleotide using human Tau primer probe set 9_10 R$_5$. See Examples 8 and 10 hereinbelow.

EXAMPLE

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example Set 1

The following examples illustrate various iterations of the invention.

Introduction to Examples 1-7

Accumulation of proteinaceous aggregates is one of the defining hallmarks of neurodegenerative diseases. How these proteins cause disease and how they are subsequently cleared has remained an enigma. Tau, a microtubule binding protein, is one such aggregated protein found in multiple neurodegenerative syndromes including Frontotemporal dementia (FTD), Alzheimer's disease (AD), Progressive Supranuclear Palsy, and Corticobasalganglionic Degeneration. Understanding tau mediated neurodegeneration may lead to important therapeutic strategies for these disorders. Studies in the examples below focus on how to prevent the behavioral effects and pathological abnormalities in mouse models of dementia by decreasing tau levels and by changing the ratio of two different tau isoforms, 3R and 4R tau.

The primary function of tau is to bind to and stabilize microtubules, which are important structural components of the cytoskeleton involved in mitosis, cytokinesis and vesicular transport. Tau is found in multiple tissues, but is particularly abundant in axons of neurons. In humans, there are six isoforms of tau that are generated by alternative splicing of exons 2, 3, and 10. Splicing of exons 2 and 3 at the N-terminus of the protein leads to inclusion of zero, one or two 29 amino acid, acidic domains and is termed 0N, 1N, or 2N tau respectively. The influence of these domains on tau function is not clear. Inclusion of exon 10 at the C-terminus leads to inclusion of the microtubule binding domain encoded by exon 10. Since there are 3 mictrotubule binding domains elsewhere in tau, this tau isoform (with exon 10 included) is termed 4R tau, where R refers to the number of repeats of microtubule binding domains. (FIG. 1). Tau without exon 10 is termed 3R tau. Since more microtubule binding domains (4R compared with 3R) probably increases the binding to microtubules, 4R tau presumably changes the microtubule binding characteristics. The ratio of 3R/4R tau is developmentally regulated, with fetal tissues expressing almost exclusively 3R tau and adult human tissues expressing approximately equal levels of 3R/4R tau. Deviations from the normal ratio of 3R/4R tau are characteristic of neurodegenerative FTD tauopathies. It is not known how changing the 3R/4R tau ratio at a later stage in the adult animal will affect tau pathogenesis.

Serine-threonine directed phosphorylation regulates the microtubule binding ability of tau. Phosphorylation promotes detachment of tau from microtubules. Other post translational modifications of tau have been described; however the significance of these is unclear. Phosphorylation of tau is also developmentally regulated with higher phosphorylation in fetal tissues and much lower phosphorylation in the adult. One characteristic of neurodegenerative disorders is aberrantly increased tau phosphorylation.

The microtubule network is involved in many important processes within the cell including structural integrity needed for maintaining morphology of cells and operating transport machinery. Since binding of tau to microtubules stabilizes microtubules, tau is likely to be a key mediator of some of these processes and disruption of normal tau in neurodegenerative diseases may disrupt some of these key cellular processes. Given the data suggesting an important role for tau in normal cellular processes, it is surprising that the tau knockout animals do not have an obvious phenotype.

One of the early indicators that tau may be important in neurodegenerative syndromes was the recognition that tau is a key component of neurofibrillary tangles in Alzheimer's disease. Along with amyloid beta containing plaques, neurofibrillary tangles are a hallmark of Alzheimer's disease and correlate significantly with cognitive impairment. 95% of tau accumulations in AD are found in neuronal processes and is termed neuritic dystrophy. The process(es) whereby this microtubule associated protein becomes disengaged from microtubules and forms accumulations of proteins and how this relates to neuronal toxicity is not well understood. Recent experiments suggest that tau may be a key mediator of amyloid beta induced toxicity. Tau knockout animals are protected from amyloid beta induced toxicity. The animals do develop amyloid beta plaques, but do not develop the behavioral phenotype typical of transgenic amyloid-3 depositing mice. Given the developmental regulation of tau isoforms and the adult onset of AD, it is important to understand whether decreasing levels of tau in the adult animal will provide neuroprotection as suggested by this experiment where tau is deleted developmentally as well as in the adult. Measuring the effect of decreasing levels of tau on neurodegeneration in Alzheimer's mice and FTD model mice is another central question of the examples below. Data from late onset Alzheimer's disease patients suggest that among patients with Alzheimer's disease increased CSF tau may lead to earlier age of onset, implying that tau is not only a component of the pathology of Alzheimer's disease, but may directly influence the course of disease. This reinforces the possibility that decreasing tau levels in patients may slow the course of Alzheimer's disease patients.

Neuronal tau inclusions are a pathological characteristic of not only Alzheimer's disease, but also a subset of Frontotemporal dementia (FTD), PSP, and CBD. The link between tau and neurodegeneration was solidified by the discovery that mutations in the tau gene cause a subset of FTD. These genetic data have also highlighted the importance of the 3R:4R ratio of tau. Many of the tau mutations that cause FTD lead to a change in tau splicing which leads to preferential inclusion of exon 10, and thus to increased 4R tau. The overall tau levels are normal. Whether the tau isoform change or the amino acid change or both cause neurodegeneration remains unknown. Recent data suggest that PSP may also be associated with an increased 4R:3R tau ratio and thus may be amenable to a similar splicing strategy.

To help understand the influence of tau ratios on neurodegeneration, a mouse model based on one of the splicing tau mutations (N279K) has been generated using a minigene that includes the tau promoter and the flanking intronic sequences of exon 10. As in humans, these mice demonstrate increased levels of 4R tau compared with transgenics expressing WT tau and develop behavioral and motor abnormalities as well as accumulations of aggregated tau in the brain and spinal cord. Very interestingly, additional transgenic lines in which N279K mutation was driven by a CMV promoter were also generated. These CMV-N279K animals have exclusively 4R tau at both fetal and adult stages and do not develop any disease. Therefore it is unlikely that N279K toxicity arises from the N279K amino acid change since CMV-N279K mice have the same mutation. Similarly, expression of increased 4R alone presumably does not cause disease since the CMV-N279K mice express equal levels of 4R tau, but do not develop disease. Rather, these data suggest that tau pathogenesis depends on the shift away from the normal 4R:3R ratio and/or the tau promoter itself. A critical unaddressed question is whether decreasing the 4R:3R ratios in the adult animals will prevent neurodegeneration.

Figure 2:
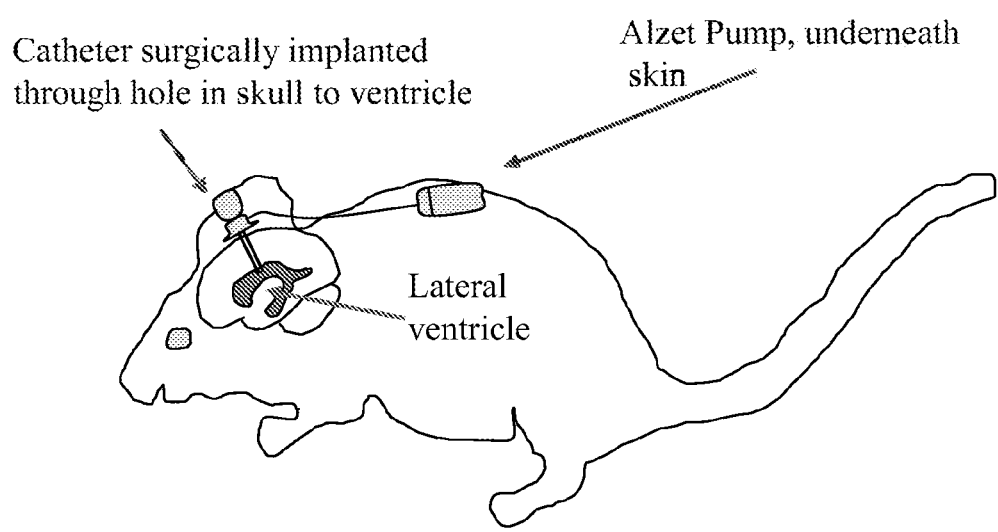
FIG. 2 depicts a diagram describing delivery of antisense oligonucleotides. Under anesthesia (inhaled isoflourane/oxygen mixture), a small hole is drilled in skull through which a catheter is placed in the lateral ventricle. The catheter is connected via plastic tubing to an osmotic pump (Alzet pump) which is embedded in a subcutaneous pocket on the back of the animal. Oligos are delivered continuously via this method. Changing the pump can be done easily by removing the osmotic pump without disturbing the indwelling catheter.

Antisense oligonucleotides are used to achieve tau knockdown and to modulate tau splicing. The inventors have pioneered the use of antisense oligonucleotides in the central nervous system. Although the oligos do not cross the blood brain barrier, this issue is solved by infusing the oligos directly into the cerebral spinal fluid (CSF) that circulates throughout the brain and the spinal cord. Direct CSF infusion of oligos is done using an osmotic pump (Alzet pump) connected via plastic tubing to a catheter implanted in the right lateral ventricle, the space within the brain filled with cerebral spinal fluid (FIG. 2). The pump delivers drug at a constant rate into the ventricle. Previous data from the inventors demonstrate a widespread distribution of oligos throughout the brain and spinal cord of both rat and Rhesus monkey, target specificity, and neuroprotection in an animal model of ALS based on expression of mutant SOD1G93A. Surprisingly, the antisense oligos penetrate deeply and evenly into the brain parenchyma targeting all regions of the brain.

Typical antisense oligos are designed to decrease gene expression by activating RNAse H, thus cleaving the target mRNA to which the oligo binds. Oligos may also be designed not to activate RNAse H, but to bind to introns or exon/intron boundaries and promote inclusion or exclusion of a particular exon. This strategy has been successful in mice for SMN, the gene whose absence causes spinal muscular atrophy. A similar strategy to promote exclusion of exon 10 and thus decrease the 4R to 3R tau ratio is described below. Decreasing the abnormal 4R:3R tau ratio may be sufficient to decrease the behavioral deficits and the pathological changes in the tau N279K mice, even though the tau protein sequence remains abnormal.

Example 1. Mouse Tau Knockdown In Vitro

Antisense oligonucleotides that decrease levels of tau mRNA in tissue culture have been identified. 80 antisense oligos designed to decrease mouse tau levels were screened by transfection into a murine cell line (FIG. 3A). From these results, 10 antisense oligos were judged to have relative good activity in this assay. These 10 oligos were tested in a dose response curve in a murine cell line (FIG. 3B). Nine of 10 oligos were active in this assay, demonstrating >80% decrease in tau mRNA compared with non-transfected controls. Two different scrambled oligos caused 15% knockdown at the highest dose and no effect on tau mRNA levels at lower doses.

Certain active oligos (i.e., oligonucleotides) in this assay, demonstrating >80% decrease in tau mRNA compared with non-transfected controls were taken forward in additional studies.

Example 2. Mouse Tau Knockdown In Vivo.
(Effect of Antisense Inhibition of Murine Tau by Systemic Administration in a Murine Model)

Antisense oligonucleotides from the study described above were selected for testing in vivo. The antisense oligonucleotides were designed as 5-10-5 MOE gapmers, and are 20 nucleosides in length, wherein the central gap segment is comprised of ten 2'-deoxynucleosides and is flanked on both sides (in the 5' and 3' directions) by wings comprising 5 nucleosides each. Each nucleoside in the 5' wing segment and each nucleoside in the 3' wing segment as a 2'-MOE modification. The internucleoside linkages throughout the gapmer are phosphorothioate (P=S) linkages. All cytosine residues throughout he gapmer are 5-methylcytosines.

From the above in vitro study (FIG. 3), 5 oligos were selected to test in vivo. First, the oligos were tested by intraperitoneal delivery of 37.5 mg/kg three times per week×3 weeks. After 3 weeks, a piece of liver and a sample of blood were collected. The blood was used to test for generic toxicity by measuring "liver enzymes", which are proteins found in the liver that are detectable in serum. In the setting of liver toxicity, these enzymes (ALT and AST) are increased. Liver enzymes were changed less than 2 fold indicating that these oligos are not likely to be toxic.

mRNA was isolated from liver and mouse Tau mRNA levels were measured by QPCR using GAPDH as a control. Three of the oligos (#2, 4, 5) decreased tau mRNA levels by about 50%, but there was substantial variability in the results, which is partly attributed to low abundance of tau mRNA in the liver samples (data not shown).

Figure 4A:
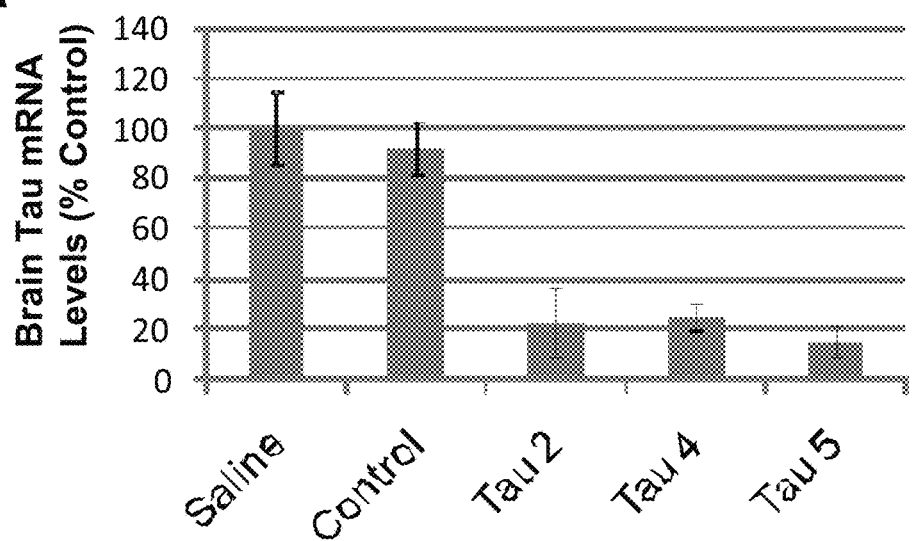
FIG. 4A-4C depict two plots and a Western blot showing antisense oligos decrease mouse tau levels in the brain. (A) Saline, control scrambled oligo, or 50 μg of antisense oligos directed against mouse tau were injected into the hippocampus by stereotactic injection. Mice were euthanized after one week and brain parenchyma was examined for mouse tau mRNA levels by QPCR. GAPDH mRNA was used to normalize samples. All three oligos used in this paradigm decreased mouse tau by >75%. Individual antisense oligos were labeled 1-5. Oligos 1 and 3 were not tested in this paradigm. (N=5 Avg+/−SD). (B, C) Since oligo Tau5 worked well in the intraparenchymal (hippocampal) injection in (A), Tau5 was further tested by infusing this oligo into the right lateral ventricle for 1 month, at 100 μg/day via an osmotic pump connected to a catheter in the right lateral ventricle. Mice were euthanized after 1 month and right temporal parietal cortex was examined for mouse tau mRNA levels (N=4, Avg+/−SD), (B) and mouse tau protein levels (C). Protein data from three saline animals and 4 Tau5 treated animals are shown. Tau protein levels are clearly reduced. GAPDH was used a loading control and shows no change.

Example: Effect of Antisense Inhibition of Tau by Direct Hippocampal Administration As a further test of the oligos, oligos 2, 4, 5 were screened by direct hippocampal injection. Saline, or a scrambled oligo, or 50 µg of antisense oligonucleotide was infused by stereotactic injection into the right hippocampus of a 60 day old non-transgenic mouse. After one week, mice were euthanized and the area surrounding the injection was isolated and used to prepare mRNA. Mouse tau mRNA levels were decreased >75% in all tau antisense oligo injected hippocampi (FIG. 4A).

Example: Effect of Antisense Inhibition of Tau by Intraventricular Administration Since the treatment paradigm for modulating behavior in the transgenic amyloid-β depositing mice will involve treatment of the entire brain using intraventricular injection of antisense oligonucleotides, the most active antisense oligo (Tau 5, FIG. 4A) was next tested by intraventricular injection.

Study 1

Figure 4B:
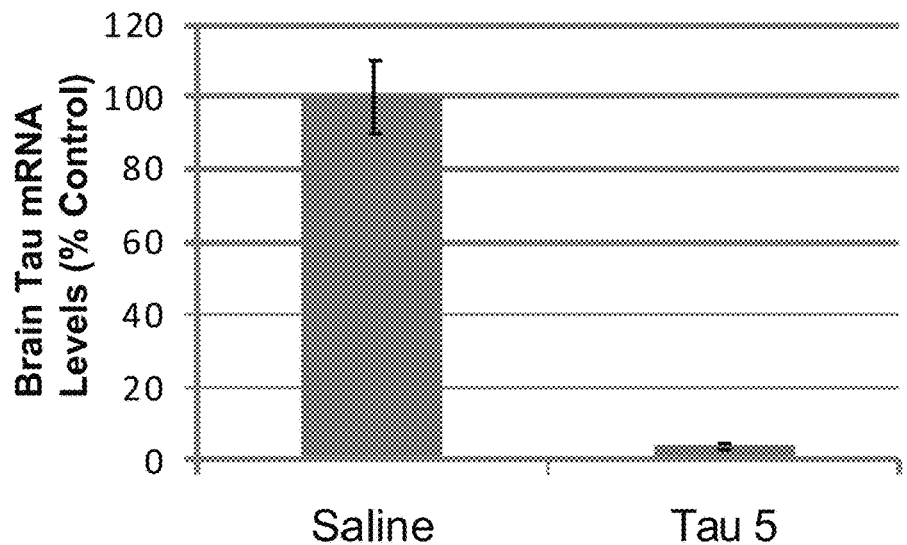
Figure 4C:
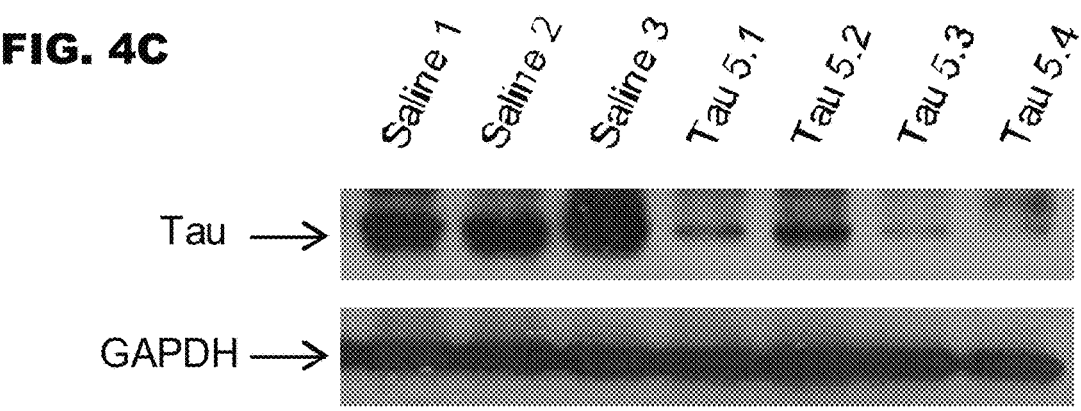

Saline or tau #5 was infused into the right lateral ventricle (of 8 week old C57BL6 mice) at 100 µg/day using an indwelling catheter connected to an Alzet osmotic pump buried in a subcutaneous pocket on the back of the animal (as described in FIG. 2). After 30 days, animals were euthanized and mRNA was prepared from a section of right frontal cortex. Tau mRNA levels were analyzed by QPCR. Using GAPDH as a normalizer, the knockdown of tau mRNA was about 95% in the animals treated with antisense oligonucleotide (FIG. 4B). Tau protein was also clearly decreased by Tau5 antisense oligonucleotide (FIG. 4C).

Study 2

Efficacy of lower doses of the Tau5 oligo (i.e., oligonucleotide) was also tested.

Figure 5:
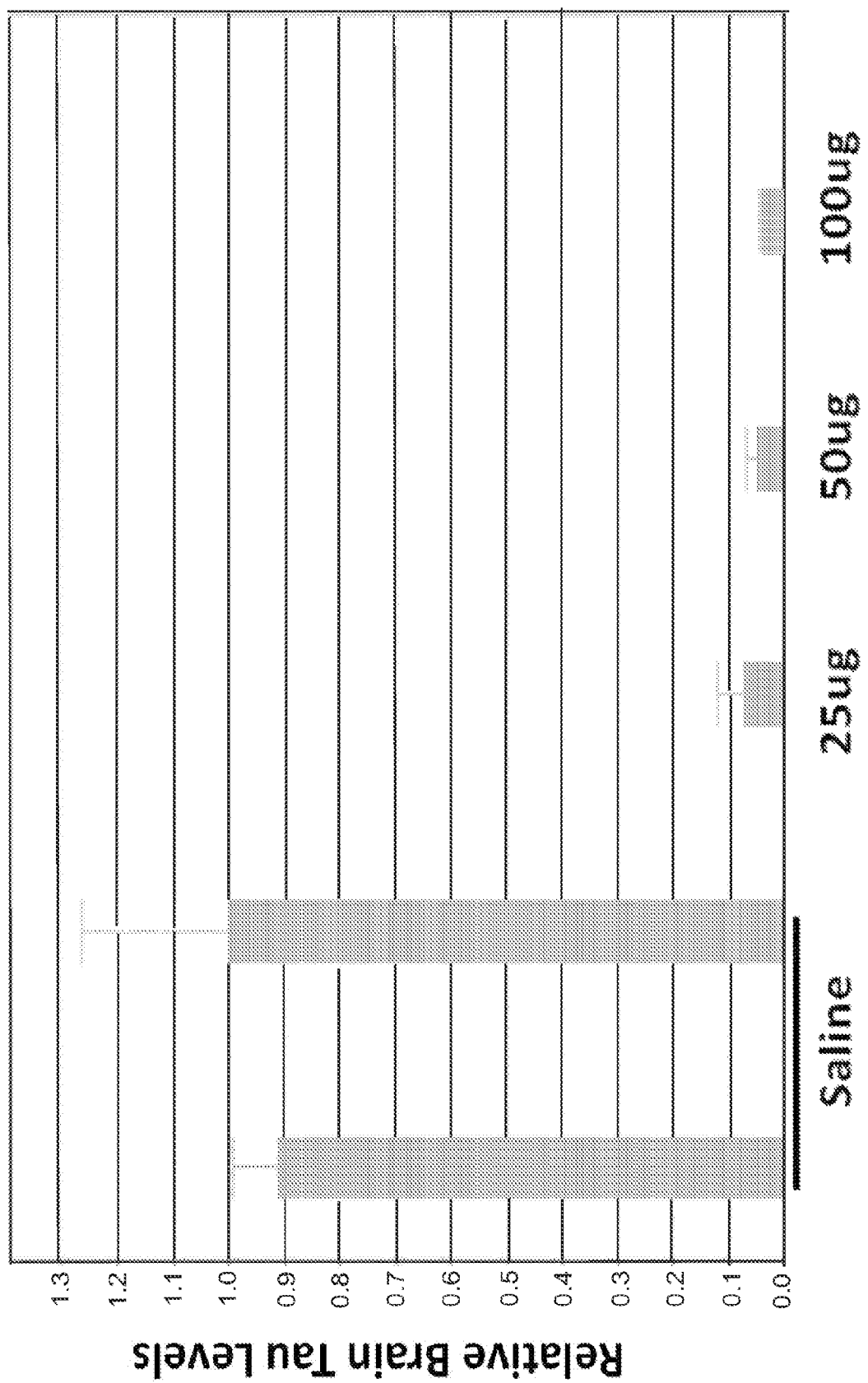
FIG. 5 depicts a plot representing the relative brain tau levels after infusion of 25, 50 and 100 μg of the knockdown oligo.

The current dose of 100 µg/day was tolerated well without any evidence of toxicity. Efficacy of lower doses of the tau5 oligo (i.e., oligonucleotide) were also tested using 25, 50 and 100 µg/day with the Alzet pump system. Four to five 8 week old non-transgenic BL6 mice per group were used. The lowest dose tested (25 µg/day) was still effective at knocking down relative brain tau levels (FIG. 5).

Study 3

Figure 6:
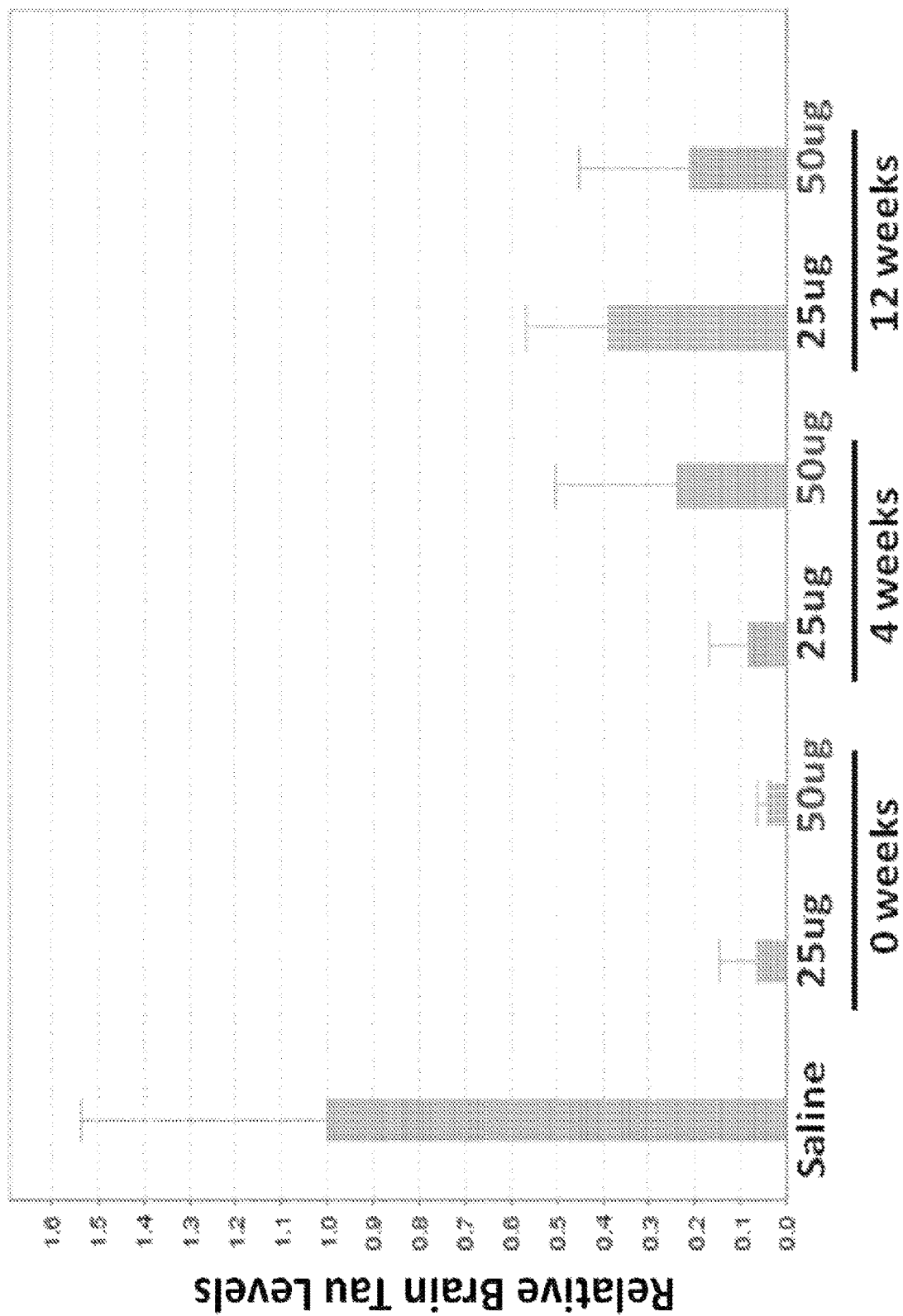
FIG. 6 depicts a plot representing the relative brain tau levels 0, 4 and 12 weeks after infusion of the knockdown oligo.

In addition, the half life of tau5 oligo after intraventricular infusion with the Alzet pump was also tested. Intraventricular infusions using 8 weeks old non-transgenic BL6 mice were as described above, using 3-6 mice per group. Tau5 oligo was infused at 25 and 50 µg/day for 1 month. Brains were then collected immediately after infusion, or 1 month, and 3 months after infusion. Brain tau levels were still significantly lower 12 weeks after infusion (FIG. 6).

Figure 7A:
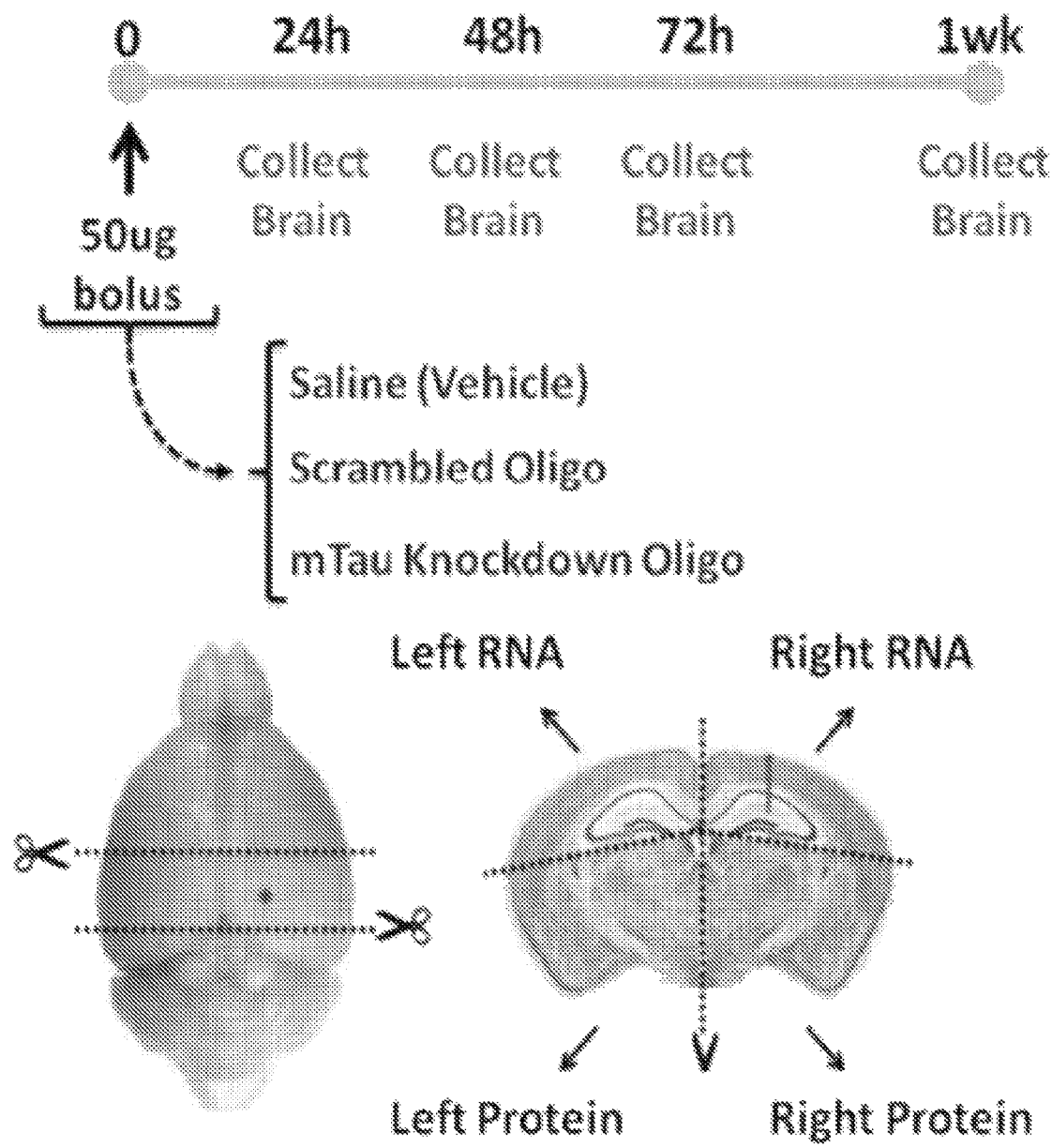
FIG. 7A-7C depict (A) the experimental setup and tissue collection, (B) a plot representing the total endogenous mouse tau mRNA levels 24, 48 and 72 hours after administration of the oligo, and (C) a Western blot of total endogenous mouse tau protein levels and GAPDH levels up to one month after administration of the oligo.
Figure 7B:
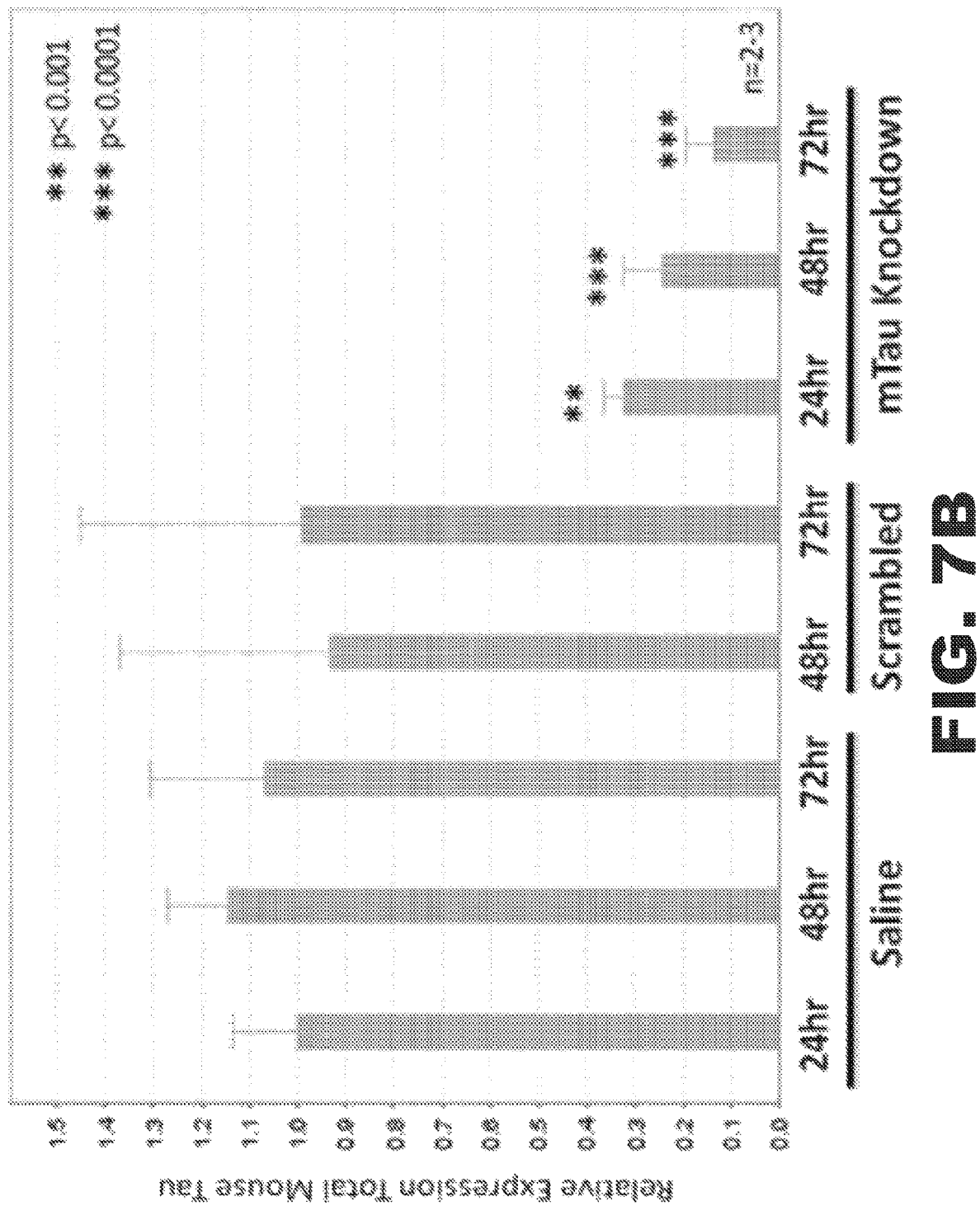
Figure 7C:
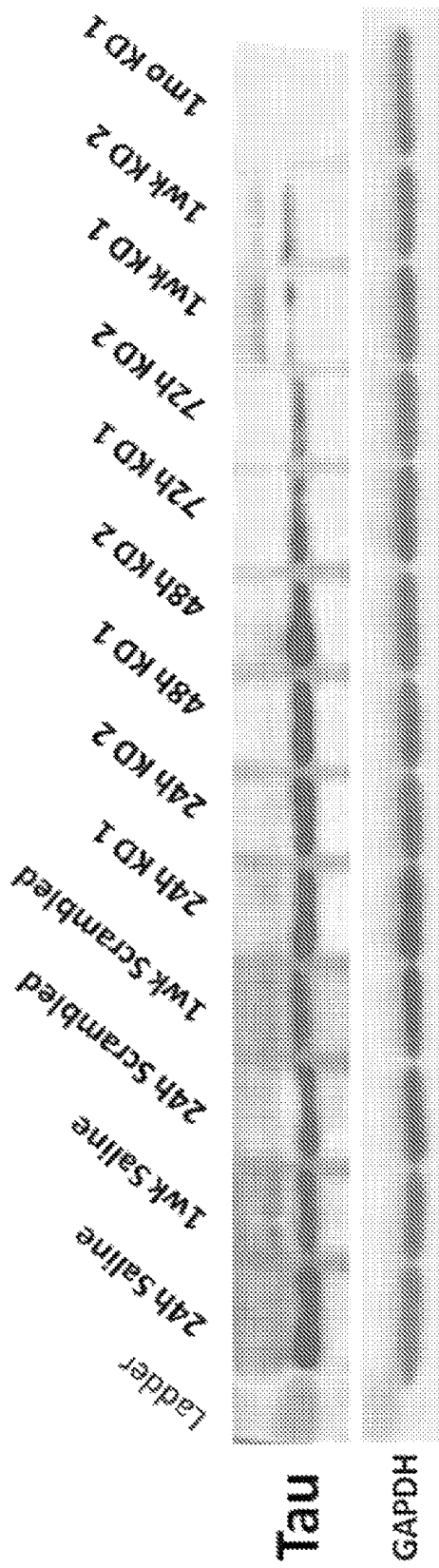

Example: Duration of Action of Tau #5 ASO by Intraventricular Administration To further characterize tau knockdown using antisense oligos, tau5 oligo was used to test duration of onset after injection of the oligo into mice (FIG. 7). In short, a 50 µg hippocampal bolus was injected (1 µl of 50 µg/µl solution was infused at 0.2 µl/min for 5 minutes) into 12 week old C57BL6 mice, brains were collected at 25 hours, 48 hours, and 72 hours post-injection (+/−2 hours). Four pieces of brain were collected—Right RNA, Right protein, Left RNA, Left protein (FIG. 7A). The right RNA and Right Protein pieces were used for qRT-PCR (FIG. 7B) and Western blot analysis (FIG. 7C), respectively. Tau mRNA levels significantly drop even after only 24 hours post bolus and continue to drop at 48 and 72 hours (FIG. 7B). Tau protein levels do not appear to decrease by the 24 and 48 hour time points by Western blot (FIG. 7C), suggesting that there is a lag between the mRNA knockdown and protein knockdown of tau. However, by 72 hours the protein levels begin to decrease such that by 1 week there is a significant decrease in tau protein levels (FIG. 7C).

Example 3. Changing Human Tau Splicing

Figure 9A:
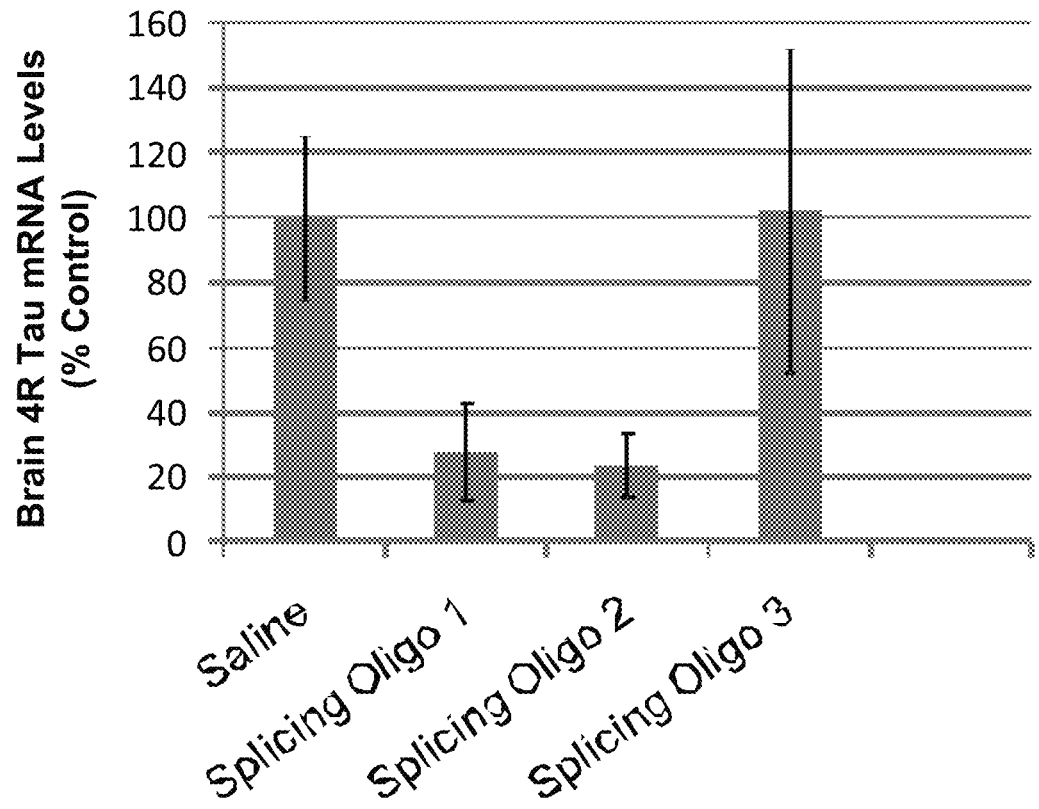
FIG. 9A-9B depict two plots showing tau splicing oligos decrease 4R tau. Oligos designed to specifically decrease 4R tau levels (50 μg) or saline were injected into the hippocampus by stereotactic injection into htau mice that express full length human tau. Mice were euthanized after one week and brain parenchyma was examined for human 4R tau mRNA (A) and for human tau 3R tau mRNA (B) by QPCR. GAPDH mRNA was used to normalize samples. (N=4 for saline, and 2 for each oligo, Avg+/−range).
Figure 9B:
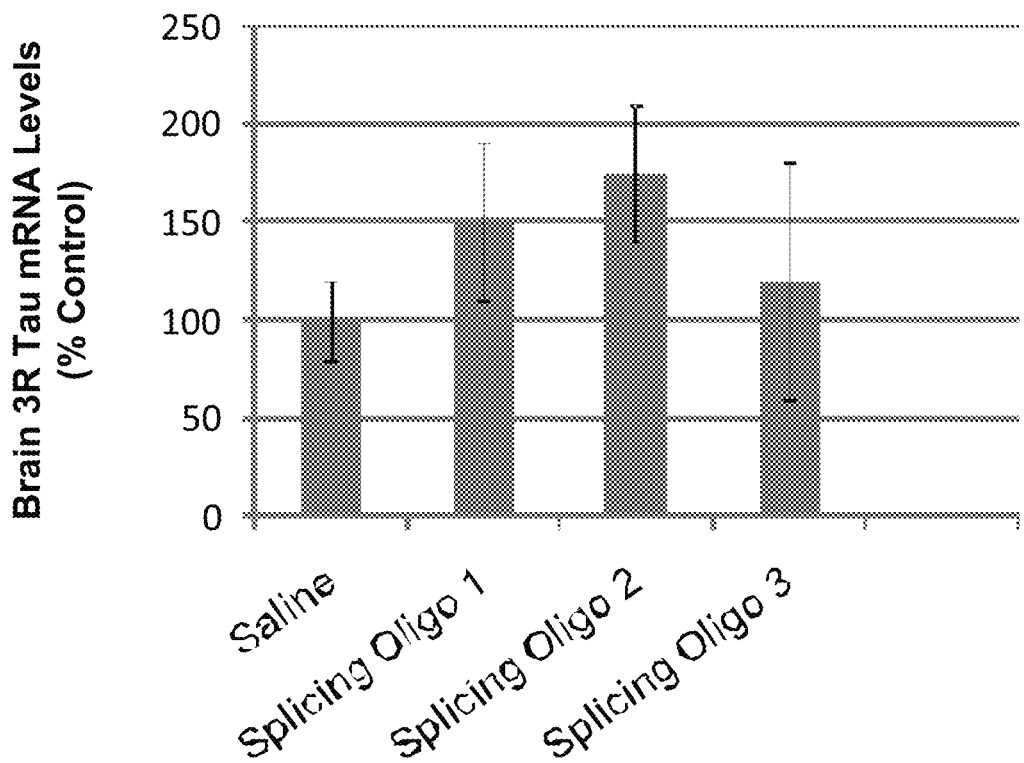

Saline or splicing oligos (i.e., "splicing oligo 1" also ISIS 415883, "splicing oligo 2" also ISIS 415885, and "splicing oligo 3" also ISIS 415887) which dramatically shifted the tau isoforms from mainly 4R with some 3R tau to mostly 3R tau with some 4R tau in an in vitro study, and designed to specifically decrease 4R tau levels, were infused into the hippocampus by stereotactic injection into htau mice that express full length human tau. Mice were euthanized after one week and brain parenchyma was examined for human 4R tau mRNA and for human 3R tau mRNA by QPCR (FIG. 9). The oligos clearly decrease 4R tau levels. They also appear to increase 3R levels. These data demonstrate the oligos are active in vivo.

The effect of tau415883 on 4R tau was also tested after intraventricular infusion with the Alzet pump was also tested. Intraventricular infusions using 14 week old non-transgenic BL6 mice were as described above, using 11-12 mice per group. Tau415883 oligo was infused at 50 µg/day for 28 days. Relative brain 4R tau levels were significantly lower (FIG. 8).

Figure 10:
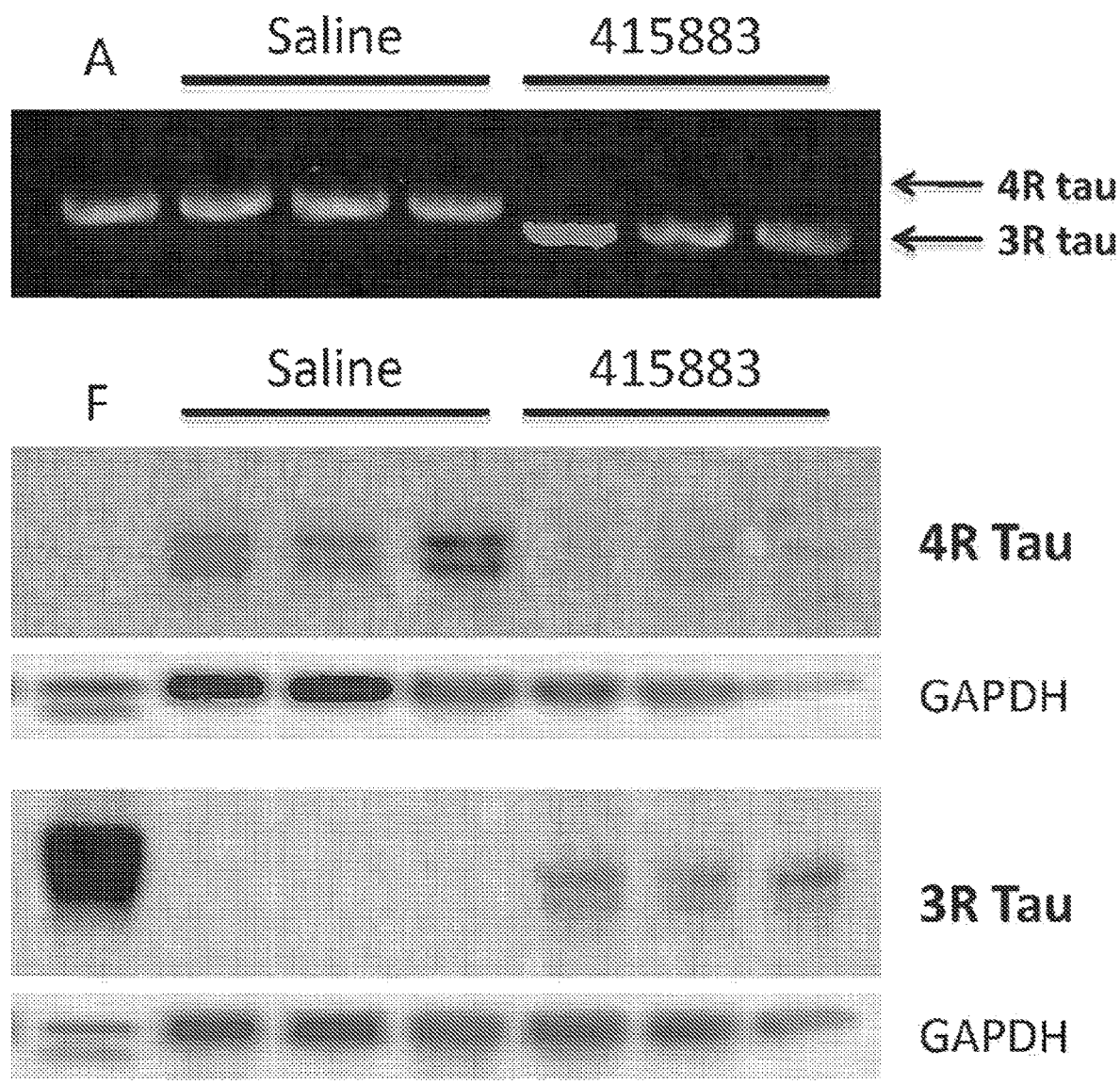
FIG. 10 depicts RT-PCR and Western blot results of a one month intraventricular infusion with a splicing oligo. 100 ng of starting RNA was used for the RT-PCR. A=Adult mouse with no pump. 20 μg protein was loaded for the Western blots. F=E18 fetal rat whole brain homogenate. 4R Tau antibody (RD4) was used at a 1:500 dilution. 3R Tau antibody (RD3) was used at a 1:500 dilution. GAPDH antibody was used at a 1:10,000 dilution.

A similar experiment was performed using a month intraventricular infusion (FIG. 10).

Example 4. PTZ Induced Seizures

Example: Effect Antisense Inhibition of Tau on PTZ Induced Seizures

Figure 11A:
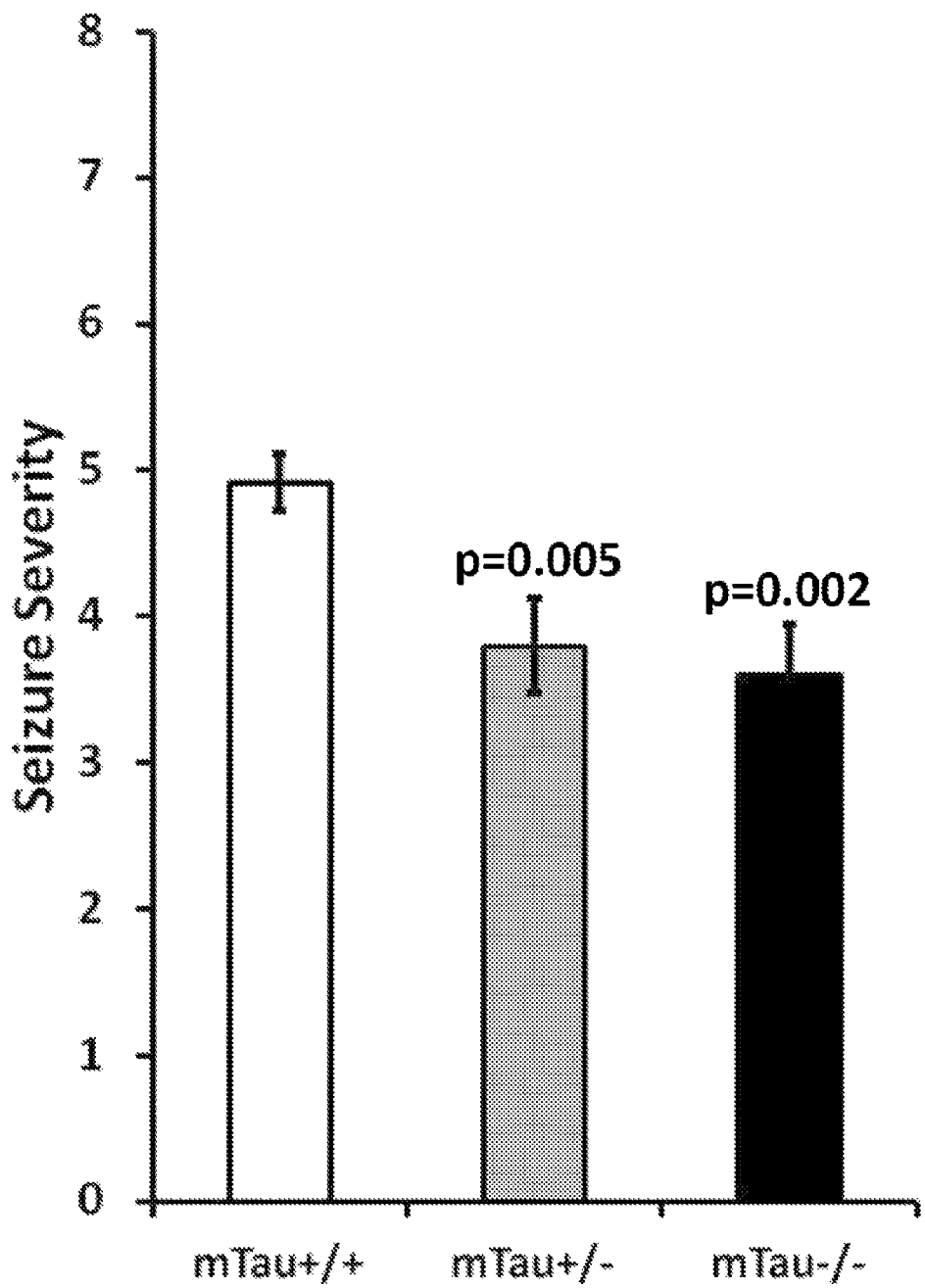
FIG. 11A-11B depict two plots of (A) seizure severity in mTau+/+, mTau+/−, and mTau−/− mice, and (B) percentage of mice with various stages of seizures in mTau+/+, mTau+/−, and mTau−/− mice.
Figure 11B:
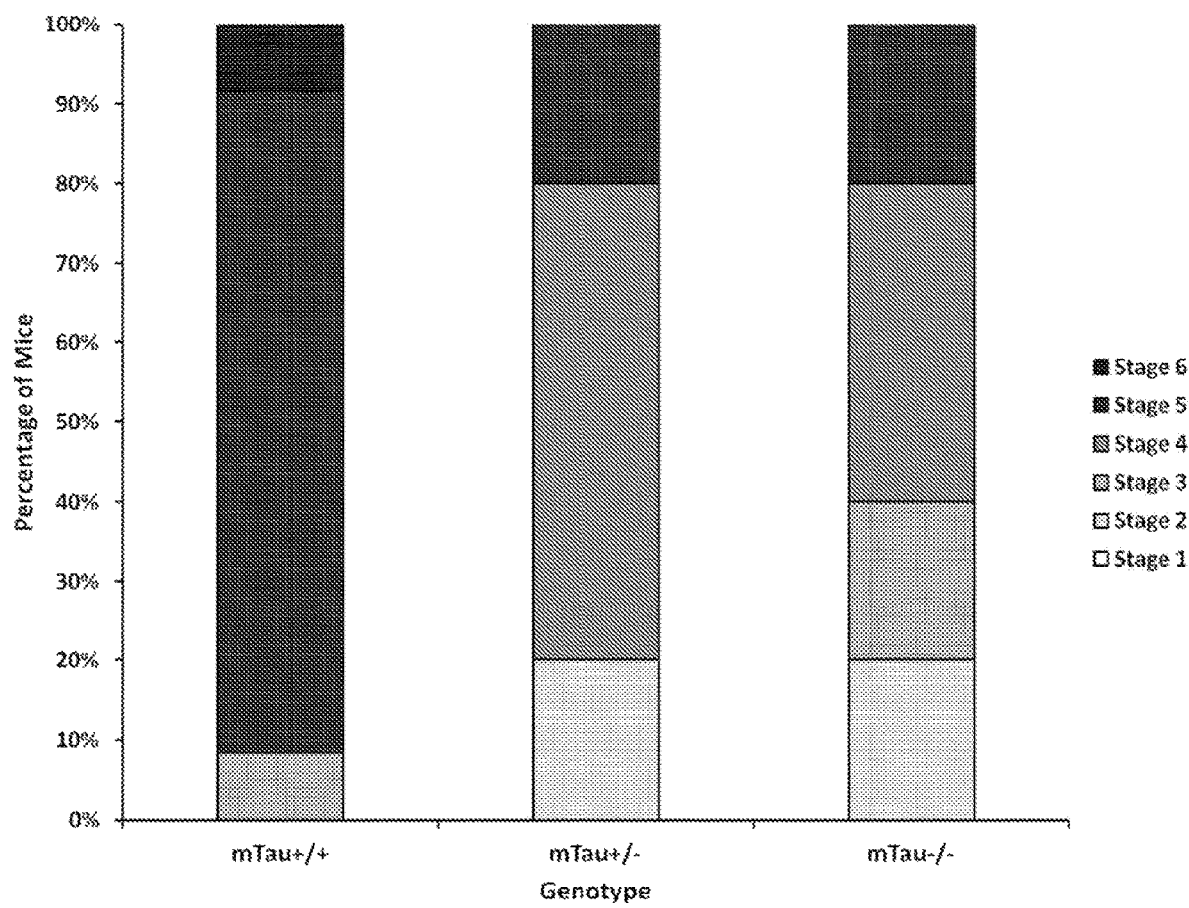

Seizures were induced and quantified in various mice using pentelenetetrazoll (PTZ). The mice are videotaped for 15 minutes and scored later in a blinded fashion. The final stage reached is recorded. In short, 50 mg/kg PTZ was injected ip into mTau−/−, and mTau+/− mice. mTau+/+ mice were used as control. Mice deficient for mTau were more resistant to PTZ induced seizures (FIGS. 11A and 11B).

Figure 12A:
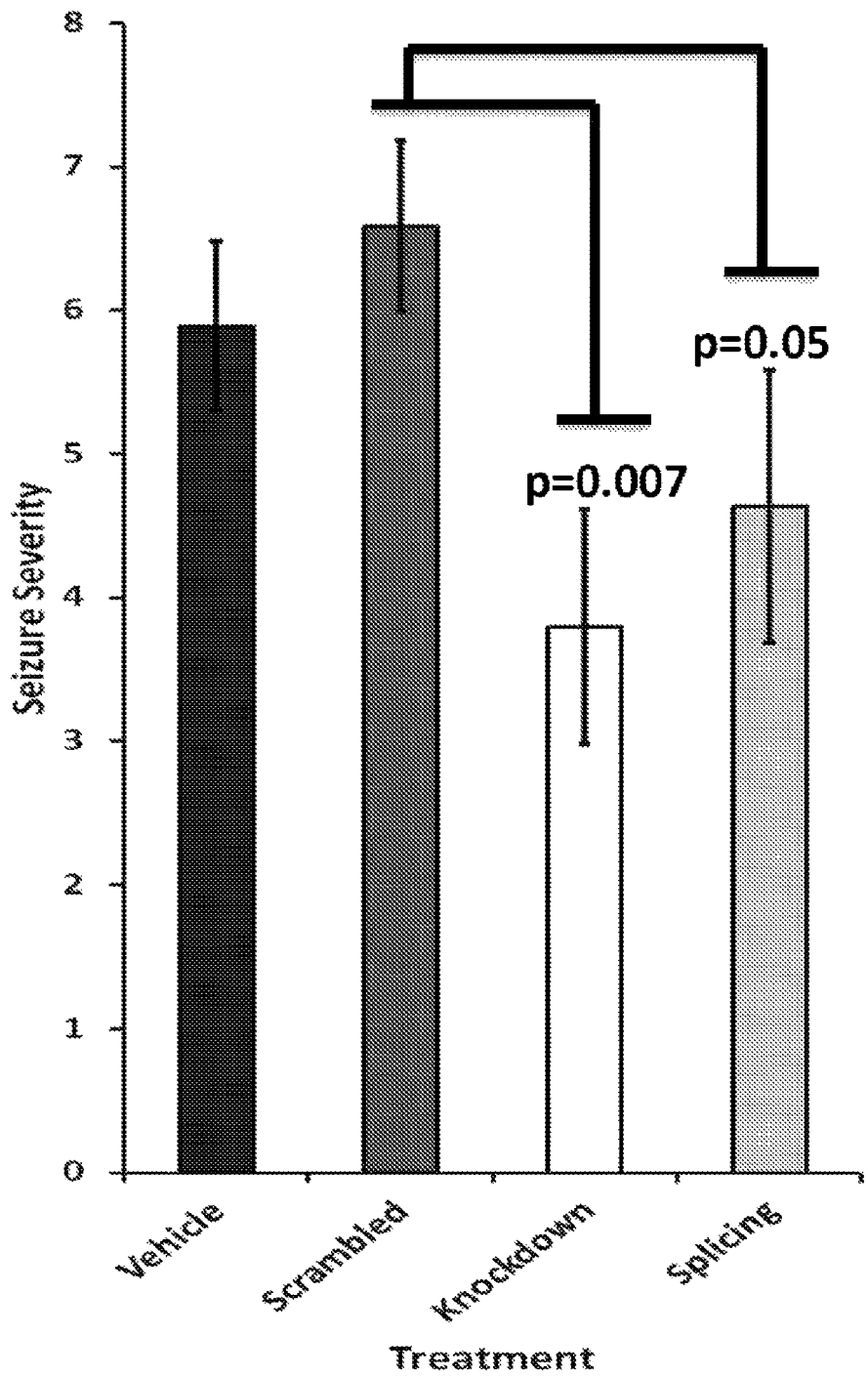
FIG. 12A-12B depict two plots of (A) seizure severity in mice treated with a knockdown oligo or a splicing oligo, and (B) percentage of mice treated with a knockdown oligo or a splicing oligo with various stages of seizures.
Figure 12B:
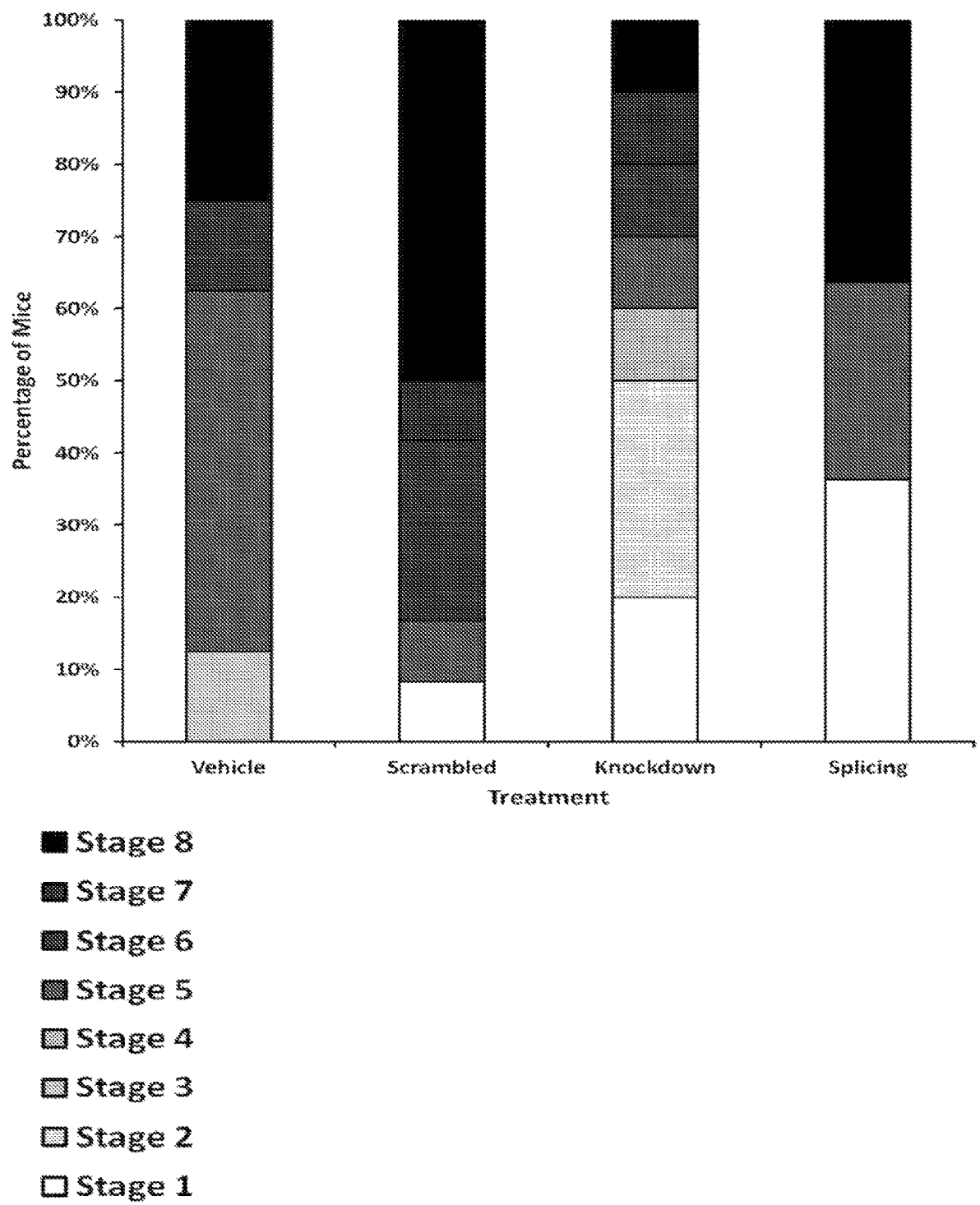

Seizures were also induced and measured in mice treated with a tau knockdown oligo or a tau splicing oligos (also ISIS 415883). In short 3 month old C57/BL6 males were dosed for 28 days with 25 µg/day of oligo. The pumps were removed, and the animals were allowed to sit for 3 weeks post-pump removal before seizure induction. Seizures were induced using 55 mg/kg of PTZ using ip injection. The mice are videotaped for 15 minutes and scored later in a blinded fashion. The results show that the knockdown and the splicing oligos were capable of protecting mice against PTZ induced seizures (FIGS. 12A and 12B).

Figure 13:
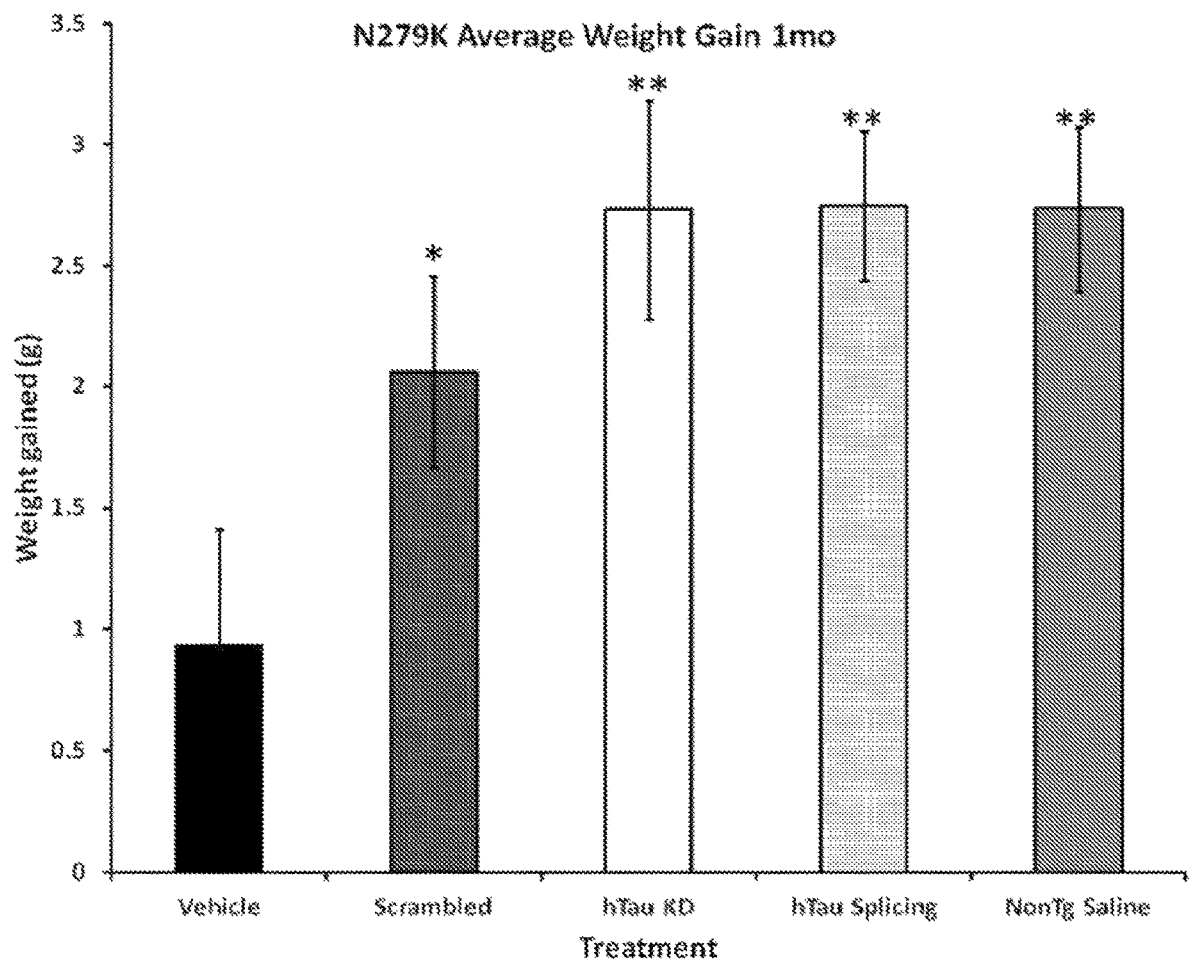
FIG. 13 depicts a plot showing the average weight gain by a N279K mouse treated with vehicle, a scrambled oligonucleotide, a human tau knockdown oligonucleotide, a human tau splicing oligonucleotide and nonTg saline.

Example 5. Effect of Knockdown and Splicing Oligonucleotides on Weight Gain in N297K Mice N279K mice treated with vehicle, a scrambled oligonucleotide, a human tau knockdown oligonucleotide, a human tau splicing oligonucleotide (i.e., ISIS 415883) and nonTg saline. The results show that mice treated with the human tau knockdown oligonucleotide, the human tau splicing oligonucleotide and nonTg saline gained significantly more weight than mice treated with vehicle alone (FIG. 13).

Example 6. Reversing Splicing Deficit in N279K Tauopathy Mice by Decreasing 4R Tau Levels Decreasing 4R tau levels in adult N279K exon 10 mutation mice may improve behavioral and pathological phenotype in these mice. Tau N279K mice are based on one of the tau mutations which causes aberrant splicing of tau, by promoting inclusion of exon 10. Inclusion of exon 10 leads to increased 4R compared with 3R tau, without affecting overall levels of tau. The mice typically develop motor and cognitive behavioral abnormalities at 6 months including deficits on rotarod and on water maze. These deficits are worse at 12 months. As is typical of a variety of tau models, approximately 25% of these animals develop severe motor weakness and die before the rest of the cohort (on average at 45 weeks old). The percentage of animals with this profound motor deficit may be measured in each group and these animals may not be included in other behavioral tests. Brain pathological changes are mild at 6 months and prominent at 1 year. The changes include increased tau and phosphotau staining in neurons and astrocytes, and increased caspase 3 activation. Pathology also included positive Gallyas silver staining in neurons, a stain that detects abnormal filaments such as those composed of aggregated tau as well as Fluorojade B positive staining, indicative of degenerating neuronal cells.

The goal of the treatment is to decrease the 4R:3R ratio in the N279K mice, which is increased by the N279K mutation and which causes preferential inclusion of exon 10. As has been demonstrated in vivo (FIG. 9), Tau splicing oligos that decrease the inclusion of Exon 10 and thus decrease the 4R:3R tau ratio may be used. Antisense oligos that alter splicing, a control oligo, or saline may be infused into the right lateral ventricle of N279K mice, at 3 months of age. Since pathology starts at 6 months of age, 3 months was chosen to be presymptomatic. The control groups are animals treated with saline alone or a control oligo. Both may be compared to animals treated with an oligo that decreases 4R:3R ratios. Each of the groups may be compared with non-transgenic, untreated mice.

The three groups of N279K mice (saline, oligo control, 4R:3R tau splicing oligo) and a group of non-transgenic mice without pumps may be examined at ages 6 months and 12 months for behavioral analysis. Including the non-transgenic mice in the behavioral studies may document that the N279K mice animals do indeed develop behavioral deficits and help understand to what degree treatment is able to prevent behavioral abnormalities. In terms of the statistical comparisons and treatment effect in the N279K mice, the important comparison may be the saline and oligo control compared to the 4R:3R tau splicing oligo. Mice that develop acute motor weakness (25% expected) may be determined to be dead when they are no longer able to right themselves after being placed on their backs for 30 seconds. There is no primary analysis planned for these animals, though tissues may be retained for any possible future analyses and the number of animals with this phenotype in each group may be scored. In conjunction with the Washington University Behavioral Core, for animals that do not develop overt weakness, radial arm Morris water maze may be analyzed at 6 months and 12 months. Rotarod performance may also be analyzed. At 1 year of age, mice may be euthanized. Just prior to euthanasia, CSF may be collected. Brains may then be collected. The left half of the brain may be fixed with 10% formalin, cyroprotected with sucrose and sectioned for immunocytochemistry of tau, phosphotau, and activated Caspase 3. Gallyas staining and fluorojade staining may also be performed. The right half of the brain may be used for biochemical analyses. Total tau mRNA and protein levels, and 4R:3R ratios may be analyzed.

Given the preliminary data described in the examples above, reversing the splicing deficit in the N279K mice with antisense oligos is likely. Previous data suggest that pathogenesis arises from the change in the ratio of 3R to 4R tau rather than the absolute levels or the missense variant in the 4R containing protein. This is evidenced by tau mice with the N279K minigene construct driven by the CMV promoter. These animals have increased levels of 4R tau both fetally and in the adult animal. However, they do not develop any tau pathology or behavioral abnormalities. Thus it is the tau promoter itself and/or the switch to increased 4R:3R that appears to be important for disease. These experiments may address an important question regarding whether changing tau ratios in the adult animal may be beneficial.

Figure 20A:
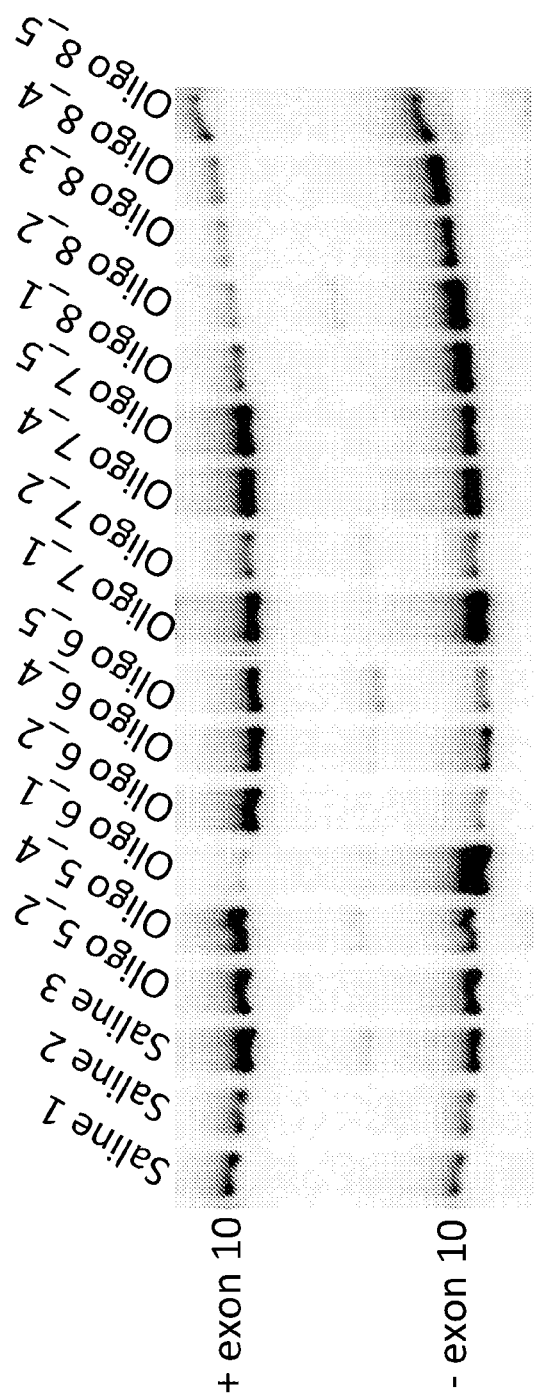
FIG. 20A-20B depict a picture (A) and a graph (B) showing ASO screen for Tau splicing in N279K mice. ICV infusion 60 micrograms/day for 28 days. Mice were sacrificed on the 29th day, and the cortex tissue around the cannula was collected.
Figure 20B:
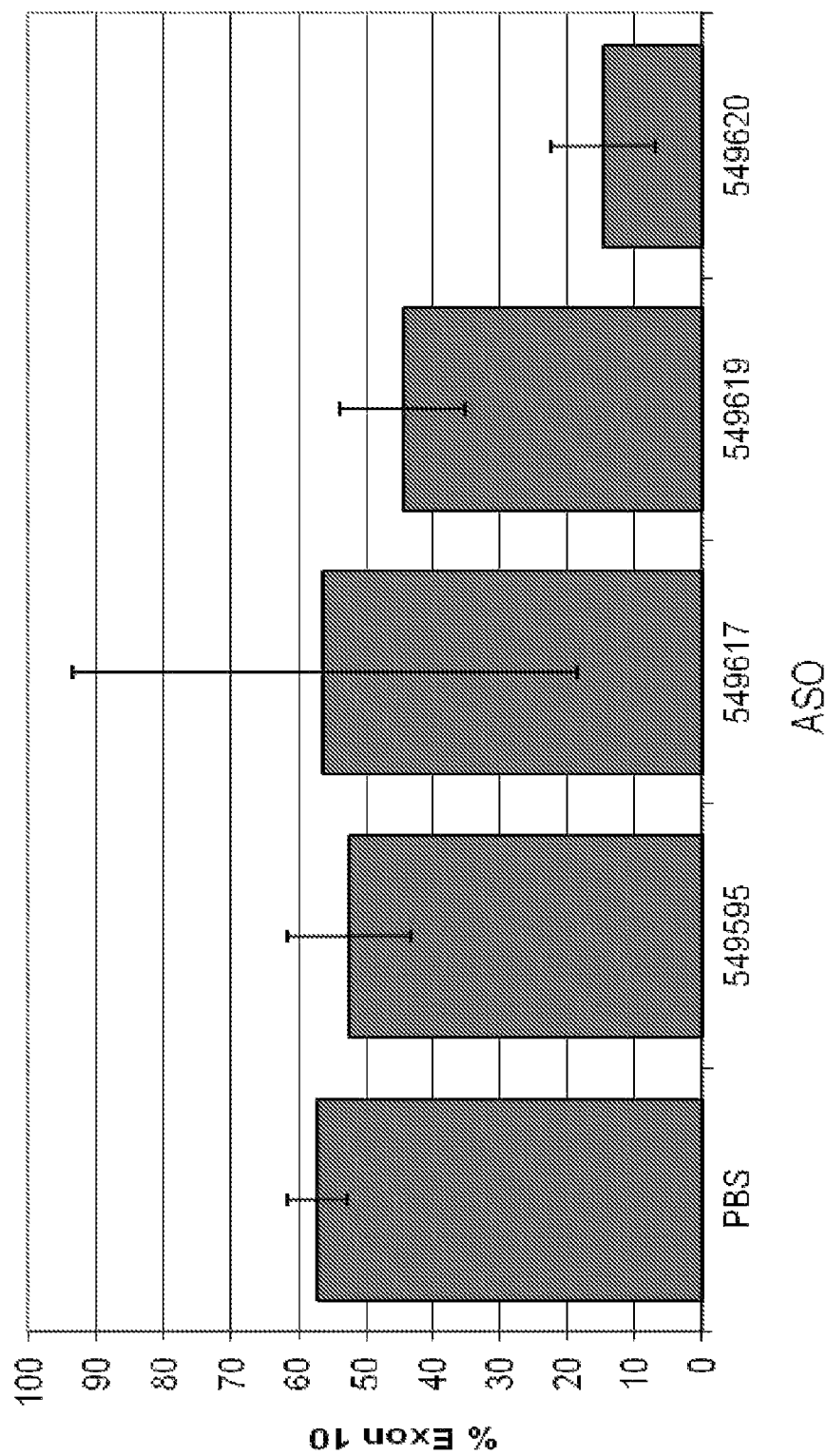
Figure 21A:
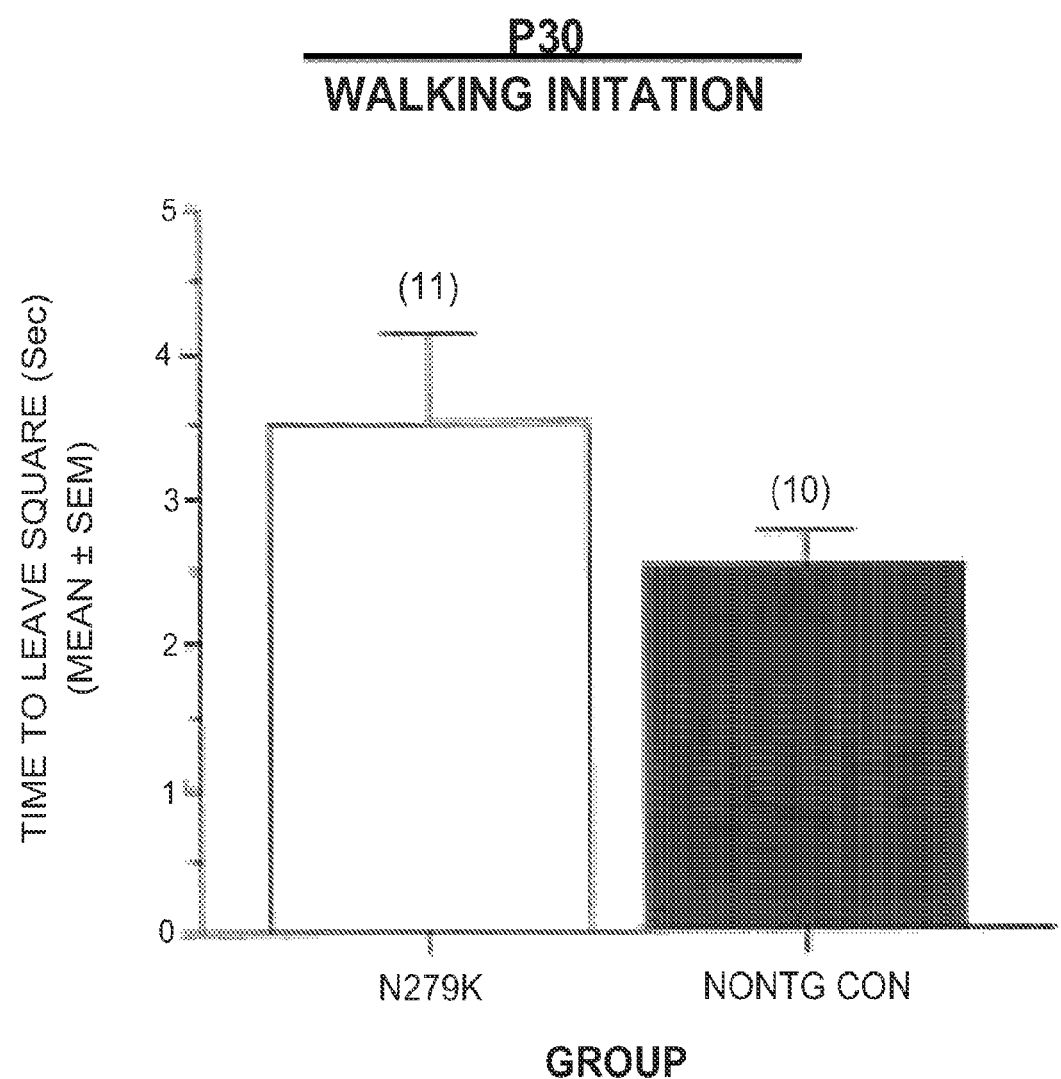
FIG. 21A-21D depicts graphs showing N279K baseline behavioral deficits.
Figure 21B:
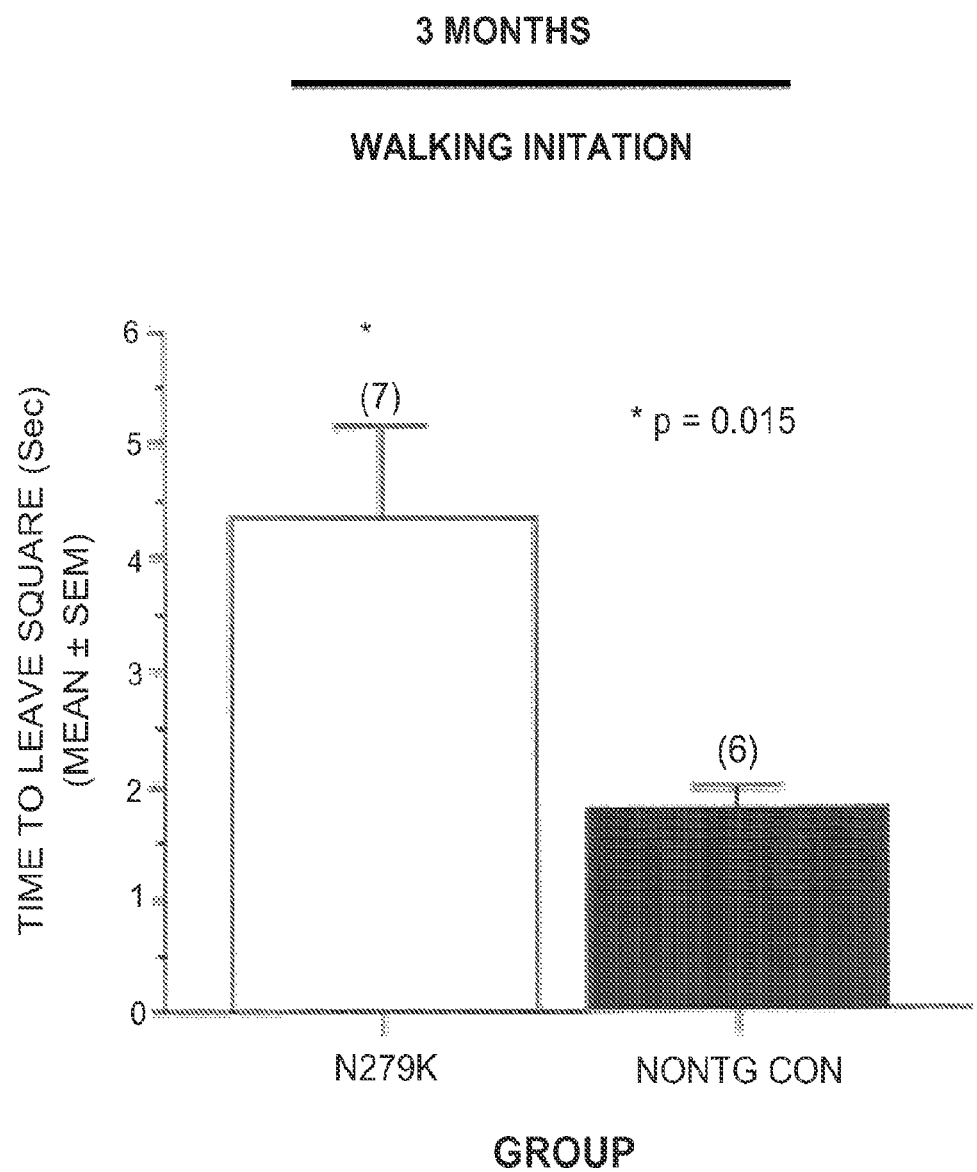
Figure 21C:
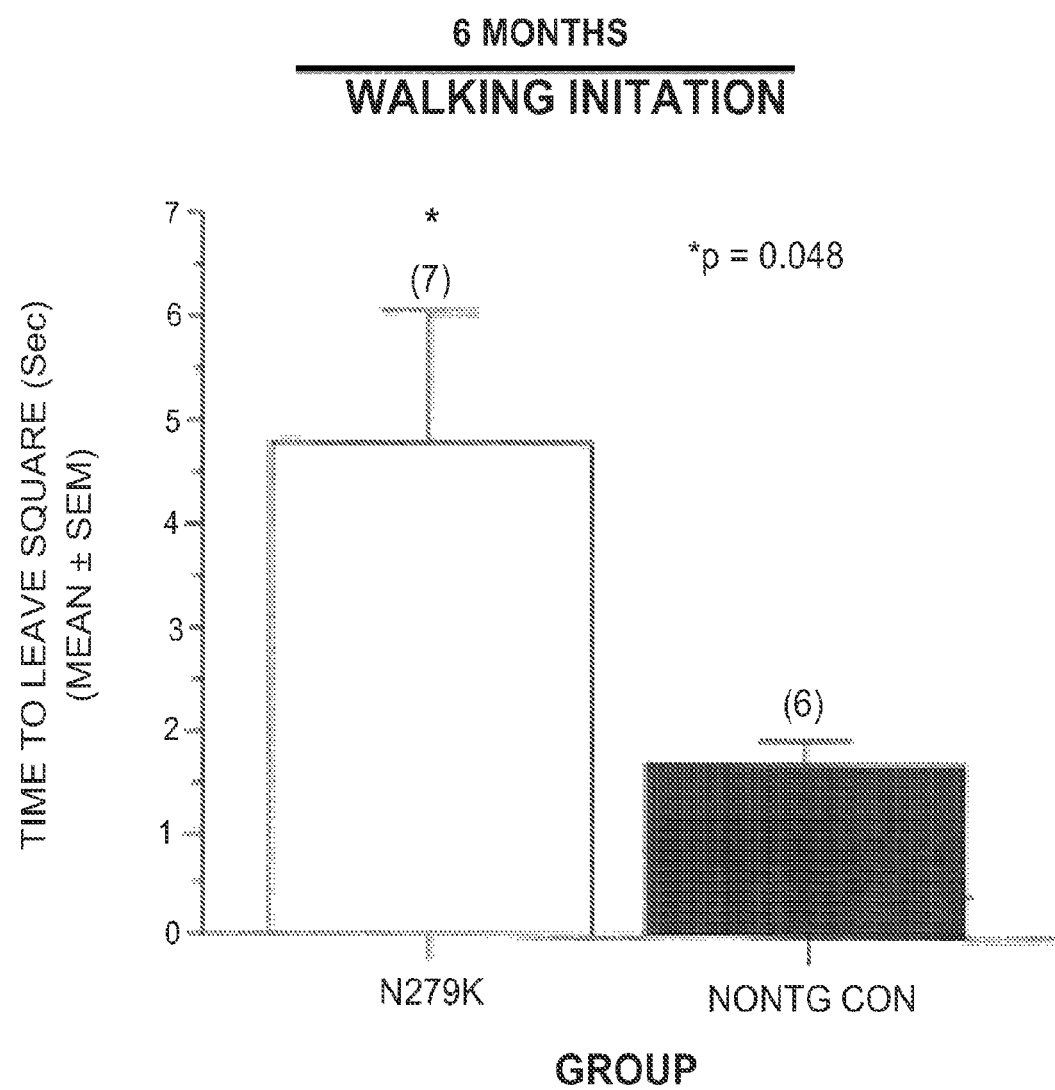
Figure 21D:
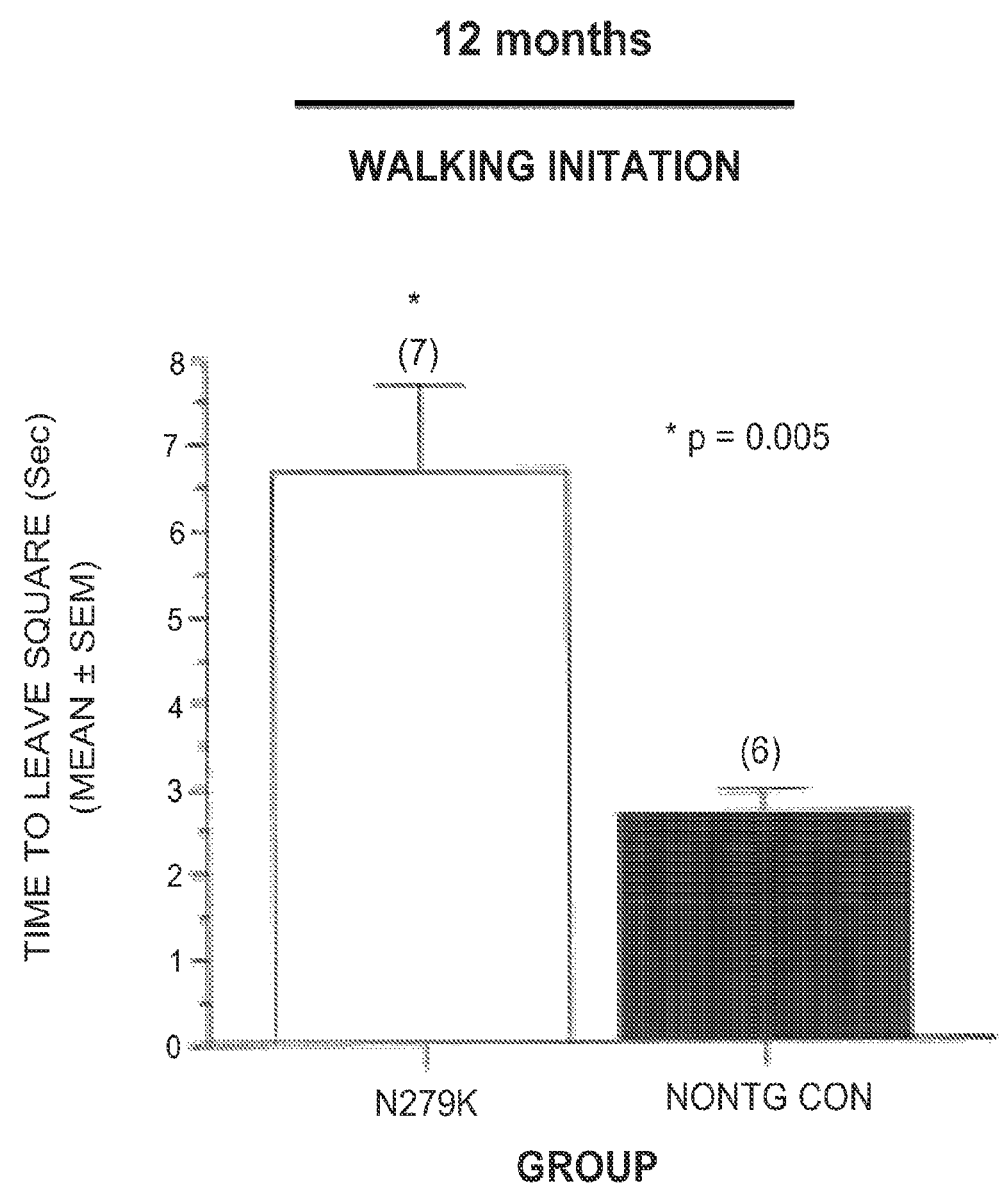
Figure 22A:
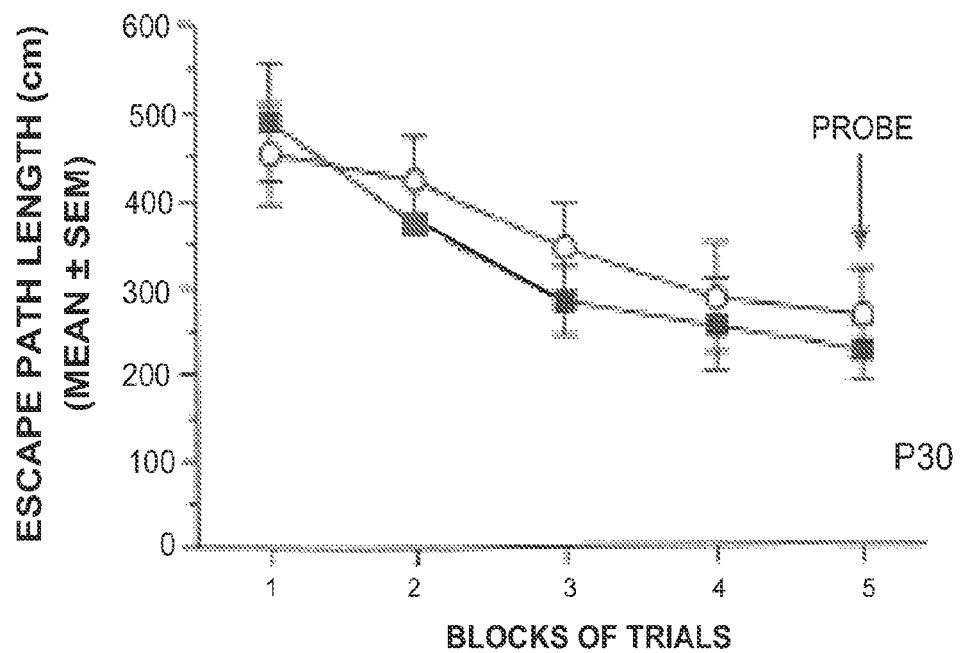
FIG. 22A-22I depicts graphs showing Morris water navigation at different timepoints.
Figure 22B:
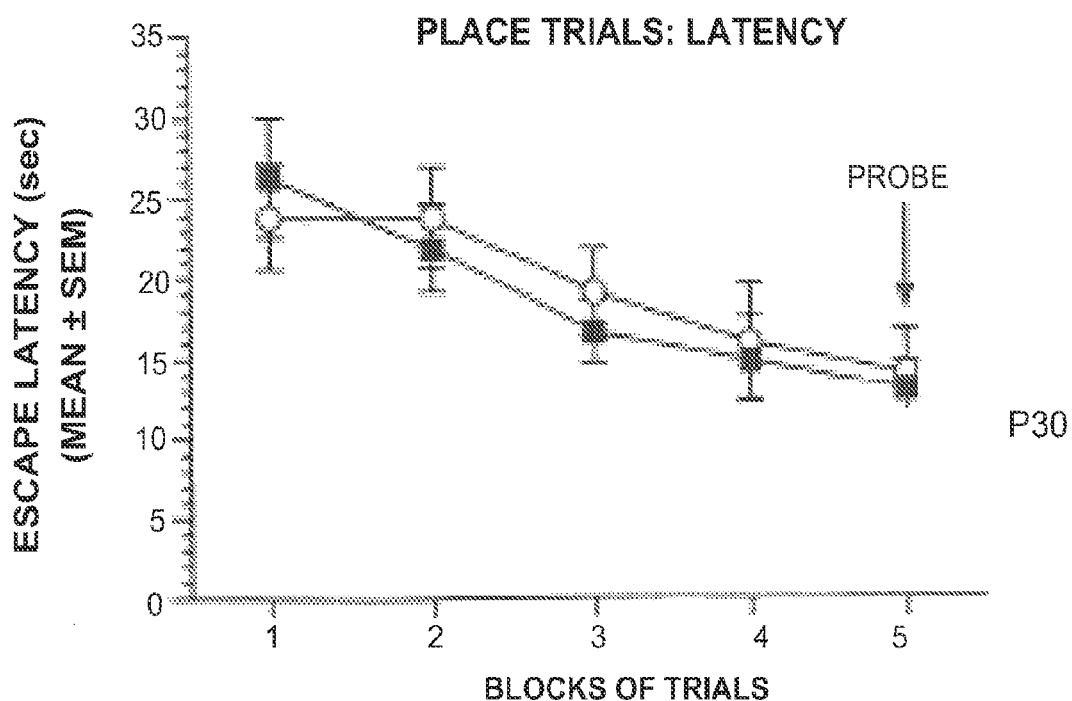
Figure 22C:
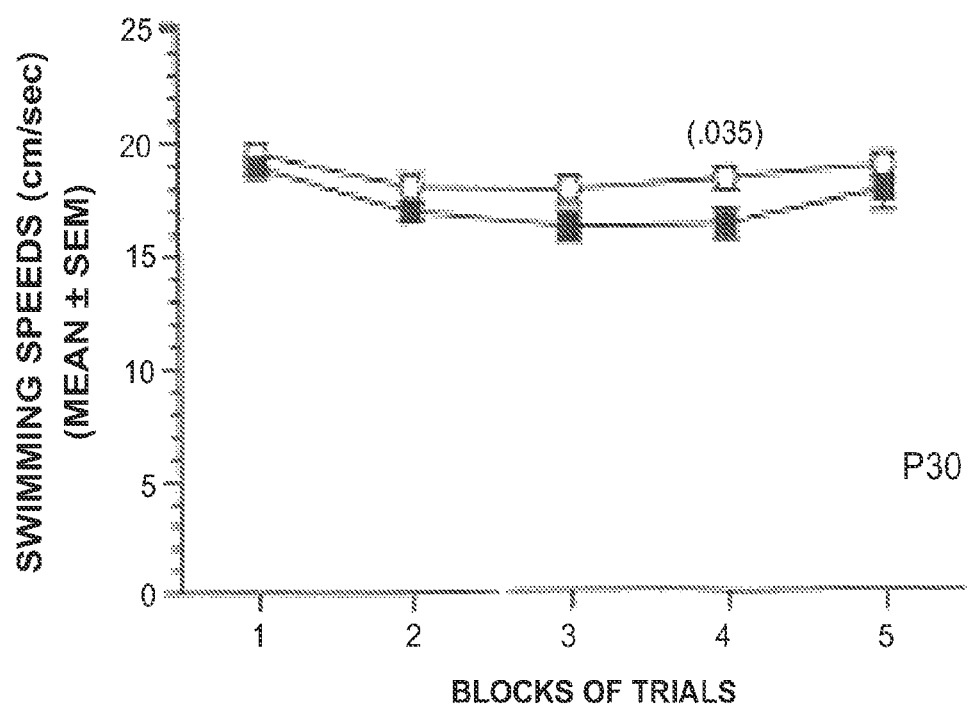
Figure 22D:
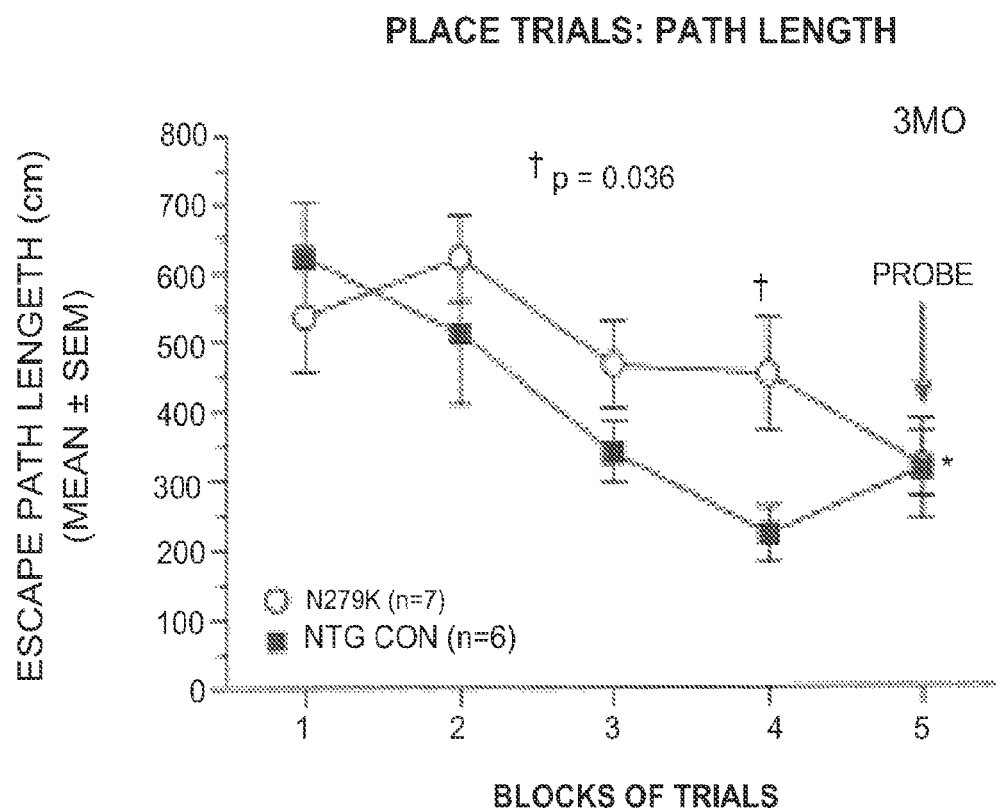
Figure 22E:
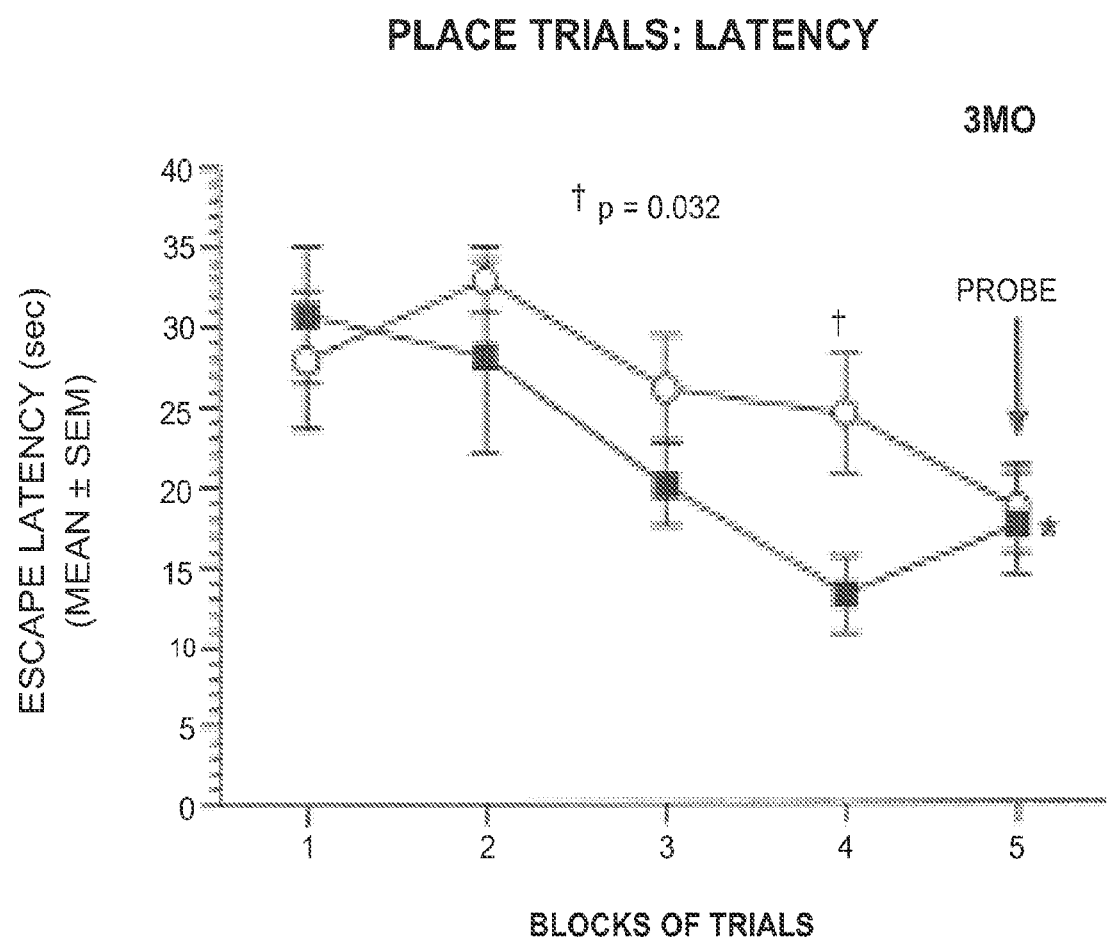
Figure 22F:
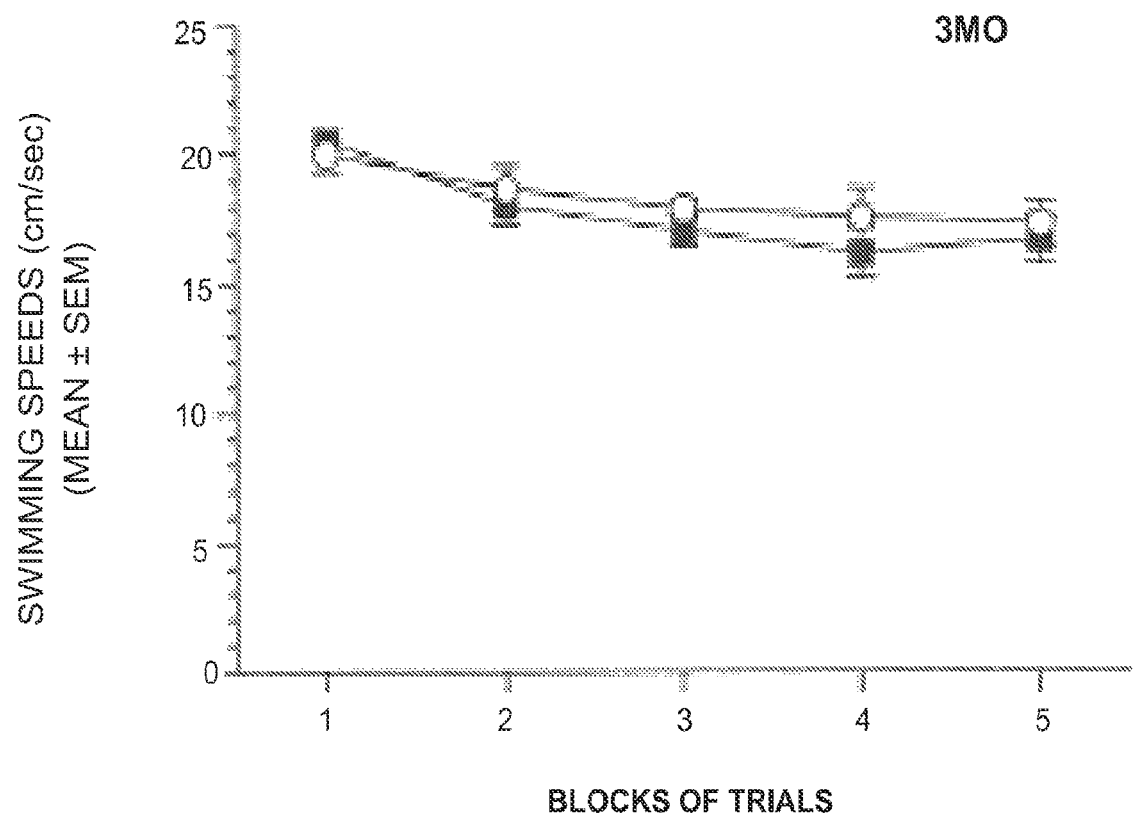
Figure 22G:
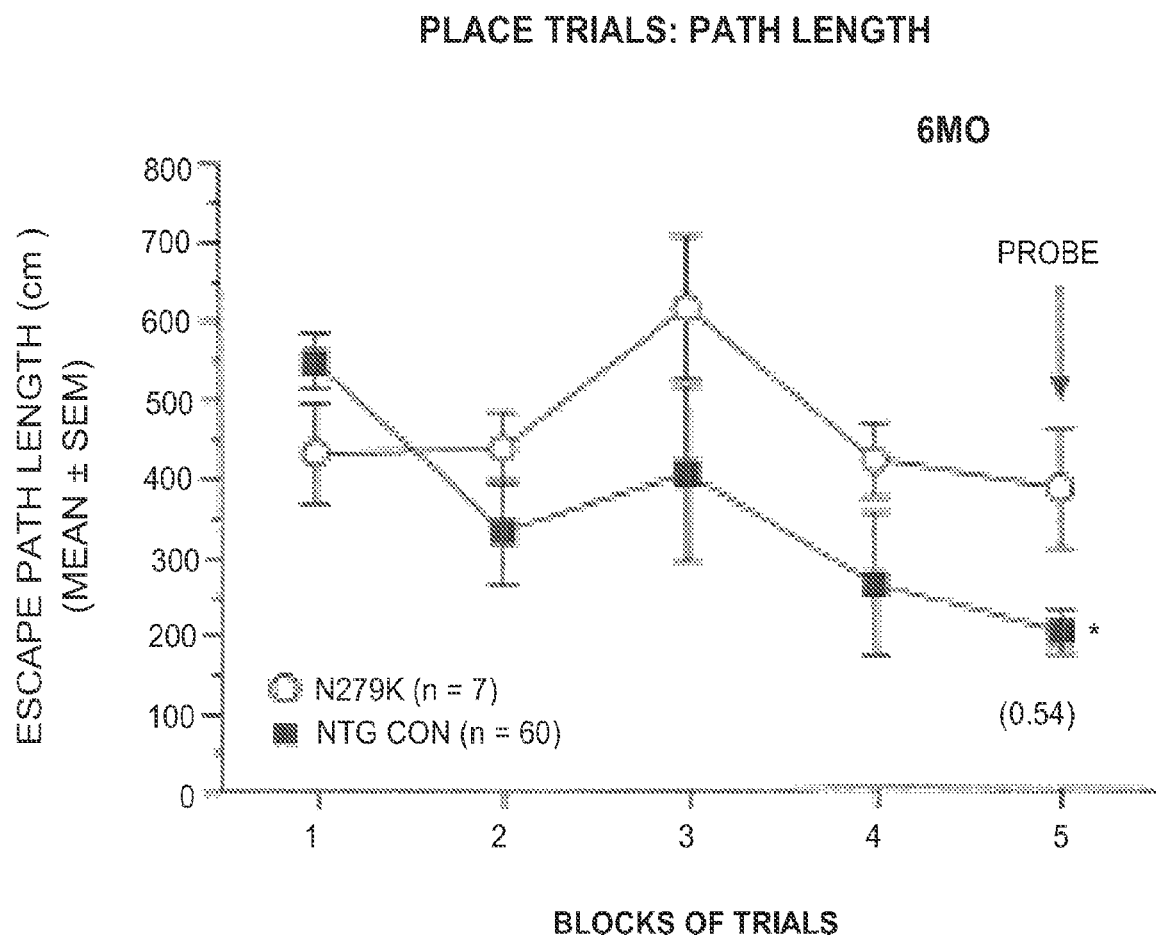
Figure 22H:
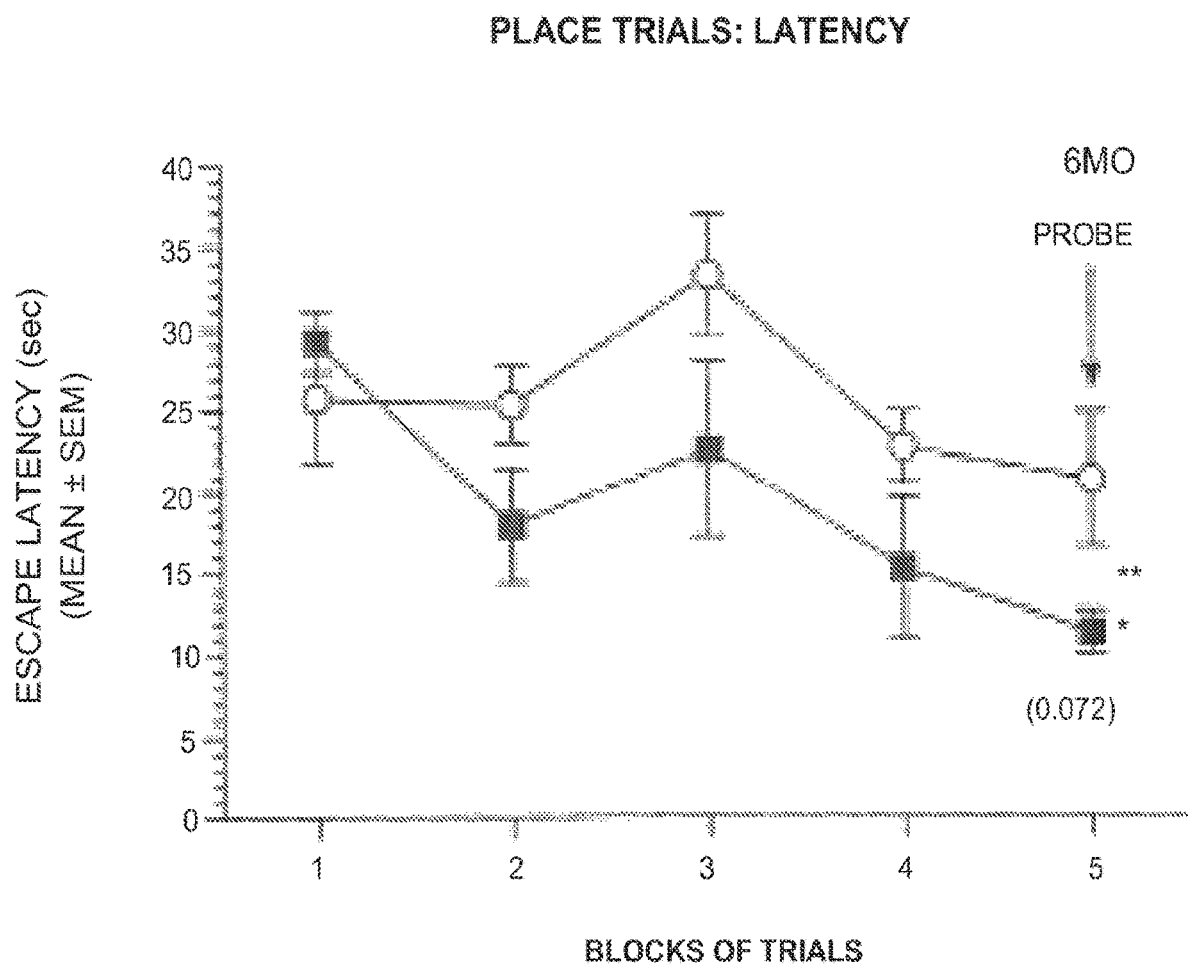
Figure 22I:
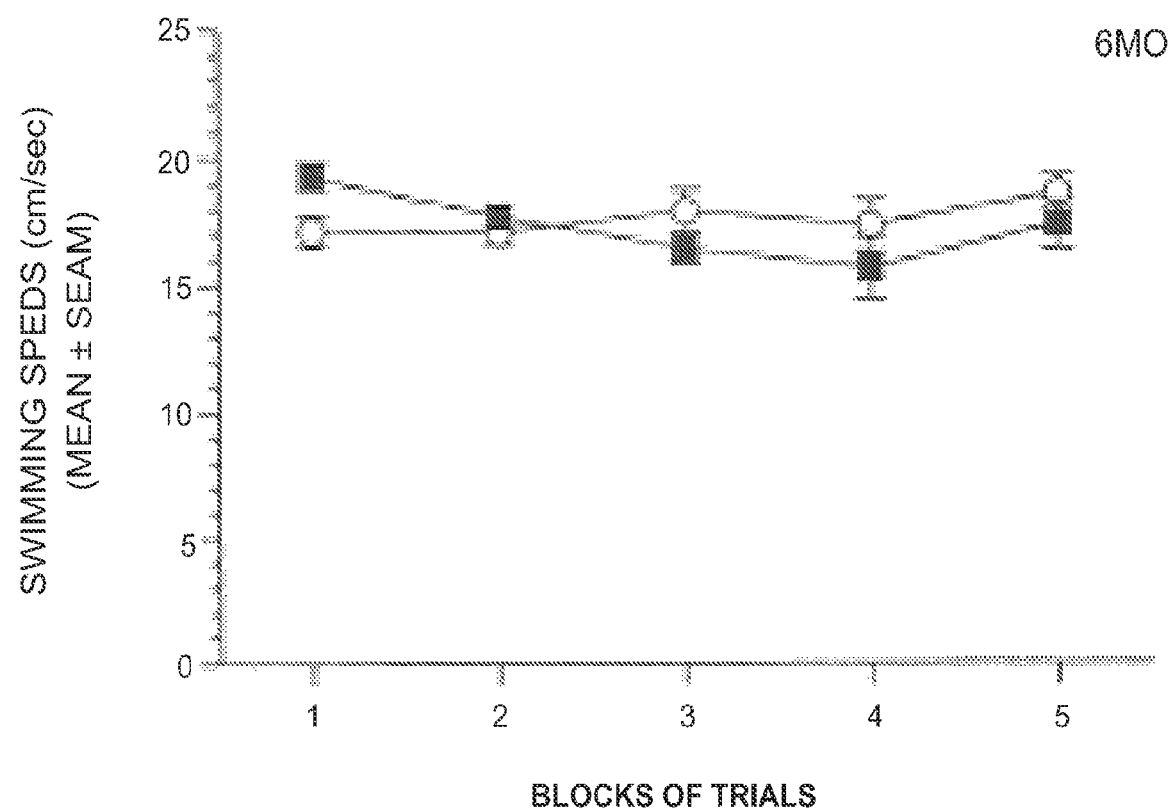
Figure 23:
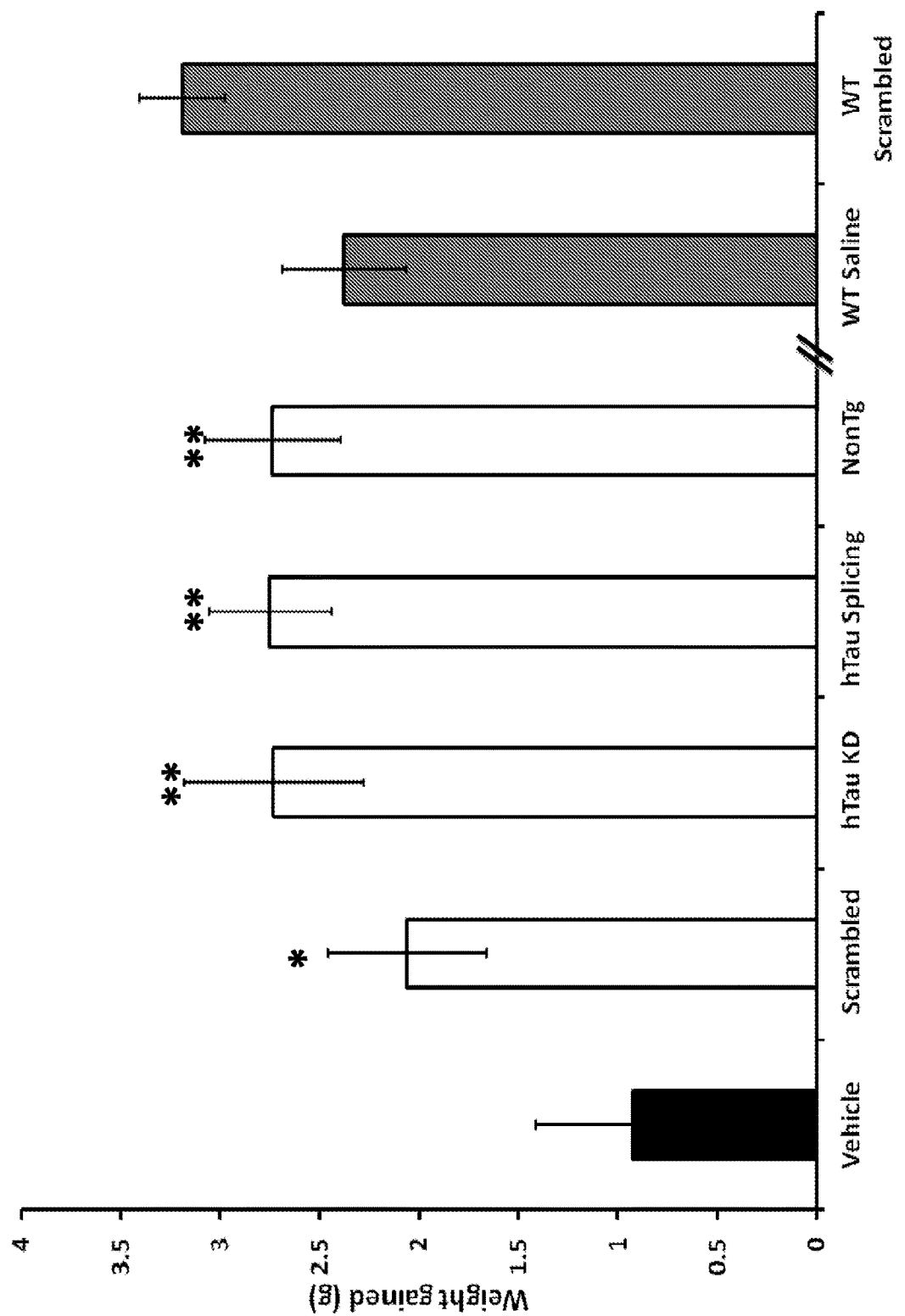
FIG. 23 depicts a graph showing N279K average weight gain after 1 month with various antisense treatments.
Figure 24:
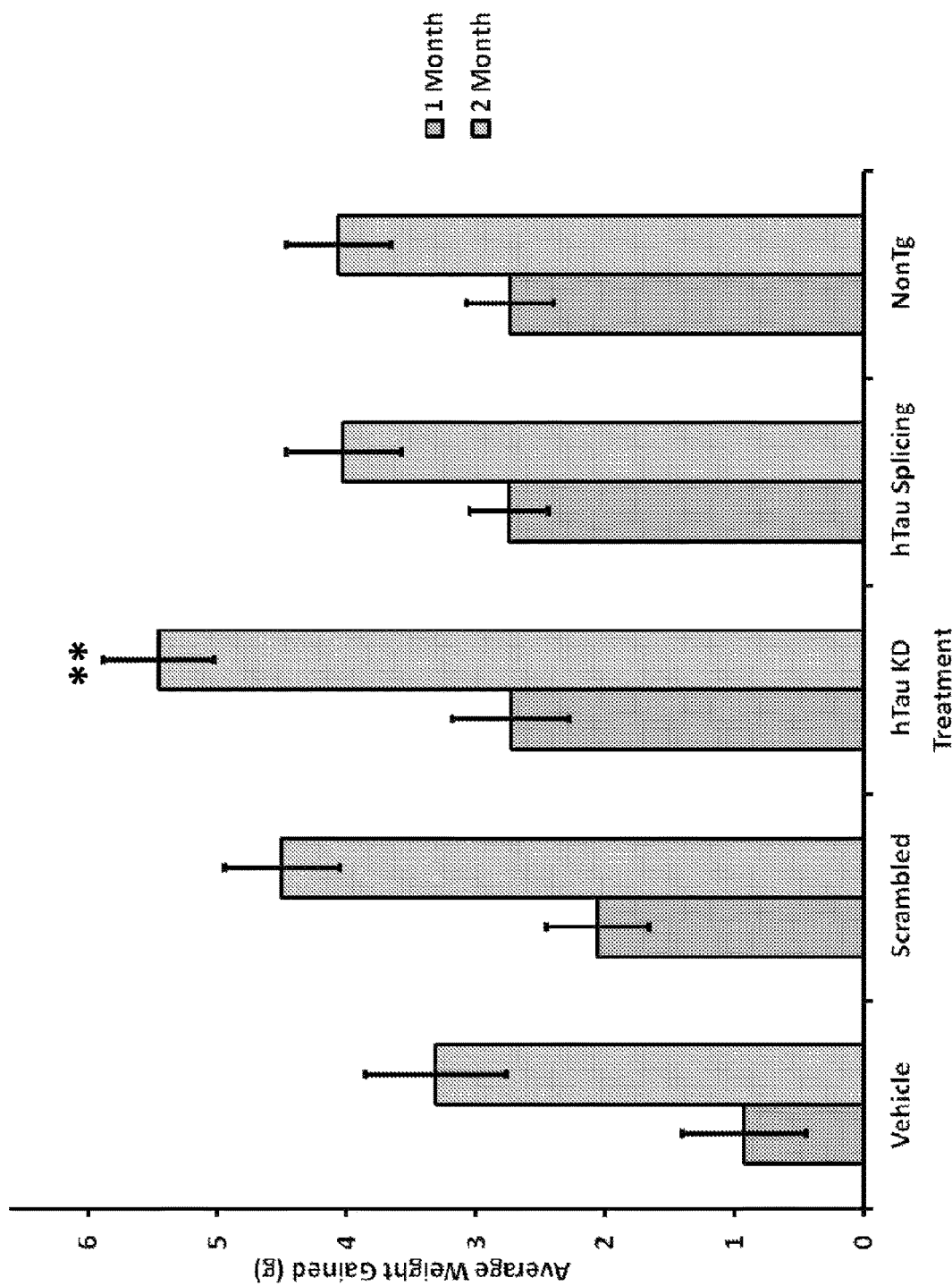
FIG. 24 depicts a graph showing N279K average weight gain after 1 and 2 months with various antisense treatments.

Example: Effect of Antisense Oligonucleotide Treatment on Human Tau Splicing in N279K Tauopathy Mice The effect of ASOs (i.e., antisense oligonucleotides) on tau splicing was tested in vivo. N279K tauopathy mice (Dawson, H. N. et al., Neurosci. 27:9155-9168, 2007) were used in this assay. Tau N279K mice are based on one of the tau mutations which causes aberrant splicing of tau by promoting inclusion of exon 10. Inclusion of exon 10 leads to increased 4R compared to 3R, without affecting overall levels of tau. The effect of ASOs in the splicing of exon 10 and the resulting 4R:3R ratio in these mice was evaluated.
Study 1
Transgenic mice were infused with PBS or 60 µg/day ASO (i.e., ISIS 549595, ISIS 549617, ISIS 549619, and ISIS 549620) for 28 days. Mice were sacrificed on the 29th day, and cortical tissue around the cannula was collected and examined for human 4R tau mRNA and for human 3R tau mRNA by QPCR (FIG. 20). Treatment with ASO decreased 4R tau levels and increased 3R levels.

Example 7. Modulating Tau Levels in Mice with Alzheimer's Disease-Like Pathology For an amyloid precursor protein (APP) transgenic model the J20 line (Table 1) may be used, which expresses an hAPP minigene with the Swedish (K670M/N671 L) and Indiana (V717F) familial Alzheimer's disease (AD) mutations under control of the PDGF promoter. Behavioral deficits in the J20 line Alzheimer's mice typically occur at 4-7 months and include deficits in the Morris water and exploration of a new environment. In addition, about 15% of the animals die early (by 6-8 months) for unclear reasons, but perhaps related to seizures. The death typically occurs in an animal that otherwise appeared well the previous day and is presumably secondary to an acute event. J20 line APP mice with one or both copies of mouse tau deleted are protected from amyloid beta induced toxicity as evidenced by better performance on the Morris water maze, open field exploration, and a normal lifespan in all the animals. Amyloid plaque deposition occurs in only a few J20 animals at 2-4 months, 50% at 6 months, and nearly 100% by 8-10 months. Tau deletion does not affect amyloid plaque levels in the J20 line.

J20 line Alzheimer's mice at age 3 months old may be treated with Tau 5 oligo, an antisense oligonucleotide that clearly decreases mouse tau mRNA and protein (FIG. 4). There may be two control groups, one may be treated with saline and another with a scrambled antisense oligonucleotide control. Since behavioral deficits become apparent between 4 and 7 months of age, and since the J20 line does not have amyloid beta accumulation at 2-4 months, 3 months was chosen as presymptomatic. Treatment may consist of placement of an intraventricular catheter connected to an osmotic pump filled with oligo or saline.

Each litter of animals may be divided into male and female groups. Males and females may then be equally and randomly assigned to a treatment paradigm. Following surgeries, cage cards indicating treatment group may be replaced with animal number assignments such that the technician following the mice may be blinded to the treatment strategy.

The three groups of J20 APP mice (saline, oligo control, antisense oligo against tau) and a group of non-transgenic mice may be examined at ages 6 months and 12 months for cognitive function on water maze, y maze, and the exploration of new environment. Including the non-transgenic mice in the behavioral studies may document that the J20 APP animals do indeed develop behavioral deficits and help understand to what degree treatment is able to prevent behavioral abnormalities. In terms of the statistical comparisons and treatment effect in the J20 APP mice, the important comparison may be the saline and oligo control compared to the antisense oligo against tau. These behavioral studies may be performed in conjunction with the Animal Behavioral Core at Washington University run by Dr. David Wozniak. This core is open to all Washington University investigators, is located within an animal facility, and has a wide array of experience with behavioral measures (hopecenter.wustl.edu/cores/animalBehavior). At one year of age animals may be euthanized. Immediately before euthanasia, cerebral spinal fluid may be drawn. Brains may then be collected. The left half of the brain may be fixed with 10% formalin, cyroprotected with sucrose and sectioned for immunocytochemistry of amyloid beta from the genu of the corpus callosum through the caudal extent of the hippocampus. The percent surface area covered by immunoreactive amyloid beta deposits (percent A13 load) as identified with a rabbit pan A13 antibody may be quantified following stereological principles as described. The right half of the brain may be used for biochemical analyses. It may be confirmed that Amyloid beta levels are not changed, including CSF amyloid beta, and that tau mRNA and protein levels are indeed decreased in the treated animals using tissue homogenate. The J20 APP do recapitulate some aspects of Alzheimer's disease, including amyloid beta deposition and cognitive changes. However, they do not develop tau pathology. Thus tau pathological examinations may not be performed for this set of experiments although tissue may be retained for potential analysis of this or any other measures suggested by future work in the field.

It is expected that decreasing overall tau levels in adult APP transgenic mice may protect the mice from amyloid 13 induced toxicity.

Methods for Examples 1-7

Screening and Identifying Effective Antisense Oligonucleotides.

The overall goal is to identify one or two antisense oligos with potent efficacy and no toxicity that may be used in the subsequent studies. Though this initial work is labor intensive and time consuming, identifying the best oligo in these initial studies will be essential for successfully completing the interesting treatment part of this project using transgenic mice. The antisense oligonucleotides are produced by Isis Pharmaceuticals, Inc. The oligonucletotides used are 20-mer phosphorothioate, 2'-O-(2-methoxyethyl) (MOE)-modified antisense oligonucleotides.

Step 1.) In Vitro Screen:

Approximately 80 oligonucleotides are typically screened in vitro in cultured cells. This process typically identifies 8-10 oligos that show good efficacy and could be used for in vivo knockdown.

Step 2.) Brain and Spinal Cord Screen:

Prior experience has demonstrated that these antisense oligos will not reach the brain and the spinal cord following delivery in the periphery (intraperitoneal, subcutaneous, or venous), presumably because the oligos do not cross the blood brain barrier. Because the oligos do not cross the blood brain barrier, the antisense oligos need to be delivered directly to the brain. Two methods are used to screen oligos in the brain. The first is a direct brain parenchymal injection. This is an excellent method for screening oligos because the technique is straightforward, does not require insertion of a pump, and leads to reproducible oligo effects after 1 week. This technique addresses the question of whether the oligo is active in the brain.

The second method for screening is intraventricular delivery through an osmotic pump for 1 month. This leads to more widespread delivery as would be required for treatment of an animal model. Cerebral spinal fluid bathes the brain and spinal cord and thus serves as a drug delivery system to the entire brain and spinal cord. To deliver drugs to the cerebral spinal fluid, a catheter is placed in the lateral ventricle. To access the lateral ventricle, a small hole is drilled in the skull (using a stereotaxic apparatus) and a catheter which is connected to an osmotic pump (Alzet) is inserted. The continuous infusion into the right lateral ventricle delivers drug to the cerebral spinal fluid, which is then widely distributed throughout the brain and spinal cord. The typical dose is 100 µg/day for 28 days, and may be optimized for individual oligos. The osmotic pump lasts for 30 days, but can be replaced with a new pump by making a small incision in the skin, disconnecting the plastic tubing, reconnecting to a new pump and then resuturing the skin. These catheters have been maintained for more than 9 months. Mice tolerate this procedure well.

Tolerability of Antisense Oligonucleotides:

Part of the screen in brain involves an assessment of the tolerability of the oligo. One concern with this technology that is often raised is the toxicity associated with many first generation antisense oligonucleotides. Use of the new "second generation" oligos has demonstrated decreased toxicities for the following reasons. First, oligo chemistry has greatly improved over the past decade. The current "second generation" oligos include modifications to increase potency and decrease immune stimulation. Second, there is now better understanding of the biology causing some immune reactions to oligos. Phosphorothioate oligodeoxynucleotides, such as those used here are well recognized to activate cells of the immune system predominantly through interaction with Toll-like receptor 9 (TLR-9), although there are TLR-9 independent pathways as well. Avoiding certain particularly immunogenic sequence motifs and the current chemistries helps to minimize this immune stimulation. Third, careful attention paid to choosing the most potent oligos, minimizes toxicity by using smaller doses. 25-50 fold less oligo is now used to produce the same effects achieved with earlier chemistries. Fourth, the current set of oligos is produced with minimal impurities and no measurable endotoxin, which were a likely source of earlier oligo related toxicities.

Despite these reassurances, the best measure of toxicity of a particular oligo for these animal studies is observation of the animal. Animals are observed behaviorally for any signs of abnormalities and weighed weekly. Loss of weight would be considered a sign of toxicity. Signs of weakness, decreased mobility, infection, and ruffed coat are monitored. This toxicity screen also involves a brain survey for inflammation including H&E, and astroglial/microglial stains. Thus far both the tau knockdown and tau splicing oligos used in these studies have been well tolerated. In addition, the exact same oligo chemistry has been well tolerated in the periphery (subcutaneous injection) by greater than 500 patients in clinical trials.

Mice

Mice used in these studies and planned studies are detailed in Table 1.

for an additional 14 days. Brains were then collected. Sections of brain were collected for RNA analysis using qRT-PCR.

Figure 14:
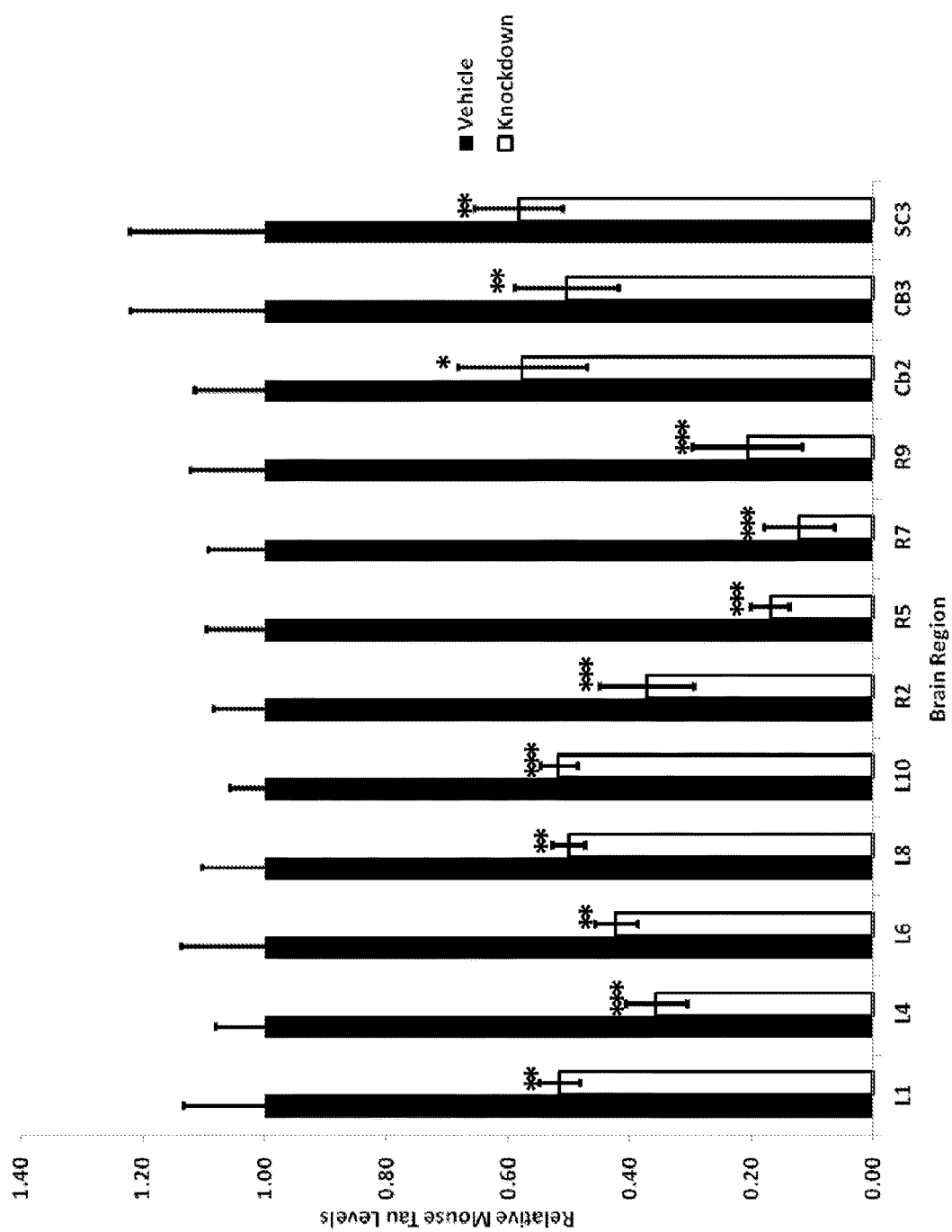
FIG. 14 depicts a graph showing the relative mouse tau levels in different brain regions with vehicle or a knockdown oligo.

Tau mRNA levels significantly decreased in all sections of the brain examined (FIG. 14).

Example 7: Effect of Antisense Inhibition of Tau in P301S Mice

The effect of treatment with ASOs #6, 9, 12, and 13 was evaluated in P301S mice. P301S mice develop filamentous tau lesions at 6 months of age that progressively result in hippocampal and entorhinal cortical atrophy by 9-12 months of age (Yoshiyama, Y. et al., Neuron 53: 337-351, 2007).

Groups of P301S mice were infused with PBS or 100 µg of antisense oligonucleotide into the right lateral ventricle by the Alzet pump for 14 days. The pumps were then removed and mice were allowed to rest for 14 days. The mice were euthanized and tissues were collected and used to prepare mRNA.

Figure 15:
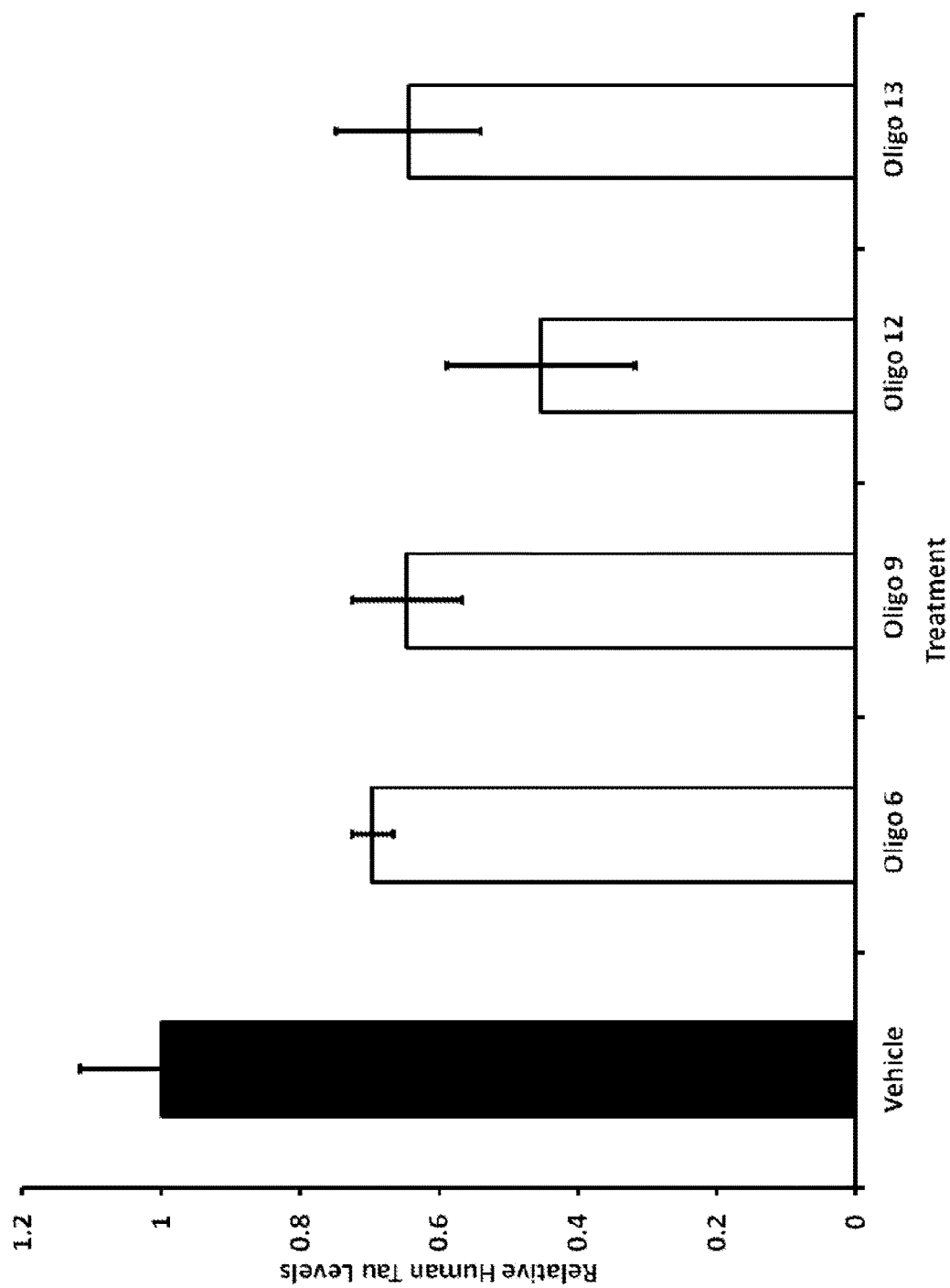
FIG. 15 depicts a graph showing the relative human tau levels in P301S mice treated with four different antisense oligos.
Figure 16:
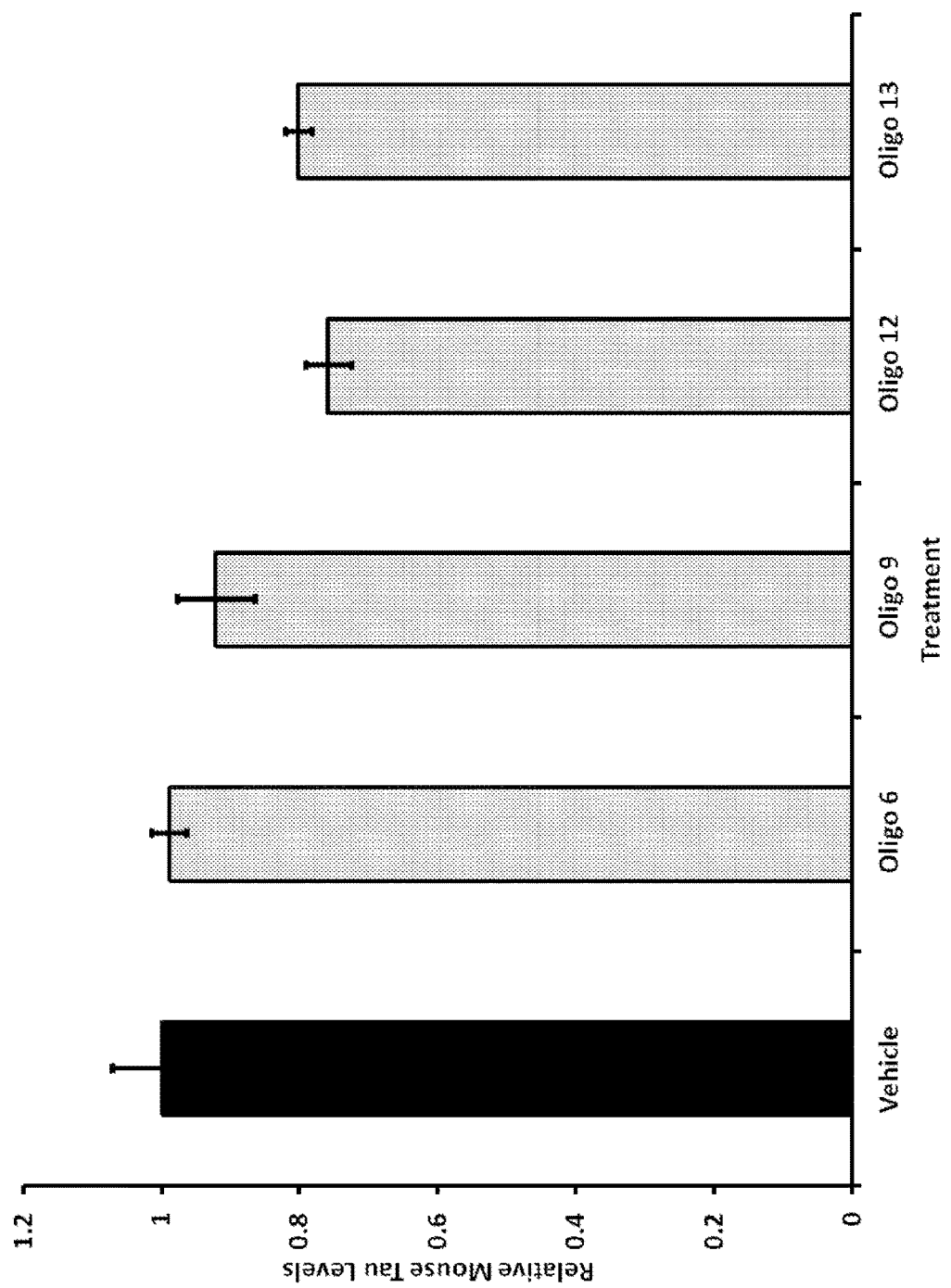
FIG. 16 depicts a graph showing the relative mouse tau levels in P301S mice treated with four different antisense oligos.
Figure 17:
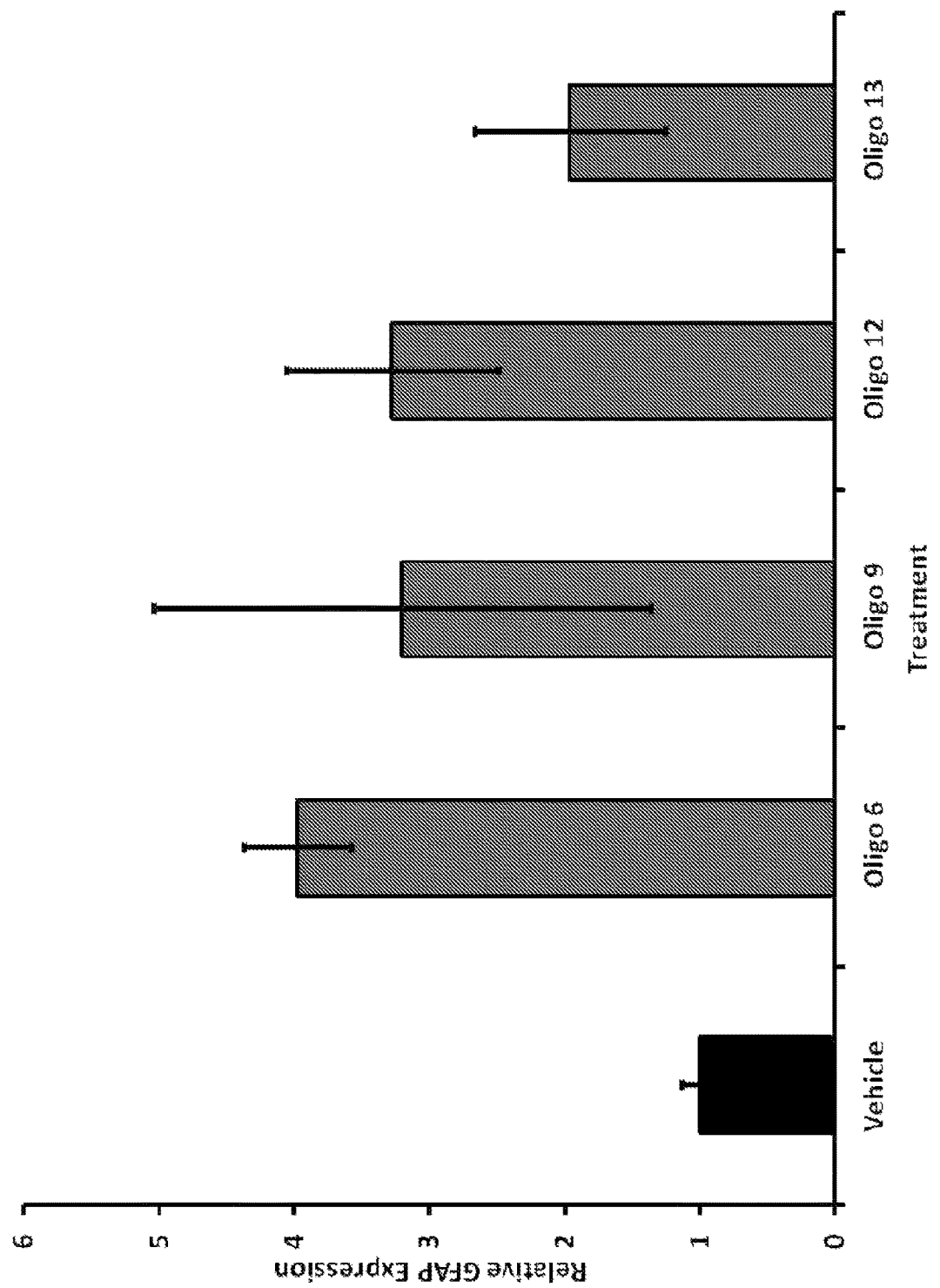
FIG. 17 depicts a graph showing the relative GFAP expression in P301S mice treated with four different antisense oligos.
Figure 18A:
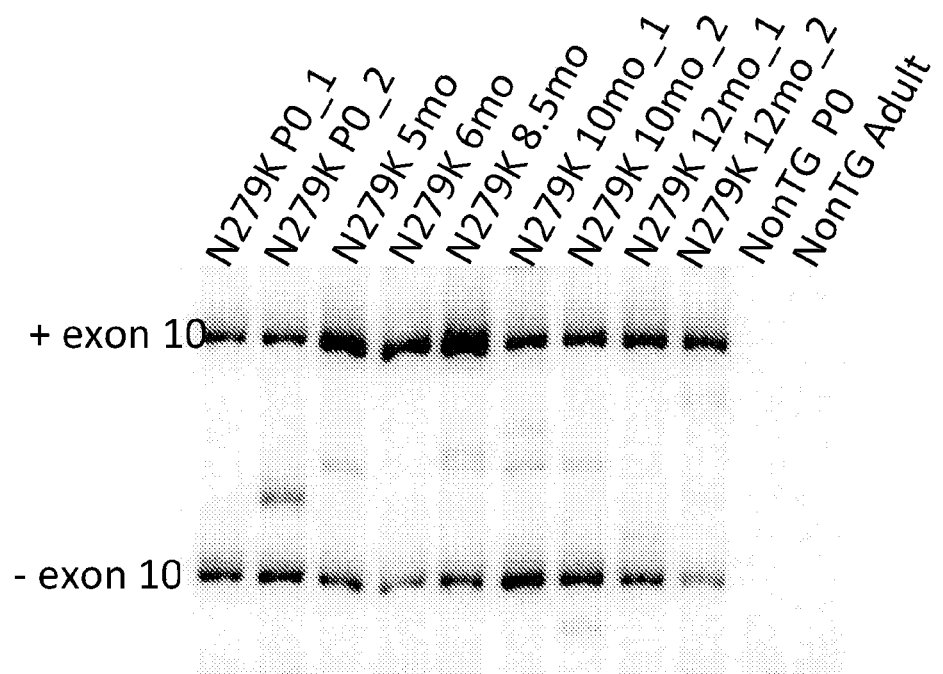
FIG. 18A-18B depict a picture (A) and a graph (B) showing tau splicing in N279K mice over time.
Figure 18B:
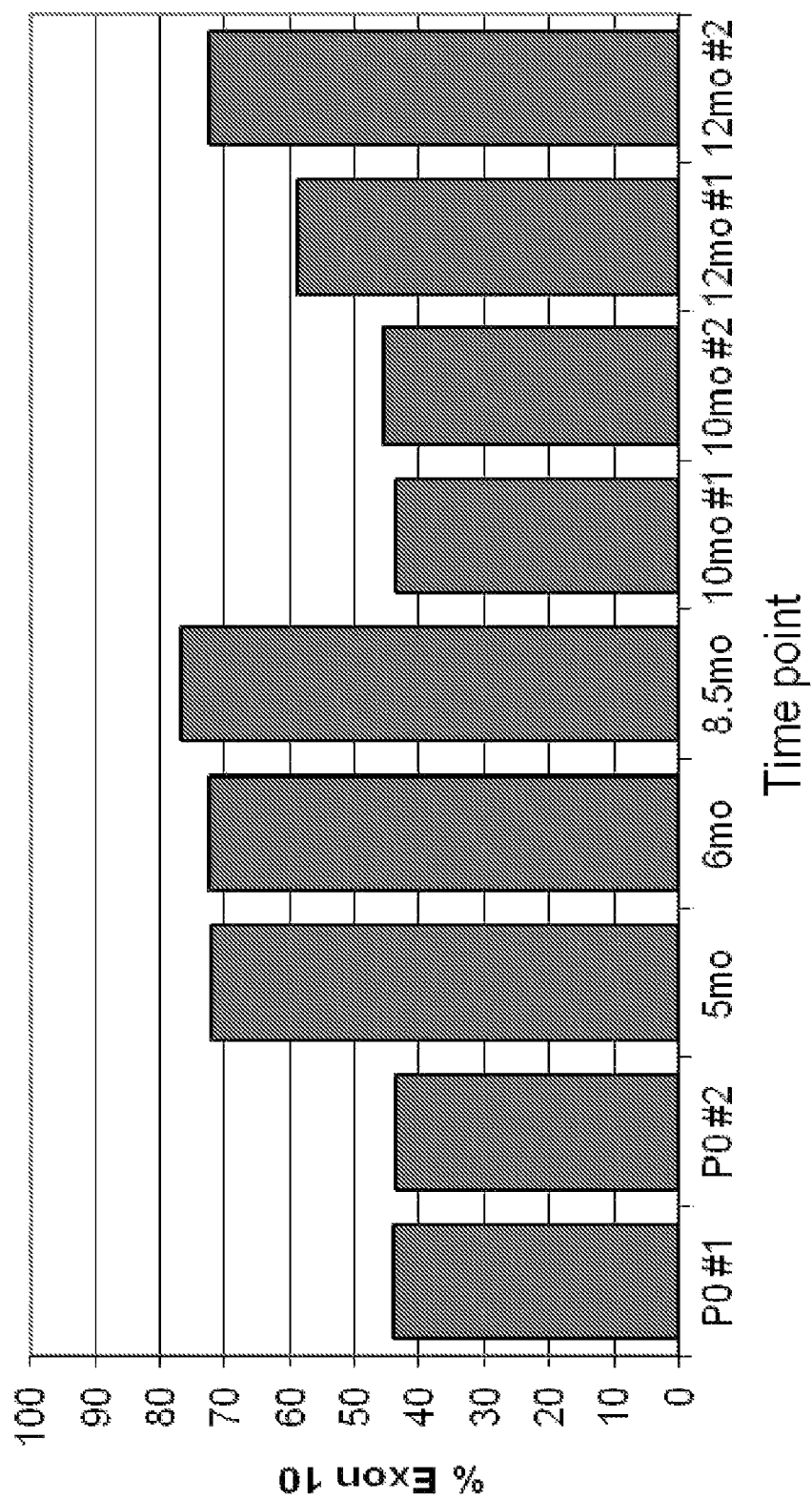
Figure 19:
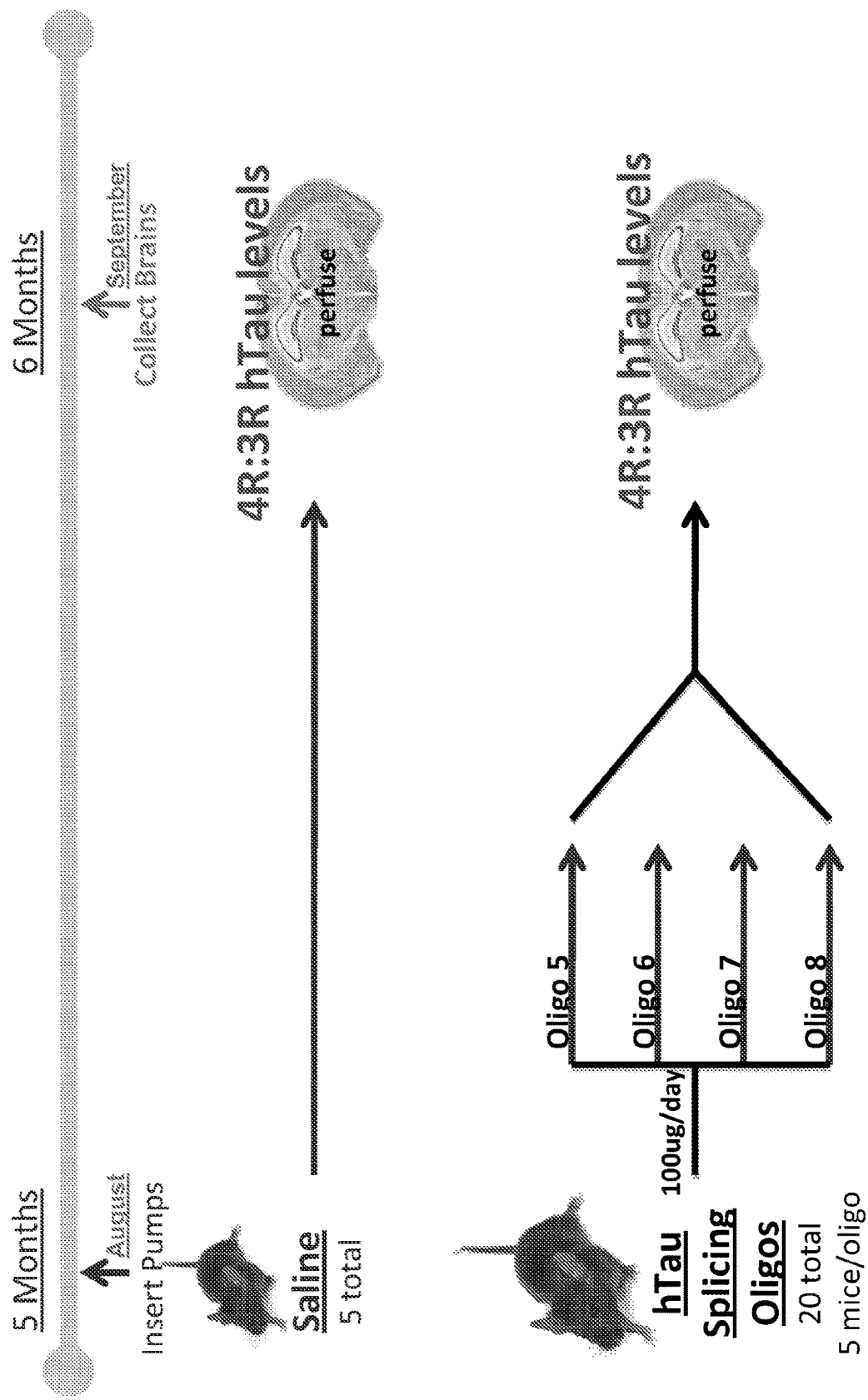
FIG. 19 depicts hTau splicing oligo screening in N279K mice.

Human tau levels and mouse tau mRNA levels were measured and were found to be decreased (FIGS. 15 and 16). Relative GFAP expression was also measured as a measure of toxicity (FIG. 17).

TABLE 1

| Mouse Line | Transgene | Promoter | Behavioral Changes | Pathology | Experimental |
|---|---|---|---|---|---|
| N279K | Human tau minigene containing Exon 10 and flanking intronic sequence | Human Tau | Deficits in radial arm water maze and rotarod at 6 months. 25% develops ever motor weakness by 6 months. | Accumulation of tau, phosphotau in neurons, astrocytes. Present at 6 months, worse at 12 months. | N279K mutation leads to increased 4R compared to 3R tau. Does decreasing 4R:3R tau ratio in adult mice improve behavior/pathology? |
| J20 APP | hAPP minigene with Swedish (K670M/N671L) and Indiana (V717F) familial AD mutations | PDGF | Deficits on Morris water maze, y maze, exploration of new environment at 4-7 months. 15% premature death for unclear reasons by 6-8 months. | Amyloid beta deposition. No obvious tau pathology | Does decreasing mouse tau in adult mice improve behavior/pathology? |

Example Set 2

Figure 27:
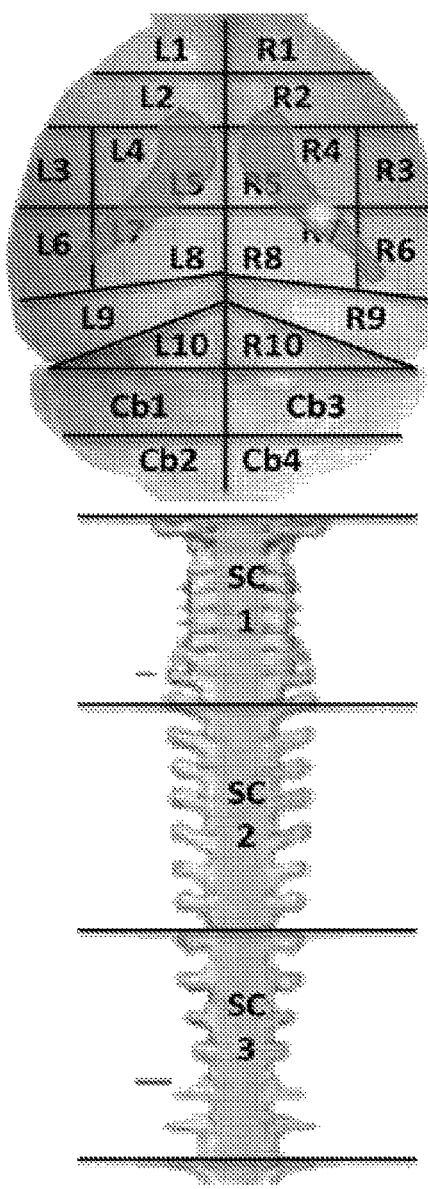
FIG. 27 provides a diagram of each CNS section used for mRNA and protein analysis in Example 6 (Example set 3).

Example 6: Evaluation of Wide-Spread Tau Knockdown In Vivo with Antisense Oligonucleotides To evaluate tau knockdown in different brain regions using antisense oligos, tau #5 oligo was used in C57/Bl6 mice (FIG. 14). A map of the brain regions is provided in FIG. 27.

C57/Bl6 mice were administered 25 µg/day tau #5 or PBS by intraventricular infusion with the Alzet pump for 28 days. Pumps were then removed and the mice were allowed to rest Example 10: Effect Antisense Inhibition of Tau on Treating Seizures Induced by Pentelenetetrazoll (PTZ) was Evaluated Groups of 3 month old C57/BL6 males were infused for 28 days with the Alzet pump at 25 µg/day of ASO. The pumps were removed, and the animals were rested for 3 weeks post-pump removal. Seizures were induced using 55 mg/kg of PTZ by intraperitoneal injection. The mice are videotaped for 15 minutes and scored later in a blinded fashion.

The results show that the knockdown and the splicing oligos (i.e., ISIS 415883) were capable of protection mice against PTZ induced seizures (FIG. 12).

Example Set 3

Example 1: In Vitro Dose-Dependent Inhibition of Tau in Human SH-SY5Y Cells with Gapmer Antisense Oligonucleotides Antisense oligonucleotides (ASO A and ASO B) were designed targeting a Tau nucleic acid (SEQ ID NO: 1) and were tested for their effects on Tau mRNA in vitro. The chimeric antisense oligonucleotides were designed as 5-10-5 MOE gapmers. The gapmers are 20 nucleosides in length, wherein the central gap segment comprises ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines. Each gapmer is targeted to the human Tau genomic sequence, designated herein as SEQ ID NO: 1 (GENBANK Accession No. NT_010783.14 truncated from nucleotides 2624000 to 2761000), as presented in Table 2.

TABLE 2

Antisense oligonucleotides targeting SEQ ID NO: 1

| ISIS No | Target Region |
|---|---|
| ASO A | Exon 2 |
| ASO B | Exon 7 |

SH-SY5Y cells were plated at a density of 20,000 cells per well and transfected using electroporation with 1,250 nM, 2,500 nM, 5,000 nM, 10,000 nM, or 20,000 nM concentrations of antisense oligonucleotide. After a treatment period of approximately 16 hours, RNA was isolated from the cells and Tau mRNA levels were measured by quantitative real-time PCR. Tau mRNA levels were adjusted according to total RNA content, as measured by RIBOGREEN®. Tau was reduced in a dose-dependent manner in ASO A and ASO B treated cells, relative to untreated control cells.

Example 2: In Vitro Dose-Dependent Reduction of 4R Isoform in Human A172 Cells with Uniformly Modified Antisense Oligonucleotides Targeting Intron 10 of Human Tau Uniformly modified antisense oligonucleotides were tested in vitro in a dose dependent study. The oligonucleotides, ASO C (also ISIS 549620), ISIS 549595, ISIS 549617, and ISIS 549619, are 18 nucleobase uniformly modified antisense oligonucleotides comprising a 2'-MOE modification on each nucleoside was designed targeting intron 10 of human Tau (i.e., SEQ ID NO: 1). Each internucleoside linkage throughout the oligonucleotide are phosphorothioate (P=S) linkages. All cytosine residues throughout the oligonucleotide are 5-methylcytosines.

The antisense oligonucleotide was tested in vitro. A172 cells were transfected using LipofectAMINE2000® with 0.3 nM, 1.0 nM, 3.0 nM, 10.0 nM, 30.0 nM, or 100.0 nM concentrations of antisense oligonucleotide. After a treatment period of approximately 24 hours, RNA was isolated from the cells and the mRNA levels of the 4R isoform and total Tau mRNA were measured by quantitative real-time PCR using primer probe set hMAPT_LTS00914_MGB (forward sequence CGGGAAGGTGCAGATAATTAATAAG, designated SEQ ID NO: 21; reverse sequence GGACGTGTTTGATATTATCCTTTGAG, designated SEQ ID NO: 22; probe sequence AGCTGGATCTTAGCAACG, designated SEQ ID NO: 23). Tau mRNA levels were adjusted according to total RNA content, as measured by RIBOGREEN®.

The half maximal inhibitory concentration (IC50) of each oligonucleotide is presented in the table below and was calculated by plotting the concentrations of oligonucleotides used versus the percent inhibition of human Tau exon 10 mRNA expression achieved at each concentration, and noting the concentration of oligonucleotide at which 50% inhibition of human Tau exon 10 mRNA expression was achieved compared to the control. The 4R isoform of Tau was reduced in a dose-dependent manner in ASO C (also ISIS 549620), ISIS 549595, ISIS 549617, and ISIS 549619-treated cells, relative to untreated control cells.

TABLE 3

Percent 4R isoform to total Tau mRNA in A172 cells

|  | 0.3 nM | 1 nM | 3 nM | 10 nM | 30 nM | 100 nM | $IC_{50}$ (nM) |
|---|---|---|---|---|---|---|---|
| ISIS 549595 | 75 | 57 | 33 | 24 | 16 | 31 | 1.3 |
| ISIS 549617 | 83 | 61 | 46 | 34 | 29 | 26 | 3.4 |
| ISIS 549619 | 82 | 78 | 51 | 39 | 21 | 17 | 4.6 |
| ASO C (ISIS 549620) | 83 | 70 | 55 | 33 | 20 | 23 | 4.0 |

Example 3: Effect of Treatment with Gapmer Antisense Oligonucleotides on Tau mRNA Levels, Tau Protein Levels, and Tau Hyperphosphorylation in P301S Transgenic Mouse Model P301S mice over-express the mutated form of human Tau (Yoshiyama, Y. et al., Neuron. 2007. 53: 337-51). The mice exhibit Tau pathology with accumulation of hyperphosphorylated Tau protein. The effect of treatment on these mice with gapmers targeting human Tau was assessed in this model.

Study 1

Groups of 3-4 P301S mice were administered ASO A and ASO B at 60 µg/day for 14 days via an intracerebroventricular pump. A control group of two mice were similarly treated with PBS. Alzet osmotic pumps were used to continuously deliver the antisense oligonucleotide. Pumps were assembled and implanted, as per the manufacturer's instructions (Durect Corporation). Animals were anesthetized with 3% isofluorane and placed in a stereotactic frame. After sterilizing the surgical site, a one cm midline incision was made over the bregma. Through the use of stereotaxic guides, a cannula was implanted into the right lateral ventricle and secured. A catheter attached to an Alzet osmotic pump was secured to the cannula and the pump was placed subcutaneously in the midcapsular area. The incision was closed with sutures. Tissue was collected from around the catheter site 4 weeks after pump implantation.

RNA Analysis

RNA was extracted from the cortex region around the catheter site and analyzed by qRT-PCR for expression levels of human and murine Tau. The data is presented in Table 4. The results indicate that oligonucleotides inhibit levels of human Tau mRNA.

TABLE 4

% inhibition of Tau mRNA compared to the PBS control

| ISIS No | human | murine |
|---|---|---|
| ASO A | 35 | 7 |
| ASO B | 55 | 24 |

Study 2

Groups of five P301S mice each (5 months old) were administered ASO B at 50 µg/day for 28 days via an intracerebroventricular pump. A control group of five mice were similarly treated with PBS. Alzet osmotic pumps were used to continuously deliver the antisense oligonucleotide. Pumps were assembled and implanted, as per the manufacturer's instructions (Durect Corporation). Animals were anesthetized with 3% isofluorane and placed in a stereotactic frame. After sterilizing the surgical site, a one cm midline incision was made over the bregma. Through the use of stereotaxic guides, a cannula was implanted into the right lateral ventricle and secured. A catheter attached to an Alzet osmotic pump was secured to the cannula and the pump was placed subcutaneously in the midcapsular area. Tissues were collected after 2 months.

RNA Analysis

RNA was extracted from the hippocampal region around the injection site and analyzed by qRT-PCR for expression levels of human and murine Tau. The results indicate that ASO B inhibited levels of human Tau mRNA by 36% and of murine Tau mRNA by 5% one month post-ASO B active infusion.

Protein Analysis

Human Tau protein in the brain was analyzed by ELISA (as previously described by Yamada et al., J. Neurosci. 2011. 31: 13110-117), as well as by western blot analysis using the total tau Tau5E2 antibody. The ELISA results indicate that ASO B inhibited levels of human Tau by 40%. The western blot results were quantified and indicate that ASO B inhibited levels of human Tau by 74%. It should be noted that the ELISA recognizes all forms of Tau, including human and mouse, whereas with the Western Blot, the human Tau can be separated from the mouse Tau by size differences. Thus, the Western Blot human Tau quantification is a more accurate representation of the human Tau specific knockdown levels.

Study 3

Groups of 5 P301S mice each (5 months old) were administered ASO B at 50 µg/day for 28 days via an intracerebroventricular pump. Another Group of 5 P301S mice (5 months old) were administered ASO B at 100 µg/day for 14 days via an intracerebroventricular pump. A control group of five mice were similarly treated with PBS. Alzet osmotic pumps were used to continuously deliver the antisense oligonucleotide. Pumps were assembled and implanted, as per the manufacturer's instructions (Durect Corporation). Animals were anesthetized with 3% isofluorane and placed in a stereotactic frame. After sterilizing the surgical site, a one cm midline incision was made over the bregma. Through the use of stereotaxic guides, a cannula was implanted into the right lateral ventricle and secured. A catheter attached to an Alzet osmotic pump was secured to the cannula and the pump was placed subcutaneously in the midcapsular area. Tissues were collected after 2 months.

Hyperphosphorylated Tau Analysis

Figure 25:
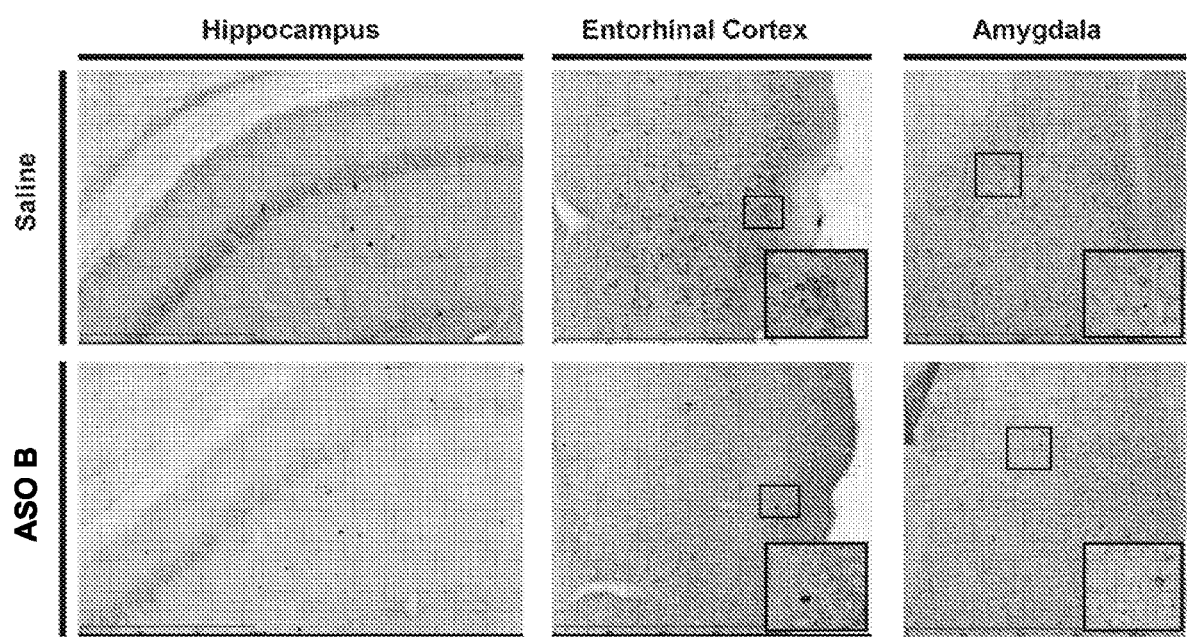
FIG. 25 provides a graphical representation of the percentage of cells stained with the antibody AT8 as a measure of hyperphosphorylated Tau in the P301S transgenic mouse model.

The monoclonal Tau antibody AT8 recognizes Tau protein phosphorylated at both serine 202 and threonine 205 (Goedert, M. et al., Neurosci. Lett. 1995. 189: 167-9) and is therefore is used in a method of detection of hyperphosphorylated Tau. This is also the most commonly used antibody to identify Tau accumulations in human Alzheimer's disease patient brains. Extensive hyperphosphorylated Tau (Ser202 and Thr205) was detected in the entorhinal cortex and the basolateral amygdala by immunohistochemistry using AT8 antibody in P301S brains at 7 months of age. The percentage of cells stained with the antibody is presented in FIG. 25 and Table 5. The results indicate that treatment with ASO B resulted in clearance of hyperphosphorylated Tau.

TABLE 5

% staining of hyperphosphorylated human Tau

| Area | Treatment | % |
|---|---|---|
| amygdala | PBS | 4.6 |
|  | ASO B 50 µg | 1.4 |
|  | ASO B 100 µg | 2.3 |
| entorhinal cortex | PBS | 8.8 |
|  | ASO B 50 µg | 5.4 |
|  | ASO B 100 µg | 6.8 |

Example 4: In Vivo Reduction of 4R Isoform in the N279K Transgenic Mouse Model with Uniformly Modified Antisense Oligonucleotides Targeting Intron 10 of Human Tau N279K mice express the human Tau mini-gene with FTD mutation (Dawson, H. N. et al., J. Neurosci. 2007. 27: 9155-68). The N279K mutation promotes the inclusion of exon 10 (4R Tau). The effect of uniformly modified antisense oligonucleotides targeting human Tau on the shifting of the 4R isoform to 3R isoform was assessed in this mouse model.

Groups of 4 N279K mice (5 months of age) were administered ASO C (also ISIS 549620) at 60 µg/day for 28 days via an intracerebroventricular pump. A control group of five mice was similarly treated with PBS. Animals were anesthetized with 3% isofluorane and placed in a stereotactic frame. Alzet osmotic pumps were used to continuously deliver the antisense oligonucleotide. Pumps were assembled and implanted, as per the manufacturer's instructions (Durect Corporation). Animals were anesthetized with 3% isofluorane and placed in a stereotactic frame. After sterilizing the surgical site, a one cm midline incision was made over the bregma. Through the use of stereotaxic guides, a cannula was implanted into the right lateral ventricle and secured. A catheter attached to an Alzet osmotic pump was secured to the cannula and the pump was placed subcutaneously in the midcapsular area. Tissues around the cannula region were collected on the 29th day.

RNA Analysis

RNA was extracted from the cortex around the cannula, and mRNA expression of the 4R and 3R isoforms of human Tau were analyzed by RT-radioactive PCR. Briefly, 1,000 ng of RNA was reverse transcribed with oligo(dT). The cDNA was then amplified in the presence of $\alpha$-$^{32}$P-dCTP. PCR products digested with Hinc II and separated by denaturing PAGE. Exon 10 included and excluded species were detected by autoradiography and quantitated by PhosphorImage analysis. The signal intensity of each cDNA band was normalized according to its G+C content. The results indicate that treatment with ASO C (also ISIS 549620) resulted in a decrease in 4R Tau by 85% of the total Tau mRNA.

Example 5: Effect of Antisense Oligonucleotides Targeting Human Tau on Behavior and Tau Accumulations in the N279K Transgenic Mouse Model The effect of gapmers and uniformly modified antisense oligonucleotides on behavioral assays was analyzed in the N279K transgenic model. ASO A, a gamer, which causes reduction of total Tau mRNA, and ASO C (also ISIS 549620), a uniform MOE oligonucleotide, which causes the shifting of the 4R Tau isoform to 3R Tau isoform, were both used in this assay.

Two groups of 6-8 N279K mice each (3 months of age) were administered ASO A or ASO C (also ISIS 549620) at 25 μg/day for 28 days via an intracerebroventricular pump. An N279K transgenic control group of eight mice were similarly treated with PBS. Another control group of eight mice was similarly treated with a scrambled oligonucleotide, ISIS 141923 (CCTTCCCTGAAGGTTCCTCC, 5-10-5 MOE gapmer with no known target (SEQ ID NO: 11)). Another transgenic littermate control group of eight mice were similarly treated with PBS. Animals were anesthetized with 3% isofluorane and placed in a stereotactic frame. Alzet osmotic pumps were used to continuously deliver the antisense oligonucleotide solution. Pumps were assembled and implanted, as per the manufacturer's instructions (Durect Corporation). Animals were anesthetized with 3% isofluorane and placed in a stereotactic frame. After sterilizing the surgical site, a one cm midline incision was made over the bregma. Through the use of stereotaxic guides, a cannula was implanted into the right lateral ventricle and secured. A catheter attached to an Alzet osmotic pump was secured to the cannula and the pump was placed subcutaneously in the midcapsular area. Behavioral studies were performed at 6.5 months of age and mice collected at 7.5 months of age.

Novel Object Recognition Analysis

Novel object recognition is used to determine if the mice can recognize an object that is familiar versus one that is novel (Bevins, R. A. and Besheer, J. Nature Protocols. 2006, 1: 1306-1311). Briefly, the animals are first exposed to two identical objects for 10 minutes; 3 hours later, they are then exposed to this same object (familiar), as well as a new object (novel) for 5 minutes. The mice were videotaped and videos were watched and scored blinded. Non-transgenic mice will spend more time with the novel object compared to the time spent with the familiar object. This is a measure of recall memory in the mice. Human patients affected by a tauopathy, such as Alzheimer's disease, also display deficits in memory recall.

The data are presented in Table 6. The results indicate that mice treated with the uniformly modified antisense oligonucleotide (ASO C also ISIS 549620) spent less time with familiar objects and more time with novel objects compared to the transgenic control.

TABLE 6

Total Percent Time spent with object over a 5 minute period

|  | Familiar | Novel |
| --- | --- | --- |
| PBS | 45 | 54 |
| ISIS 141923 | 38 | 62 |
| ASO A | 36 | 64 |
| ASO C (also ISIS 549620) | 25 | 75 |
| Non-Tg mice | 38 | 62 |

Nestlet Building Activity Analysis

As a general measure of mouse performance, nestlet building activity was accessed. Mice instinctually build nests when provided with nestlets. Impaired resting performance indicates either an overall cognitive and/or motor deficit. Human tauopathy patients present with general cognition dysfunction and may also present with motor problems. Nestlet building activity (Deacon, R. M. Nat. Protocol. 2006. 1: 1117-9) was initiated by providing the mice with 3.0 grams of pressed cotton material and leaving the mice overnight to assemble a nest. Male nest building activity was assessed. The mice first shred the tightly packed material, then arrange it into a nest. The nesting activity was scored on a five-point scale with '0' being 'no nest' and '5' being a perfect nest surrounding the mouse. Any untorn material left after a bout of nesting was also weighed and provided a further analysis of nesting behavior. A higher untorn nestlet weight signifies a lower quality nest. The nesting scores and untorn nestlet weights are presented in Table 7. Treatment with both the gapmer antisense oligonucleotide (ASO A) and the uniformly modified antisense oligonucleotide (ASO C also ISIS 549620) led to increase in nesting scores and decrease in untorn material as compared to control, indicating improvement of nesting behavior in the mice.

TABLE 7

Nestlet building activity

|  | score | Untorn nestlet weight (g) |
| --- | --- | --- |
| PBS | 1.8 | 2.2 |
| ISIS 141923 | 2.3 | 1.6 |
| ASO A | 2.4 | 1.2 |
| ASO C (also 549620) | 4.4 | 0.8 |
| Non-Tg mice | 4.4 | 0.5 |

Walking Initiation Analysis

The N279K mice display age progressive deficits in walking initiation. Walking initiation in mice may be, in part, equated to the parkinsonism component of FTDP-17. Bradykinesia, or slowed initiation of movement, is a common feature in parkinsonism disorders. To measure walking initiation in mice, the mice were placed in the center of a 21 cm×21 cm square and time taken for all four paws of the mouse to completely leave the square was measured using a stopwatch. The data are presented in Table 8. The results indicate that mice treated with both the gapmer antisense oligonucleotide (ASO A) and the uniformly modified antisense oligonucleotide (ASO C also ISIS 549620) initiated walking at time intervals faster than the N279K PBS and ISIS 141923 controls.

TABLE 8

| Time to leave square (sec) | |
|---|---|
| | (Sec) |
| PBS | 10.8 |
| ISIS 141923 | 10.1 |
| ASO A | 9.7 |
| ASO C (also ISIS 549620) | 7.0 |
| Non-Tg mice | 3.4 |

Hyperphosphorylated Tau Analysis

Figure 26:
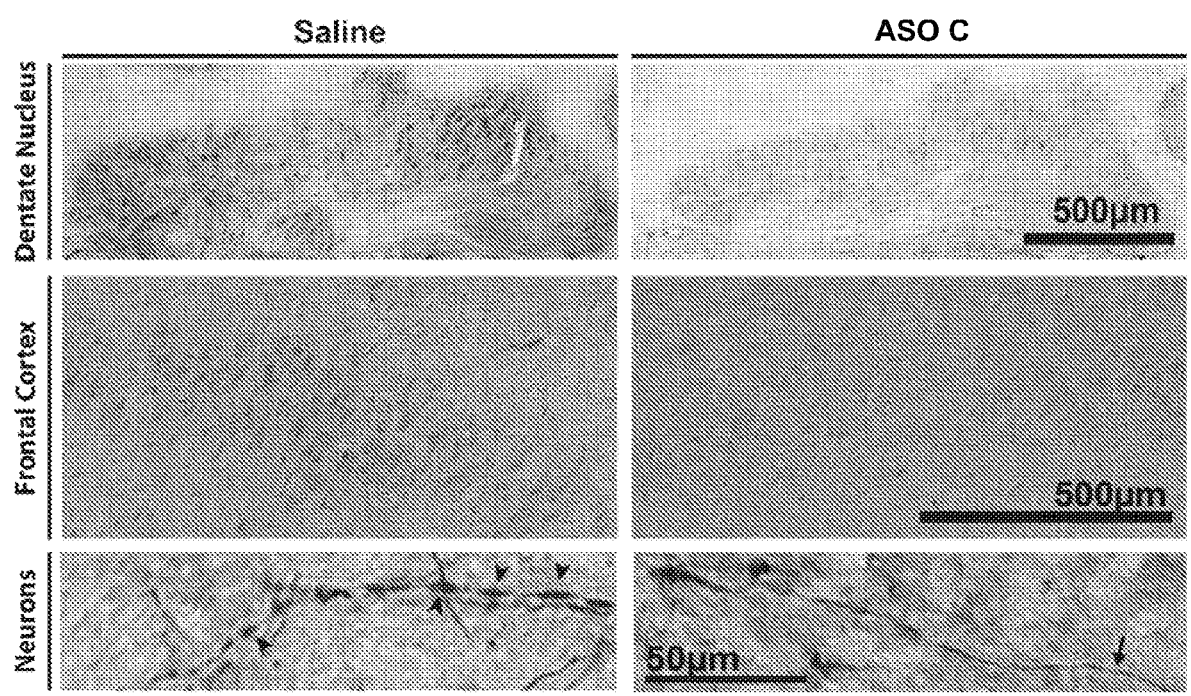
FIG. 26 provides a graphical representation of the percentage of cells stained with the antibody AT8 as a measure of hyperphosphorylated Tau in the N279K transgenic mouse model.

Mice treated with the uniformly modified antisense oligonucleotide (ASO C also ISIS 549620) were euthanized at 7 months of age. The frontal cortex and the dentate nucleus were assessed by immunohistochemistry with the Tau13 antibody, which binds specifically to human Tau protein. The percentage of cells stained with Tau13 somatodendritic accumulations is presented in Table 9 and FIG. 26. The results indicate that mice treated with ASO C (also ISIS 549620) had a decrease in the presence of human Tau inclusions compared to the PBS control. The dentate nucleus is, in part, responsible for the initiation of voluntary movements. So a clearance of Tau deposition in the dentate nucleus may be responsible for the improvement in walking initiation in the ASO C (also ISIS 549620) treated mice as compared to the PBS control.

TABLE 9

| Human Tau inclusions (%) | | |
|---|---|---|
| | PBS | ASO C (also ISIS 549620) |
| Frontal cortex | 16 | 4 |
| Dentate nucleus | 29 | 16 |

Example 6: Effect of Antisense Inhibition of Tau on PTZ Induced Seizures

The effect of antisense inhibition of Tau on treating seizures induced by pentelenetetrazoll (PTZ) was evaluated. The mice were treated with a gapmer antisense oligonucleotide (ASO D) and a uniformly modified antisense oligonucleotide (ISIS 415883). ASO D is a chimeric antisense oligonucleotides 20 nucleosides in length, wherein the central gap segment comprises ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification (i.e., a 5-10-5 MOE gapmer). The internucleoside linkages throughout each gapmer are phosphorothioate linkages. All cytosine residues throughout each gapmer are 5-methylcytosines. Each gapmer is targeted to the human Tau genomic sequence, designated herein as SEQ ID NO: 1 (GENBANK Accession No. NT_010783.14 truncated from nucleotides 2624000 to 2761000), as presented in Table 1. ISIS 141923, an oligonucleotide with no known target (i.e., a "scrambled oligonucleotide") and PBS were used as controls.

Groups of 3 month old C57/BL6 males were administered ASO at 25 µg/day for 28 days via an intracerebroventricular pump. A control group of mice were similarly treated with PBS. The pumps were removed, and the animals were rested for 3 weeks post-pump removal. Seizures were induced using 55 mg/kg of PTZ by intraperitoneal injection. The mice are videotaped for 15 minutes and scored later in a blinded fashion. The final stage reached was recorded.

Figure 28:
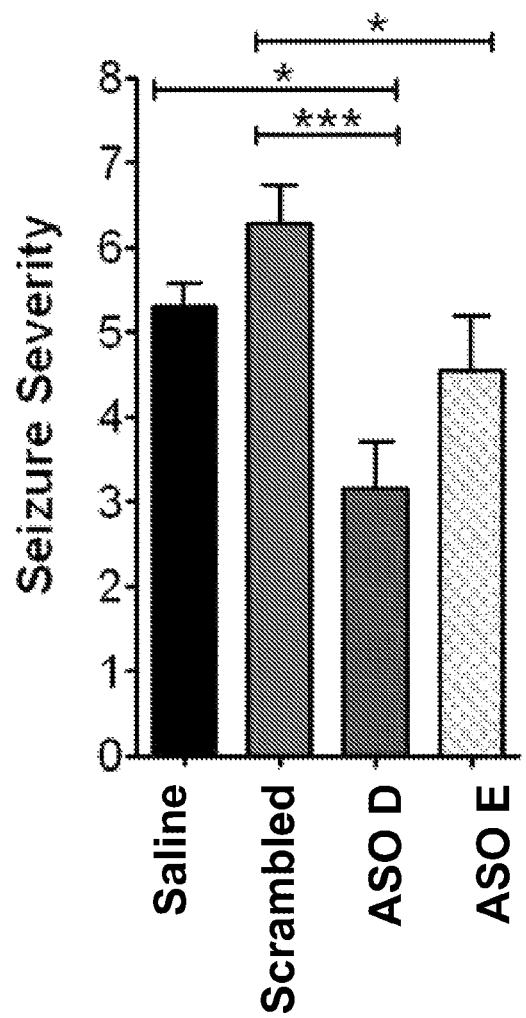
FIG. 28 provides a bar graph showing seizure severity.

Seizure severity was rated on a scale of 0-8 with '0' denoting 'no seizures', 1 denoting 'immobility', 2 denoting 'jerk or twitch', 3 denoting 'tail extension', 4 'denoting forelimb clonus', 5 denoting 'generalized seizure', 6 denoting 'running or jumping', 7 denoting 'tonic extension', and '8' denoting 'death'. The results show that both ASO D and ISIS 415883 were capable of protecting mice against PTZ induced seizures as compared to the scrambled oligonucleotide control (FIG. 28 and Table 10).

Figure 29A:
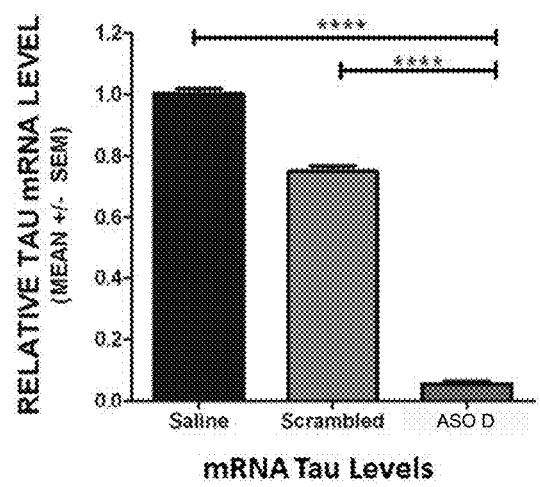
FIG. 29A-29B provide a bar graph showing Tau mRNA (A) and Tau protein (B) levels.
Figure 29B:
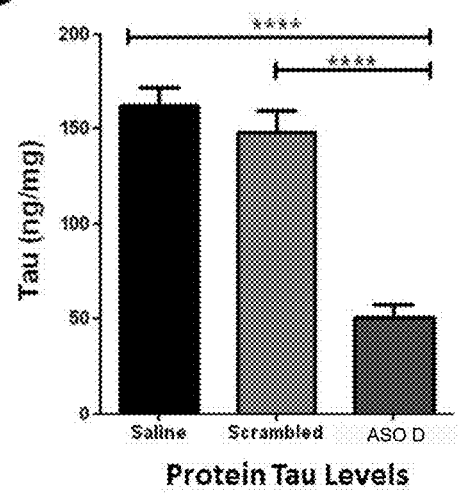

Tau mRNA and protein levels from a 3 mm coronal tissue section around the catheter of the mice treated with ASO D were measured and the data is presented in Table 11 and FIG. 29. The results show that ASO D significantly reduced both mRNA (FIG. 29A) and protein levels (FIG. 29B) of Tau. This correlates well with the decrease in seizure severity of the mice.

Tau isoform of mice treated with ISIS 415883 were measured and the data is presented in Table 12. The results show treatment with ISIS 415883 shifted the Tau isoforms from mainly 4R with some 3R Tau to mostly 3R Tau with some 4R Tau. This is demonstrated with a significant decrease in 4R tau levels while maintaining normal total tau levels.

Figure 30:
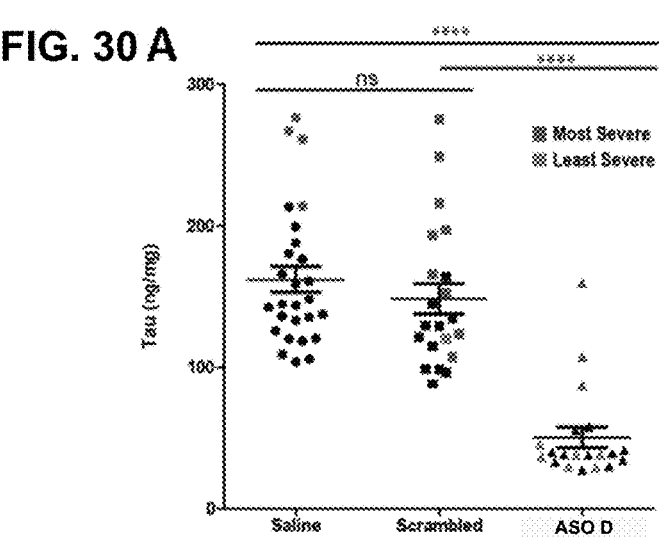
FIG. 30A-30B provide a scatter plot showing seizure severity plotted against Tau levels. (A) shows Tau protein levels in PBS, ISIS 141923-treated, and Tau5-treated groups. (B) shows the correlation of Tau protein levels with seizure score in a linear regression plot.
Figure 30B:
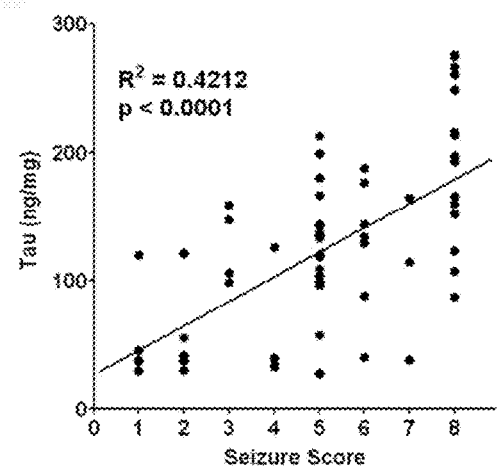

The levels of Tau protein and corresponding seizure severity of the mice treated with ASO D were analyzed in individual mice. As shown in Table 13 and FIG. 30A, it was noted that those mice that demonstrated higher levels of Tau were also those to experience the most severe seizures (stage 8 or death), while those mice that demonstrated reduced levels of Tau only had first stage or the least severe seizures of the group. Based on this observation, the total Tau level in each mouse of the study was plotted against the final seizure stage that the mouse reached. There is a significant correlation using Spearman's Correlation ($p<0.0001$) between the total amount of Tau in each mouse and the induced seizure severity, as shown in the linear regression of FIG. 30B. This suggests that inhibition of Tau results in protection against seizure activity in a chemically-induced model.

TABLE 10

| Seizure severity (average in each group) | |
|---|---|
| PBS | 5.4 |
| ISIS 141923 | 6.3 |
| ASO D | 3.4 |
| ISIS 415883 | 4.6 |

TABLE 11

% inhibition of mRNA and protein levels in mice treated with knockdown oligo (ASO D)

| | mRNA | Protein |
|---|---|---|
| ISIS 141923 | 25 | 8 |
| ASO D | 95 | 70 |

TABLE 12

% Tau 4R Tau isoform and total Tau in mice treated with splicing oligo (ISIS 415883)

|  | 4R isoform | Total Tau |
|---|---|---|
| ISIS 141923 | N/A | 25 |
| ISIS 415883 | 90 | 26 |

TABLE 13

Tau protein levels and seizure severity in mice treated with knockdown oligo (ASO D)

| Mouse # | Tau (ng/mg) | Seizure Stage |
|---|---|---|
| PBS 1 | 120 | 5 |
| PBS 2 | 142 | 5 |
| PBS 3 | 177 | 6 |
| PBS 4 | 181 | 5 |
| PBS 5 | 276 | 8 |
| PBS 6 | 267 | 8 |
| PBS 7 | 214 | 8 |
| PBS 8 | 148 | 3 |
| PBS 9 | 144 | 5 |
| PBS 10 | 106 | 3 |
| PBS 11 | 135 | 5 |
| PBS 12 | 118 | 5 |
| PBS 13 | 143 | 6 |
| PBS 14 | 159 | 3 |
| PBS 15 | 167 | 5 |
| PBS 16 | 188 | 6 |
| PBS 17 | 120 | 5 |
| PBS 18 | 200 | 5 |
| PBS 19 | 137 | 5 |
| PBS 20 | 261 | 8 |
| PBS 21 | 213 | 5 |
| PBS 22 | 133 | 5 |
| PBS 23 | 109 | 5 |
| PBS 24 | 104 | 5 |
| PBS 25 | 136 | 5 |
| PBS 26 | 126 | 4 |
| ISIS 141923 1 | 129 | 6 |
| ISIS 141923 2 | 129 | 6 |
| ISIS 141923 3 | 120 | 1 |
| ISIS 141923 4 | 165 | 7 |
| ISIS 141923 5 | 134 | 6 |
| ISIS 141923 6 | 166 | 8 |
| ISIS 141923 7 | 275 | 8 |
| ISIS 141923 8 | 249 | 8 |
| ISIS 141923 9 | 123 | 8 |
| ISIS 141923 10 | 99 | 5 |
| ISIS 141923 11 | 107 | 8 |
| ISIS 141923 12 | 193 | 8 |
| ISIS 141923 13 | 96 | 5 |
| ISIS 141923 14 | 153 | 8 |
| ISIS 141923 15 | 144 | 6 |
| ISIS 141923 16 | 197 | 8 |
| ISIS 141923 17 | 98 | 3 |
| ISIS 141923 18 | 88 | 6 |
| ISIS 141923 19 | 216 | 8 |
| ISIS 141923 20 | 115 | 7 |
| ISIS 141923 21 | 121 | 2 |
| ASO D 1 | 39 | 7 |
| ASO D 2 | 40 | 6 |
| ASO D 3 | 38 | 1 |
| ASO D 4 | 58 | 5 |
| ASO D 5 | 160 | 8 |
| ASO D 6 | 87 | 8 |
| ASO D 7 | 55 | 2 |
| ASO D 8 | 40 | 4 |
| ASO D 9 | 38 | 1 |
| ASO D 10 | 41 | 2 |
| ASO D 11 | 30 | 2 |
| ASO D 12 | 33 | 4 |
| ASO D 13 | 27 | 5 |
| ASO D 14 | 45 | 1 |
| ASO D 15 | 38 | 2 |
| ASO D 16 | 30 | 1 |
| ASO D 17 | 30 | 1 |
| ASO D 18 | 37 | 1 |
| ASO D 19 | 34 | 4 |
| ASO D 20 | 107 | 8 |

Example 7: Evaluation of Oligonucleotide Distribution in P301S Mice

The distribution of oligonucleotide in P301S mice after infusion of ASO D was analyzed.

P301S mice at 5 months age were administered ASO D at 50 µg/day for 28 days via an intracerebroventricular pump. A control group of P301S mice were similarly treated with PBS. The pumps were removed, and the animals were rested for 28 days post-pump removal. The mice were euthanized and brain tissue and eyes were collected. Brain sections throughout the whole brain were stained with an antibody against the oligonucleotide (developed in-house) and were counterstained with DAPI.

The results show widespread distribution of ASO D throughout the brain sections of the mice. Sections of 50 µm in thickness were taken throughout the entire left hemisphere and stained with the oligonucleotide antibody. For detection, an Alexa-Fluor-546 anti-rabbit secondary antibody was used and a DAPI counter-stain was applied. The presence of a red or pink fluorescence intensity signified the presence of the oligonucleotide. These results demonstrate that ASO D is widely distributed throughout the entire brain following infusion into the right lateral ventricle.

The eyes of the mice were post-fixed, embedded in paraffin, sliced at 6 µm thickness, and mounted onto slides. The sections were stained with an antibody against the oligonucleotide and sections were counterstained with DAPI. The results show significant presence of ASO D in the retinal layers of the eye as well as in the outer layer of the lens in the eye sections of mice treated with ASO D. The same Alexa-Fluor-546 anti-rabbit secondary antibody was used to detect the oligonucleotide antibody. Due to the high level of autofluorescence in the retina because of the retinal pigment epithelium, the green FITC channel was applied to show exactly where the autofluorescence was coming from. Previous studies have shown the presence of hyperphosphorylated Tau in the eyes in patients with Alzheimer's disease and glaucoma (Frost, S. Digital Teleretinal Screen. 2012, 91-100; Ho, W. L. Et al., Molecular Vision, 2012, 18: 2700-2710; Gupta, N. et al., Can. J. Ophthalmol. 2008, 43: 53-60). Hence, this result suggests that an ASO tau treatment can in fact reach the retinal cell layers and may potentially decrease aberrant tau species that may be impeding vision or used as a clinical marker for measuring reduction of tau expression in the CNS.

Example 8: Inhibitory Effect of Uniform 2'-MOE Modified Oligonucleotides on Human Tau Exon 10

Several modified oligonucleotides were evaluated for their effect on inhibiting human Tau exon 10 expression in vitro. ISIS 617782 and 617781 were included in the study for comparison.

"Start site" indicates the 5'-most nucleoside to which the modified oligonucleotide is targeted in the human gene sequence. "Stop site" indicates the 3'-most nucleoside to which the modified oligonucleotide is targeted in the human gene sequence. Each modified oligonucleotide listed in the table below is targeted to the human Tau genomic sequence, designated herein as SEQ ID NO: 1 (GENBANK Accession No NT_010783.15 truncated from nucleotides 9240000 to 9381000).

The half maximal inhibitory concentration (IC50) of each oligonucleotide is presented in the table below and was calculated by plotting the concentrations of oligonucleotides used versus the percent inhibition of human Tau exon 10 mRNA expression achieved at each concentration, and noting the concentration of oligonucleotide at which 50% inhibition of human Tau exon 10 mRNA expression was achieved compared to the control. Results are presented below.

TABLE 14

Inhibitory effect of uniform 2'-MOE modified oligonucleotides on human Tau exon 10 expression

| ISIS NO | Sequence | 0.1 nM | 0.3 nM | 1.0 nM | 3.0 nM | 10 nM | 30 nM | $IC_{50}$ (nM) | SEQ ID NO: X Start Site | SEQ ID NO: X Stop Site | SEQ ID NO |
|---------|----------|--------|--------|--------|--------|-------|-------|-------|------------|-----------|--------|
| 617782 | $U_mG_mA_mA_mG_mG_mU_mA_mC_mU_mC_mA_mC_mA_mC_mU_mG_mC_mC_mG_m$ | 100 | 89 | 80 | 55 | 34 | 16 | 4.33 | 121914 | 121934 | 30 |
| 617781 | $U_mA_mU_mC_mU_mG_mC_mA_mC_mC_mU_mU_mU_mG_mG_mU_mA_mG_m$ | 100 | 95 | 79 | 82 | 65 | 41 | 20.25 | 121820 | 121837 | 31 |
| 415883 | TCTTATTAATTATCTGCACC | 77 | 63 | 41 | 28 | 16 | 11 | 0.65 | 121828 | 121847 | 12 |

ISIS 617782 is 21 nucleosides in length, wherein each nucleoside has a 2'-OCH₃ modification and is denoted as the subscript "m". Each internucleoside linkage throughout the modified oligonucleotide are phosphorothioate internucleoside linkages (P=S).

ISIS 617781 is 18 nucleosides in length, wherein each nucleoside has a 2'-OCH₃ modification and is denoted as the subscript "m". Each internucleoside linkage throughout the modified oligonucleotide are phosphorothioate internucleoside linkages (P=S).

ISIS 415883 is 20 nucleosides in length, wherein each nucleoside has a 2'-MOE modification. Each internucleoside linkage throughout the modified oligonucleotide are phosphorothioate internucleoside linkages (P=S). All cytosine residues throughout the modified oligonucleotides are 5-methylcytosines.

A172 cells were transfected using Lipofectamine2000® with 0, 0.1, 0.3, 1, 3, 10, or 30 nM concentration of modified oligonucleotide as specified in the table below. After a treatment period of approximately 24 hours, RNA was isolated from the cells and the mRNA levels of Tau transcripts containing exon 10 were measured by quantitative real-time PCR. Human Tau primer probe set 9_10 R5 was used to measure mRNA levels of 617782 and human Tau primer probe set 10_11 was used for ISIS 617781 and 415883.

Human Tau primer probe set 9_10 R5 (forward sequence CACTGAGAACCTGAAGCACC, designated herein as SEQ ID NO: 24; reverse sequence GGACGTTGCTAAGATCCAGCT, designated herein as SEQ ID NO: 25; probe sequence TTAATTATCTGCACCTTCCCGCCTCC, designated herein as SEQ ID NO: 26). Human Tau exon 10 mRNA levels were adjusted according to total RNA content, as measured by RIBOGREEN®.

Human primer probe set 10_11 (forward sequence GGATAATATCAAACACGTCCCG, designated herein as SEQ ID NO: 27; reverse sequence TGCCTAATGAGCCACACTTG, designated herein as SEQ ID NO: 28; probe sequence GTCTACAAACCAGTTGACCTGAGC, designated herein as SEQ ID NO: 29).

Example 9: Effects of Uniform 2'-MOE Modified Oligonucleotides on Human Tau Exon 10

A series of modified oligonucleotides were designed to target exon 10 of human Tau and were screened for their effects in reducing exon 10 inclusion in vitro. They are 18 nucleosides in length, wherein each nucleoside has a 2'-MOE modification. Each internucleoside linkage throughout the modified oligonucleotide are phosphorothioate internucleoside linkages (P=S). All cytosine residues throughout the modified oligonucleotides are 5-methylcytosines.

"Start site" indicates the 5'-most nucleoside to which the modified oligonucleotide is targeted in the human gene sequence. "Stop site" indicates the 3'-most nucleoside to which the modified oligonucleotide is targeted in the human gene sequence. Each modified oligonucleotide listed in the tables below is targeted to the human Tau genomic sequence, designated herein as SEQ ID NO: 32 (GENBANK Accession No NT_010783.15 truncated from nucleotides 9240000 to 9381000).

A172 cells were transfected using Lipofectamine2000® with 5 nM concentration of modified oligonucleotide. After a treatment period of approximately 24 hours, RNA was isolated from the cells and the mRNA levels of Tau transcripts containing exon 10 were measured by quantitative real-time PCR. Human primer probe set 10_11 was used to measure mRNA levels. Tau exon 10 mRNA levels were adjusted according to total RNA content, as measured by RIBOGREEN®. Results are presented as percent of Tau exon 10 mRNA expression, relative to untreated control levels and is denoted as "% UTC."

Human primer probe set 10_11 (forward sequence GGATAATATCAAACACGTCCCG, designated herein as SEQ ID NO: 27; reverse sequence TGCCTAATGAGCCACACTTG, designated herein as SEQ ID NO: 28; probe sequence GTCTACAAACCAGTTGACCTGAGC, designated herein as SEQ ID NO: 29).

TABLE 15

Effects of uniform 2'-MOE modified oligonucleotides on human Tau
exon 10 using Primer Probe Set 10_11

| ISIS No. | Sequence | % UTC | SEQ ID NO: 1 Start Site | SEQ ID NO: 1 Stop Site | Mismatches | SEQ ID No. |
|---|---|---|---|---|---|---|
| 549595 | GGACGTGTGAAGGTACTC | 20 | 121924 | 121941 | 0 | 15 |
| 549617 | GCCCAAGAAGGATTTATT | 31.8 | 122012 | 122029 | 0 | 16 |
| 549619 | TCCTGAGAGCCCAAGAAG | 41.7 | 122020 | 122037 | 0 | 17 |
| 549620 | CAGATCCTGAGAGCCCAA | 35.6 | 122024 | 122041 | 0 | 18 |

Example 10: Effects of Uniform 2'-MOE Modified Oligonucleotides on Human Tau Exon A series of modified oligonucleotides were designed to target exon 10 of human Tau and were screened for their effects in reducing exon 10 inclusion in vitro. The modified oligonucleotides are 18 nucleosides in length, wherein each nucleoside has a 2'-MOE modification. Each internucleoside linkage throughout the modified oligonucleotide are phosphorothioate internucleoside linkages (P=S). All cytosine residues throughout the modified oligonucleotides are 5-methylcytosines.

"Start site" indicates the 5'-most nucleoside to which the modified oligonucleotide is targeted in the human gene sequence. "Stop site" indicates the 3'-most nucleoside to which the modified oligonucleotide is targeted in the human gene sequence. Each modified oligonucleotide listed in the tables below is targeted to the human Tau genomic sequence, designated herein as SEQ ID NO: 32 (GENBANK Accession No NT_010783.15 truncated from nucleotides 9240000 to 9381000).

A172 cells were transfected using Lipofectamine2000® with 5 nM concentration of modified oligonucleotide. After a treatment period of approximately 24 hours, RNA was isolated from the cells and the mRNA levels of Tau transcripts containing exon 10 were measured by quantitative real-time PCR. Human Tau primer probe set 9_10 $R_5$ was used to measure mRNA levels. Tau exon 10 mRNA levels were adjusted according to total RNA content, as measured by RIBOGREEN®. Results are presented as percent of Tau exon 10 mRNA expression, relative to untreated control levels and is denoted as "% UTC."

Human Tau primer probe set 9_10 $R_5$ (forward sequence CACTGAGAACCTGAAGCACC, designated herein as SEQ ID NO: 24; reverse sequence GGACGTTGCTAAGATCCAGCT, designated herein as SEQ ID NO: 25; probe sequence TTAATTATCTGCACCTTCCCGCCTCC, designated herein as SEQ ID NO: 26).

TABLE 16

Effects of uniform 2'-MOE modified oligonucleotides on human
Tau exon 10 using Human Tau primer probe set 9_10 R5

| ISIS NO | Sequence | % UTC | SEQ ID NO: 1 Start Site | SEQ ID NO: 1 Stop Site | SEQ ID NO |
|---|---|---|---|---|---|
| 549595 | GGACGTGTGAAGGTACTC | 26 | 121924 | 121941 | 15 |
| 549619 | TCCTGAGAGCCCAAGAAG | 42 | 122020 | 122037 | 17 |
| 549620 | CAGATCCTGAGAGCCCAA | 35 | 122024 | 122041 | 18 |

The invention claimed is:

1. A method of treating Alzheimer's disease in a human subject in need thereof, the method comprising administering to the human subject a therapeutically effective amount of a modified single-stranded antisense oligonucleotide consisting of (i) 20 to 30 linked nucleosides and having a nucleobase sequence that is selected from the group consisting of SEQ ID NOs.: 12, 13, and 14; or (ii) 18 to 30 linked nucleosides and having a nucleobase sequence that is selected from the group consisting of SEQ ID NOs.: 15, 16, 17, and 18.

2. The method of claim 1, wherein the modified single-stranded antisense oligonucleotide has a nucleobase sequence that is set forth in SEQ ID NO: 12.

3. The method of claim 1, wherein the modified single-stranded antisense oligonucleotide has a nucleobase sequence that is set forth in SEQ ID NO: 13.

4. The method of claim 1, wherein the modified single-stranded antisense oligonucleotide comprises at least one modified nucleoside.

5. The method of claim 4, wherein the modified single-stranded antisense oligonucleotide comprises at least one modified nucleoside comprising a modified sugar moiety.

6. The method of claim 5, wherein the modified single-stranded antisense oligonucleotide comprises at least one modified nucleoside comprising a bicyclic sugar moiety.

7. The method of claim 6, wherein the modified single-stranded antisense oligonucleotide comprises at least one modified nucleoside comprising a bicyclic sugar moiety having a 2'-4' bridge, wherein the 2'-4' bridge is selected from —O—CH$_2$—; —O—CH$_2$—CH$_2$; and —O—CH(CH$_3$)—.

8. The method of claim 4, wherein the modified single-stranded antisense oligonucleotide comprises at least one modified nucleoside comprising a modified non-bicyclic sugar moiety.

9. The method of claim 8, wherein the modified single-stranded antisense oligonucleotide comprises at least one modified nucleoside comprising a non-bicyclic sugar moiety comprising a 2'-O-methoxyethyl (2'-MOE) or 2'-OMe.

10. The method of claim 1, wherein the modified single-stranded antisense oligonucleotide comprises:
  a gap segment consisting of linked deoxynucleosides;
  a 5' wing segment consisting of linked nucleosides;
  a 3' wing segment consisting of linked nucleosides;
    wherein the gap segment is positioned immediately adjacent to and between the 5' wing segment and the 3' wing segment and wherein each nucleoside of each wing segment comprises a modified sugar moiety.

11. The method of claim 5, wherein each nucleoside of the modified single-stranded antisense oligonucleotide comprises a modified sugar moiety.

12. The method of claim 1, wherein the modified single-stranded antisense oligonucleotide comprises at least one modified internucleoside linkage.

13. The method of claim 12, wherein each internucleoside linkage of the modified single-stranded antisense oligonucleotide is a modified internucleoside linkage.

14. The method of claim 12, wherein at least one internucleoside linkage is a phosphorothioate internucleoside linkage.

15. The method of claim 14, wherein the modified single-stranded antisense oligonucleotide comprises at least one phosphodiester internucleoside linkage.

16. The method of claim 13, wherein each internucleoside linkage is a phosphorothioate internucleoside linkage.

17. The method of claim 1, wherein the modified single-stranded antisense oligonucleotide comprises at least one modified nucleobase.

18. The method of claim 17, wherein the modified nucleobase is a 5-methylcytosine.

19. The method of claim 1, wherein the modified single-stranded antisense oligonucleotide comprises at least one modified internucleoside linkage, at least one modified nucleobase, and at least one modified sugar moiety.

20. The method of claim 19, wherein the at least one modified internucleoside linkage comprises a phosphorothioate internucleoside linkage.

21. The method of claim 20, wherein each cytosine of the modified single-stranded antisense oligonucleotide is 5-methylcytosine.

22. The method of claim 21, wherein each sugar moiety of the modified single-stranded antisense oligonucleotide is 2'-MOE.

23. The method of claim 19, wherein the modified single-stranded antisense oligonucleotide comprises:
- a gap segment consisting of linked deoxynucleosides;
- a 5' wing segment consisting of linked nucleosides;
- a 3' wing segment consisting of linked nucleosides; wherein the gap segment is positioned immediately adjacent to and between the 5' wing segment and the 3' wing segment and wherein each nucleoside of each wing segment comprises a modified sugar moiety.

24. The method of claim 23, wherein each nucleoside of each wing segment comprises 2'-MOE.

25. The method of claim 24, wherein the at least one modified internucleoside linkage comprises a phosphorothioate internucleoside linkage.

26. The method of claim 25, wherein each cytosine of the modified single-stranded antisense oligonucleotide is 5-methylcytosine.

27. The method of claim 1, wherein the modified single-stranded antisense oligonucleotide has a nucleobase sequence that is set forth in SEQ ID NO:14.

28. The method of claim 1, wherein the modified single-stranded antisense oligonucleotide has a nucleobase sequence that is set forth in SEQ ID NO:15.

29. The method of claim 1, wherein the modified single-stranded antisense oligonucleotide has a nucleobase sequence that is set forth in SEQ ID NO:16.

30. The method of claim 1, wherein the modified single-stranded antisense oligonucleotide has a nucleobase sequence that is set forth in SEQ ID NO: 17.

31. The method of claim 1, wherein the modified single-stranded antisense oligonucleotide has a nucleobase sequence that is set forth in SEQ ID NO:18.

32. The method of claim 2, wherein each cytosine of the modified single-stranded antisense oligonucleotide is 5-methylcytosine, each sugar moiety of the modified single-stranded antisense oligonucleotide is 2'-MOE, and wherein each internucleoside linkage of the modified single-stranded antisense oligonucleotide is a phosphorothioate internucleoside linkage.

33. The method of claim 3, wherein each cytosine of the modified single-stranded antisense oligonucleotide is 5-methylcytosine, each sugar moiety of the modified single-stranded antisense oligonucleotide is 2'-MOE, and wherein each internucleoside linkage of the modified single-stranded antisense oligonucleotide is a phosphorothioate internucleoside linkage.

34. The method of claim 27, wherein each cytosine of the modified single-stranded antisense oligonucleotide is 5-methylcytosine, each sugar moiety of the modified single-stranded antisense oligonucleotide is 2'-MOE, and wherein each internucleoside linkage of the modified single-stranded antisense oligonucleotide is a phosphorothioate internucleoside linkage.

35. The method of claim 28, wherein each cytosine of the modified single-stranded antisense oligonucleotide is 5-methylcytosine, each sugar moiety of the modified single-stranded antisense oligonucleotide is 2'-MOE, and wherein each internucleoside linkage of the modified single-stranded antisense oligonucleotide is a phosphorothioate internucleoside linkage.

36. The method of claim 29, wherein each cytosine of the modified single-stranded antisense oligonucleotide is 5-methylcytosine, each sugar moiety of the modified single-stranded antisense oligonucleotide is 2'-MOE, and wherein each internucleoside linkage of the modified single-stranded antisense oligonucleotide is a phosphorothioate internucleoside linkage.

37. The method of claim 30, wherein each cytosine of the modified single-stranded antisense oligonucleotide is 5-methylcytosine, each sugar moiety of the modified single-stranded antisense oligonucleotide is 2'-MOE, and wherein each internucleoside linkage of the modified single-stranded antisense oligonucleotide is a phosphorothioate internucleoside linkage.

38. The method of claim 31, wherein each cytosine of the modified single-stranded antisense oligonucleotide is 5-methylcytosine, each sugar moiety of the modified single-stranded antisense oligonucleotide is 2'-MOE, and wherein each internucleoside linkage of the modified single-stranded antisense oligonucleotide is a phosphorothioate internucleoside linkage.

* * * * *